United States Patent
Tsuchiya et al.

(10) Patent No.: US 6,649,656 B1
(45) Date of Patent: Nov. 18, 2003

(54) ANTHRANILIC ACID DERIVATIVES

(75) Inventors: Naoki Tsuchiya, Tokyo (JP); Susumu Takeuchi, Tokyo (JP); Takumi Takeyasu, Tokyo (JP); Naoki Hase, Tokyo (JP); Takao Yamori, Tokyo (JP); Takashi Tsuruo, Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/744,388

(22) PCT Filed: Jul. 23, 1999

(86) PCT No.: PCT/JP99/03969

§ 371 (c)(1),
(2), (4) Date: Apr. 4, 2001

(87) PCT Pub. No.: WO00/05198

PCT Pub. Date: Feb. 3, 2000

(30) Foreign Application Priority Data

| Jul. 24, 1998 | (JP) | 10-209410 |
| Sep. 11, 1998 | (JP) | 10-258486 |
| Dec. 25, 1998 | (JP) | 10-369808 |
| Dec. 25, 1998 | (JP) | 10-369809 |

(51) Int. Cl.[7] ............... A61K 31/195; A61K 31/215; C07C 235/38; C07C 237/57
(52) U.S. Cl. ........... 514/535; 514/562; 514/563; 560/12; 560/18; 560/36; 560/45; 560/48; 562/430; 562/432; 562/441; 562/455; 562/457
(58) Field of Search ............. 560/12, 18, 36, 560/15, 48; 562/430, 432, 441, 455, 457; 514/535, 562, 563

(56) References Cited

U.S. PATENT DOCUMENTS 5,808,144 A * 9/1998 Hasegawa et al. .......... 562/455

FOREIGN PATENT DOCUMENTS

| EP | 0 763 523 A1 | 3/1997 |
| JP | A 1-287066 | 11/1989 |
| JP | A 1-106818 | 4/1990 |
| JP | A 5-9170 | 1/1993 |
| JP | A 7-33743 | 2/1995 |
| JP | A 7-97350 | 4/1995 |
| JP | A 7-285858 | 10/1995 |
| WO | WO 90/12001 | 10/1990 |
| WO | WO 95/25723 | 9/1995 |
| WO | WO 95/32943 | 12/1995 |
| WO | 97/19910 | 6/1997 |

OTHER PUBLICATIONS

Hasegawa et al., Chemical Abstracts, vol. 127:81253, 1997.*
Journal of Medicinal Chemistry, 1997, vol. 40, No. 4, 395–407, "Novel Naphthalene Derivatives as Inhibitors of Human Immunoglobulin E Antibody Production", M. Hasegawa, et al.

* cited by examiner

Primary Examiner—Richard L. Raymond
(74) Attorney, Agent, or Firm—Sughrue Mion, PLLC

(57) ABSTRACT

The present invention relates to an anthranilic acid derivative expressed by the following formula (1) or the following formula (2), or its pharmacologically permissible salt or solvate.

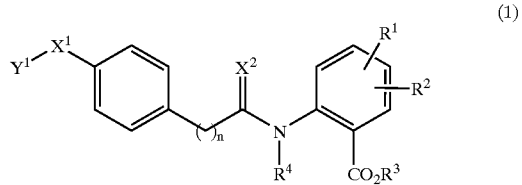

(1)

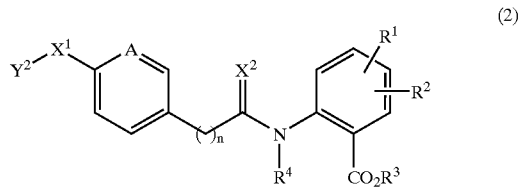

(2)

11 Claims, No Drawings

ANTHRANILIC ACID DERIVATIVES

This application is a 371 of PCT/JP99/03969, filed Jul. 23, 1999.

TECHNICAL FIELD

The present invention relates to a new anthranilic acid derivative expressed by the formula (1) or the formula (2), its pharmacologically permissible salts or solvated products (which may be collectively called as "the anthranilic acid derivative of the present invention" hereinafter), a pharmaceutical composition composed thereof and a preventive and/or therapeutic agent composed thereof. More particularly, it relates to a new anthranilic acid derivative having benzene skeleton or pyridine skeleton on the principal anthranilic acid skeleton and further having a benzene skeleton or a naphthalene skeleton substituted by a side chain containing hetero-atom, i.e. a derivative having three aromatic groups at the same time, its pharmacologically permissible salt or solvated product, a pharmaceutical composition composed thereof and a preventive and/or therapeutic agent composed thereof.

Further, the anthranilic acid derivative of the present invention is a compound clinically applicable as a carcinostatic agent owing to its strong cytotoxic action and also clinically applicable as a preventive and/or therapeutic agent for allergic diseases owing to its activity to suppress the formation of IgE antibody.

BACKGROUND ARTS

Examples of the compound having naphthalene skeleton and anthranilic acid skeleton at the same time are those disclosed in the specification of JP-A 1-287066 (hereinunder, JP-A means "Japanese Unexamined Patent Application"). The specification describes compounds such as N-(2-naphthoyl)anthranylbenzoic acid and shows that these compounds have antiallergic activity or 5-lipoxygenase inhibiting activity. However, these compounds consist of a bicyclic aromatic ring derivative substituted by hydroxyl group or alkoxy group and directly bonded to an anthranilic acid skeleton through an amide bond, and there is no description or suggestion in the specification whether these compounds have cytotoxic action or IgE antibody production suppressing action or not.

Compounds having naphthalene skeleton and anthranilic acid skeleton and exhibiting antiallergic activity and IgE antibody production suppressing activity are described in the specifications of JP-A 1-106818, International Application WO90/12001 and JP-A 7-285858. However, these compounds are different from the compound of the present invention because there is no compound having a principal skeleton containing three aromatic rings at the same time in these compounds.

International Application WO95/32943 and a document "Journal of Medicinal Chemistry (J.Med.Chem.) vol.40, No.4, sections 395–407 (1997)" describe compounds having naphthalene skeleton and anthranilic acid skeleton and exhibiting antiallergic activity and IgE antibody production suppressing activity. Further, International Application WO97/19910 describes compounds having benzene skeleton and anthranilic acid skeleton and exhibiting antiallergic activity and IgE antibody production suppressing activity. However, these compounds are also different from the compound of the present invention because the substituent corresponding to the side chain of benzene skeleton or naphthalene skeleton is limited to alkoxy groups, alkenyloxy groups or aralkyloxy groups. Furthermore, the specification merely describes the presence of antiallergic activity and IgE antibody production suppressing activity in these compounds having the above specific substituents.

Compounds having pyridine ring skeleton and anthranilic acid skeleton and exhibiting antibacterial activity are described in the specification of International Application WO95/25723. The specification further describes that the substituent of the pyridine ring includes phenyloxy group and phenylthio group which may have substituents. However, there is no detailed explanation on the kind of the substituents. In the compounds of the present invention, for example, the pyridine ring is always substituted by phenyloxy group, phenylthio group, phenylsulfonyl group, phenylsulfinyl group, phenylcarbonyl group, phenylmethyl group, naphthyloxy group, naphthylthio group, naphthylsulfonyl group, naphthylsulfinyl group, naphthylcarbonyl group or naphthylmethyl group and furthermore the phenyl group or the naphthyl group constitutes the mother nucleus and always substituted by alkoxy group, aryloxy group, etc., which may contain hetero-atoms and, accordingly, the compound of the present invention is different from the compounds described in the above specification. Further, there is no comment on the IgE antibody production suppressing activity in the specification.

Meanwhile, the creation of a new compound having strong cytotoxic action is extremely important in the development of an excellent carcinostatic agent. Since the carcinostatic activity and carcinostatic spectrum of a compound are highly dependent upon its chemical structure in general, it is highly possible to enable the development of a carcinostatic agent having excellent characteristics compared with conventional carcinostatic agents practically in use at present from a cytotoxic compound having a new structure different from the structure of known compounds.

Examples of known low-molecular compound having benzene skeleton or aryl skeleton and exhibiting cytotoxic activity are substituted phenylsulfonyl derivative (JP-A 5-9170), 2-arylquinolinol derivative (JP-A 7-33743) and benzoylacetylene derivative (JP-A 7-97350).

However, the fact that a compound having benzene skeleton or aryl skeleton together with anthranilic acid skeleton has cytotoxic activity or carcinostatic activity is utterly unknown.

The object of the present invention is to provide a new compound usable as a clinically applicable therapeutic agent for cancer and preventive and/or therapeutic agent for allergic diseases.

DISCLOSURE OF THE INVENTION

As a result of vigorous investigation performed by the inventors of the present invention to achieve the above purpose, the inventors have found the following items 1 to 16 and completed the present invention.

In the description of atomic group expressing substituent, etc., the mark "—" showing the direction of bond is described in a group supposed to have ambiguous bonding form, however, the mark may be omitted for a group having clear bonding form.

1. The anthranilic acid derivative expressed by the following formula (1) or the following formula (2) or its pharmacologically permissible salt or solvate.

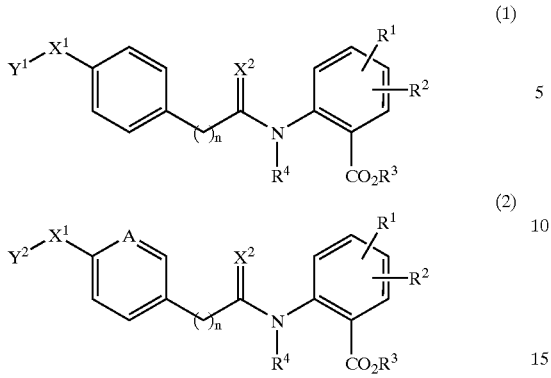

(1)

(2)

<<in the formulas, $Y^1$ is the group of the following formula (3)-1 or (3)-2.

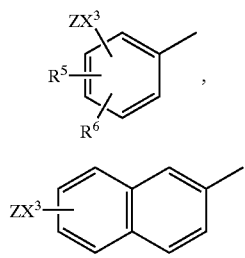

(3)-1

(3)-2

{in the formulas, Z is a straight-chain, branched or cyclic saturated, unsaturated or aromatic C1 to C12 hydrocarbon group substituted by one or more —$NR^{10}R^{11}$, —$COOR^{12}$, —(C=O)$NR^{13}R^{14}$, —(C=O)$R^{15}$ or $OR^{16}$ [the C1 to C12 hydrocarbon group is optionally substituted by a substituent L (L is a C1 to C6 alkyl group, a halogen atom, —$NO_2$ or —CN)], a 3 to 8-membered saturated ring containing one or plural —$NR^{17}$—, —O— or —S— in the ring and optionally containing one or more —C(=O)— groups in the ring, a C1 to C4 straight or branched-chain saturated or unsaturated hydrocarbon group having one or two double bonds or triple bonds and optionally substituted by the above 3 to 8-membered ring, or a C5 to C10 straight or branched-chain saturated or unsaturated hydrocarbon group substituted by a monocyclic or bicyclic aromatic ring containing one or more heteroatoms selected from oxygen, nitrogen and sulfur atom in the ring (the aromatic ring is optionally substituted by the substituent L).

the groups $R^{10}$, $R^{11}$, $R^{12}$, $R^{13}$, $R^{14}$, $R^{15}$, $R^{16}$, and $R^{17}$ are each independently hydrogen atom, a straight or branched-chain C1 to C6 alkyl group which is optionally substituted, a C7 to C11 aralkyl group which is optionally substituted, a C6 to C10 aryl group which is optionally substituted (the substituent is a halogen atom, —OH, a C1 to C4 alkoxy group, —CN, —$NO_2$ or —$COOR^{18}$), or a group selected from the following formulas (4)-1, (4)-2 and (4)-3. The groups $R^{10}$ and $R^{11}$, or $R^{13}$ and $R^{14}$ may together form a 3 to 12-membered ring optionally containing one or more —O—, —S—, —$NR^{18}$— or —(C=O)— groups.

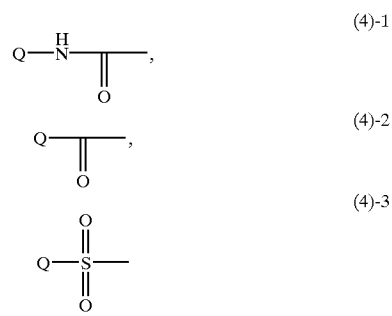

(4)-1

(4)-2

(4)-3

[in the formulas, Q is a C1 to C10 alkyl group which is optionally substituted, a C2 to C6 alkenyl group which is optionally substituted, a C1 to C6 alkoxy group which is optionally substituted, a C7 to C11 aralkyl group which is optionally substituted, a C7 to C11 aralkyloxy group which is optionally substituted (the substituent is a halogen atom, —OH, —CN, —$NO_2$, —$COOR^{19}$ or phenoxy group), dimethylamino group, morpholino group or a monocyclic or bicyclic aromatic hydrocarbon group which may have one or more hetero-atoms selected from oxygen, nitrogen and sulfur atoms. [when a monocyclic or bicyclic aromatic hydrocarbon group which may have one or more hetero-atoms is selected in the above case, the ring is optionally substituted at arbitrary positions independently by one or plural substituents selected from halogen atom, —OH, —$NO_2$, —CN, —$COOR^{19}$, $NR^{19}R^{20}$, straight or branched-chain C1 to C6 alkyl group, straight or branched-chain C1 to C6 alkoxy group (in this case, the substituents at adjacent positions may form an acetal bond), straight or branched-chain C1 to C6 alkylthio group, straight or branched-chain C1 to C6 alkylsulfonyl group, straight or branched-chain C1 to C6 acyl group, straight or branched-chain C1 to C6 acylamino group, trihalomethyl group, trihalomethoxy group, phenyl group, or phenoxy group which is optionally substituted by one or more halogen atoms], the groups $R^{19}$ and $R^{20}$ are each independently hydrogen atom or a C1 to C4 alkyl group], the group $R^{18}$ is hydrogen atom or a C1 to C4 alkyl group, the group $X^3$ is —(C=O)—, —O—, —S—, —(S=O)—, $SO_2$, —$NR^{21}$—, *—$NR^{21}$(C=O) or *—(C=O)$NR^{21}$ (the sign (*—) representing a bond means the bonding to the benzene ring or the naphthalene ring in the formula (3)-1 or the formula (3)-2, the group $R^{21}$ is hydrogen atom or a C1 to C4 hydrocarbon group which is optionally substituted by a halogen, the groups $R^5$ and $R^6$ are each independently hydrogen atom, a halogen atom, —$NO_2$, —$CO_2H$, —CN, —$OR^{22}$, —NH(C=O)$R^{22}$, —(C=O)$NHR^{22}$ or a C1 to C4 straight or branched-chain saturated or unsaturated hydrocarbon group which is optionally substituted by halogen atom, the group $R^{22}$ is a C1 to C3 hydrocarbon group which is optionally substituted by hydrogen atom or halogen atom}, the group $Y^2$ is the formula (3)-1, the formula (3)-2, the following formula (5)-1 or the following formula (5)-2,

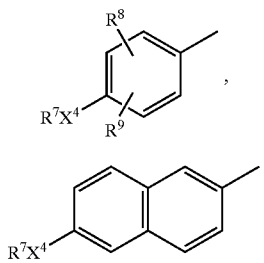

(5)-1

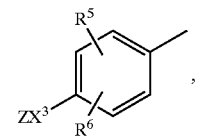

(5)-2

<in the formulas, the group $R^7$ is hydrogen atom or a substituted or unsubstituted straight-chain, branched or alicyclic saturated or unsaturated C1 to C12 hydrocarbon group having one or two double bonds or triple bonds [in this case, the substituent is a halogen atom, $-NO_2$, $-CN$, a substituted or unsubstituted phenyl group (in this case, the substituent is a halogen atom, $-NO_2$, $-CN$, $-CF_3$ or a C1 to C4 hydrocarbon group), or a substituted or unsubstituted 5 to 8-membered cycloalkyl group (in this case, the substituent is a halogen atom or a C1 to C4 hydrocarbon group)], the group $X^4$ is $-(C=O)-$, $-O-$, $-S-$, $-(S=O)-$, $-(O=S=O)-$, $-NR^{23}-$, *$-NR^{23}CO$ or *$-CONR^{23}$ (the group $R^{23}$ is hydrogen atom or a C1 to C4 hydrocarbon group, which is optionally substituted by halogen atom. In this case, the sign (*$-$) means the bonding to the benzene ring or the naphthalene ring of the formula (5)-1 or the formula (5)-2. The group $R^7$ is not hydrogen atom when the group $X^4$ is $-(C=O)-$, $-(S=O)-$, $-(O=S=O)-$ or *$-NR^{23}(C=O)-$, the groups $R^8$ and $R^9$ are each independently hydrogen atom, a halogen atom, $-NO_2$, $-CO_2H$, $-CN$, $-OR^{24}$, $-NH(C=O)R^{24}$, $-(C=O)NHR^{24}$ or a straight or branched-chain saturated or unsaturated C1 to C4 hydrocarbon group which is optionally substituted by halogen atom (the group $R^{24}$ is hydrogen atom or a C1 to C3 hydrocarbon group which is optionally substituted by halogen atom)>, the group $X^1$ is $-(C=O)-$, $-O-$, $-S-$, $-(S=O)-$, $-(O=S=O)-$ or $-CH_2-$, the group $X^2$ is O or S, the groups $R^1$ and $R^2$ are each independently hydrogen atom, a halogen atom, $-NO_2$, $-CO_2H$, $-CN$, $-OR^{25}$, $-NH(C=O)R^{25}$, $-(C=O)NHR^{25}$ or a C1 to C4 straight or branched-chain saturated or unsaturated hydrocarbon group which is optionally substituted by halogen atom, the group $R^{25}$ is hydrogen atom or a C1 to C3 hydrocarbon group which is optionally substituted by halogen atom, the groups $R^3$ and $R^4$ are each independently hydrogen atom or a C1 to C4 hydrocarbon group, the group A is N, N→O or $N^+-CH_3$, and n is an integer of 0 to 3.>>.

2. The above anthranilic acid derivative wherein $Y^2$ is the group of the formula (3)-1 or the formula (3)-2 or its pharmacologically permissible salt or solvate.

3. An anthranilic acid derivative expressed solely by the formula (1), or its pharmacologically permissible salt or solvate.

4. An anthranilic acid derivative expressed solely by the formula (2) wherein the group $Y^2$ is expressed by the formula (3)-1 or the formula (3)-2, or its pharmacologically permissible salt or solvate.

5. An anthranilic acid derivative expressed solely by the formula (2) wherein the group $Y^2$ is expressed by the formula (5)-1 or the formula (5)-2, or its pharmacologically permissible salt or solvate.

6. An anthranilic acid derivative of the formula (1) wherein the group $Y^1$ is expressed by the following formula (9)-1, (9)-2 or (9)-3, or its pharmacologically permissible salt or solvate.

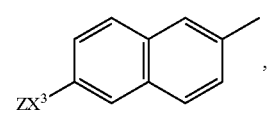

(9)-1

(9)-2

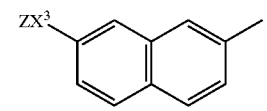

(9)-3

<in the formula, the definitions of Z, $X^3$, $R^5$ and $R^6$ are same as those of the formula (3)1 or the formula (3)-2>

7. An anthranilic acid derivative of the formula (2) wherein the group $Y^2$ is expressed by the formula (5)-1, the formula (5)-2, the formula (9)-1, the formula (9)-2 or the formula (9)-3, or its pharmacologically permissible salt or solvate.

8. The anthranilic acid derivative of the formula (1) or the formula (2) wherein the group Z is a straight-chain, branched or cyclic saturated, unsaturated or aromatic C1 to C12 hydrocarbon group substituted by one or more $-NR^{10}R^{11}$, $-COOR^{12}$, $-(C=O)NR^{13}R^{14}$, $-(C=O)R^{15}$ or $-OR^{16}$ [the C1 to C12 hydrocarbon group is optionally further substituted by substituent L (L is a C1 to C6 alkyl group, halogen atom, $-NO_2$ or $-CN$)], or its pharmacologically permissible salt or solvate.

9. An anthranilic acid derivative of the formula (1) or the formula (2) wherein the group Z is a saturated 3 to 8-membered ring containing one or plural $-NR^{17}-$, $-O-$ or $-S-$ groups and optionally containing one or more $-C(=O)-$ groups in the ring, or a C1 to C4 straight or branched-chain saturated or unsaturated hydrocarbon group having one or two double bonds or triple bonds and optionally substituted by the above 3 to 8-membered ring, or its pharmacologically permissible salt or solvate.

10. The anthranilic acid derivative of the formula (1) or the formula (2) wherein the group Z is a C5 to C10 straight or branched-chain saturated or unsaturated hydrocarbon group substituted by a monocyclic or bicyclic aromatic ring containing one or more hetero-atoms selected from oxygen, nitrogen and sulfur atom in the ring (the aromatic ring is optionally substituted by a substituent L), or its pharmacologically permissible salt or solvate.

11. A pharmaceutical composition composed of the above anthranilic acid derivative or its pharmacologically permissible salt or solvate, and a pharmaceutically permissible carrier.

12. The above pharmaceutical composition having cytotoxic activity.

13. A therapeutic agent for cancer composed of the above pharmaceutical composition.
14. The above pharmaceutical composition having IgE antibody production suppressing action.
15. A preventive or therapeutic agent for allergic diseases composed of the above pharmaceutical composition.
16. The above preventive or therapeutic agent wherein said allergic diseases are bronchial asthma, allergic rhinitis, allergic conjunctivitis, atopic dermatitis, anaphylactic shock, mite allergy, pollinosis, food allergy, urticaria, ulcerative colitis, eosinophilic gastroenteritis or drug-induced rash.

BEST MODE FOR CARRYING OUT THE INVENTION

The present invention is described in more detail as follows.

In the formula (1) expressing the anthranilic acid derivative of the present invention, $Y^1$ is a group selected from the formula (3)-1 and the formula (3)-2.

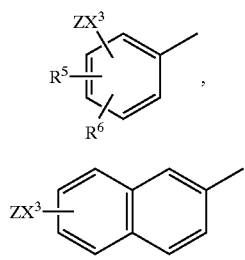

(3)-1

(3)-2

In the formulas, $ZX^3$, $R^5$ and $R^6$ are substituted one for each to the benzene ring or the naphthalene ring, however, the group $ZX^3$— is preferably positioned at a site expressed in the following formulas (9)-1 to (9)-3.

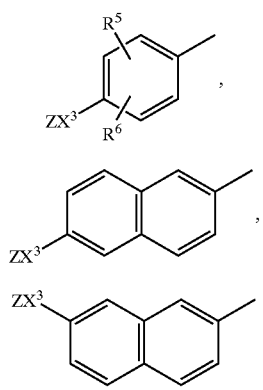

(9)-1

(9)-2

(9)-3

$R^5$ and $R^6$ are each independently hydrogen atom, a halogen atom, —$NO_2$, —$CO_2H$, —CN, —$OR^{22}$, —NH(C=O)$R^{22}$ or —(C=O)NH$R^{22}$ or a C1–C4 straight or branched-chain saturated or unsaturated hydrocarbon group which may be substituted by halogen atom, and preferably hydrogen atom, a halogen atom, —$NO_2$, —CN, —OH, —$OCH_3$, —NH(C=O)$CH_3$, —(C=O)NHCH$_3$ or a C1–C4 straight or branched-chain saturated or unsaturated hydrocarbon group which may be substituted by halogen atom. More preferably, it is hydrogen atom, a halogen atom, —$CH_3$, —OH or —$OCH_3$ and, especially, hydrogen atom.

In the formula (3)-1 or the formula (3)-2, Z is a C1—C12 (the carbon number is restricted to those allowable from its structure) straight, branched or cyclic saturated or unsaturated hydrocarbon group or aromatic hydrocarbon group substituted by one or more substituents selected from —$NR^{10}OR^{11}$, —$COOR^{12}$, —(C=O)$NR^{13}R^{14}$, —(C=O)$R^{15}$ and —$OR^{16}$ and optionally substituted by a substituent L, or a saturated 3 to 8-membered ring having one or plural $NR^{17}$, O or S in the ring and optionally containing one or more —C(=O)— groups in the ring or a C5–C10 straight or branched-chain saturated or unsaturated hydrocarbon group substituted by a C1–C4 straight or branched-chain or unsaturated hydrocarbon group having one or two double bonds or triple bonds and optionally substituted by the above 3 to 8-membered ring or by a monocyclic or bicyclic aromatic ring (which may be substituted by the substituent L) containing one or more hetero-atoms selected from oxygen, nitrogen and sulfur. The carbon number of the C1–C12 hydrocarbon group of Z is the number of carbon atoms of the main chain and the carbon numbers of the substituents are not included in the carbon number.

When the group Z is a C1–C12 straight, branched or cyclic saturated or unsaturated hydrocarbon or an aromatic hydrocarbon, it is for example methyl group, ethyl group, propyl group, butyl group, isobutyl group, hexyl group, 2-ethylpropyl group, 1,1-dimethylethyl group, allyl group, methallyl group, cyclohexyl group, cyclooctyl group, cyclopentylmethyl group, cyclohexenylmethyl group, 1-decalyl group, phenyl group, benzyl group and phenylpropyl group, and especially preferably methyl group, ethyl group, cyclohexyl group, cyclopentylmethyl group, benzyl group or phenylpropyl group. These hydrocarbon groups are substituted by one or more —$NR^{10}R^{11}$, —$COOR^{12}$, —(C=O)$NR^{13}R^{14}$, —(C=O)$R^{15}$ or —$OR^{16}$ groups.

In the definitions of the formula (3)-1 and the formula (3)-2, the group Z is a saturated 3 to 8-membered ring containing one, or plural —$NR^{17}$—, —O— or —S— groups in the ring and optionally containing one or more —C(=O)— groups, or a C1–C4 straight or branched-chain saturated hydrocarbon group or unsaturated hydrocarbon group containing one or two double bonds or triple bonds wherein these hydrocarbon groups may be substituted by the above 3 to 8-membered ring.

When Z is a C1–C4 straight or branched-chain saturated hydrocarbon group or unsaturated hydrocarbon group containing one or two double bonds or triple bonds wherein these hydrocarbon groups may be substituted by a saturated 3 to 8-membered ring containing one or plural —$NR^{17}$—, —O— or —S— groups in the ring and optionally containing one or more —C(=O)— groups, the number of carbon atoms of the C1–C4 hydrocarbon does not include the carbon number of the ring. The substitution position of the main chain on the ring is an arbitrary carbon atom constituting the ring. In the above sentence, the main chain means a C1–C4 straight or branched-chain saturated hydrocarbon group or unsaturated hydrocarbon group containing one or two double bonds or triple bonds.

When the group Z is a saturated 3 to 8-membered ring containing one or plural —$NR^{17}$—, —O— or —S— groups in the ring and optionally containing one or more —C(=O)— groups, the substitution position of the group $X^3$ defined in the formula (3)-1 and the formula (3)-2 is an arbitrary carbon atom constituting the ring.

The saturated 3 to 8-membered ring containing one or plural —$NR^{17}$—, —O— or —S— groups in the ring and optionally containing one or more —C(=O)— groups is, for example, pyrrolidine ring, piperidine ring, pyrrolidone ring, piperazine ring, morpholine ring, thiomorpholine ring, tetrahydropyran ring and tetrahydrothiophene ring and especially preferably pyrrolidine ring, piperidine ring and piperazine ring.

In the C1–C4 straight or branched-chain saturated hydrocarbon group or unsaturated hydrocarbon group having one or two double bonds or triple bonds and substituted by a 3 to 8-membered ring, the straight-chain group is e.g. methyl group, ethyl group, n-propyl group, n-butyl group, 2-propenyl group, 3-butenyl group and 2-propynyl group, preferably methyl group, ethyl group, n-propyl group or n-butyl group, especially preferably methyl group or ethyl group.

The branched-chain group is e.g. isopropyl group, t-butyl group and 2-methylpropyl group and, among the above examples, isopropyl group and t-butyl group are preferable. In the definition in the formula (3)-1 and the formula (3)-2, the group Z is a C5–C10 straight or branched-chain saturated or unsaturated hydrocarbon group substituted by monocyclic or bicyclic aromatic ring (the aromatic ring may be substituted by a substituent L) containing one or more hetero-atoms selected from oxygen, nitrogen and sulfur atom in the ring.

The term "C5–C10" means the total number of carbon atoms including the carbon atoms of substituents.

The monocyclic or bicyclic aromatic ring containing one or more hetero-atoms selected from oxygen, nitrogen and sulfur atom in the ring is, for example, pyridine ring, furan ring, thiophene ring, quinoline ring, pyrazole ring, imidazole ring, thiazole ring, triazole ring, benzofuran ring, thianaphthalene ring, indole ring and benzimidazole ring. Among the above examples, pyridine ring, furan ring, thiophene ring and quinoline ring are preferable and pyridine ring is especially preferable.

Examples of the C5–C10 straight or branched-chain saturated or unsaturated hydrocarbon group substituted by these aromatic rings are 4-pyridylmethyl group, 3-furanylmethyl group, 3-thiophenylethyl group, 2-quinolin-4-ylmethyl group and 3-pyridylethyl group and especially preferably 4-pyridylmethyl group.

The monocyclic or bicyclic aromatic ring containing one or more hetero-atoms selected from oxygen, nitrogen and sulfur atom in the ring may be substituted by a substituent L, and such substituent L is selected from C1–C6 alkyl group, halogen atom, —NO$_2$ and —CN, for example, methyl group, ethyl group, isobutyl group, 1-ethylpropyl group, chloro group, bromo group, nitro group and nitrile group and, among the above examples, methyl group, ethyl group and chloro group are preferable.

The groups $R^{10}$, $R^{11}$, $R^{12}$, $R^{13}$, $R^{14}$, $R^{15}$, $R^{16}$ and $R^{17}$ are each independently hydrogen atom, a C1–C6 straight or branched-chain alkyl group which may have substituent, a C7–C11 aralkyl group which may have substituent, a C6–C10 aryl group which may have substituent (these substituents are halogen atom, OH, C1–C4 alkoxy group, —CN, —NO$_2$ or —COOR$^{18}$), or a group selected from the formula (4)-1, the formula (4)-2 and the formula (4)-3 or $R^{10}$ and $R^{11}$, or $R^{13}$ and $R^{14}$ together form a 3 to 12-membered ring which may contain one or more —O—, —S—, —NR$^{18}$— or —(C=O)— groups in the ring. Preferable examples of the groups $R^{10}$, $R^{11}$, $R^{12}$, $R^{13}$, $R^{14}$, $R^{15}$, $R^{16}$ and $R^{17}$ are hydrogen atom, a C1–C6 straight or branched-chain alkyl group which may have substituents, a C7–C11 aralkyl group which may have substituents, a C6–C10 aryl group which may have substituents (these substituents are C1–C4 alkoxy group or COOR$^{18}$) or a group selected from the formula (4)-1, the formula (4)-2 and the formula (4)-3.

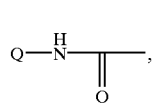

When these groups are hydrogen atom, a C1–C6 straight or branched-chain alkyl group which may have substituents, a C7–C11 aralkyl group which may have substituents or a C6–C10 aryl group which may have substituents, examples of the groups are hydrogen atom, methyl group, ethyl group, isopropyl group, n-butyl group, pentyl group, hexyl group, benzyl group, phenyl group and naphthyl group, preferably methyl group, ethyl group, benzyl group and phenyl group. These group may be substituted by halogen atom, —OH, a C1–C4 alkyl group, —CN, —NO$_2$ or —COOR$^{18}$, and the substituent is preferably —Cl, —OH, ethoxy group, —CN or —COOH.

When the groups $R^{10}$ and $R^{11}$ or $R^{13}$ and $R^{14}$ together form a 3 to 12-membered ring, the ring may contain O, S or NR$^{18}$. Concretely, the ring is e.g. pyrrolidine ring, piperidine ring, pyrrolidone ring, piperazine ring, morpholine ring, thiomorpholine ring, etc., and above all, pyrrolidine ring, piperidine ring, piperazine ring and morpholine ring are preferable. When the ring is e.g. piperazine ring, the nitrogen atom of the ring may be substituted by a C1–C4 lower alkyl group, i.e. $R^{18}$, and in this case, the substituent is especially preferably methyl group or isopropyl group.

In the formula (3)-1 or the formula (3)-2, the group $X^3$ is —(C=O)—, —O—, —S—, —(S=O)—, —(O=S=O)—, —NR$^{21}$, *—NR$^{21}$(C=O)— or *—(C=O)NR$^{21}$ (the sign (*—) representing a bond means the bonding to the benzene ring or the naphthalene ring). The group is e.g. —(C=O)—, —O—, —S—, —N(CH$_3$)(C=O)— or —(C=O)NCH$_3$ and especially preferably —O— or —S—.

In the formula (4)-1, the formula (4)-2 and the formula (4)-3, the group Q is a C2–C10 alkyl group which may have substituents, a non-substituted C1–C6 alkenyl group which may have substituents, a C1–C6 alkoxy group which may have substituents, a C7–C11 aralkyl group which may have substituents, a C7–C11 aralkyloxy group which may have substituents, dimethylamino group, morpholino group or a monocyclic or bicyclic aromatic hydrocarbon group which may contain one or plural hetero-atoms selected from oxygen, nitrogen and sulfur atom in the ring.

When the group Q is a C1–C10 alkyl group which may have substituents, a C1–C6 alkenyl group which may have substituents, a C1–C6 alkoxy group which may have substituents, a C7–C11 aralkyl group which may have substituents, a C7–C11 aralkyloxy group which may have substituents, the concrete examples of the group are methyl group, ethyl group, propyl group, heptyl group, methoxy group, allyl group, benzyl group, phenylpropyl group and benzyloxy group. These groups may be substituted by halogen atom, —OH, —CN, —NO$_2$, —COOR$^{19}$ or phenoxy group. Concretely, preferable substituent is chloro group, —OH, —COOH or phenoxy group.

When the group Q is a monocyclic or bicyclic aromatic hydrocarbon group which may contain one or plural heteroatoms selected from oxygen, nitrogen and sulfur atoms in the ring, any one of the groups described in the following formula (10) can be selected as the aromatic hydrocarbon group.

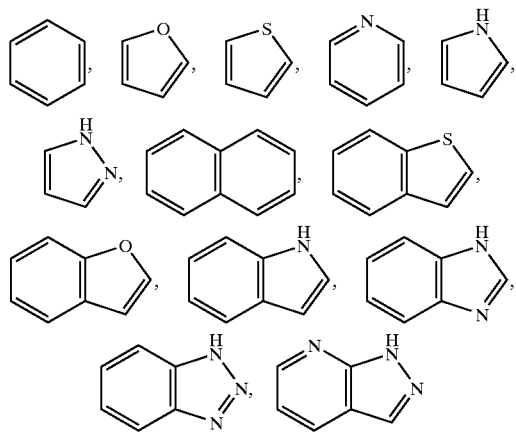

These groups are bonded to the amide group, carboxyl group or sulfonyl group in the formula (4)-1, the formula (4)-2 or the formula (4)-3 as the group Q at an arbitrary possible position, and may be bonded with the following groups at the remaining positions. Namely, the groups may be substituted by one or plural groups independently selected from halogen atom, —OH, —NO$_2$, —CN, —COOR$^{19}$, —NR$^{19}$R$^{20}$, a straight or branched-chain C1–C6 alkyl group, a straight or branched-chain C1–C6 alkoxy group (in this case, an acetal bond may be formed at the sites adjacent to each other as the substituents), a straight or branched-chain C1–C6 alkylthio group, a straight or branched-chain C1–C6 alkylsulfonyl group, a straight or branched-chain C1–C6 acyl group, a straight or branched-chain C1–C6 acylamino group, trihalomethyl group, trihalomethoxy group, phenyl group, or phenoxy group which may be substituted by one or more halogen atoms. In the above description, R$^{19}$ and R$^{20}$ are each hydrogen atom or a C1–C4 lower alkyl group.

Concrete examples of preferable substituents are —COOH, —F, —Cl, —Br, —NO$_2$, —OH, —NH$_2$, —NHCH$_3$, —N(CH$_3$)$_2$, —NH(C=O)CH$_3$, —(C=O)CH$_3$, —CF$_3$, —OCF$_3$, —CN, —OCH$_3$, —Ph, —CH$_3$, —(O=S=O)—, —CH$_3$, —SCH$_3$ and —OPh.

In the above formula (2), Y$^2$ is the group of formula (3)-1, the formula (3)-2, the formula (5)-1 or the formula (5)-2. Among the groups expressed by the formula (3)-1 or the formula (3)-2, the preferable groups are, as mentioned before, the groups of the formula (9)-1, (9)-2 or (9)-3.

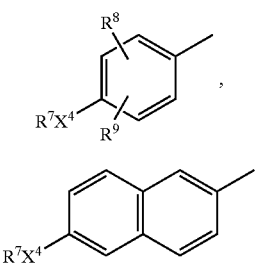

(5)-1

(5)-2

In the formula (5)-1 or the formula (5)-2, the group R$^7$ is hydrogen atom or optionally substituted straight, branched or alicyclic C1–C12 saturated hydrocarbon group or unsaturated hydrocarbon group containing one or two double bonds or triple bonds [in this case, the substituent is halogen atom, —NO$_2$, —CN, an optionally substituted phenyl group (the substituent is halogen atom, —NO$_2$, —CN, —CF$_3$ or a C$_1$–C4 hydrocarbon group) or an optionally substituted 5 to 8-membered cycloalkyl group (the substituent is halogen atom or a C$_1$–C4 hydrocarbon group)].

Each of the above groups has a total carbon number of 1 to 12 including the substituents. The cyclic saturated hydrocarbon group or unsaturated hydrocarbon group having one or two double bonds or triple bonds does not include aromatic rings such as benzene ring and hetero-aromatic ring, and the ring is directly bonded to the group X$^4$ in the formula (5)-1 or the formula (5)-2. That is to say, the cyclic means alicyclic. In other words, these rings are free from oxygen, sulfur, nitrogen atom and carbonyl group in the ring, and the preferable examples of the ring are cyclopropane ring, cyclobutane ring, cyclopentane ring, cyclohexane ring, cyclooctane ring cycloheptane ring, cyclododecane ring, norbornene ring and cyclohexene ring. Cyclopentane ring, cyclohexane ring, cyclooctane ring and cyclododecane ring are more preferable among the above examples.

The straight-chain saturated hydrocarbon group or unsaturated hydrocarbon group having one or two double bonds or triple bonds is, for example, methyl group, ethyl group, n-propyl group, n-butyl group, n-hexyl group, n-octyl group, n-dodecyl group, 2-propenyl group, 3-butenyl group, 4-hexenyl group, 3-hexenyl group, 3-nonenyl group, 2,4-hexadienyl group and 2-propynyl group, preferably methyl group, ethyl group, n-propyl group, n-butyl group, n-hexyl group, 2-propenyl group, 3-butenyl group, 4-hexenyl group, 3-hexenyl group, 2,4-hexadienyl group or 2-propynyl group.

The branched saturated or unsaturated hydrocarbon group is, for example, isopropyl group, t-butyl group, ethylpropyl group, ethylpentyl group, 4-methylpentyl group, 2-ethylbutyl group, 2-methylpropyl group, 2-methylbutyl group, 2,4,4-trimethylpentyl group, 2-methylheptyl group, 3-methyl-1-(2-methylpropyl)butyl group, 2-methyl-1-(methylethyl)propyl group, 3-methyl-3-butenyl group, 3-methyl-2-butenyl group, 1-vinyl-2-propenyl group, 4-methyl-3-pentenyl group, 1-allyl-3-butenyl group, 1-ethyl-2-propenyl group, 1-propyl-2-propenyl group and 1-ethyl-2-propynyl group. Symmetric groups are preferable among the above groups. Especially preferable groups are ethylpropyl group and 2-ethylbutyl group.

The substituent of R$^7$ is halogen atom, —NO$_2$, —CN, a substituted or non-substituted phenyl group (the substituent is selected from halogen atom, —NO$_2$, —CN, —CF$_3$ and C$_1$–C4 hydrocarbon group) and a substituted or non-substituted 5 to 8-membered cycloalkyl group (the substituent is selected from halogen atom and a C$_1$–C4 hydrocarbon group).

In the substituent of R$^7$, the substituted or non-subsititted phenyl group (the substituent is selected from halogen atom, —NO$_2$—, —CN, —CF$_3$ and a C1–C4 hydrocarbon group) is, for example, phenyl group, m-fluorophenyl group, p-chlorophenyl group, m-iodophenyl group, p-fluorophenyl group, 2,4-dichlorophenyl, 3,5-difluorophenyl group, p-nitrophenyl group, m-nitrophenyl group, p-methylthiophenyl group, o-cyanophenyl group, p-cyanophenyl group, m-trifluoromethylphenyl group, p-methylphenyl group, p-isopropylphenyl group, p-t-butylphenyl group and 3,4-dimethylphenyl group.

The 5 to 8-membered cycloalkyl group as the substituent of the group R$^7$ may be substituted by halogen atom or C1–C4 hydrocarbon group. Preferable examples of the C1–C4 hydrocarbon group are methyl group and ethyl group. Namely, examples of the optionally substituted 5 to 8-membered cycloalkyl group are cyclopentyl group, cyclohexyl group, cycloheptyl group, cyclooctyl group, 2-chlorocyclohexyl group, 2-methylcyclohexyl group, 2-ethylcyclohexyl group, 3-methylcyclohexyl group, 4-methylcyclohexyl group, 4-(i-propyl)cyclohexyl group, 2,6-dimethylcyclohexyl group and 3,5-dimethylcyclohexyl group.

The group $R^7$ is preferably hydrogen atom, a straight or branched-chain C1–C12 saturated hydrocarbon group or unsaturated hydrocarbon group having one or two double bonds or triple bonds and optionally substituted by halogen atom, or a group expressed by the following formulas.

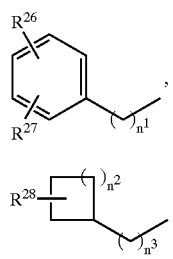

(11)-1

(11)-2

[in the formula, $n^1$ is an integer of 1 to 3, $n^3$ is an integer of 0 to 3, $n^2$ is an integer of 0 to 9 (when $n^3$ is 0) or an integer of 2 to 5 (when $n^3$ is an integer of 1 to 3), $R^{26}$ and $R^{27}$ are each independently hydrogen atom, halogen atom, $NO_2$, CN, $CF_3$ or a C1–C4 hydrocarbon group, and $R^{28}$ is hydrogen atom or a C1–C4 hydrocarbon group]. (The groups $R^{26}$ and $R^{27}$ are more preferably hydrogen atom, halogen atom or $NO_2$).

The group $R^7$ is especially preferably hydrogen atom or a group selected from the groups expressed by the following formula (12).

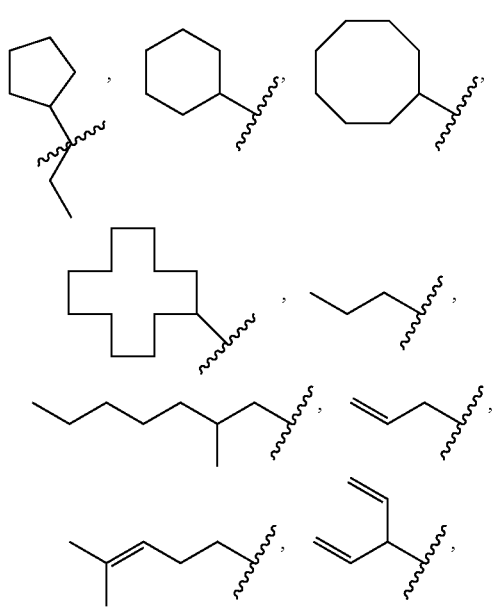

(12)

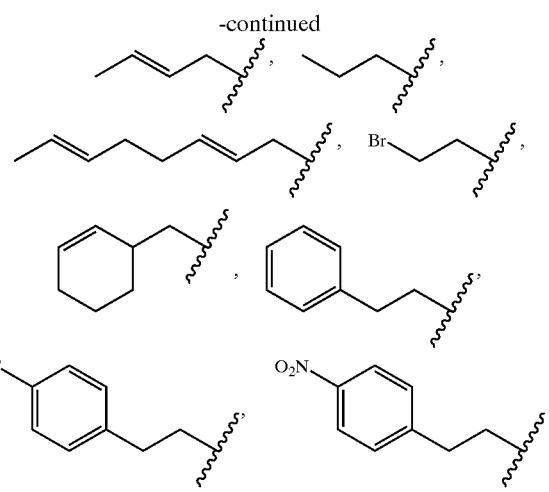

The group $X^4$ in the formula (5)-1 or the formula (5)-2 is —(C=O)—, —O—, —S—, —(S=O)—, —(O=S=O)—, —$NR^{23}$—, *—$NR^{23}$(C=O)— or *—(C=O)$NR^{23}$. (The sign (—) representing a bond is bonded to the benzene ring or the naphthalene ring having $R^8$ and $R^9$, $R^{23}$ is hydrogen atom or a C1–C4 hydrocarbon group which may be substituted by halogen atom. $R^7$ is not hydrogen atom when $X^4$ is —(C=O)—, —(S=O)—, —(O=S=O)— or *—$NR^{23}$(C=O)—.). $X^4$ is preferably —O—, —S—, —(S=O)— or —(O=S=O)—, more preferably —O— or —S— and especially preferably —O—.

$R^{23}$ is preferably hydrogen atom, methyl group or ethyl group, especially preferably hydrogen atom.

In the formula (5)-1 and the formula (5)-2, the groups $R^8$ and $R^9$ are each independently hydrogen atom, halogen atom, —$NO_2$, —$CO_2H$, —CN, —$OR^{24}$, —NH(C=O)$R^{24}$, —(C=O)$NHR^{24}$ or a straight or branched-chain saturated or unsaturated C1–C4 hydrocarbon group which may be substituted by halogen atom (the group $R^{24}$ is hydrogen atom or a C1–C3 hydrocarbon group which may be substituted by halogen atom.). It is preferably hydrogen atom, halogen atom, —$NO_2$, —CN, —OH, —$OCH_3$, —NH(C=O)$CH_3$, —(C=O)$NHCH_3$ or a straight or branched-chain saturated or unsaturated C1–C4 hydrocarbon group which may be substituted by halogen atom. It is more preferably hydrogen atom, halogen atom, —$CH_3$, —$OCH_3$, —OH, ethyl group, isopropyl group, t-butyl group, allyl group or trifluoromethyl group, further preferably hydrogen atom, halogen atom, —$CH_3$, —$OCH_3$, —OH or trifluoromethyl group and especially preferably hydrogen atom.

When the group $R^{24}$ is a C1–C3 hydrocarbon group which may be substituted by halogen, it is, for example, methyl group, ethyl group, isopropyl group and trifluoromethyl group and preferably methyl group or trifluoromethyl group.

In the formula (1) or the formula (2), $X^1$ is —(C=O)—, —O—, —S—, —(S=O)—, —(O=S=O)— or —$CH_2$—, preferably —O—, —S—, —(S=O)— or —(O=S=O)—, especially preferably —O— or —S—.

In the formula (1) or the formula (2), $X^2$ is O or S, preferably O.

In the formula (1) or the formula (2), $R^1$ and $R^2$ are each independently hydrogen atom, halogen atom, —$NO_2$, —$CO_2H$, —CN, —$OR^{25}$, —NH(C=O)$R^{25}$, —(C=O)$NHR^{25}$ or a C1–C4 straight or branched-chain saturated or unsaturated hydrocarbon group which may be substituted by halogen atom. Concrete examples of the groups are hydrogen atom, chloro group, bromo group, —$NO_2$, —$CO_2H$, —CN, methoxy group, ethoxy group, chloromethoxy group, butoxy group, acetylamide group, propionylamide group, methylaminocarbonyl group, butylaminocarbonyl group, methyl group, bromoethyl group, allyl group and chloropropenyl group, and preferably hydrogen atom, halogen atom (especially chloro group), —OH, —NO₂, —CO₂H, —CN, methoxy group, chloromethoxy group, acetylamide group, methylaminocarbonyl group or methyl group.

In the formula (1) or the formula (2), $R^3$ and $R^4$ are each independently hydrogen atom or a C1–C4 hydrocarbon group. Concrete examples of the groups are hydrogen atom, methyl group, ethyl group, propyl group and butyl group and preferably hydrogen atom or methyl group.

In the formula (1) or the formula (2), n is an integer of 0 to 3, preferably 0 or 1.

In the formula (2), A is N, N→O or $N^+$—CH₃, preferably N or N or N→O, more preferably N.

The anthranilic acid derivative of the present invention or its pharmacologically permissible salt can be converted into solvate at need. The solvent usable in the conversion process is water, methanol, ethanol, (n- or i-)propyl alcohol, (n- or t-)butanol, acetonitrile, acetone, methyl ethyl ketone, chloroform, ethyl acetate, diethyl ether, t-butyl methyl ether, benzene, toluene, DMSO, DMF, etc., preferably water, methanol, ethanol, (n- or i-)propyl alcohol or acetonitrile.

When the compound of the formula (1) or the formula (2) has CO₂H group in the molecule, the anthranilic acid derivative of the present invention can be converted as necessary into a non-toxic cation salt or its solvate. Examples of such salt are alkali metal ion such as Na⁺ and K⁺, alkaline earth metal ion such as Mg²⁺ and Ca²⁺, metal ion such as Al³⁺ and Zn²⁺, or organic base such as ammonia, triethylamine, ethylenediamine, propanediamine, pyrrolidine, piperidine, piperazine, pyridine, lysine, choline, ethanolamine, N,N-dimethylethanolamine, 4-hydroxypiperidine, glucosamine, and N-methylglucamine, preferably Na⁺, Ca²⁺, lysine, choline, N,N-dimethylethanolamine and N-methylglucamine. The solvents for forming the solvates of these salts are, for example, water, methanol, ethanol, (n- or i-)propyl alcohol, (n- or t-)butanol, acetonitrile, acetone, methyl ethyl ketone, chloroform, ethyl acetate, diethyl ether, t-butyl methyl ether, benzene, toluene, DMF and DMSO, especially preferably water, methanol, ethanol, (n- or i-)propyl alcohol and acetonitrile.

When the compound of the formula (1) or the formula (2) contains primary, secondary or tertiary amine group in the molecule, the anthranilic acid derivative of the present invention can be converted as necessary into an acid addition salt or its solvate. The acid for the production of the acid addition salt is a mineral acid such as hydrochloric acid, sulfuric acid and nitric acid or an organic acid such as acetic acid, benzoic acid, fumaric acid, maleic acid, methanesulfonic acid and toluenesulfonic acid. Preferable acids among the above examples are hydrochloric acid, sulfuric acid, acetic acid, fumaric acid, maleic acid, methanesulfonic acid and toluenesulfonic acid. The solvent for the production of the solvate of the salt is, for example, water, methanol, ethanol, (n- or i-)propyl alcohol, (n- or t-)butanol, acetonitrile, acetone, methyl ethyl ketone, chloroform, ethyl acetate, diethyl ether, t-butyl methyl ether, benzene, toluene, DMF and DMSO, and preferably water, methanol, ethanol, (n- or i-)propyl alcohol and acetonitrile.

Concrete preferable examples of the compounds expressed by the formula (1) or the formula (2) of the present invention are compounds described in the Table 1 to the Table 43, their pharmacologically permissible salts or their solvates.

TABLE 1

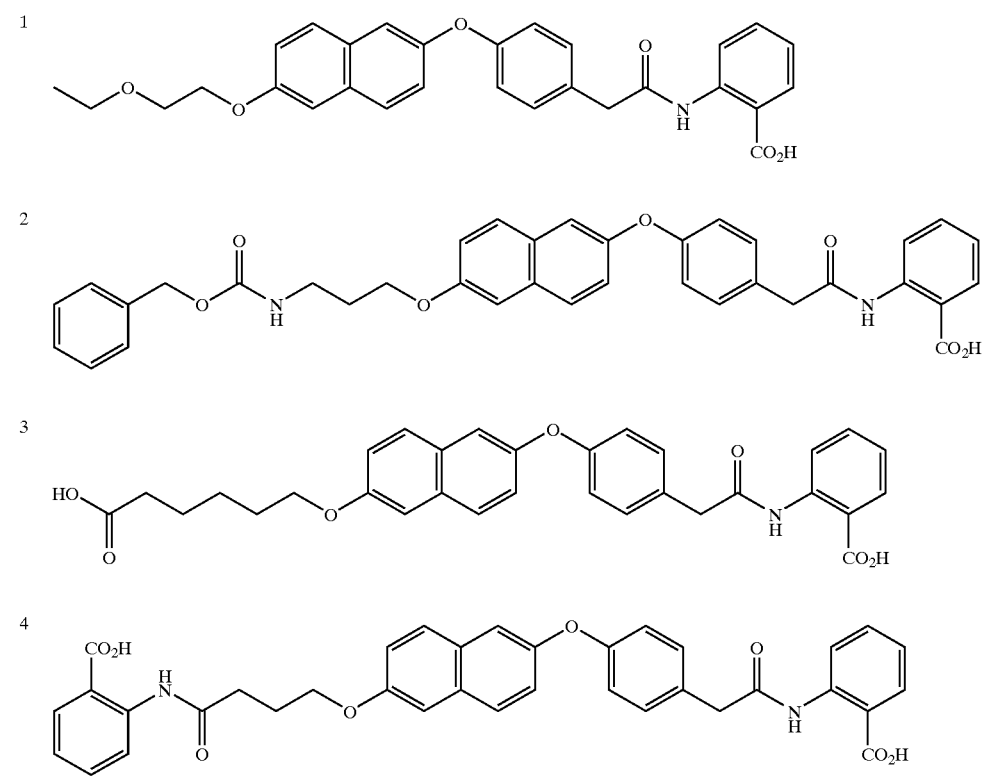

TABLE 1-continued

TABLE 1-continued

| | |
|---|---|
| 14 | [structure: piperidine-CH2CH2-O-naphthalene-O-phenyl-CH2-C(=O)-NH-phenyl-CO2H] |
| 15 | [structure: pyrrolidine-CH2CH2-O-naphthalene-O-phenyl-CH2-C(=O)-NH-phenyl-CO2H] |
| 16 | [structure: benzyl-O-cyclohexyl-O-naphthalene-O-phenyl-CH2-C(=O)-NH-phenyl-CO2H] |
| 17 | [structure: HO-cyclohexyl-O-naphthalene-O-phenyl-CH2-C(=O)-NH-phenyl-CO2H] |
| 18 | [structure: H2N-cyclohexyl-O-naphthalene-O-phenyl-CH2-C(=O)-NH-phenyl-CO2H] |
| 19 | [structure: H2N-cyclohexyl-O-naphthalene-O-phenyl-CH2-C(=O)-NH-phenyl-CO2H] |
| 20 | [structure: acetamido-phenyl-CH2CH2-O-naphthalene-O-phenyl-CH2-C(=O)-NH-phenyl-CO2H] |
| 21 | [structure: MeO-CH2CH2-O-naphthalene-O-phenyl-C(=O)-NH-phenyl-CO2H] |
| 22 | [structure: EtO-CH2CH2-O-naphthalene-O-phenyl-C(=O)-NH-phenyl-CO2H] |

TABLE 1-continued
23 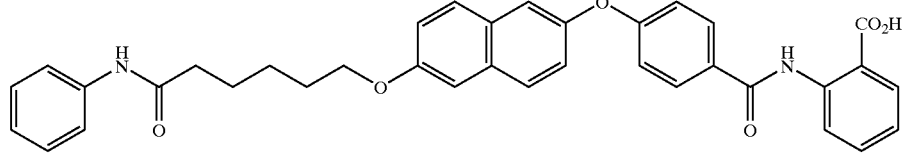
24 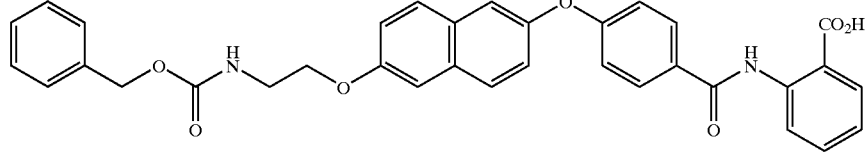
25 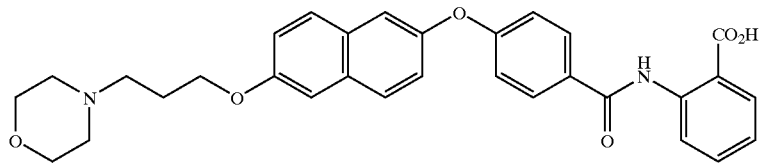
26 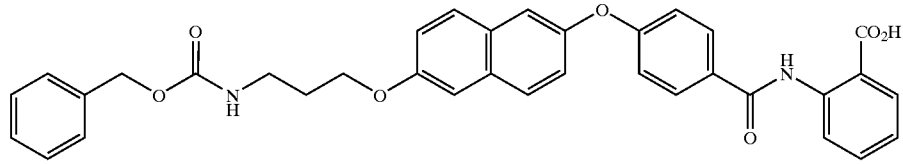
27 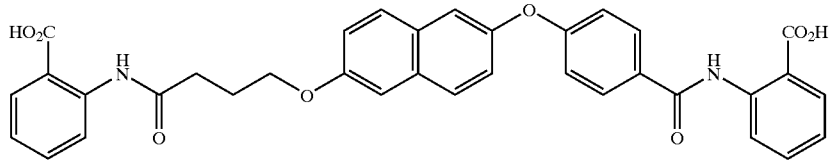
28 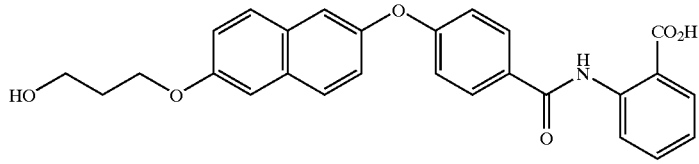
29 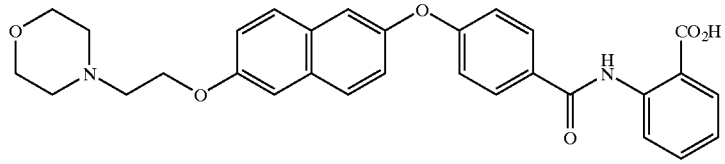
30 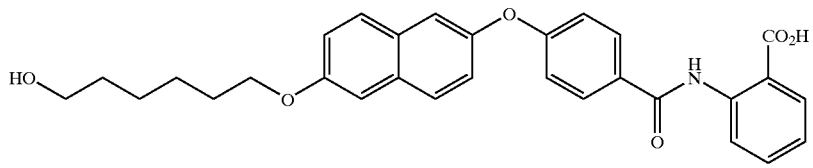

TABLE 2
| | |
|---|---|
| 31 | 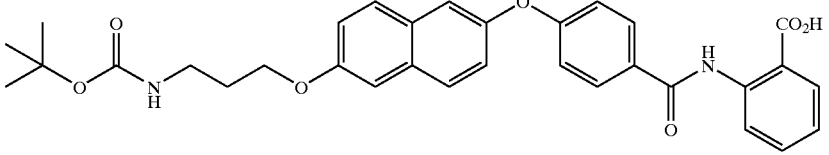 |
| 32 | 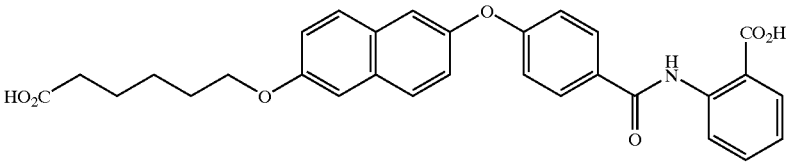 |
| 33 | 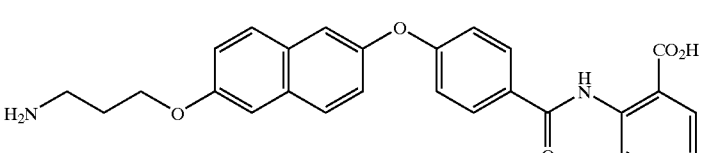 |
| 34 | 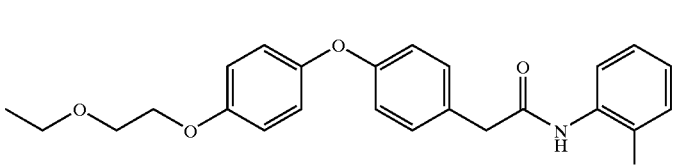 |
| 35 | 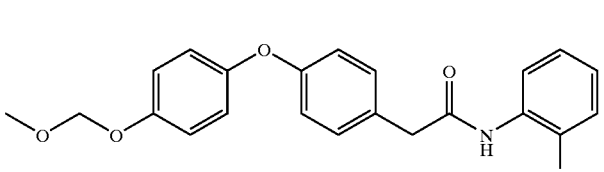 |
| 36 | 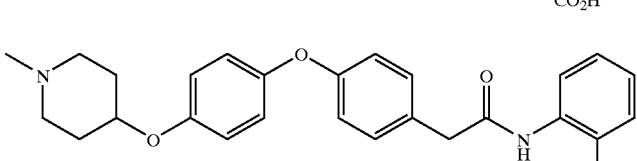 |
| 37 | 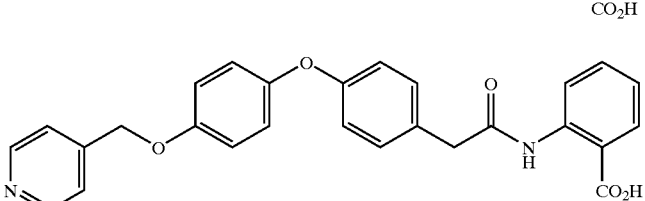 |
| 38 | 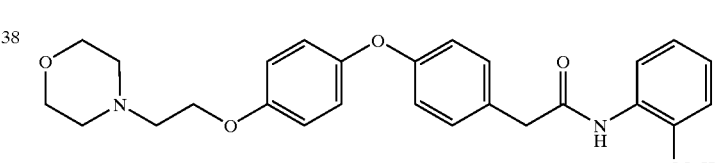 |
| 39 | 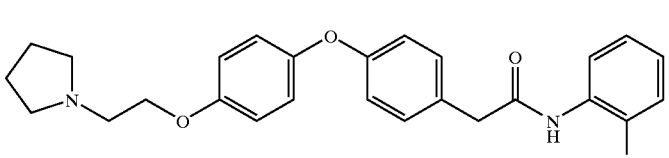 |

TABLE 2-continued

| 40 | (structure) |
| 41 | (structure) |
| 42 | (structure) |
| 43 | (structure) |
| 44 | (structure) |
| 45 | (structure) |
| 46 | (structure) |
| 47 | (structure) |

TABLE 2-continued

| 48 | (structure) |
| 49 | (structure) |
| 50 | (structure) |
| 51 | (structure) |
| 52 | (structure) |
| 53 | (structure) |
| 54 | (structure) |
| 55 | (structure) |

TABLE 2-continued
| 56 | 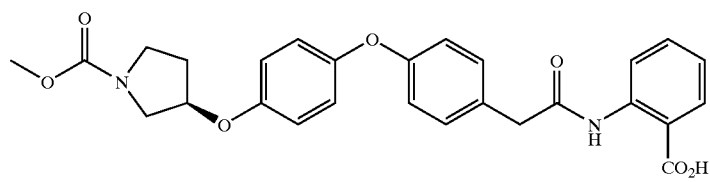 |
| 57 | 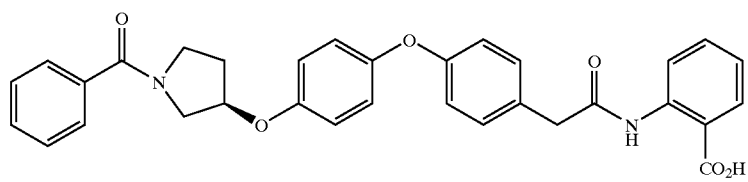 |
| 58 | 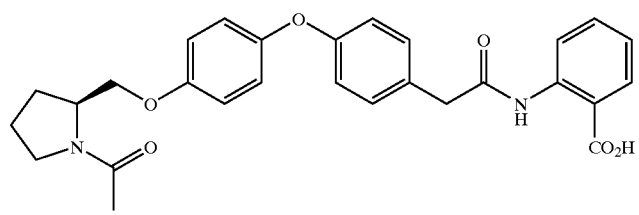 |
| 59 | 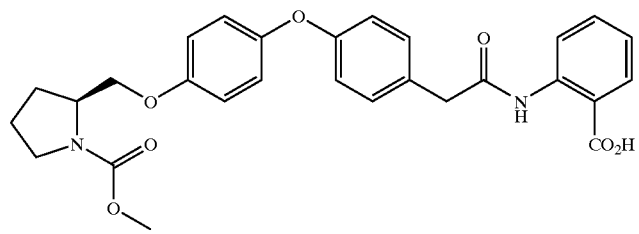 |
TABLE 3
| 60 | 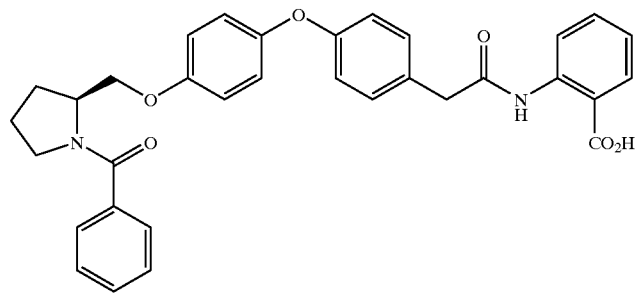 |
| 61 | 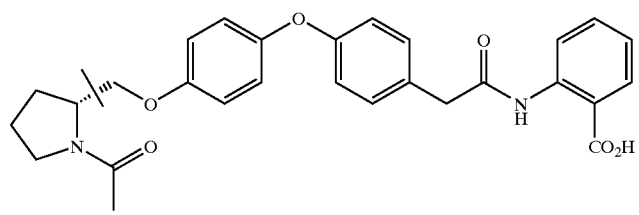 |

TABLE 3-continued
62
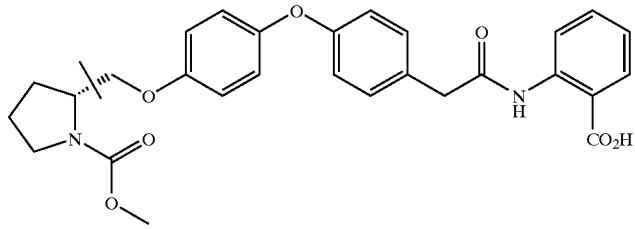
63
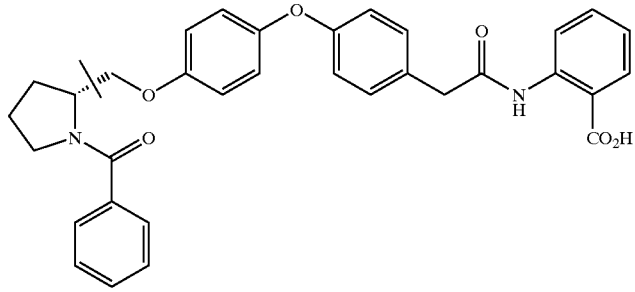
64
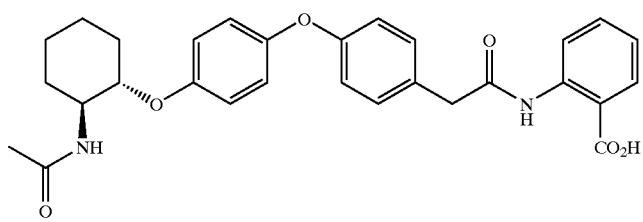
65
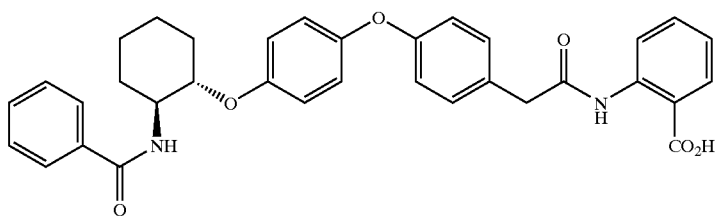
66
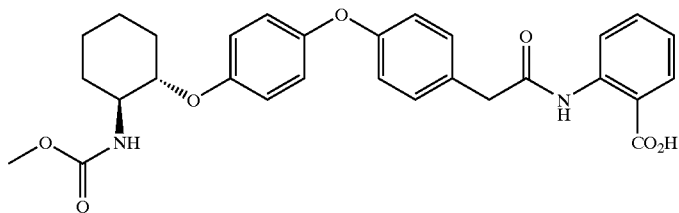
67
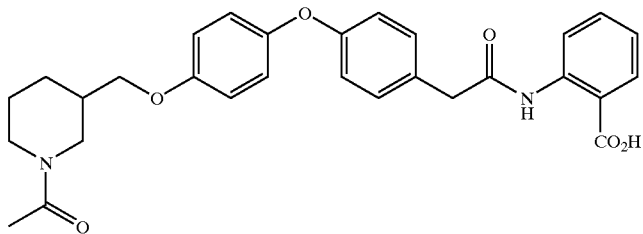

TABLE 3-continued
68 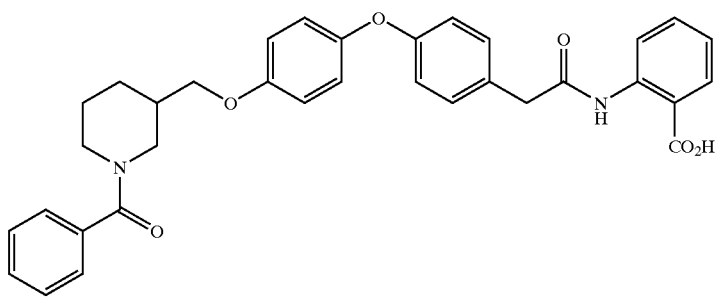
69 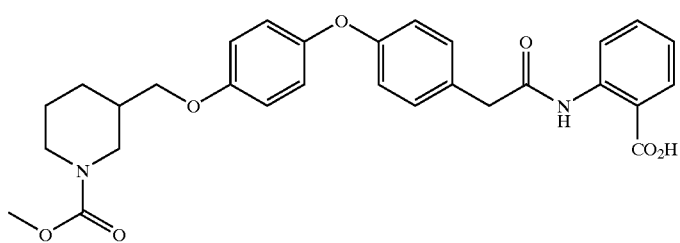
70 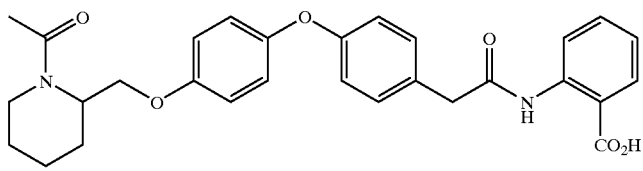
71 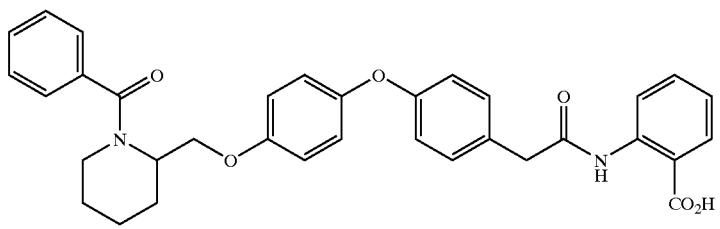
72 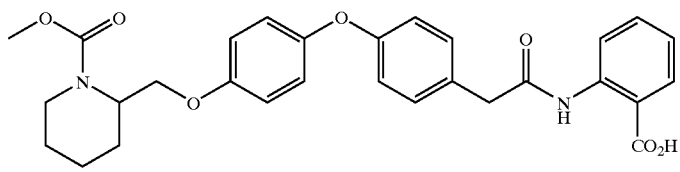
73 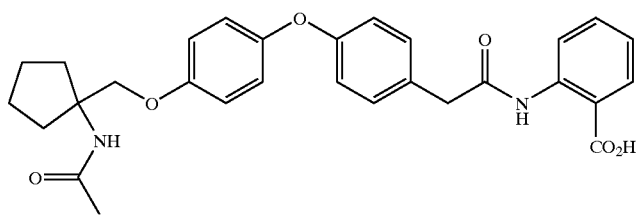

TABLE 3-continued
74 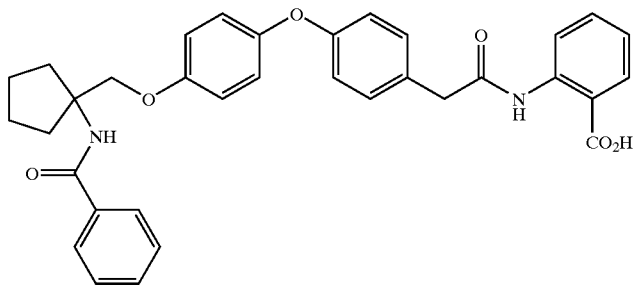
75 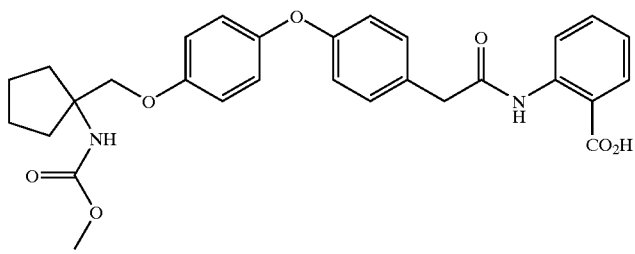
76 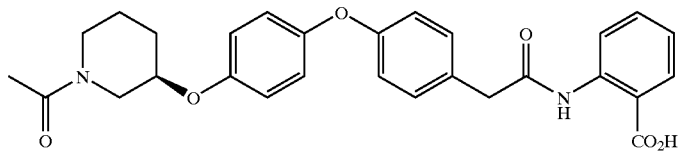
77 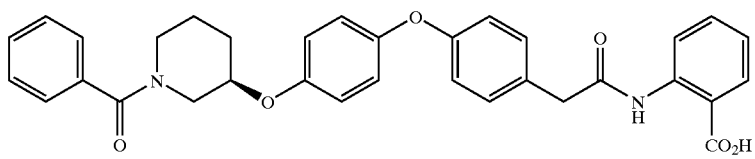
78 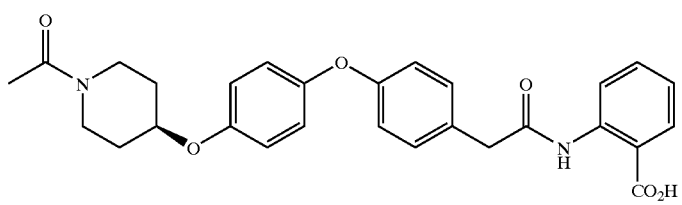
79 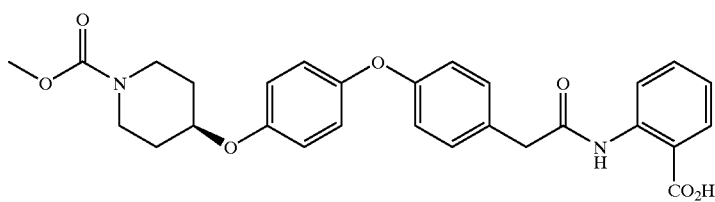
80 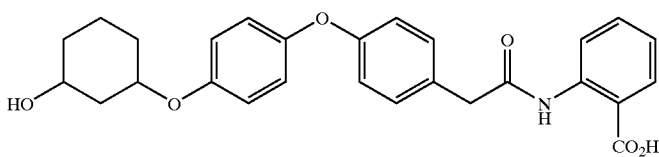

TABLE 3-continued
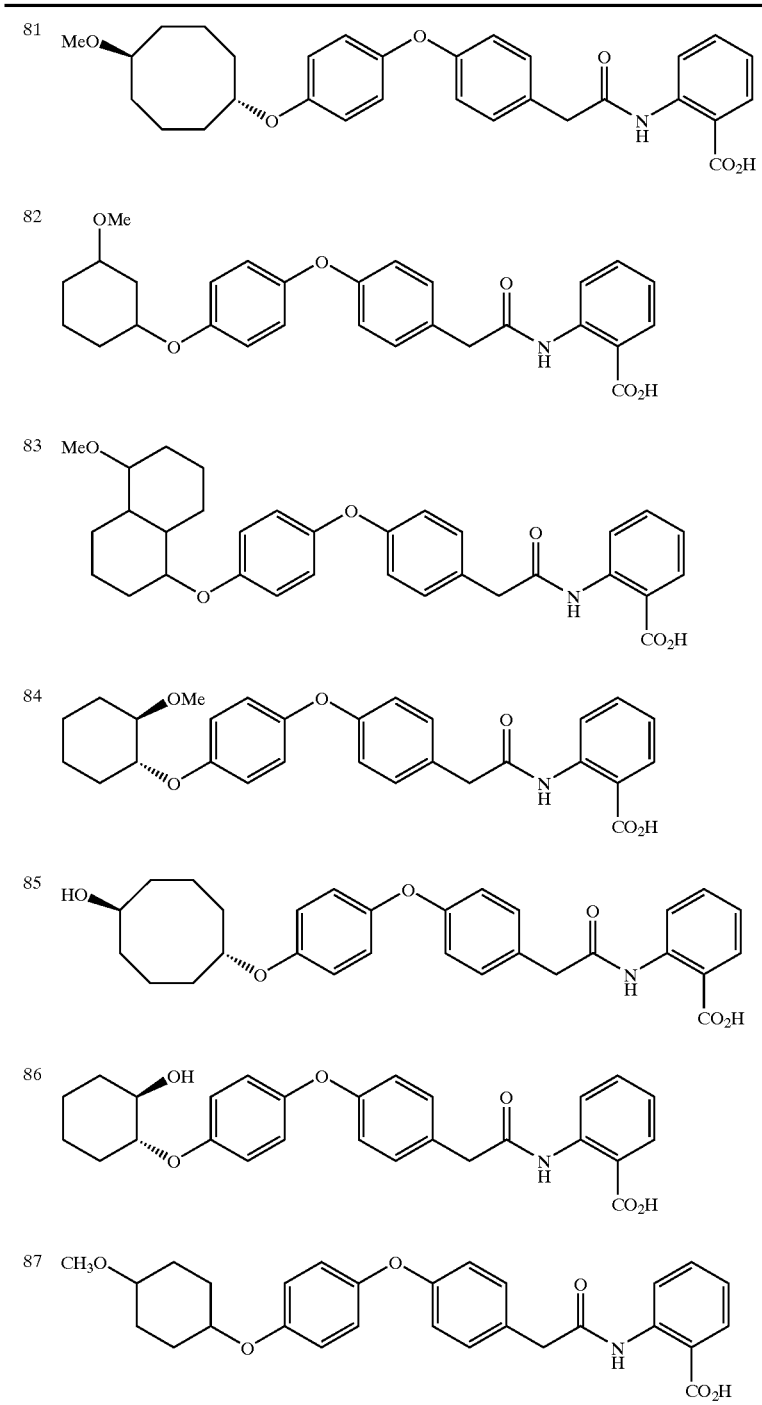
TABLE 4
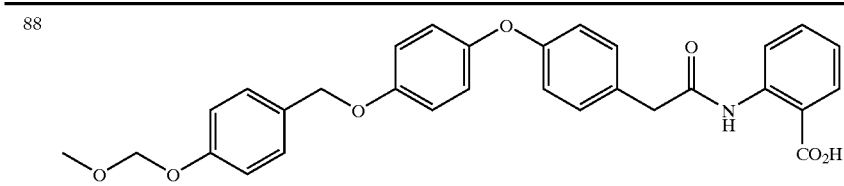

TABLE 4-continued
| 89 | 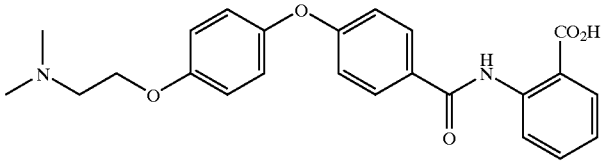 |
| --- | --- |
| 90 | 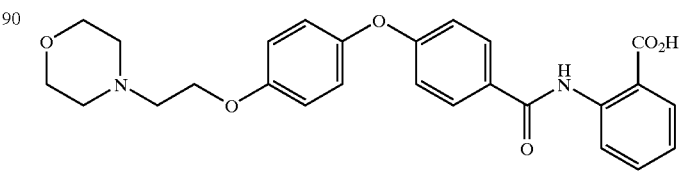 |
| 91 | 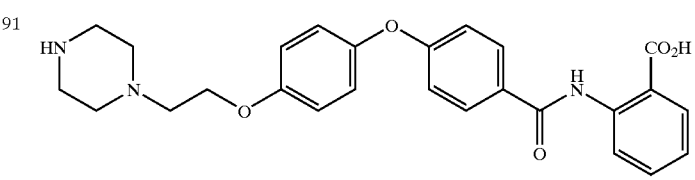 |
| 92 | 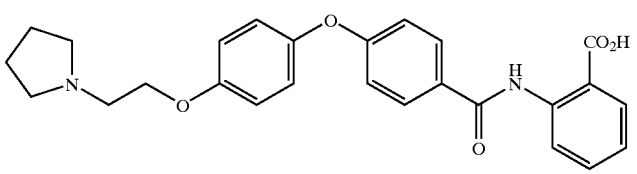 |
| 93 | 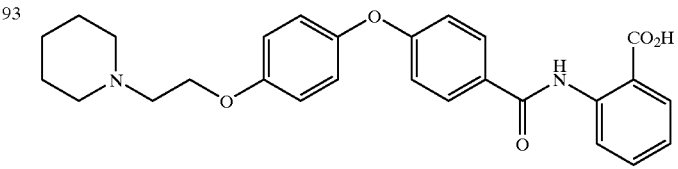 |
| 94 | 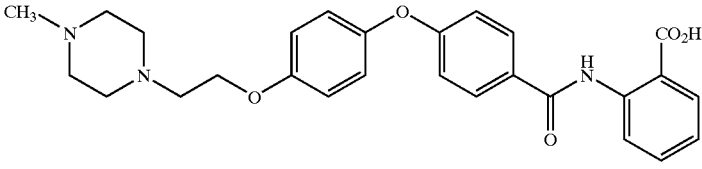 |
| 95 | 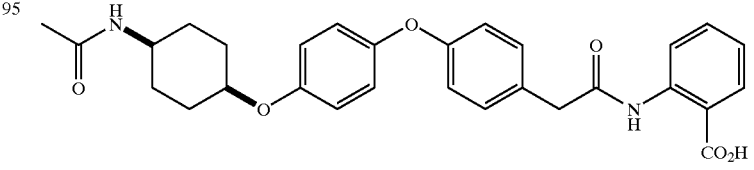 |
| 96 | 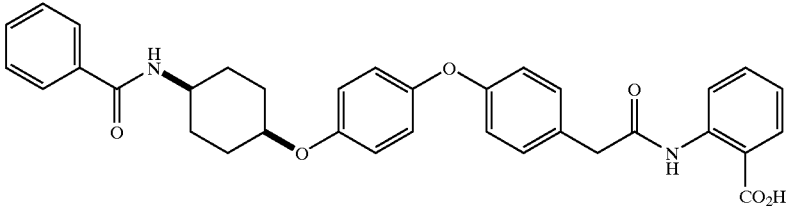 |

TABLE 4-continued

TABLE 4-continued

| 104 | (isobutyramide-cyclohexyl-O-phenyl-O-phenyl-CH2C(O)NH-2-carboxyphenyl) |
| 105 | (butyramide-cyclohexyl-O-phenyl-O-phenyl-CH2C(O)NH-2-carboxyphenyl) |
| 106 | (pivalamide-cyclohexyl-O-phenyl-O-phenyl-CH2C(O)NH-2-carboxyphenyl) |
| 107 | (isovaleramide-cyclohexyl-O-phenyl-O-phenyl-CH2C(O)NH-2-carboxyphenyl) |
| 108 | (valeramide-cyclohexyl-O-phenyl-O-phenyl-CH2C(O)NH-2-carboxyphenyl) |
| 109 | (hexanamide-cyclohexyl-O-phenyl-O-phenyl-CH2C(O)NH-2-carboxyphenyl) |
| 110 | (cyclohexanecarboxamide-cyclohexyl-O-phenyl-O-phenyl-CH2C(O)NH-2-carboxyphenyl) |
| 111 | (4-nitrobenzamide-cyclohexyl-O-phenyl-O-phenyl-CH2C(O)NH-2-carboxyphenyl) |

TABLE 4-continued
112 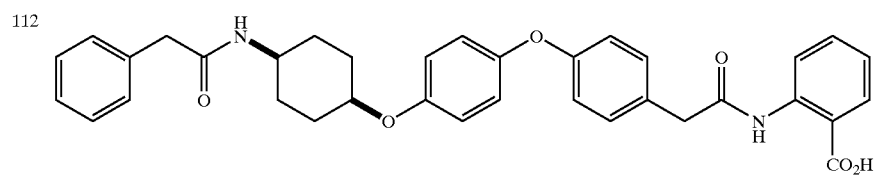
113 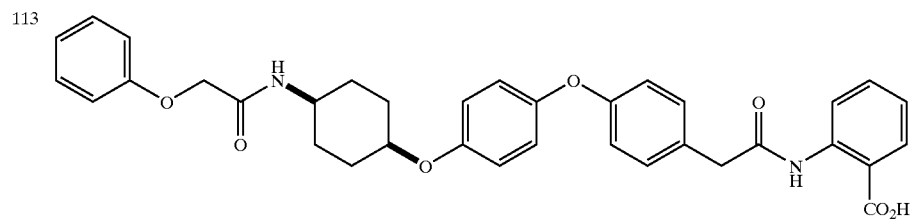
114 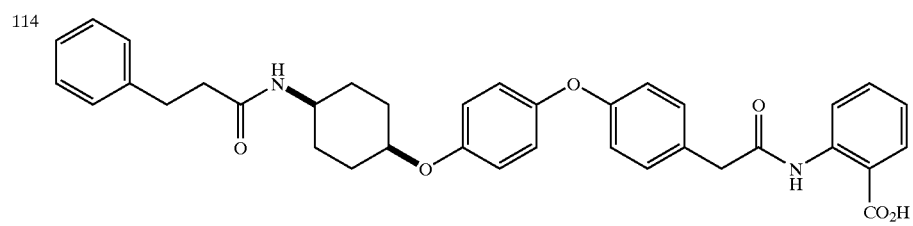
115 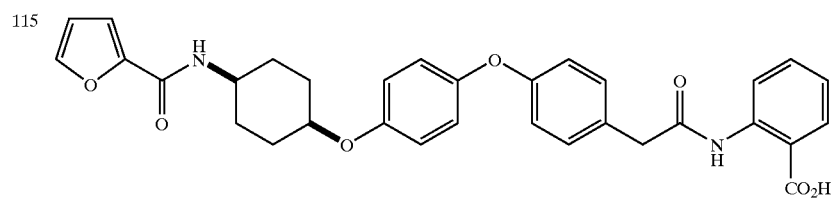
116 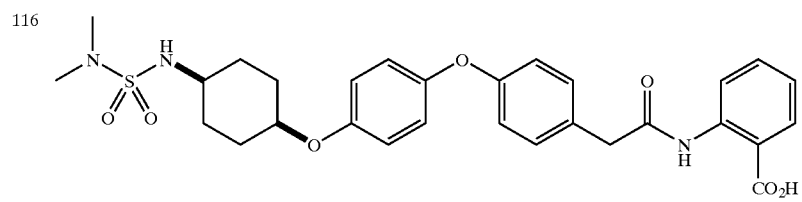
117 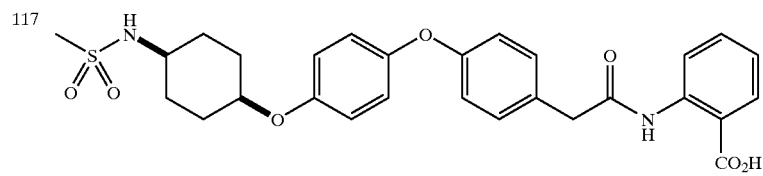
TABLE 5
118 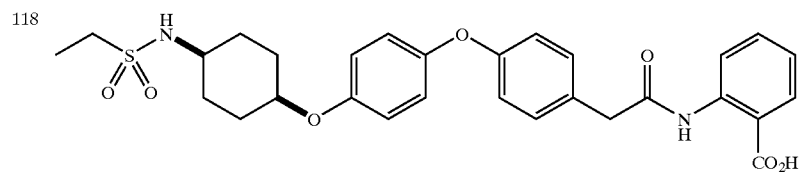

TABLE 5-continued

TABLE 5-continued
126 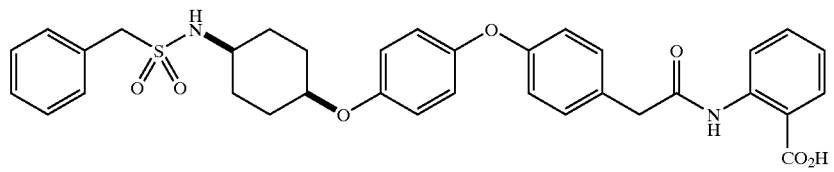
127 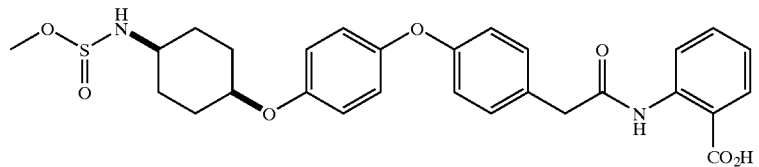
128 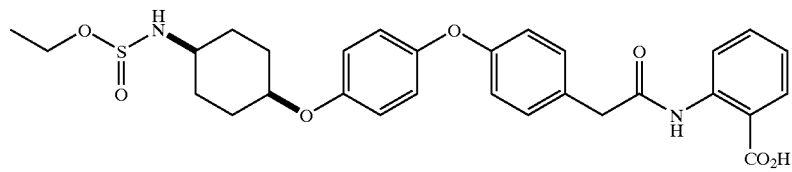
129 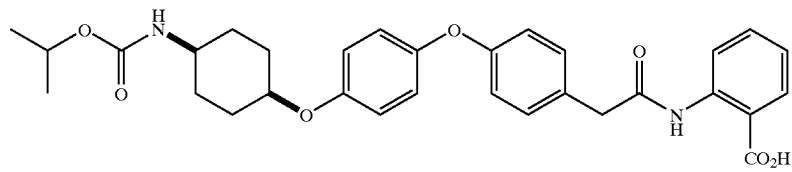
130 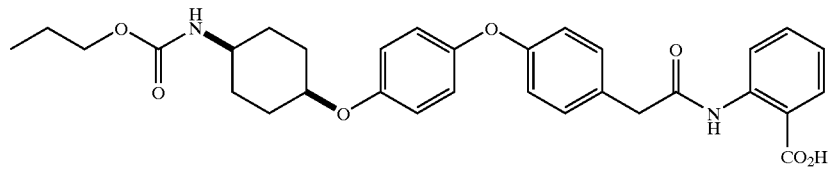
131 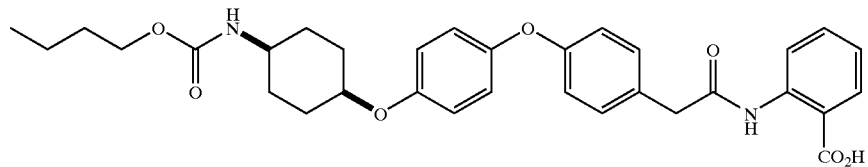
132 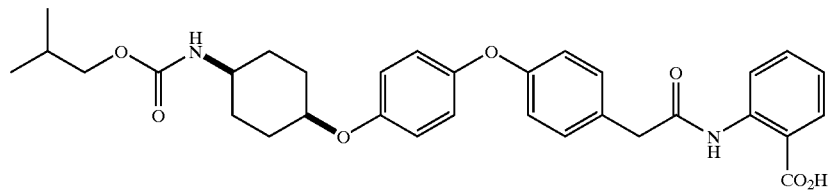
133 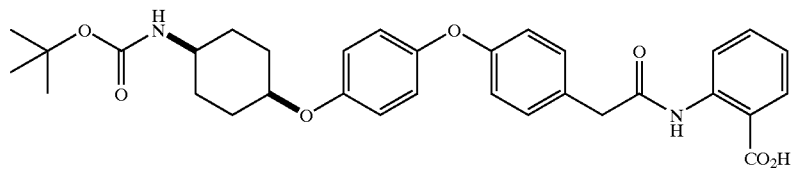

TABLE 5-continued
134 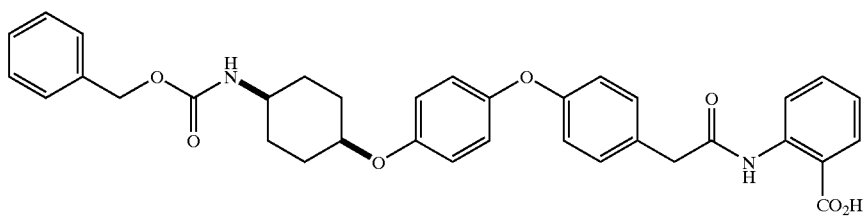
135 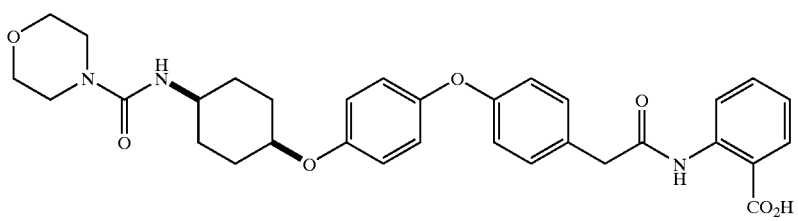
136 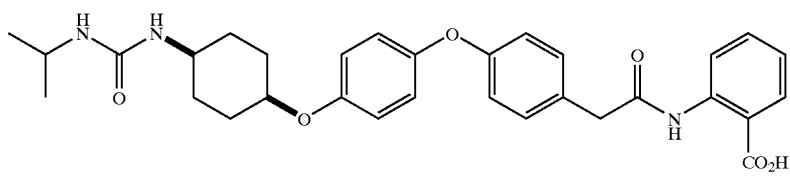
137 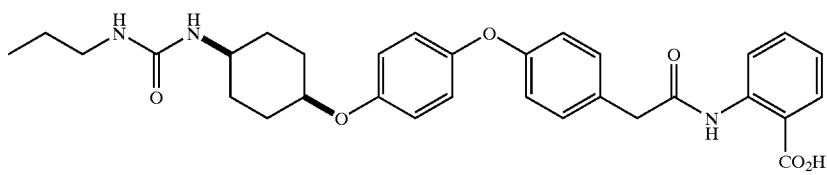
138 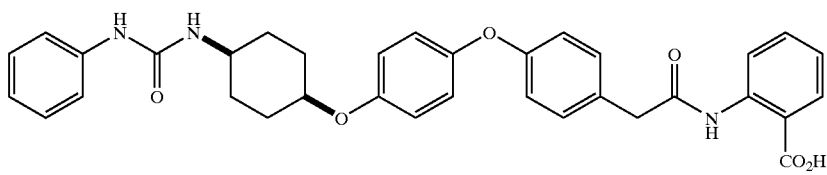
139 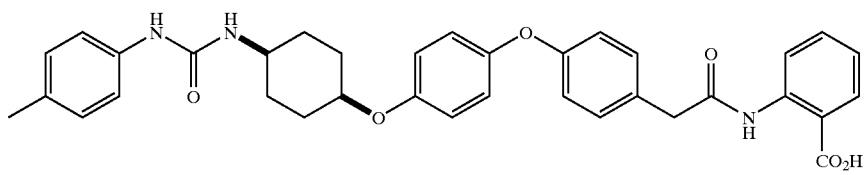
140 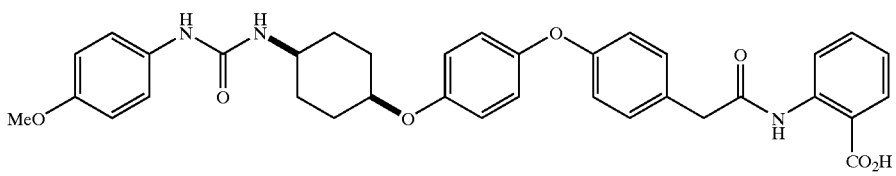
141 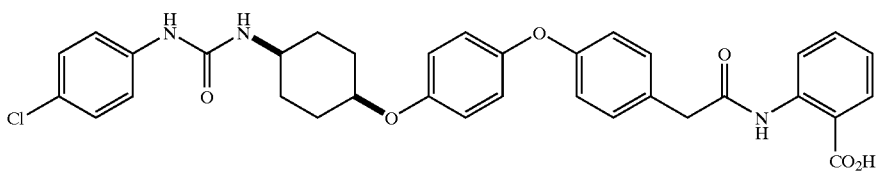

TABLE 5-continued
142 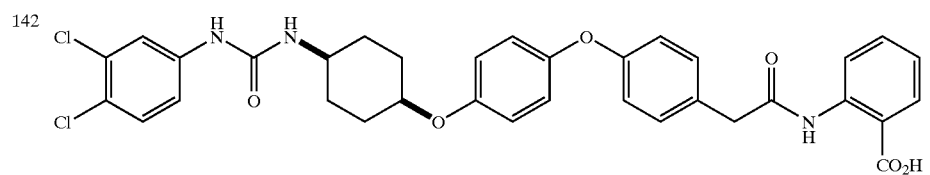
143 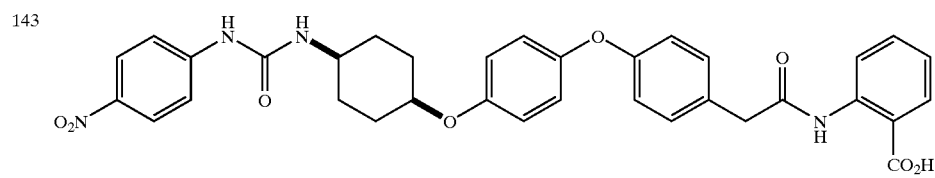
144 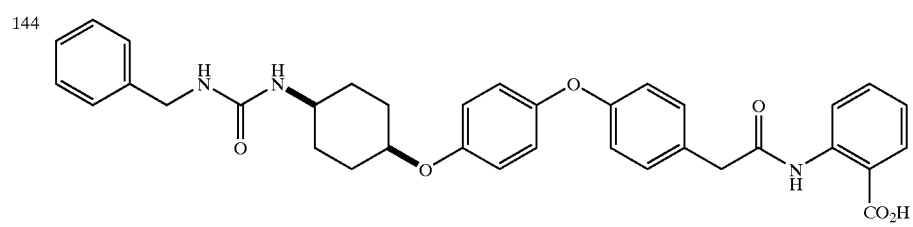
145 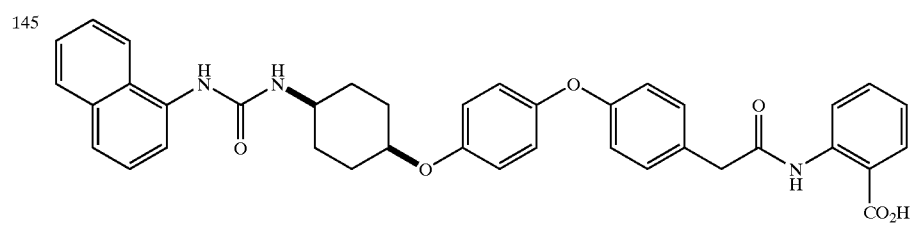
146 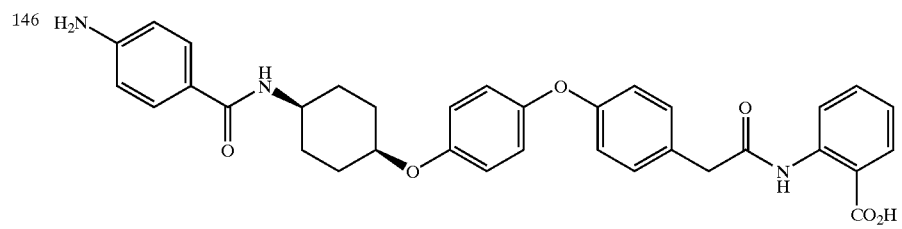
147 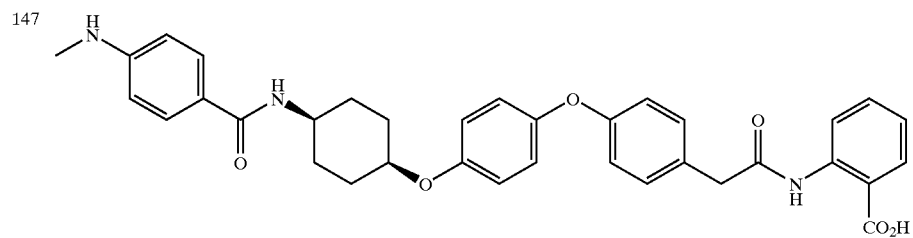

TABLE 6
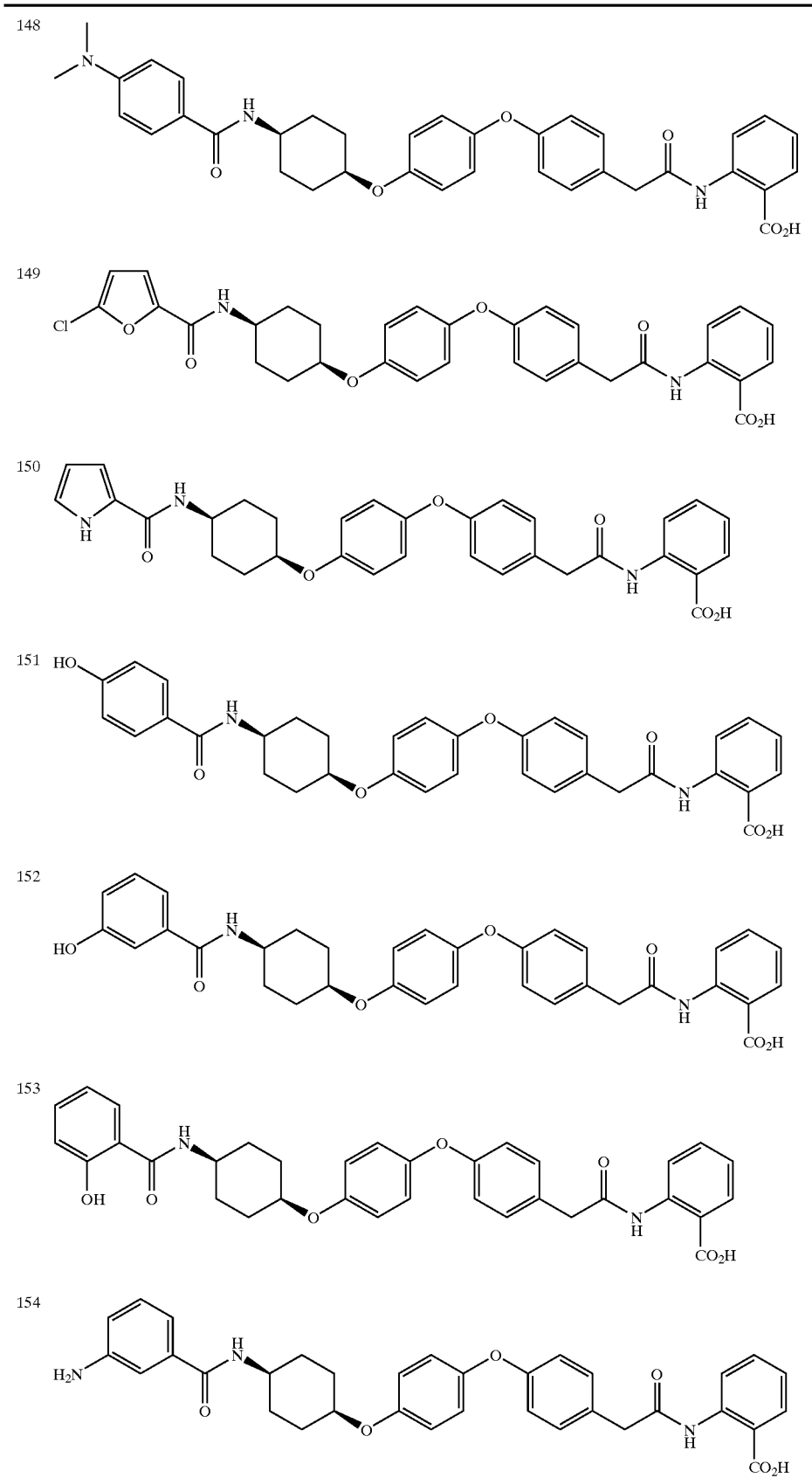

TABLE 6-continued
155
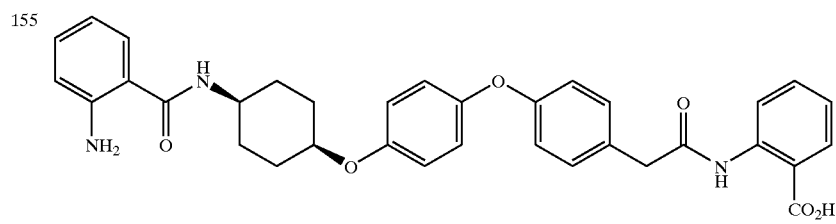
156
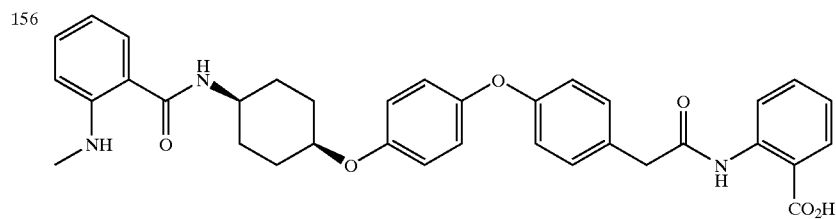
157
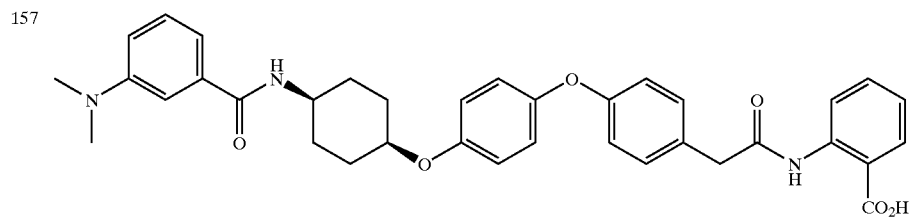
158
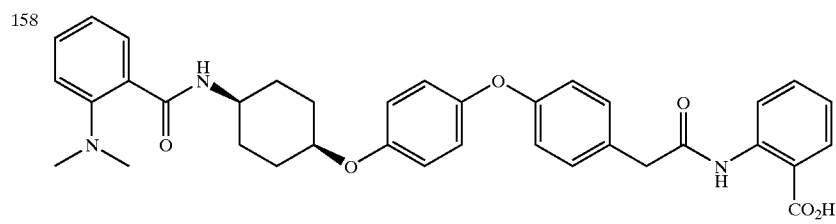
159
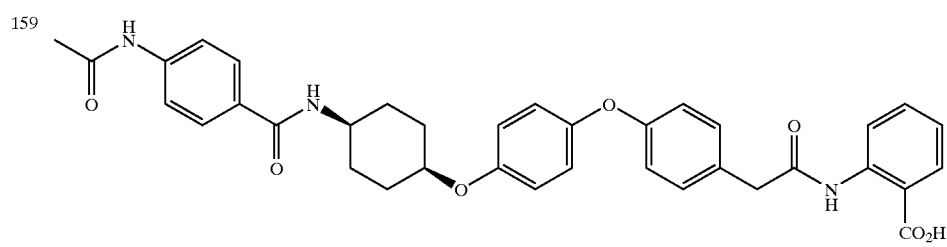
160
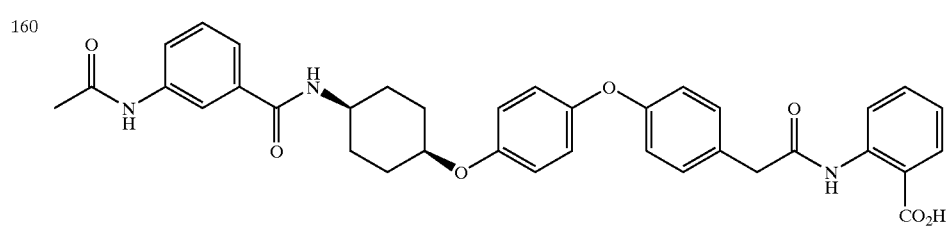

TABLE 6-continued
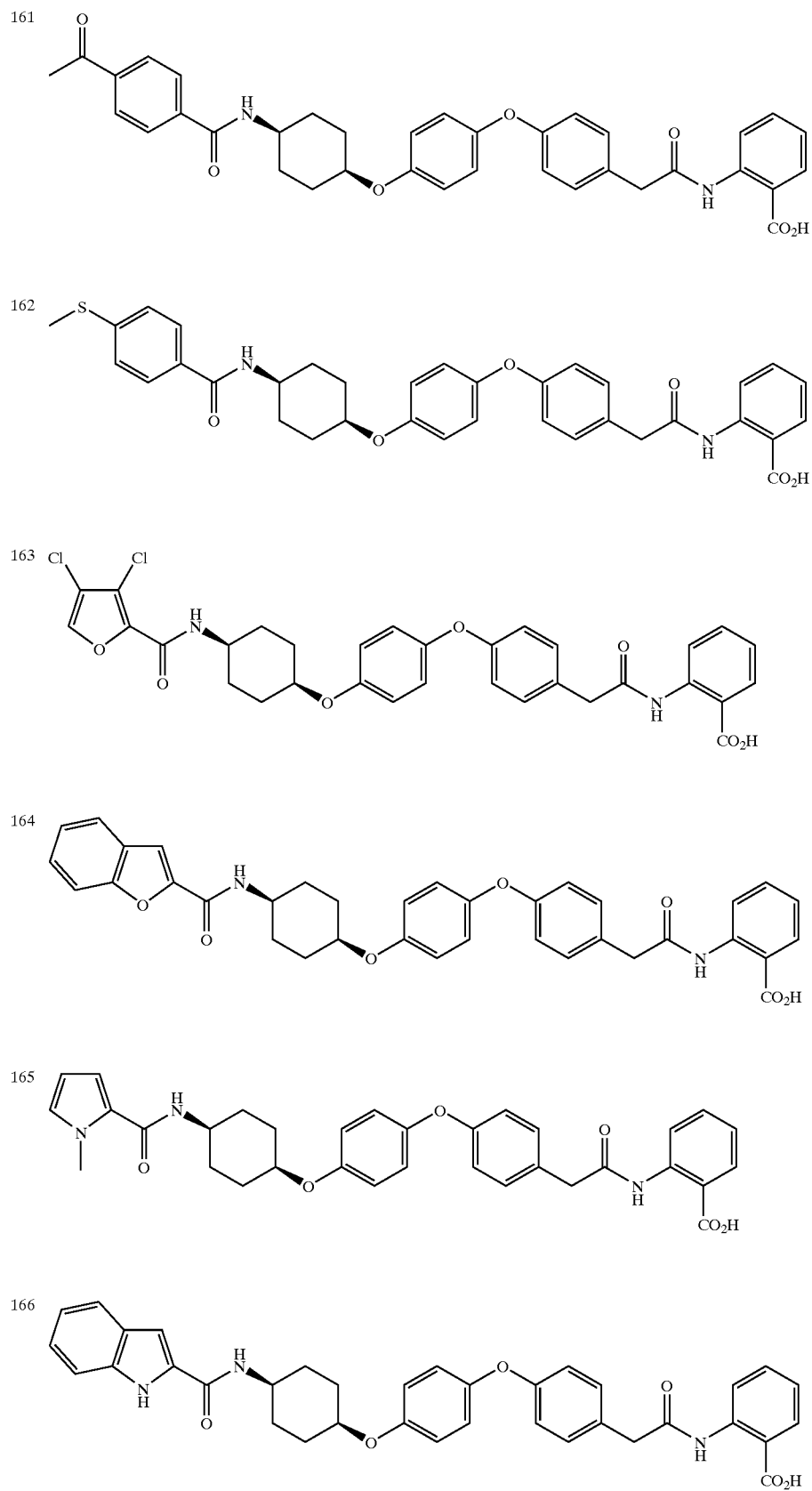

TABLE 6-continued
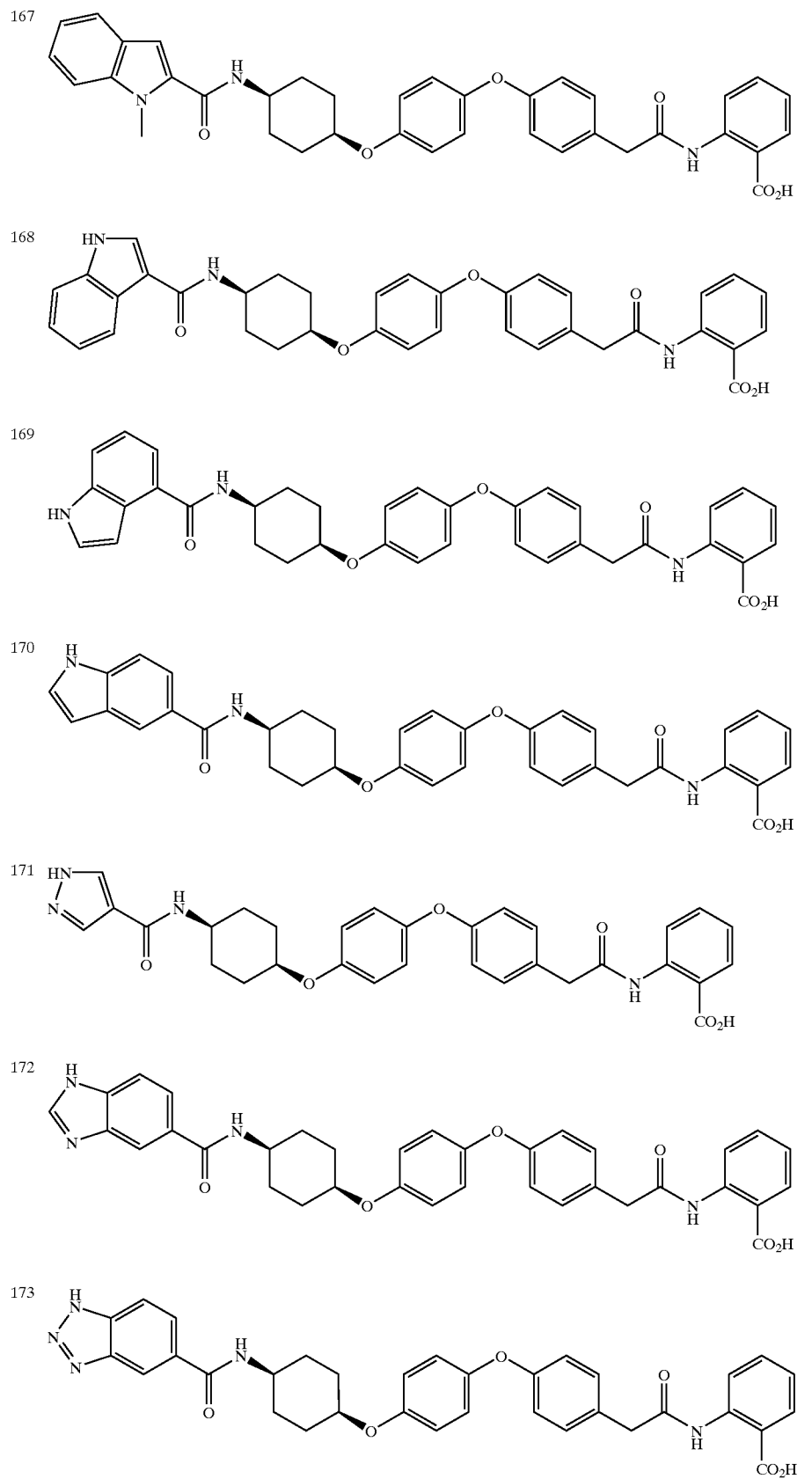

TABLE 6-continued
174 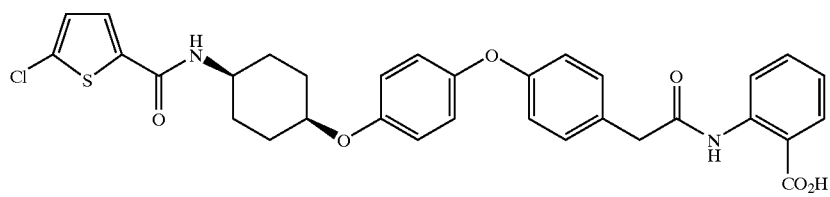
175 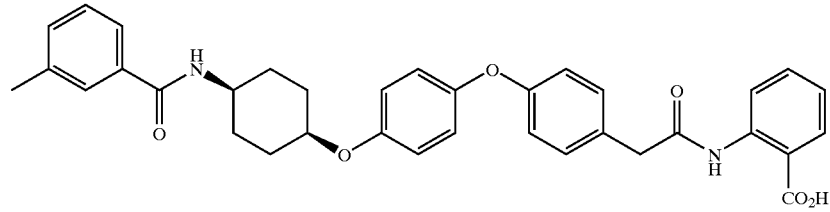
176 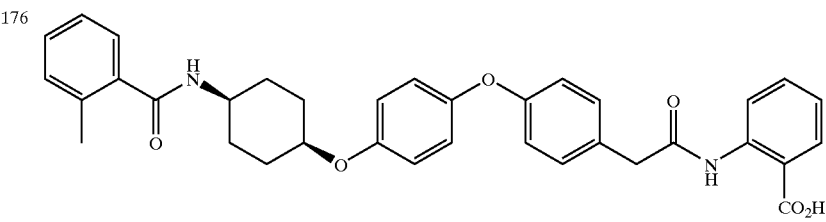
177 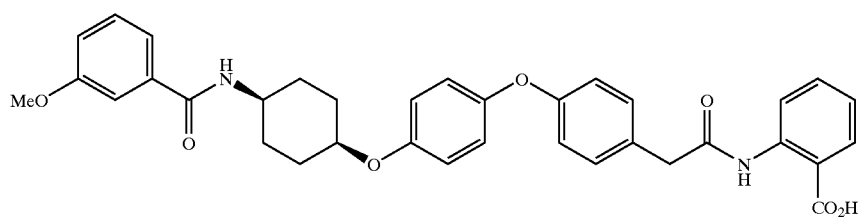
TABLE 7
178 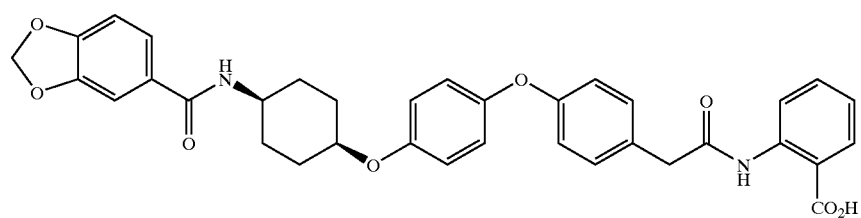
179 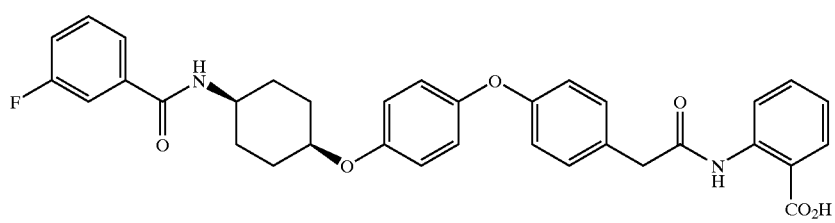

TABLE 7-continued

| 180 | 2-F-C6H4-C(O)NH-cyclohexyl-O-C6H4-O-C6H4-CH2-C(O)NH-C6H4-2-CO2H |
| 181 | 3-Cl-C6H4-C(O)NH-cyclohexyl-O-C6H4-O-C6H4-CH2-C(O)NH-C6H4-2-CO2H |
| 182 | 2-Cl-C6H4-C(O)NH-cyclohexyl-O-C6H4-O-C6H4-CH2-C(O)NH-C6H4-2-CO2H |
| 183 | 4-Br-C6H4-C(O)NH-cyclohexyl-O-C6H4-O-C6H4-CH2-C(O)NH-C6H4-2-CO2H |
| 184 | 3-CF3-C6H4-C(O)NH-cyclohexyl-O-C6H4-O-C6H4-CH2-C(O)NH-C6H4-2-CO2H |
| 185 | 4-CF3-C6H4-C(O)NH-cyclohexyl-O-C6H4-O-C6H4-CH2-C(O)NH-C6H4-2-CO2H |
| 186 | 2-OCF3-C6H4-C(O)NH-cyclohexyl-O-C6H4-O-C6H4-CH2-C(O)NH-C6H4-2-CO2H |

TABLE 7-continued
187 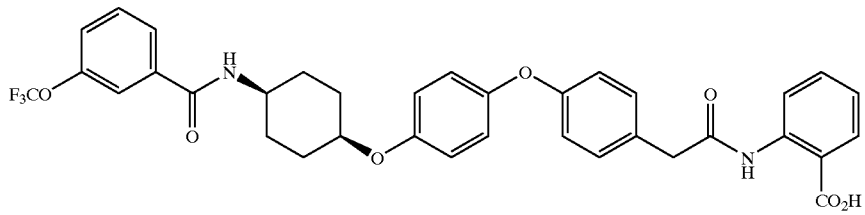
188 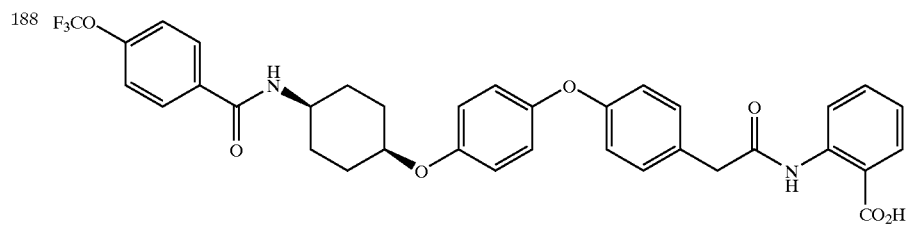
189 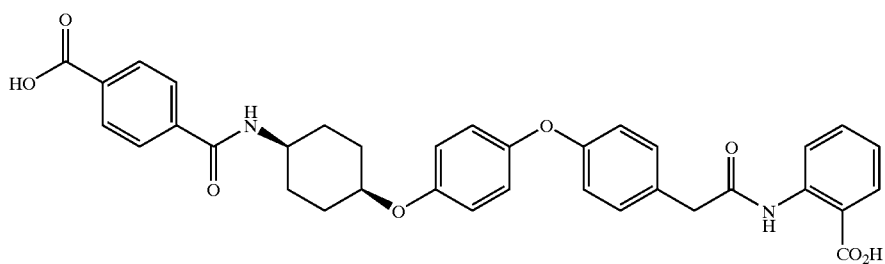
190 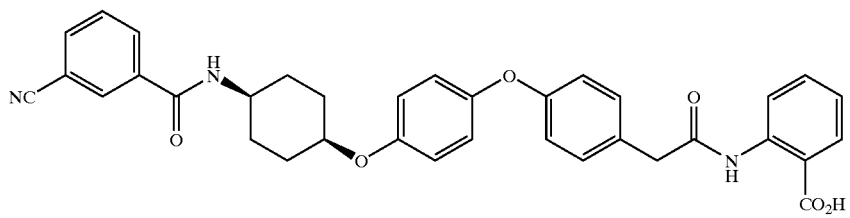
191 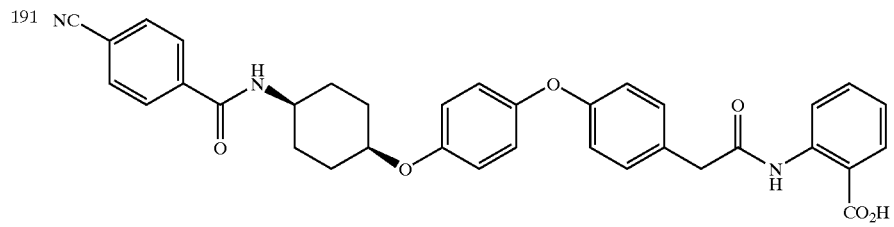
192 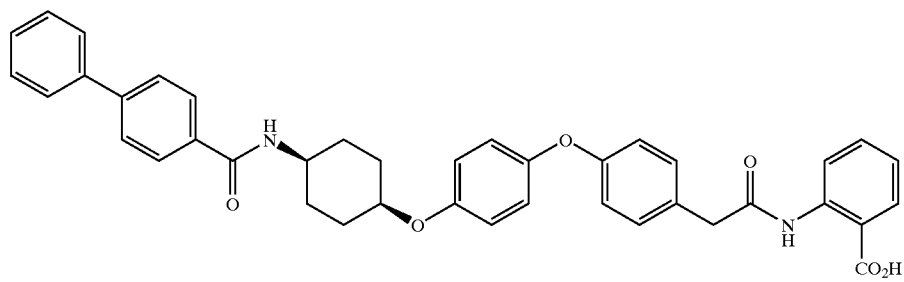

TABLE 7-continued
193
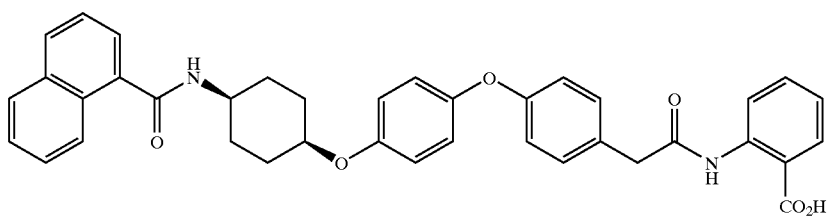
194
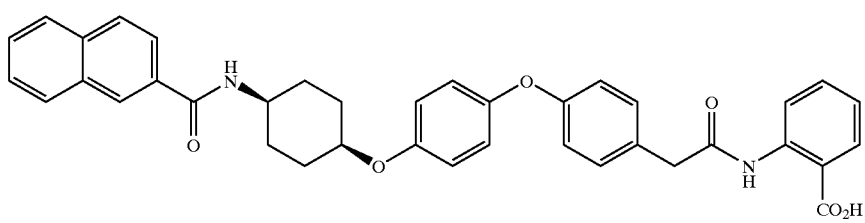
195
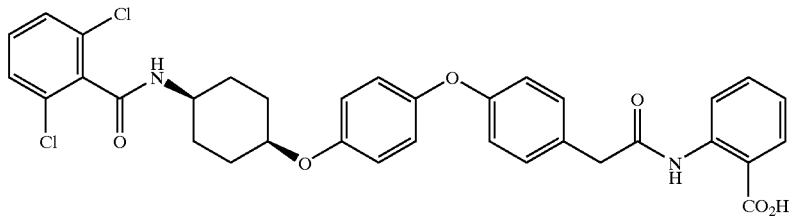
196
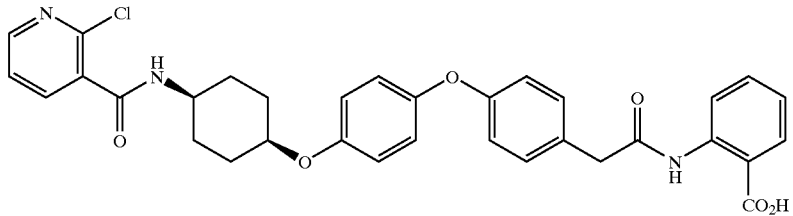
197
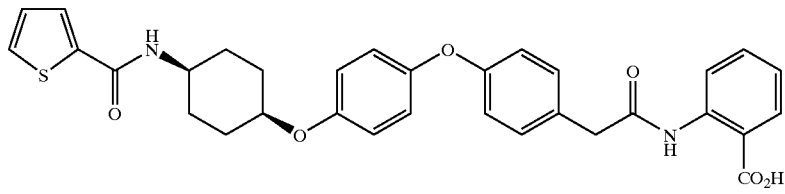
198
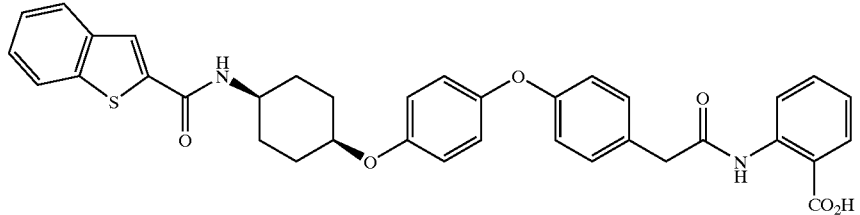
199
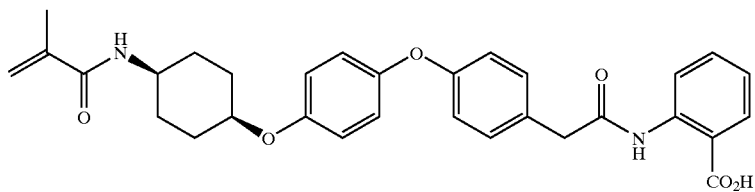

TABLE 7-continued

TABLE 7-continued
| 207 | 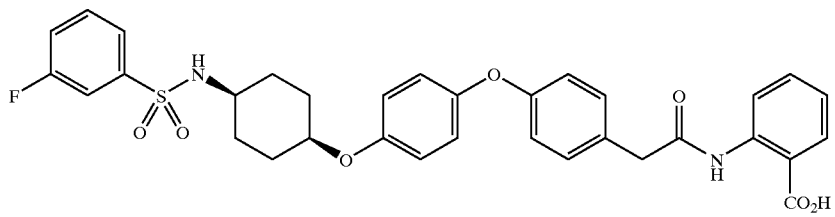 |
TABLE 8
| 208 | 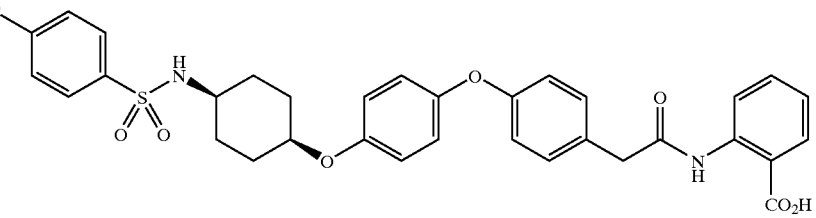 |
| 209 | 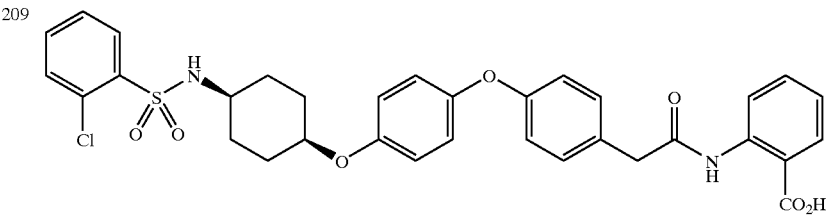 |
| 210 | 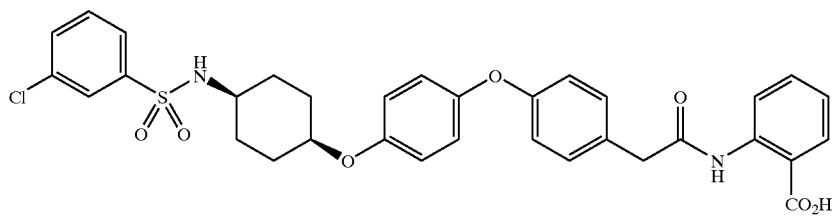 |
| 211 | 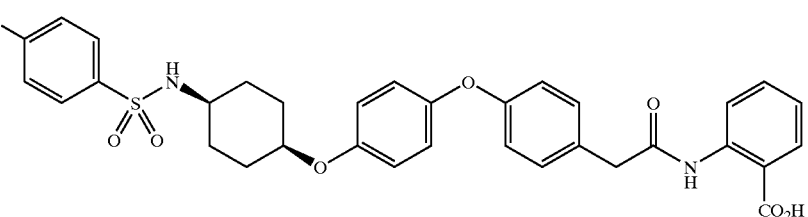 |
| 212 | 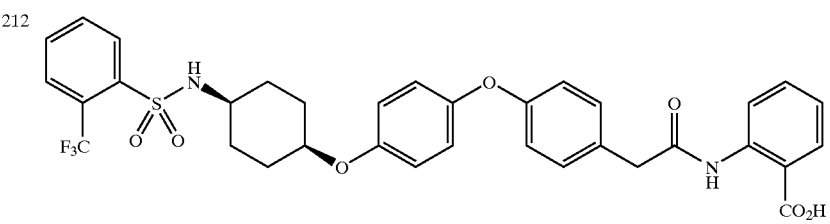 |

TABLE 8-continued
213 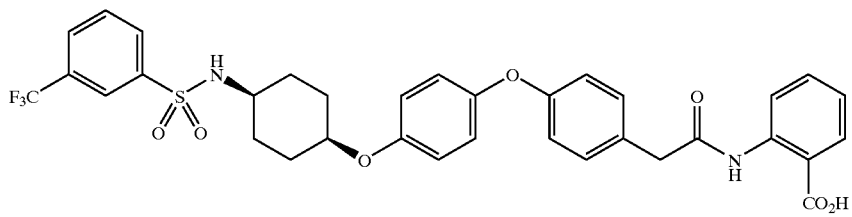
214 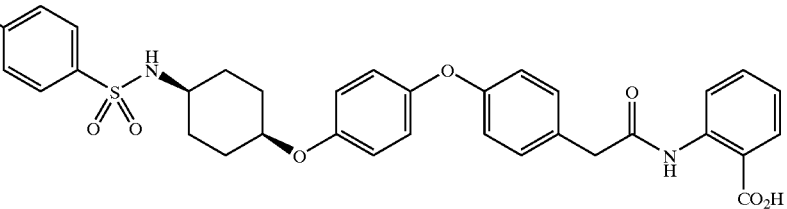
215 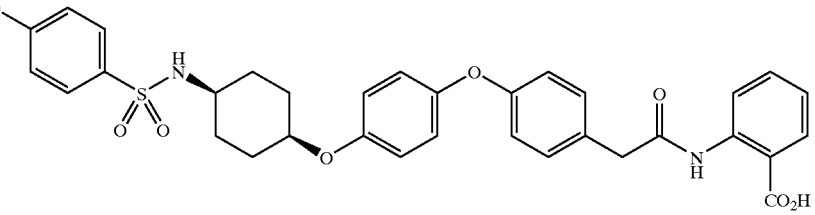
216 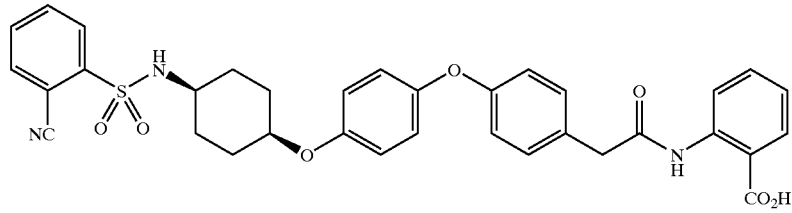
217 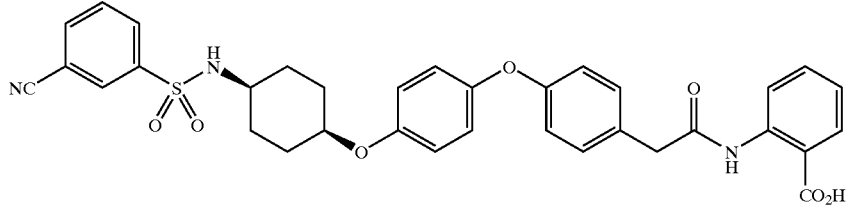
218 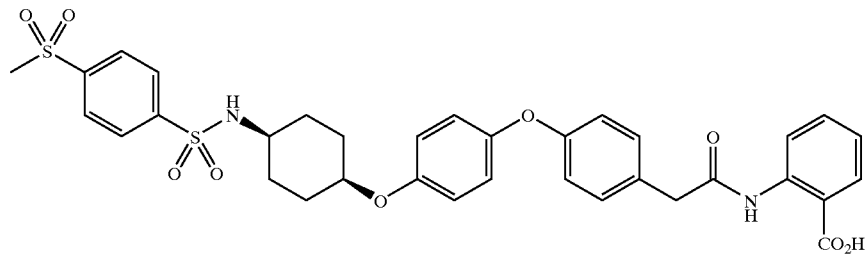
219 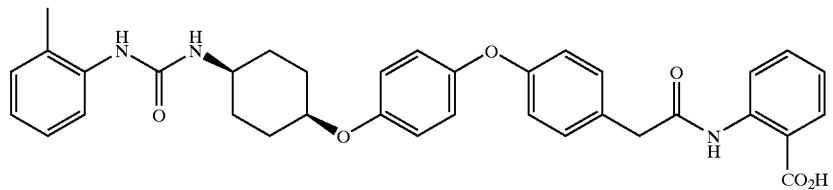

TABLE 8-continued

| 220 | 3-methylphenyl urea cyclohexyl-O-phenyl-O-phenyl-CH₂C(O)NH-phenyl-CO₂H |
| 221 | 2-fluorophenyl urea cyclohexyl-O-phenyl-O-phenyl-CH₂C(O)NH-phenyl-CO₂H |
| 222 | 3-fluorophenyl urea cyclohexyl-O-phenyl-O-phenyl-CH₂C(O)NH-phenyl-CO₂H |
| 223 | 3,4-difluorophenyl urea cyclohexyl-O-phenyl-O-phenyl-CH₂C(O)NH-phenyl-CO₂H |
| 224 | 2-chlorophenyl urea cyclohexyl-O-phenyl-O-phenyl-CH₂C(O)NH-phenyl-CO₂H |
| 225 | 3-chlorophenyl urea cyclohexyl-O-phenyl-O-phenyl-CH₂C(O)NH-phenyl-CO₂H |
| 226 | 4-bromophenyl urea cyclohexyl-O-phenyl-O-phenyl-CH₂C(O)NH-phenyl-CO₂H |
| 227 | 2-methoxyphenyl urea cyclohexyl-O-phenyl-O-phenyl-CH₂C(O)NH-phenyl-CO₂H |

TABLE 8-continued

TABLE 8-continued
236 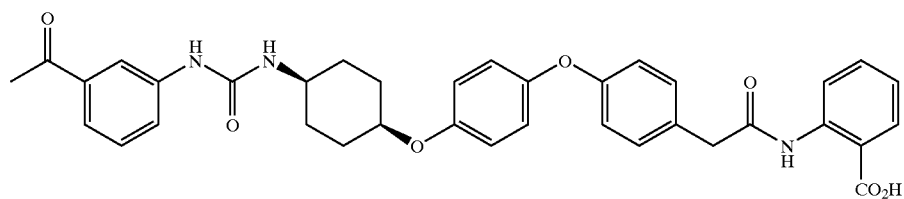
237 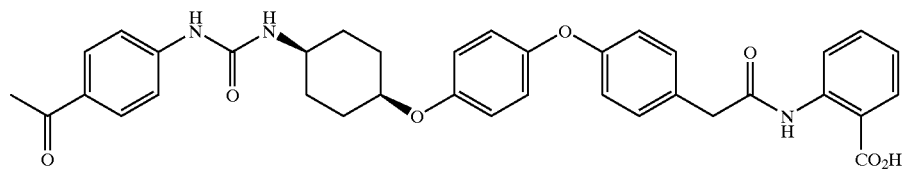
TABLE 9
238 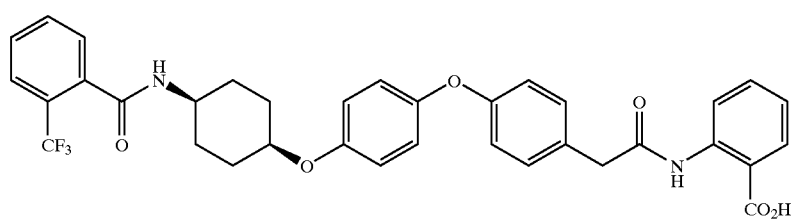
239 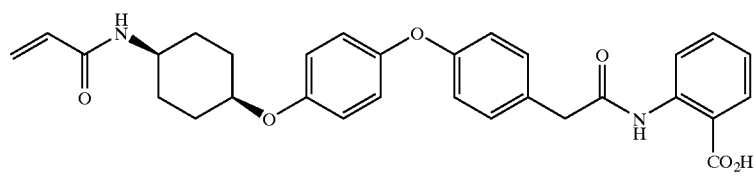
240 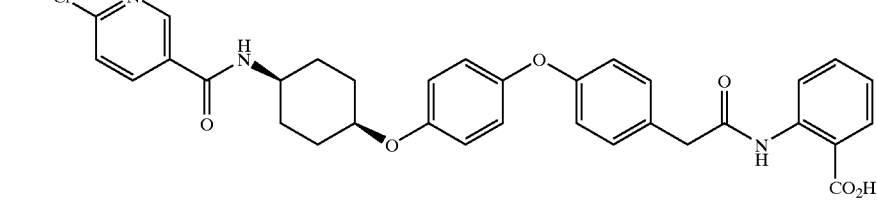
241 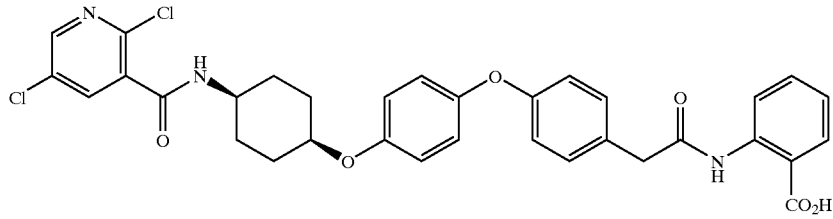
242 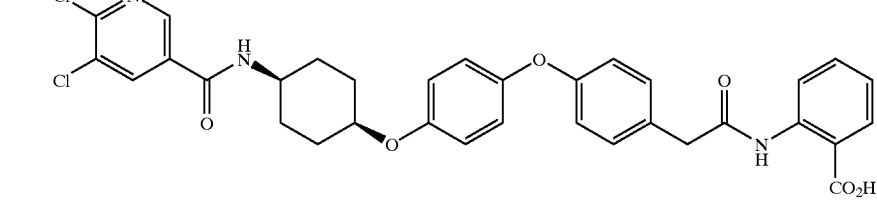

TABLE 9-continued
243 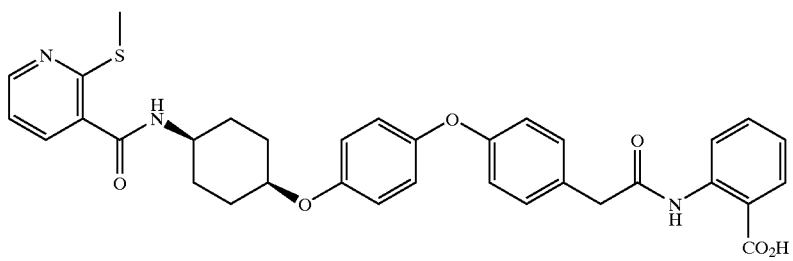
244 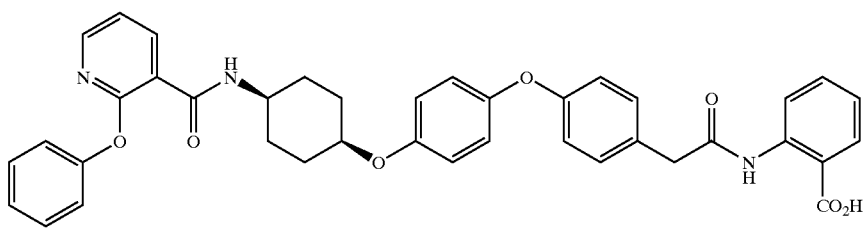
245 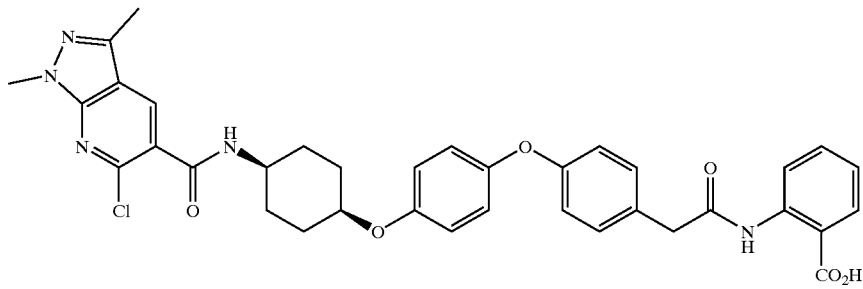
246 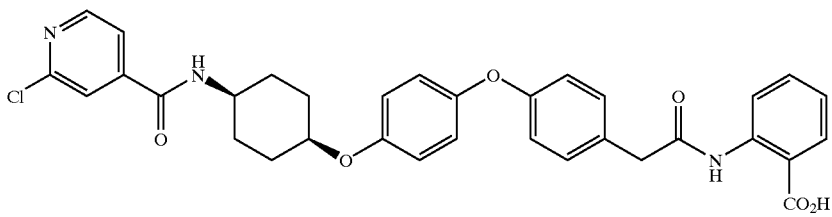
247 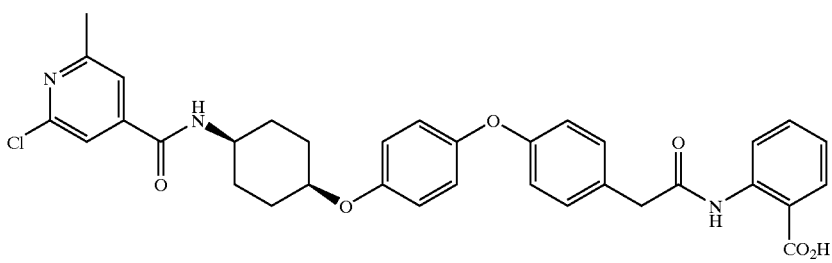
248 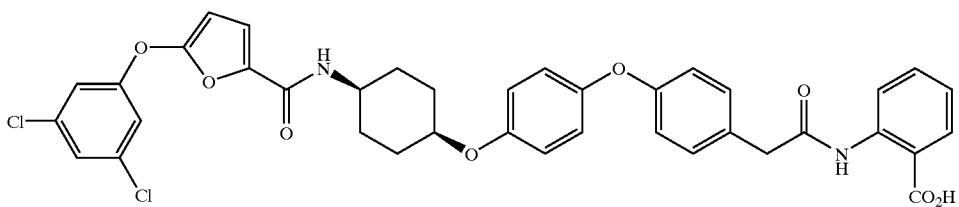

US 6,649,656 B1
TABLE 9-continued
| 249 | 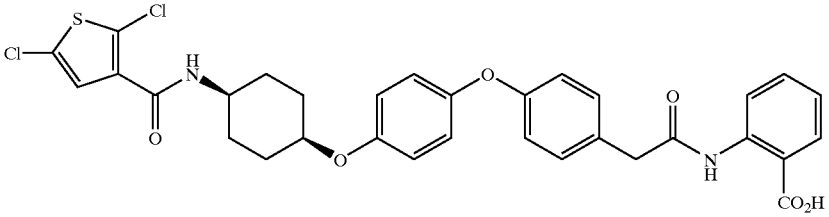 |
| 250 | 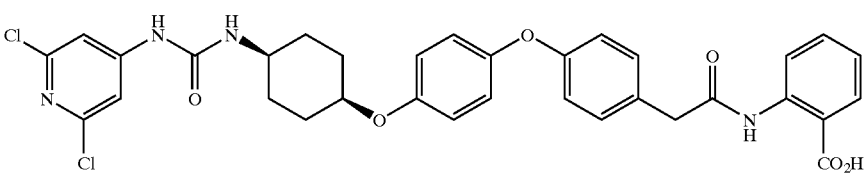 |
| 251 | 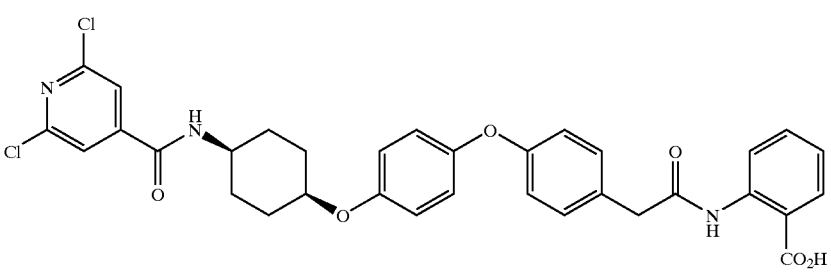 |
| 252 | 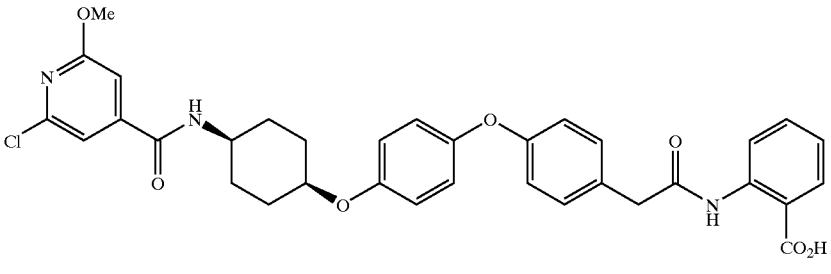 |
| 253 | 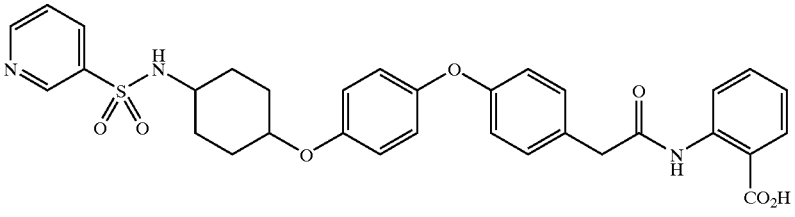 |
| 254 | 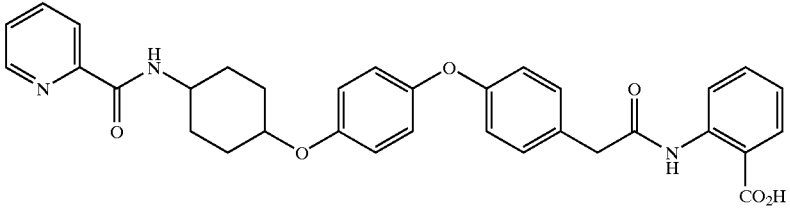 |
| 255 | 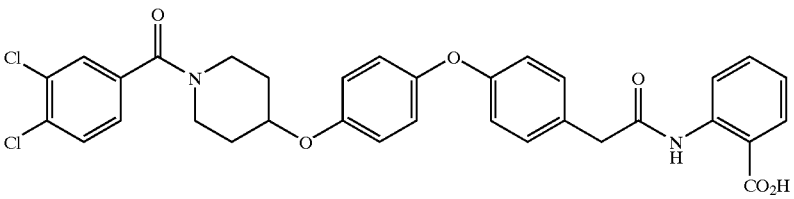 |

TABLE 9-continued

| 256 | (structure) |
| 257 | (structure) |
| 258 | (structure) |
| 259 | (structure) |
| 260 | (structure) |
| 261 | (structure) |
| 262 | (structure) |
| 263 | (structure) |

TABLE 9-continued
264 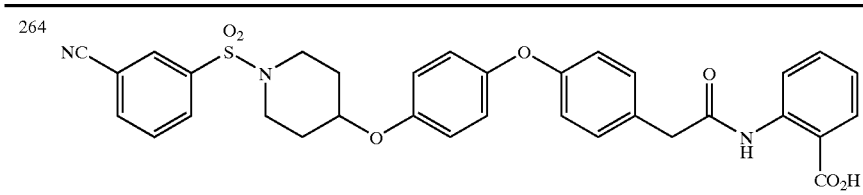
265 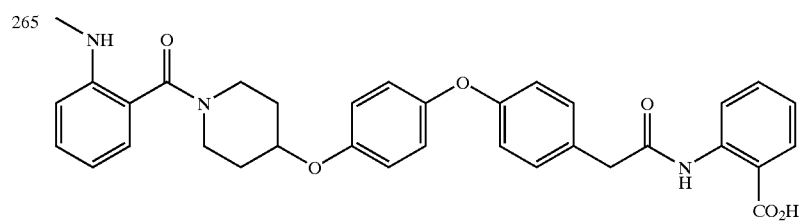
266 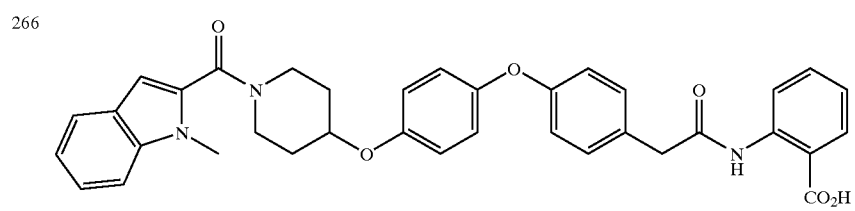
267 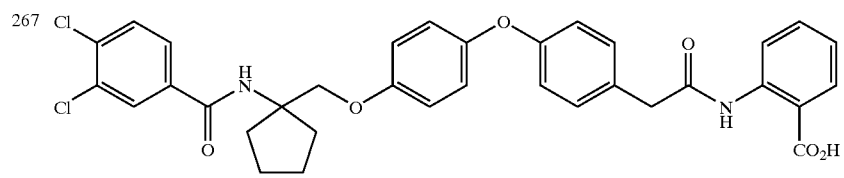
TABLE 10
268 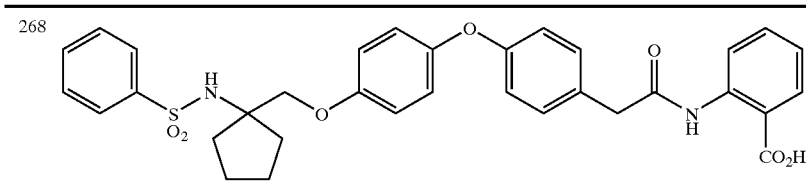
269 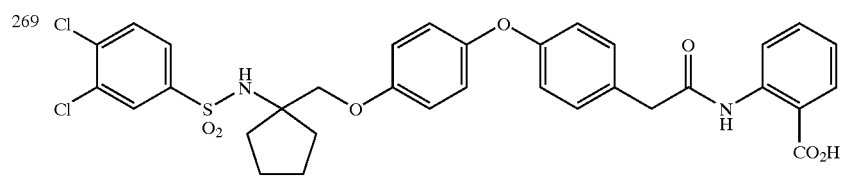
270 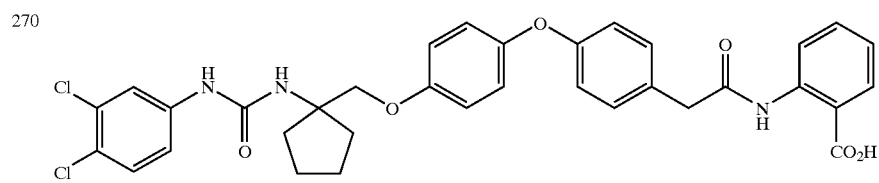
271 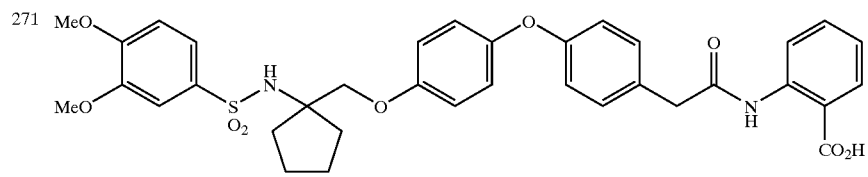

TABLE 10-continued

TABLE 10-continued
280 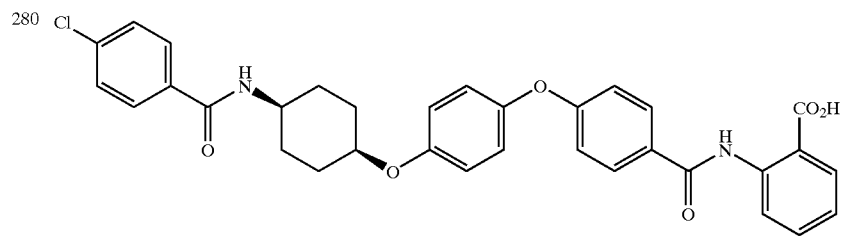
281 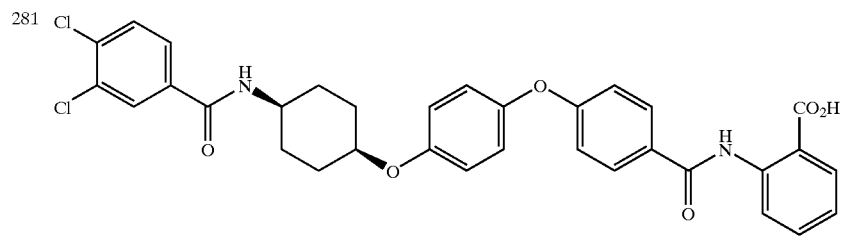
282 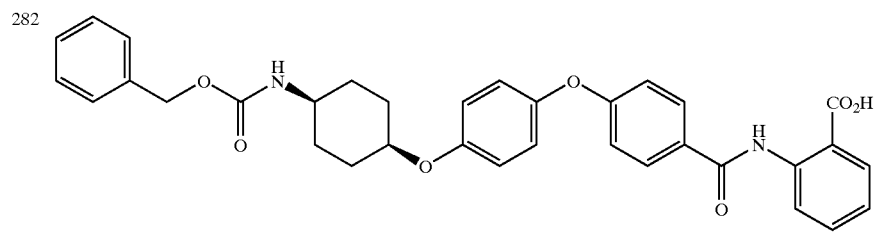
283 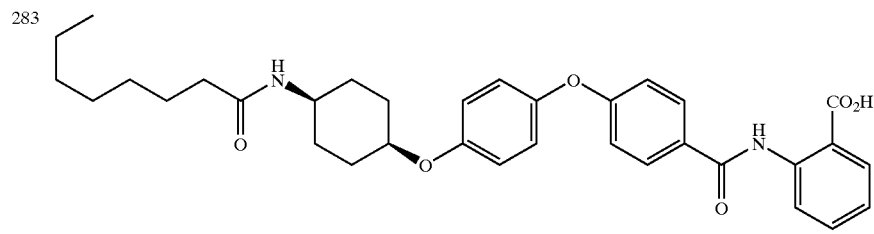
284 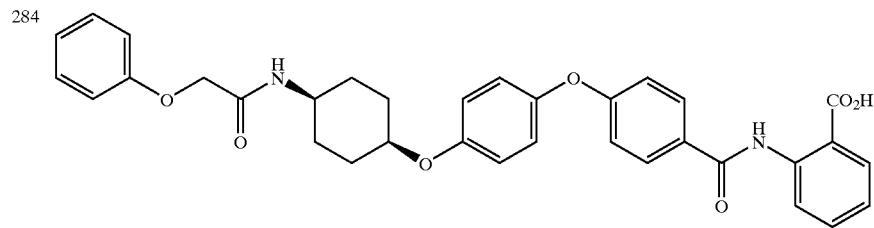
285 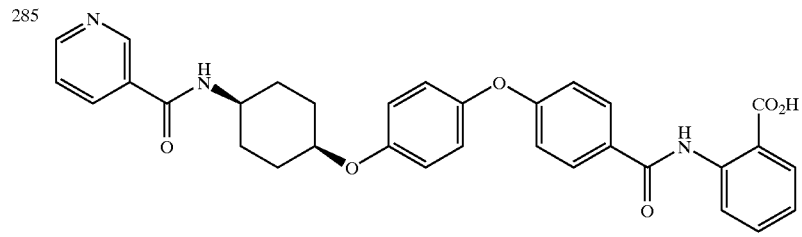

TABLE 10-continued

| 286 | (structure) |
| 287 | (structure) |
| 288 | (structure) |
| 289 | (structure) |
| 290 | (structure) |
| 291 | (structure) |
| 292 | (structure) |

TABLE 10-continued
293 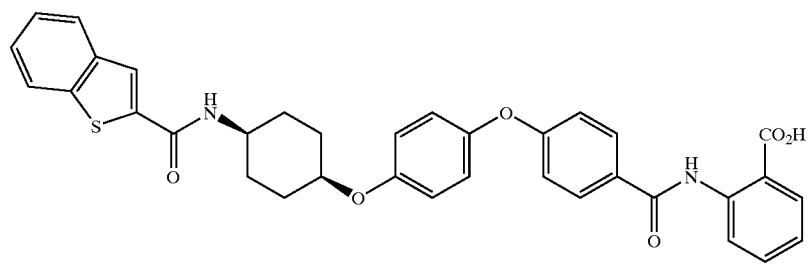
294 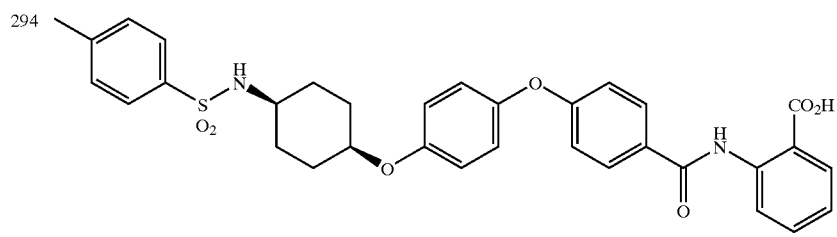
295 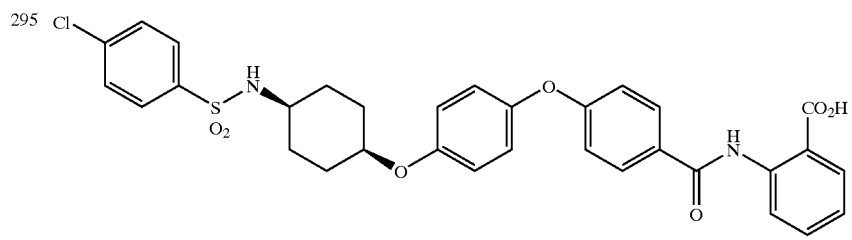
296 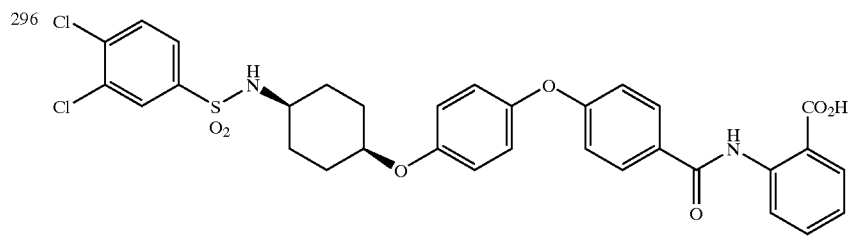
297 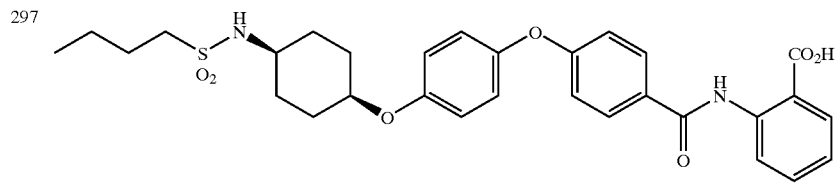
TABLE 11
298 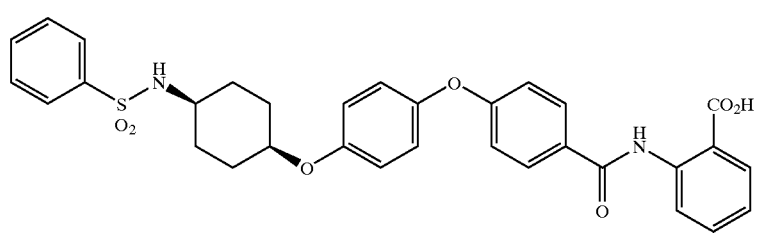

TABLE 11-continued
299 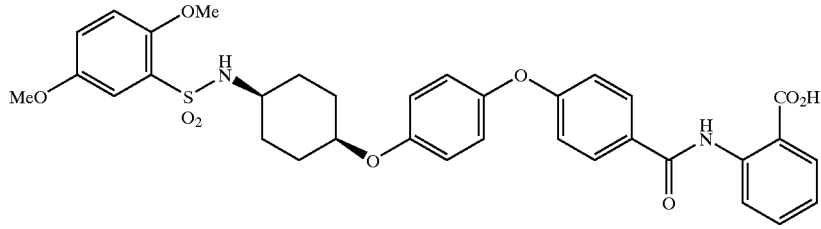
300 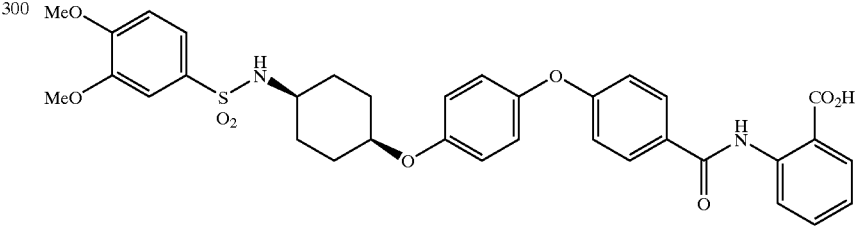
301 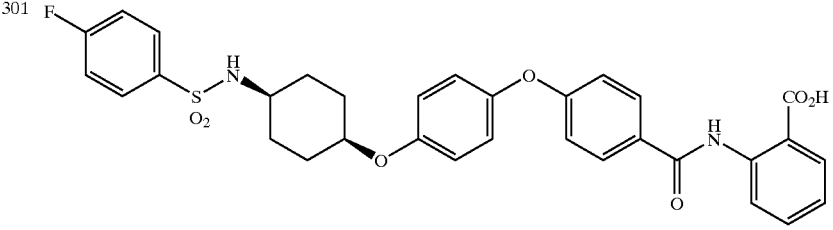
302 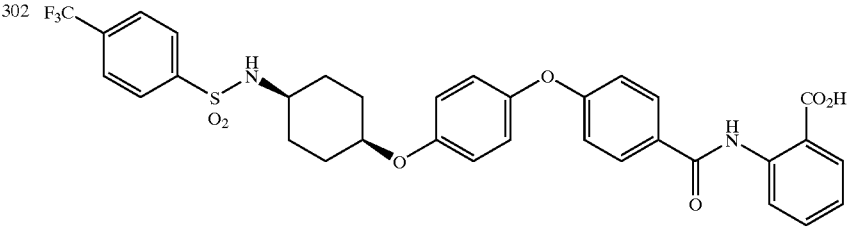
303 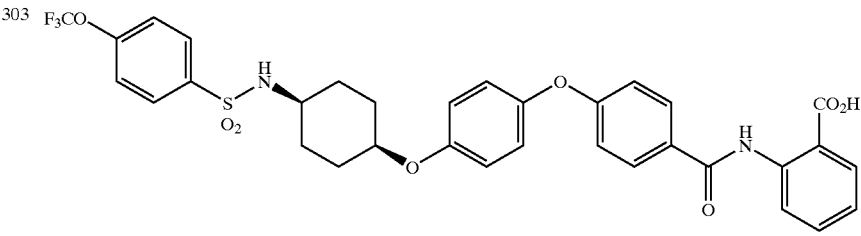
304 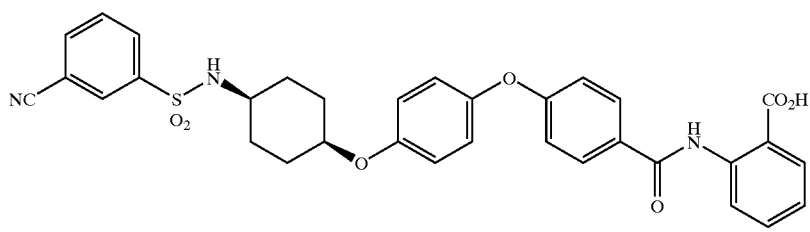

TABLE 11-continued

TABLE 11-continued
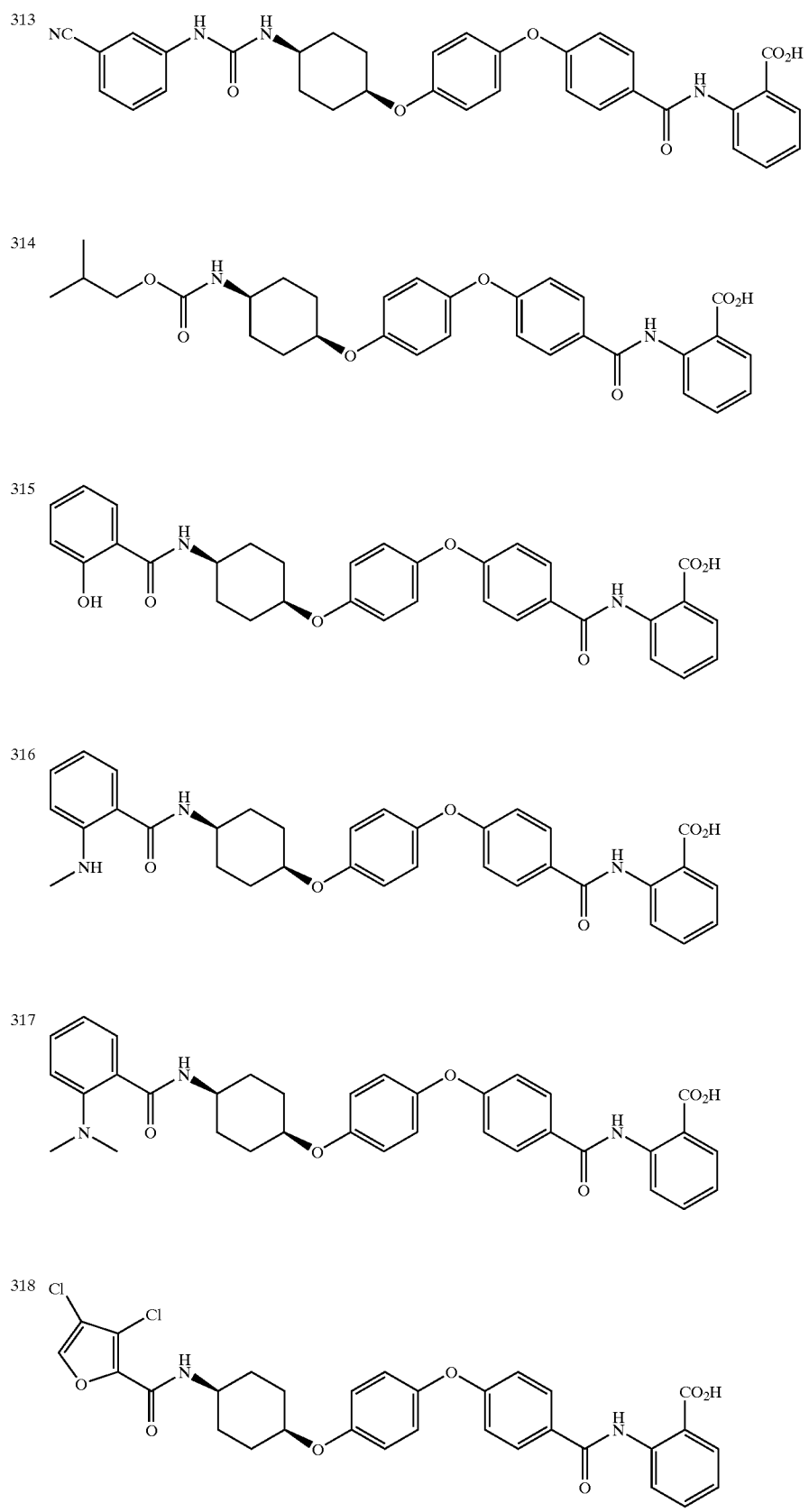

TABLE 11-continued
319 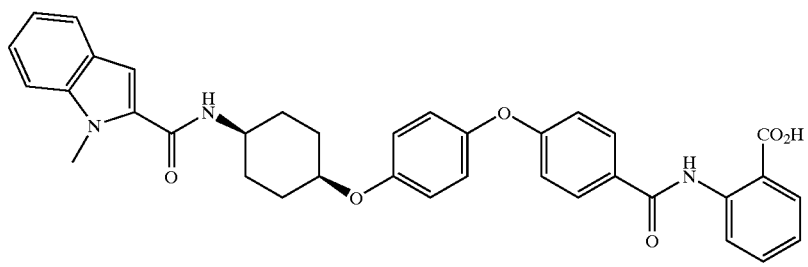
320 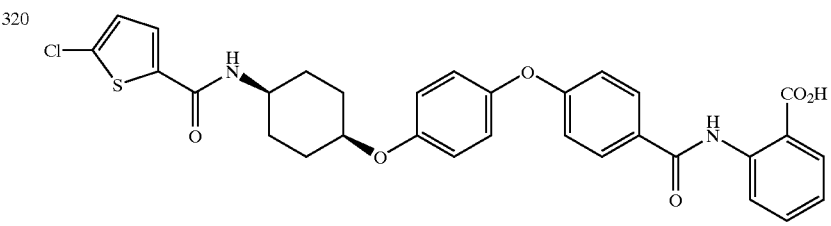
321 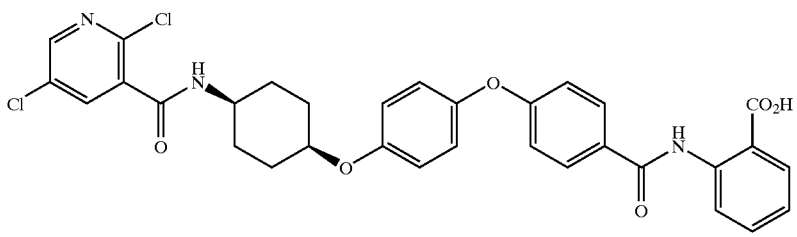
322 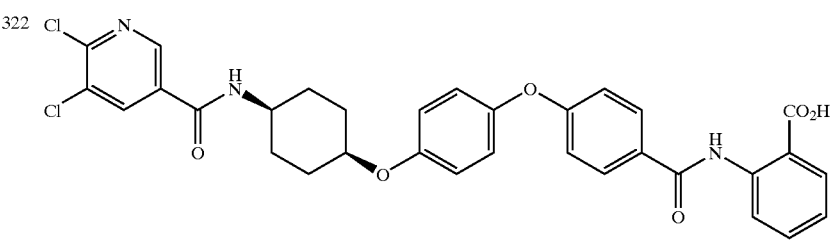
323 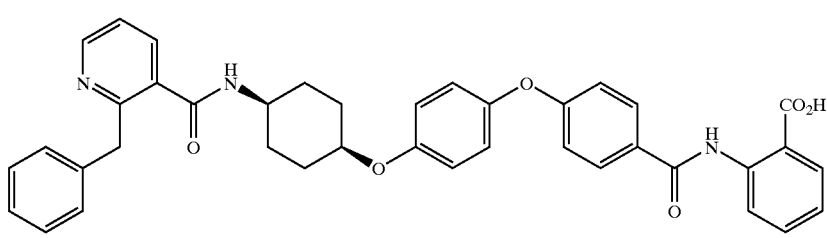
324 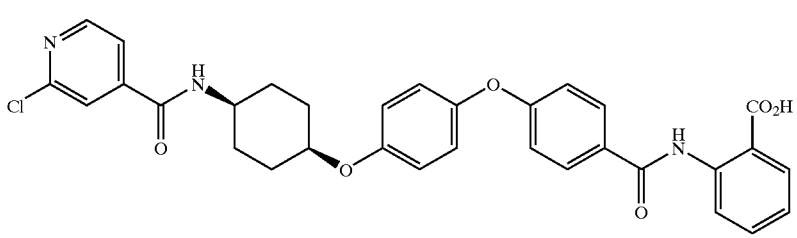

TABLE 11-continued
325 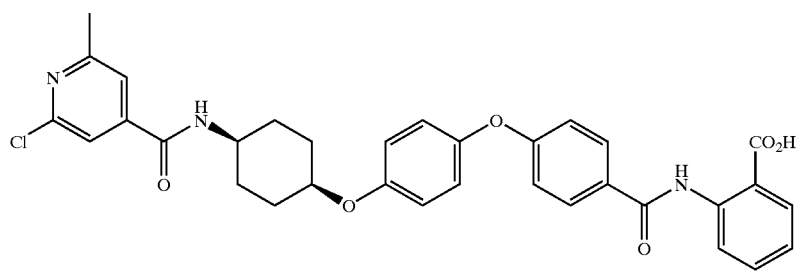
326 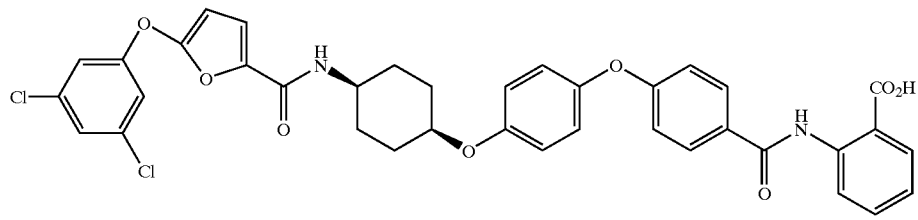
327 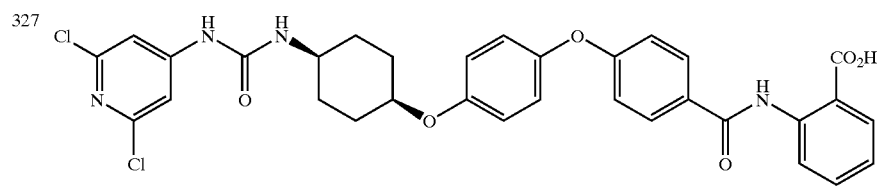
TABLE 12
328 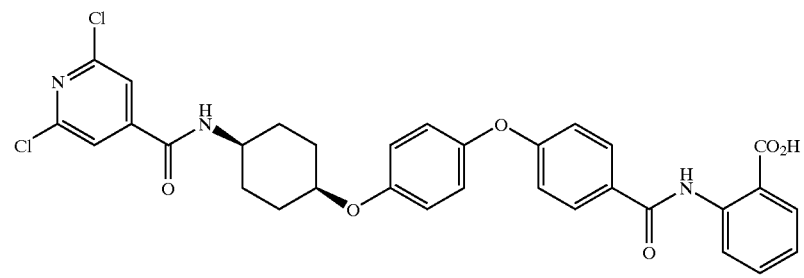
329 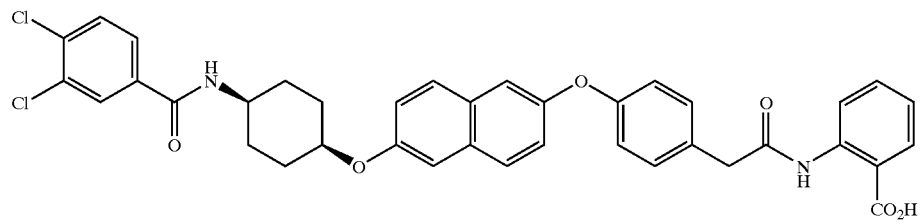
330 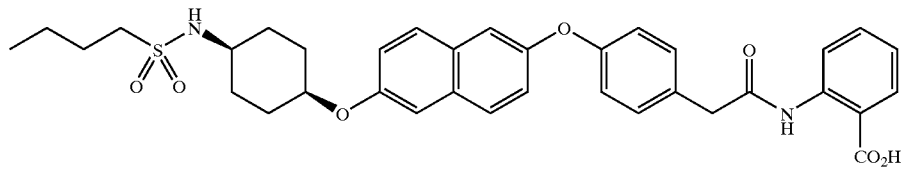

TABLE 12-continued
| 331 | 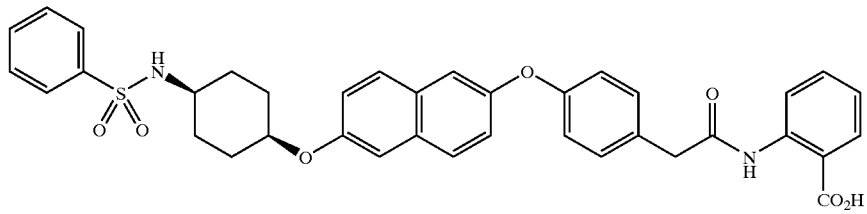 |
| --- | --- |
| 332 | 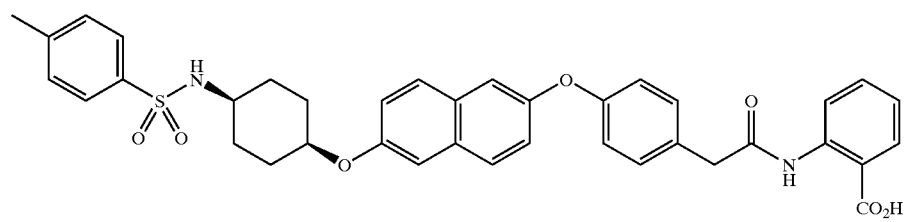 |
| 333 | 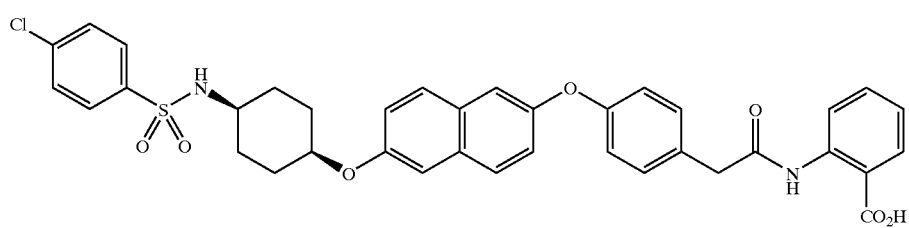 |
| 334 | 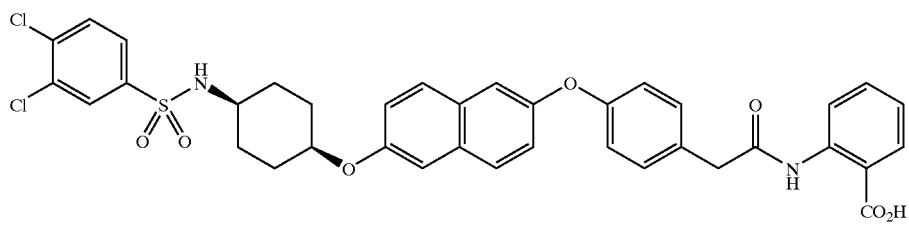 |
| 335 | 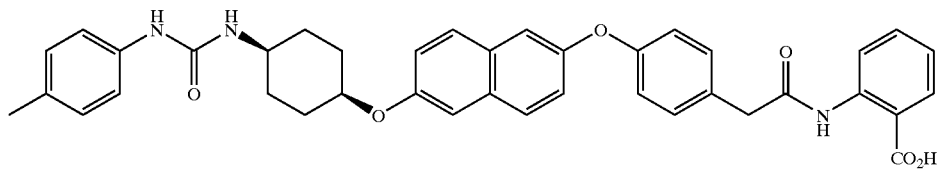 |
| 336 | 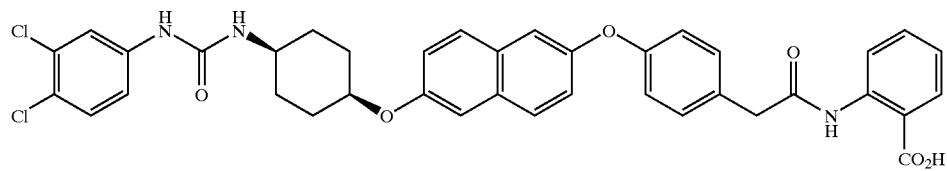 |
| 337 | 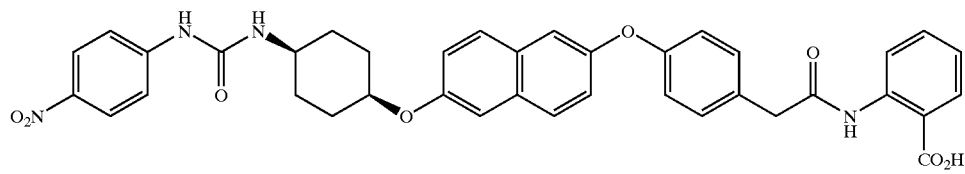 |

TABLE 12-continued
338 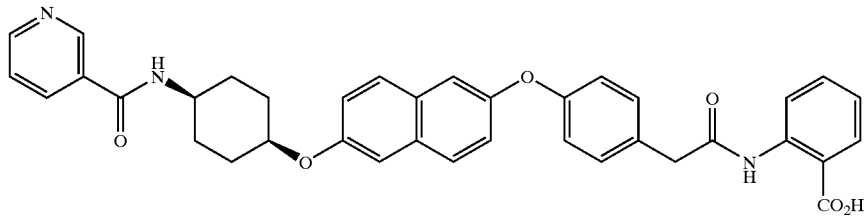
339 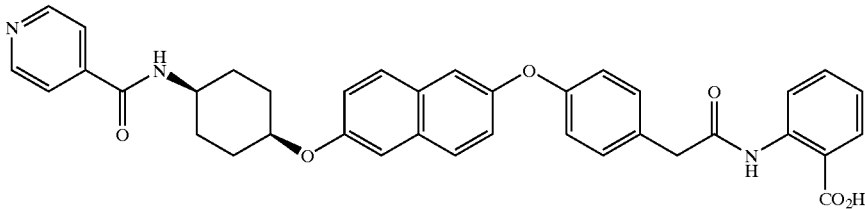
340 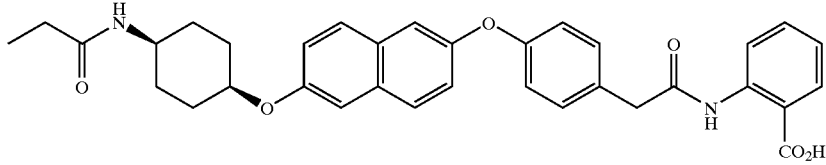
341 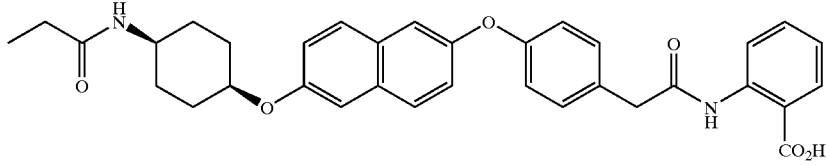
342 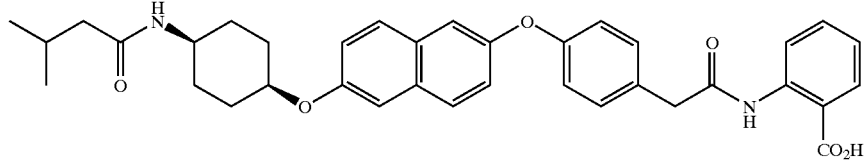
343 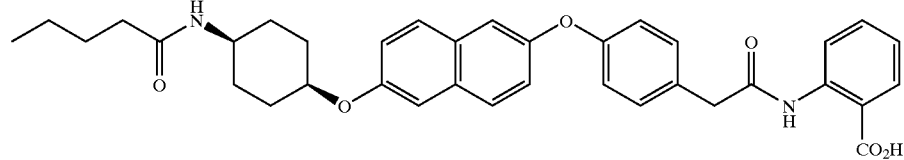
344 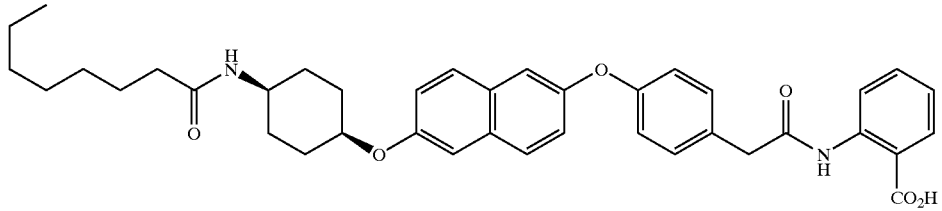
345 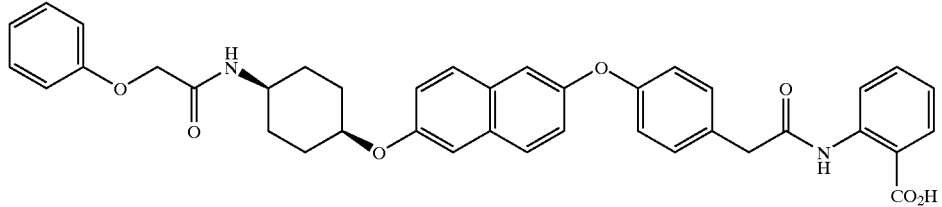

TABLE 12-continued
346 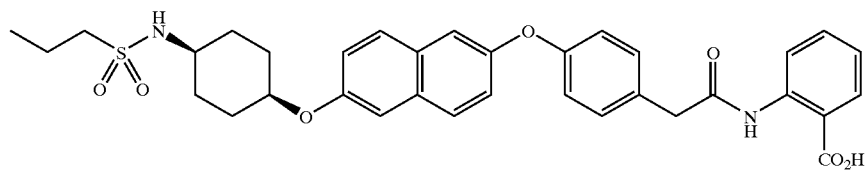
347 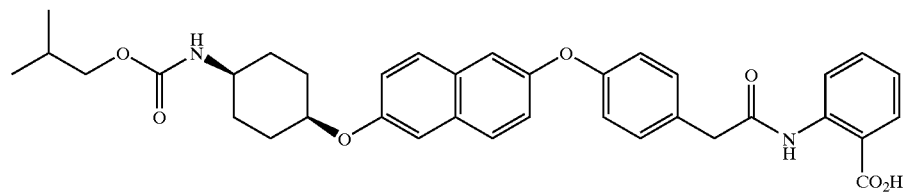
348 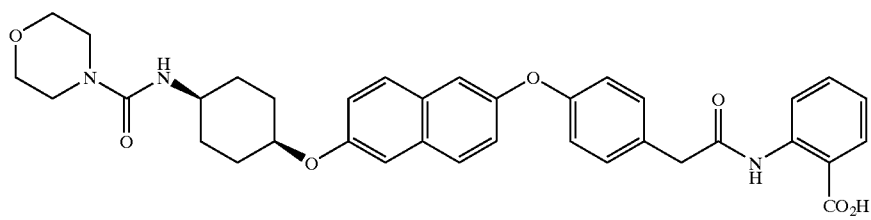
349 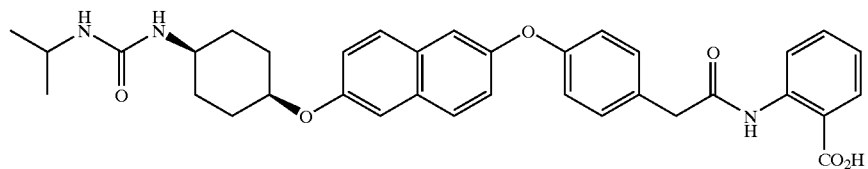
350 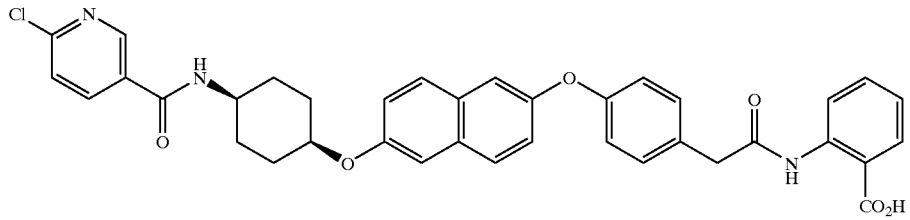
351 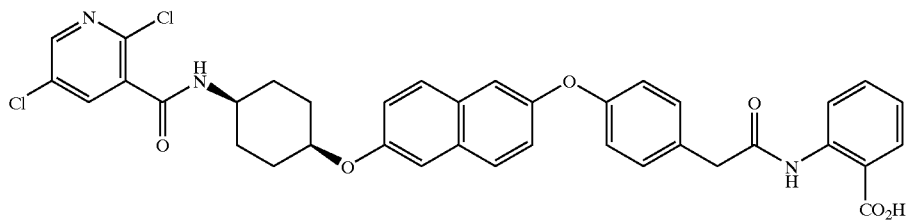
352 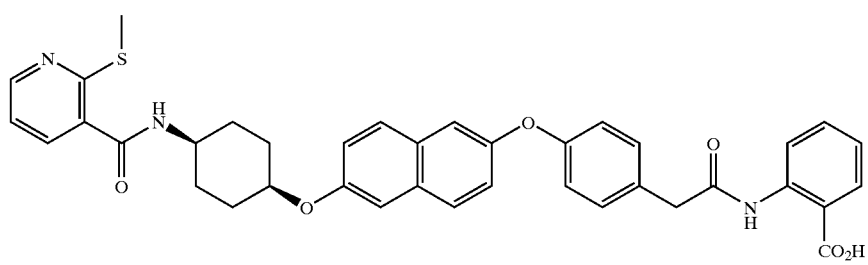

TABLE 12-continued
| | |
|---|---|
| 353 | 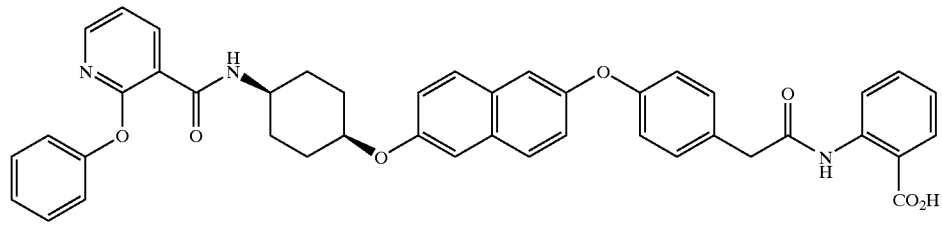 |
| 354 | 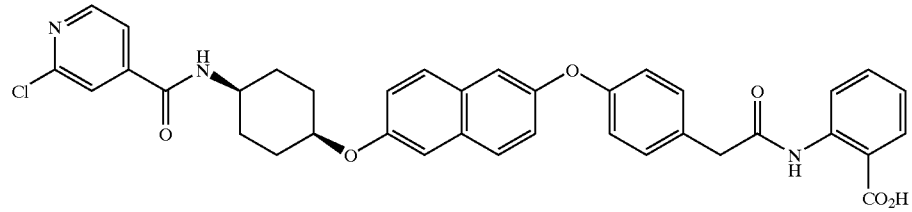 |
| 355 | 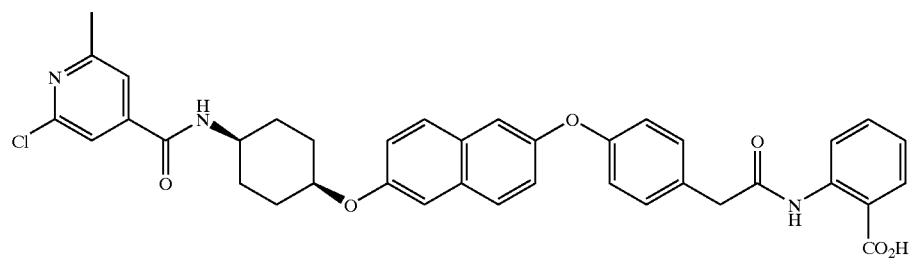 |
| 356 | 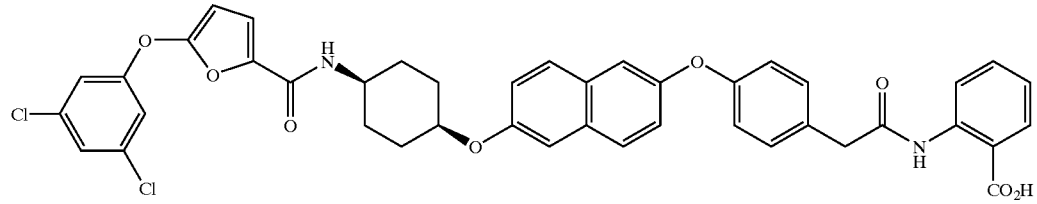 |
| 357 | 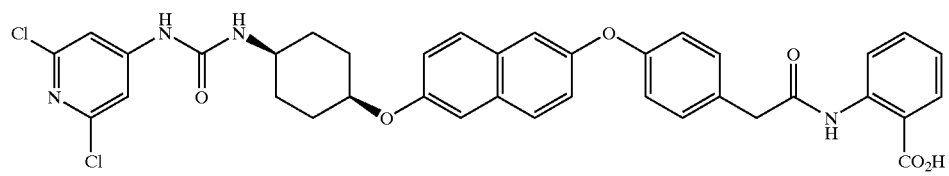 |
TABLE 13
| | |
|---|---|
| 358 | 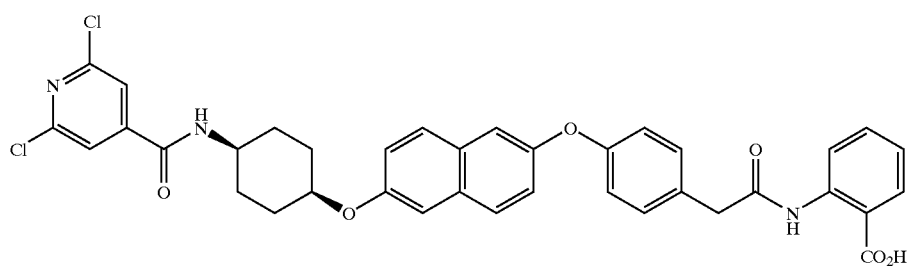 |

TABLE 13-continued
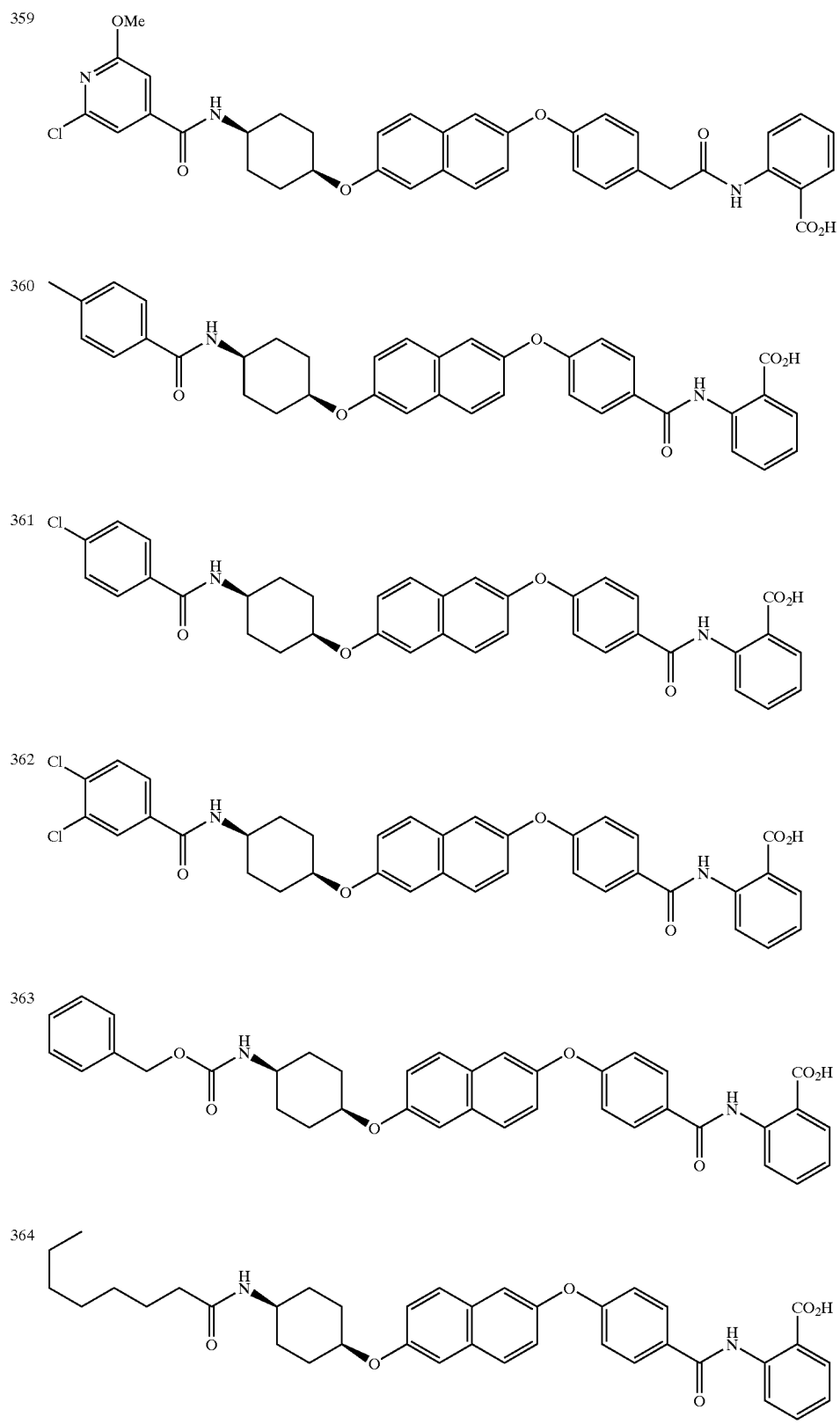

TABLE 13-continued
365 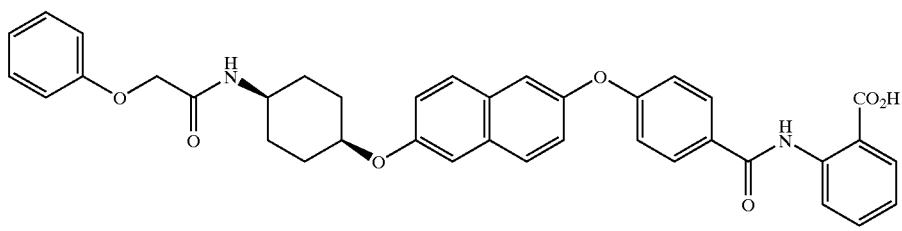
366 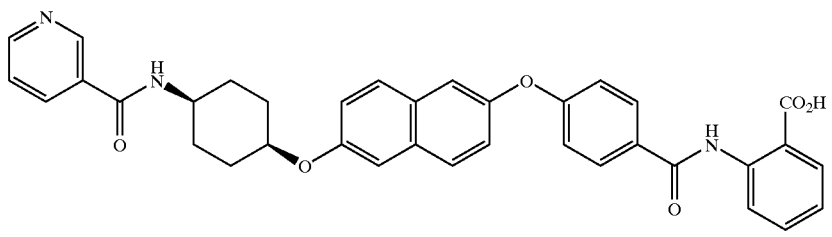
367 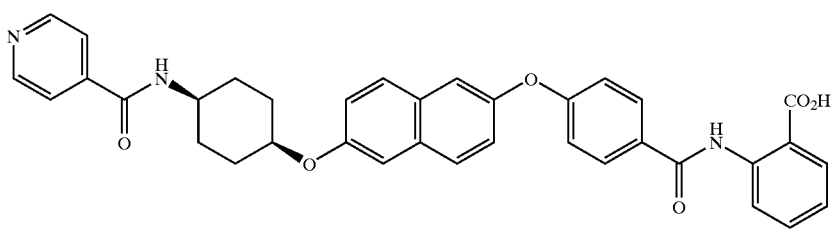
368 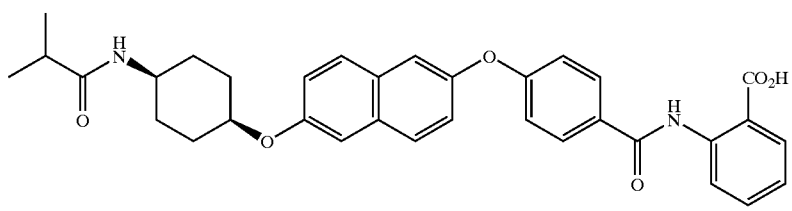
369 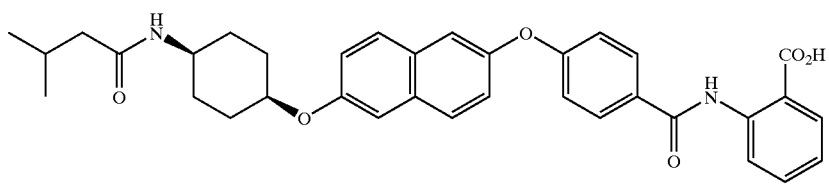
370 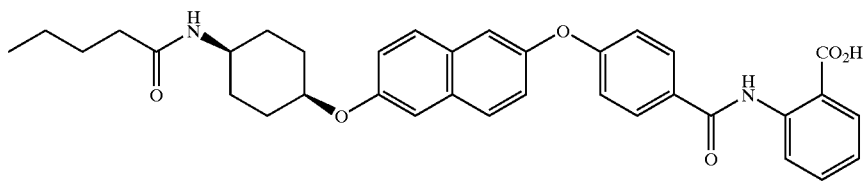
371 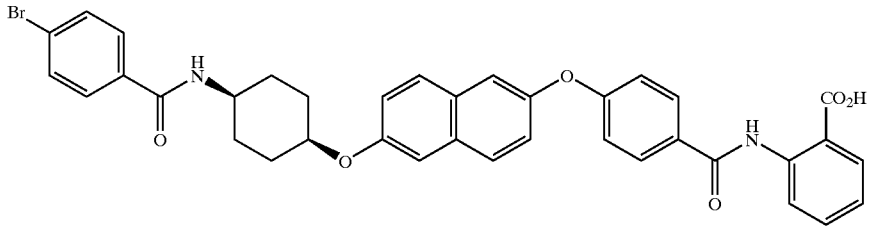

TABLE 13-continued
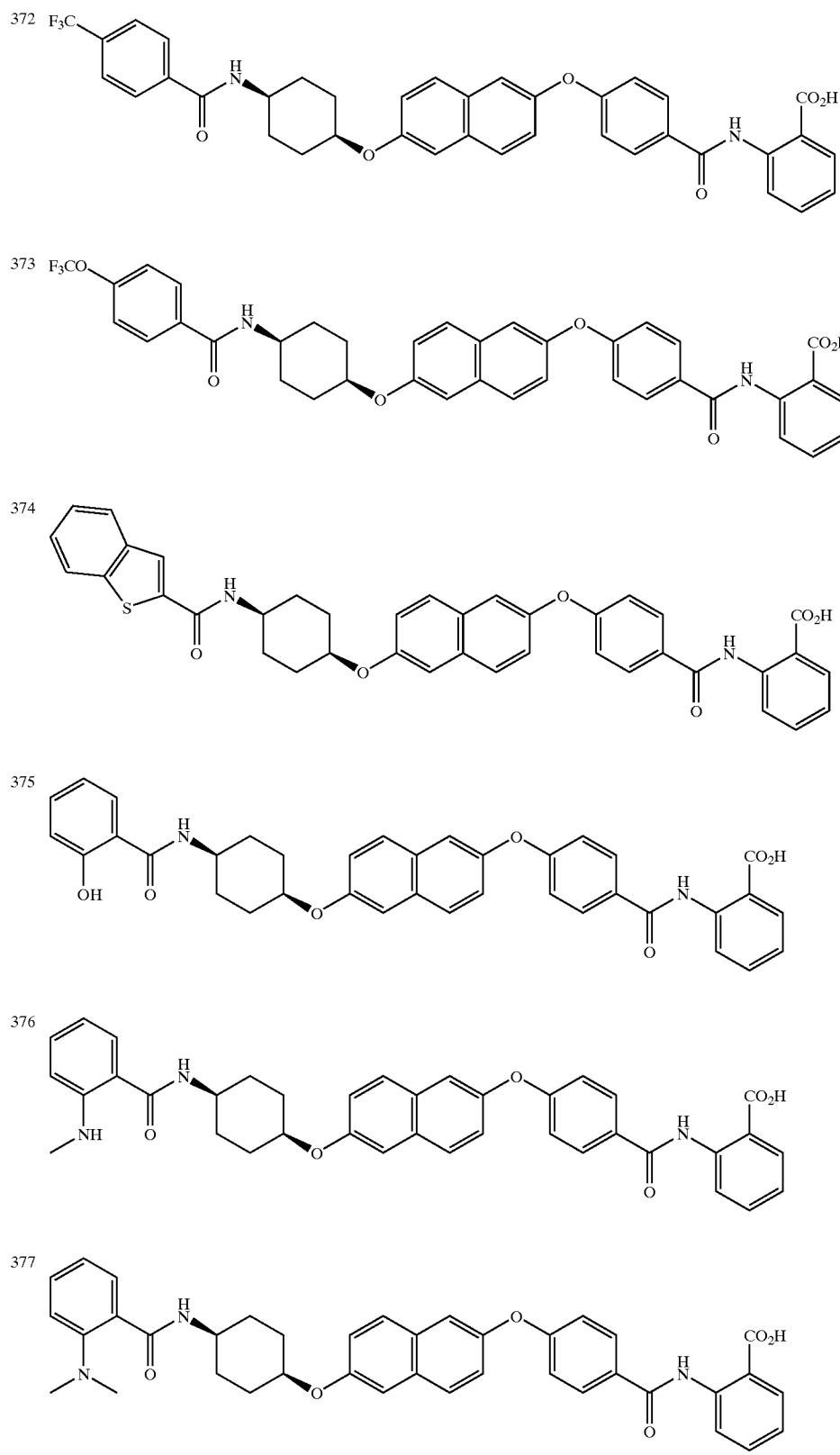

US 6,649,656 B1
123
124
TABLE 13-continued
378 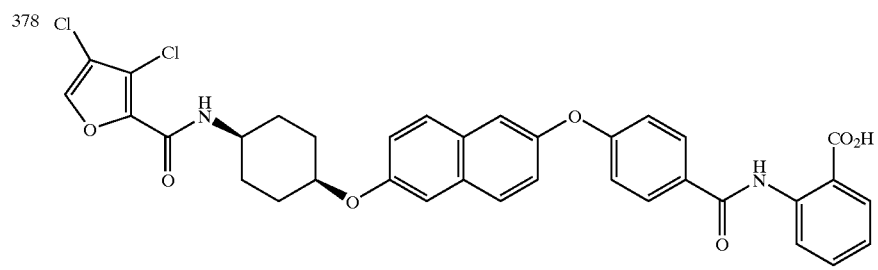
379 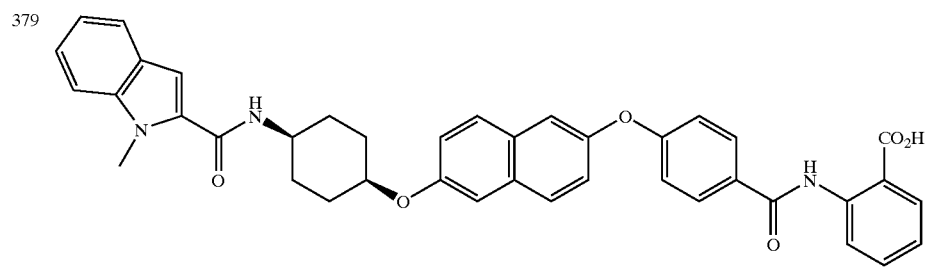
380 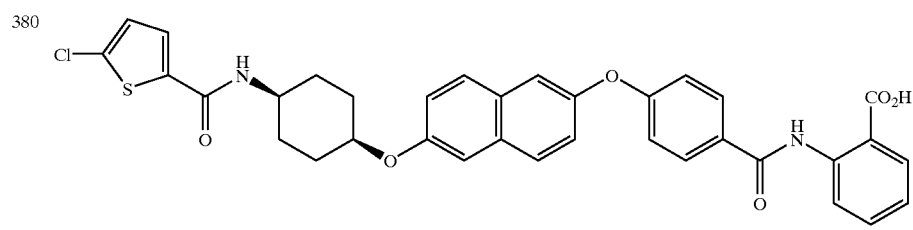
381 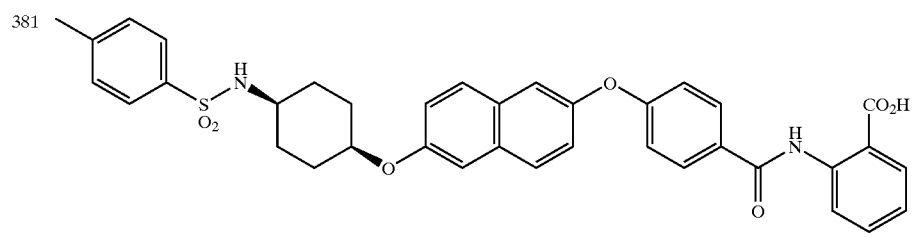
382 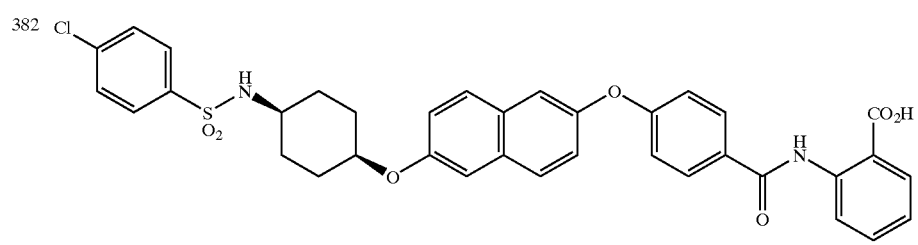
383 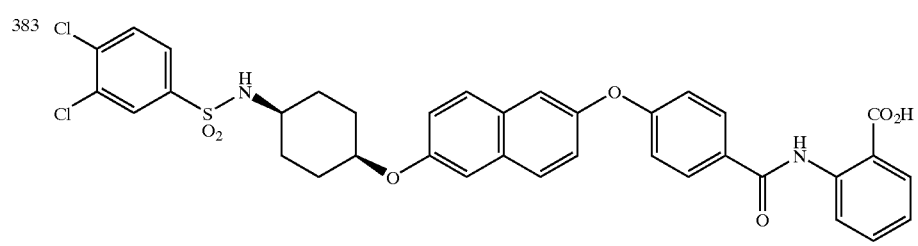

TABLE 13-continued
384 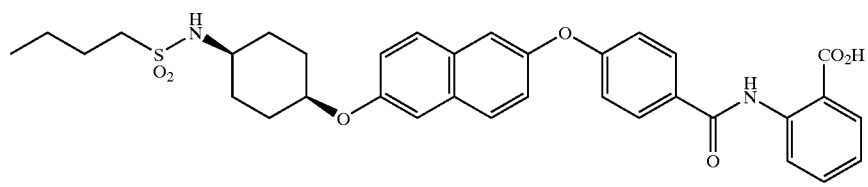
385 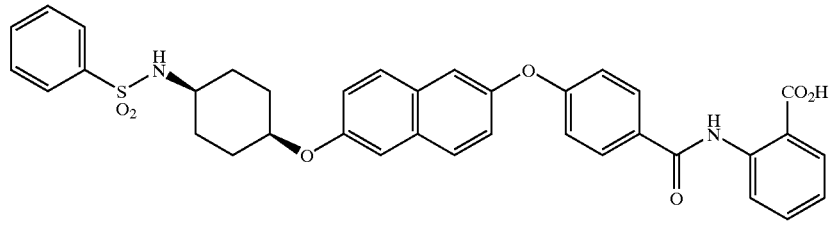
386 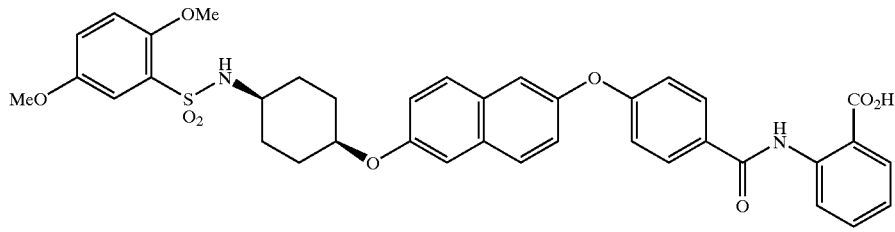
387 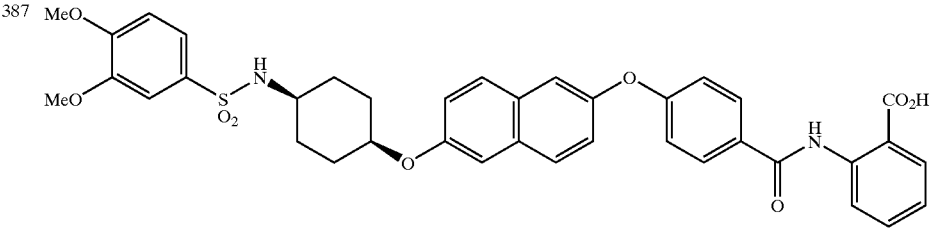
TABLE 14
388 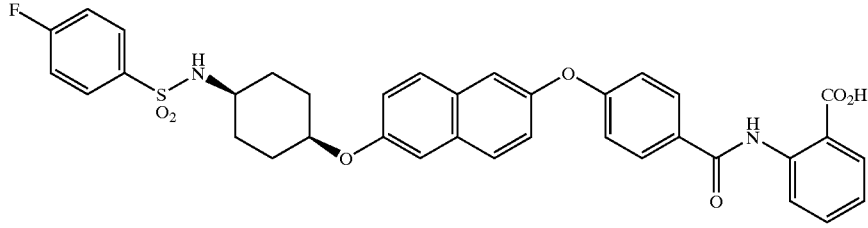
389 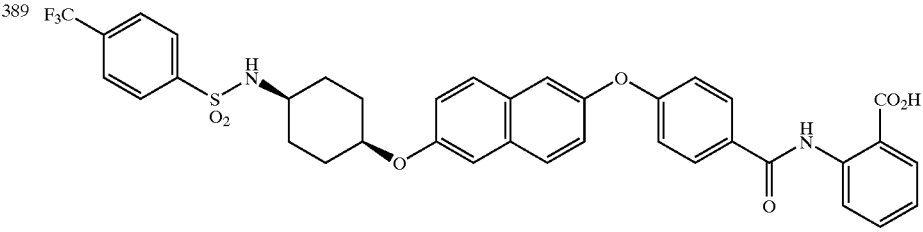

TABLE 14-continued
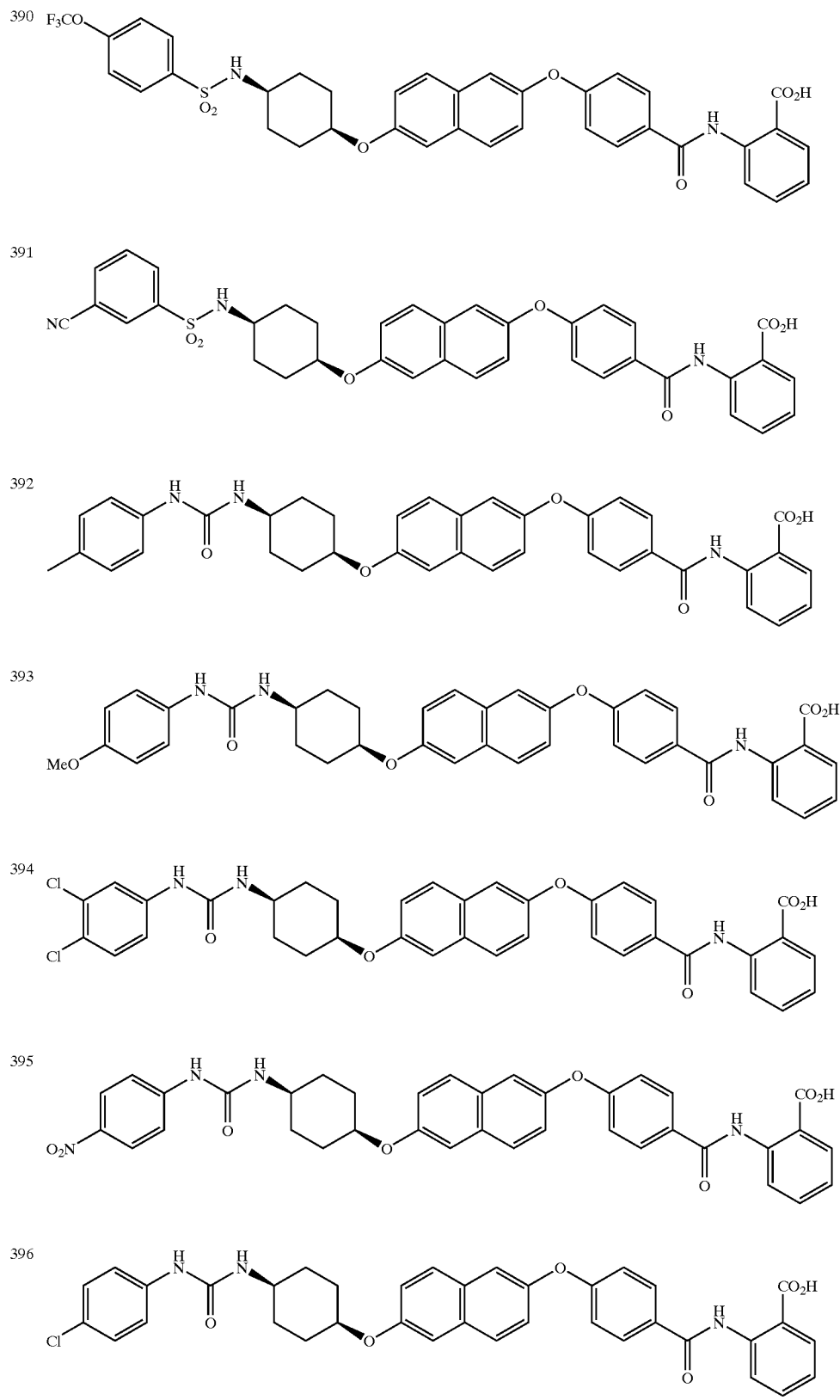

TABLE 14-continued
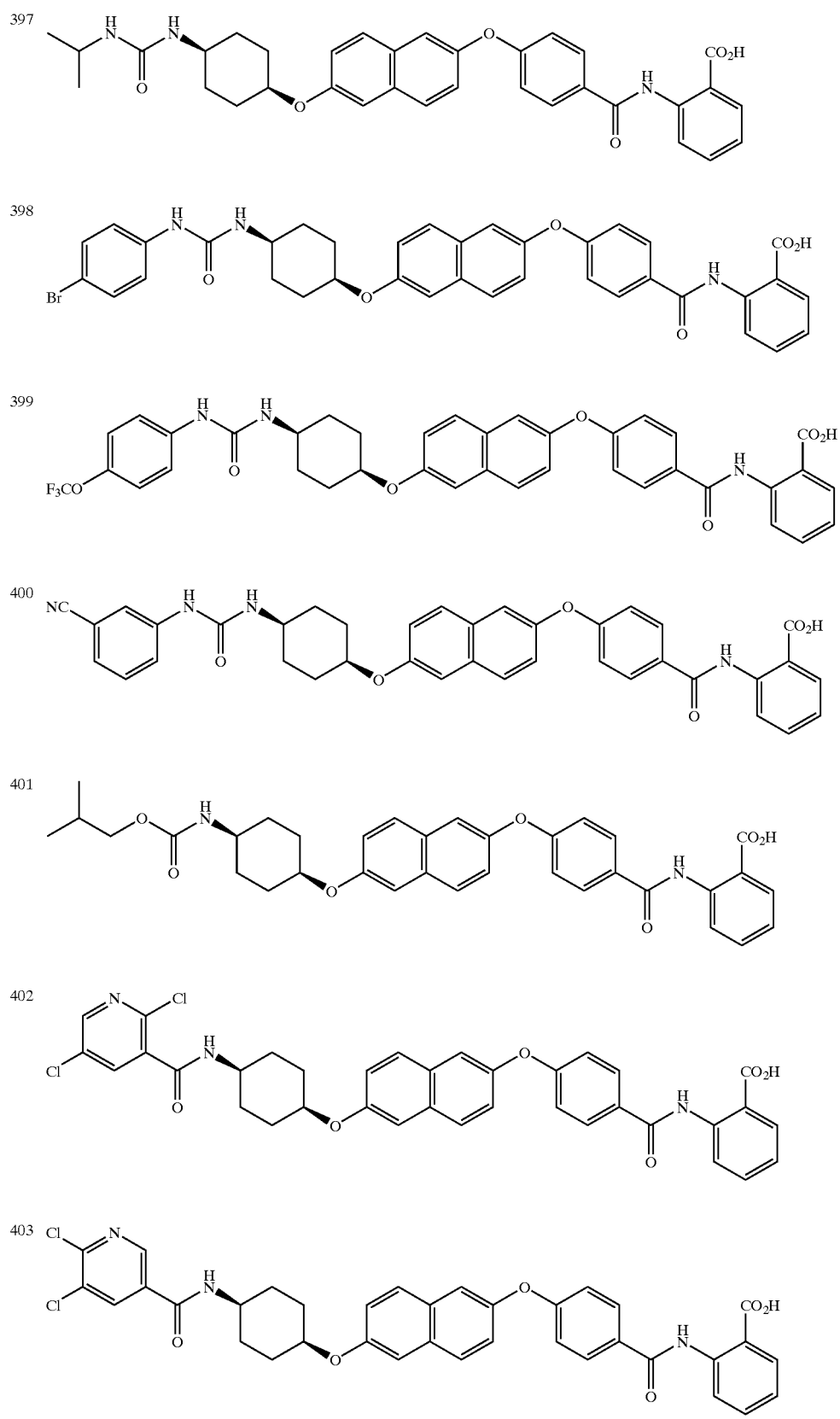

TABLE 14-continued
| | |
|---|---|
| 404 | 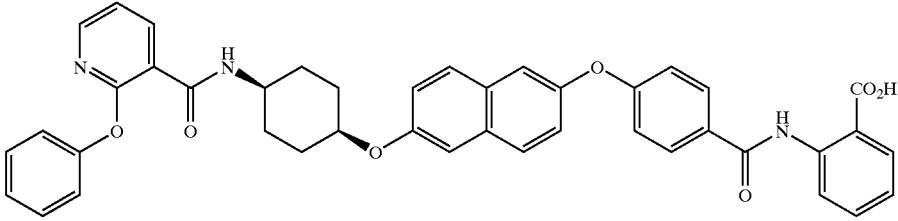 |
| 405 | 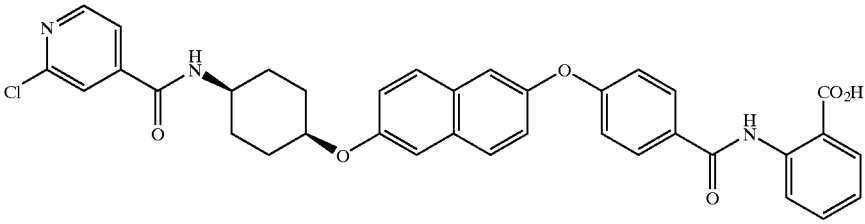 |
| 406 | 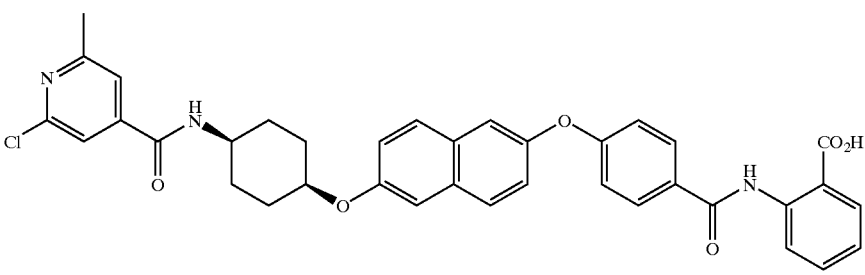 |
| 407 | 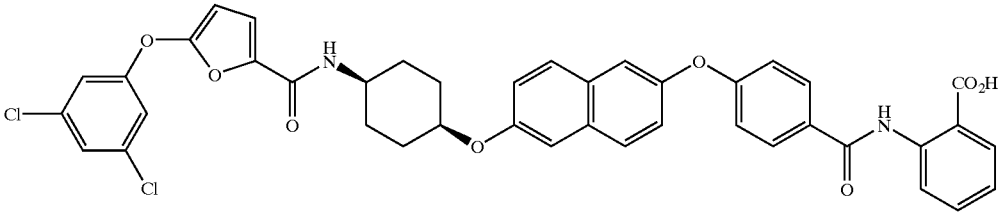 |
| 408 | 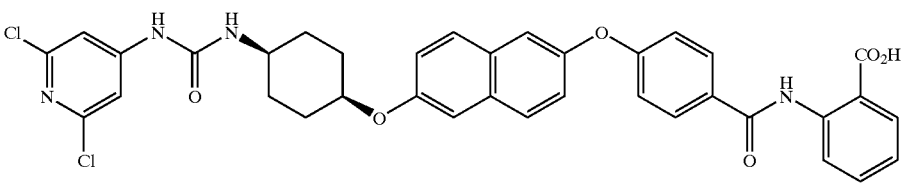 |
| 409 | 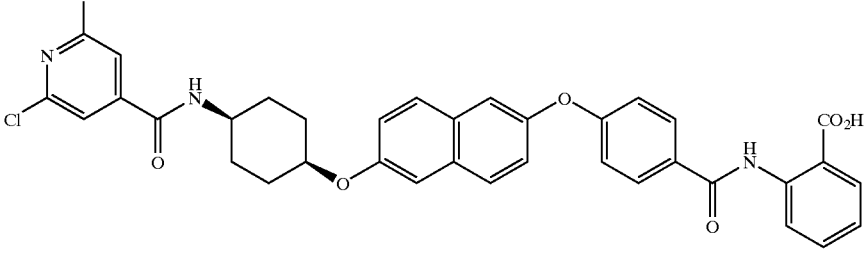 |
| 410 | 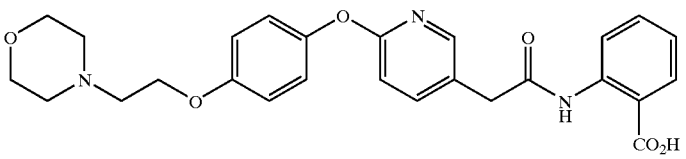 |

TABLE 14-continued
411 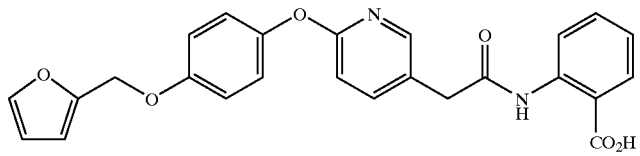
412 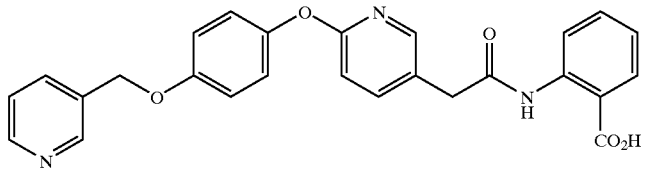
413 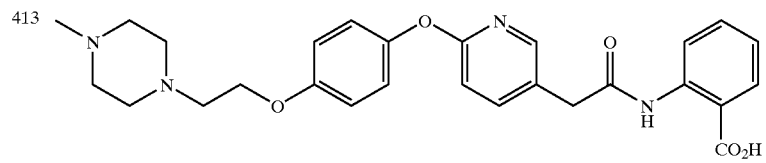
414 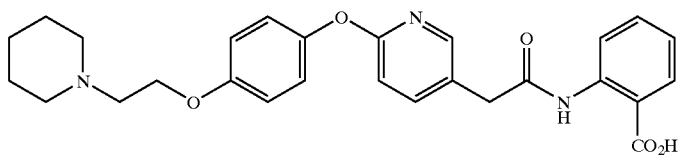
415 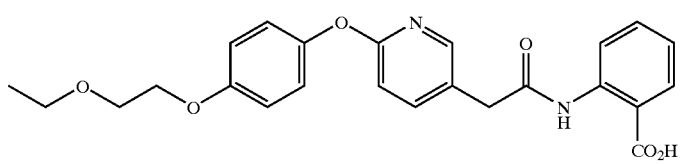
416 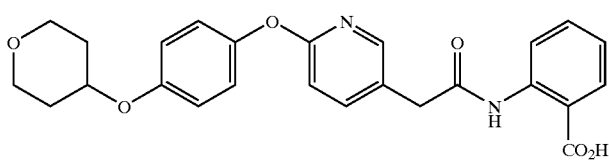
417 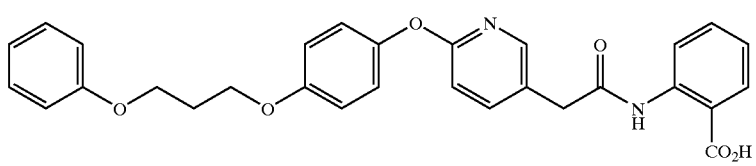
TABLE 15
418 

TABLE 15-continued

| 419 | (structure) |
| 420 | (structure) |
| 421 | (structure) |
| 422 | (structure) |
| 423 | (structure) |
| 424 | (structure) |
| 425 | (structure) |
| 426 | (structure) |
| 427 | (structure) |

TABLE 15-continued
428 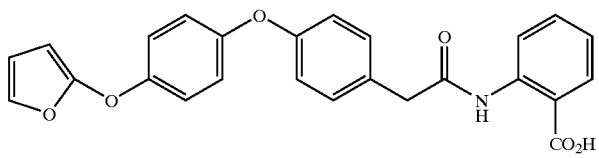
TABLE 16
429 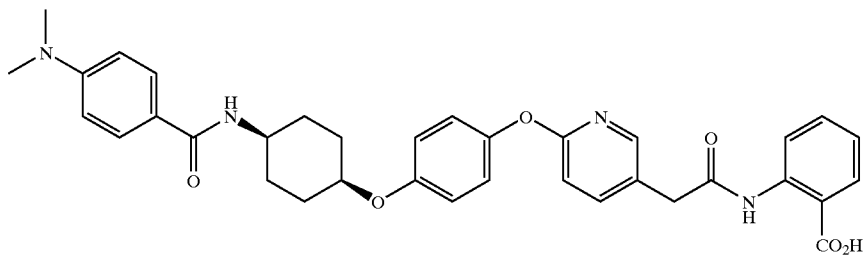
430 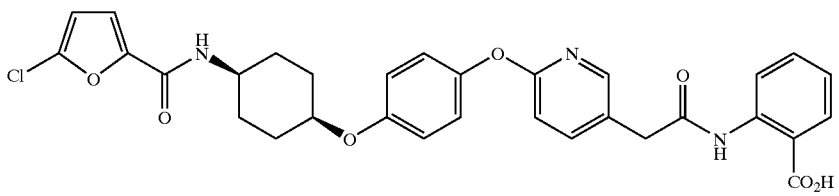
431 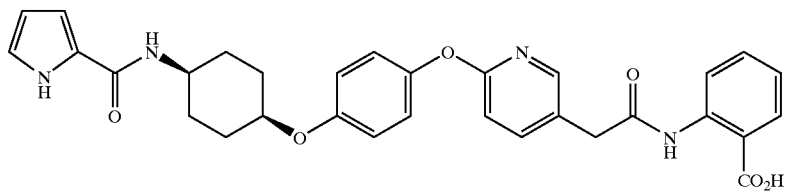
432 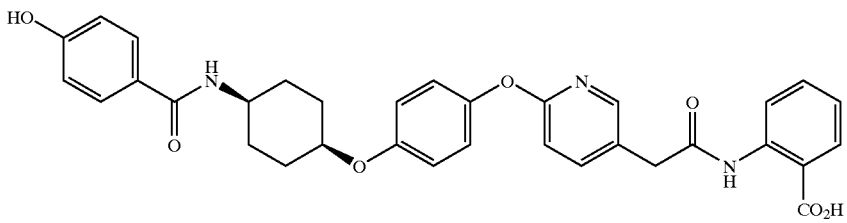
433 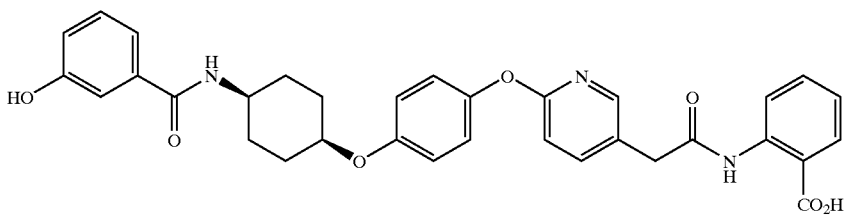
434 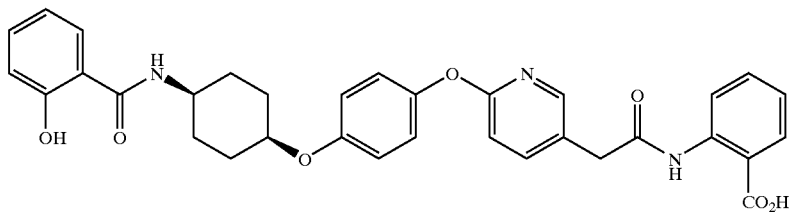

TABLE 16-continued
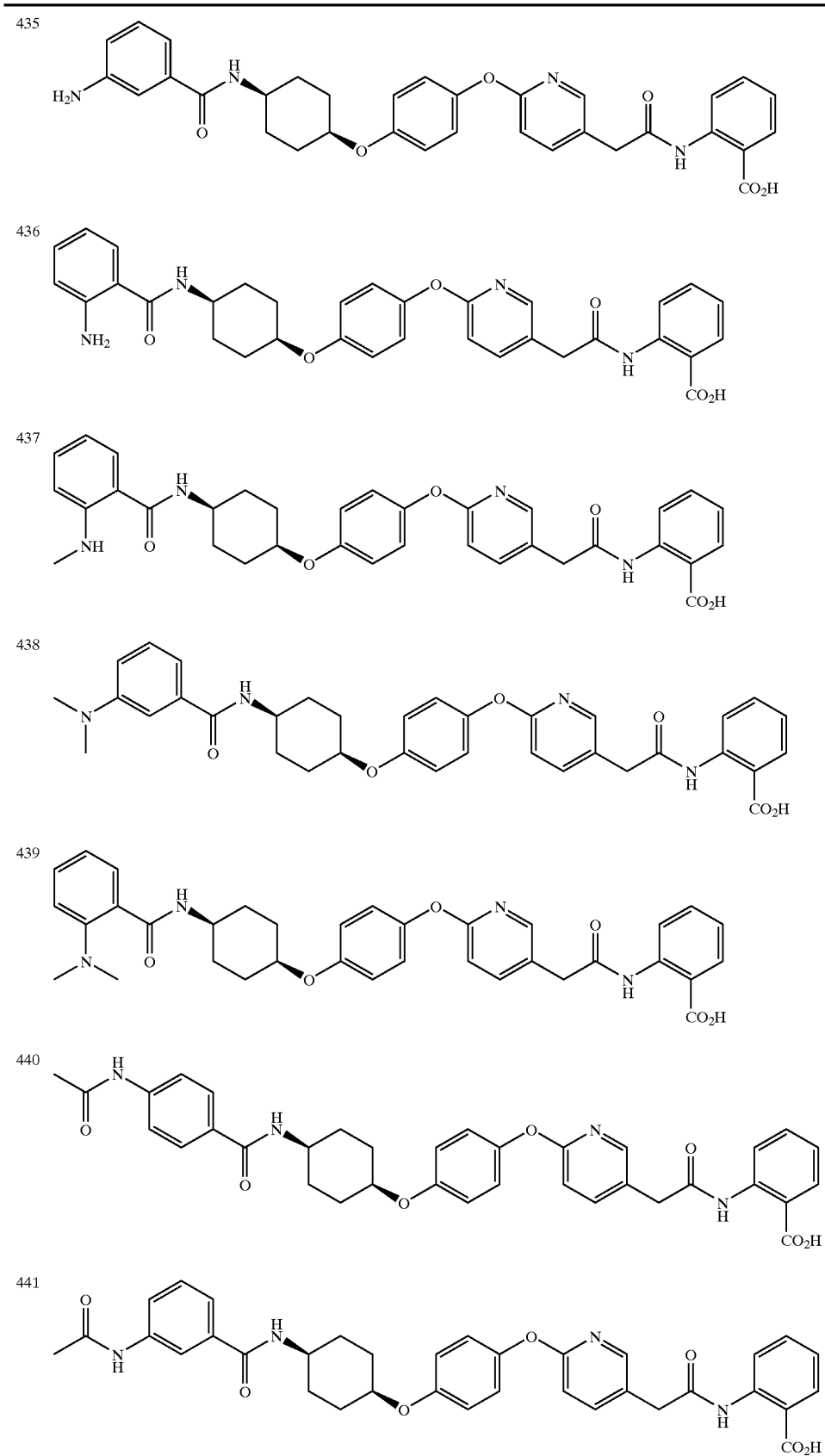

TABLE 16-continued
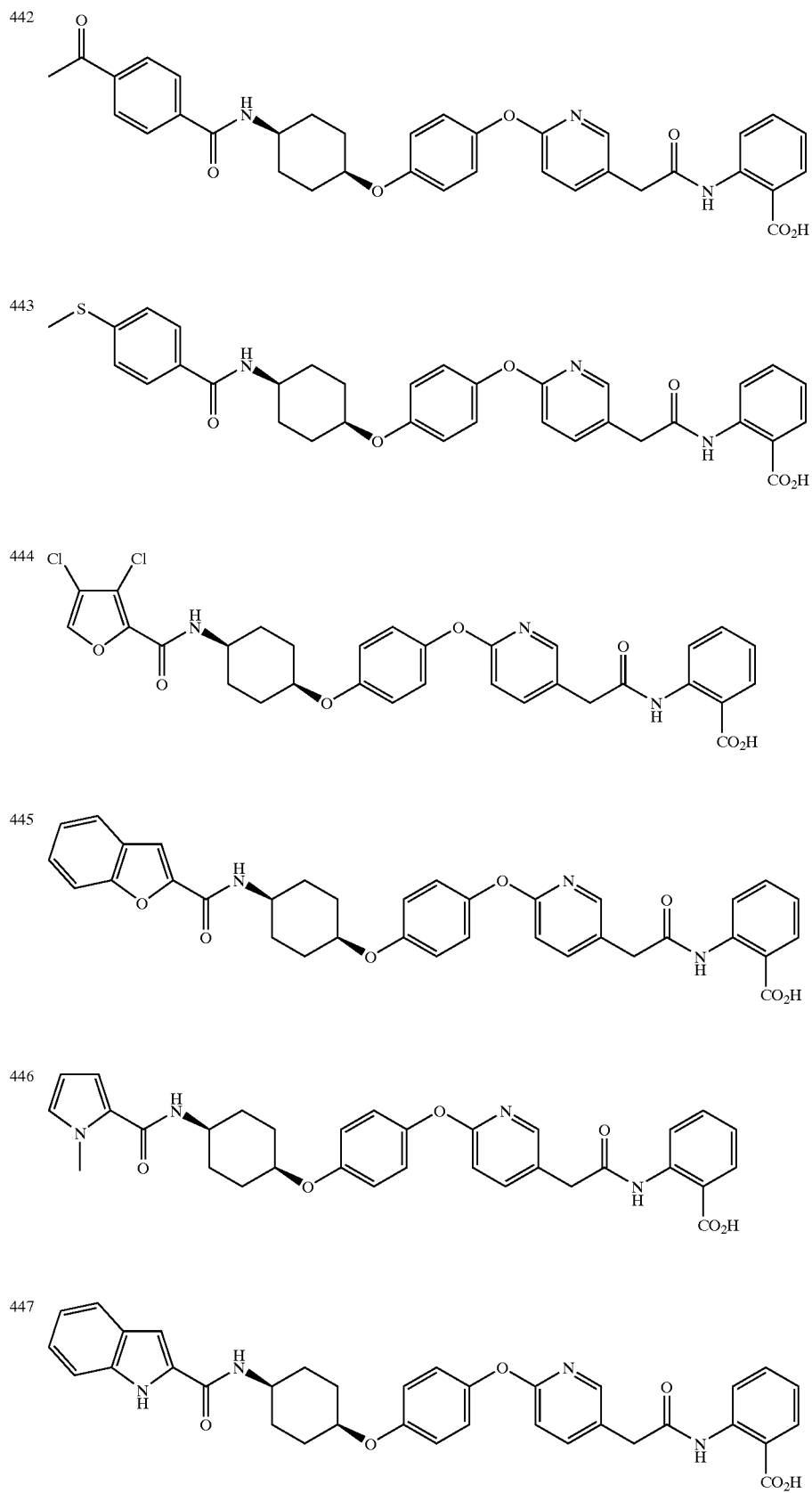

TABLE 16-continued
448
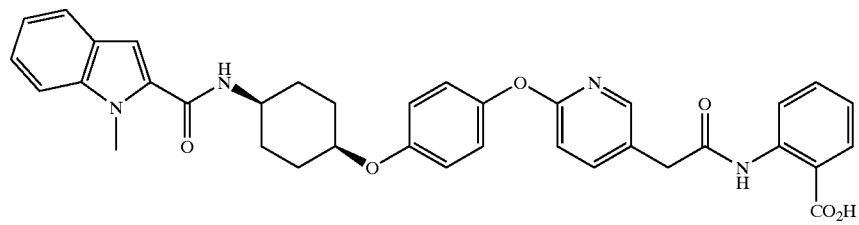
449
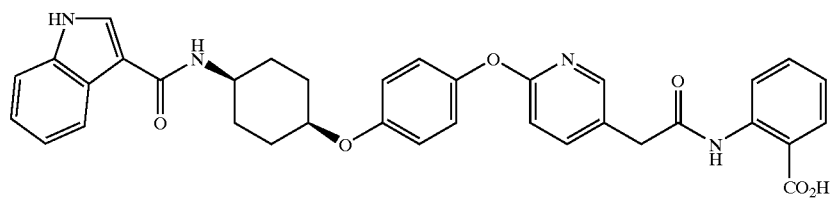
450
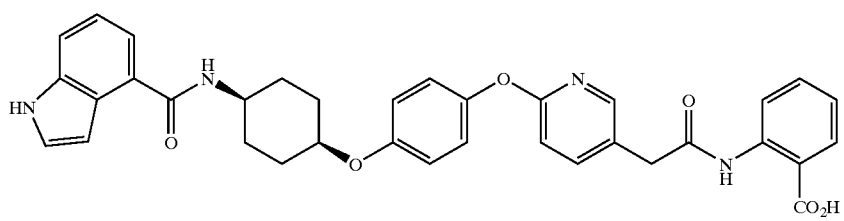
451
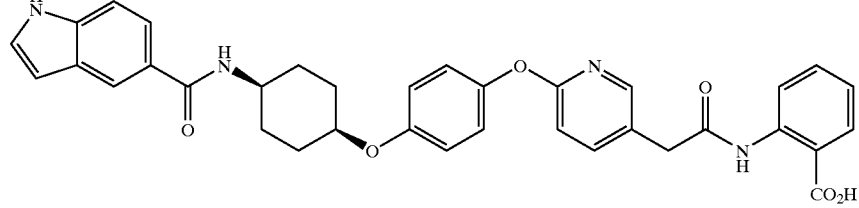
452
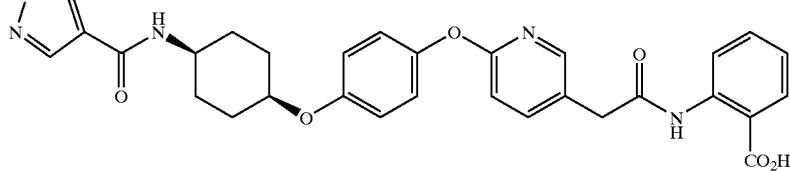
453
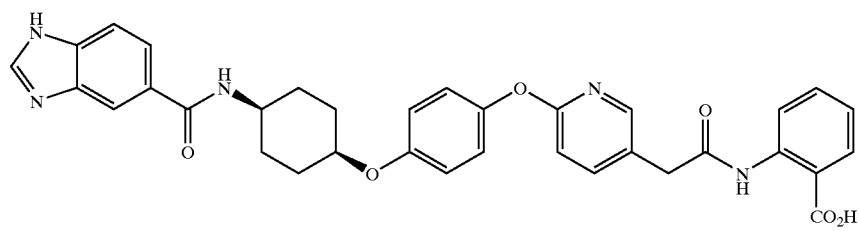
454
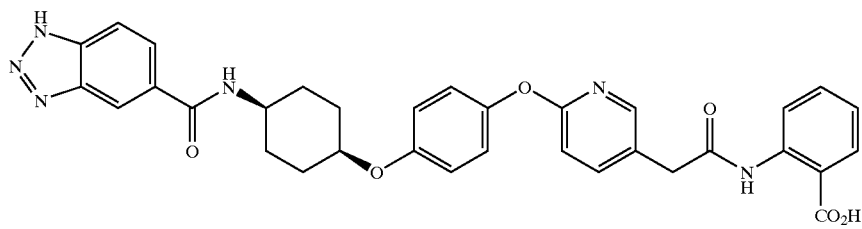

TABLE 16-continued
455 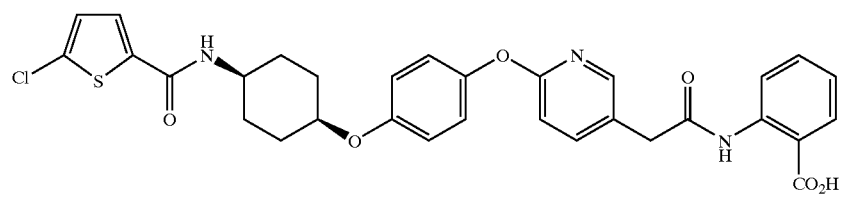
456 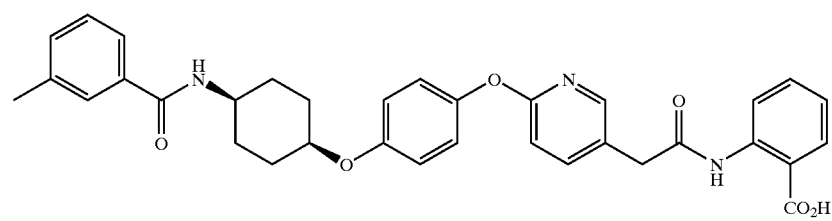
457 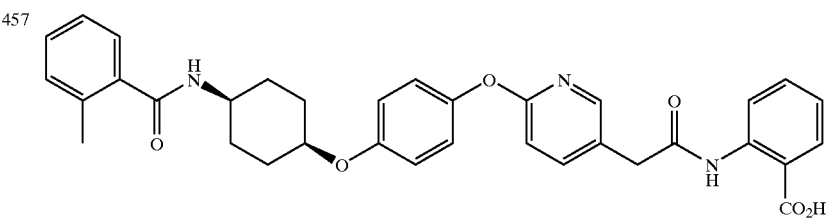
458 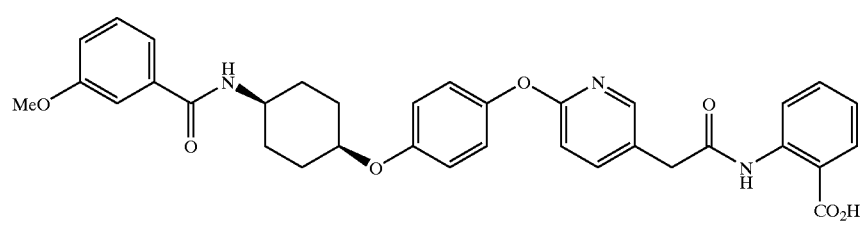
TABLE 17
459 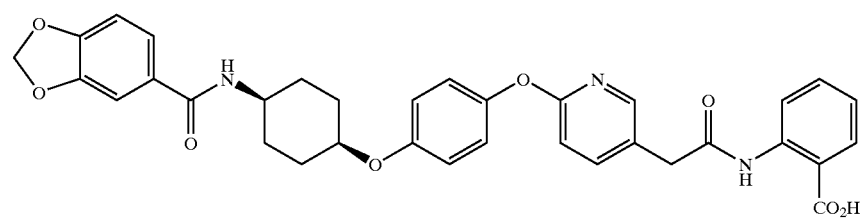
460 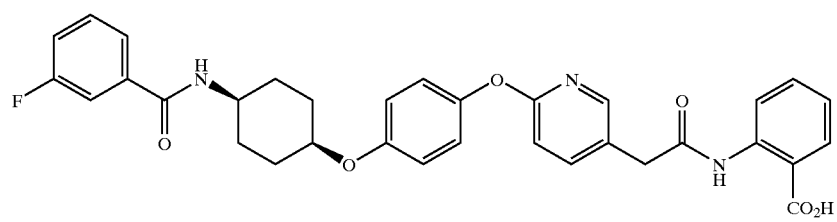

TABLE 17-continued

| 461 | 2-fluorobenzamide derivative |
| 462 | 3-chlorobenzamide derivative |
| 463 | 2-chlorobenzamide derivative |
| 464 | 4-bromobenzamide derivative |
| 465 | 3-trifluoromethylbenzamide derivative |
| 466 | 4-trifluoromethylbenzamide derivative |
| 467 | 2-trifluoromethoxybenzamide derivative |

TABLE 17-continued
468 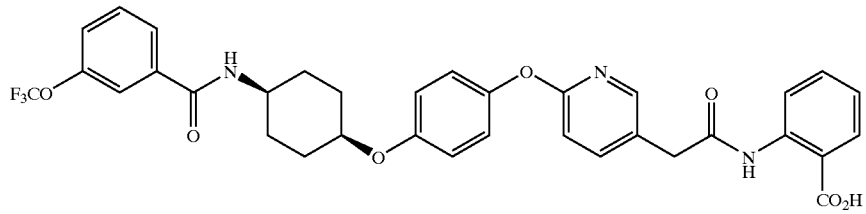
469 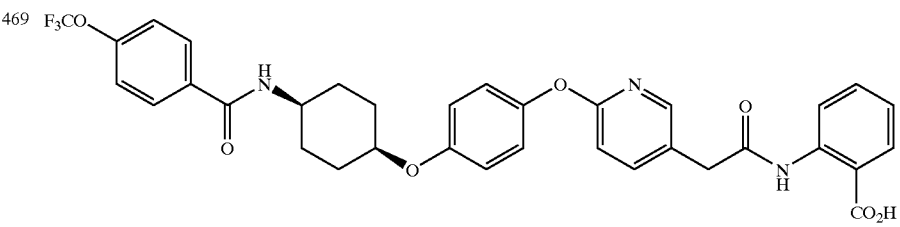
470 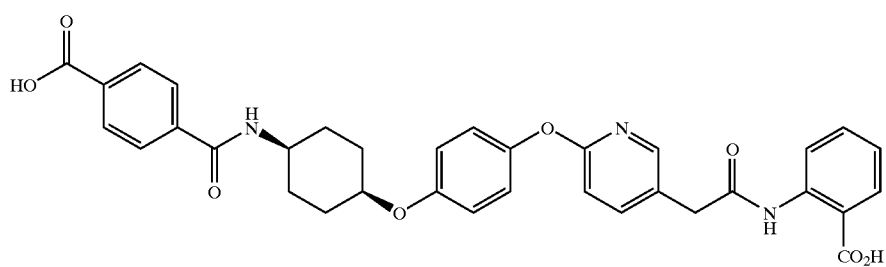
471 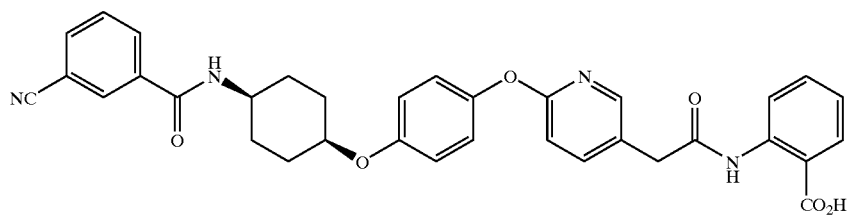
472 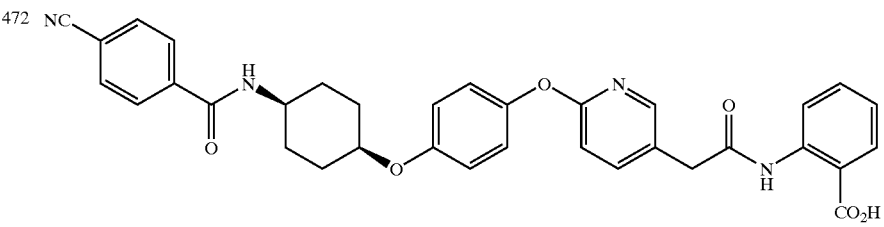
473 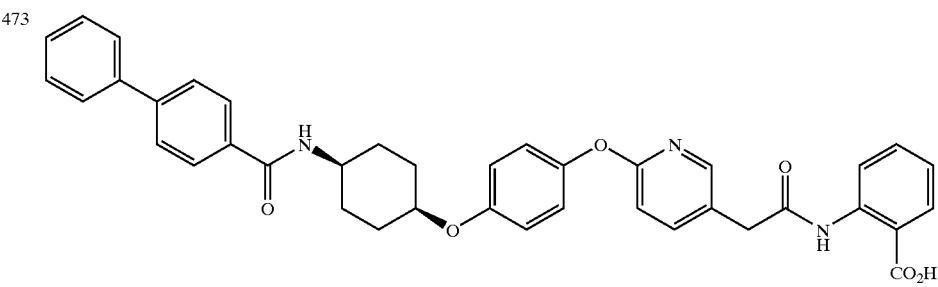

TABLE 17-continued
| 474 | 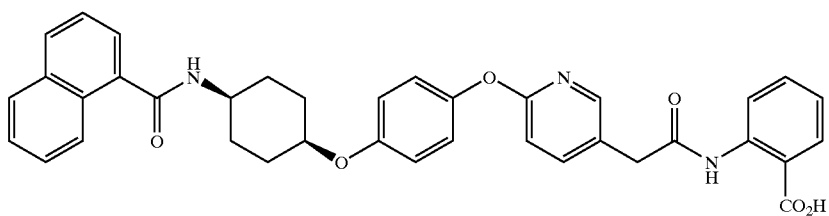 |
| 475 | 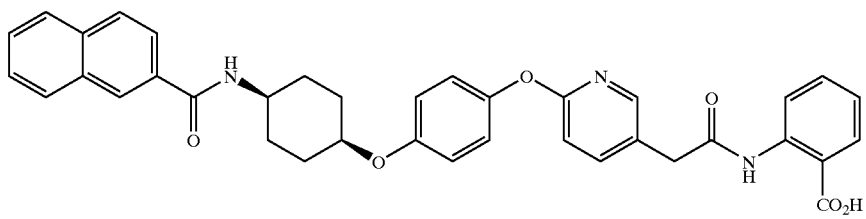 |
| 476 | 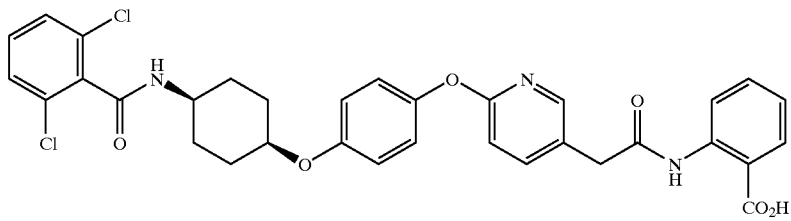 |
| 477 | 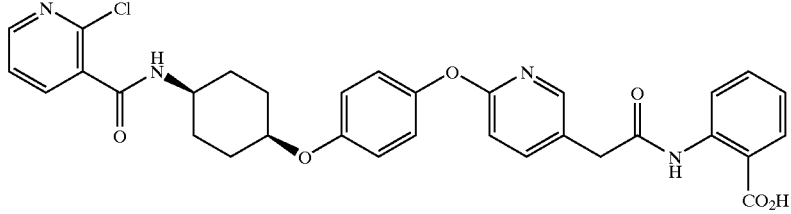 |
| 478 | 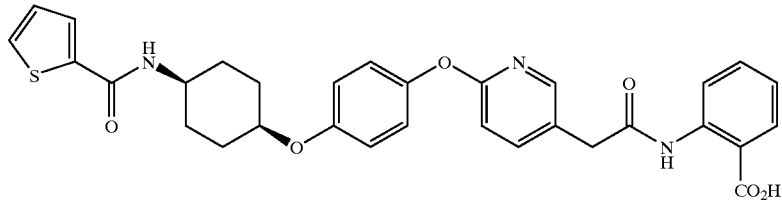 |
| 479 | 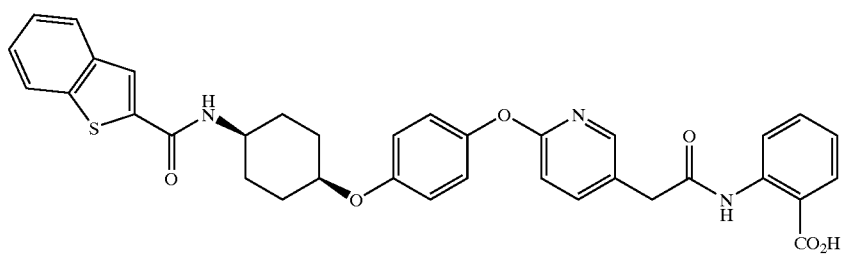 |
| 480 | 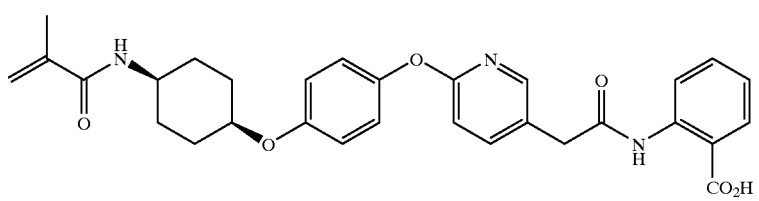 |

TABLE 17-continued
481 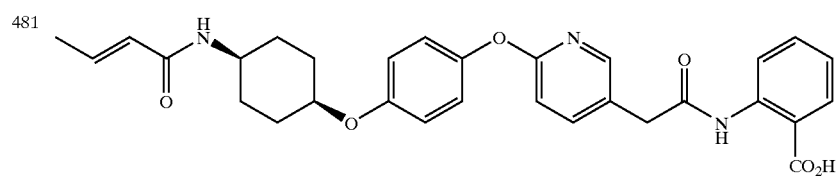
482 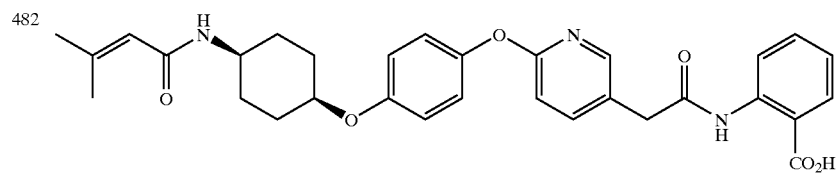
483 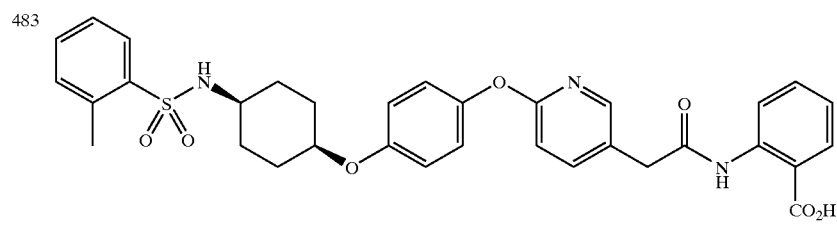
484 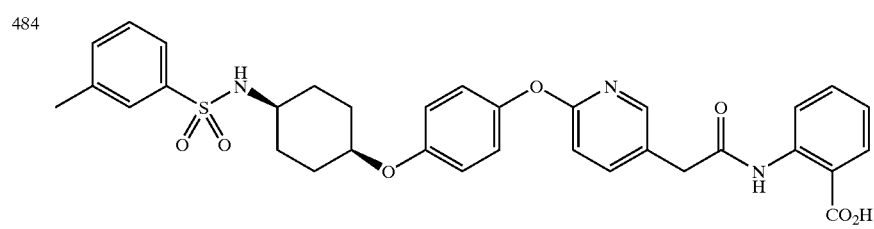
485 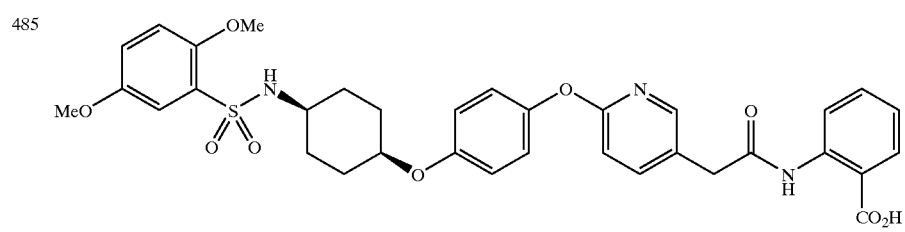
486 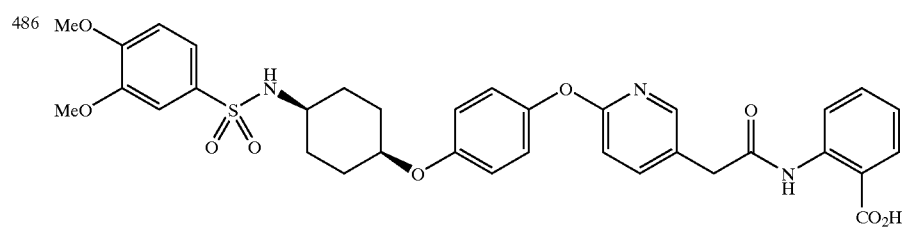
487 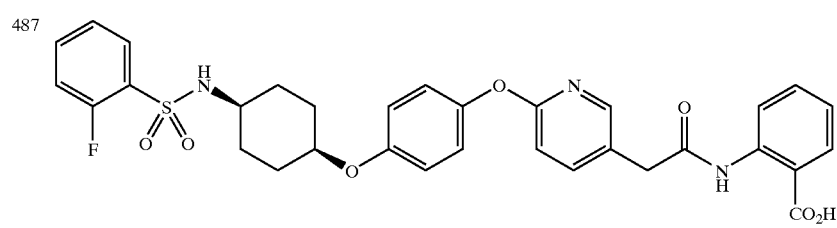

TABLE 17-continued
488 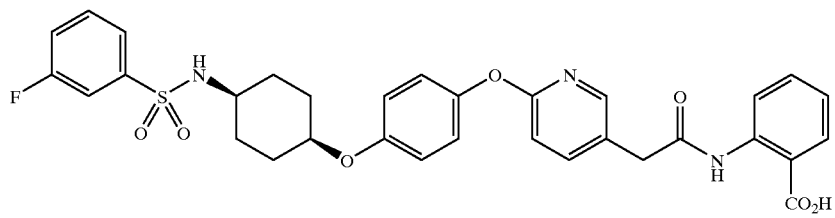
TABLE 18
489 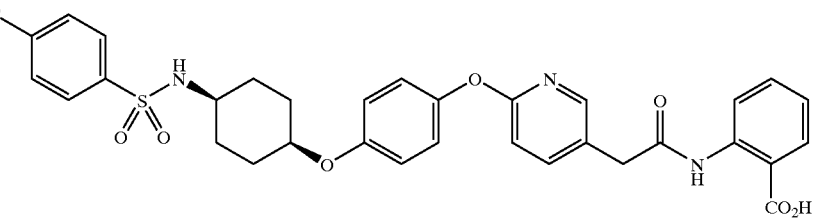
490 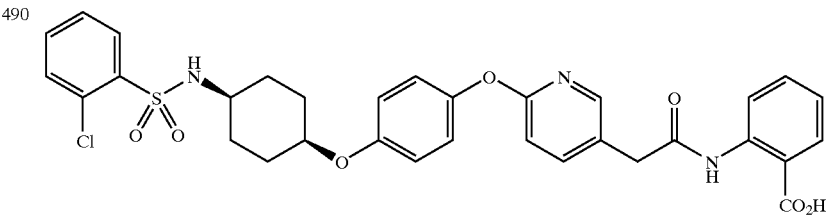
491 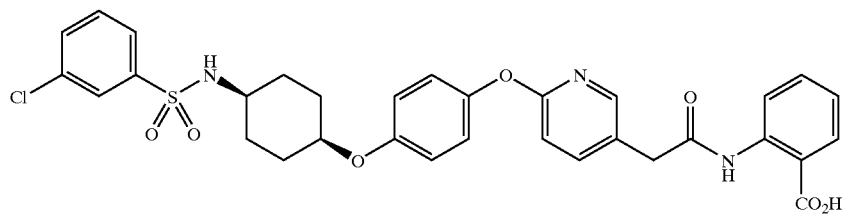
492 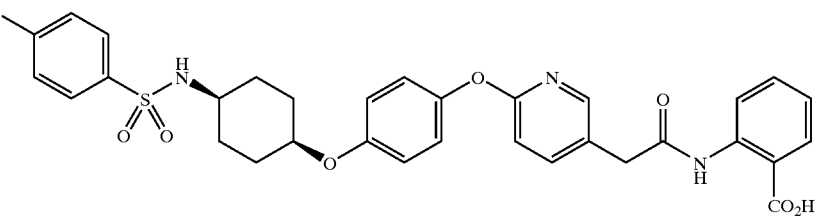
493 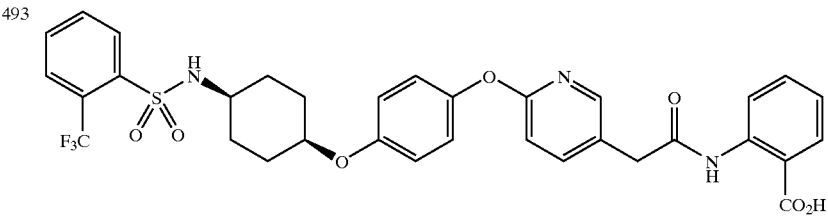

TABLE 18-continued
494 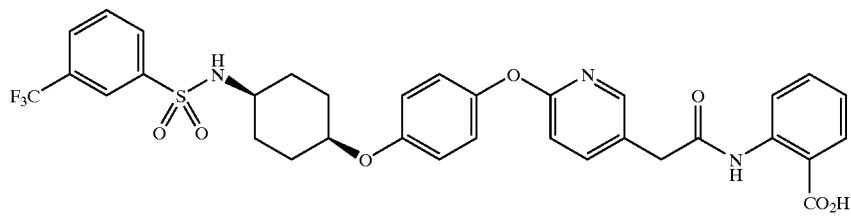
495 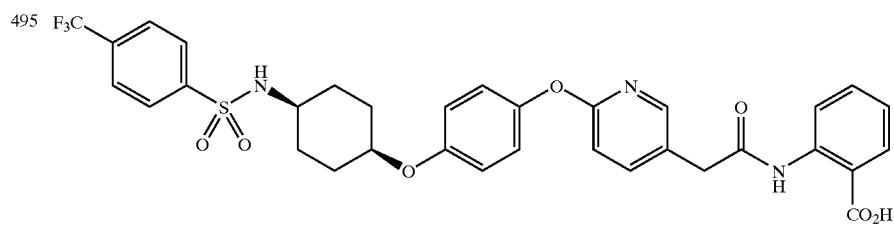
496 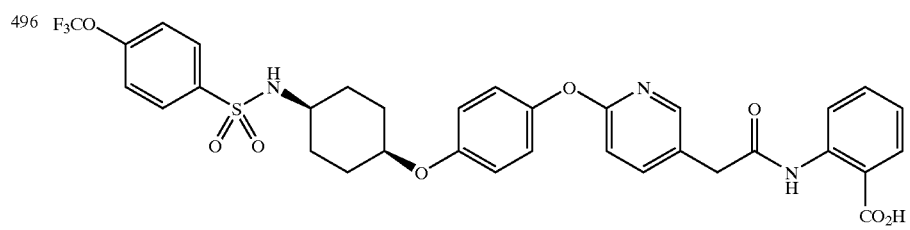
497 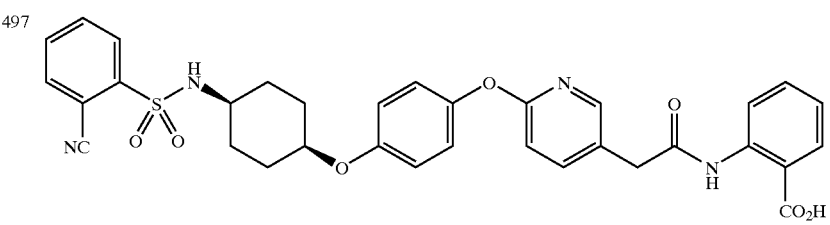
498 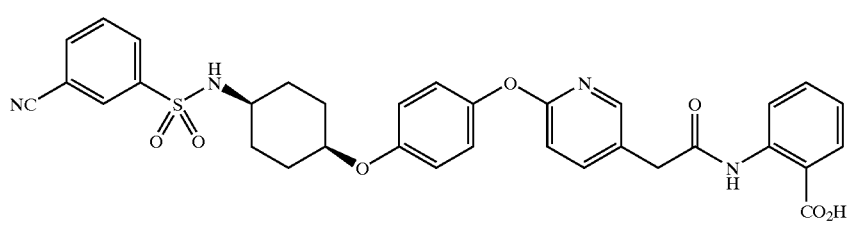
499 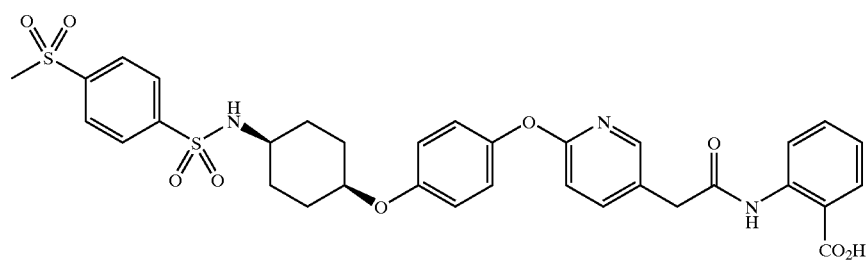
500 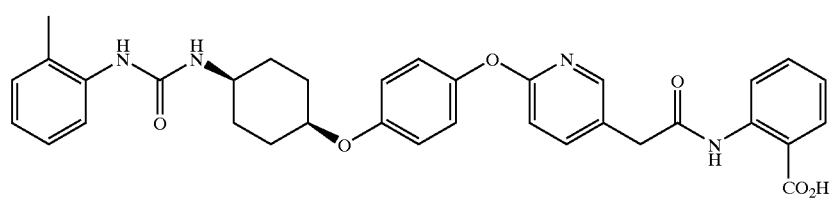

TABLE 18-continued
501 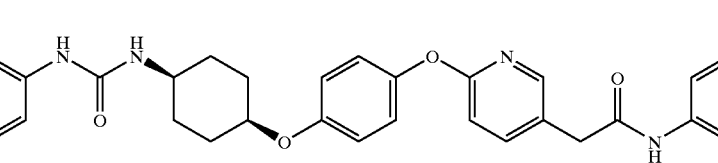
502 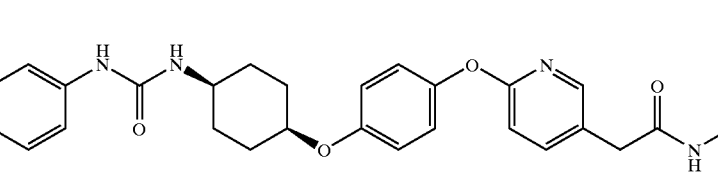
503 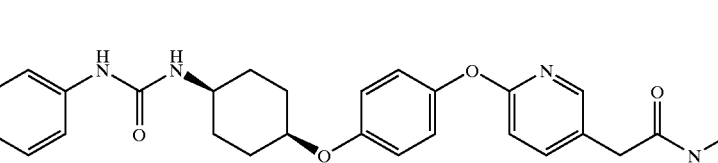
504 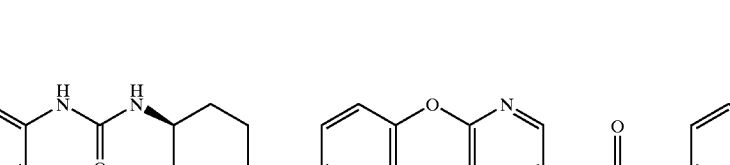
505 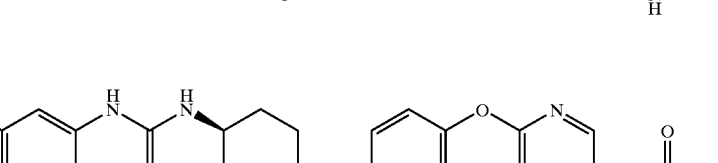
506 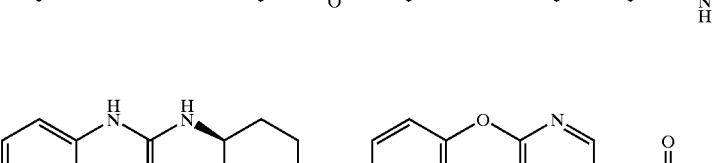
507 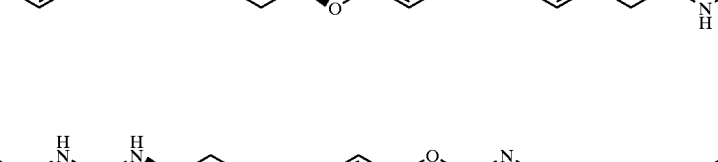
508

TABLE 18-continued

TABLE 18-continued
517 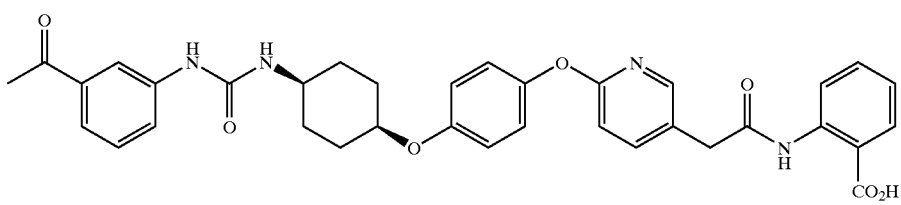
518 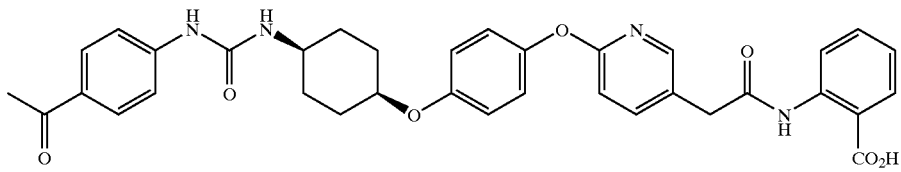
TABLE 19
519 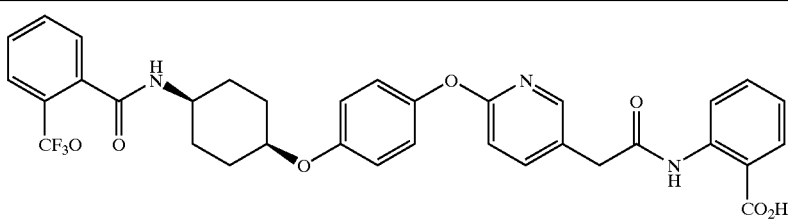
520 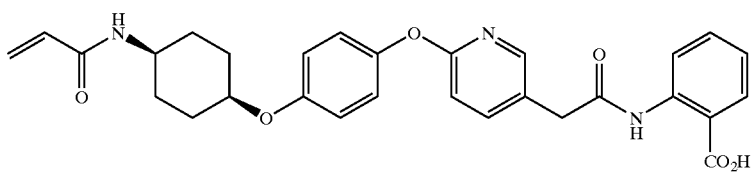
521 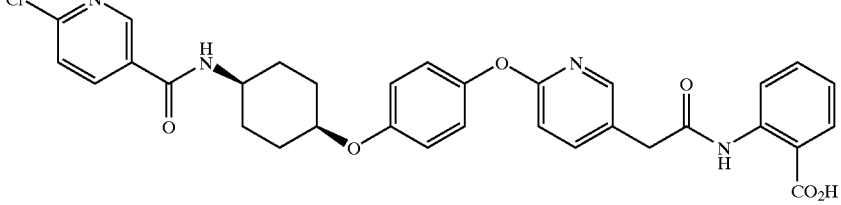
522 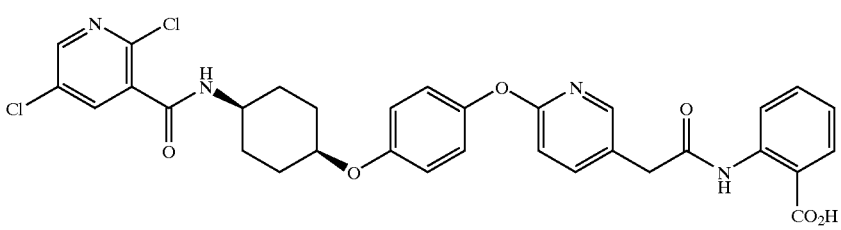
523 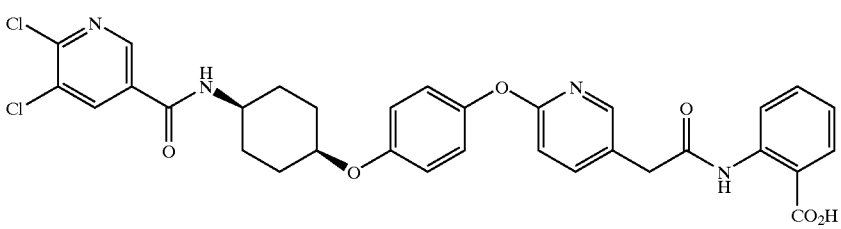

TABLE 19-continued
524 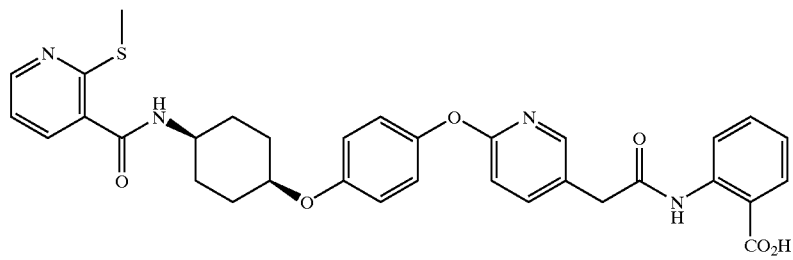
525 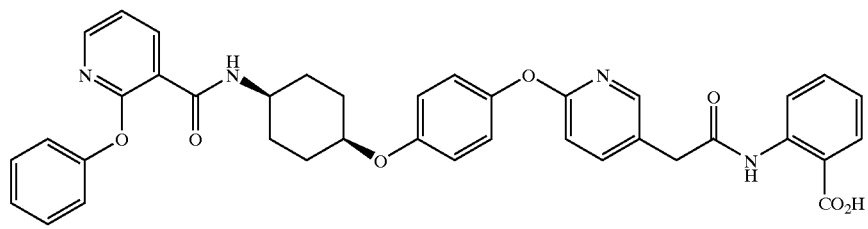
526 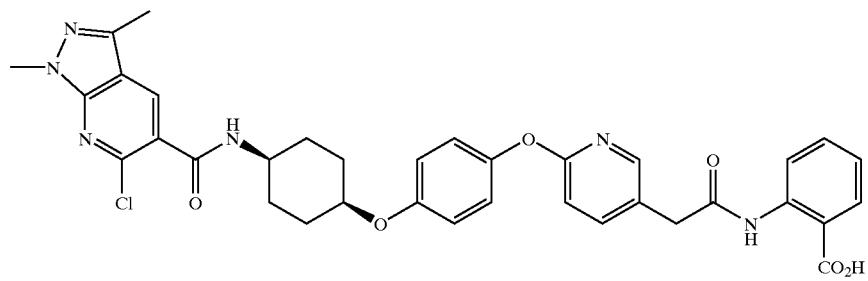
527 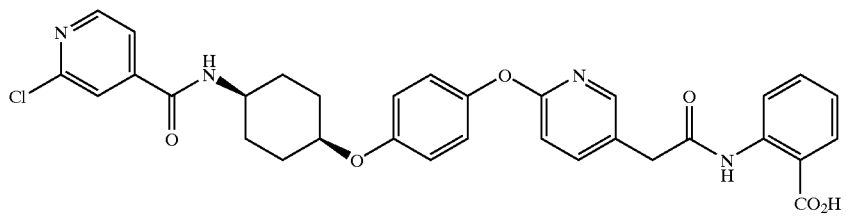
528 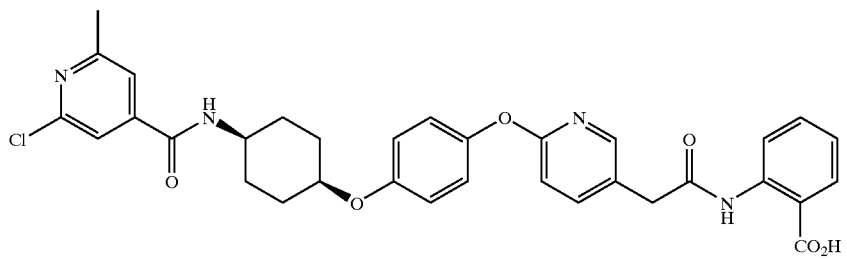
529 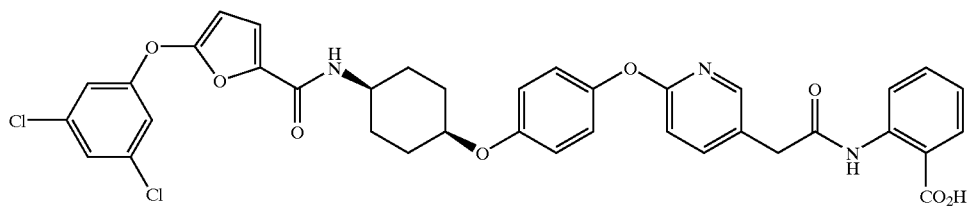

TABLE 19-continued
| 530 | 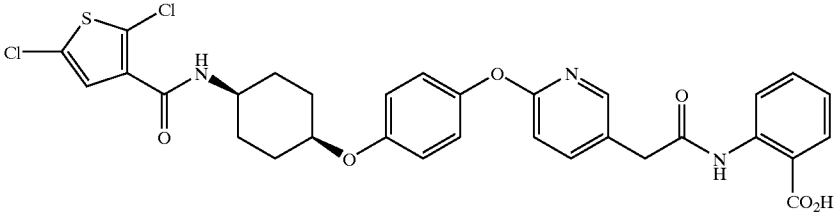 |
| --- | --- |
| 531 | 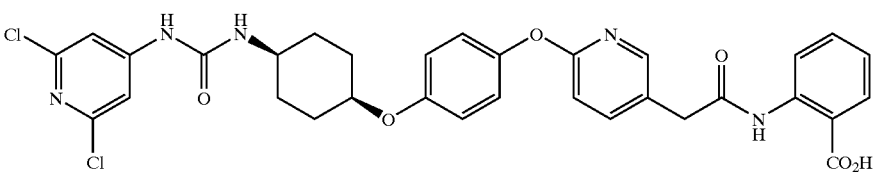 |
| 532 | 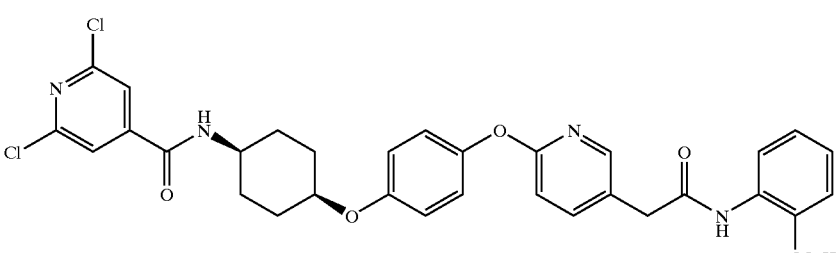 |
| 533 | 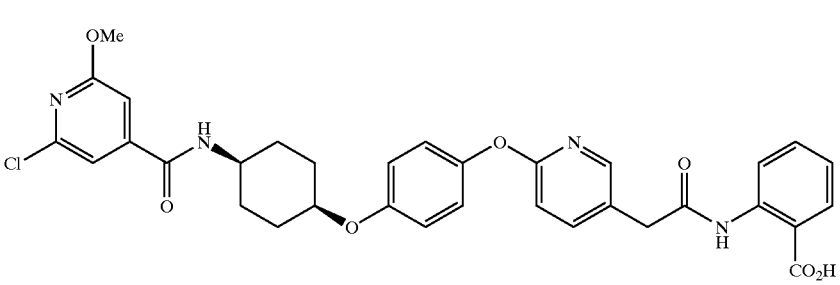 |
| 534 | 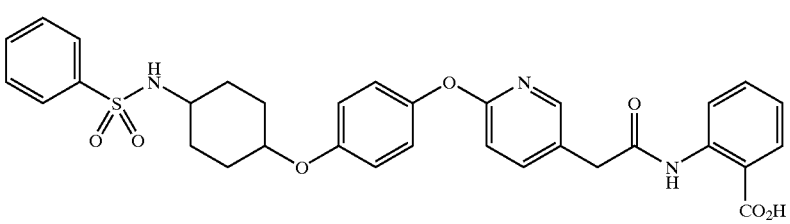 |
| 535 | 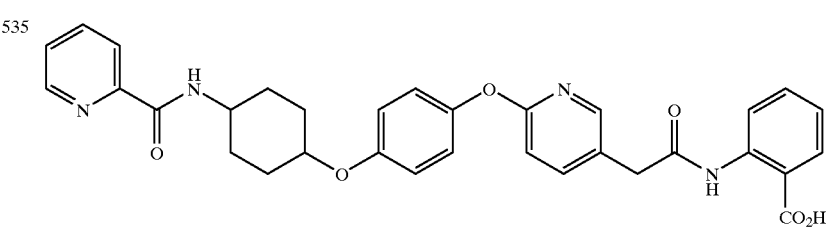 |
| 536 | 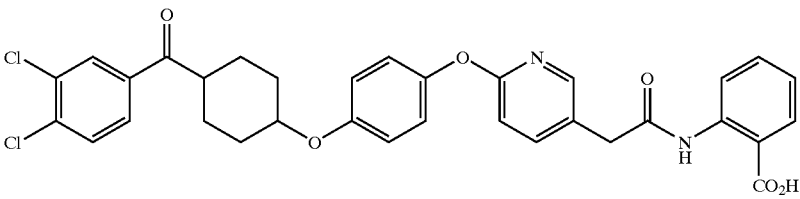 |

TABLE 19-continued

| 537 | (structure) |
| 538 | (structure) |
| 539 | (structure) |
| 540 | (structure) |
| 541 | (structure) |
| 542 | (structure) |
| 543 | (structure) |
| 544 | (structure) |

TABLE 19-continued
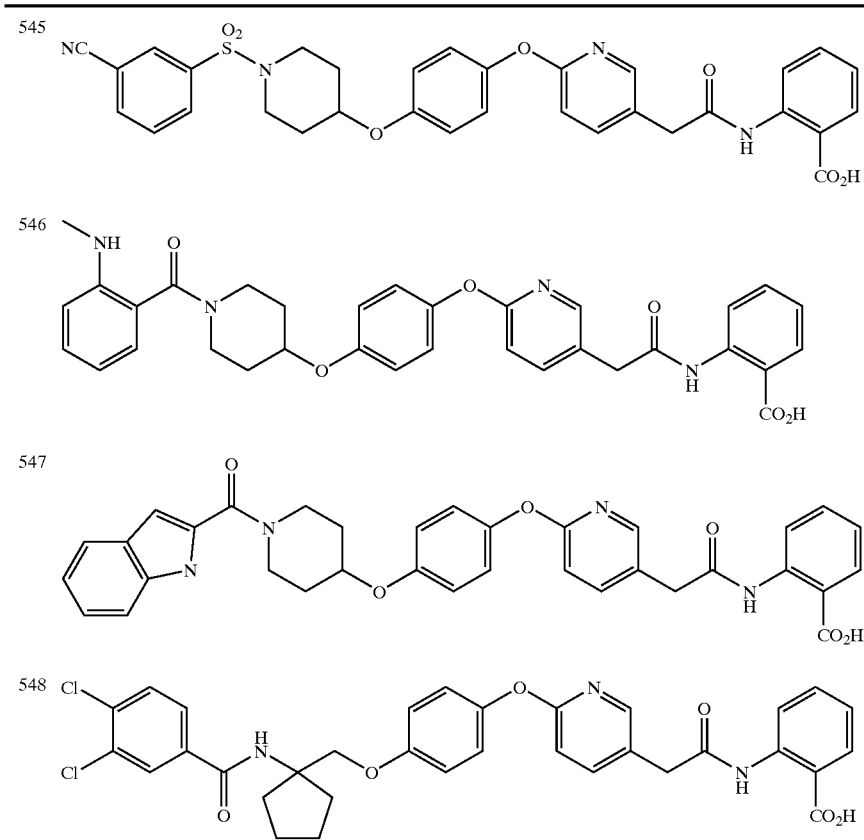
TABLE 20
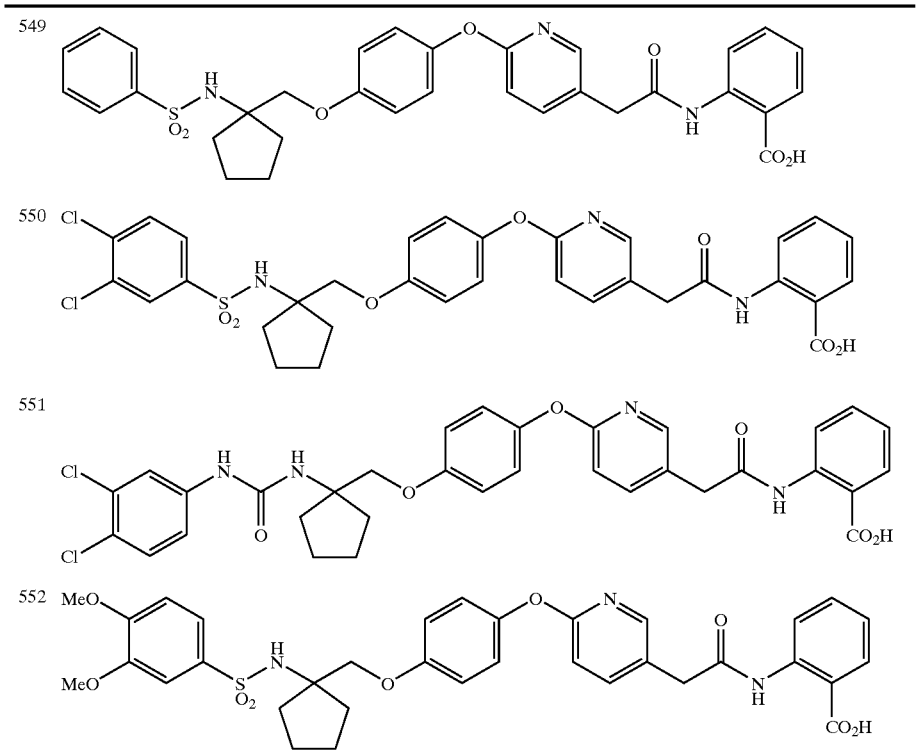

TABLE 20-continued

TABLE 20-continued
561 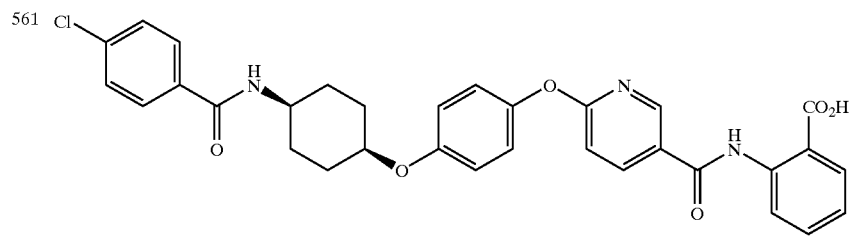
562 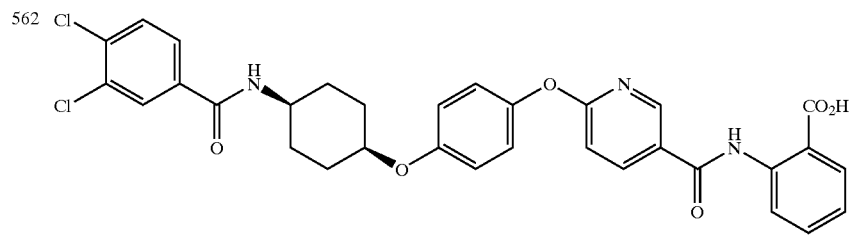
563 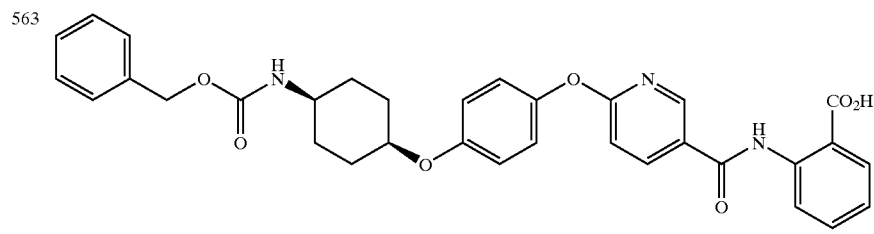
564 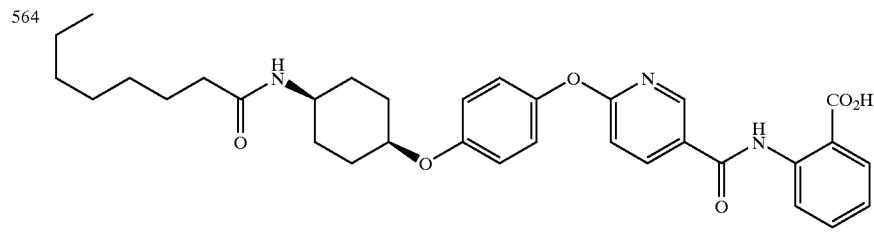
565 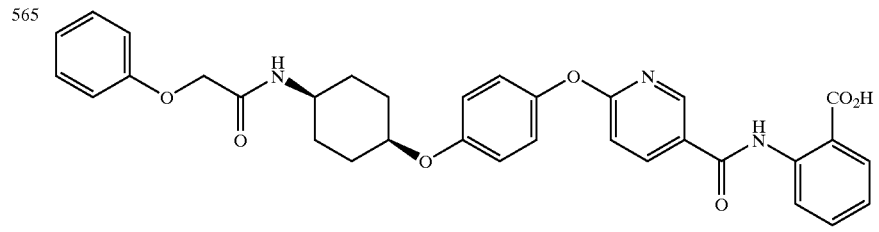
566 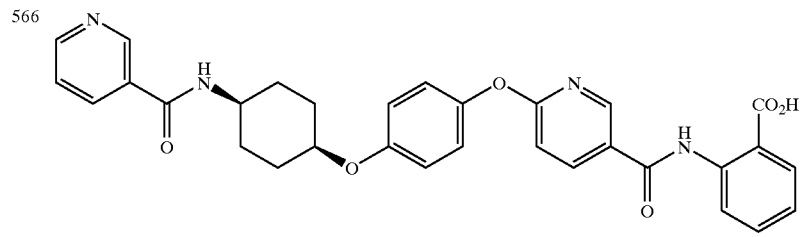

TABLE 20-continued
567 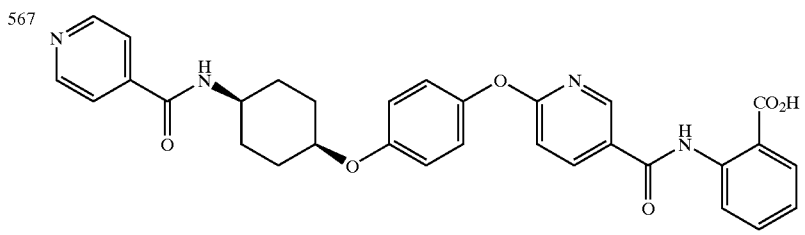
568 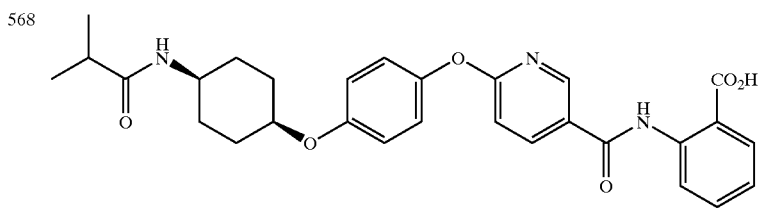
569 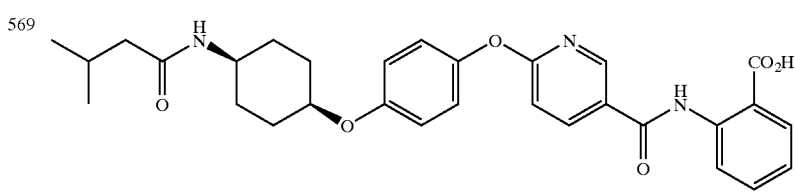
570 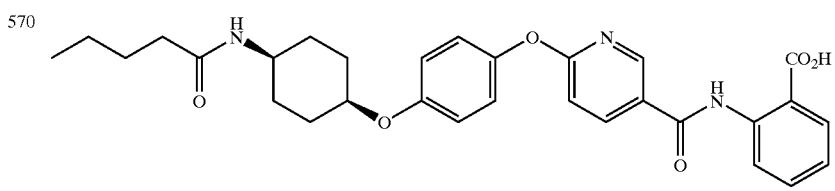
571 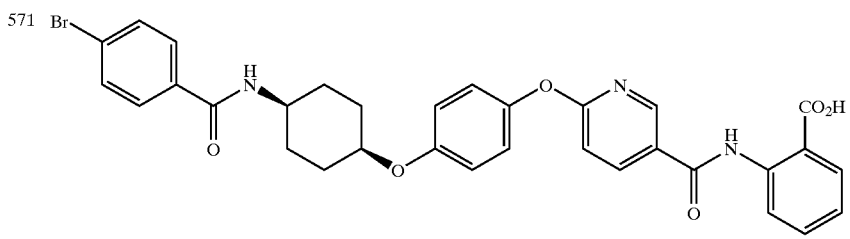
572 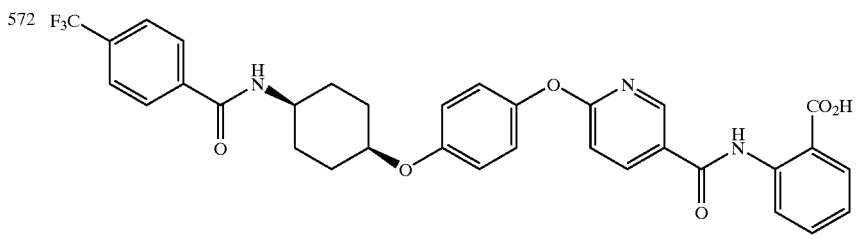
573 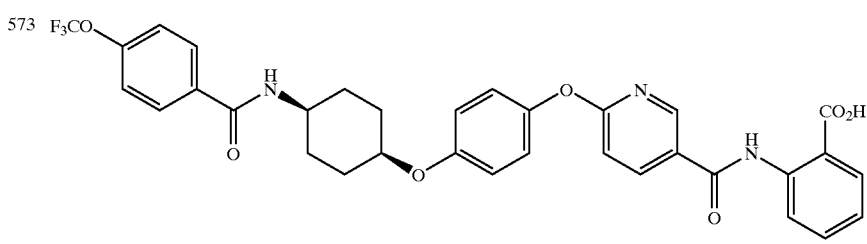

TABLE 20-continued
574 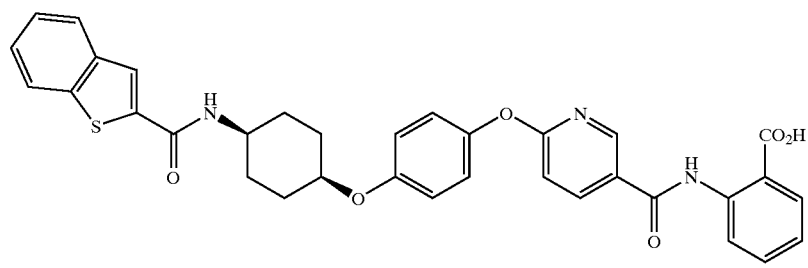
575 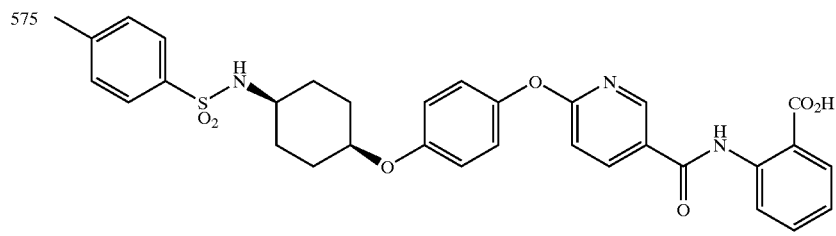
576 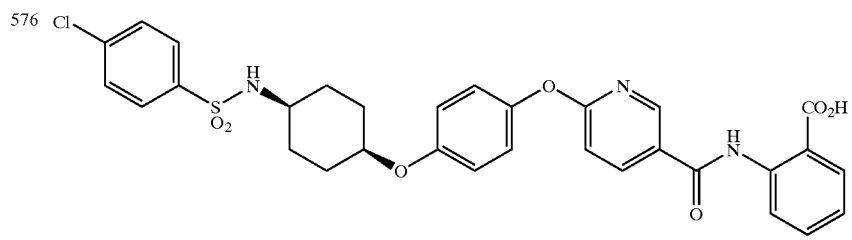
577 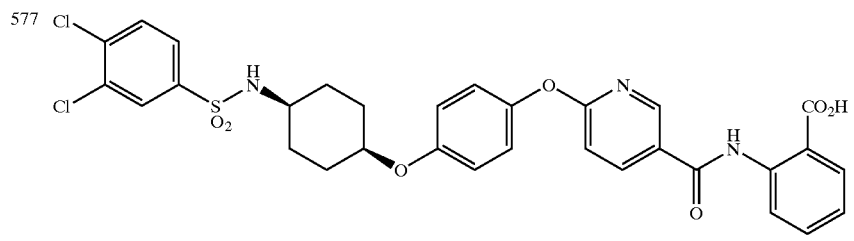
578 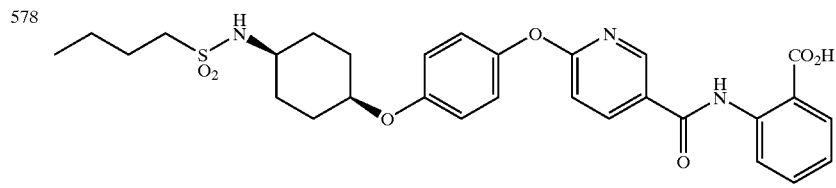
TABLE 21
579 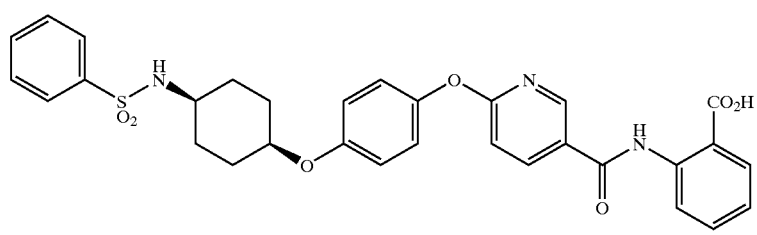

TABLE 21-continued
580 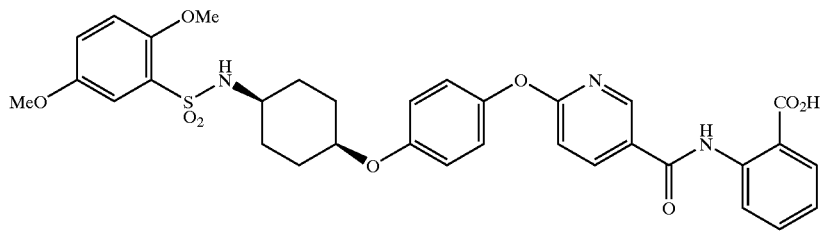
581 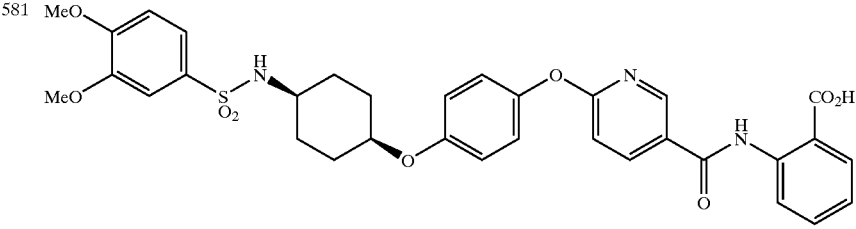
582 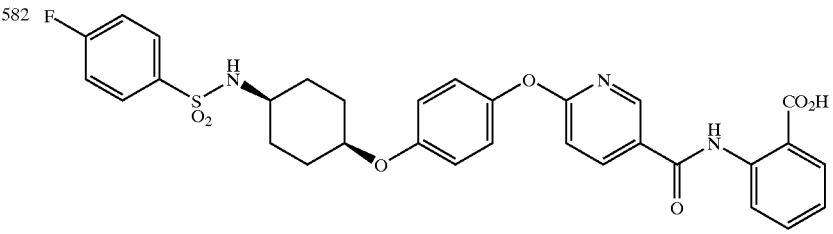
583 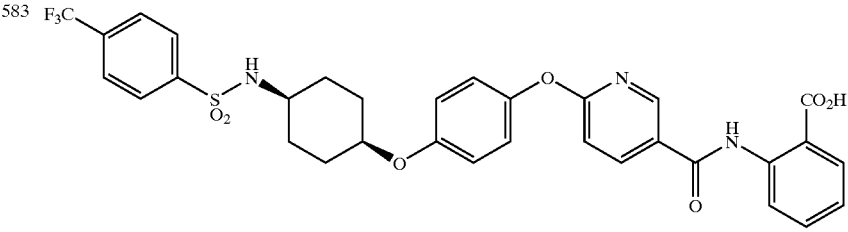
584 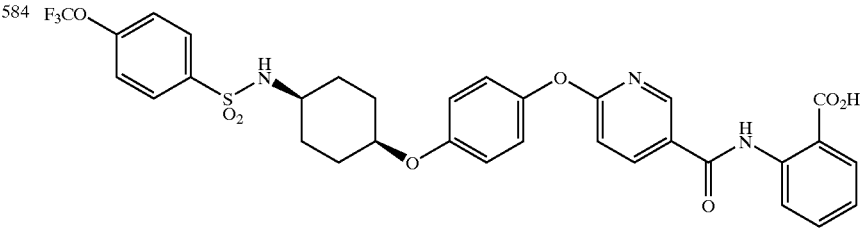
585 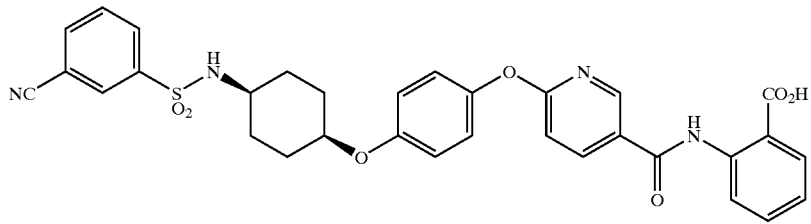

TABLE 21-continued

TABLE 21-continued
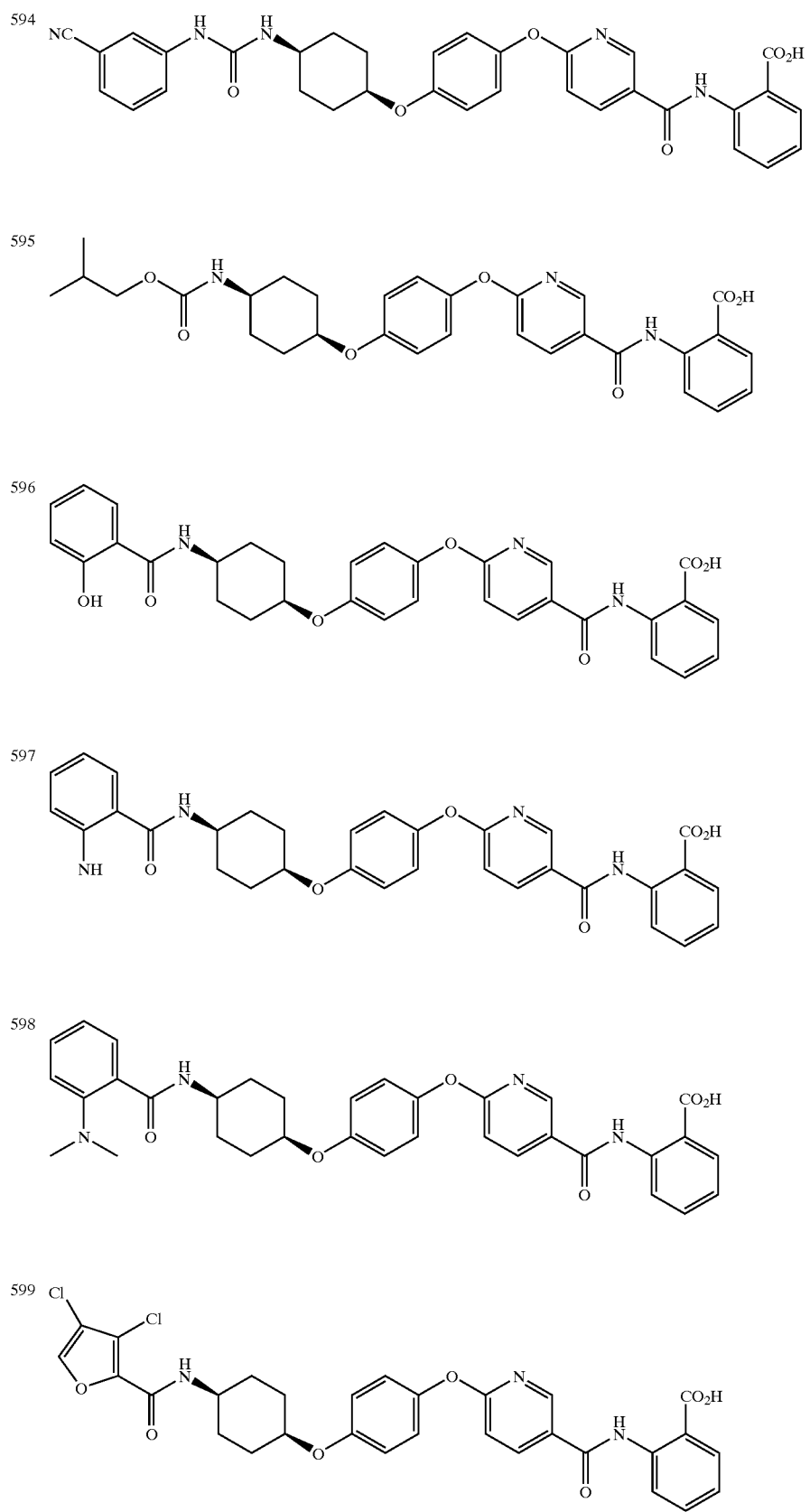

TABLE 21-continued
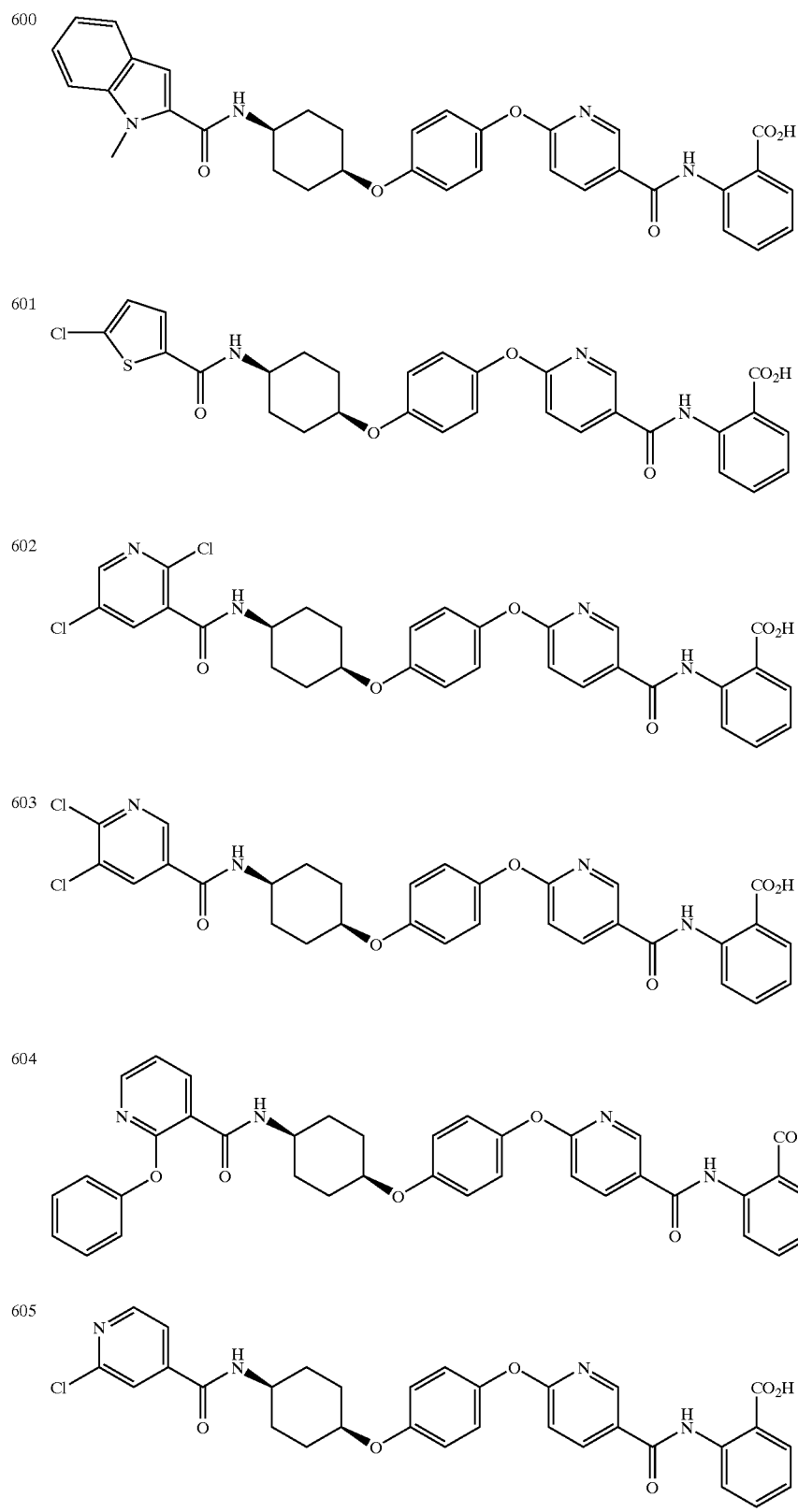

TABLE 21-continued
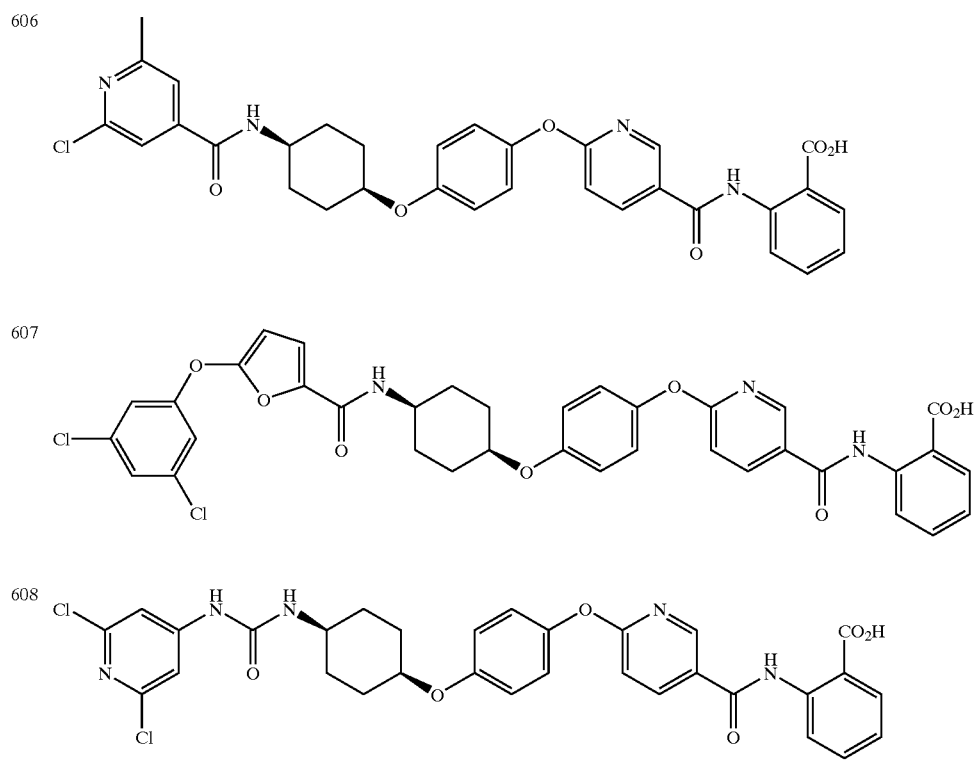
TABLE 22
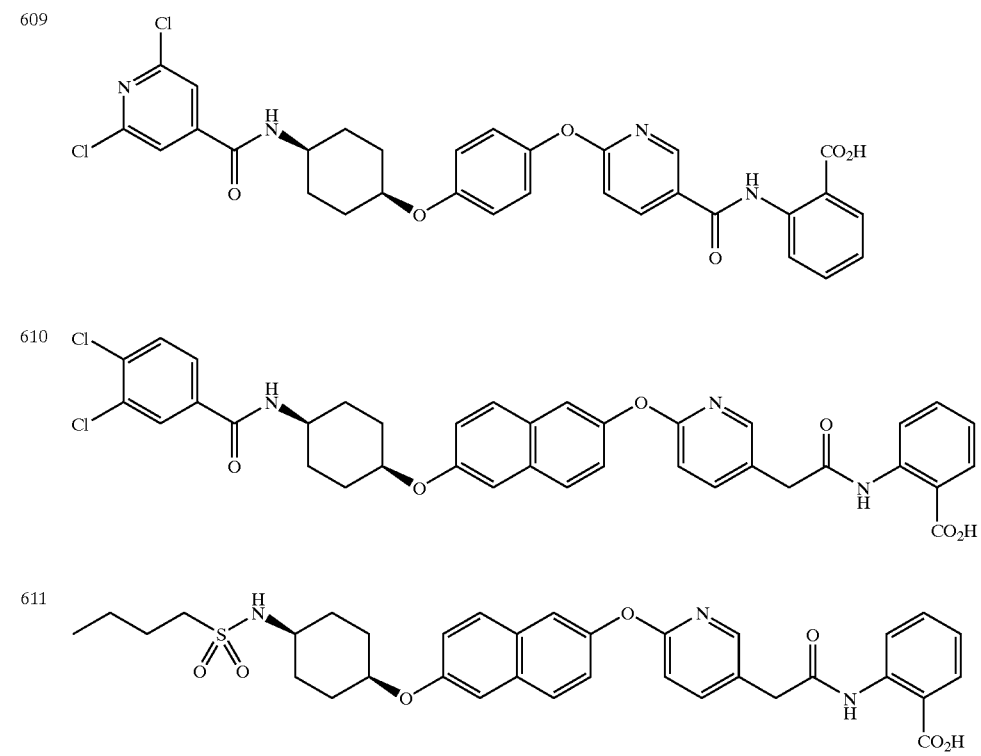

TABLE 22-continued
612
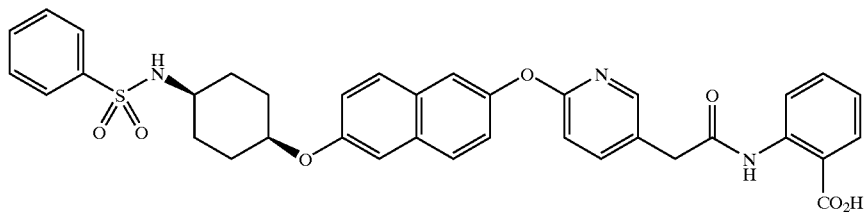
613
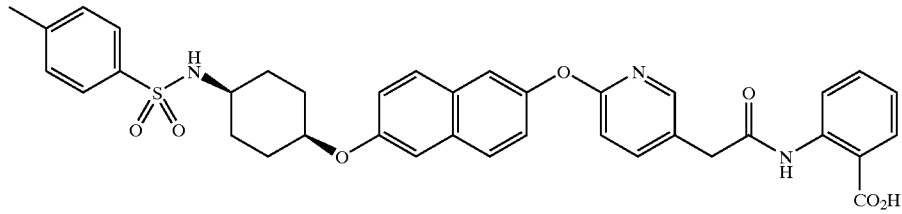
614
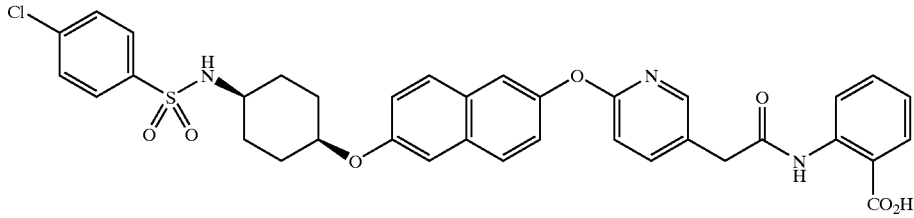
615
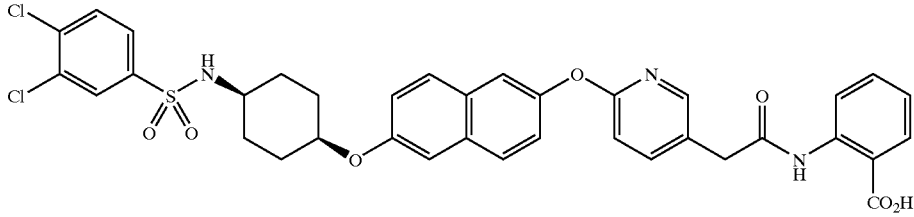
616
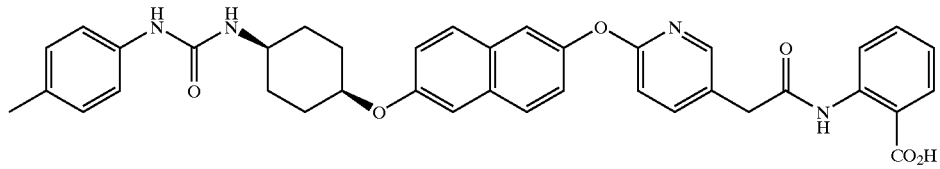
617
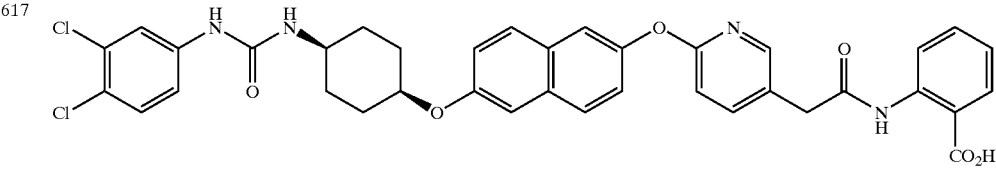
618
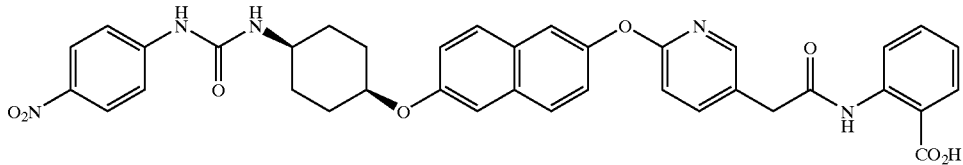

TABLE 22-continued
619 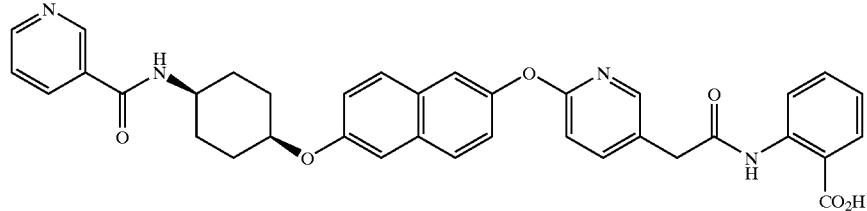
620 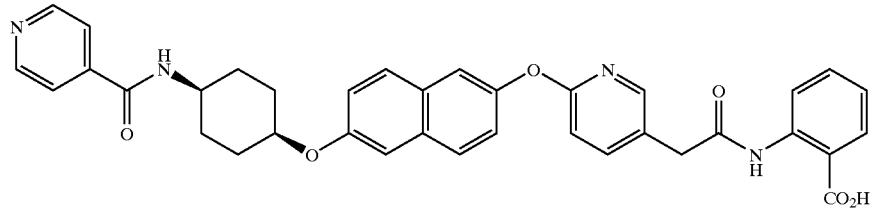
621 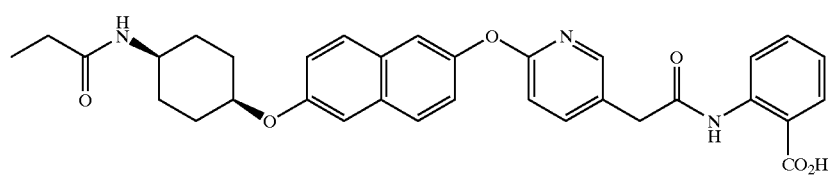
622 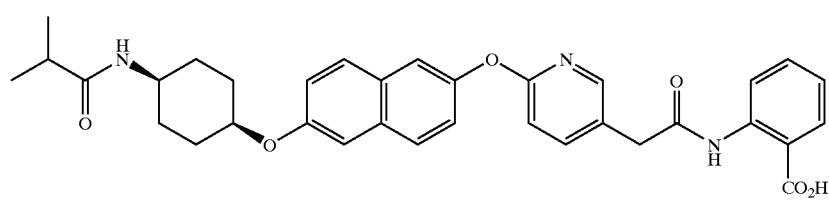
623 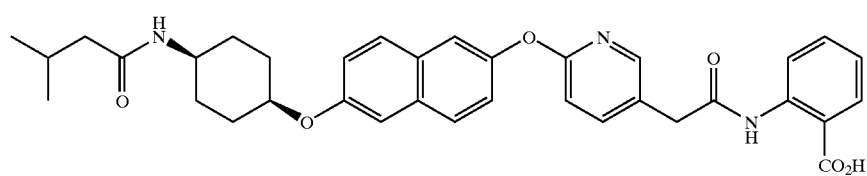
624 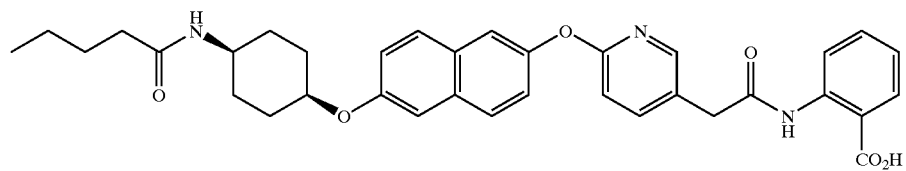
625 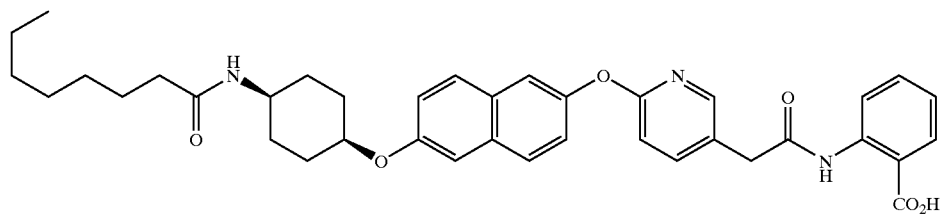

TABLE 22-continued
626 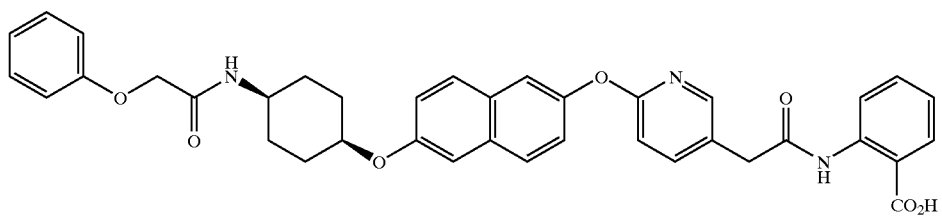
627 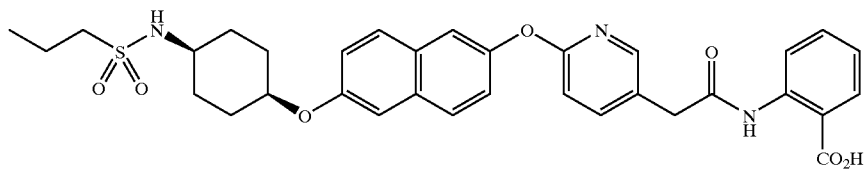
628 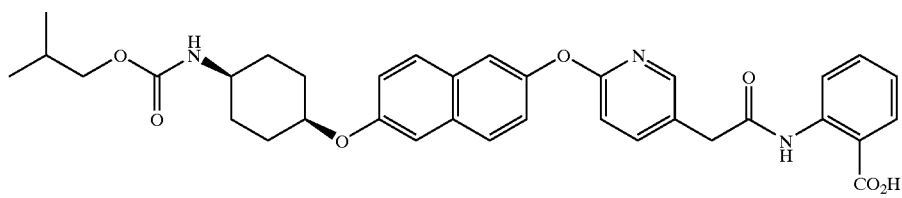
629 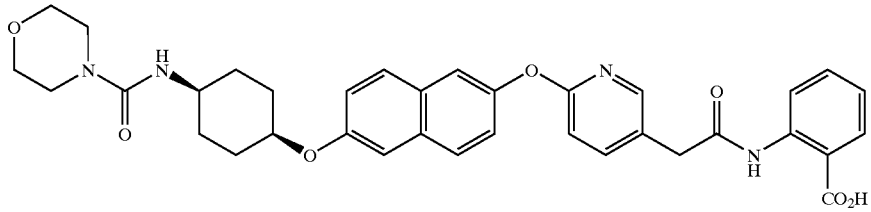
630 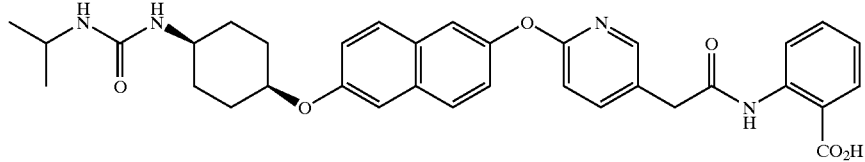
631 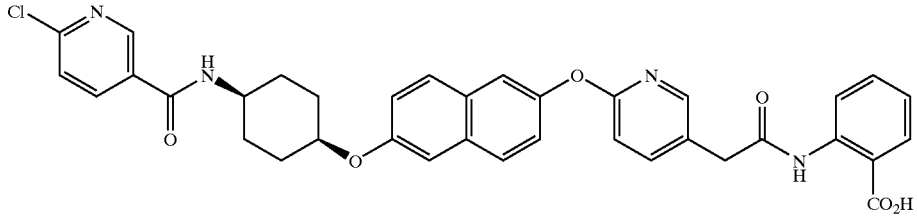
632 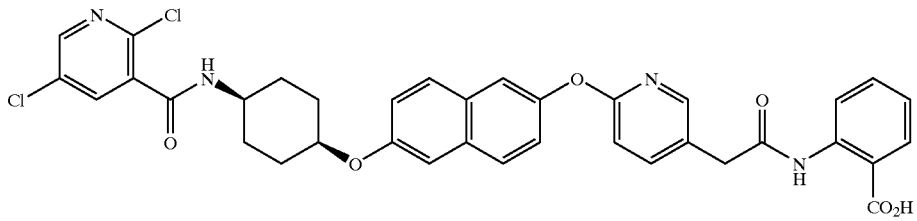

TABLE 22-continued
633 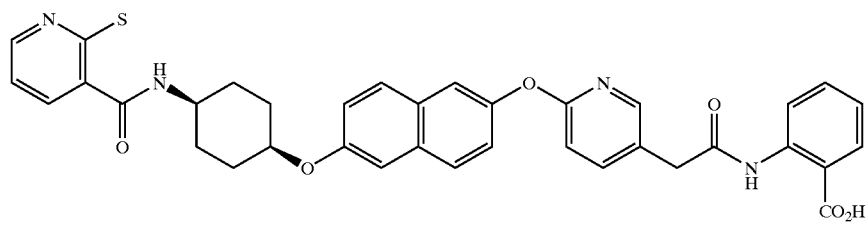
634 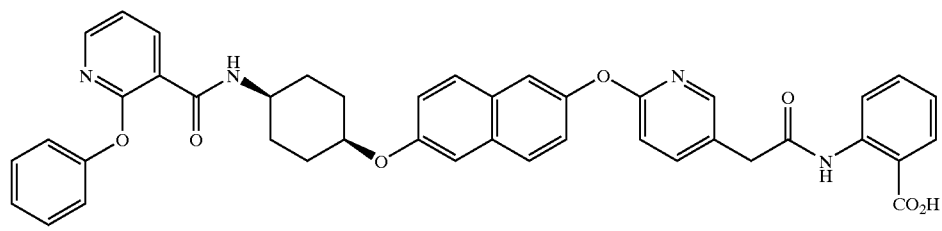
635 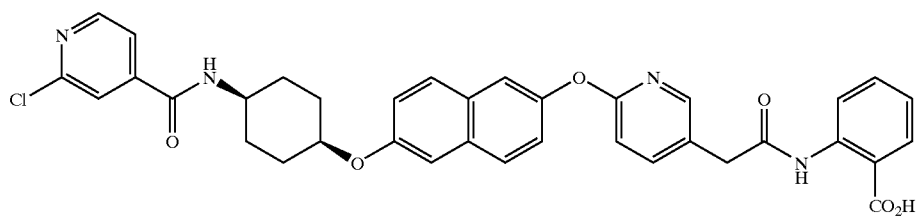
636 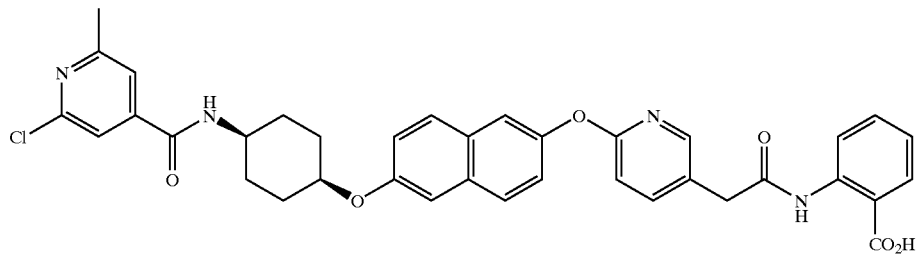
637 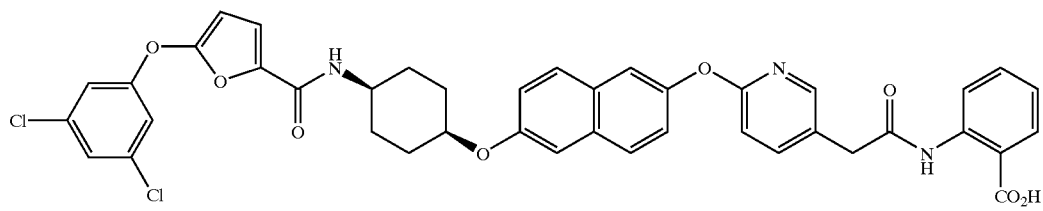
638 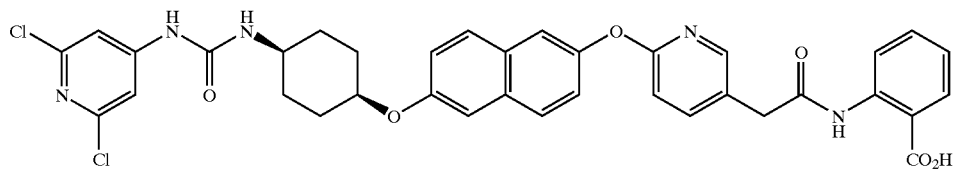

TABLE 23
639 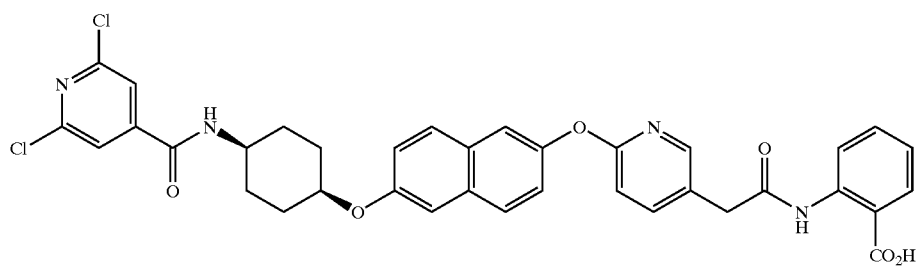
640 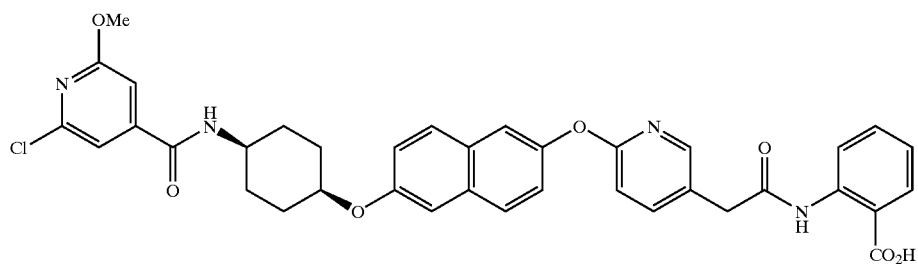
641 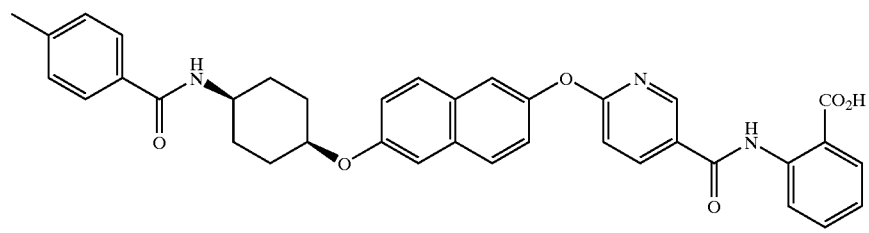
642 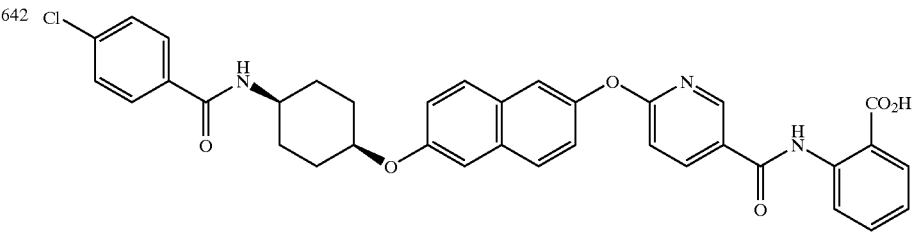
643 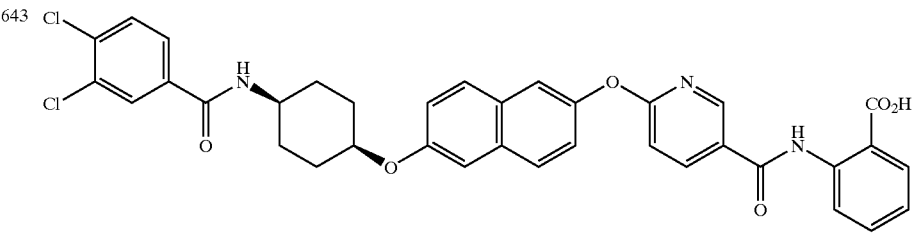
644 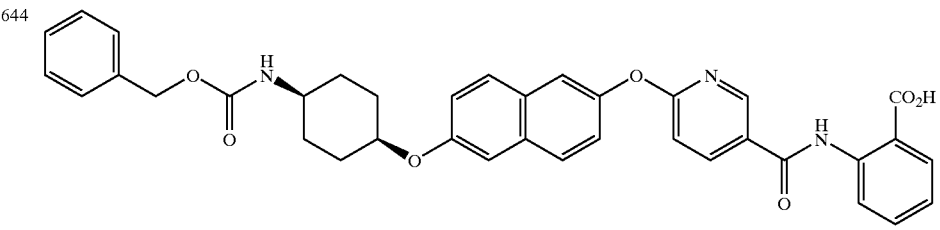

TABLE 23-continued
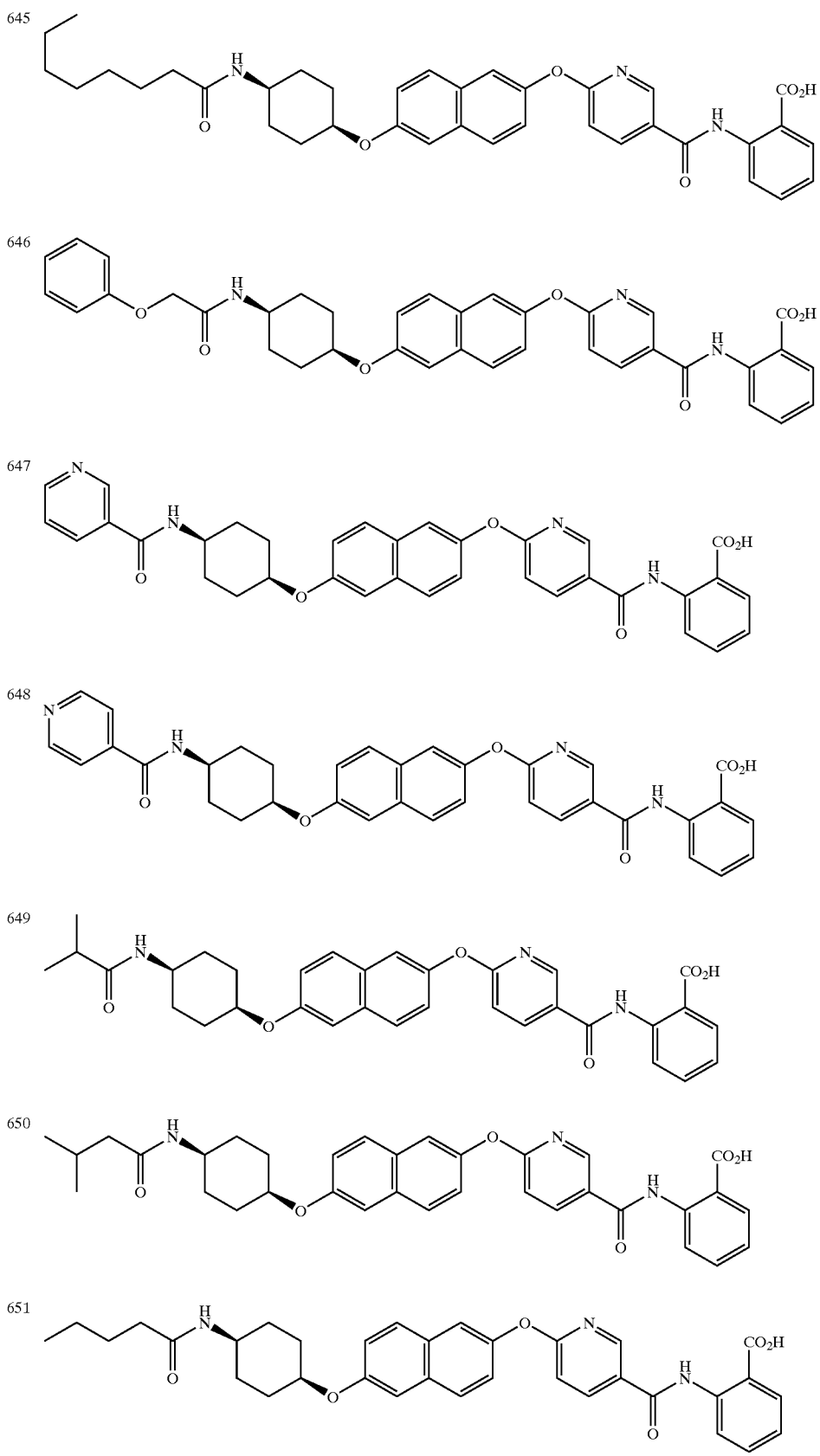

TABLE 23-continued
652 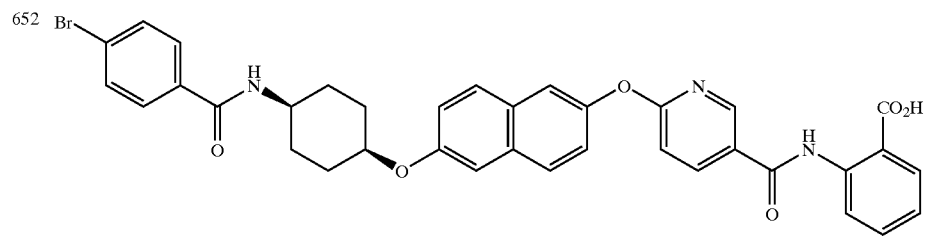
653 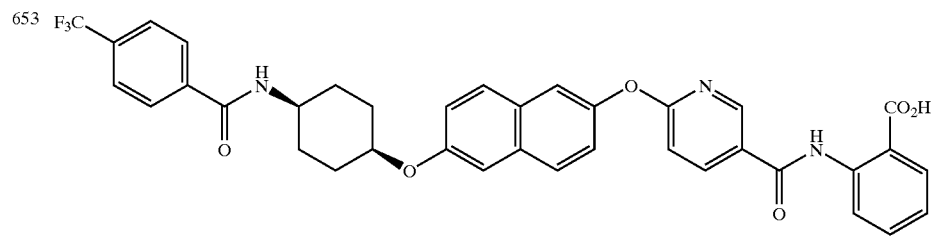
654 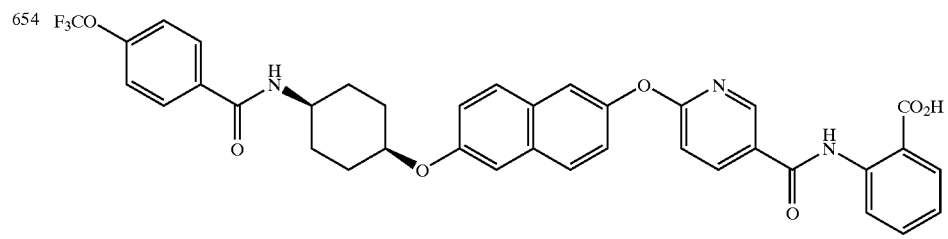
655 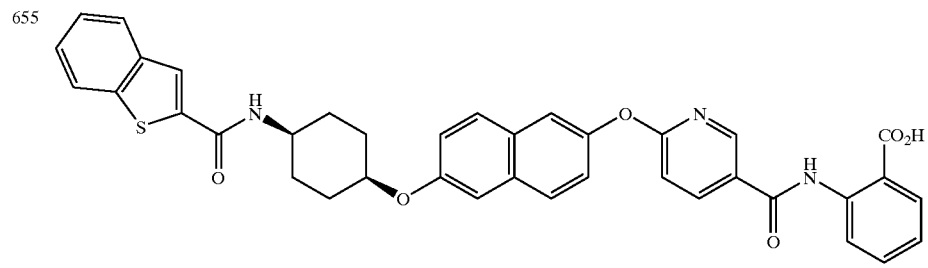
656 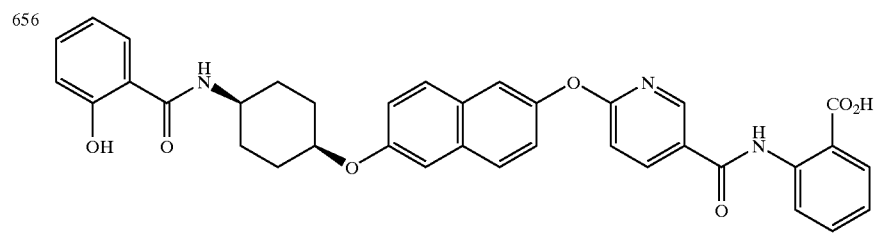
657 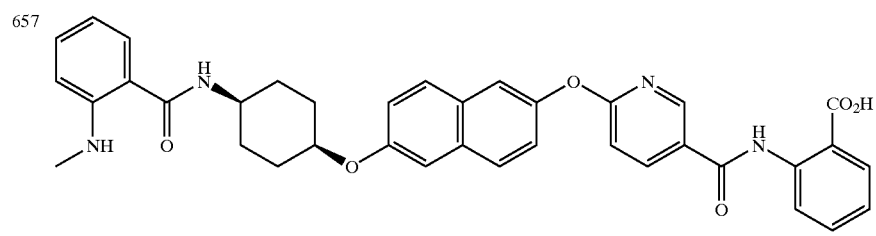

TABLE 23-continued
658
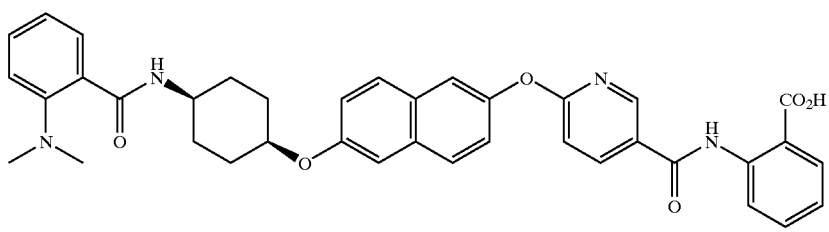
659
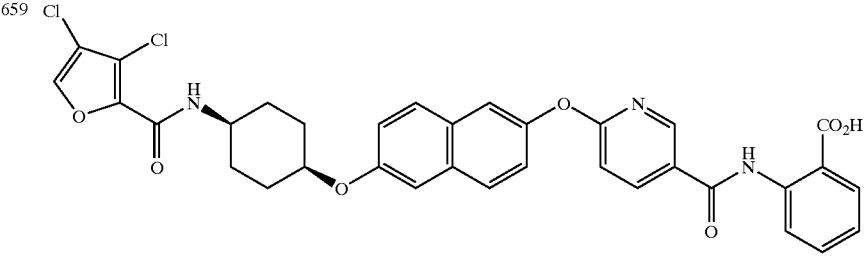
660
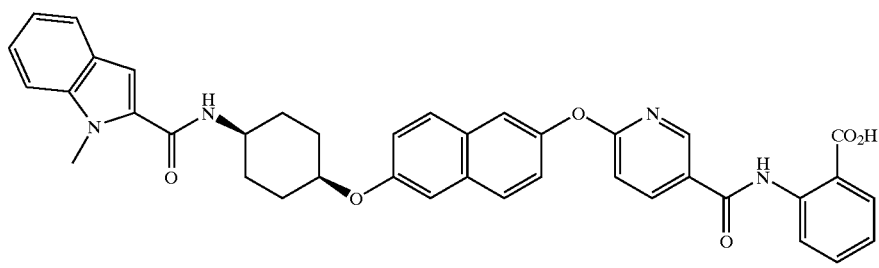
661
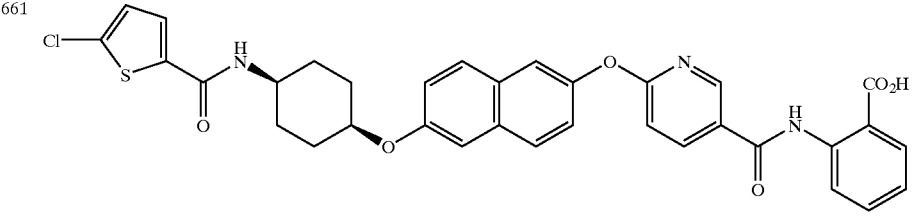
662
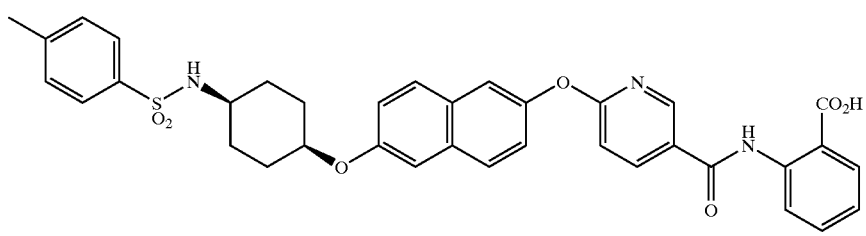
663
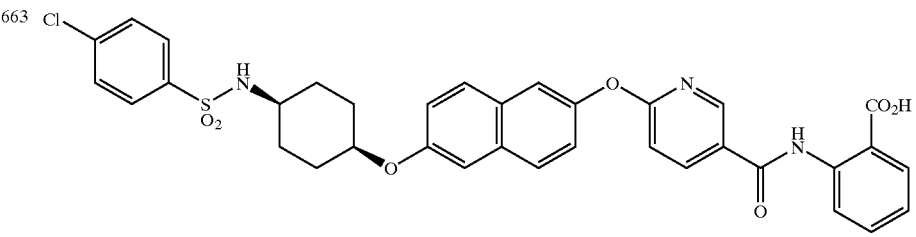

TABLE 23-continued
664 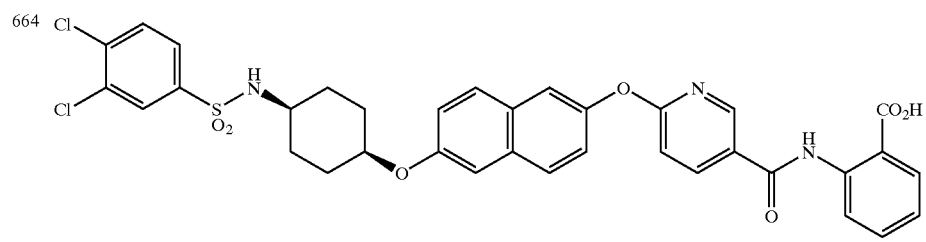
665 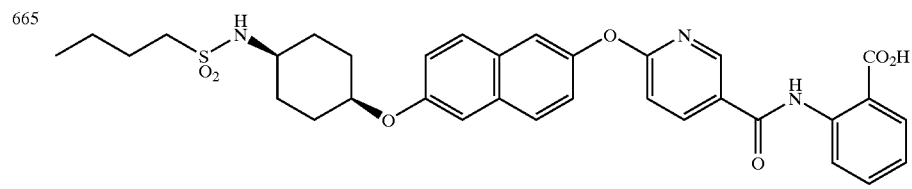
666 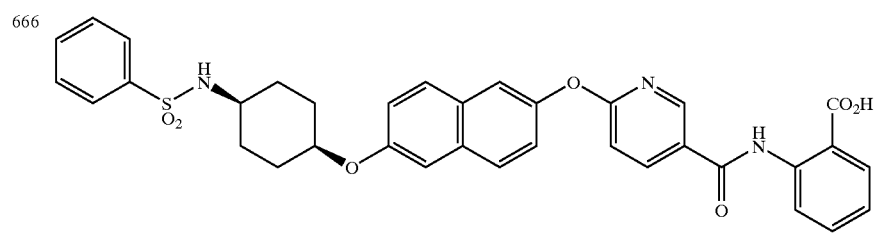
667 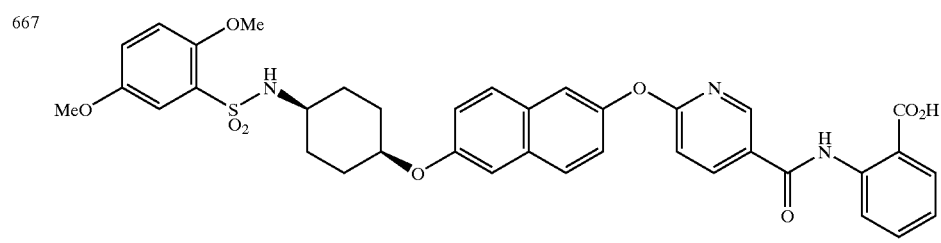
668 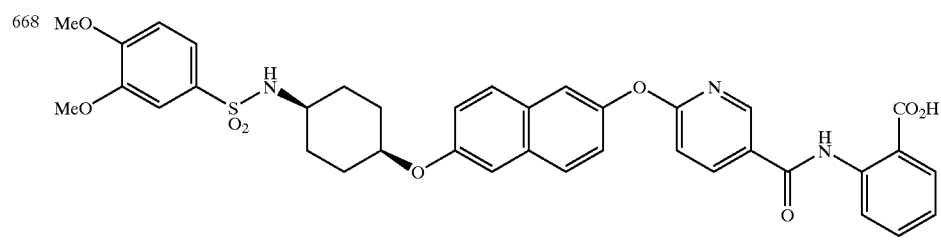
TABLE 24
669 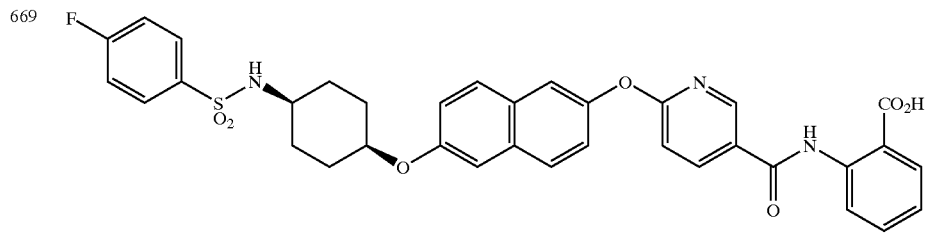

TABLE 24-continued
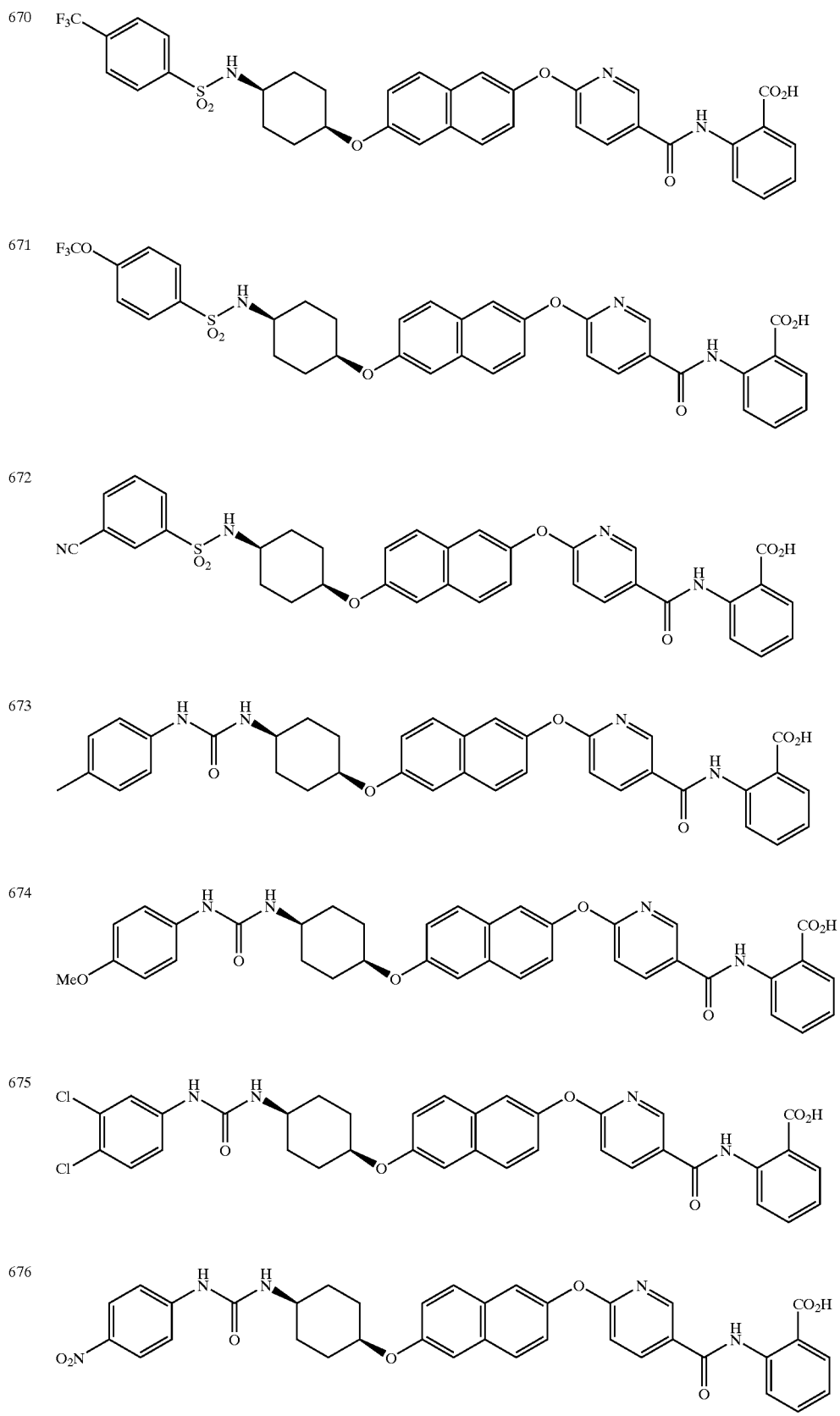

TABLE 24-continued
| 677 |  |
| 678 | 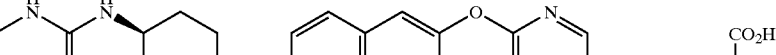 |
| 679 | 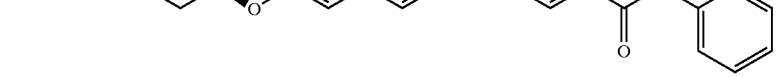 |
| 680 |  |
| 681 | 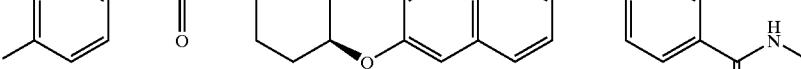 |
| 682 |  |
| 683 | 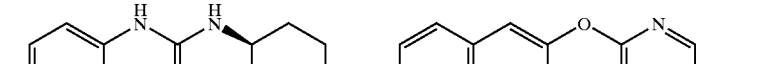 |

TABLE 24-continued
684 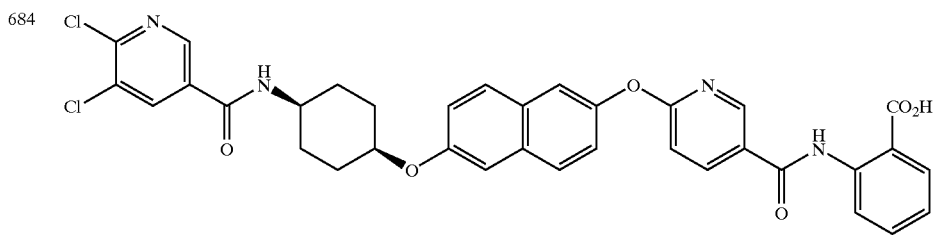
685 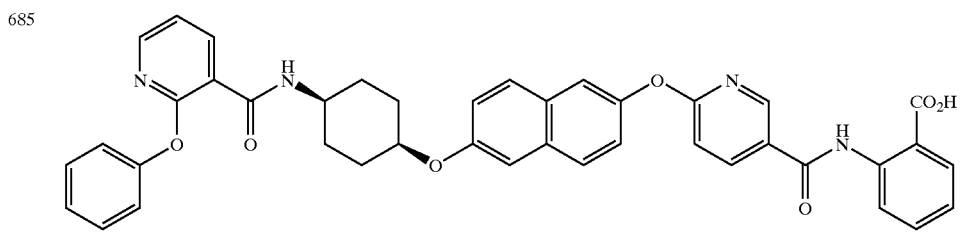
686 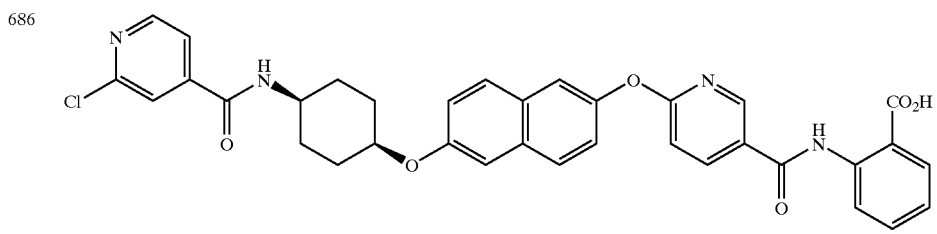
687 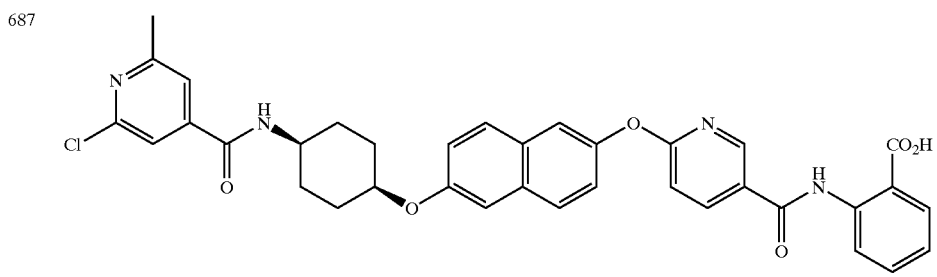
688 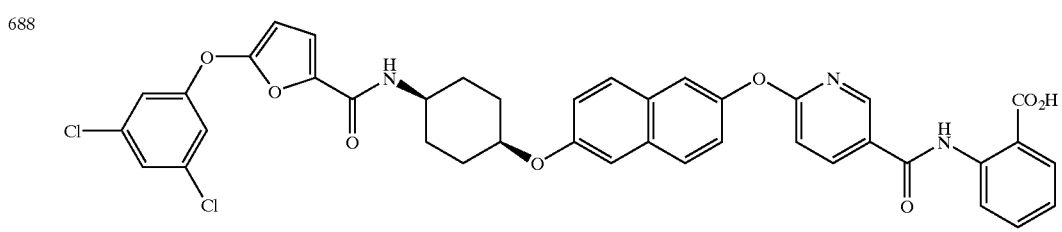
689 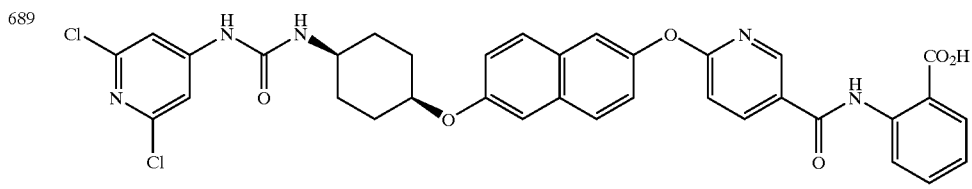

TABLE 24-continued
690 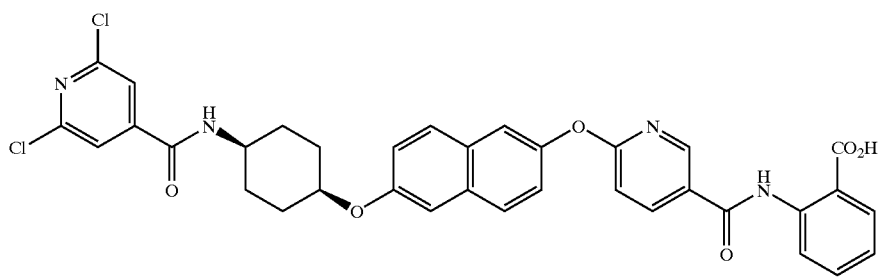
TABLE 25
691 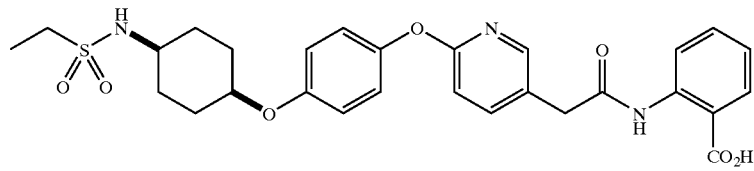
692 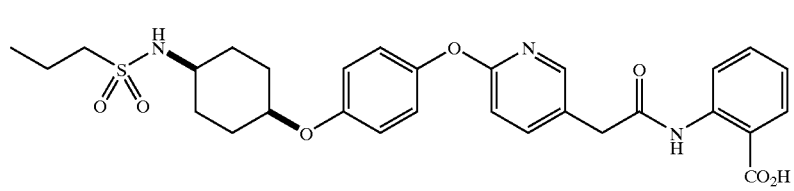
693 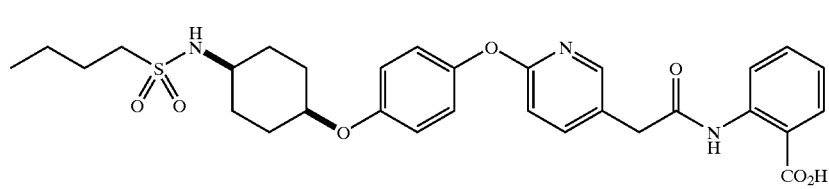
694 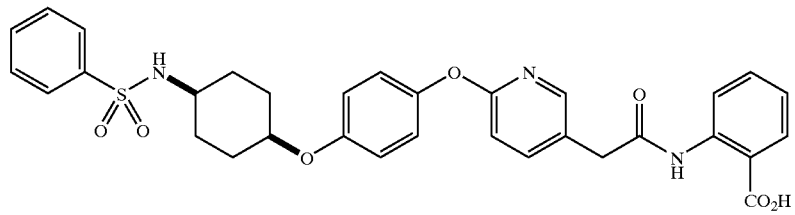
695 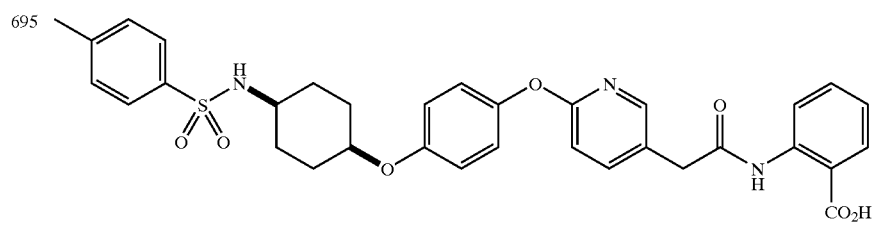
696 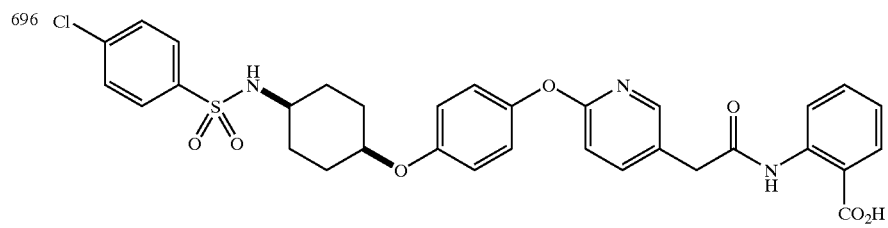

TABLE 25-continued
697 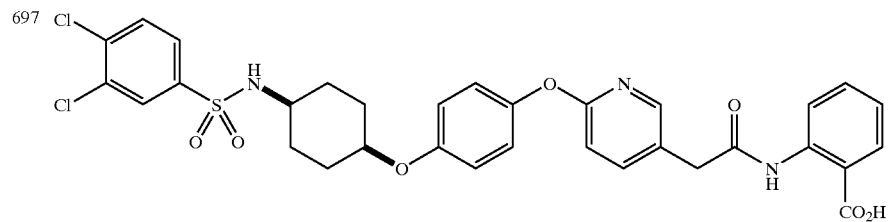
698 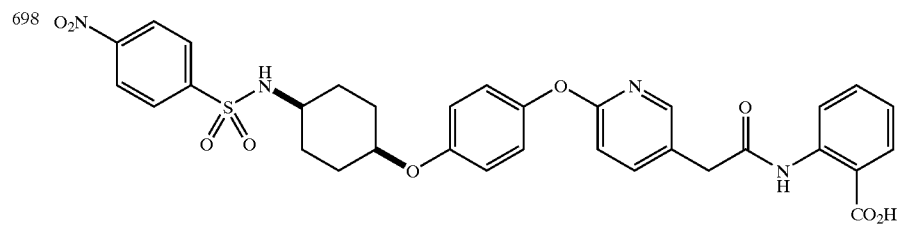
699 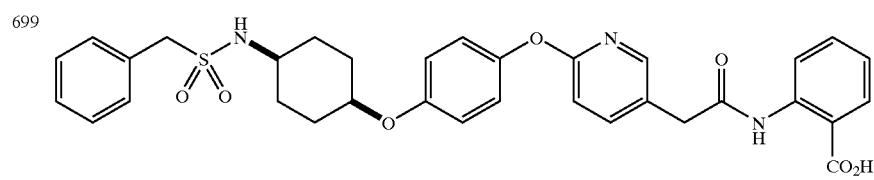
700 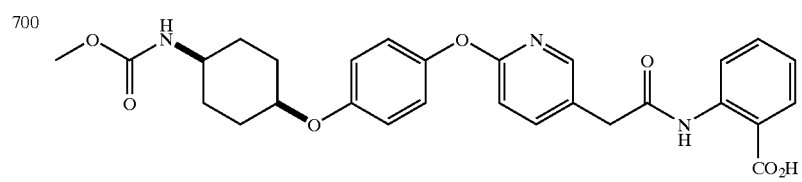
701 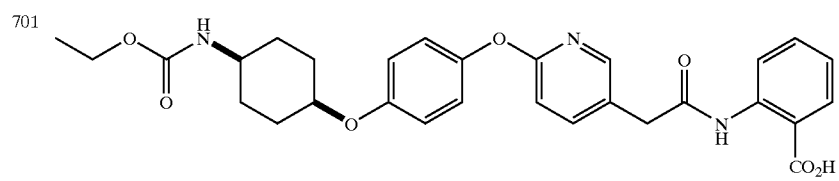
702 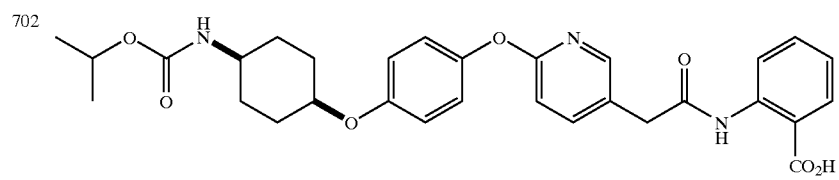
703 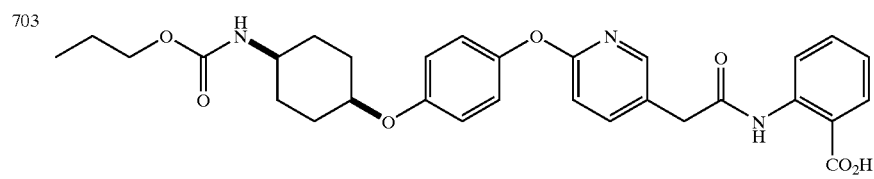
704 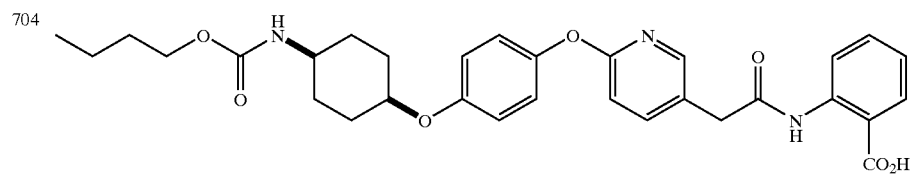

TABLE 25-continued
| 705 | 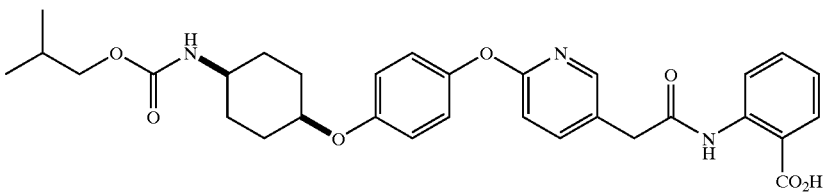 |
| --- | --- |
| 706 | 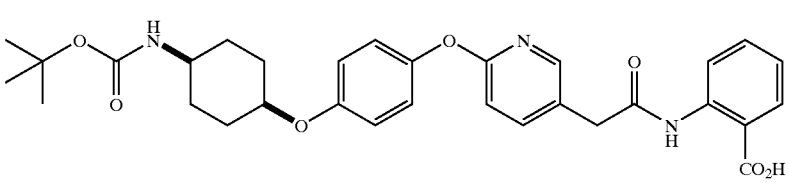 |
| 707 | 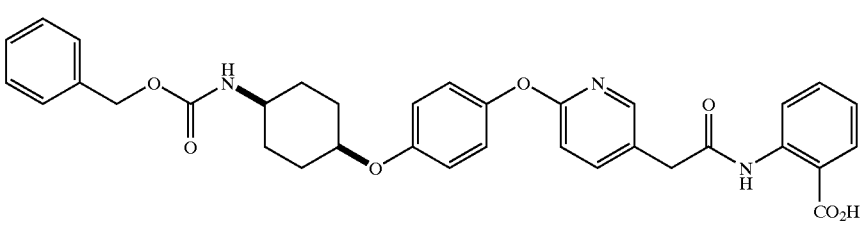 |
| 708 | 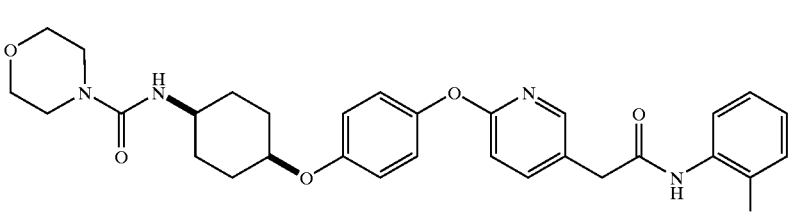 |
| 709 | 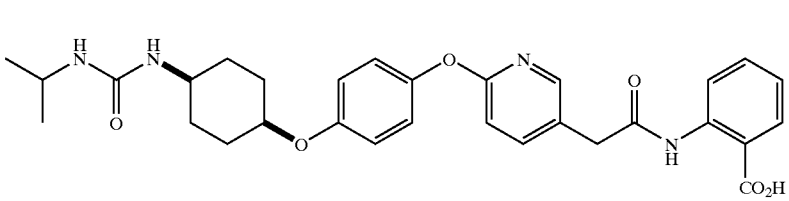 |
| 710 | 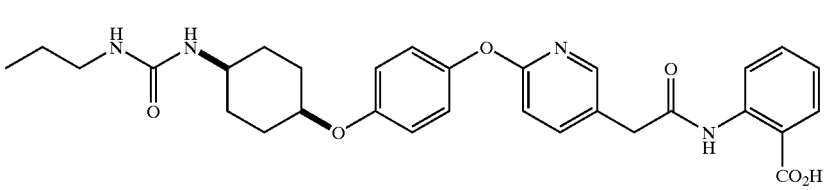 |
| 711 | 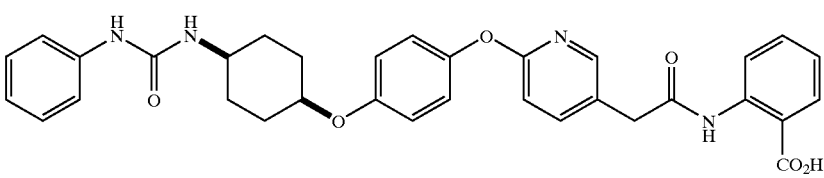 |
| 712 | 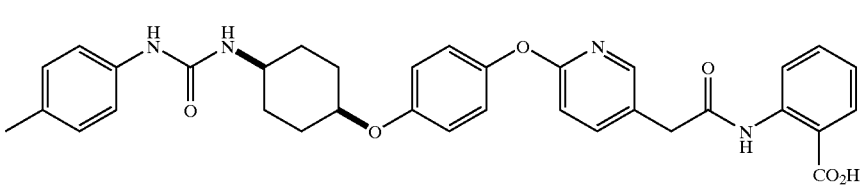 |

TABLE 25-continued
713 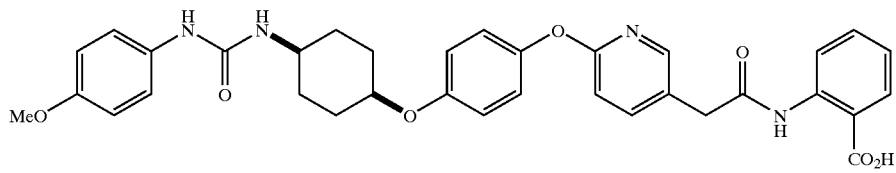
714 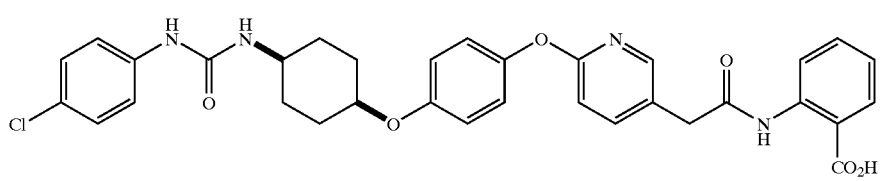
715 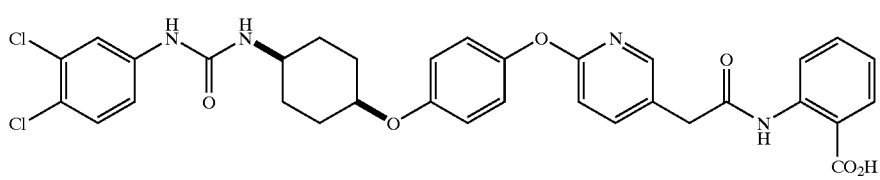
716 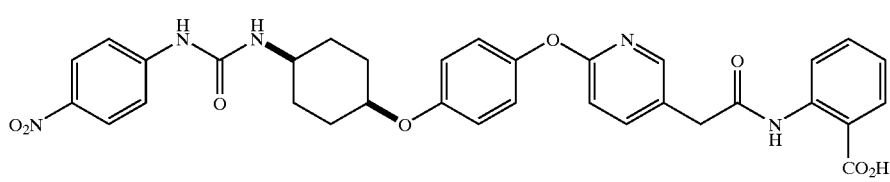
717 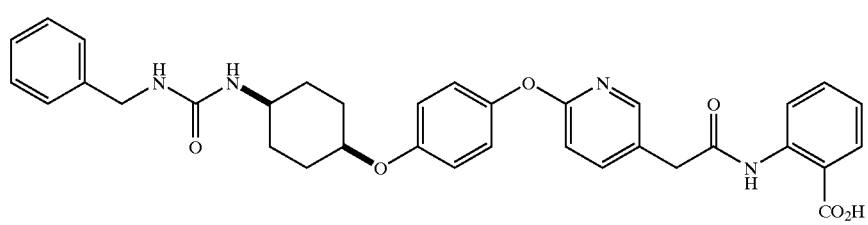
718 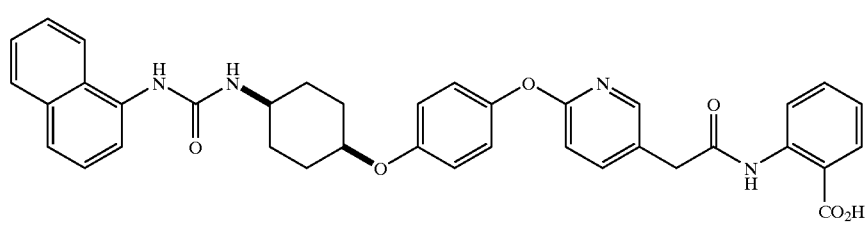
719 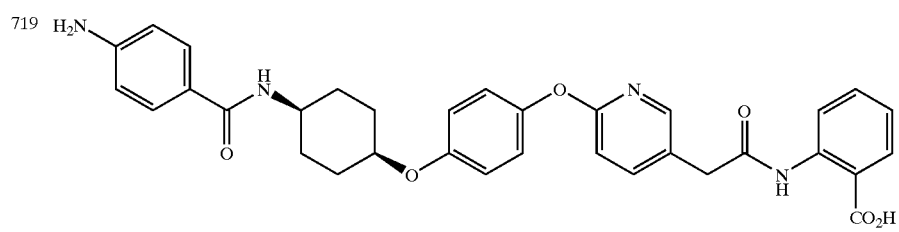

TABLE 25-continued
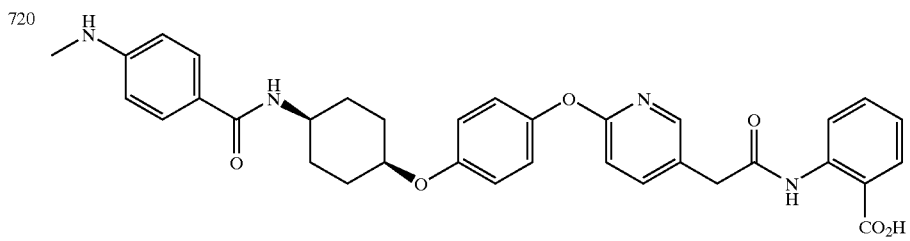
TABLE 26
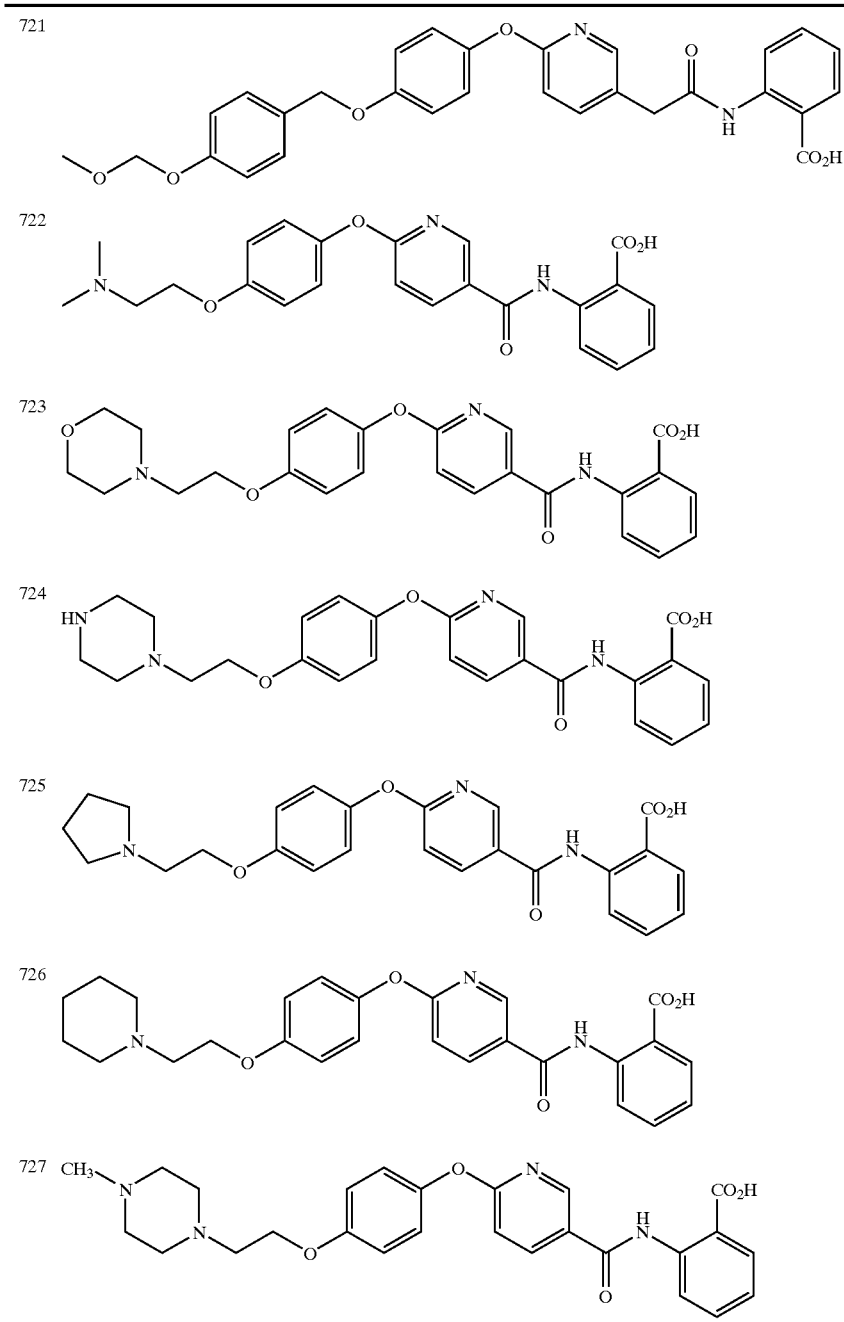

TABLE 26-continued
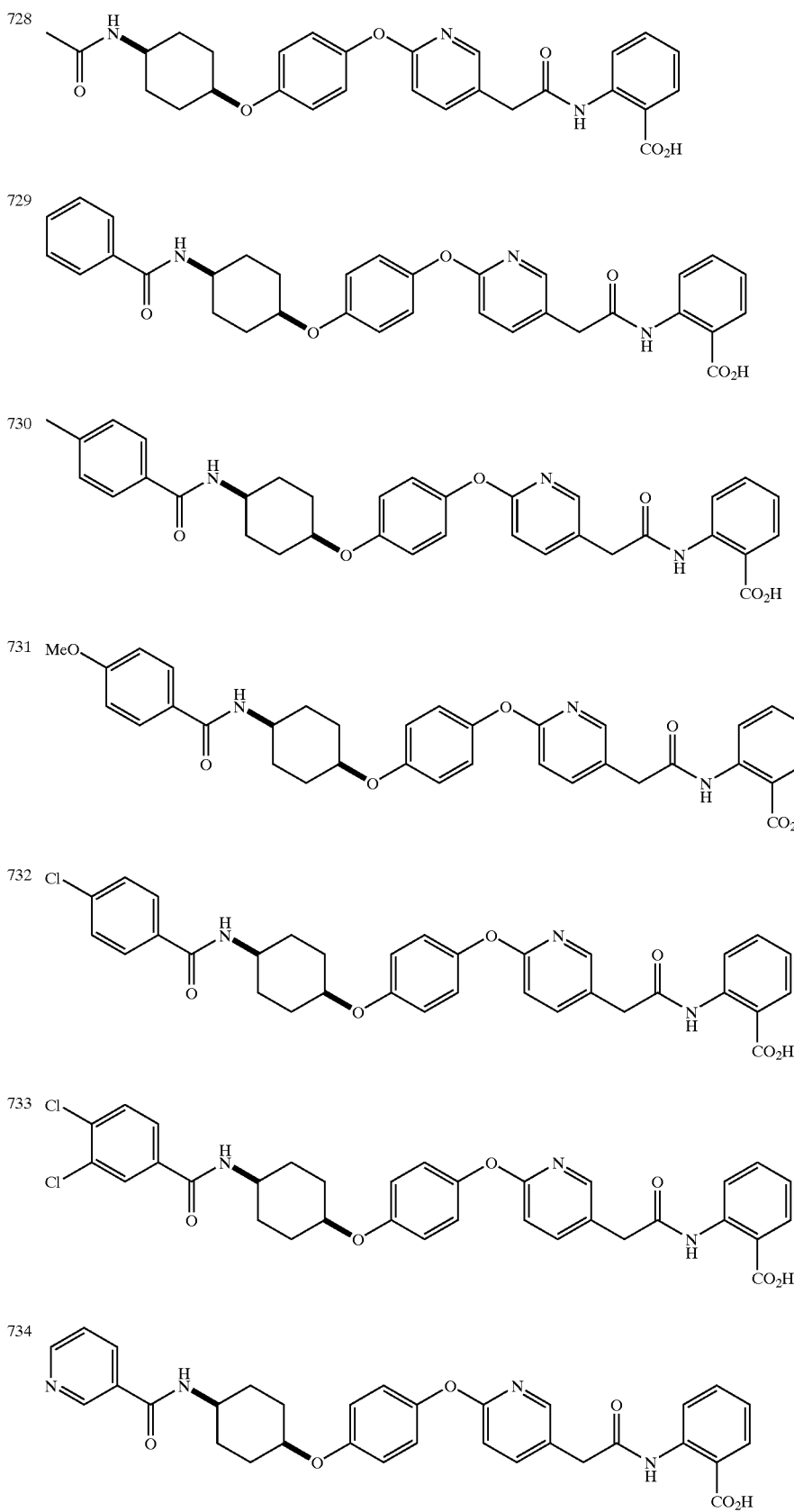

TABLE 26-continued
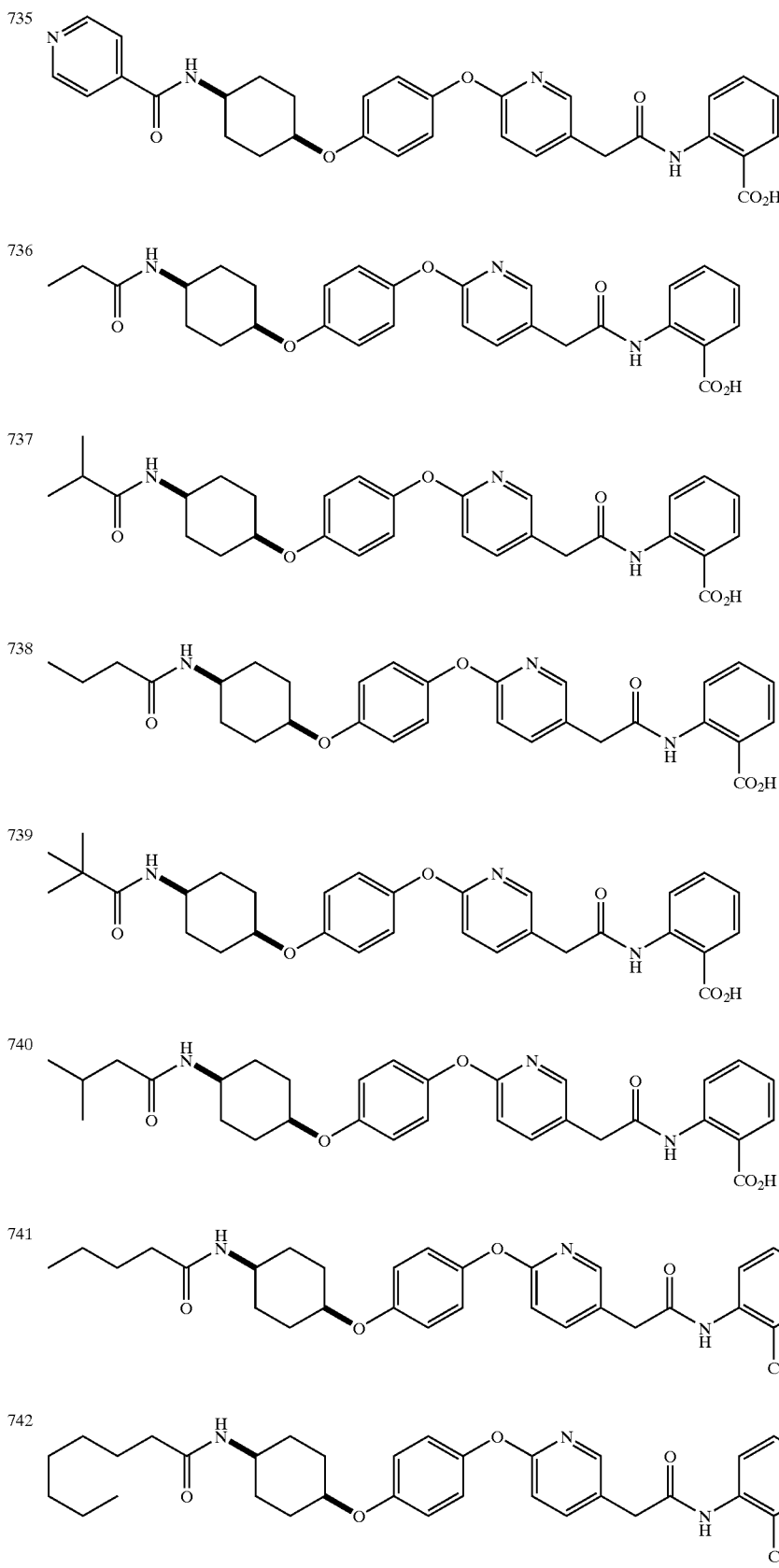

TABLE 26-continued
743 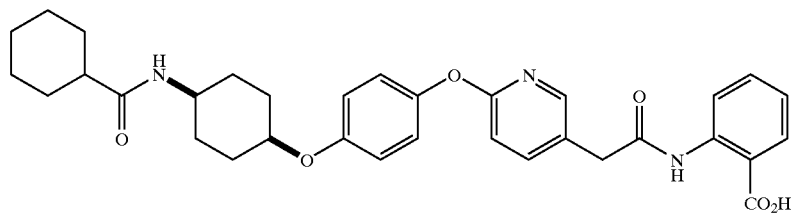
744 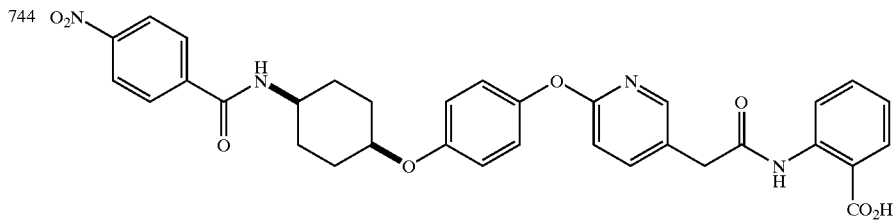
745 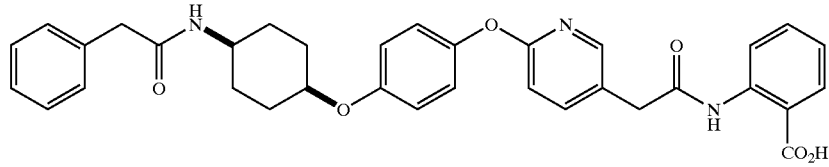
746 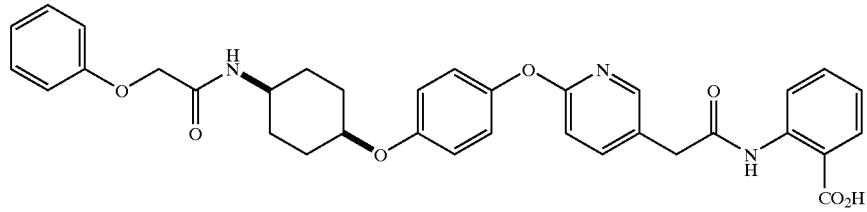
747 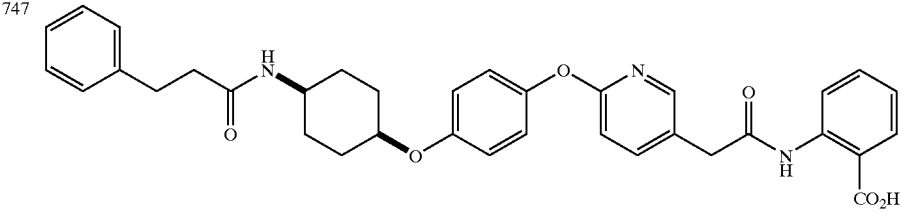
748 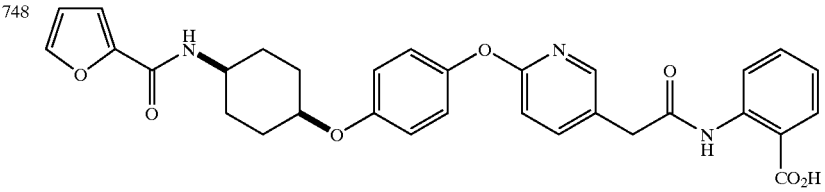
749 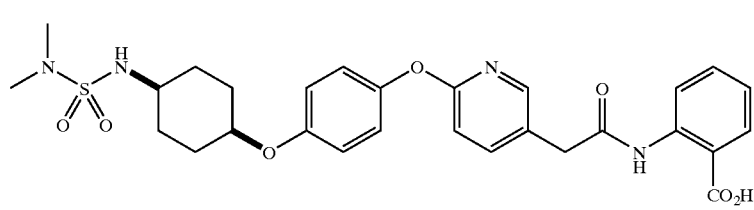

TABLE 26-continued
750 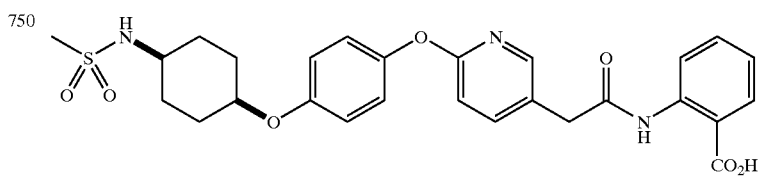
TABLE 27
751 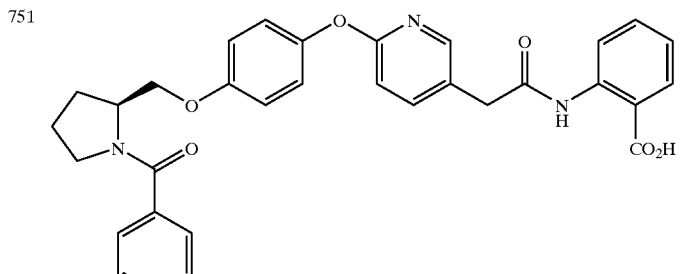
752 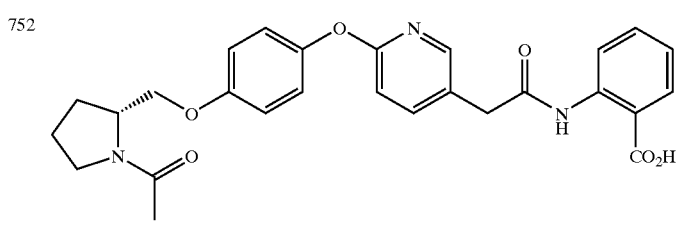
753 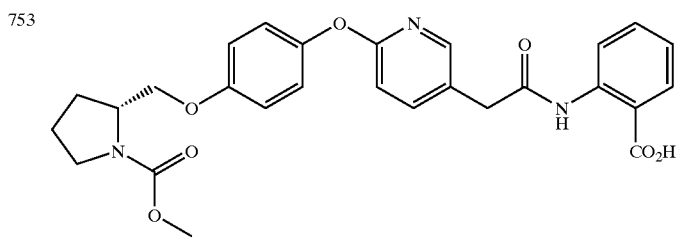
754 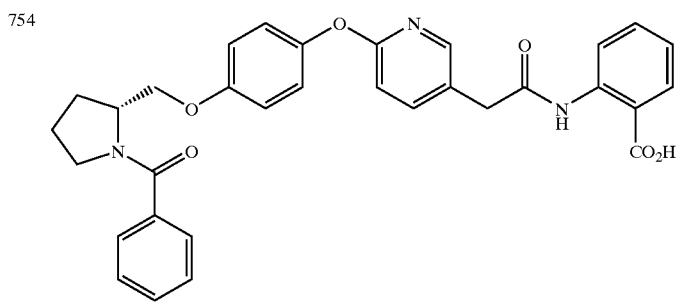
755 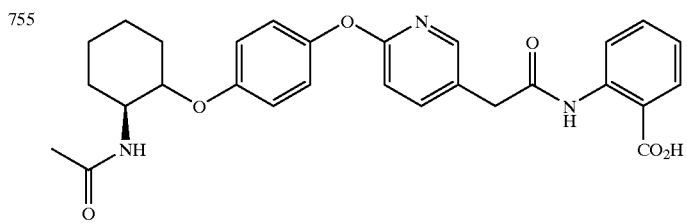

TABLE 27-continued
756 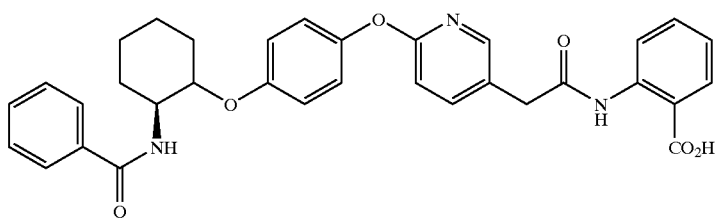
757 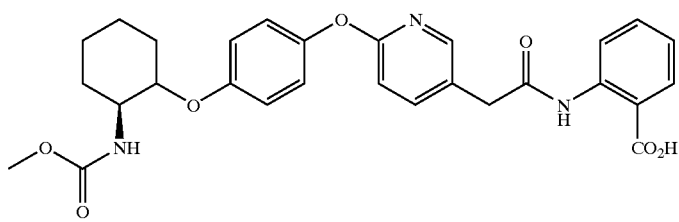
758 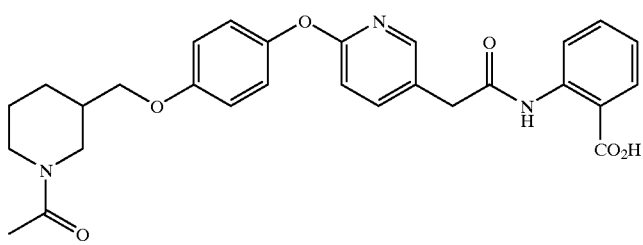
759 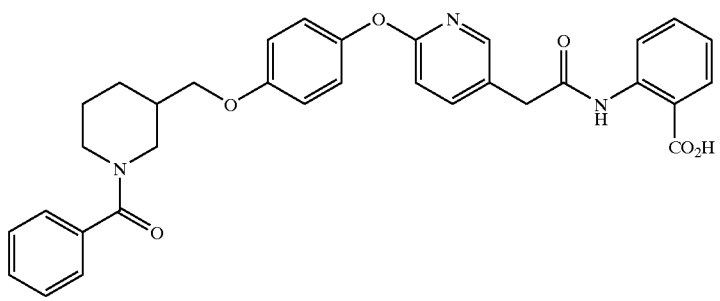
760 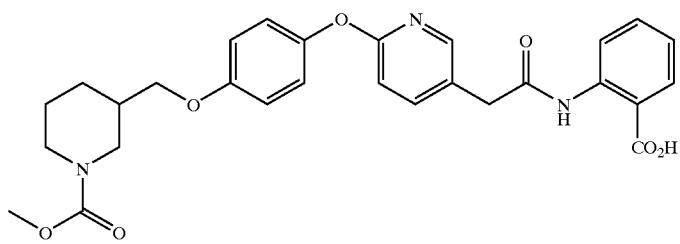
761 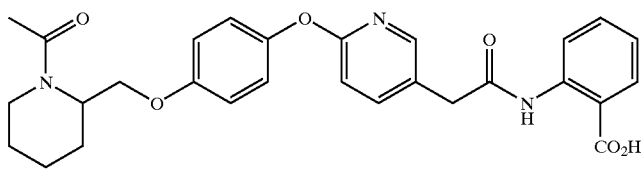

TABLE 27-continued
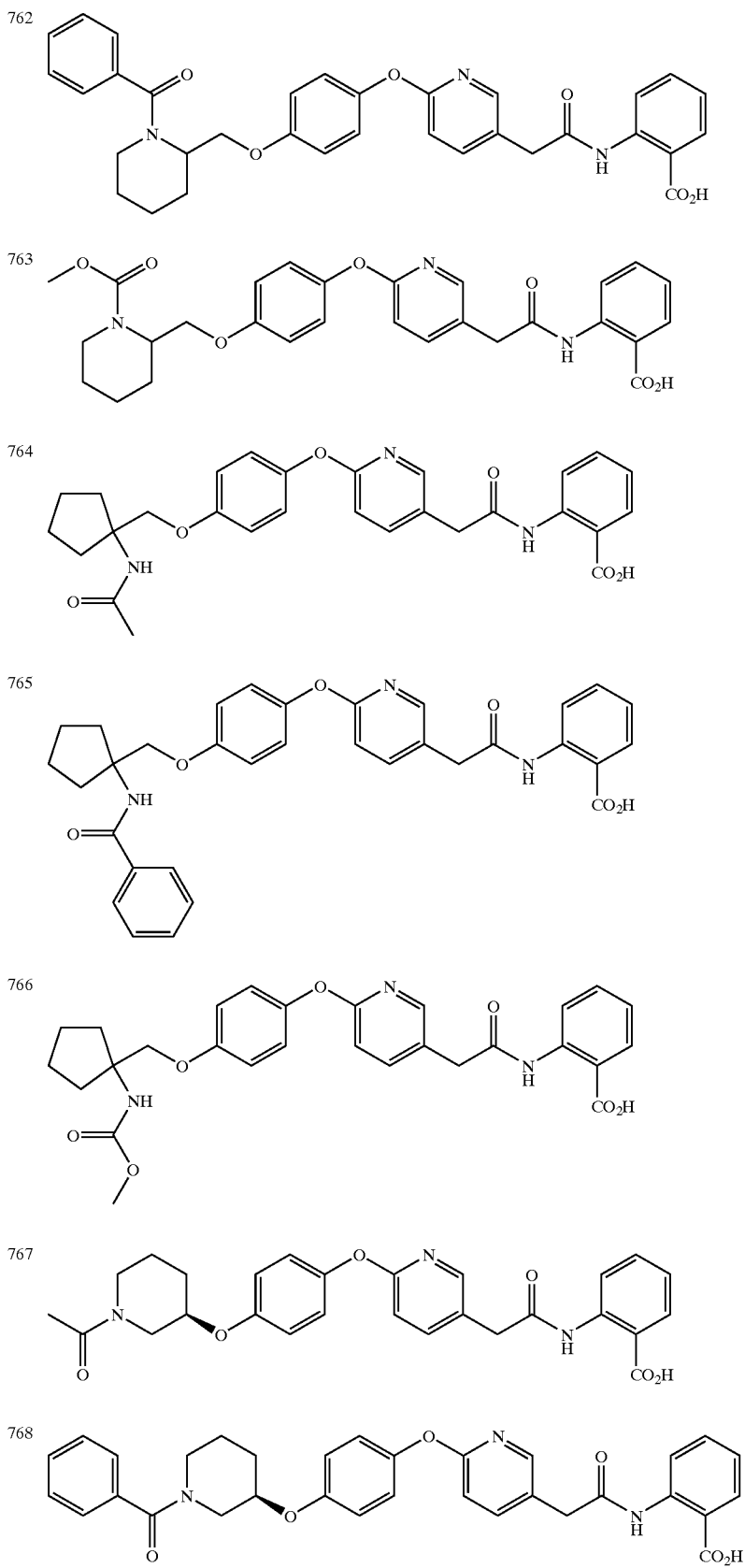

TABLE 27-continued
769 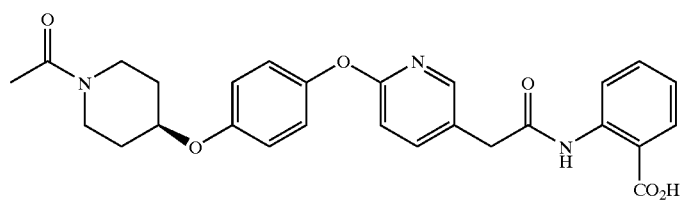
770 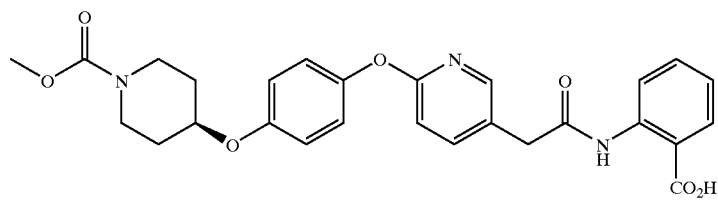
771 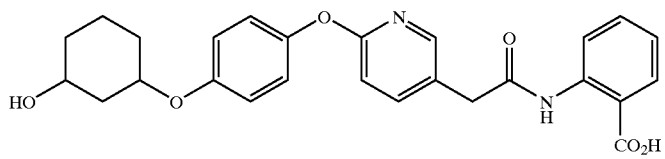
772 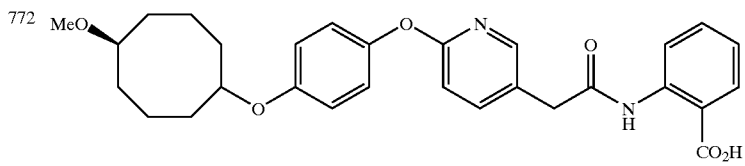
773 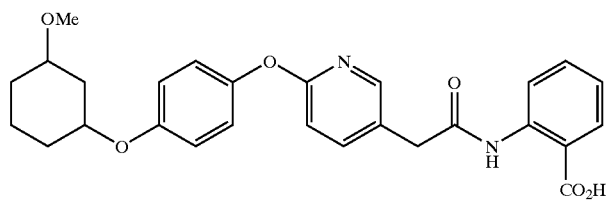
774 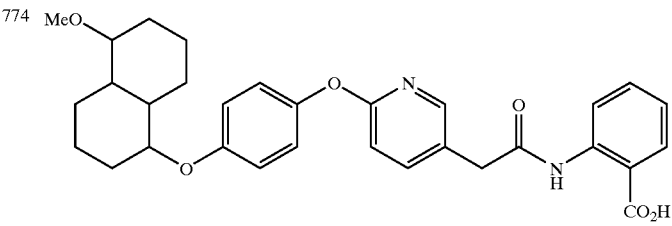
775 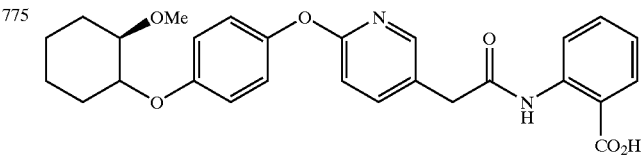
776 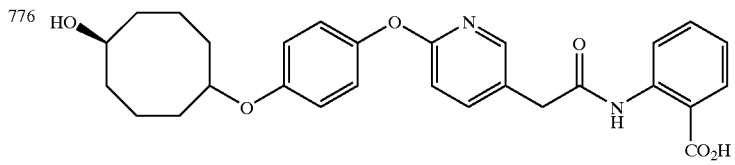

TABLE 27-continued
| | |
|---|---|
| 777 | 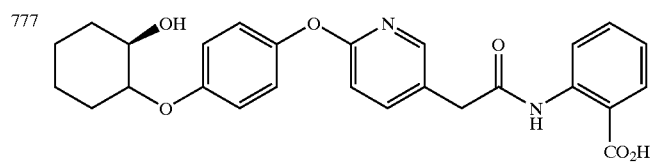 |
| 778 | 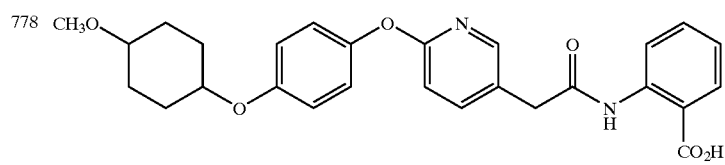 |
TABLE 28
| | |
|---|---|
| 779 | 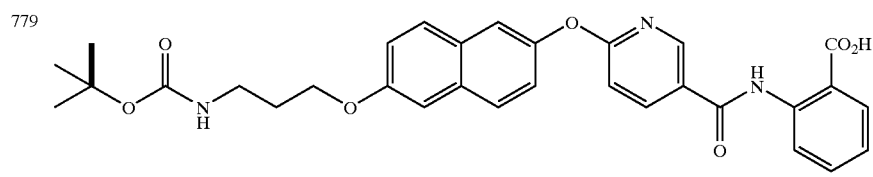 |
| 780 | 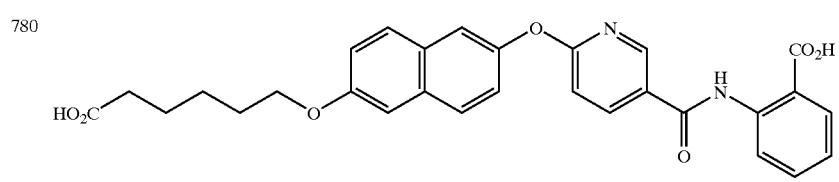 |
| 781 | 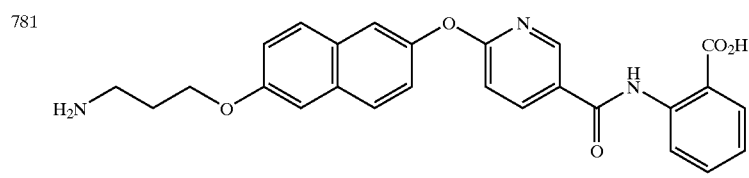 |
| 782 | 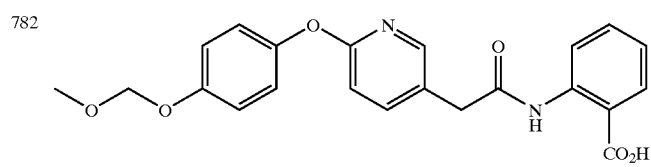 |
| 783 | 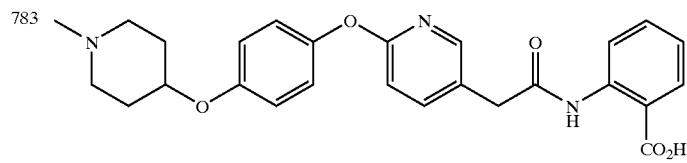 |
| 784 | 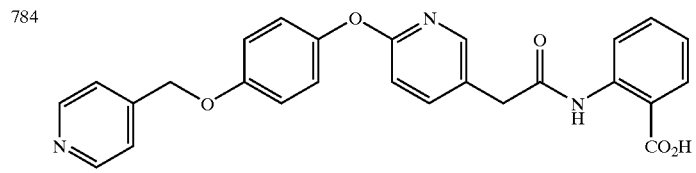 |

TABLE 28-continued

| 785 | (structure) |
| 786 | (structure) |
| 787 | (structure) |
| 788 | (structure) |
| 789 | (structure) |
| 790 | (structure) |
| 791 | (structure) |
| 792 | (structure) |

TABLE 28-continued
793 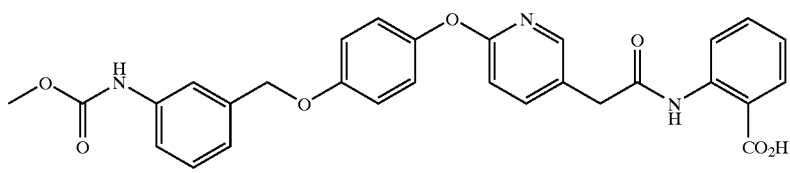
794 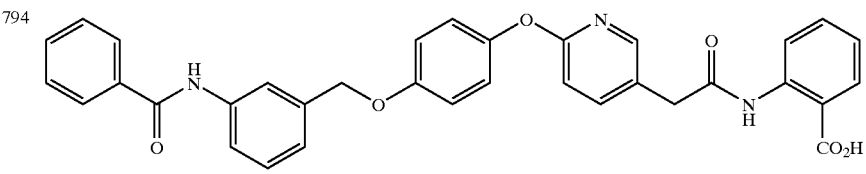
795 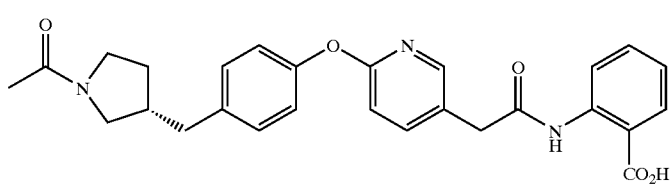
796 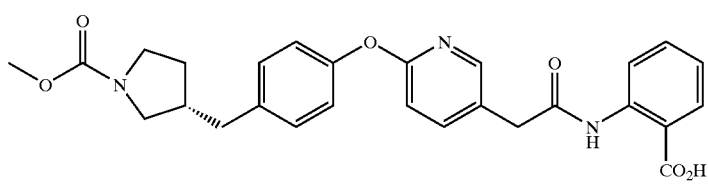
797 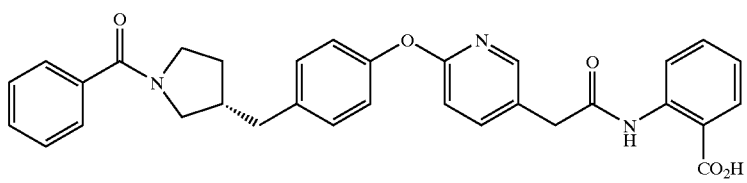
798 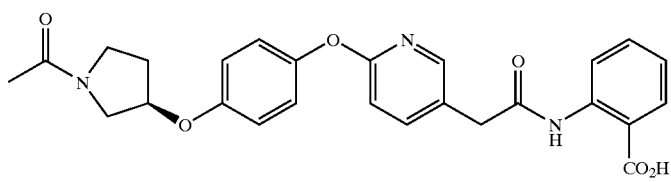
799 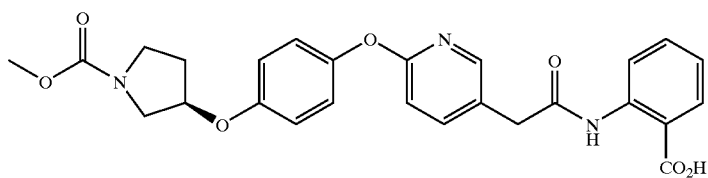
800 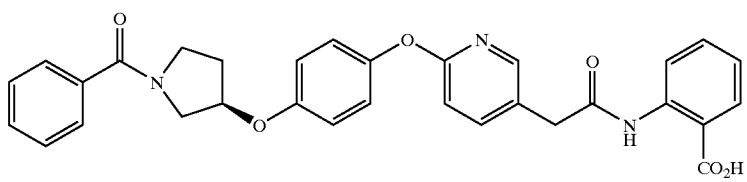

TABLE 28-continued
801 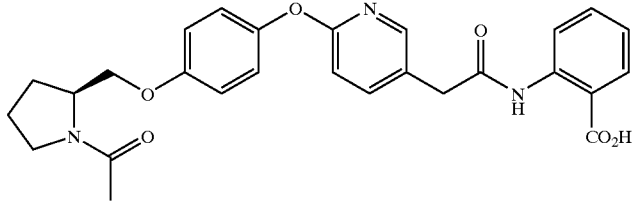
802 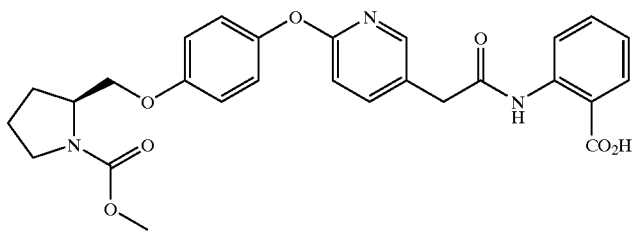
TABLE 29
803 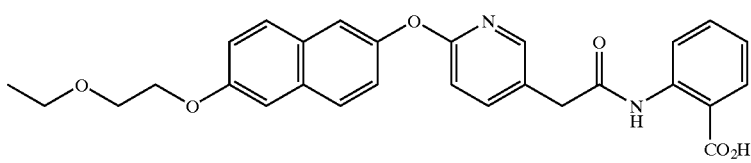
804 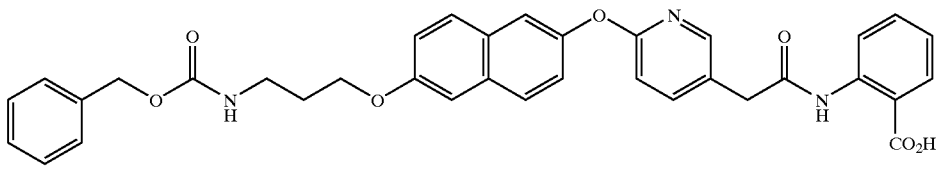
805 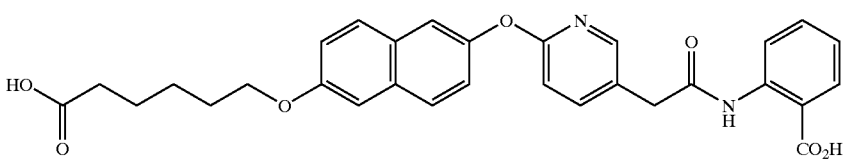
806 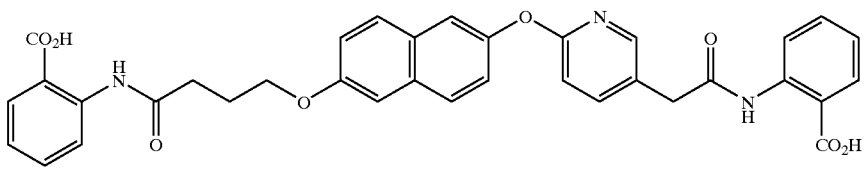
807 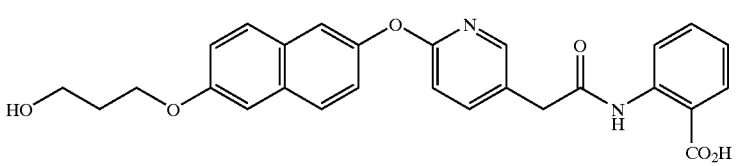
808 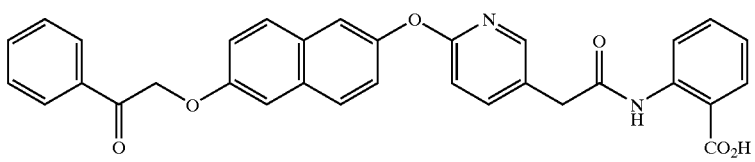

TABLE 29-continued

| | |
|---|---|
| 809 | [structure: morpholine-N-CH2CH2-O-naphthalene-O-pyridine-CH2-C(O)NH-phenyl-CO2H] |
| 810 | [structure: N-methylpiperidine-O-naphthalene-O-pyridine-CH2-C(O)NH-phenyl-CO2H] |
| 811 | [structure: HO-CH2CH2CH2-O-naphthalene-O-pyridine-CH2-C(O)NH-phenyl-CO2H] |
| 812 | [structure: ethyl-O-CH2CH2-O-naphthalene-O-pyridine-CH2-C(O)NH-phenyl-CO2H] |
| 813 | [structure: piperazine-CH2CH2-O-naphthalene-O-pyridine-CH2-C(O)NH-phenyl-CO2H] |
| 814 | [structure: morpholine-CH2CH2-O-naphthalene-O-pyridine-CH2-C(O)NH-phenyl-CO2H] |
| 815 | [structure: 4-pyridyl-CH2-O-naphthalene-O-pyridine-CH2-C(O)NH-phenyl-CO2H] |
| 816 | [structure: piperidine-CH2CH2-O-naphthalene-O-pyridine-CH2-C(O)NH-phenyl-CO2H] |
| 817 | [structure: pyrrolidine-CH2CH2-O-naphthalene-O-pyridine-CH2-C(O)NH-phenyl-CO2H] |

TABLE 29-continued
| 818 | 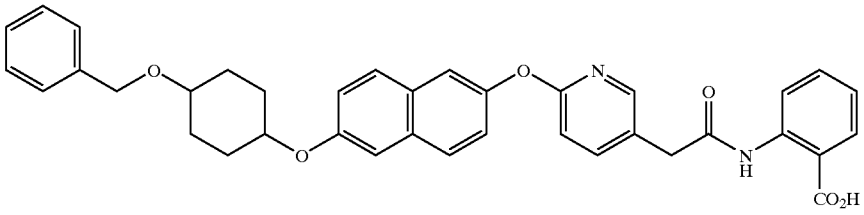 |
| 819 | 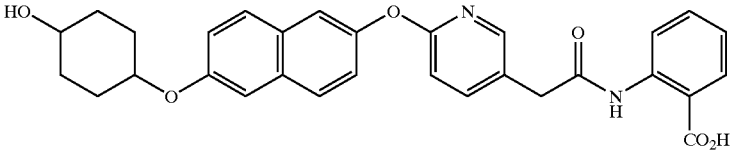 |
| 820 | 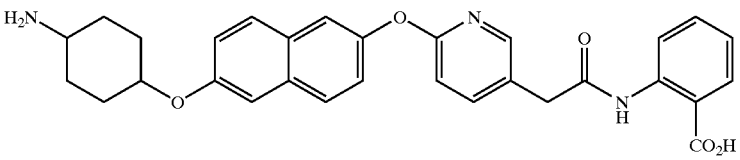 |
| 821 | 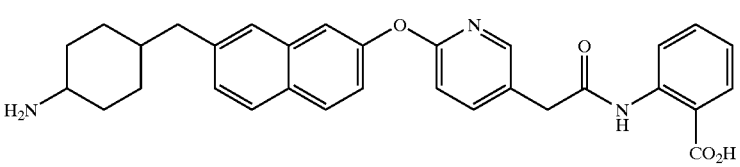 |
| 822 | 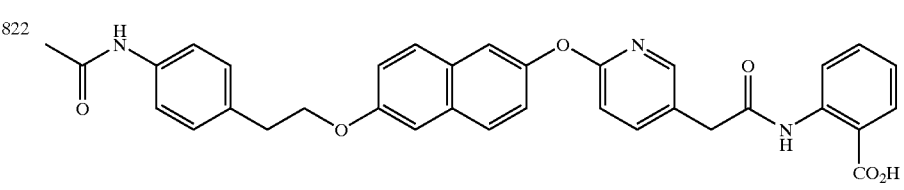 |
| 823 | 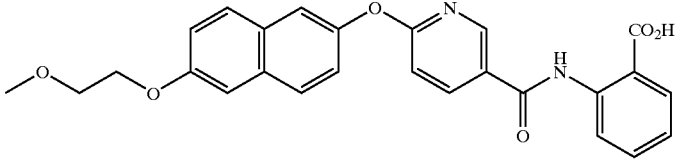 |
| 824 | 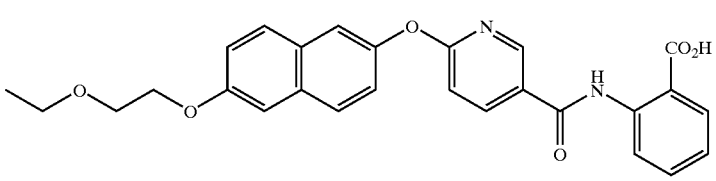 |
| 825 | 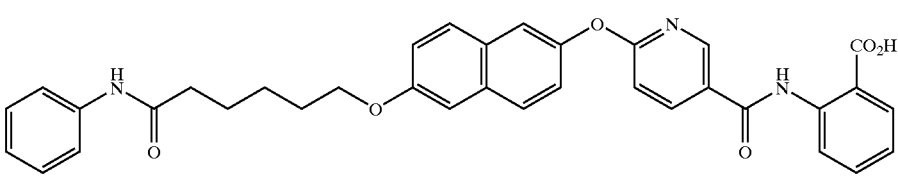 |
| 826 | 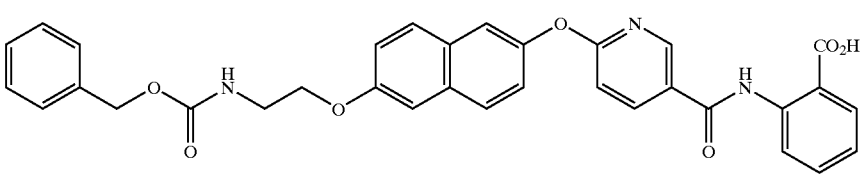 |

TABLE 29-continued
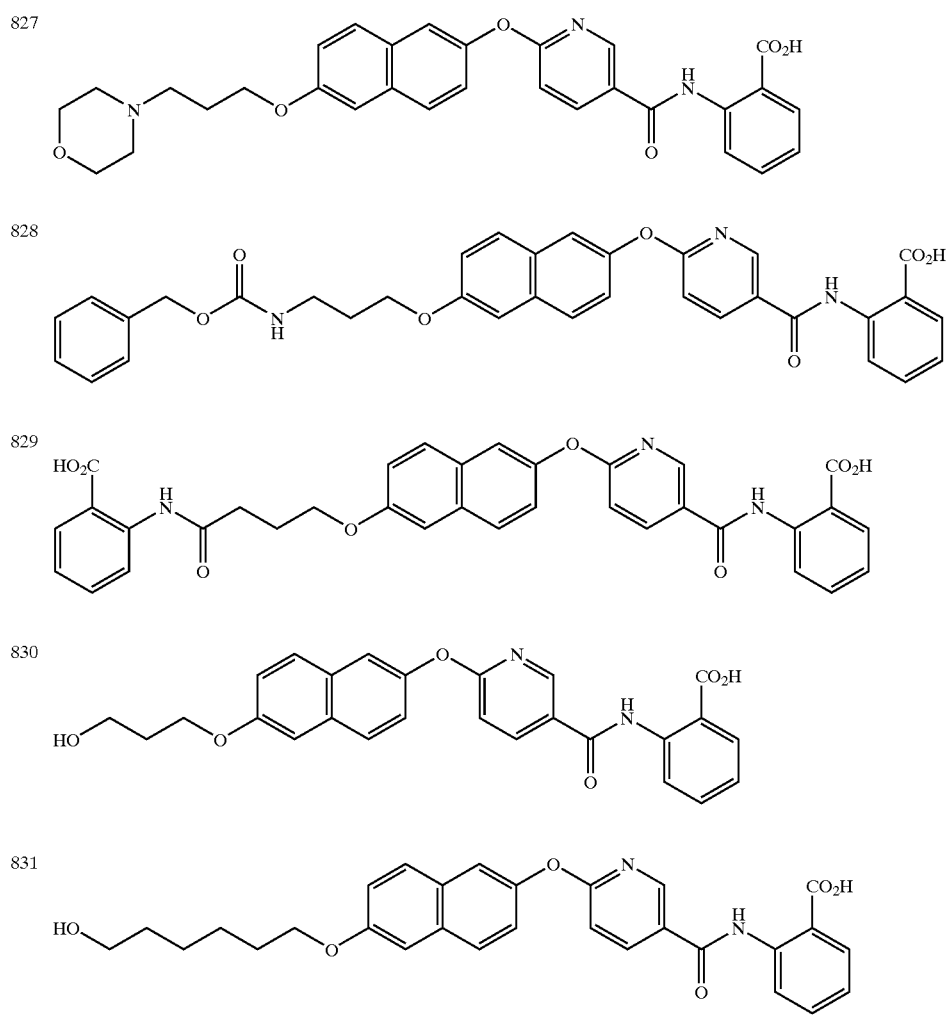
TABLE 30
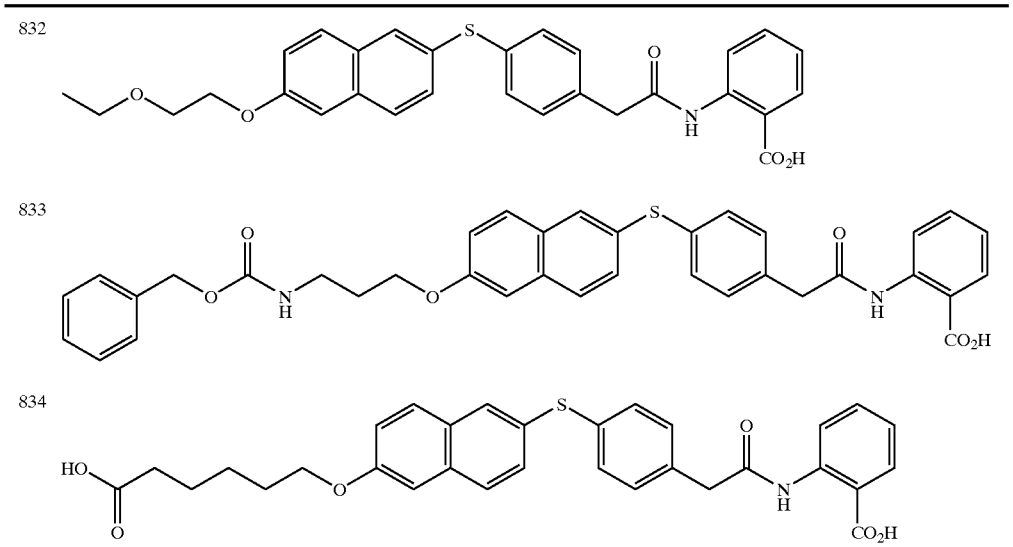

TABLE 30-continued

TABLE 30-continued
844 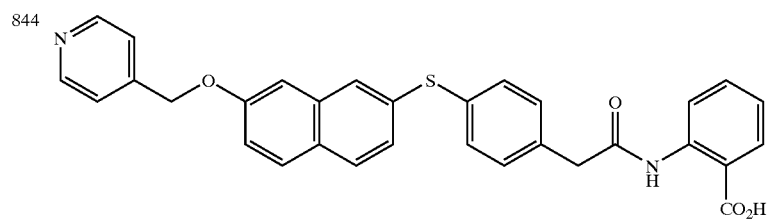
845 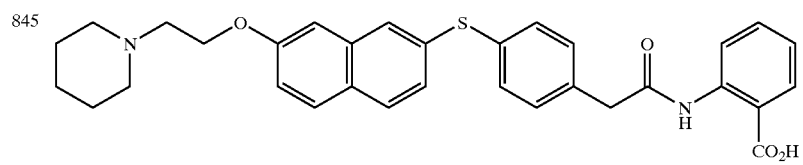
846 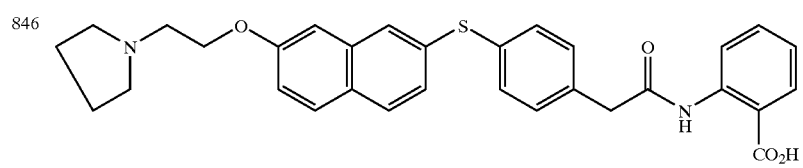
847 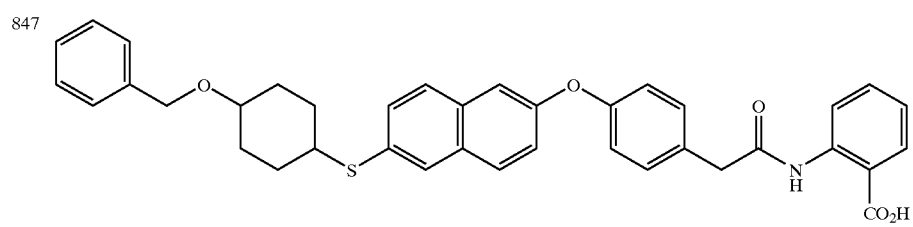
848 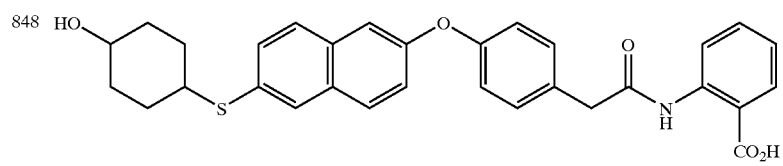
849 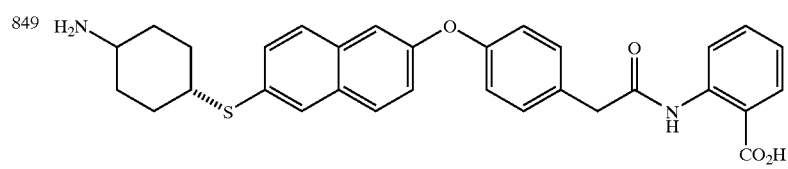
850 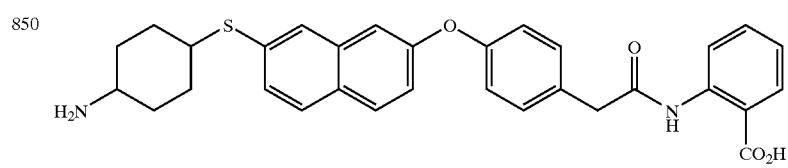
851 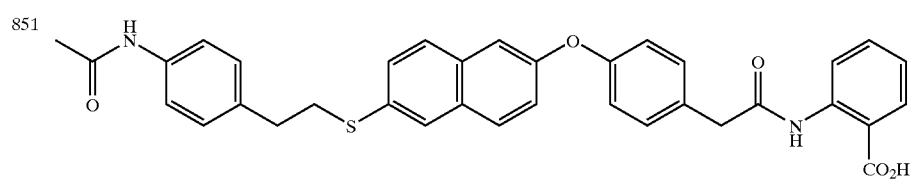

TABLE 30-continued

| 852 | (structure) |
| 853 | (structure) |
| 854 | (structure) |
| 855 | (structure) |
| 856 | (structure) |
| 857 | (structure) |
| 858 | (structure) |
| 859 | (structure) |
| 860 | (structure) |

TABLE 30-continued
861 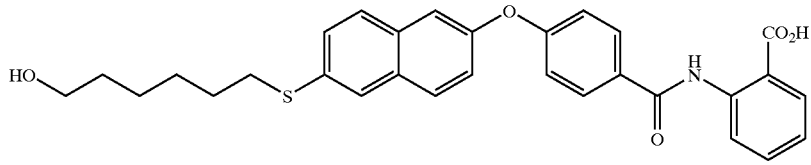
TABLE 31
862 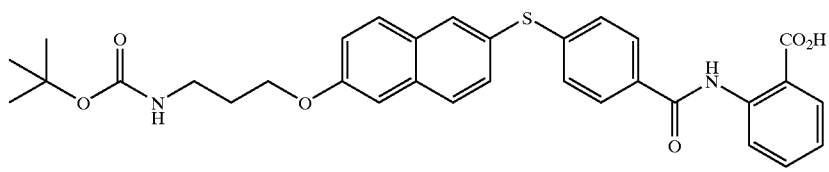
863 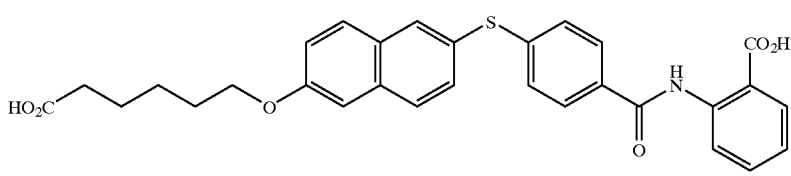
864 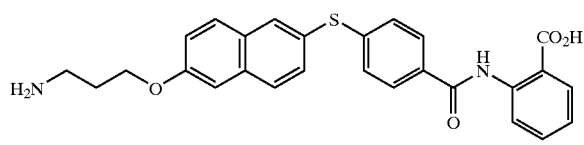
865 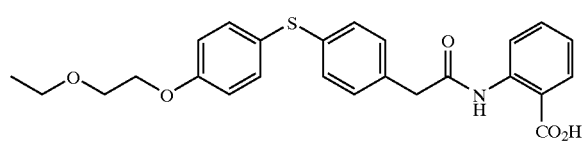
866 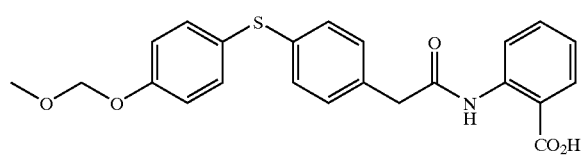
867 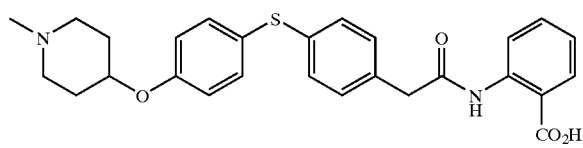
868 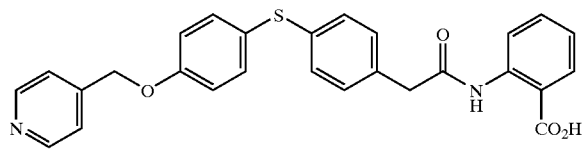
869 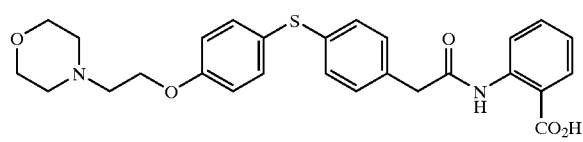

TABLE 31-continued

| | |
|---|---|
| 870 | (structure) |
| 871 | (structure) |
| 872 | (structure) |
| 873 | (structure) |
| 874 | (structure) |
| 875 | (structure) |
| 876 | (structure) |
| 877 | (structure) |
| 878 | (structure) |
| 879 | (structure) |

TABLE 31-continued
| 880 |  |
| 881 | 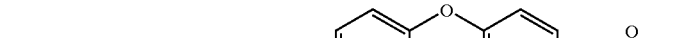 |
| 882 |  |
| 883 | 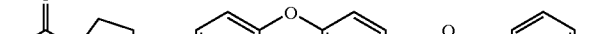 |
| 884 |  |
| 885 | 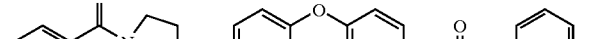 |
| 886 | 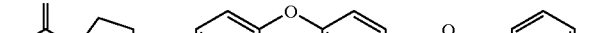 |
| 887 |  |
| 888 |  |

TABLE 31-continued
889 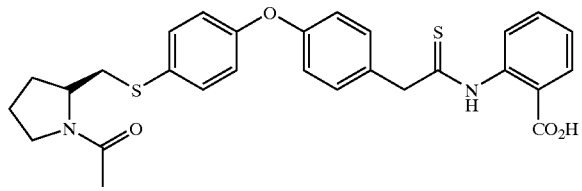
890 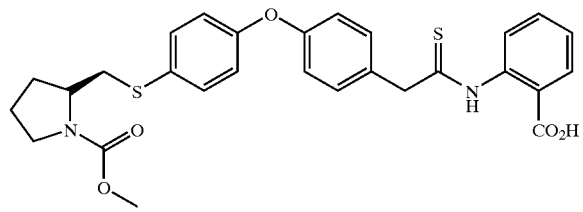
TABLE 32
891 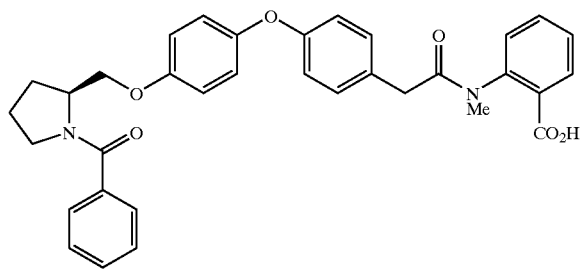
892 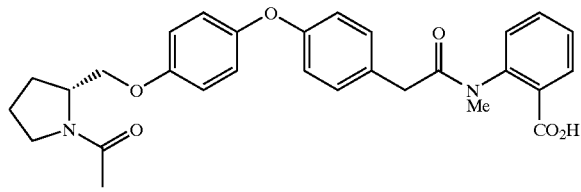
893 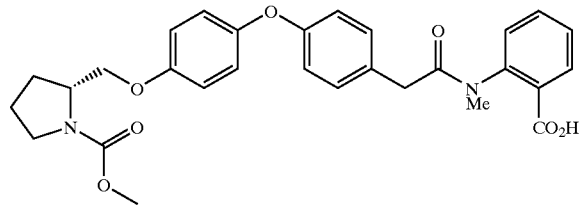
894 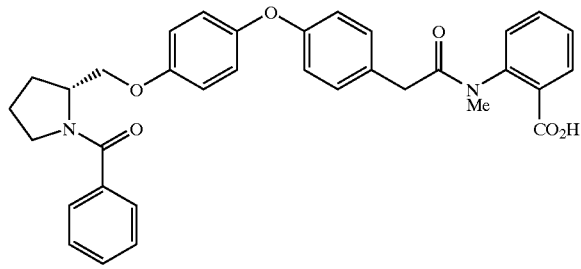

TABLE 32-continued
895 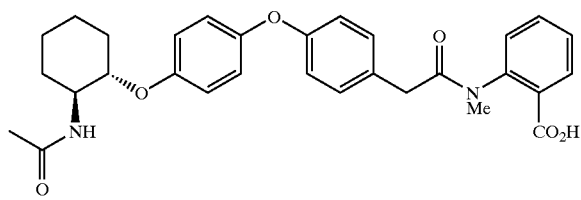
896 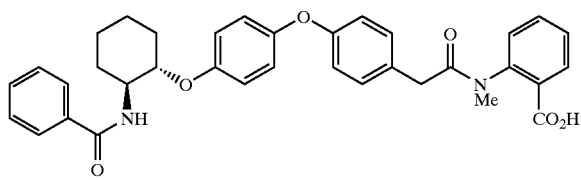
897 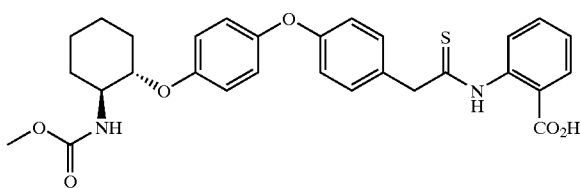
898 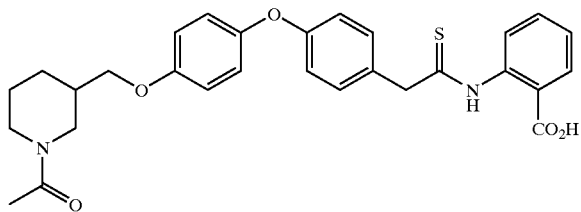
899 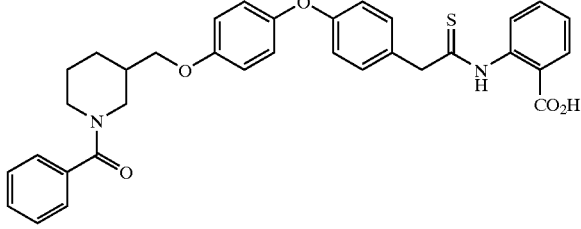
900 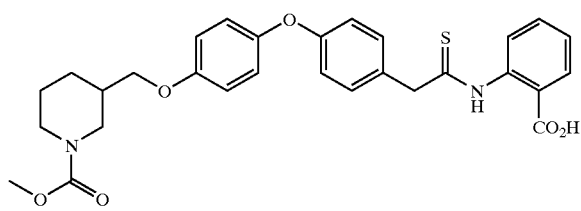
901 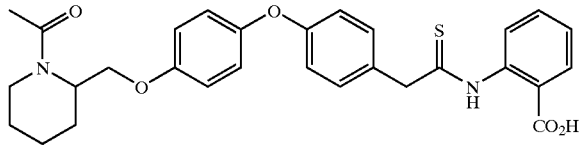

TABLE 32-continued
902 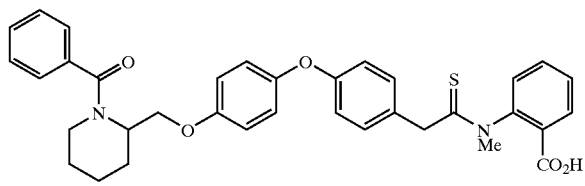
903 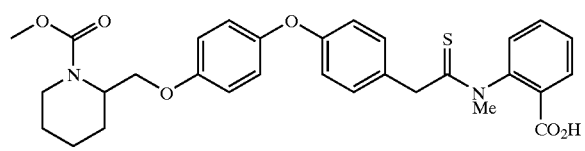
904 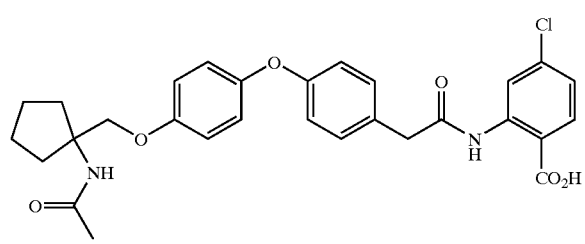
905 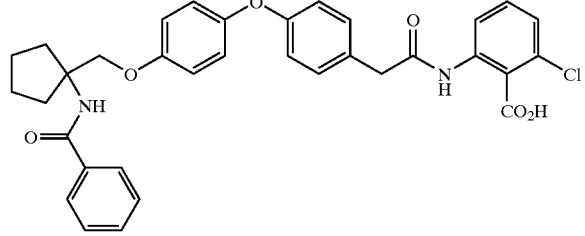
906 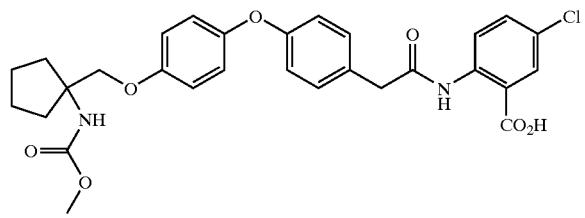
907 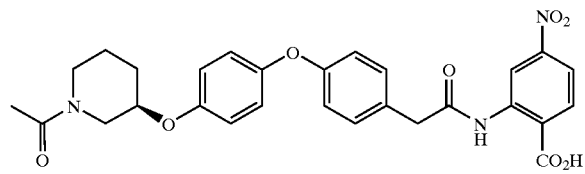
908 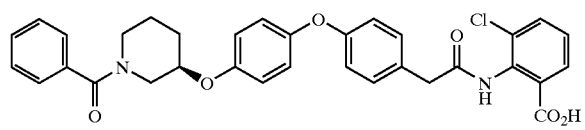
909 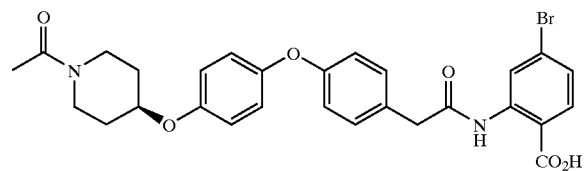

TABLE 32-continued

| 910 | (structure) |
| 911 | (structure) |
| 912 | (structure) |
| 913 | (structure) |
| 914 | (structure) |
| 915 | (structure) |
| 916 | (structure) |
| 917 | (structure) |
| 918 | (structure) |

TABLE 33

| | |
|---|---|
| 919 | |
| 920 | |
| 921 | |
| 922 | |
| 923 | |
| 924 | |
| 925 | |
| 926 | |

TABLE 33-continued
927 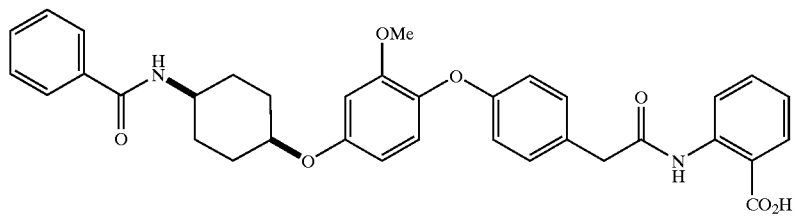
928 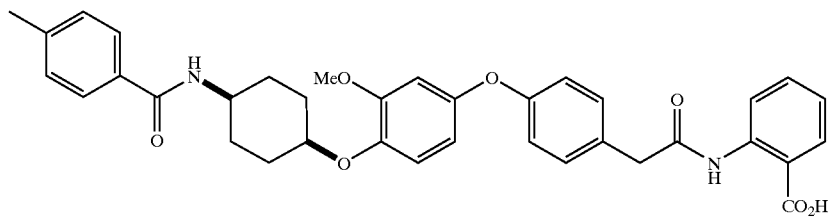
929 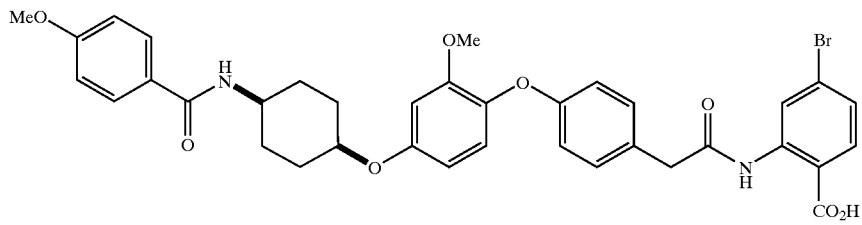
930 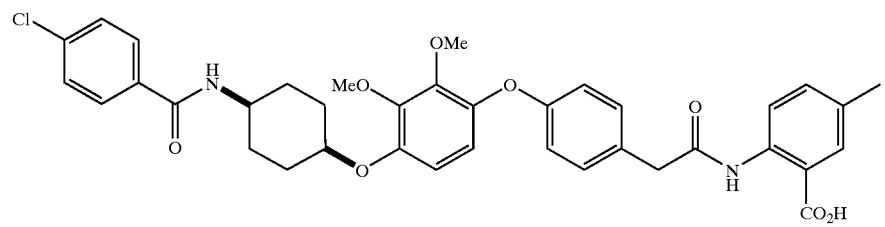
931 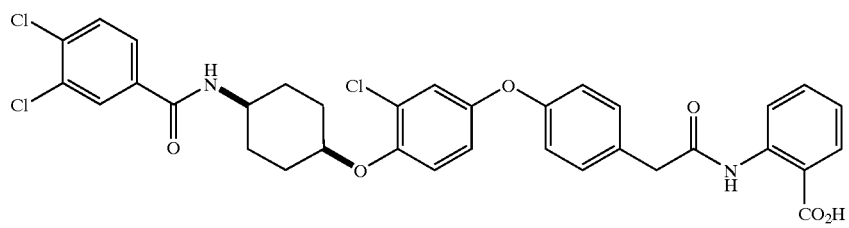
932 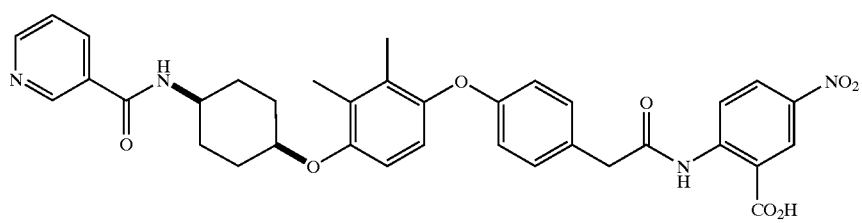
933 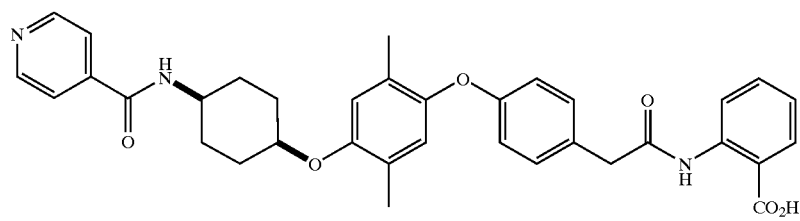

TABLE 33-continued
934 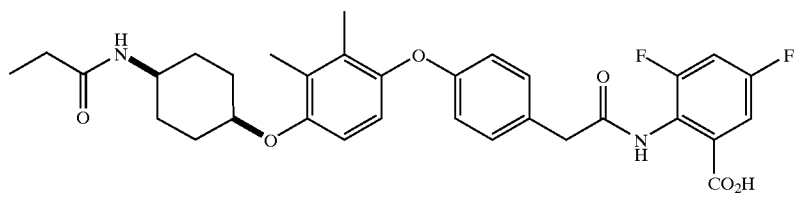
935 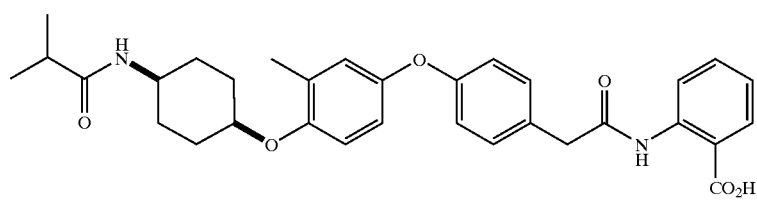
936 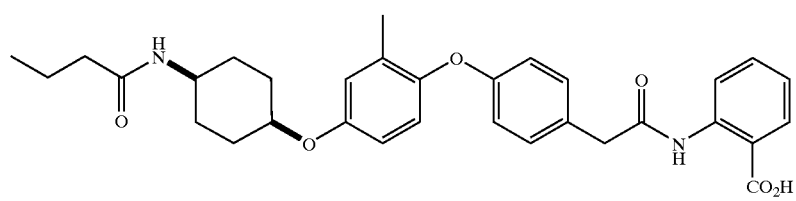
937 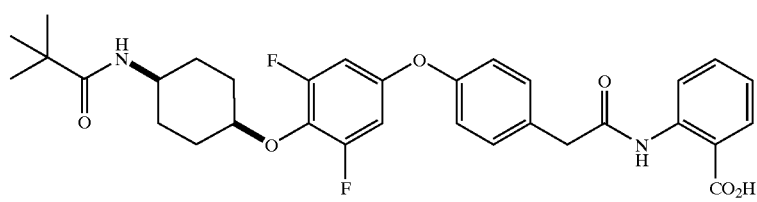
938 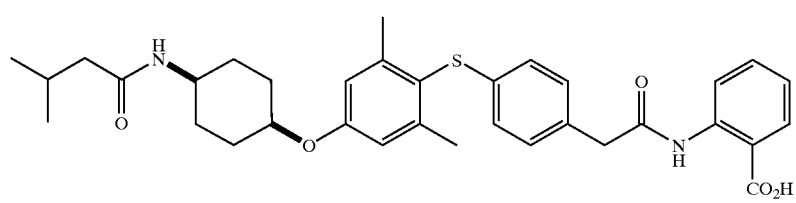
939 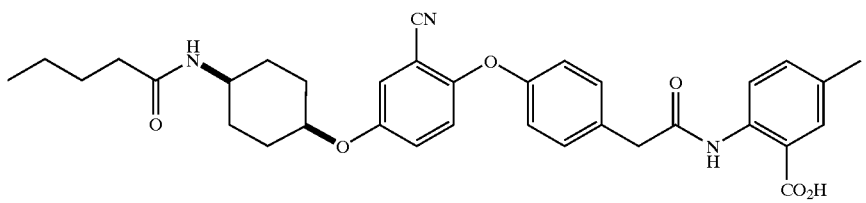
940 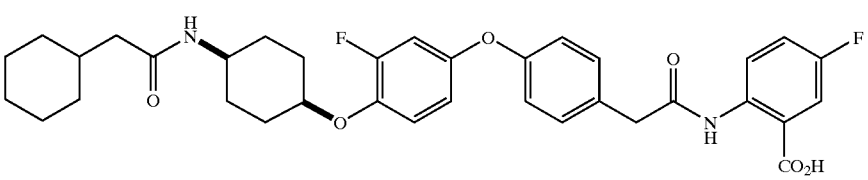

TABLE 33-continued
941 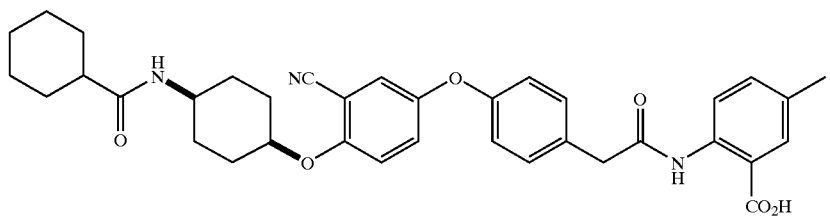
942 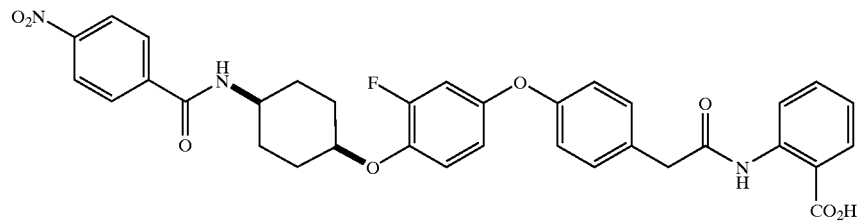
943 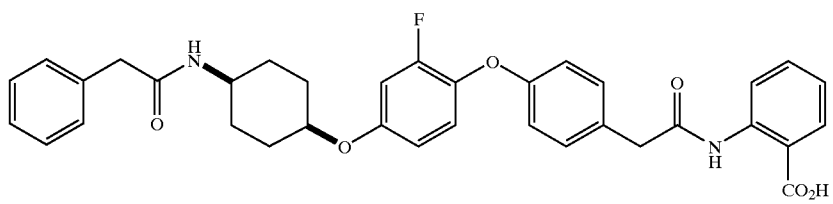
944 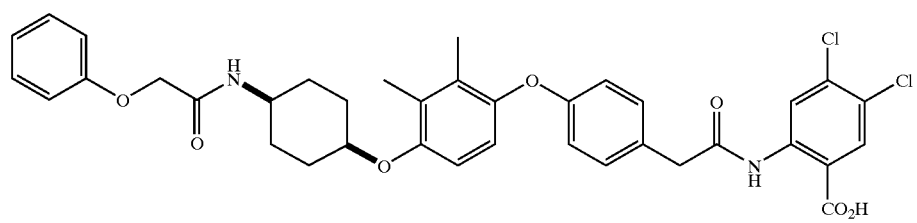
945 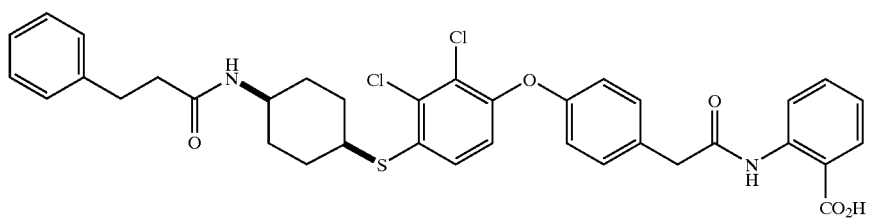
946 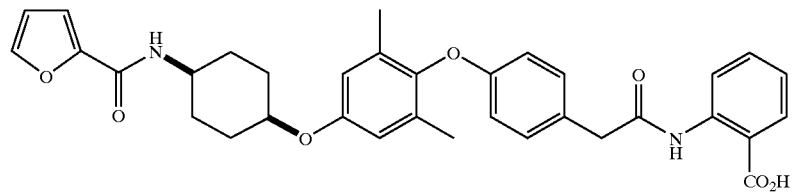
947 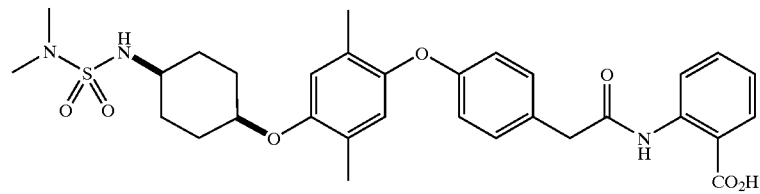

TABLE 33-continued
948 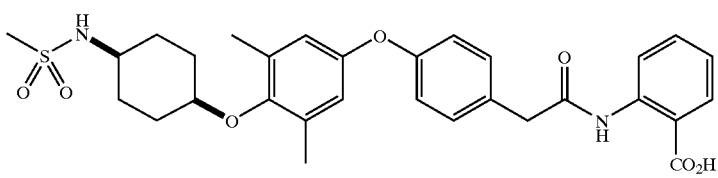
TABLE 34
949 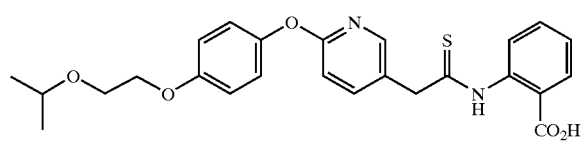
950 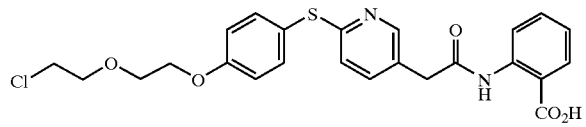
951 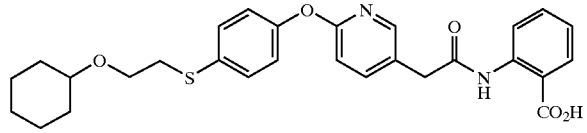
952 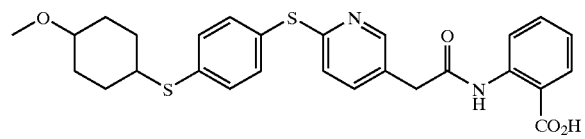
953 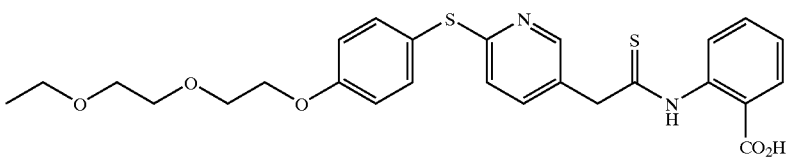
954 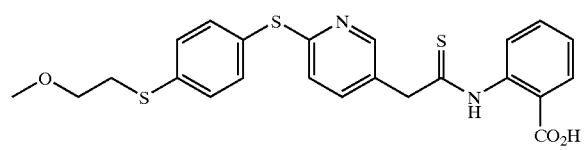
955 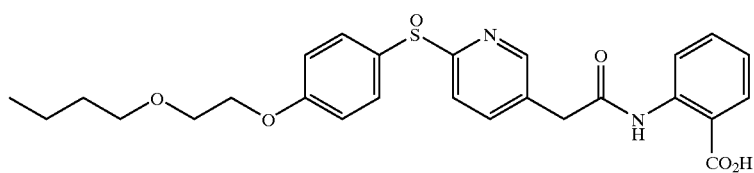
956 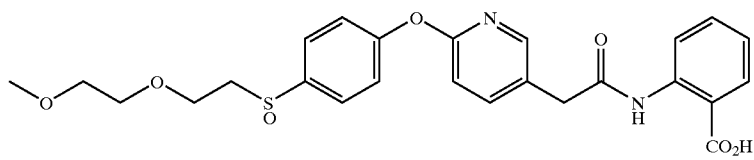

TABLE 34-continued
957 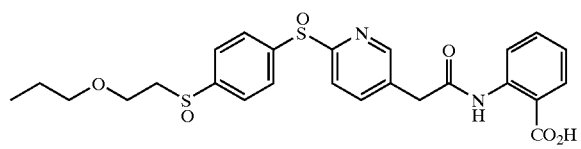
958 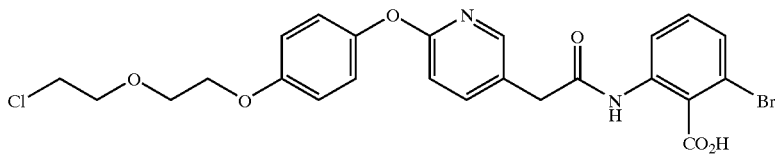
959 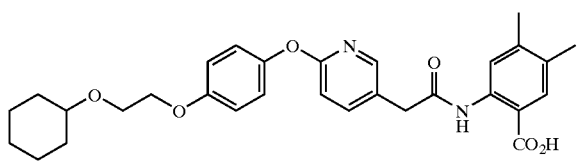
960 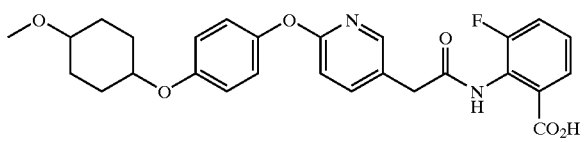
961 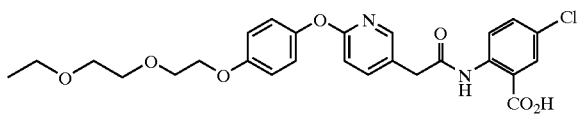
962 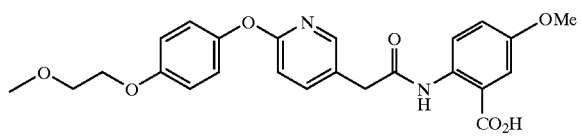
963 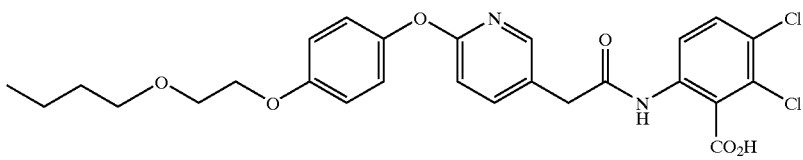
964 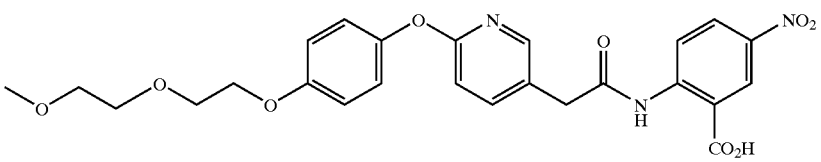
965 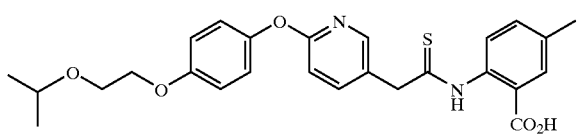
966 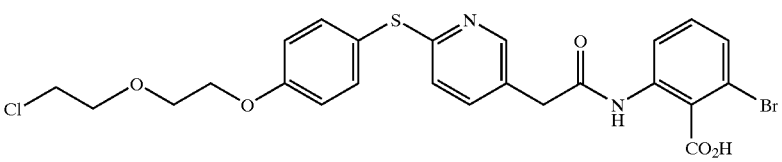

TABLE 34-continued
| 967 | 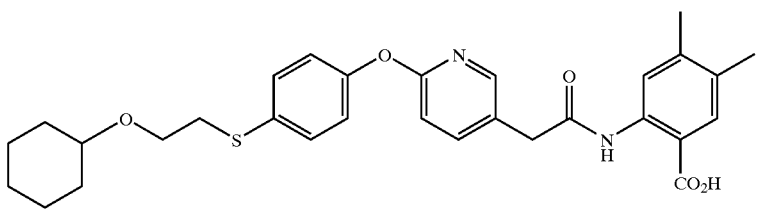 |
| 968 | 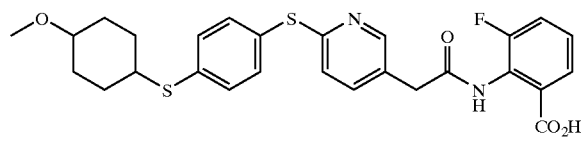 |
| 969 | 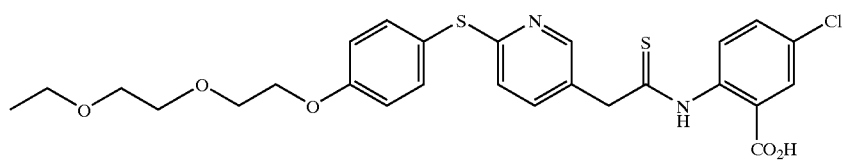 |
| 970 | 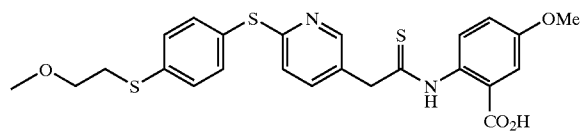 |
| 971 | 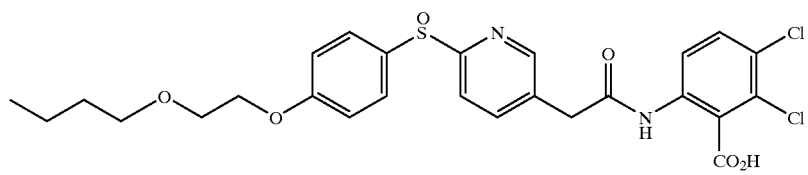 |
| 972 | 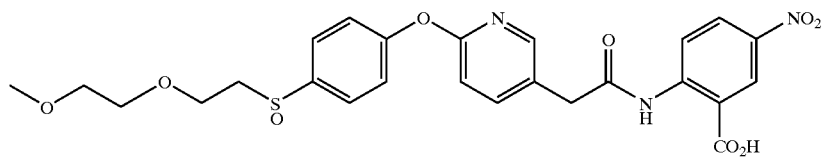 |
| 973 | 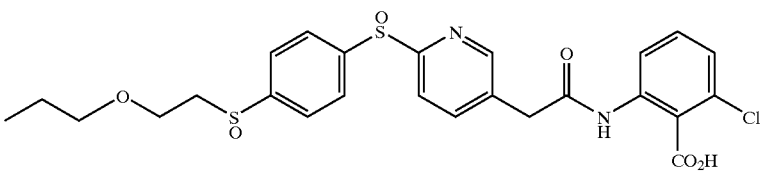 |
| 974 | 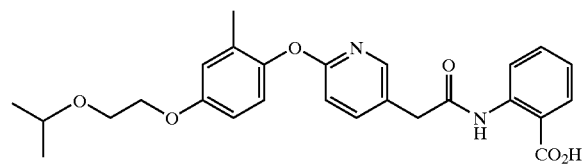 |
| 975 | 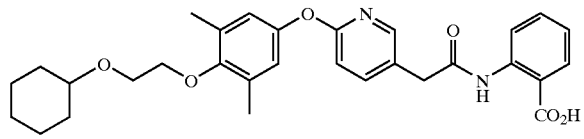 |

TABLE 34-continued
976 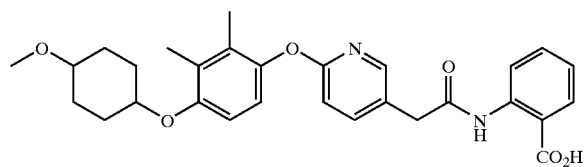
977 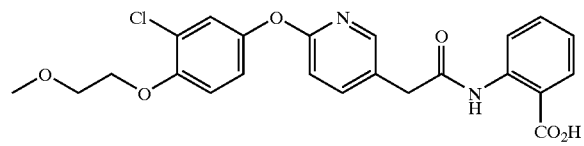
978 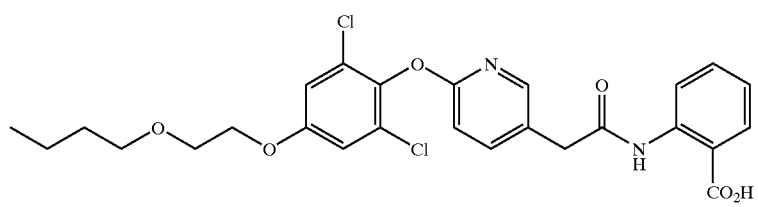
979 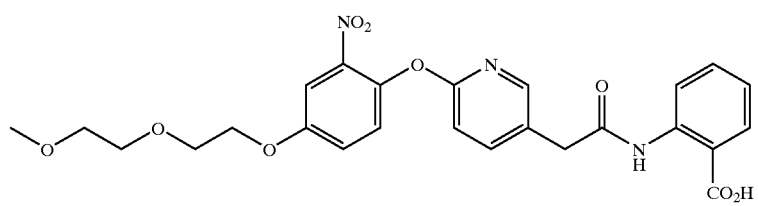
980 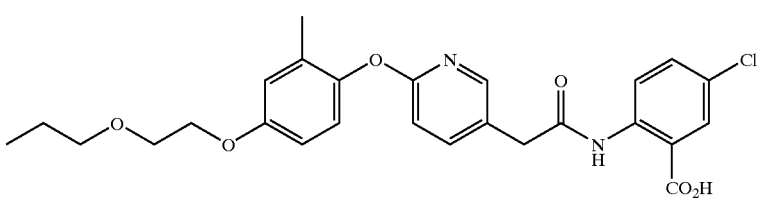
TABLE 35
981 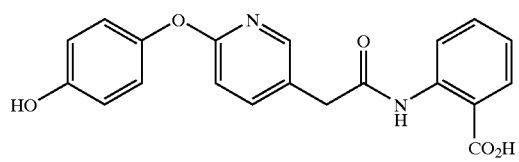
982 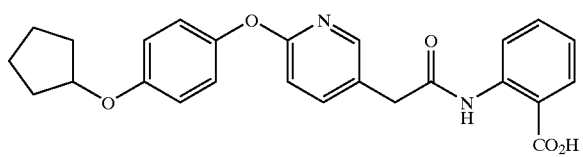
983 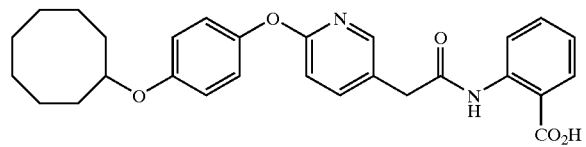

TABLE 35-continued
984 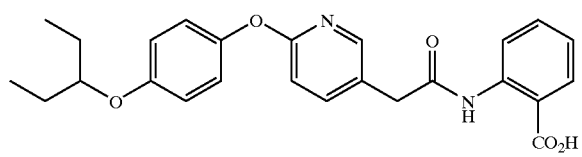
985 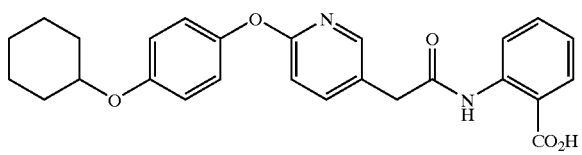
986 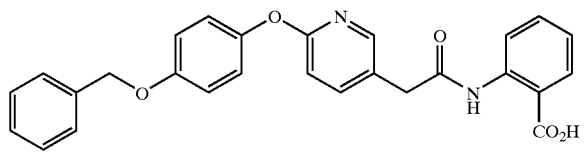
987 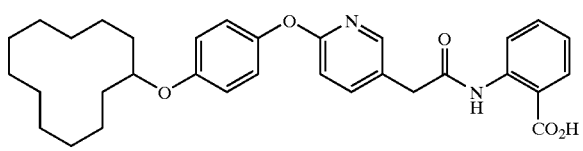
988 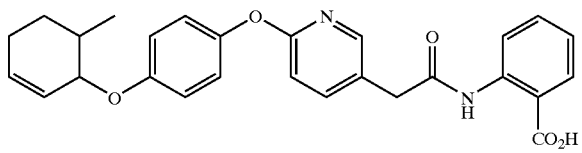
989 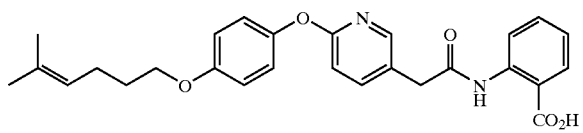
990 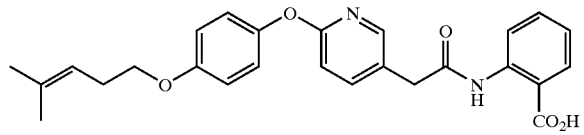
991 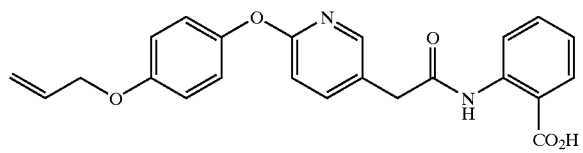
992 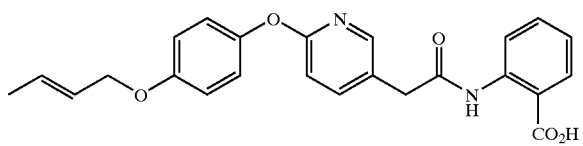
993 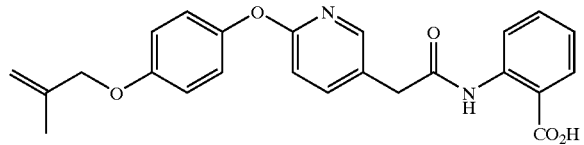

TABLE 35-continued

| 994 | (structure) |
| 995 | (structure) |
| 996 | (structure) |
| 997 | (structure) |
| 998 | (structure) |
| 999 | (structure) |
| 1000 | (structure) |
| 1001 | (structure) |
| 1002 | (structure) |
| 1003 | (structure) |

TABLE 35-continued
1004 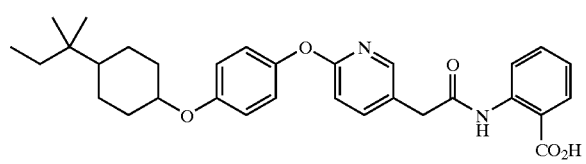
1005 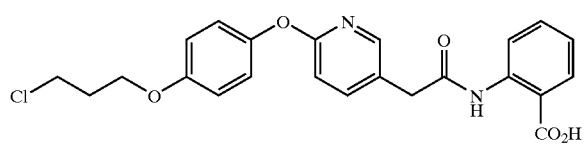
1006 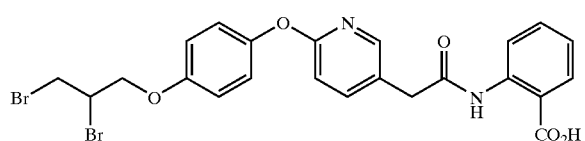
1007 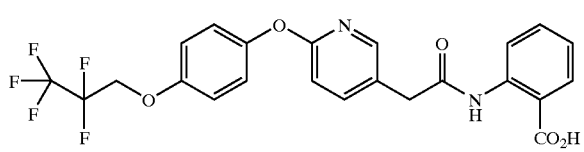
1008 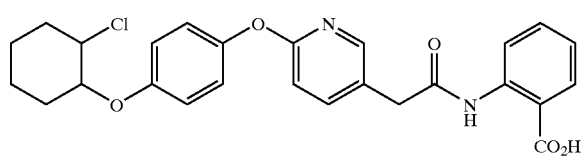
1009 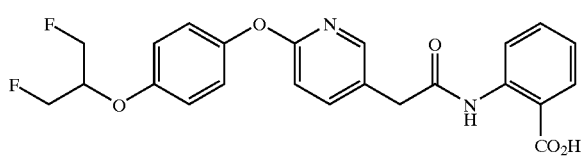
1010 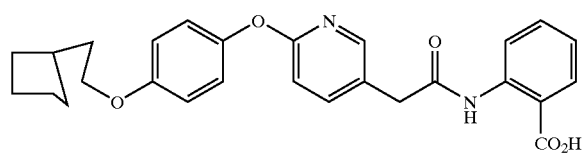
TABLE 36
1011 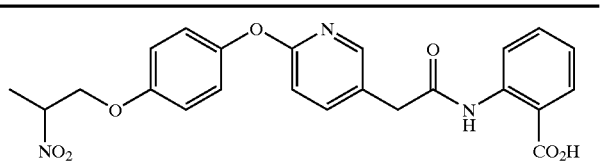
1012 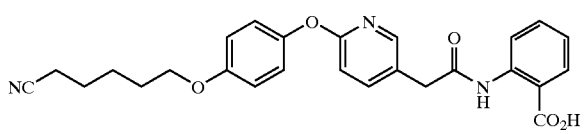

TABLE 36-continued

| 1013 | (structure) |
| 1014 | (structure) |
| 1015 | (structure) |
| 1016 | (structure) |
| 1017 | (structure) |
| 1018 | (structure) |
| 1019 | (structure) |
| 1020 | (structure) |
| 1021 | (structure) |
| 1022 | (structure) |

TABLE 36-continued

| 1023 | (3-cyanobenzyl)oxy-phenoxy-pyridine-CH2-C(O)NH-phenyl-2-CO2H |
| 1024 | pent-4-ynyloxy-phenoxy-pyridine-CH2-C(O)NH-phenyl-2-CO2H |
| 1025 | (pent-1-yn-3-yl)oxy-phenoxy-pyridine-CH2-C(O)NH-phenyl-2-CO2H |
| 1026 | benzylthio-phenoxy-pyridine-CH2-C(O)NH-phenyl-2-CO2H |
| 1027 | (pent-3-yl)thio-phenoxy-pyridine-CH2-C(O)NH-phenyl-2-CO2H |
| 1028 | cyclohexylthio-phenoxy-pyridine-CH2-C(O)NH-phenyl-2-CO2H |
| 1029 | (3-methylbut-2-enyl)thio-phenoxy-pyridine-CH2-C(O)NH-phenyl-2-CO2H |
| 1030 | (4-trifluoromethylbenzyl)thio-phenoxy-pyridine-CH2-C(O)NH-phenyl-2-CO2H |
| 1031 | (3-nitrobenzyl)thio-phenoxy-pyridine-CH2-C(O)NH-phenyl-2-CO2H |

TABLE 36-continued
| 1032 | 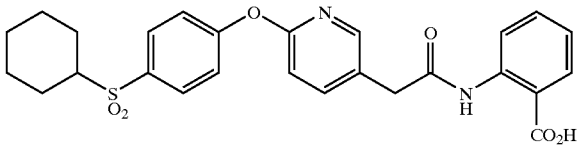 |
| 1033 | 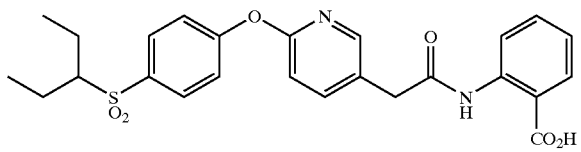 |
| 1034 | 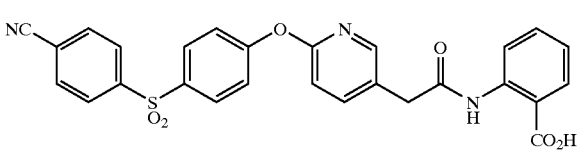 |
| 1035 | 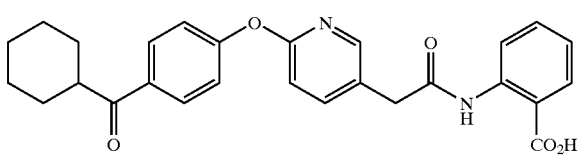 |
| 1036 | 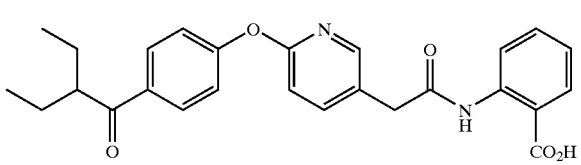 |
| 1037 | 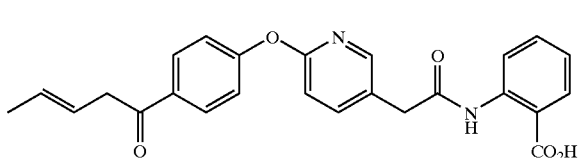 |
| 1038 | 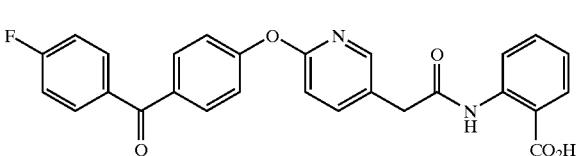 |
| 1039 | 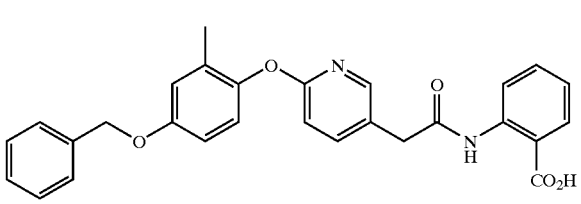 |
| 1040 | 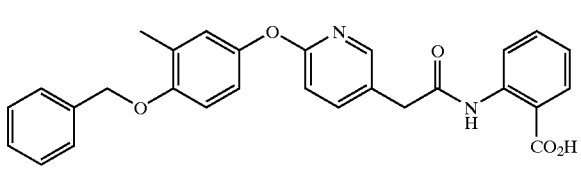 |

TABLE 37
1041 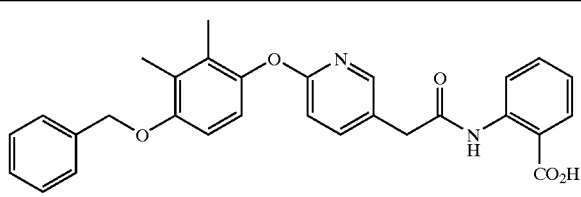
1042 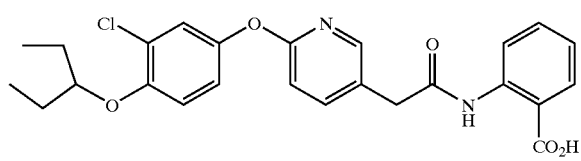
1043 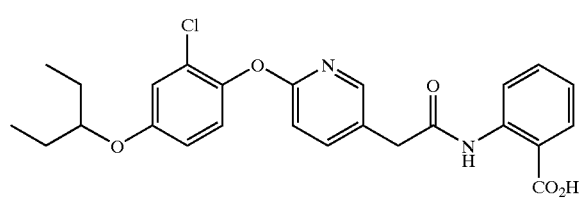
1044 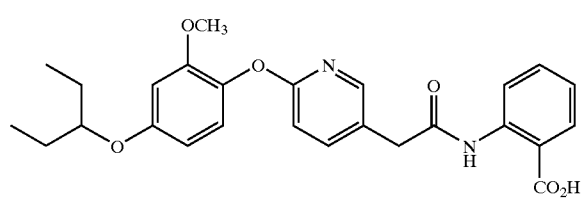
1045 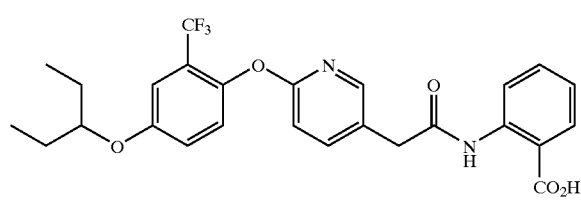
1046 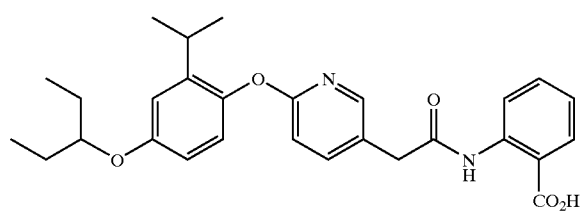
1047 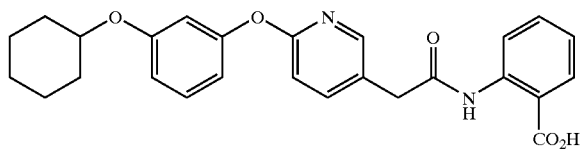
1048 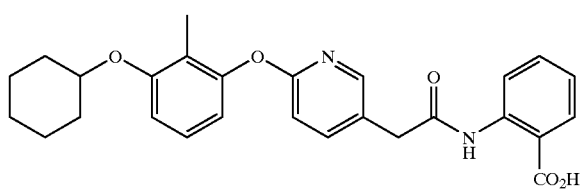

TABLE 37-continued
| 1049 | 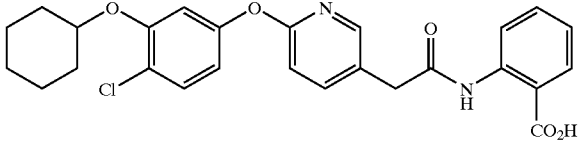 |
| 1050 | 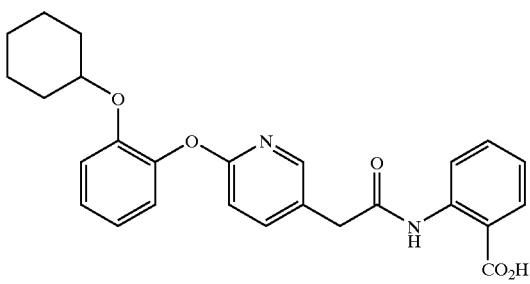 |
| 1051 | 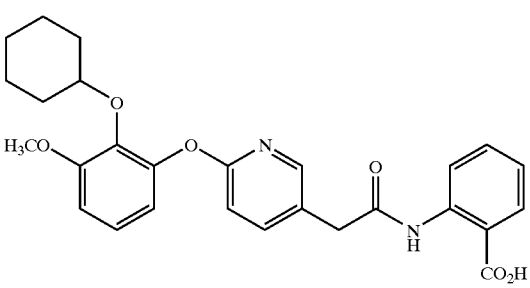 |
| 1052 | 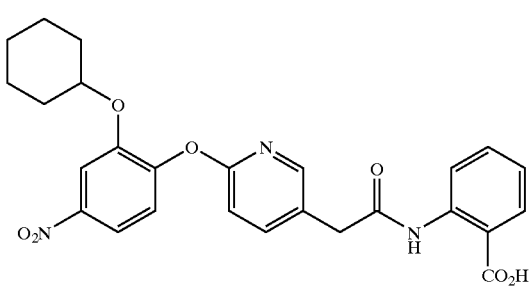 |
| 1053 | 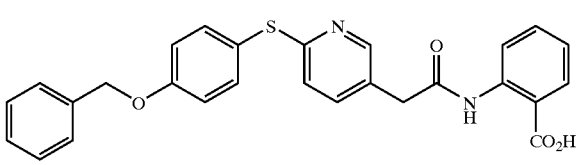 |
| 1054 | 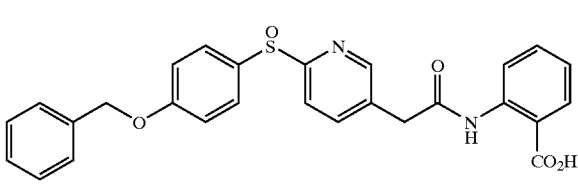 |
| 1055 | 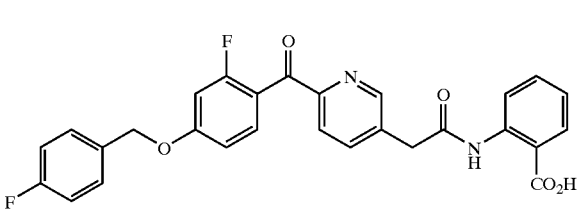 |

TABLE 37-continued
| 1056 | 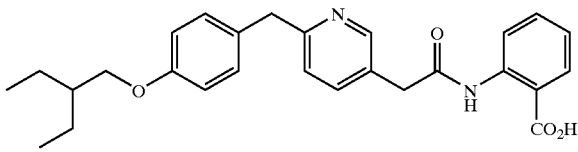 |
| 1057 | 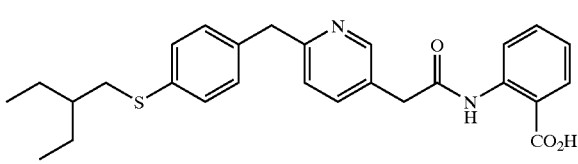 |
| 1058 | 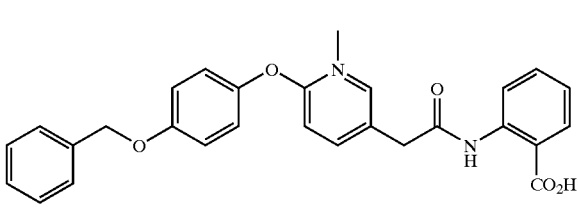 |
| 1059 | 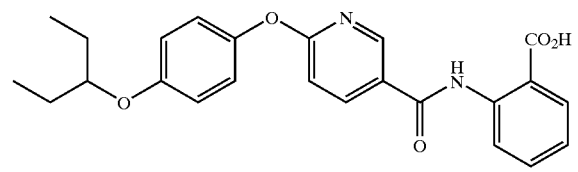 |
| 1060 | 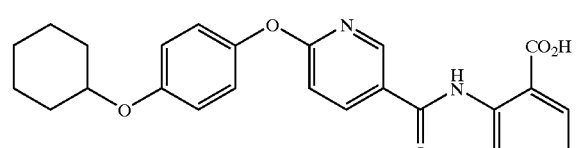 |
| 1061 | 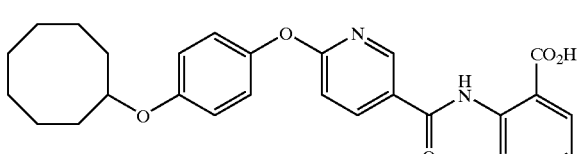 |
| 1062 | 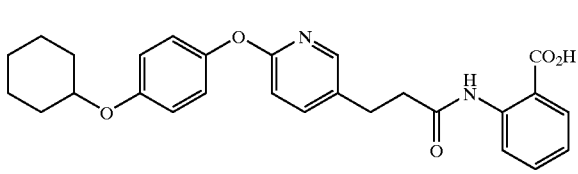 |
| 1063 | 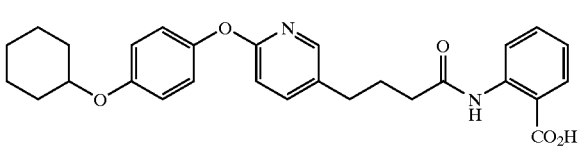 |
| 1064 | 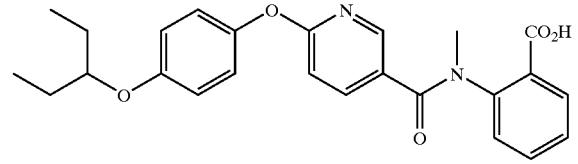 |

TABLE 37-continued
1065 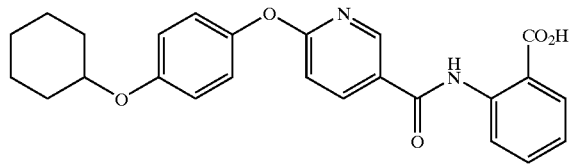
1066 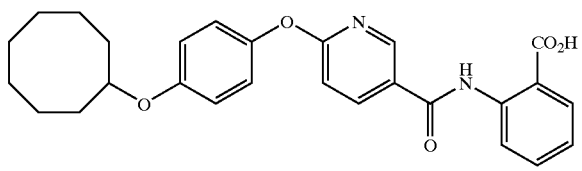
1067 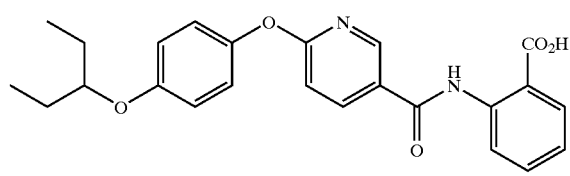
1068 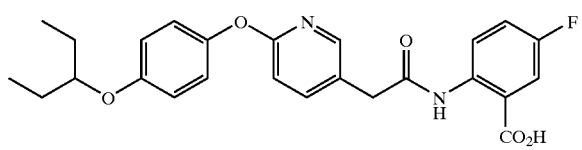
1069 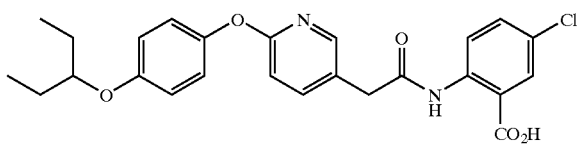
1070 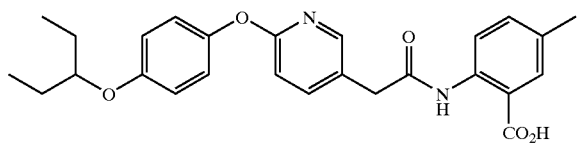
TABLE 38
1071 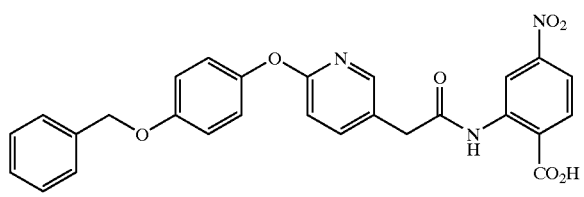
1072 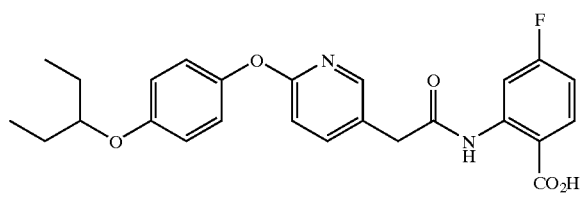

TABLE 38-continued
1073 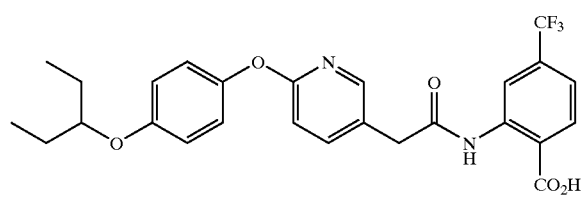
1074 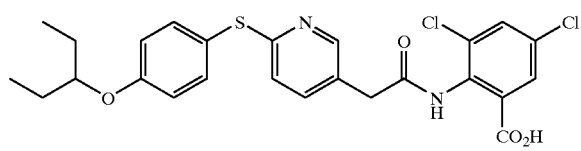
1075 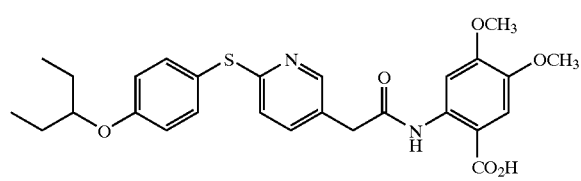
1076 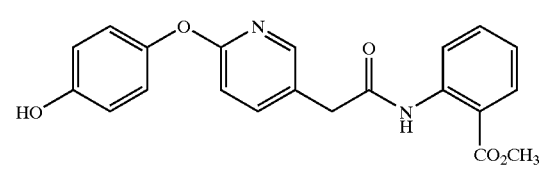
1077 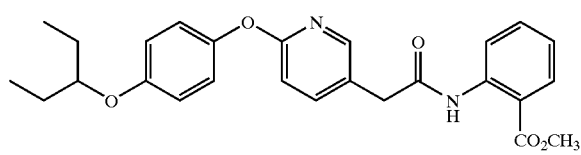
1078 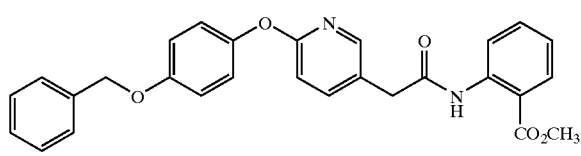
1079 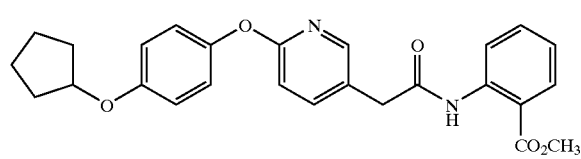
1080 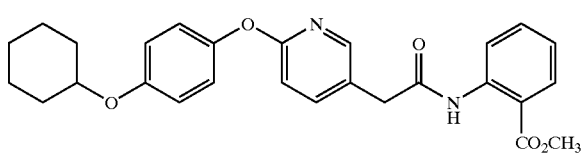
1081 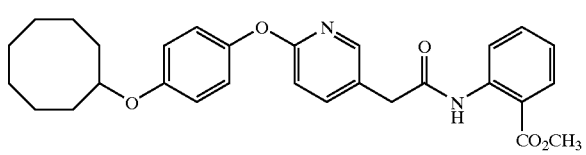

TABLE 38-continued

| | |
|---|---|
| 1082 | *[structure]* |
| 1083 | *[structure]* |
| 1084 | *[structure]* |
| 1085 | *[structure]* |
| 1086 | *[structure]* |
| 1087 | *[structure]* |
| 1088 | *[structure]* |
| 1089 | *[structure]* |
| 1090 | *[structure]* |
| 1091 | *[structure]* |

TABLE 38-continued

| | |
|---|---|
| 1092 | (structure) |
| 1093 | (structure) |
| 1094 | (structure) |
| 1095 | (structure) |
| 1096 | (structure) |
| 1097 | (structure) |
| 1098 | (structure) |
| 1099 | (structure) |
| 1100 | (structure) |

TABLE 39
1101 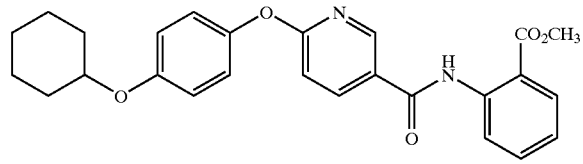
1102 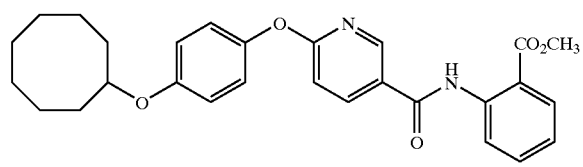
1103 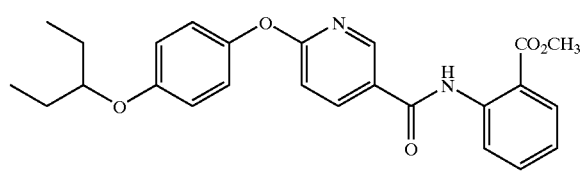
1104 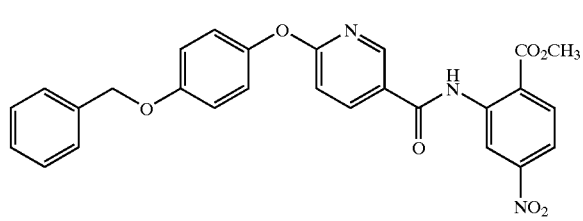
1105 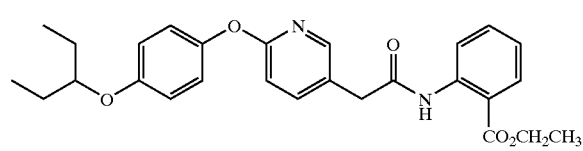
1106 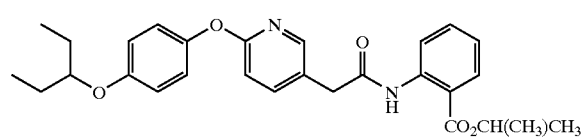
1107 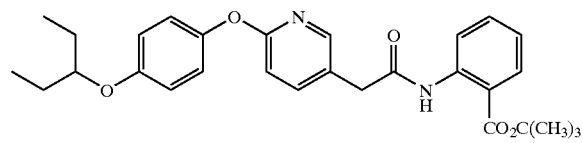
1108 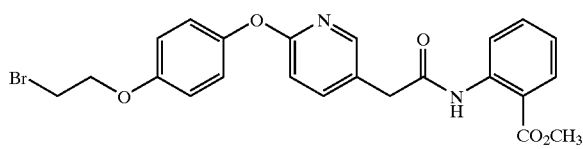
1109 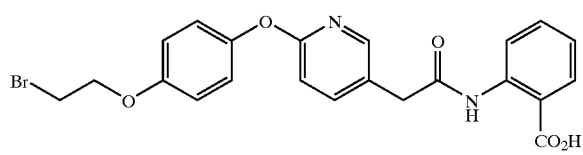

TABLE 39-continued

| | |
|---|---|
| 1110 | (structure) |
| 1111 | (structure) |
| 1112 | (structure) |
| 1113 | (structure) |
| 1114 | (structure) |
| 1115 | (structure) |
| 1116 | (structure) |
| 1117 | (structure) |
| 1118 | (structure) |
| 1119 | (structure) |

TABLE 39-continued
1120 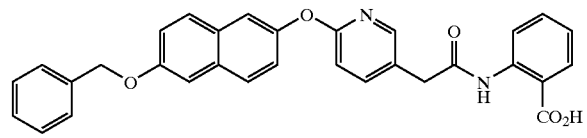
1121 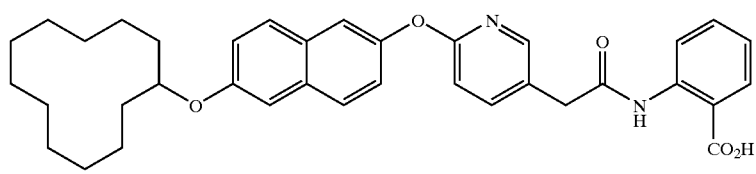
1122 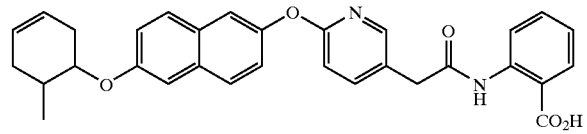
1123 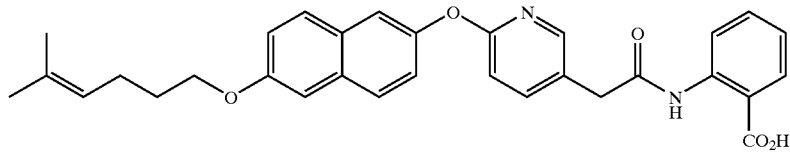
1124 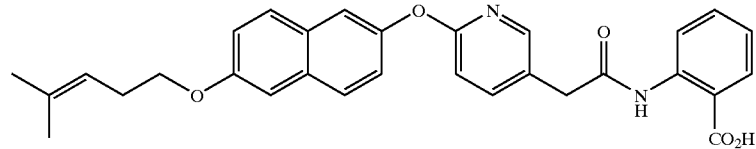
1125 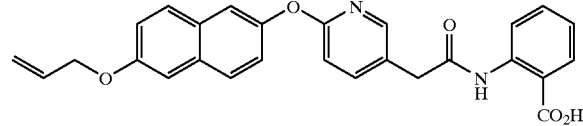
1126 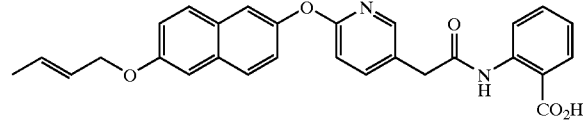
1127 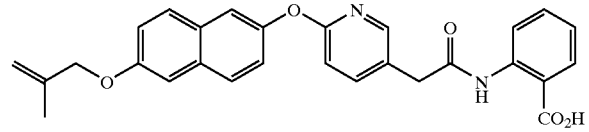
1128 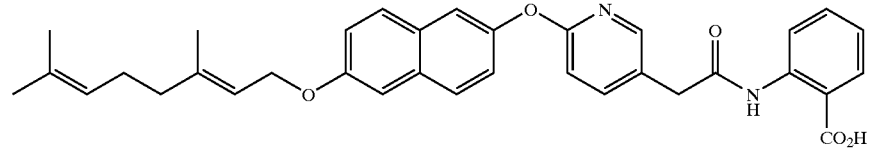
1129 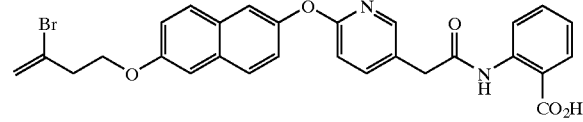

TABLE 39-continued
| 1130 | 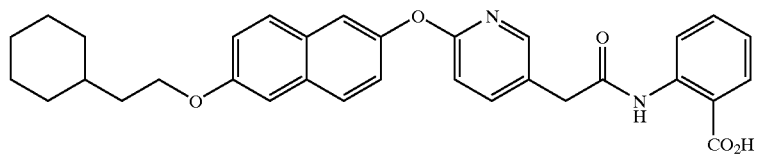 |
TABLE 40
| 1131 | 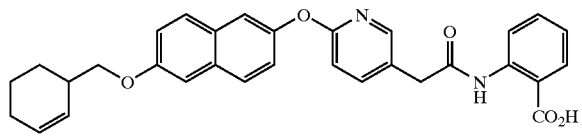 |
| 1132 | 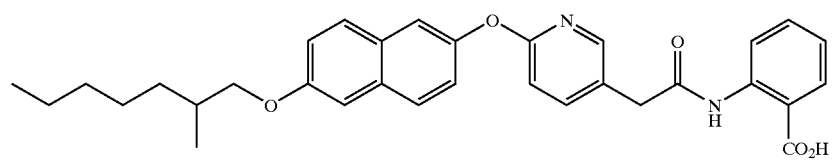 |
| 1133 | 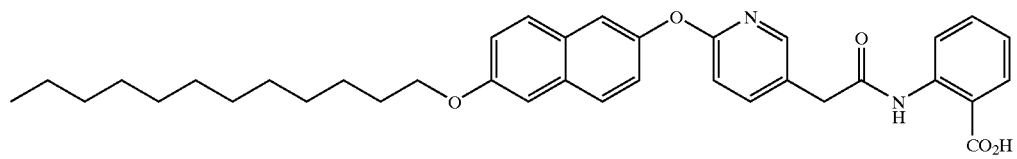 |
| 1134 | 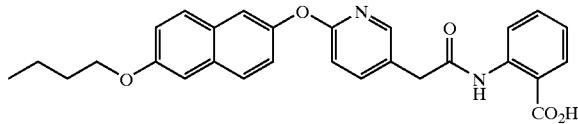 |
| 1135 | 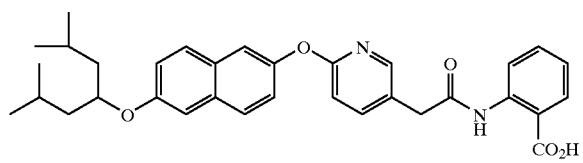 |
| 1136 | 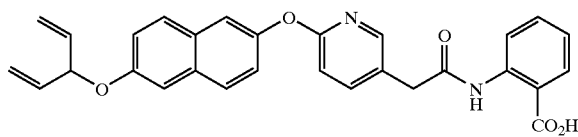 |
| 1137 | 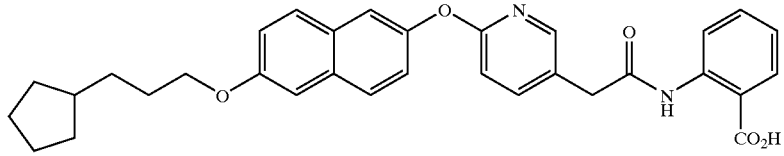 |
| 1138 | 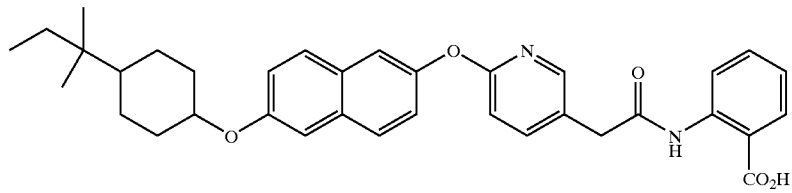 |

TABLE 40-continued
1139 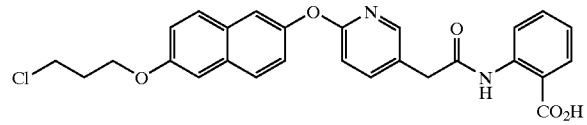
1140 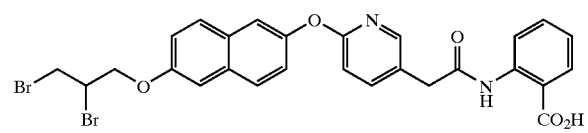
1141 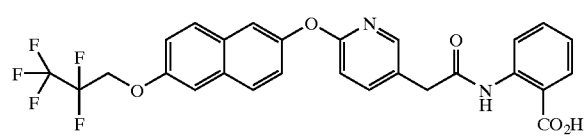
1142 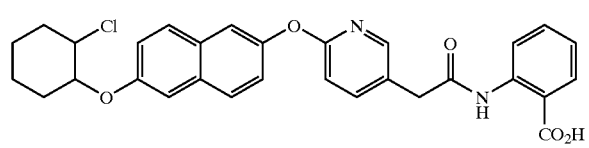
1143 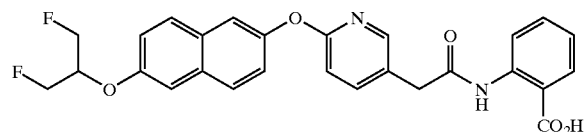
1144 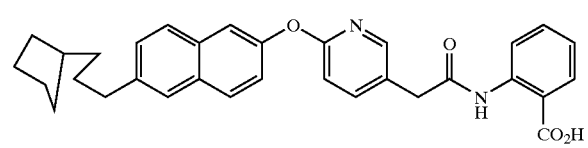
1145 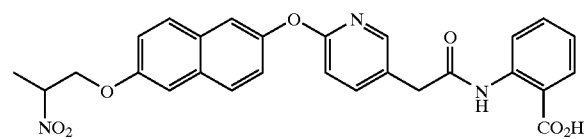
1146 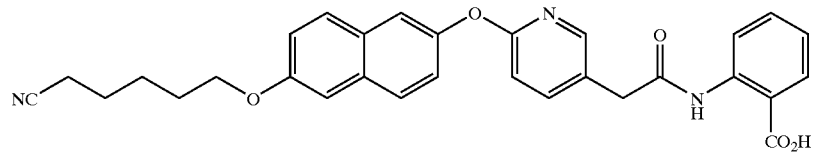
1147 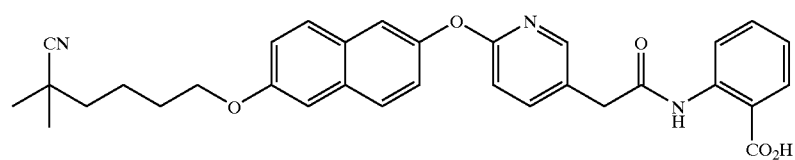
1148 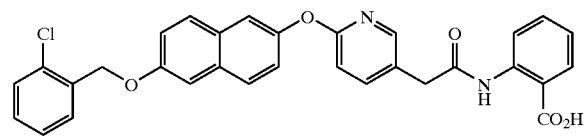

TABLE 40-continued
| 1149 | 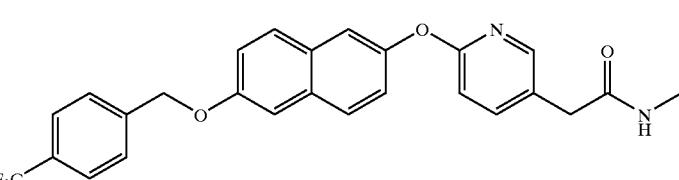 |
| 1150 | 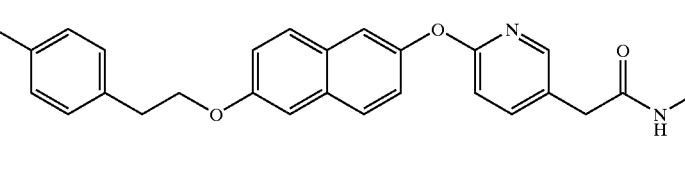 |
| 1151 | 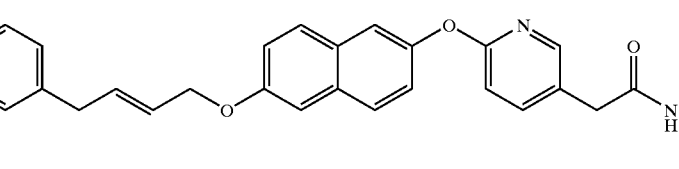 |
| 1152 | 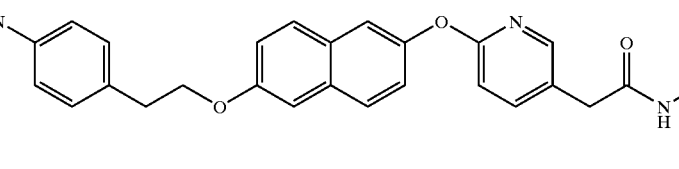 |
| 1153 | 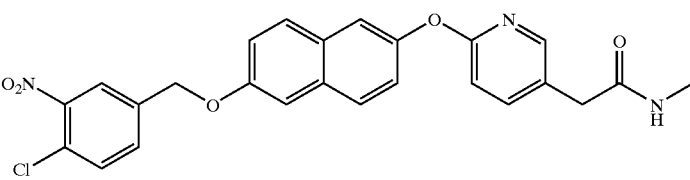 |
| 1154 | 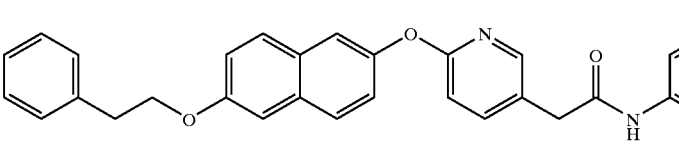 |
| 1155 | 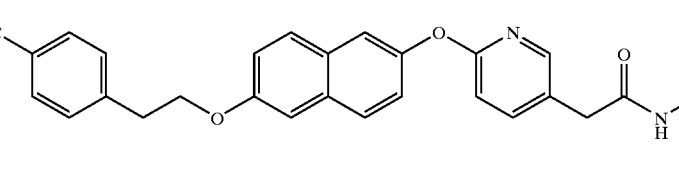 |
| 1156 | 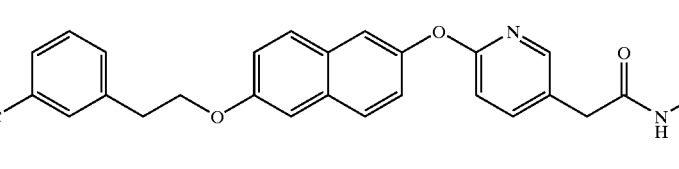 |
| 1157 | |

TABLE 40-continued
1158 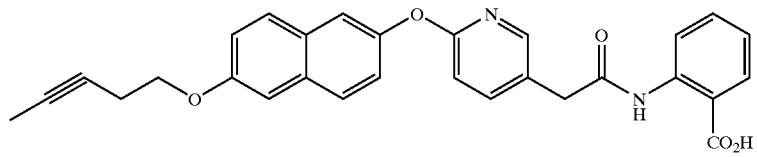
1159 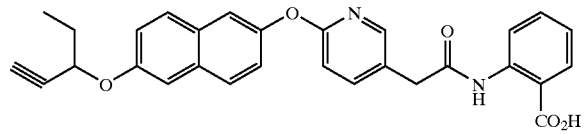
1160 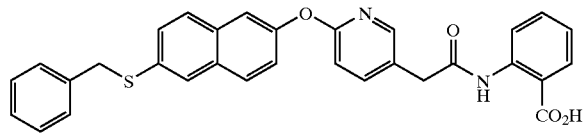
TABLE 41
1161 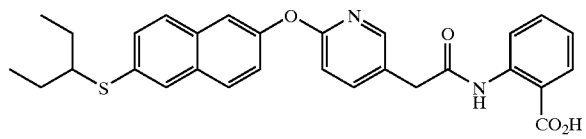
1162 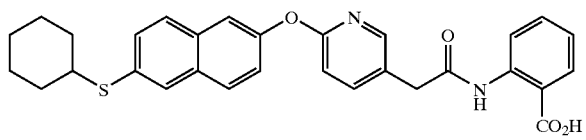
1163 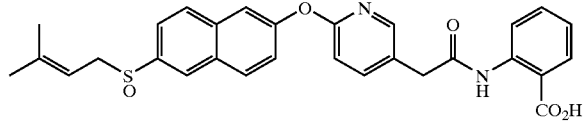
1164 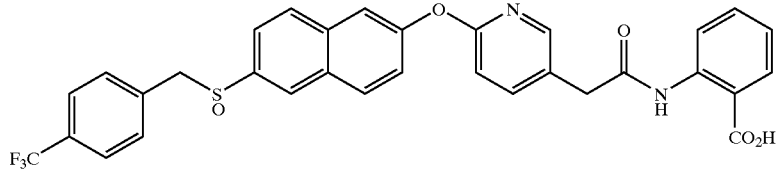
1165 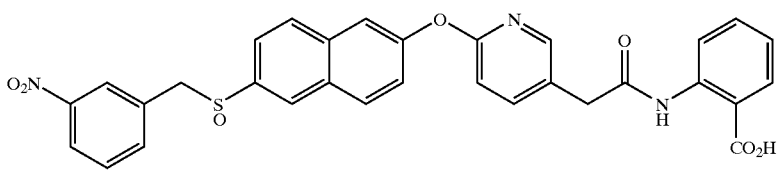
1166 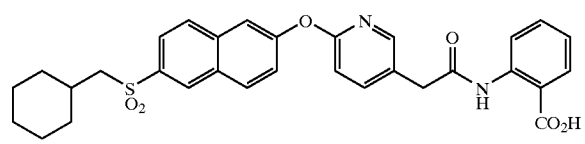

TABLE 41-continued
| | |
|---|---|
| 1167 | 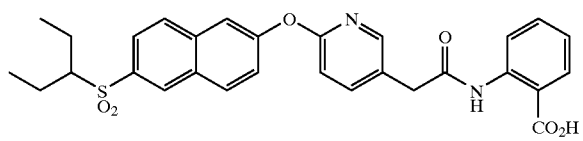 |
| 1168 | 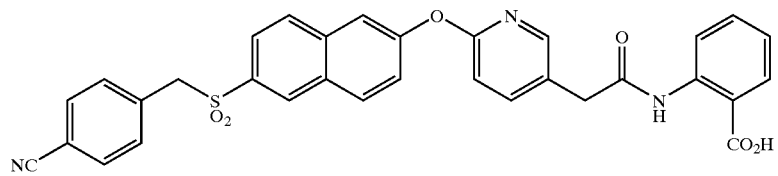 |
| 1169 | 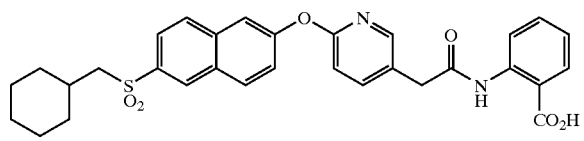 |
| 1170 | 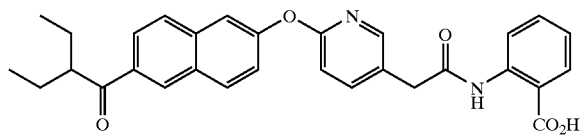 |
| 1171 | 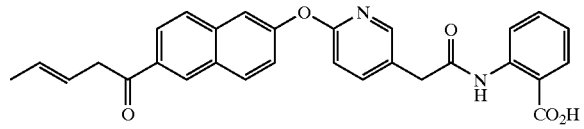 |
| 1172 | 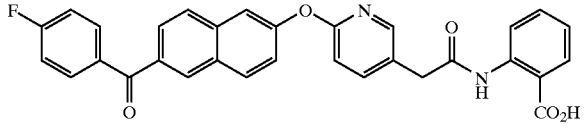 |
| 1176 | 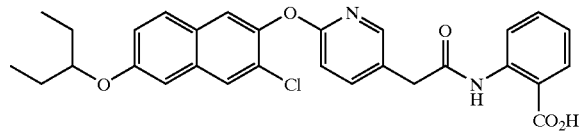 |
| 1181 | 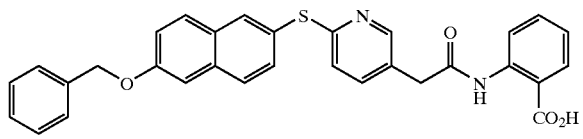 |
| 1182 | 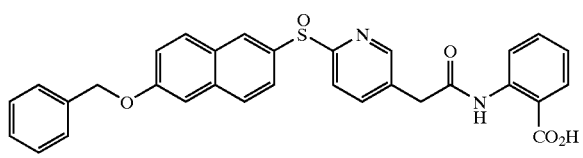 |
| 1184 | 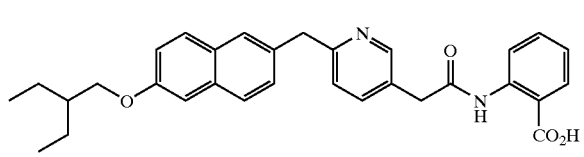 |

TABLE 41-continued
1185 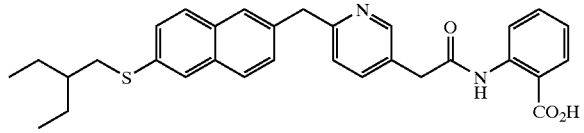
1186 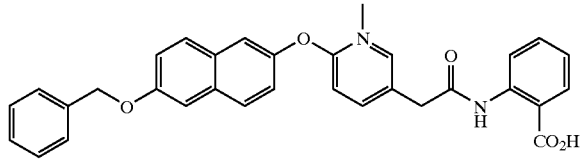
1187 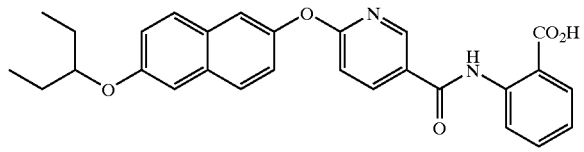
1188 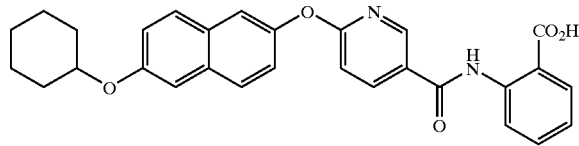
1189 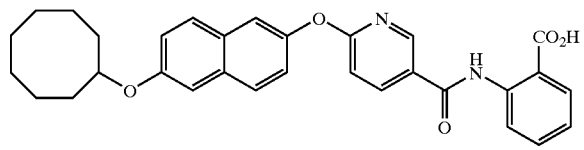
1190 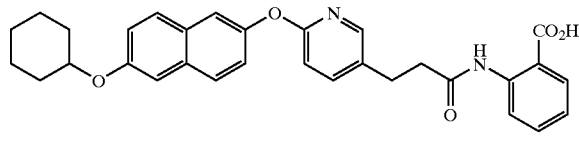
TABLE 42
1191 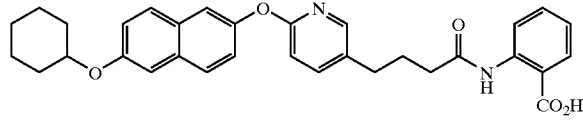
1192 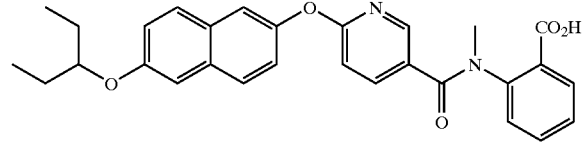
1193 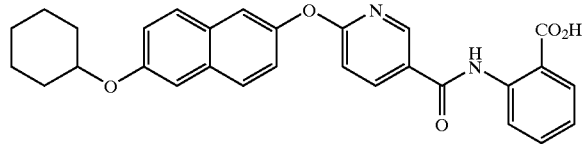

TABLE 42-continued
1194 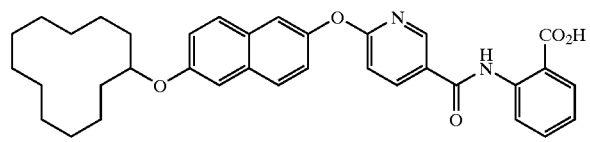
1195 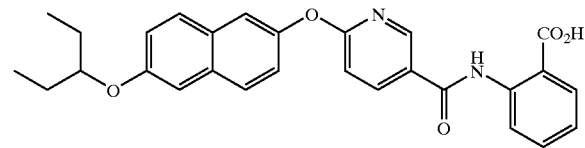
1196 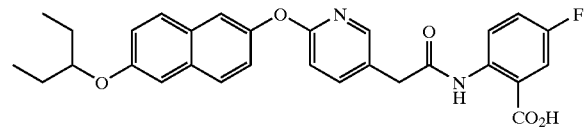
1197 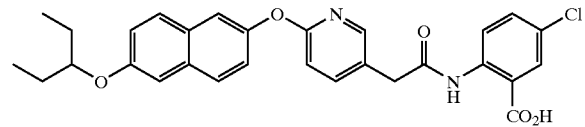
1198 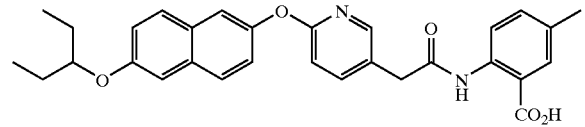
1199 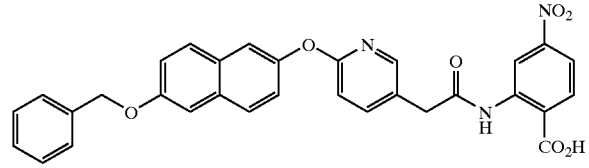
1200 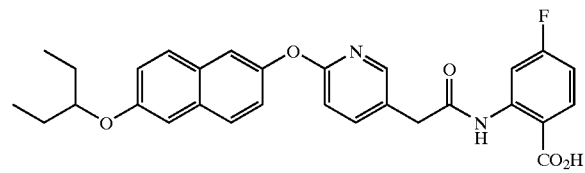
1201 
1202 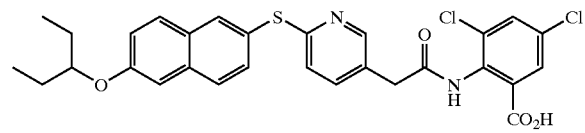
1203 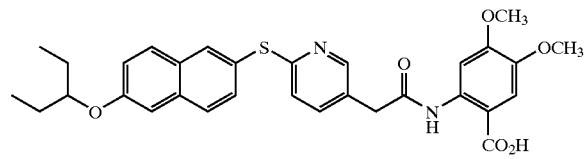

TABLE 42-continued
1204 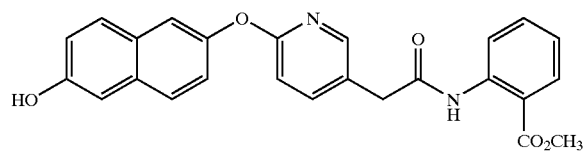
1205 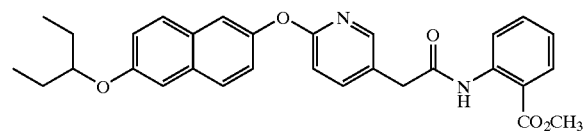
1206 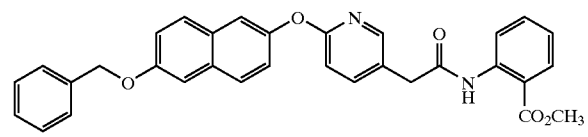
1207 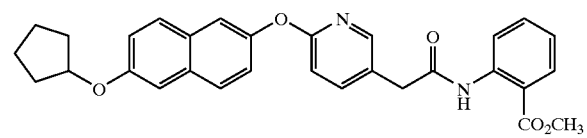
1208 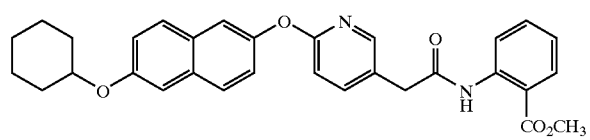
1209 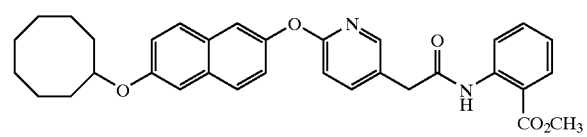
1210 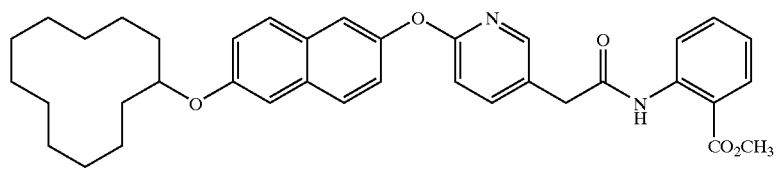
1211 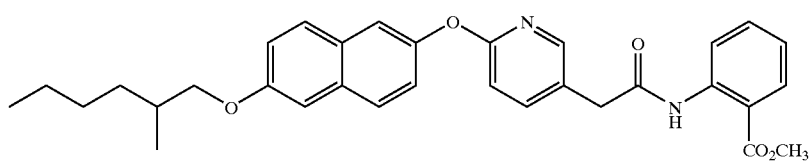
1212 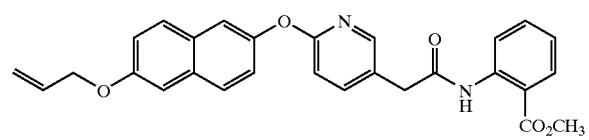
1213 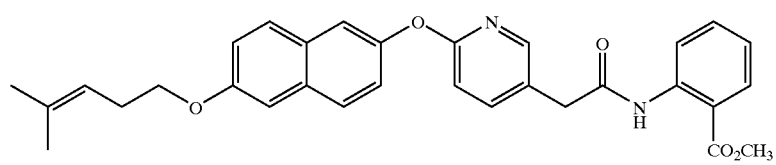

TABLE 42-continued
1214 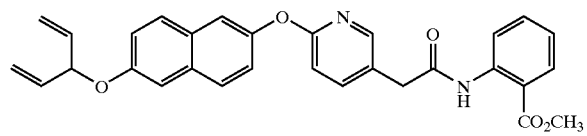
1215 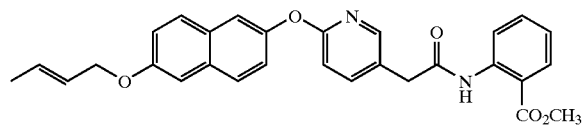
1216 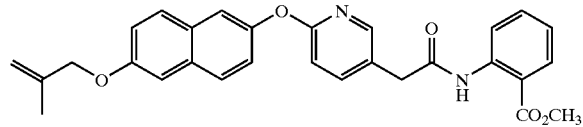
1217 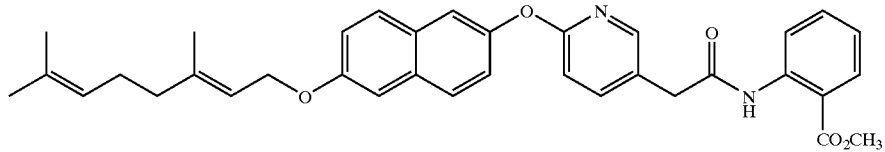
1218 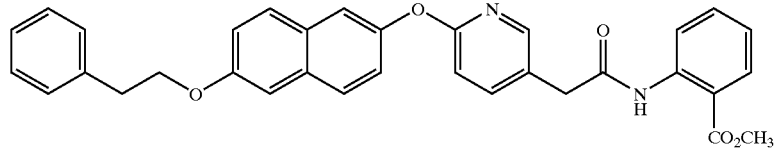
1219 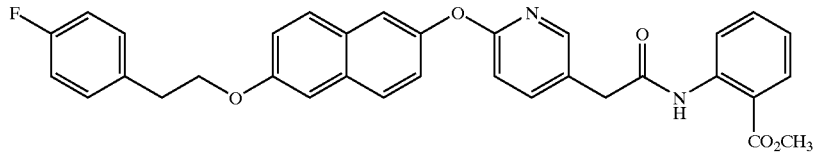
1220 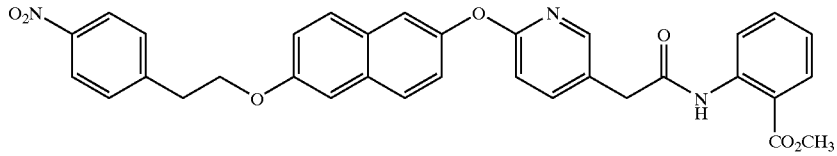
TABLE 43
1221 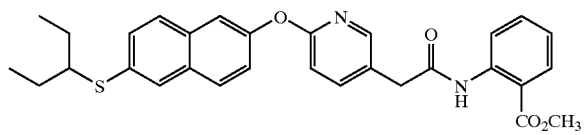
1222 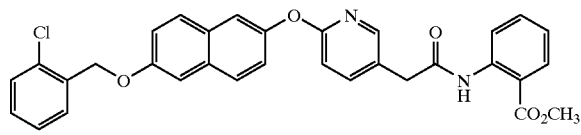

TABLE 43-continued
1223 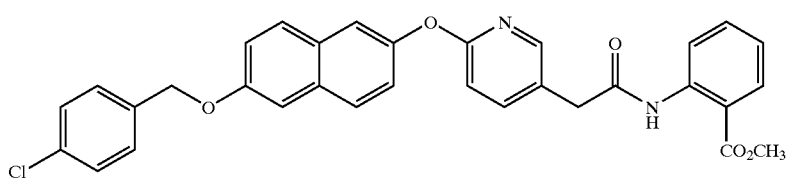
1224 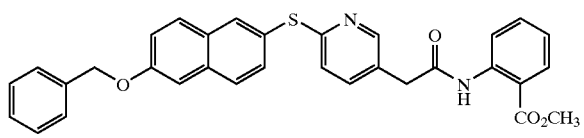
1225 
1226 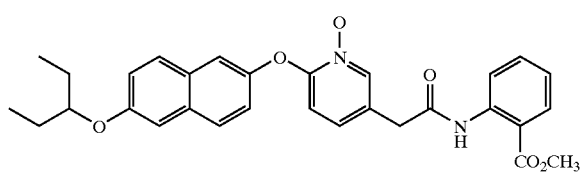
1227 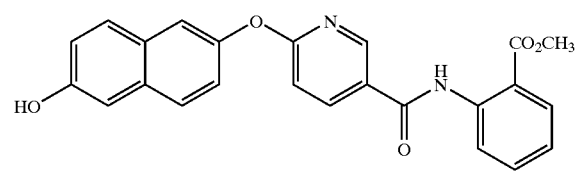
1228 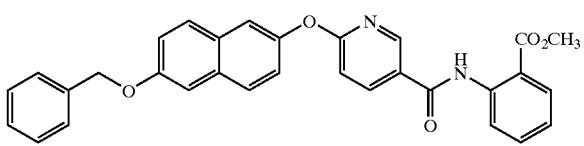
1229 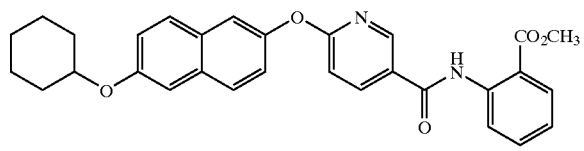
1230 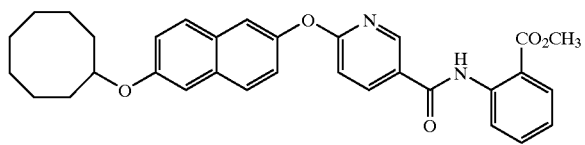
1231 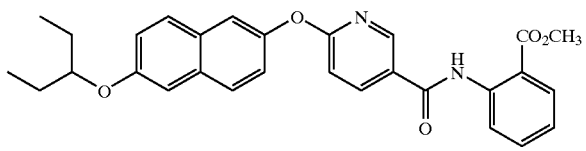

TABLE 43-continued
| 1232 | 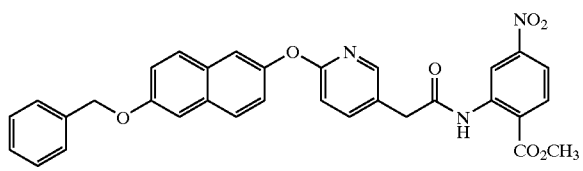 |
| 1233 | 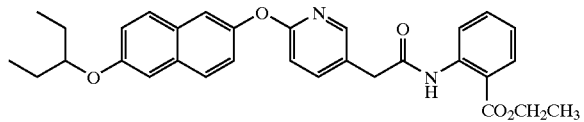 |
| 1234 | 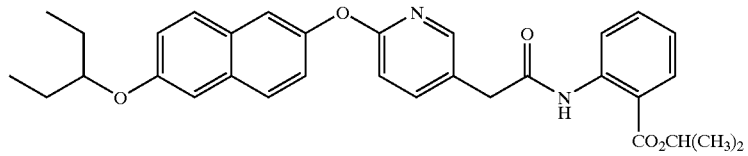 |
| 1235 | 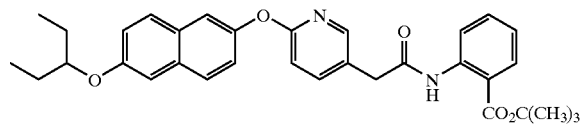 |
| 1236 | 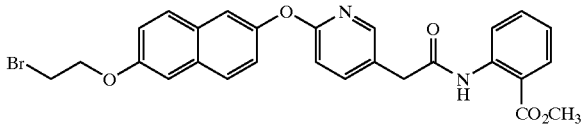 |
| 1237 | 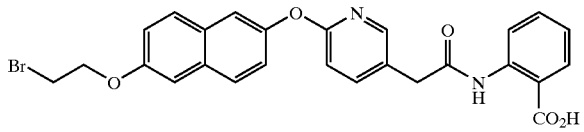 |
| 1238 | 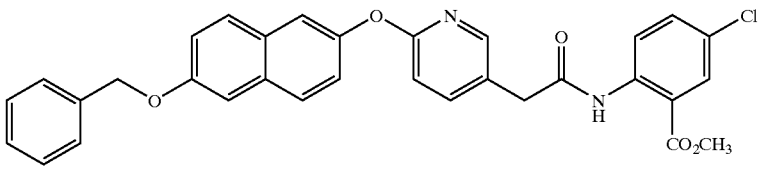 |
| 1239 | 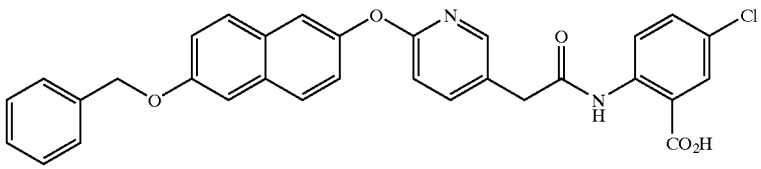 |
| 1240 | 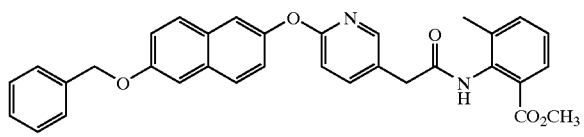 |
| 1241 | 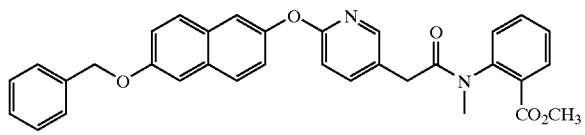 |

TABLE 43-continued

| | |
|---|---|
| 1242 | 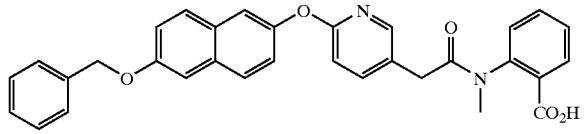 |
| 1243 | 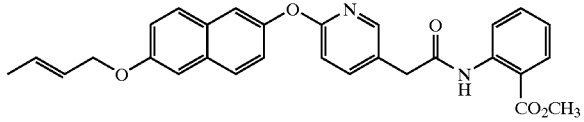 |
| 1244 | 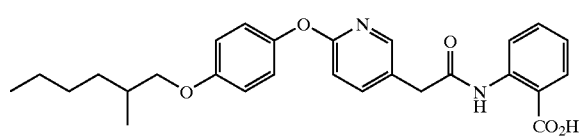 |
| 1245 | 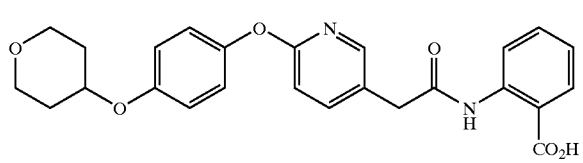 |
| 1246 | 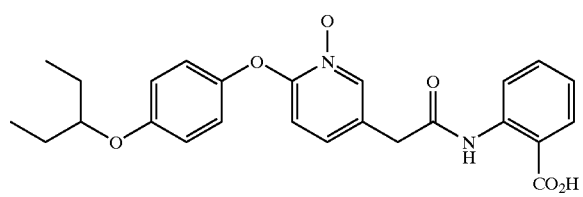 |

The anthranilic acid derivative of the present invention has strong cytotoxic activity and/or IgE antibody production suppressing activity. Concretely, as for cytotoxic activity, LC50 or GI50 is 5,000 nM or less, preferably 0.05 nM to 1,000 nM, more preferably 0.05 nM to 500 nM. As for IgE antibody production suppressing activity, IC50 is 1,000 nM or less, preferably 0.05 nM to 500 nM, more preferably 0.05 M to 100 nM.

The anthranilic acid derivative of the present invention having such an excellent cytotoxic activity can be used as a therapeutic agent clinically applicable to cancer. Since the anthranilic acid derivative of the present invention further has excellent IgE antibody production suppressing activity, compounds having relatively weak cytotoxicity among the above compounds are rather suitable for the use as a preventing agent and/or therapeutic agent clinically applicable to various allergic diseases.

The derivative of the present invention expressed by the aforementioned formula (1) or formula (2) or its pharmacologically permissible salt can be produced for example according to the following scheme.

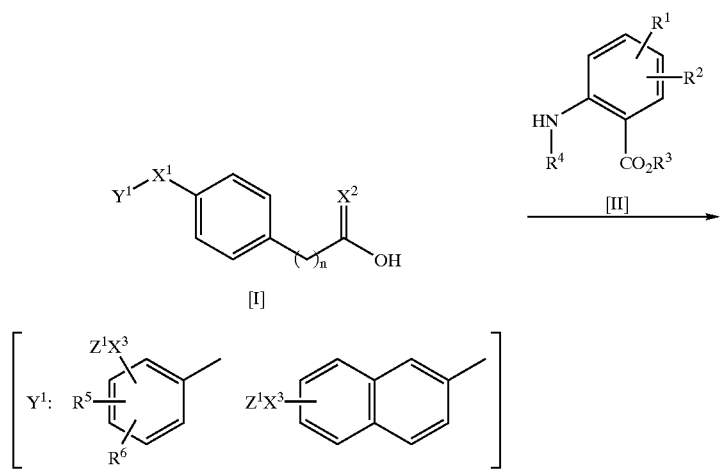

-continued
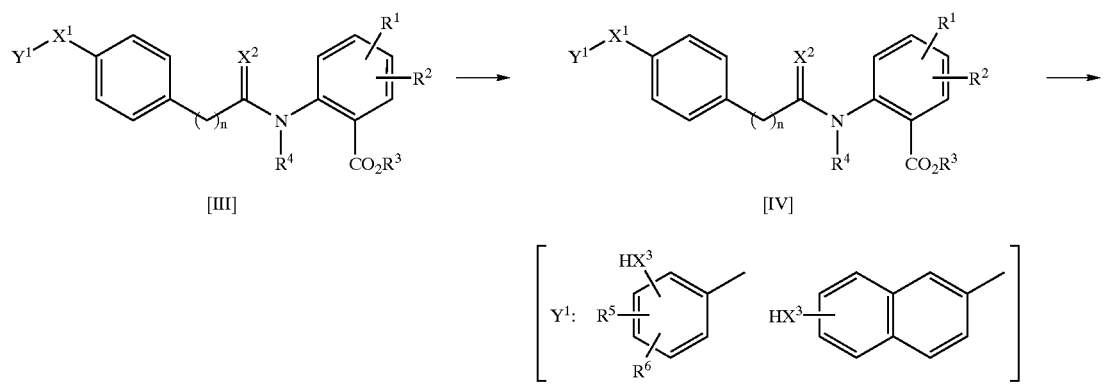
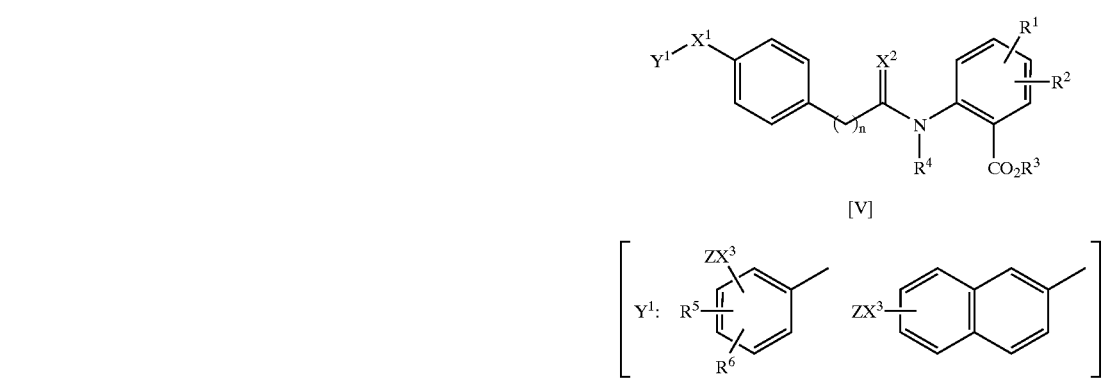
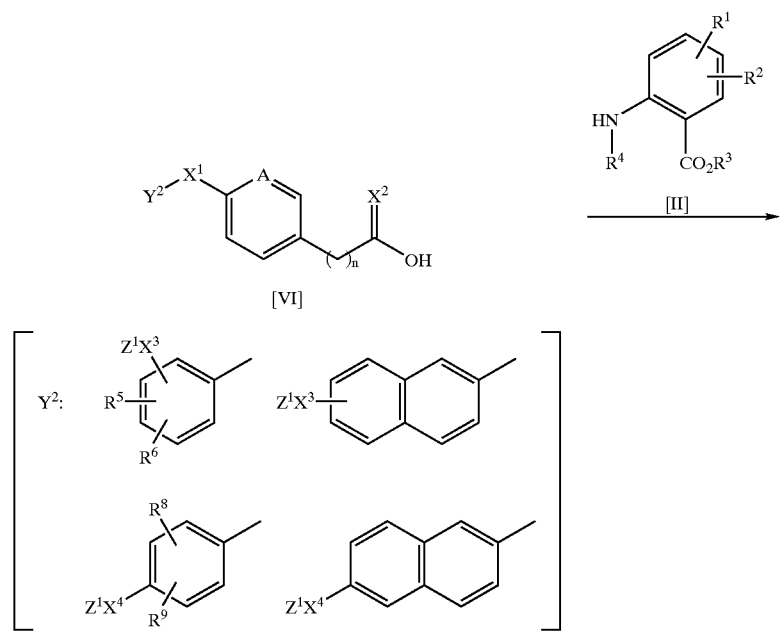

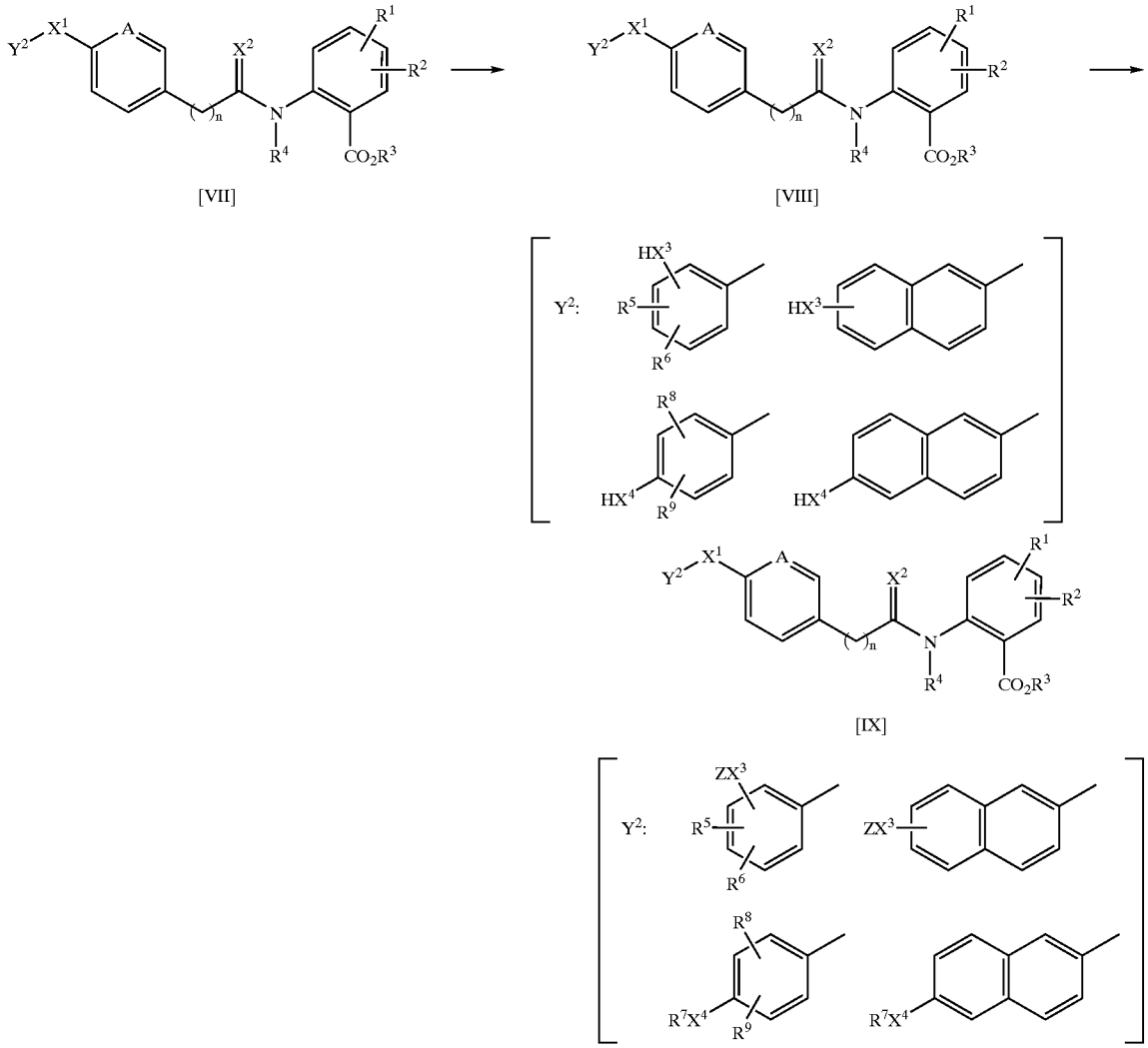

Namely, an aryl derivative [I] or [VI] having a group expressed by $Z^1X^3$ or $Z^1X^4$ ($Z^1$ is hydrogen atom, a general protecting group such as benzyl group, benzoyl group, methoxymethyl group, acetyl group or trimethylsilyl group, the group Z defined in the formula (3)-1 and the formula (3)-2 or the group $R^7$ defined in the formula (5)-1 or the formula (5)-2) and a carboxylic acid group is coupled with an anthranilic acid derivative [II] under a proper condition to enable the production of the compounds [III] and [VII] from the starting compounds [I] and [VI], respectively. The group $Z^1$ of the produced compound [III] or [VII] is deprotected to obtain respective intermediate [IV] or [VIII] and a side chain Z is introduced into the compound [IV] to obtain the compound [V] or a side chain Z or a group $R^7$ is introduced into the compound [VIII] to obtain a compound [IX]. When the group —$CO_2R^3$ is an ester, the product can be converted as necessary into a carboxylic acid by hydrolyzing the ester of the compound [V] or [IX]. When the group $Z^1$ in the compound [III] or [VII] is Z or $R^7$ defined before, the compound [III] or [VII] becomes the objective compound [V] or [IX], respectively, and when the group —$CO_2R^3$ is an ester, the ester [III] and [VII] can be converted as necessary into a carboxylic acid by hydrolysis.

The definitions of the groups A, Z, $X^1$ to $X^4$, $R^1$ to $R^9$ and n in the above formulas are same as the definitions in the formulas (1), (2), (3)-1, (3)-2, (5)-1 and (5)-2. There is no restriction on the production process of the starting substances [I] and [VI], and these compounds can be produced by known conventional methods.

The compounds [V] and [IX] are concretely synthesizable as follows.

The condensation of the compound [I] or [VI] to the compound [II] can be roughly classified into a method through an acid halide and an activation method without passing through an acid halide and either method is principally a known method.

In the case of passing through an acid halide, the objective compounds [III] and [VII] can be produced from the compounds [I] and [II] and the compounds [VI] and [II], respectively, by treating the compound [I] or [VI] with a proper halogenation agent such as oxalyl chloride and thionyl chloride in the presence or absence of an additive such as DMF in a proper solvent (e.g. methylene chloride or tetrahydrofuran) and reacting the produced acid halide with the compound [II] in the presence or absence of a proper base (e.g. triethylamine or potassium carbonate).

In the activation method which does not go through an acid halide, the objective compounds [III] and [VII] can be produced from the compounds [I] and [II] and the compounds [VI] and [II], respectively, by activating the compound [I] or [VI] with a proper activation agent such as mixed acid anhydride, carbodiimides, imidazolation agent, halophosphoric acid esters or cyanophosphoric acid esters in a proper solvent (e.g. methylene chloride or tetrahydrofuran) and reacting the activated compound with the compound [II].

The group $Z^1$ in $Z^1X^3$ of the compounds [III] and [VII] may be Z and in $Z^2X^4$ may be $R^1$ itself. When $X^3$ is —O—, —S—, —$NR^{21}$ or —(C=O)$NR^{21}$ (in this case, the carbonyl group is bonded to the benzene ring or naphthalene ring in the formula (3)-1 or the formula (3)-2, and the definition of $R^{21}$ is same as the definition in the formula (3)-1 and the formula (3)-2) or $X^4$ is —O—, —S—, —$NR^{23}$— or —(C=O)$NR^{23}$ (in this case, the carbonyl group is bonded to the benzene ring or naphthalene ring in the formula (5)-1 or the formula (5)-2 and the definition of $R^{23}$ is same as the definition in the formula (5)-1 and the formula (5)-2), the compound [IV] or [VIII] can be used as an intermediate after deprotection by using a proper protecting group (for example, ethers of benzyl group, allyl group, etc., silyl ethers of t-butyldimethylsilyl group, etc., esters of benzoyl group, etc., carbonates such as allyl carbonate, etc. when $X^3$ or $X^4$ is —O—; thioethers of benzyl group, etc., thioesters of benzoyl group, etc., thiocarbonates of t-butyl carbonate, etc. when it is —S—; benzyl group, formyl group, etc. when it is —$NR^{21}$— or —$NR^{23}$—; and t-butyldimethylsilyloxy group, methylthio group, etc. when it is —(C=O)$NR^{21}$ or —(C=O)$NR^{23}$), and the compound [V] can be produced by introducing Z into the compound [IV] or the compound [IX] can be produced by introducing Z or $R^7$ into the compound [VIII] to facilitate the development of synthesis. For example, when $X^3$ or $X^4$ in the compound [III] or [VII] is —O—, the debenzylated intermediate [IV] or [VIII] can be produced from the compound [III] or [VII] by hydrogenation by the use of benzyl group as the group $Z^1$. Further, the introduction of Z into the compound [IV] gives the compound [V] and the introduction of Z or $R^7$ into the compound [VIII] gives the compound [IX]. In this case, $R^3$ is preferably a C1–C4 hydrocarbon group among the groups defined in the formula (1) and the formula (2) from the viewpoint of the handling in synthesis. In other words, the compound of the formula (1) or formula (2) wherein $R^3$ is hydrogen atom is produced preferably by introducing the group Z into the intermediate [IV] or introducing the group Z or the group $R^7$ into the intermediate [VIII] and hydrolyzing the group $CO_2R^3$ (i.e. the group $R^3$ is a C1–C4 hydrocarbon group).

There is no particular restriction on the method for introducing the group Z of the formula (3)-1 and the formula (3)-2 or the group $R^7$ of the formula (5)-1 and the formula (5)-2 into the compound [IV] or [VIII], and the introduction can be carried out for example by using a reactant $ZX^5$, $R^7X^5$, etc. An alcohol and an alkyl halide are concrete examples of $ZX^5$ or $R^7X^5$ when $X^3$ and $X^4$ are —O—. The objective compound [V] containing introduced group Z or the compound [IX] containing introduced group Z or $R^7$ can be produced, in the case of using an alcohol as the $ZX^5$ or $R^7X^5$, by using ZOH or $R^7$OH, triphenyl phosphine (which may be replaced with tributyl phosphine, etc.), diethyl azodicarboxylate [which may be replaced with diisopropyl azodicarboxylate or 1,1-azobis(N,N-dimethylformamide)] and carrying out Mitsunobu synthesis or its analogous reaction in a proper solvent (e.g. N-methylmorpholine or tetrahydrofuran) at a proper temperature condition. In the case of using an alkyl halide, etc., i.e. using a halogen atom as the eliminable group $X^5$, the objective compound [V] or [IX] can be produced by carrying out the reaction in the presence of a proper base such as sodium hydride, potassium carbonate or triethylamine in a proper solvent (e.g. dimethylformamide, tetrahydrofuran, acetonitrile or methylene chloride) under a proper temperature condition.

When the group $X^3$ is —$NR^{21}$ or the group $X^4$ is —$NR^{23}$, the group Z in the formula (3)-1 or the formula (3)-2 or the group $R^7$ in the formula (5)-1 or the formula (5)-2 can be introduced by the above reaction similar to the case that the group $X^3$ or $X^4$ is —O—. When the group $X^3$ or $X^4$ is —S—, the compound $ZX^5$ is an alkyl halide derivative, etc. In the case of synthesizing a compound containing —NH—, —$NH_2$—, —$CO_2H$, —OH, —SH, etc., in the group Z of the compound [V] or [IX] and further containing a substituent introduced into these functional groups, a compound of formula $Z^2X^5$ (there is no particular definition of $Z^2$, however, it is a group produced by introducing a proper protecting group into —NH, —$NH_2$, —$CO_2H$, —OH or —SH in the side chain) having proper protecting group introduced into —NH, —$NH_2$, —$CO_2H$, —OH or —SH is synthesized beforehand, the synthesized compound is made to react with the compound [IV] or [VIII] by the aforementioned method to introduce the group $Z^2$, the protecting group of —NH—, —$NH_2$, —$CO_2H$, —OH or —SH in the group $Z^2$ is removed, the product is used as an intermediate and various substituents are introduced into the intermediate to obtain the objective new compound having the group Z. When the group —$CO_2R^3$ is an ester, it can be induced as necessary into a carboxylic acid compound by hydrolyzing the ester —$CO_2R^3$.

Concrete example of the synthesizing process is the protection of the amino group of trans-4-aminocyclohexanol with benzyl group beforehand to obtain a dibenzyl compound, Mitsunobu reaction of the product with an intermediate [IV] or [VIII], debenzylation of the product to obtain an amino compound and the reaction with a reagent having a group to be introduced, for example, an acid chloride, sulfonyl chloride, etc., to obtain an amide compound, a sulfonamide compound, etc., as the objective compound. When the group —$CO_2R^3$ is an ester, a carboxylic acid compound can be produced as necessary by hydrolyzing the group —$CO_2R^3$. Also in this case, the group $R^3$ is preferably a C1–C4 lower hydrocarbon group among the above definition in the formula (1) and the formula (2) from the viewpoint of handleability in synthesis, namely, a compound wherein $R^3$ is hydrogen atom is preferably produced by the hydrolysis of —$CO_2R^3$.

A compound of the formula (1) or (2) wherein $X^1$, $X^3$ and $X^4$ are each —(S=O)— or —(O=S=O)— or A is N→O can be produced by oxidizing a corresponding compound wherein $X^1$, $X^3$ or $X^4$ are S or A is N. Although there is no particular restriction on the stage for oxidizing S or N in the above case, the objective oxidized product can be produced e.g. by oxidizing the non-oxidized compound [V] or [IX] with a general oxidizing agent such as peroxide or NBS.

A compound of the formula (1) or (2) wherein $X^3$ or $X^4$ is —(C=O)— can be synthesized e.g. by introducing ZCO or $R^7$CO by Friedel-Crafts reaction at an arbitrary reaction stage. As an alternative, in the case of using a compound having carboxylic acid group at a position corresponding to the $X^3$ or $X^4$ on the benzene ring or naphthalene ring of the formula (3)-1, (3)-2, (5)-1 or (5)-2, the carboxylic acid can be converted into a ketone by activating the carboxylic acid with carbodiimidazole, etc., converting into an amide with N-methoxy-N-methylamine and reacting with a Grignard reagent of group Z or group $R^7$ or lithium anion. When a raw material having carboxylic acid group at a position corresponding to the group $X^3$ or $X^4$ of the formula (3)-1, (3)-2, (5)-1 or (5)-2 is unavailable, a compound having methyl group, aldehyde group or —CH$_2$OH at the corresponding position can be converted into carboxylic acid by oxidization. A compound having cyano group at the corresponding group can be converted into carboxylic acid by the hydrolysis of the cyano group. Further, even a compound having only hydrogen atom at the corresponding position can be converted into a carboxylic acid e.g. by the carboxylation with carbon dioxide.

When the group $X^3$ is —NR$^{21}$(C=O) or the group $X^4$ is —NR$^{23}$(C=O) (in this case, the N of —NR$^{21}$(C=O) is bonded to the benzene ring or naphthalene ring in the formula (3)-1 or the formula (3)-2 and the N of —NR$^{23}$(C=O) is bonded to the benzene ring or naphthalene ring in the formula (5)-1 or the formula (5)-2. The definition of $R^{21}$ is same as the one shown in the formula (3)-1 and the formula (3)-2 and that of $R^{23}$ is same as the one shown in the formula (5)-1 and the formula (5)-2.), the objective compound [V] or [IX] can be synthesized by reacting, at an arbitrary reaction stage, the compound [IV] or [VIII] with an acid chloride of the compound of the formula ZCO$_2$H or its activated product in the case that the group —X$^3$H of the compound [IV] or [VIII] is —NHR$^{21}$ or reacting the compound [VIII] with an acid chloride of the formula R$^7$CO$_2$H or ZCO$_2$H or its activated product in the case that the group —X$^4$H of the compound [VIII] is —NHR$^{23}$.

When the group $X^3$ is —(C=O)NR$^{21}$ or the group $X^4$ is —(C=O)NR$^{23}$ (in this case, the carbonyl group of —(C=O)NR$^{21}$ is bonded to the benzene ring or naphthalene ring in the formula (3)-1 or the formula (3)-2 and the carbonyl group of —(C=O)NR$^{23}$ is bonded to the benzene ring or naphthalene ring in the formula (5)-1 or the formula (5)-2. The definition of $R^{21}$ is same as the one expressed in the formula (3)-1 and the formula (3)-2 and that of $R^{23}$ is same as the one expressed in the formula (5)-1 and the formula (5)-2.), the objective compound can be synthesized by coupling, at an arbitrary reaction stage, a corresponding amine with a compound produced by activating a carboxylic acid with carbodiimidazole or oxalyl chloride, etc., using a compound having carboxylic acid group at a position corresponding to the $X^3$ or the $X^4$ of the formula (3)-1, the formula (3)-2, the formula (5)-1 or the formula (5)-2.

When the group $R^4$ is an alkyl group, the objective compound is synthesized, although there is no restriction on the synthesis method, preferably by N-alkylating an anthranilic acid derivative [II] with a general alkylation agent, e.g. an alkyl halide such as an alkyl iodide before the coupling of the derivative with a compound [I] or [VI] in the above scheme and then coupling the alkylation product with the compound [I] or [VI].

Although there is no particular restriction on the process for the synthesis of the compounds [I] and [VI] which are raw materials for the above scheme, these compounds can be synthesized with reference to the description of the International Application WO95/32943 and the International Application 97/19910 or by the following method.

In the case of n is zero, these compounds can be synthesized according to the following scheme.

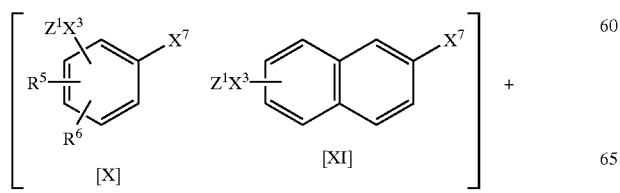

[X]     [XI]

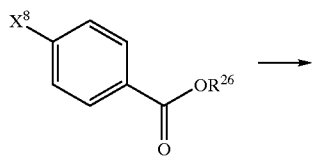

[XIV]

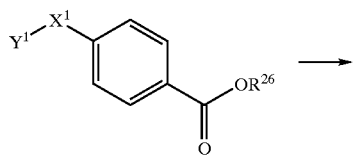

[XV]

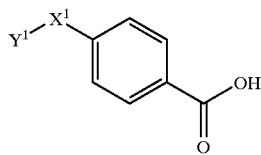

[I]

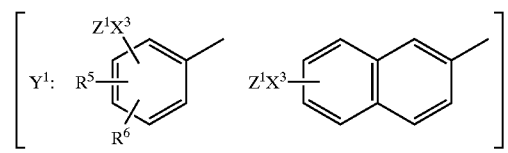

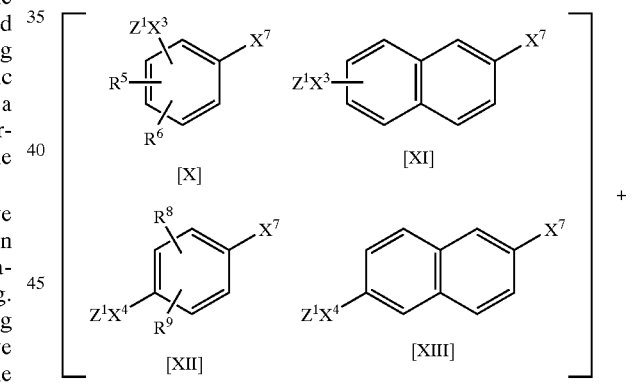

[X]     [XI]

[XII]     [XIII]

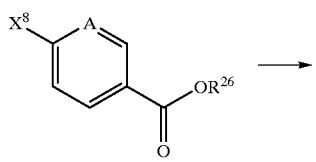

[XVI]

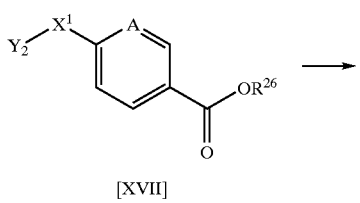

[XVII]

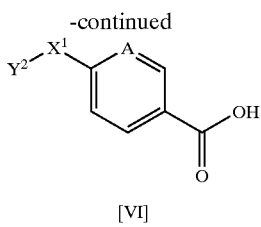

[VI]

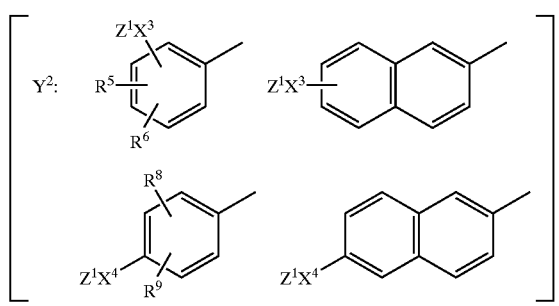

In the above scheme, the definitions of $R^5$, $R^6$, $R^8$, $R^9$, $X^1$, $X^3$, $X^4$ and A are same as the definitions in the formula (1), the formula (2), the formula (3)-1, the formula (3)-2, the formula (5)-1 and the formula (5)-2. The definition of $Z^1$ is same as the aforementioned definition. The group $R^{26}$ is hydrogen atom or a C1–C4 hydrocarbon group. As shown in the above scheme, these compounds can be produced by coupling the compound [X], [XI], [XII] or [XIII] having $X^7$ as a nucleophilic site with the compound [XIV] or [XVI] having a proper eliminable group such as halogen atom on $X^8$ using a proper base reagent and a proper solvent, concretely, the compound [XV] can be synthesized by coupling the compound [X] or [XI] with the compound [XIV] and the compound [XVII] can be synthesized by coupling the compound [X], [XI], [XII] or [XIII] with the compound [XVI]. When the group $R^{26}$ is a hydrocarbon group, the compound [XV] and [XVII] can be converted into the corresponding carboxylic acid [I] and [VI] by the hydrolysis of the ester. Concretely, it can be synthesized by the following method.

In the case of producing the compound [XV] by the reaction of the compound [X] or [XI] with the compound [XIV] and in the case that the group $X^1$ is —O— or —S—, the objective compound [XV] can be synthesized by reacting the compound [X] or [XI] wherein $X^7$ is —OH or —SH with the compound [XIV] wherein $X^8$ is F in the presence of a proper base reagent such as potassium carbonate (other examples of the reagent are sodium carbonate, potassium bicarbonate, etc.) in a proper solvent such as N,N-dimethylacetamide (other examples of the solvent are N,N-dimethylformamide, tetrahydrofuran, methylene chloride, etc.) under a proper temperature condition comprising the reaction at room temperature or under heating. In the above case, the group $R^{26}$ of the compound [XIV] is preferably a C1–C4 hydrocarbon group from the viewpoint of the handleability in synthesis. In other words, it is preferable to obtain the carboxylic acid [I] by the ester hydrolysis of the compound [XV]. In the case of producing the compound [XVII] by the reaction of the compound [X], [XI], [XII] or [XIII] and in the case that the group $X^1$ is —O— or —S—, the compound [XVII] can be synthesized by reacting the compound [X], [XI], [XII] or [XIII] wherein the group $X^7$ is —OH or —SH with the compound [XVI] wherein the group $X^8$ is —Cl in the presence of a proper base reagent such as sodium hydride (other examples of the reagent are potassium carbonate, sodium carbonate and potassium bicarbonate) in a proper solvent such as N,N-dimethylformamide under a proper temperature condition comprising the reaction at 0° C. or under heating. Also in the above case, the group $R^{26}$ of the compound [XVI] is preferably a C1–C4 hydrocarbon group from the viewpoint of the handleability in synthesis. In other words, it is preferable to obtain the carboxylic acid [VI] by the ester hydrolysis of the compound [XVII].

In the case of n is 1, these compounds can be synthesized according to the following scheme.

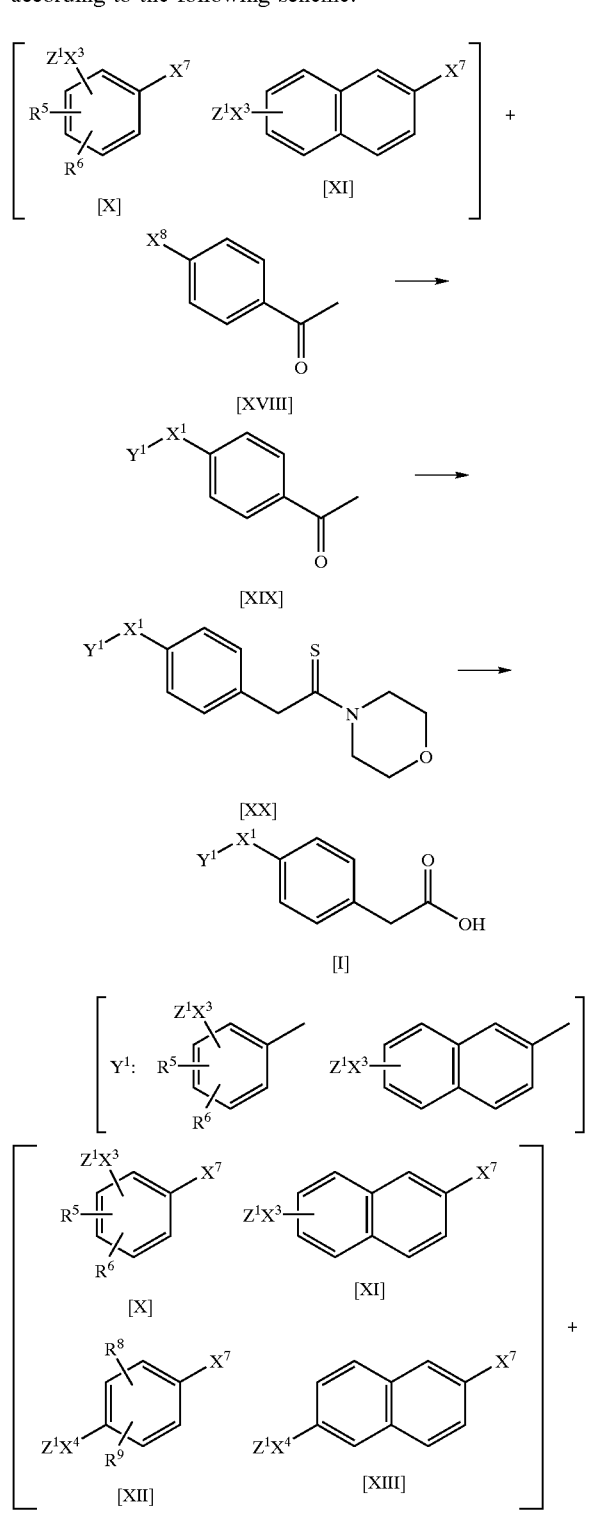

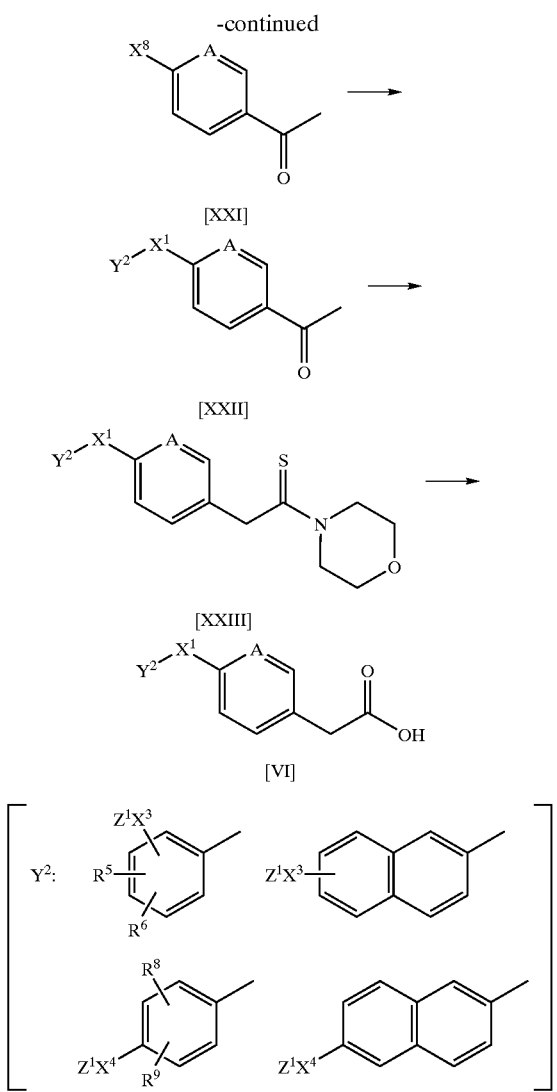

In the above scheme, the definitions of $R^5$, $R^6$, $R^8$, $R^9$, $X^1$, $X^3$, $X^4$ and A are same as the definitions in the formula (1), the formula (2), the formula (3)-1, the formula (3)-2, the formula (5)-1 and the formula (5)-2, and the definition of $Z^1$ is same as aforementioned definition. As shown in the above scheme, these compound can be produced by coupling the compound [X], [XI], [XII] or [XIII] having $X^7$ as a nucleophilic site with the compound [XVIII] or [XXI] having a proper eliminable group such as halogen atom on the group $X^8$ using a proper base reagent and a proper solvent to synthesize the compound [XIX] from the compound [X] or [XI] or synthesize the compound [XXII] from the compound [X], [XI], [XII] or [XIII] and the product is subjected to rearrangement reaction to synthesize the thioamide [XX] from the compound [XIX] or synthesize the compound [XXIII] from the compound [XXII]. Furthermore, the products [XX] and [XXIII] can be converted into the compounds [I] and [VI] by hydrolysis. Concretely, the synthesis can be performed as follows.

In the case of producing the compound [XIX] by the reaction of the compound [X] or [XI] with the compound [XVIII] and in the case that the group $X^1$ is —O— or —S—, the objective compound [XIX] can be synthesized by reacting the compound [X] or [XI] wherein $X^7$ is —OH or —SH with the compound [XVIII] wherein $X^8$ is —F in the presence of a proper base reagent such as potassium carbonate (other examples of the reagent are sodium carbonate, potassium bicarbonate and sodium hydride) in a proper solvent such as N,N-dimethylacetamide under a proper temperature condition comprising the reaction at room temperature or under heating. The product can be converted into the compound [I] by heating in the presence of S and morpholine to effect the rearrangement reaction and hydrolyzing the resultant thioamide [XX].

In the case of producing the compound [XXII] by the reaction of the compound [X], [XI], [XII] or [XIII] and in the case that the group $X^1$ is —O— or —S—, the compound [XXII] can be synthesized by reacting the compound [X], [XI], [XII] or [XIII] wherein the group $X^7$ is —OH or —SH with the compound [XXI] wherein the group $X^8$ is —Cl in the presence of a proper base reagent such as sodium hydride (other examples of the reagent are potassium carbonate, sodium carbonate and potassium bicarbonate) in a proper solvent such as N,N-dimethylformamide under a proper temperature condition comprising the reaction at 0° C. or under heating. The product can be converted into the compound [VI] by heating in the presence of S and morpholine to effect the rearrangement reaction and hydrolyzing the resultant thioamide [XXIII].

Although there is no particular restriction on the process for the synthesis of the compounds [I] and [VI] wherein n is 2 or 3 and $X^1$ is —O— or —S—, these compounds can be synthesized with reference to a coupling method described in the paper of Journal of Medicinal Chemistry vol.40, no.4, sections 395–407 (1997) or similar methods.

Similarly, the compounds [I] and [VI] wherein n is 0 or 3 and $X^1$ is —(C=O)— or —$CH_2$— can be synthesized, although there is no restriction on the process, with reference to a coupling method described in the paper of Journal of Medicinal Chemistry vol.40, no.4, sections 395–407 (1997) or similar methods.

The anthranilic acid derivative of the present invention and its pharmacologically permissible salt can be administered by peroral means or parenteral means such as intravenous injection, subcutaneous injection, intramuscular injection, transcutaneous administration, rectal infusion, nasal administration, eye instillation or by inhalation.

The form of the oral administration drug is, for example, tablet, pill, granule, powder, liquid, suspension, syrup or capsule.

A tablet can be formed by conventional method using an excipient such as lactose, starch and crystalline cellulose, a binder such as carboxymethylcellulose, methylcellulose and polyvinylpyrrolidone, a disintegrant such as sodium alginate, sodium bicarbonate and sodium laurylsulfate; etc.

A pill, granule and powder are also formable by conventional method using the above excipients, etc.

A liquid agent, suspension and syrup can be formed by conventional method using a glycerol ester such as tricaprylin and triacetin; an alcohol such as ethanol; water; a vegetable oil such as corn oil, cottonseed oil, coconut oil, almond oil, peanut oil and olive oil; etc.

A capsule can be formed by filling a granule, powder or liquid agent into a capsule made of gelatin, etc.

The agent for intravenous, subcutaneous or intramuscular administration is, for example, an injection composed of an aseptic aqueous or non-aqueous solution agent. The aqueous solution agent is produced e.g. by using physiological salt solution. The non-aqueous solution agent is produced e.g. by using propylene glycol, polyethylene glycol, a vegetable oil such as olive oil, an injectable organic ester such as ethyl oleate, etc. These drugs may be incorporated as necessary with isotropic agent, antiseptic agent, wetting agent, emulsifying agent, dispersing agent, stabilizing agent, etc., and aseptized by proper treatments such as filtration through a bacteria-retaining filter, compounding of a disinfectant, heating treatment, irradiation treatment, etc. As an alternative, it can be used by preparing an aseptic solid preparation and dissolving the agent in aseptic water or an aseptic solvent for injection immediately before use.

The agent for percutaneous administration is an ointment agent, a cream agent, etc. These agents can be produced, by conventional method using an oil and fat such as castor oil or olive oil or petrolatum, etc., for an ointment agent and a fatty oil, diethylene glycol, an emulsifier such as sorbitan monofatty acid ester, etc., for a cream agent.

A conventional suppository such as gelatin soft capsule is used for the rectal administration.

The preparation for transnasal administration is supplied in the form of a liquid or powdery composition. The base for the liquid agent is water, salt solution, phosphate buffer solution, acetate buffer solution, etc., and the agent may further contain a surfactant, an antioxidant, a stabilizer, a preservative and a thickening agent. The base for the powdery agent is preferably a water-absorbing material, for example, easily water-soluble polyacrylic acid salts such as sodium polyacrylate, potassium polyacrylate and ammonium polyacrylate; cellulose lower alkyl ethers such as methylcellulose, hydroxyethylcellulose, hydroxypropylcellulose and carboxymethylcellulose sodium; polyethylene glycol polyvinylpyrrolidone, amylose, pullullan etc.; celluloses such as a scarcely water-soluble crystalline cellulose, α-cellulose and crosslinked carboxymethylcellulose sodium; starches such as hydroxypropyl starch, carboxymethyl starch, crosslinked starch, amylose, amylopectin and pectin; proteins such as gelatin, casein and casein sodium; gums such as gum arabic, tragacanth gum and glucomannan; crosslinked vinyl polymers such as polyvinylpolypyrrolidone, crosslinked polyacrylic acid and its salt, crosslinked polyvinyl alcohol and polyhydroxyethyl methacrylate; etc., or their mixture. The powdery agent may be incorporated further with an antioxidant, a colorant, a preservative, an antiseptic agent, a decay modifying agent, etc. Such liquid agent and powdery agent can be administered e.g. by using a spraying tool.

The eye instillation agent is an aqueous or non-aqueous instillation. The aqueous instillation can be produced by using sterilized pure water, physiological salt solution or proper aqueous solvent as the solvent, and includes an aqueous eye drop produced by using only a sterilized pure water as the solvent; a viscous eye drop added with a thickening agent such as carboxymethylcellulose, methylcellulose, hydroxypropylcellulose and polyvinylpyrrolidone; an aqueous suspension eye drop added with a surfactant or a suspension agent such as a polymer thickener; a solubilized eye drop added with a solubilizing agent such as a nonionic surfactant; etc. The non-aqueous instillation uses a non-aqueous solvent for injection as the solvent and includes a non-aqueous eye drop produced by using vegetable oil, liquid paraffin, mineral oil, propylene glycol, etc.; a non-aqueous suspension eye drop produced by using a thixotropic colloid such as aluminum monostearate as a suspension agent; etc. These preparations may be incorporated as necessary with an isotonic agent, a preservative, a buffer agent, an emulsifier, a stabilizing agent, etc., or aseptized by proper treatments such as filtration through a bacteria-retaining filter, compounding of a disinfectant, heating treatment, irradiation treatment, etc. As an alternative, it can be used by preparing an aseptic solid preparation and dissolving or suspending the agent in a proper aseptic solution immediately before use.

The dosage form for the administration to the eye other than an ophthalmic instillation is an eye ointment formed by using petrolatum, etc.; an application liquid produced by using dilute iodine tincture, zinc sulfate solution, methyl chloride rosaniline liquid, etc.; a scattering agent to directly apply fine powder of active component; an insertion agent produced by compounding or impregnating an active component in a proper base or a material and used by inserting into the eyelid, etc.

A solution or suspension of an active component and a conventional excipient for medicine is used for the inhalation, for example, in the form of an aerosol spray for inhalation. As an alternative, an active component having dried powdery form is administered by an inhalator or other device to enable the direct contact of the active component with the lung.

The administration dose of the compound of the present invention depends upon the kind of disease, administration path, condition, age, sex, body weight, etc., of the patient, etc. It is about 0.1 to 1,000 mg/day/head, preferably 1 to 300 mg/day/head in oral administration and about 0.1 to 100 mg/day/head, preferably 0.1 to 30 mg/day/head in parenteral administration such as intravenous, subcutaneous, intramuscular, percutaneous, rectal or nasal administration, ophthalmic instillation and inhalation, and the drug is prepared preferably to satisfy the above condition.

In the case of using the compound of the present invention as a preventing agent, such preparations may be administered beforehand according to each symptom by the administration method known as a method for the administration of preventing agent.

As shown in the following Examples, the anthranilic acid derivative of the present invention is effective for suppressing the highly proliferative L929 cell at a low concentration. Since the derivative is also effective for suppressing the proliferation of various other human cancer cells at a low concentration, it is extremely useful as a carcinostatic agent. Furthermore, as shown in the following Examples, the derivative also suppresses the production of IgE antibody from human lymphocyte by an antigen non-specific stimulation (IL-4+IL-10 (interleukin 10)+antiCD40Ab (anti-CD40 antibody)). Accordingly, the anthranilic acid derivative of the present invention is useful also as a preventive and/or therapeutic agent for allergic diseases caused by the production of IgE antibody such as bronchial asthma, allergic rhinitis, allergic conjunctivitis, atopic dermatitis, anaphylactic shock, mite allergy, pollinosis, food allergy, urticaria, ulcerative colitis, eosinophilic gastroenteritis and drug-induced rash.

EXAMPLES

The present invention is explained concretely by the following Reference Examples and Examples. The experiment was performed on the following group of compounds, however, the present invention is not restricted by these Examples. The $^1$H-NMR peaks originated from carboxylic acid, hydroxyl group, amine or amide were sometimes unobservable. Although it is not particularly described, the amine compound may take the form of hydrochloride.

When the following Reference Example or Example contains the sentence of "the following compound was synthesized by a similar method using the corresponding substrate", the used reagent was synthesized by the use of a substrate analogized from the product. In the case that the judgement by analogy was difficult, the substrate was clearly

Reference Example 1

Synthesis of 1-(4-(6-benzyloxy-2-naphthyloxy)phenyl)ethan-1-one

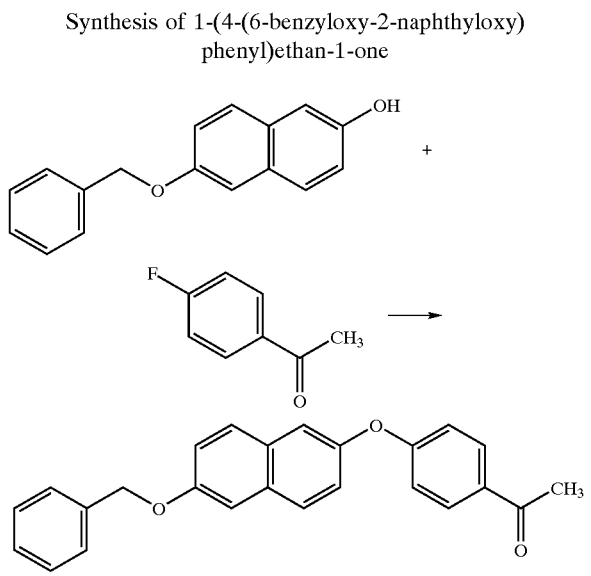

4-Fluoroacetophenone (969 μl, 8.00 mmol) was added to dry N,N-dimethylacetamide (12 ml) solution of 6-benzyloxy-2-naphthol (500 mg, 2.00 mmol) and potassium carbonate (553 mg, 4.00 mmol) in nitrogen atmosphere and stirred at 150° C. for 5 hours. After completing the reaction, 10% citric acid was added to the reaction liquid, extracted with methylene chloride, washed with water, dried with magnesium sulfate and concentrated. The obtained residue was purified by silica gel chromatography to obtain the subject compound (707 mg, 1.92 mmol). The result of $^1$H-NMR was consistent with the above structure.

Yield: 96%

$^1$H-NMR (CDCl$_3$); δ7.94 (d, 2H, J=8.88 Hz), 7.76 (d, 1H, J=8.91 Hz), 7.68 (d, 1H, J=9.88 Hz), 7.51–7.19 (m, 9H), 7.02 (d, 2H, J=8.91 Hz), 5.19 (s, 2H), 2.57 (s, 3H).

Reference Example 2

The following compounds were synthesized by a method similar to the Reference Example 1 using substrates corresponding to respective compounds. The results of $^1$H-NMR were consistent with the above structures.

1-(4-(4-Benzyloxyphenoxy)phenyl)ethan-1-one
  Yield: 73%
  $^1$H-NMR (CDCl$_3$): δ2.56 (s, 3H), 5.07 (s, 2H), 6.97 (m, 6H), 7.42 (m, 5H), 7.91 (m, 2H).
4-(4-Benzyloxyphenyloxy)benzoic acid methyl ester
  Yield: 55%
  $^1$H-NMR (CDCl$_3$); δ7.97 (d, 2H, J=8.90 Hz), 7.31–7.46 (m, 5H), 7.00 (s, 4H), 6.93 (d, 2H, J=8.90 Hz), 5.07 (s, 2H), 3.89 (s, 3H).

In this case, 4-fluorobenzoic acid methyl ester was used in place of 4-fluoroacetophenone.

Reference Example 3

Synthesis of 1-(morpholin-4-yl)-2-(4-(6-benzyloxyphenoxy-2-naphthyloxy)phenyl)ethane-1-thione

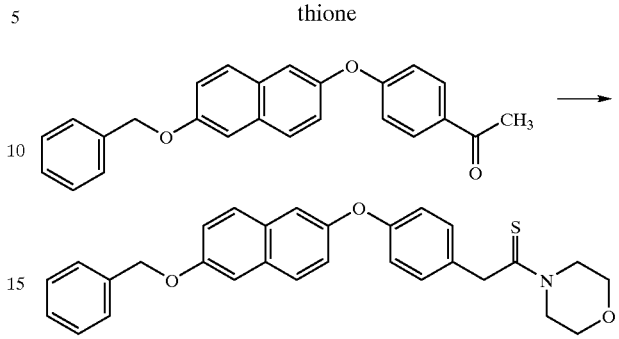

The 1-(4-(6-benzyloxy-2-naphthyloxy)phenyl)ethan-1-one (3.6 g, 9.77 mmol) obtained by the Reference Example 1 was dissolved in morpholine (15 ml) in nitrogen atmosphere, added with sulfur (1.57 g, 48.8 mmol) and stirred at 120° C. for 18 hours. After completing the reaction, methanol was added to the reaction liquid and the formed precipitate was filtered to obtain the subject compound (3.73 g, 7.94 mmol) as the precipitate. The result of $^1$H-NMR was consistent with the above structure.

Yield: 81%

$^1$H-NMR (CDCl$_3$); δ7.72 (d, 1H, J=8.91 Hz), 7.63 (d, 1H, J=9.88 Hz), 7.50–7.18 (m, 11H), 6.99 (d, 2H, J=8.59 Hz), 5.18 (s, 2H), 4.36 (t, 2H, J=4.94 Hz), 4.33 (s, 2H), 3.76 (t, 2H, J=4.78 Hz), 3.67 (t, 2H, J=4.94 Hz), 3.46 (t, 2H, J=4.78 Hz).

Reference Example 4

The following compound was synthesized by a method similar to the Reference Example 3 using the corresponding substrate. The result of $^1$H-NMR was consistent with the structure.

1-Morpholin-4-yl)-2-(4-(4-benzyloxyphenoxy)phenyl)ethane-1-thione.
  Yield: 84%
  $^1$H-NMR (CDCl$_3$); δ7.23–7.46 (m, 7H), 6.96 (m, 6H), 5.05 (s, 2H), 4.34 (m, 2H), 4.30 (s, 2H), 3.74 (m, 2H), 3.64 (m, 2H), 3.45 (m, 2H).

Reference Example 5

Synthesis of 4-(6-benzyloxy-2-naphthoxy)phenylacetic acid

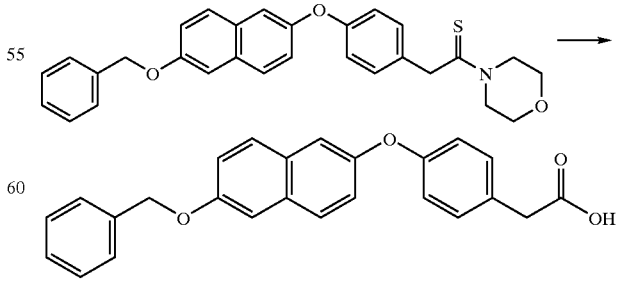

An aqueous solution (10 ml) of 50% sodium hydroxide was added to 70% ethanol solution (50 ml) of the 1-(morpholin-4-yl)-2-(4-(6-benzyloxyphenoxy-2-naphthyloxy)phenyl)-ethane-1-thione (3.73 g, 7.94 mmol) obtained by the Reference Example 3 and the mixture was stirred at 100° C. for a night. After completing the reaction, the reaction liquid was added with 6N hydrochloric acid to adjust the pH to about 2, extracted with ethyl acetate, washed with water, dried with magnesium sulfate and concentrated. The obtained crude product was recrystallized from acetonitrile to obtain the subject compound (2.10 g, 5.46 mmol). The result of $^1$H-NMR was consistent with the above structure.

Yield: 69%

$^1$H-NMR (DMSO-d$_6$); δ12.38 (br, 1H), 7.93 (d, 1H, J=8.91 Hz), 7.86 (d, 1H, J=8.88 Hz), 7.61–7.24 (m, 11H), 7.08 (d, 2H, J=8.48 Hz), 5.30 (s, 2H), 3.65 (s, 2H).

Reference Example 6

The following compound was synthesized by a method similar to the Reference Example 5 using a corresponding substrate. The result of $^1$H-NMR was consistent with the structure.

4-(4-Benzyloxyphenoxy)phenylacetic acid

Yield: 86%

$^1$H-NMR (DMSO-d$_6$); δ12.12 (s, 1H), 7.31–7.14 (m, 5H), 7.06 (d, 2H, J=8.41 Hz), 6.85 (m, 4H), 6.70 (d, 2H, J=8.41 Hz), 4.92 (s, 2H), 3.36 (s, 2H).

Reference Example 7

Synthesis of 4-(6-benzyloxy-2-naphthyloxy)benzoic acid

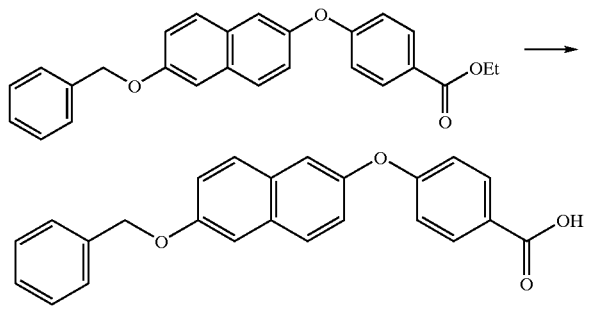

4-(6-Benzyloxy-2-naphthyloxy)benzoic acid ethyl ester (10.6 g, 26.2 mmol) was dissolved in a 2:1 mixture of THF and methanol (150 ml), added with 4N lithium hydroxide (33 ml) and stirred at room temperature. After completing the reaction, the reaction liquid was adjusted to pH 2 or thereabout with 1N hydrochloric acid, extracted with ethyl acetate, washed with water, dried with magnesium sulfate and concentrated to obtain the subject compound (8.70 g, 23.4 mmol). The result of $^1$H-NMR was consistent with the above structure.

Yield: 88%

$^1$H-NMR (DMSO-d$_6$); δ12.79 (brs, 1H), 7.94 (d, 2H, J=8.91 Hz), 7.90 (d, 1H, J=8.91 Hz), 7.82 (d, 1H, J=8.91 Hz), 7.56–7.25 (m, 9H), 7.05 (d, 2H, J=8.74 Hz), 5.23 (s, 2H).

Reference Example 8

The following compound was synthesized by a method similar to the Reference Example 7 using a corresponding substrate. The result of $^1$H-NMR was consistent with the structure.

4-(4-Benzyloxyphenyloxy)benzoic acid

Yield: 89%

$^1$H-NMR (DMSO-d$_6$); δ7.90 (d, 2H, J=8.91 Hz), 7.47–7.30 (m, 5H), 7.08 (s, 4H), 6.95 (d, 2H, J=8.91 Hz), 5.10 (s, 2H).

In this case, the methyl ester of the subject compound was used as the substrate.

Reference Example 9

Synthesis of 6-(4-benzyloxyphenoxy)-3-acetylpyridine

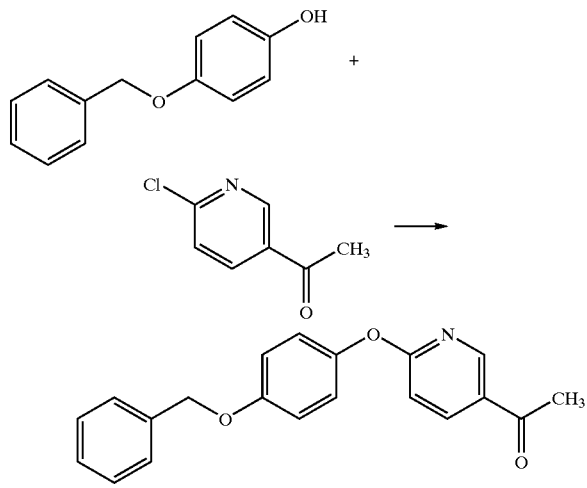

Dried DMF solution (50 ml) of sodium hydride (60% in oil, 7.24 g, 181 mmol) was cooled with ice in nitrogen atmosphere, dried DMF solution (50 ml) of hydroquinone monobenzyl ether (36.2 g, 181 mmol) was dropped into the above solution spending 10 minutes under ice cooling and the mixture was stirred for 1.5 hours under ice cooling. Dried DMF solution (110 ml) of 6-chloro-3-acetylpyridine (26.7 g, 172 mmol) was dropped into the above mixture spending 15 minutes and stirred for 2 hours under ice cooling. After completing the reaction, the reaction liquid was acidified with 6N hydrochloric acid, added with water, extracted with ethyl acetate, washed with water (400 ml×3), dried with magnesium sulfate and concentrated. The residue was recrystallized from 2-propanol (300 ml) to obtain the subject compound (43.3 g, 136 mmol). The result of $^1$H-NMR was consistent with the above structure.

Yield: 75%

$^1$H-NMR (CDCl$_3$); δ8.76 (d, 1H, J=2.64 Hz), 8.24 (dd, 1H, J=2.64, 8.58 Hz), 7.46–7.31 (m, 5H), 7.10–7.00 (m, 4H), 6.94 (d, 1H, J=8.58 Hz), 5.08 (s, 2H), 2.56 (s, 3H).

Reference Example 10

The following compounds were synthesized by a method similar to the Reference Example 9 using corresponding substrates. The results of $^1$H-NMR were consistent with the structures.

6-(6-Benzyloxy-2-naphthyloxy)-3-acetylpyridine

Yield: 26%

$^1$H-NMR (CDCl$^3$); δ2.57 (s, 3H), 5.20 (s, 2H), 7.01 (d, 1H, J=8.78 Hz), 7.79–7.14 (m, 11H), 8.27 (dd, 1H, J=2.44 Hz, 6.10 Hz), 8.76 (d, 1H, J=2.44 Hz).

6-(4-Benzyloxyphenoxy)pyridine-3-carboxylic acid methyl ester
Yield: 81%
¹H-NMR (CDCl₃); δ8.81 (d, 1H, J=2.64 Hz), 8.25 (dd, 1H, J=2.31, 8.58 Hz), 7.46–7.31 (m, 5H), 7.08 (d, 2H, J=8.90 Hz), 7.02 (d, 2H, J=9.24 Hz), 6.90 (d, 1H, J=8.58 Hz), 5.07 (s, 2H), 3.91 (s, 3H).

In this case, 6-chloro-nicotinic acid methyl ester was used as the substrate in place of 6-chloro-3-acetylpyridine. Similar substrates were used in the synthesis of the following carboxylic acid methyl esters of the Reference Example 10.

6-(4-Benzyloxyphenylthio)pyridine-3-carboxylic acid methyl ester
Yield: 49%
¹H-NMR (CDCl₃); δ8.81 (d, 1H, J=2.63 Hz), 8.27 (dd, 1H, J=2.31, 8.58 Hz), 7.55–7.16 (m, 6H), 7.05 (d, 2H, J=8.91 Hz), 6.92 (d, 1H, J=7.57 Hz), 6.71 (d, 1H, J=8.58 Hz), 4.11 (s, 2H), 3.92 (s, 3H).

6-(4-(1-Ethylpropylthio)phenoxy)pyridine-3-carboxylic acid methyl ester
Yield: 80%
¹H-NMR (CDCl₃); δ8.83 (d, 1H, J=2.31 Hz), 8.28 (dd, 1H, J=1.97, 8.24 Hz), 7.45 (d, 2H, J=8.25 Hz), 7.08 (d, 2H, J=8.24 Hz), 6.94 (d, 1H, J=8.57 Hz), 3.92 (s, 3H), 2.96 (m, 1H), 1.63 (m, 4H), 1.03 (t, 6H, J=7.26 Hz).

6-(2-Methyl-4-benzyloxyphenoxy)pyridine-3-carboxylic acid methyl ester
Yield: 58%
¹H-NMR (CDCl₃); δ8.81 (d, 1H, J=2.31 Hz), 8.25 (dd, 1H, J=2.31, 8.91 Hz), 7.47–7.31 (m, 5H), 6.99 (d, 1H, J=8.91 Hz), 6.91–6.83 (m, 3H), 5.05 (s, 2H), 3.91 (s, 3H), 2.12 (s, 3H).

6-(3-Methyl-4-benzyloxyphenoxy)pyridine-3-carboxylic acid methyl ester
Yield: 51%
¹H-NMR (CDCl₃); δ8.82 (dd, 1H, J=0.66, 2.31 Hz), 8.25 (dd, 1H, J=2.31, 8.58 Hz), 7.47–7.31 (m, 5H), 6.96–6.87 (m, 4H), 5.08 (s, 2H), 3.91 (s, 3H), 2.29 (s, 3H).

Reference Example 11

Synthesis of 6-(4-benzyloxyphenoxy)pyridine-3-carboxylic acid

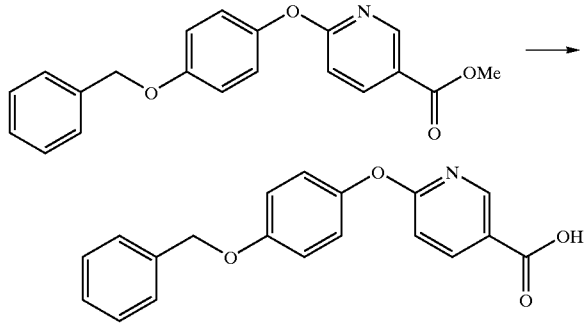

A THF-MeOH (2/1) solution (750 ml) of 6-(4-benzyloxyphenoxy)pyridine-3-carboxylic acid methyl ester (78.6 g, 234 mmol) obtained by the Reference Example 10 was added with 4N-lithium hydroxide solution (87.8 ml, 351 mmol) at room temperature (inner temperature: 15–20° C.) and stirred at room temperature (20–30° C.) for 4 hours. After completing the reaction, the reaction liquid was added with 10% aqueous solution of citric acid (600 ml) (inner temperature: 20–30° C.) to adjust the pH to about 4. The product was extracted with ethyl acetate (500 ml×3), washed with water (500 ml×1), dried with magnesium sulfate and concentrated. The residue was recrystallized from isopropanol (90 ml) to obtain the subject compound (59.9 g, 18.6 mmol). The result of ¹H-NMR was consistent with the above structure.
Yield: 80%
¹H-NMR (DMSO-d₆); δ13.14 (br, 1H), 8.65 (d, 1H, J=2.31 Hz), 8.26 (dd, 1H, J=2.31, 8.58 Hz), 7.48–7.31 (m, 5H), 7.13–7.03 (m, 5H), 5.12 (s, 2H).

Reference Example 12

The following compounds were synthesized by a method similar to the Reference Example 11 using corresponding substrates. The results of ¹H-NMR were consistent with the structures.

6-(4-Benzyloxyphenylthio)pyridine-3-carboxylic acid
Yield: 94%
¹H-NMR (DMSO-d₆); δ13.17 (br, 1H), 8.65 (d, 1H, J=2.31 Hz), 8.28 (dd, 1H, J=2.30, 8.57 Hz), 7.40–7.21 (m, 7H), 7.13–7.07 (m, 3H), 4.24 (s, 2H).

6-(4-(1-Ethylpropylthio)phenoxy)pyridine-3-carboxylic acid
Yield: 79%
¹H-NMR (CDCl₃); δ8.90 (d, 1H, J=2.30 Hz), 8.33 (dd, 1H, J=2.31, 8.25 Hz), 7.45 (d, 2H, J=8.25 Hz), 7.09 (d, 2H, J=7.91 Hz), 6.97 (d, 1H, J=8.91 Hz), 2.96 (m, 1H), 1.63 (m, 4H), 1.02 (t, 6H, J=7.26 Hz).

6-(2-Methyl-4-benzyloxyphenoxy)pyridine-3-carboxylic acid
Yield: 100%
¹H-NMR (DMSO-d₆); δ8.59 (d, 1H, 1.98 Hz), 8.23 (dd, 1H, J=1.98, 8.57 Hz), 7.48–7.31 (m, 5H), 7.01–6.98 (m, 2H), 6.92 (d, 1H, J=8.57 Hz), 6.87 (dd, 1H, J=2.97, 8.58 Hz), 5.10 (s, 2H), 2.02 (s, 3H).

6-(3-Methyl-4-benzyloxyphenoxy)pyridine-3-carboxylic acid
Yield: 100%
¹H-NMR (DMSO-d₆); δ8.61 (d, 1H, J=1.98 Hz), 8.22 (dd, 1H, J=1.98, 8.25 Hz), 7.50–7.31 (m, 5H), 7.05–6.98 (m, 4H), 5.13 (s, 2H), 2.21 (s, 3H).

Reference Example 13

Synthesis of N-methoxy-N-methyl(6-(4-benzyloxyphenoxy)-3-pyridyl)formamide

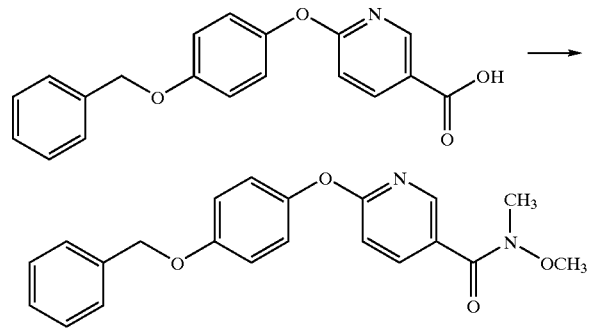

Dried THF solution (300 ml) of 6-(4-benzyloxyphenoxy)pyridine-3-carboxylic acid (58.1 g, 181 mmol) obtained by the Reference Example 11 was cooled with ice (inner temperature 3° C.) in nitrogen atmosphere, oxalyl chloride (17.4 ml, 199 mmol) was dropped into the solution (inner temperature 3–7° C.) spending 7 minutes, and the mixture was added with DMF (3 ml) and stirred for 1 hour under ice cooling or at room temperature (3 to 20° C.). The reaction liquid was concentrated and dried by evacuating with a vacuum pump. The residual THF solution (300 ml) was cooled with ice (inner temperature 3° C.) in nitrogen atmosphere, N,O-dimethylhydroxylamine hydrochloride (21.2 g, 217 mmol) was added thereto, triethylamine (60 ml, 434 mmol) was dropped into the mixture (inner temperature 5–8° C.) and stirred over a night under ice cooling to room temperature (7–20° C.). After completing the reaction, the reaction liquid was added with water (400 ml), extracted with ethyl acetate (400 ml×3), washed with water (400 ml×3), dried with magnesium sulfate and concentrated. The residue was purified by silica gel chromatography to obtain the subject compound (54 g, 148 mmol). The result of $^1$H-NMR was consistent with the above structure.

Yield: 82%

$^1$H-NMR (CDCl$_3$); δ8.63 (dd, 1H, J=0.66, 2.31 Hz), 8.08 (dd, 1H, J=2.31, 8.58 Hz), 7.47–7.30 (m, 5H), 7.11–6.94 (m, 4H), 6.90 (dd, 1H, J=0.66, 8.58 Hz), 5.07 (s, 2H), 3.57 (s, 3H), 3.37 (s, 3H).

Reference Example 14

The following compounds were synthesized by a method similar to the Reference Example 13 using corresponding substrates. The results of $^1$H-NMR were consistent with the structures.

N-Methoxy-N-methyl(6-(4-benzyloxyphenylthio)-3-pyridyl)formamide
  Yield: 91%
  $^1$H-NMR (CDCl$_3$); δ8.63 (d, 1H, J=2.31 Hz), 8.10 (dd, 1H, J=2.31, 8.58 Hz), 7.65–7.21 (m, 6H), 7.09–7.02 (m, 3H), 6.92 (d, 1H, J=8.57 Hz), 4.11 (s, 2H), 3.57 (s, 3H), 3.38 (s, 3H).

N-Methoxy-N-methyl(6-(4-(1-ethylpropyllthio)phenoxy)-3-pyridyl)formamide
  Yield: 85%
  $^1$H-NMR (CDCl$_3$); δ8.64 (d, 1H, J=2.31 Hz), 8.11 (dd, 1H, J=2.31, 8.58 Hz), 7.45 (d, 2H, J=8.58 Hz), 7.09 (d, 2H, J=8.57 Hz), 6.93 (d, 1H, J=8.57 Hz), 3.58 (s, 3H), 3.38 (s, 3H), 2.95 (m, 1H), 1.62 (m, 4H), 1.02 (t, 6H, J=7.26 Hz).

N-Methoxy-N-methyl(6-(2-methyl-4-benzyloxyphenoxy)-3-pyridyl)formamide
  Yield: 72%
  $^1$H-NMR (CDCl$_3$); δ8.63 (d, 1H, J=2.31 Hz), 8.08 (ddd, 1H, J=0.66, 2.31, 8.58 Hz), 7.47–7.33 (m, 5H), 7.00 (d, 1H, J=8.58 Hz), 6.91–6.83 (m, 3H), 5.05 (s, 2H), 3.58 (s, 3H), 3.37 (s, 3H), 2.13 (s, 3H).

N-Methoxy-N-methyl(6-(3-methyl-4-benzyloxyphenoxy)-3-pyridyl)formamide
  Yield: 66%
  $^1$H-NMR (CDCl$_3$); δ8.64 (d, 1H, J=2.31 Hz), 8.07 (dd, 1H, J=2.31, 8.58 Hz), 7.47–7.33 (m, 5H), 6.97–6.87 (m, 4H), 5.09 (s, 2H), 3.58 (s, 3H), 3.37 (s, 3H), 2.30 (s, 3H).

Reference Example 15

Synthesis of 6-(4-benzyloxyyhenoxy)-3-acetylpyridine

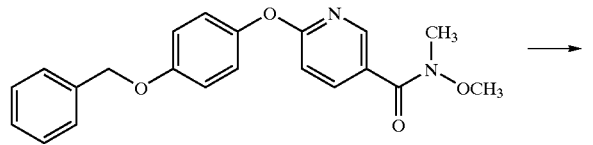

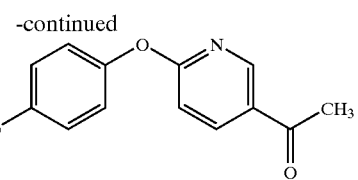

Dried THF solution (250 ml) of N-methyl-N-methoxy(6-(4-benzyloxyphenoxy)-3-pyridyl)formamide (53.3 g, 147 mmol) obtained by the Reference Example 13 was cooled in a bath of −78° C. (inner temperature −70° C.) in nitrogen atmosphere, methyllithium (1.03 M/Et20, 171 ml, 176 mmol) was dropped into the solution spending 25 minutes (inner temperature −70 to −55° C.) and the mixture was stirred in a bath of −78° C. for 1 hour (inner temperature −70 to −55° C.). After completing the reaction, the reaction liquid was added with methanol (20 ml) in cooled state and stirred for 3 minutes. The cooling bath was removed and saturated aqueous solution of ammonium chloride (300 ml) was added to the liquid. The product was extracted with ethyl acetate (200 ml×3), washed with water (200 ml×1), dried with magnesium sulfate and concentrated. The residue was recrystallized from isopropanol (300 ml) to obtain the subject compound (41.9 g, 131 mmol). The result of $^1$H-NMR was consistent with the above structure.

Yield: 89%

$^1$H-NMR (CDCl$_3$); δ8.76 (d, 1H, J=2.64 Hz), 8.24 (dd, 1H, J=2.64, 8.58 Hz), 7.46–7.31 (m, 5H), 7.10–7.00 (m, 4H), 6.94 (d, 1H, J=8.58 Hz), 5.08 (s, 2H), 2.56 (s, 3H).

Reference Example 16

The following compounds were synthesized by a method similar to the Reference Example 15 using corresponding substrates. The results of $^1$H-NMR were consistent with the structures.

6-(4-Benzyloxyphenylthio)-3-acetylpyridine
  Yield: 77%
  $^1$H-NMR (CDCl$_3$); δ8.75 (d, 1H, J=2.30 Hz), 8.26 (dd, 1H, J=2.31, 8.58 Hz), 7.37–7.21 (m, 7H), 7.06 (d, 2H, J=8.91 Hz), 6.96 (d, 1H, J=8.58 Hz), 4.12 (s, 2H), 2.57 (s, 3H).

6-(4-(1-Ethylpropylthio)phenoxy)-3-acetylpyridine
  Yield: 97%
  $^1$H-NMR (CDCl$_3$); δ8.77 (d, 1H, J=2.64 Hz), 8.26 (dd, 1H, J=2.31, 8.91 Hz), 7.45 (d, 2H, J=8.58 Hz), 7.08 (d, 2H, J=8.24 Hz), 6.97 (d, 1H, J=8.58 Hz), 2.96 (m, 1H),2.57 (s, 3H), 1.63 (m, 4H), 1.03 (t, 6H, J=7.26 Hz).

6-(2-Methyl-4-benzyloxyphenoxy)-3-acetylpyridine
  Yield: 100%
  $^1$H-NMR (CDCl$_3$); δ8.75 (d, 1H, J=2.30 Hz), 8.24 (dd, 1H, J=2.30, 8.58 Hz), 7.47–7.31 (m, 5H), 6.99 (d, 1H, J=8.58 Hz), 6.94–6.83 (m, 4H), 5.05 (s, 2H), 2.56 (s, 3H), 2.12 (s, 3H).

6-(3-Methyl-4-benzyoxyphenoxy)-3-acetylpyridine
  Yield: 100%
  $^1$H-NMR (CDCl$_3$); δ8.76 (d, 1H, J=2.31 Hz), 8.23 (dd, 1H, J=2.31, 8.58 Hz), 7.47–7.33 (m, 5H), 6.97–6.91 (m, 4H), 5.09 (s, 2H), 2.56 (s, 3H), 2.30 (s, 3H).

Reference Example 17

Synthesis of 1-(morpholin-4-yl)-2-(6-(4-benzyloxyphenoxy)-3-pyridyl)ethane-1-thione

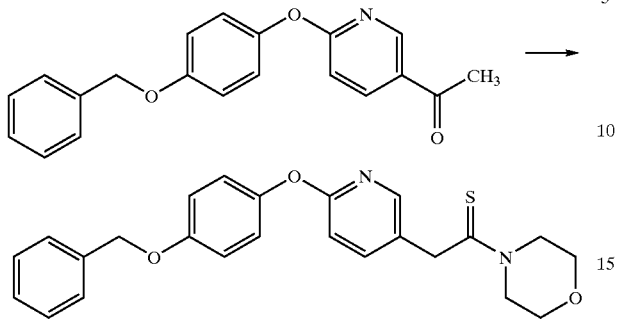

Sulfur (8.21 g, 256 mmol) was added to a morpholine solution (200 ml) of 6-(4-benzyloxyphenoxy)-3-acetylpyridine (40.8 g, 128 mmol) obtained by the Reference Example 9 in nitrogen atmosphere and stirred for 5 hours in a bath of 120° C. After completing the reaction, the reaction liquid was concentrated and purified by silica gel chromatography to obtain the subject compound (30.6 g, 73 mmol). The result of $^1$H-NMR was consistent with the above structure.

Yield: 57%

$^1$H-NMR (CDCl$_3$); δ8.03 (d, 1H, J=2.64 Hz), 7.78 (dd, 1H, J=2.64, 8.58 Hz), 7.45–7.30 (m, 5H), 7.08–6.98 (m, 4H), 6.86 (d, 1H, J=8.58 Hz), 5.06 (s, 2H), 4.33 (dd, 2H, J=4.94, 4.95 Hz), 4.24 (s, 2H), 3.75 (dd, 2H, J=4.62, 5.28 Hz), 3.67 (dd, 2H, J=4.29, 5.28 Hz), 3.51 (dd, 2H, J=4.29, 5.28 Hz).

Reference Example 18

The following compounds were synthesized by a method similar to the Reference Example 17 using corresponding substrates. The results of $^1$H-NMR were consistent with the structures.

1-(Morpholin-4-yl)-2-(6-(6-benzyloxy-2-naphthyloxy)-3-pyridyl)ethane-1-thione

Yield: 45%

$^1$H-NMR (CDCl$_3$); δ3.53 (m, 2H, J=2.64 Hz), 3.69 (m, 2H), 3.76 (m, 2H), 4.25 (s, 2H), 4.34 (m, 2H), 5.19 (s, 2H), 6.94 (d, 1H, J=8.58 Hz), 7.22–7.84 (m, 12H), 8.05 (d, 1H, J=2.48 Hz).

2-(6-(4-(1-Ethylpropylthio)phenoxy)-3-pyridyl)-1-(morpholin-4-yl)ethane-1-thione Yield: quant.

$^1$H-NMR (CDCl$_3$); δ8.06 (d, 1H, J=2.31 Hz), 7.81 (dd, 1H, J=2.64, 8.58 Hz), 7.42 (d, 2H, J=8.58 Hz), 7.05 (d, 2H, J=8.58 Hz), 6.90 (d, 1H, J=8.58 Hz), 4.33 (m, 2H), 3.76 (m, 2H), 3.74 (s, 2H), 3.67 (m, 2H), 3.52 (m, 2H), 2.93 (m, 1H), 1.61 (m, 4H), 1.02 (t, 6H, J=7.26 Hz).

2-(6-(2-Methyl-4-benzyloxyphenoxy)-3-pyridyl)-1-(morpholin-4-yl)ethane-1-thione

Yield: 84%

$^1$H-NMR (CDCl$_3$); δ8.02 (d, 1H, J=2.31 Hz), 7.78 (dd, 1H, J=2.31, 8.58 Hz), 7.46–7.33 (m, 5H), 6.98 (d, 1H, J=8.58 Hz), 6.89 (d, 1H, J=2.64 Hz), 6.83 (d, 2H, J=8.58 Hz), 5.04 (s, 2H), 4.36–4.31 (m, 4H), 4.23 (s, 2H), 3.73–3.65 (m, 2H), 3.52–3.48 (m, 2H), 2.12 (s, 3H).

2-(6-(3-Methyl-4-benzyloxyphenoxy)-3-pyridyl)-1-(morpholin-4-yl)ethane-1-thione

Yield: 80%

$^1$H-NMR (CDCl$_3$); δ8.03 (d, 1H, J=2.64 Hz), 7.77 (dd, 1H, J=2.64, 8.58 Hz), 7.46–7.27 (m, 5H), 6.95 (s, 1H), 6.89 (s, 2H), 6.85 (d, 1H, J=8.58 Hz), 5.07 (s, 2H), 4.34–4.31 (m, 4H), 4.23 (s, 2H), 3.68–3.65 (m, 2H), 3.53–3.49 (m, 2H), 2.28 (s, 3H).

Reference Example 19

Synthesis of 2-(6-(4-benzyloxyphenoxy)-3-pyridyl)acetic acid

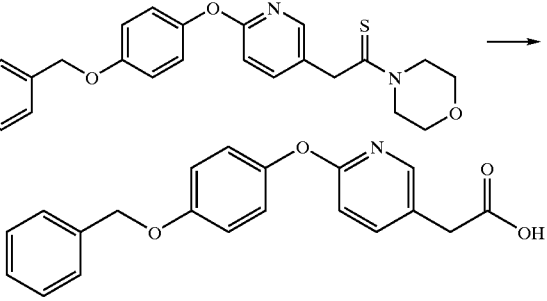

1-Morpholin-4-yl)-2-(6-(4-benzyloxyphenoxy)-3-pyridyl)ethane-1-thione (28.9 g, 71 mmol) obtained by the Reference Example 17 was dissolved in a mixture (2:1, 300 ml) of ethanol-30% aqueous solution of sodium hydroxide and stirred for 1 hour in a bath of 100° C. After completing the reaction, the reaction product was acidified by the addition of 50% aqueous solution of citric acid (250 ml), extracted with methylene chloride (250×3), washed with water, dried with magnesium sulfate and concentrated to obtain the subject compound (22.8 g, 68.0 mmol). The result of $^1$H-NMR was consistent with the above structure.

Yield: 96%

$^1$H-NMR (CDCl$_3$); δ9.90 (br, 1H), 8.08 (s, 1H), 7.61 (dd, 1H, J=2.64, 8.58 Hz), 7.45–7.31 (m, 5H), 7.06–6.96 (m, 4H), 6.80 (d,1H, J=8.58 Hz), 5.04 (s, 2H), 3.56 (s, 2H).

Reference Example 20

The following compounds were synthesized by a method similar to the Reference Example 19 using corresponding substrates. The results of $^1$H-NMR were consistent with the structures.

2-(6-(6-Benzyloxy-2-naphthyloxy)-3-pyridyl)acetic acid

Yield: 73%

$^1$H-NMR (CDCl$_3$); δ3.62 (s, 2H), 5.18 (s, 2H), 6.92 (d, 1H, J=8.25 Hz), 7.23–7.76 (m, 12H), 8.10 (s, 1H).

2-(6-(4-Benzyloxyphenylthio)-3-pyridyl)acetic acid

Yield: 38%

$^1$H-NMR (DMSO-d$_6$); δ12.44 (br, 1H), 8.01 (s, 1H), 7.74 (d, 1H, J=8.25 Hz), 7.38–7.21 (m, 7H), 7.05 (d, 2H, J=8.91 Hz), 6.97 (d, 1H, J=8.25 Hz), 4.22 (s, 2H), 3.58 (s, 2H).

2-(6-(4-(1-Ethylpropylthio)phenoxy)-3-pyridyl)acetic acid

Yield: 24% (two steps from the Reference Example 18)

$^1$H-NMR (CDCl$_3$); δ10.34 (br, 1H), 8.12 (d, 1H, J=2.31 Hz), 7.66 (dd, 1H, J=2.31, 8.58 Hz), 7.42 (d, 2H, J=8.58 Hz), 7.04 (d, 2H, J=8.58 Hz), 6.86 (d, 1H, J=8.58 Hz), 3.60 (s, 2H), 2.93 (m, 1H), 1.61 (m, 4H), 1.01 (t, 6H, J=7.26 Hz).

2-(6-(2-Methyl-4-benzyloxyphenoxy)-3-pyridyl)acetic acid

Yield: 78%

$^1$H-NMR (CDCl$_3$); δ8.03 (dd, 1H, J=2.64, 17.49 Hz), 7.62 (d, 1H, J=8.25 Hz, 7.45–7.30 (m, 5H), 6.97 (d, 1H, J=8.58 Hz), 6.89 (d, 1H, J=2.64 Hz), 6.84–6.78 (m, 2H), 5.04 (s, 2H), 2.14 (s, 2H), 2.08 (s, 3H).

2-(6-(3-Methyl-4-benzyloxyphenoxy)-3-pyridyl)acetic acid

Yield: 55%

$^1$H-NMR (CDCl$_3$); δ8.08 (d, 1H, J=2.31 Hz), 7.62 (dd, 1H, J=2.31, 8.25 Hz), 7.46–7.30 (m, 5H), 6.94 (s, 1H), 6.90–6.89 (m, 2H), 6.83 (d, 1H, J=8.58 Hz), 5.07 (s, 2H), 3.60 (s, 2H), 2.28 (s, 3H).

Reference Example 21

Synthesis of 2-((4-(6-benzyloxy-2-naphthyloxy)phenyl)acetylamino)benzoic acid methyl ester

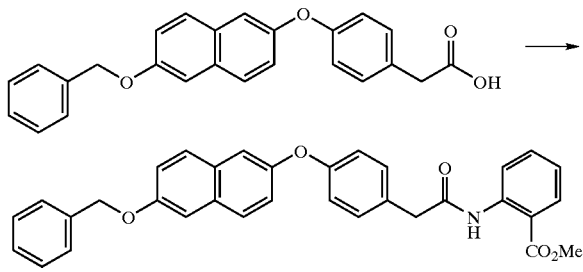

Oxalyl chloride (3.84 ml, 44.1 mmol) was dropped into a dry methylene chloride solution (200 ml) of 4-(6-benzyloxy-2-naphthoxy)phenylacetic acid (15.4 g, 40.06 mmol) obtained by the Reference Example 5 in nitrogen atmosphere, 5 drops of DMF were added with a pipette and the mixture was stirred for 2.5 hours at 35° C. The reaction liquid was concentrated and the residue was dissolved in dry methylene chloride (200 ml). The obtained solution was dropped into a dry methylene chloride. solution (200 ml) of methyl anthranylate (5.18 ml, 40.06 mmol) and triethylamine (6.14 ml, 44.1 mmol) under ice cooling in nitrogen atmosphere, and the mixture was stirred as it is for 1.5 hours and then for a night at room temperature. After completing the reaction, water is added to the reaction liquid, extracted twice with chloroform, washed with saturated sodium chloride solution, dried with anhydrous sodium sulfate and concentrated. The residue was purified by silica gel chromatography to obtain the subject compound (17.5 g, 33.8 mmol). The result of $^1$H-NMR was consistent with the above structure. Colorless acicular crystal.

Yield: 84%

$^1$H-NMR (CDCl$_3$); δ3.75 (s, 2H), 3.88 (s, 3H), 5.17 (s, 2H), 7.02–7.11 (m, 3H), 7.20–7.26 (m, 3H), 7.32–7.56 (m, 9H), 7.62 (d, J=9.6 Hz, 1H), 7.70 (d, J=8.9 Hz, 1H), 8.01 (dd, J=1.7, 8.2 Hz, 1H), 8.73 (dd, J=1.0, 8.3 Hz, 1H), 11.08 (br.s, 1H).

Reference Example 22

The following compounds were synthesized by a method similar to the Reference Example 21 using corresponding substrates. The results of $^1$H-NMR were consistent with the structures.

2-((4-(6-Benzyloxy-2-naphthyloxy)phenyl)carbonylamino)benzoic acid methyl ester

Yield: 93%

$^1$H-NMR (CDCl$_3$); δ3.95 (s, 3H), 5.20 (s, 2H), 7.00–7.15 (m, 2H), 7.20–7.30 (m, 4H), 7.35–7.45 (m, 4H), 7.49 (d, J=1.0 Hz, 2H), 7.50–7.60 (m, 1H), 7.60–7.70 (m, 1H), 7.76 (d, J=8.9 Hz, 1H), 8.04 (dd, J=2.0, 9.9 Hz, 2H), 8.10 (d, J=1.7 Hz, 1H), 8.90 (dd, J=1.0, 9.5 Hz, 1H), 12.0 (brs, 1H).

2-((4-(4-Benzyloxyphenoxy)phenyl)carbonylamino)benzoic acid methyl ester

Yield: 87%

$^1$H-NMR (CDCl$_3$); δ12.00 (m, 1H), 8.91 (m, 1H), 8.02 (m, 3H), 7.61 (m, 1H), 6.98–7.45 (m, 12H), 5.08 (s, 2H), 3.97 (s, 3H).

2-(2-(4-(4-Benzyloxyphenoxy)phenyl)acetylamino)benzoic acid methyl ester

Yield: 75%

$^1$H-NMR (CDCl$_3$); δ3.72 (2H, s), 3.87 (3H, s), 5.04 (2H, s), 6.91–7.02 (6H, m), 7.06 (1H, td, J=8.6, 1.6 Hz), 7.24–7.46 (7H, m), 7.52 (1H, td, J=8.0, 1.6 Hz), 7.99 (1H, dd, J=8.2, 1.6 Hz), 8.71 (1H, dd, J=8.6, 1.3 Hz), 11.03 (1H, brs).

Reference Example 23

Synthesis of 2-(2-(4-(6-hydroxy-2-naphthyloxy)phenyl)acetylamino)benzoic acid methyl ester

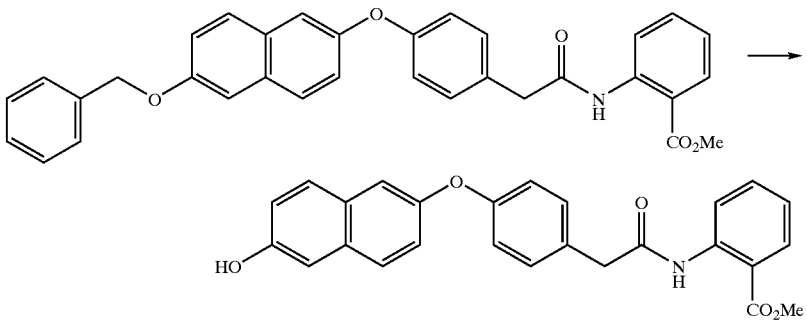

2-((4-(6-Benzyloxy-2-naphthyloxy)phenyl)acetylamino)benzoic acid methyl ester (15.0 g, 29.0 mmol) obtained by the Reference Example 21 was dissolved in chloroform (150 ml) under heating and Pd-black (1.57 g) was added to the solution. The reaction system was stirred for a night at room temperature in hydrogen atmosphere. The reaction liquid was filtered with celite and the filtrate was concentrated. The residue was recrystallized from acetonitrile to obtain the subject compound (10.5 g, 24.5 mmol). The result of $^1$H-NMR was consistent with the above structure. Light brown granular crystal.

Yield: 92%

$^1$H-NMR (CDCl$_3$); δ3.76 (s, 2H), 3.89 (s, 3H), 5.26 (brs, 1H), 7.02–7.15 (m, 5H), 7.22 (dd, J=2.3, 8.9 Hz, 1H), 7.31–7.37 (m, 3H), 7.53 (dt, J=1.7, 8.9 Hz, 1H), 7.60 (d, J=9.2 Hz, 1H), 7.64 (d, J=8.9 Hz, 1H), 8.01 (dd, J=1.7, 8.3 Hz, 1H), 8.72 (d, J=8.3 Hz, 1H), 11.10 (brs, 1H).

Reference Example 24

The following compounds were synthesized by a method similar to the Reference Example 23 using corresponding substrates. The results of $^1$H-NMR were consistent with the structures.

2-((4-(6-Hydroxy-2-naphthyloxy)phenyl)carbonylamino)benzoic acid methyl ester

Yield: 92%

$^1$H-NMR (CDCl$_3$); δ3.88 (s, 3H), 5.26 (brs, 1H), 6.90–7.20 (m, 6H), 7.35 (brs, 1H), 7.50–7.70 (m, 3H), 7.90–8.05 (m, 3H), 8.84 (d, J=7.6 Hz, 1H), 11.95 (brs, 1H).

2-((4-(4-Hydroxyphenoxy)phenyl)carbonylamino)benzoic acid methyl ester

Yield: 93%

$^1$H-NMR (DMSO-d$_6$); δ11.63 (brs, 1H), 9.57 (brs, 1H), 8.65 (d, 1H, J=8.25 Hz), 8.10 (dd, 1H, J=7.91, 1.32 Hz), 8.02 (d, 2H, J=8.58 Hz), 7.76 (dd, 1H, J=8.58, 7.26, 1.65 Hz), 7.32 (dd, 1H, J=7.92, 7.26, 0.99 Hz), 7.13 (d, 2H, J=8.91 Hz), 7.07 (d, 2H, J=8.91 Hz), 6.92 (d, 2H, J=8.91 Hz), 3.98 (s, 3H).

2-(2-(4-(4-Hydroxyphenoxy)phenyl)acetylamino)benzoic acid methyl ester

Yield: 66%

$^1$H-NMR (DMSO-d$_6$); δ3.70 (2H, s), 3.78 (3H, s), 6.76 (2H, d, J=8.9 Hz), 6.88 (4H, d-like, J=8.6 Hz), 7.18 (1H, t, J=7.5 Hz), 7.30 (2H, d, J=8.6 Hz), 7.59 (1H, t, J=7.8 Hz), 7.89 (1H, dd, J=7.9, 1.7 Hz), 8.29 (1H, d, J=7.6 Hz), 9.31 (1H, s), 10.61 (1H, brs).

Example 1

The following compounds were synthesized by a method similar to the Reference Example 21 using corresponding substrates. The results of $^1$H-NMR were consistent with the structures.

2-(2-(6-(4-Benzyloxyphenoxy)-3-pyridyl)acetylamino)benzoic acid methyl ester (Compound No. 1078)

Yield: 36%

$^1$H-NMR (CDCl$_3$); δ11.16 (brs, 1H), 8.68 (dd, 1H, J=0.66, 8.58 Hz), 8.16 (d, 1H, J=2.31 Hz), 7.99 (dd, 1H, J=1.65, 8.24 Hz), 7.70 (dd, 1H, J=2.31, 8.57 Hz), 7.53–7.29 (m, 6H), 7.09–6.96 (m, 5H), 6.87 (d, 1H, J=8.58 Hz), 5.03 (s, 2H), 3.86 (s, 3H), 3.68 (s, 2H).

2-(2-(6-(6-Benzyloxy-2-naphthyloxy)-3-pyridyl)acetylamino)benzoic acid methyl ester (Compound No. 1120)

Yield: 58%

$^1$H-NMR (CDCl$_3$); δ3.72 (s, 2H), 3.91 (s, 3H), 5.18 (s, 2H), 6.96 (d, 1H, J=8.58 Hz), 7.06–7.77 (m, 14H), 8.02 (dd, 1H, J=1.65, 8.08 Hz), 8.18 (d, 1H, J=2.47 Hz), 8.70 (d, 1H, J=7.42 Hz), 11.19 (br, 1H).

2-(2-(6-(4-(1-Ethylpropylthio)phenoxy)-3-pyridyl)acetylamino)benzoic acid methyl ester (Compound No. 1093)

Yield: 69%

$^1$H-NMR (CDCl$_3$); δ11.18 (brs, 1H), 8.69 (d, 1H, J=8.58 Hz), 8.19 (d, 1H, J=2.31 Hz), 8.01 (dd, 1H, J=1.65, 8.25 Hz), 7.75 (dd, 1H, J=2.64, 8.25 Hz), 7.53 (ddd, 1H, J=1.65, 7.26, 8.58 Hz), 7.42 (d, 2H, J=8.58 Hz), 7.07 (m, 3H), 6.93 (d, 1H, J=8.57 Hz), 3.89 (s, 3H), 3.72 (s, 2H), 2.91 (m, 1H), 1.60 (m, 4H), 1.01 (t, 6H, J=7.25 Hz).

2-(2-(6-(2-Methyl-4-benzyloxyphenoxy)-3-pyridyl)acetylamino)benzoic acid methyl ester (Compound No. 1094)

Yield: 21%

$^1$H-NMR (CDCl$_3$); δ11.15 (brs, 1H), 8.69 (d, 1H, J=8.58 Hz), 8.14 (s, 1H, 7.98 (d, 1H, J=7.91 Hz), 7.69 (dd, 1H, J=2.31, 8.58 Hz), 7.51 (dd, 1H, J=7.58, 8.25 Hz), 7.44–7.31 (m, 5H), 7.06 (dd, 1H, J=7.58, 7.91 Hz), 6.98 (d, 1H, J=8.58 Hz), 6.88–6.79 (m, 3H), 5.03 (s, 2H), 3.86 (s, 3H), 3.68 (s, 2H), 2.16 (s, 3H).

2-(2-(6-(3-Methyl-4-benzyloxyphenoxy)-3-pyridyl)acetylamino)benzoic acid methyl ester (Compound No. 1095)

Yield: 62%

$^1$H-NMR (CDCl$_3$); δ11.18 (brs, 1H), 8.68 (d, 1H, J=8.24 Hz), 8.17 (d, 1H, J=2.31 Hz), 8.01 (dd, 1H, J=1.65, 8.24 Hz), 7.71 (dd, 1H, J=2.31, 8.24 Hz), 7.53 (ddd, 1H, J=1.65, 7.26, 8.90 Hz), 7.46–7.30 (m, 5H), 7.08 (ddd, 1H, J=0.99, 7.26, 8.24 Hz), 6.97–6.86 (m, 4H), 5.07 (s, 2H), 3.89 (s, 3H), 3.69 (s, 2H), 2.28 (s, 3H).

2-(2-(6-(4-Benzyloxyphenylthio)-3-pyridyl)acetylamino)benzoic acid methyl ester (Compound No. 1096)

Yield: 81%

$^1$H-NMR (CDCl$_3$); δ11.17 (brs, 1H), 8.68 (d, 1H, J=8.58 Hz), 8.18 (d, 1H, J=2.31 Hz), 8.00 (dd, 1H, J=1.32, 7.92 Hz), 7.74 (dd, 1H, J=2.31, 8.58 Hz), 7.52 (ddd, 1H, J=1.32, 7.26, 8.58 Hz), 7.33–7.20 (m, 7H), 7.11–7.03 (m, 3H), 6.91 (d, 1H, J=8.25 Hz), 4.08 (s, 2H), 3.88 (s, 3H), 3.71 (s, 2H).

2-((6 -(4-Benzyloxyphenoxy)-3-pyridyl)carbonylamino)benzoic acid methyl ester (Compound No. 1100)

Yield: 65%

$^1$H-NMR (CDCl$_3$); δ12.08 (brs, 1H), 8.89 (s, 1H), 8.88 (d, 1H, J=6.6 Hz), 8.33 (dd, 1H, J=2.31, 8.58 Hz), 8.08 (dd, 1H, J=1.65, 7.92 Hz), 7.60 (t, 1H, J=7.26 Hz), 7.47–7.31 (m, 6H), 7.16–6.99 (m, 5H), 5.08 (s, 2H), 3.94 (s, 3H).

4-Nitro-2-(2-(6-(4-benzyloxyphenoxy)-3-pyridyl)acetylamino)benzoic acid methyl ester (Compound No. 1104)

Yield: 52% (in this case, coupled with 4-nitroanthranilic acid)

$^1$H-NMR (CDCl$_3$); δ11.21 (brs, 1H), 9.60 (m, 1H), 8.17 (m, 2H), 7.88 (m, 1H), 7.71 (m, 1H), 7.43–7.25 (m, 5H), 7.10–6.89 (m, 5H), 5.06 (s, 2H), 3.96 (s, 3H), 3.74 (s, 2H).

5-Chloro-2-(2-(6-(4-benzyloxyphenoxy)-3-pyridyl)acetylamino)benzoic acid methyl ester (Compound No. 1110)

Yield: 72% (in this case, coupled with 5-chloroanthranilic acid)

$^1$H-NMR (CDCl$_3$); δ11.05 (brs, 1H), 8.67 (d, 1H, J=8.91 Hz), 8.15 (d, 1H, J=2.64 Hz), 7.97 (d, 1H, J=2.64 Hz), 7.69 (dd, 1H, J=2.31, 8.57 Hz), 7.49–7.30 (m, 6H), 7.07 (d, 2H, J=8.90 Hz), 6.98 (d, 2H, J=9.24 Hz), 6.89 (d, 1H, 8.58 Hz), 5.05 (s, 2H), 3.89 (s, 3H), 3.69 (s, 2H).

3-Methyl-2-(2-(6-(4-benzyloxyphenoxy)-3-pyridyl)acetylamino)benzoic acid (Compound No. 1112)

Yield: 20% (in this case, coupled with 3-methylanthranilic acid)

$^1$H-NMR (DMSO-d$_6$); δ11.94 (brs, 1H), 8.05 (s, 1H), 7.79 (d, 1H, J=8.58 Hz), 7.68 (d, 1H, J=7.25 Hz), 7.49–7.30 (m, 5H), 7.16 (d, 1H, J=7.59 Hz), 7.04 (s, 4H), 7.04 (m, 1H), 6.92 (d, 1H, J=8.24 Hz), 5.10 (s, 2H), 3.62 (s, 2H), 2.08 (s, 3H).

2-(2-(N-Methyl-6-(4-benzyloxyphenoxy)-3-pyridyl)acetylamino)benzoic acid methyl ester (Compound No. 1113)

Yield: 59%

$^1$H-NMR (CDCl$_3$); δ8.02 (dd, 1H, J=1.65, 7.92 Hz), 7.65–7.55 (m, 2H), 7.51–7.30 (m, 7H), 7.22 (d, 1H, J=7.58 Hz), 7.04 (d, 2H, J=9.24 Hz), 6.97 (d, 2H, J=9.24 Hz), 6.77 (d, 1H, J=8.24 Hz), 5.05 (s, 2H), 3.83 (s, 3H), 3.25 (s, 2H), 3.20 (s, 3H).

2-(2-(6(6-Benzyloxy-2-naphthoxy)-3-pyridyl)acetylamino)
benzoic acid methyl ester (Compound No. 1206)
Yield: 58%
$^1$H-NMR (CDCl$_3$); δ11.19 (br, 1H), 8.70 (d, 1H, J=7.42 Hz), 8.18 (d, 1H, J=2.47 Hz), 8.02 (dd, 1H, J=1.65, 8.08 Hz), 7.77–7.06 (m, 14H), 6.96 (d, 1H, J=8.58 Hz), 5.18 (s, 2H), 3.91 (s, 3H); 3.72 (s, 2H).

Example 2

The following compounds were synthesized by a method similar to the Reference Example 23 using corresponding substrates. The results of $^1$H-NMR were consistent with the structures.
2-(2-(6-(4-Hydroxyphenoxy)-3-pyridyl)acetylamino)
benzoic acid methyl ester (Compound No. 1076)
Yield: 78%
$^1$H-NMR (DMSO-d$_6$); δ10.63 (brs, 1H), 9.36 (brs, 1H), 8.20 (dd, 1H, J=0.99, 8.58 Hz), 8.08 (d, 1H, J=2.31 Hz), 7.89 (dd, 1H, J=1.32, 7.92 Hz), 7.78 (dd, 1H, J=2.31, 8.58 Hz), 7.59 (ddd, 1H, J=1.65, 6.93, 8.58 Hz), 7.19 (ddd, 1H, J=0.99, 6.93, 8.25 Hz), 6.94–6.89 (m, 3H), 6.77 (d, 2H, J=8.9 Hz), 3.79 (s, 3H), 3.74 (s, 2H).
2-(2-(6-(6-Hydroxy-2-naphthyloxy)-3-pyridyl)acetylamino)
benzoic acid methyl ester (Compound No. 1204)
Yield: 82%
$^1$H-NMR CDCl$_3$); δ3.72 (s, 2H), 3.91 (s, 3H), 5.18 (brs, 1H), 6.97 (d, 1H, J=8.25 Hz), 7.07–8.18 (m, 11H), 8.69 (d, 1H, J=7.92 Hz).
2-((6-(4-Hydroxyphenoxy)-3-pyridyl)carbonylamino)
benzoic acid methyl ester (Compound No. 1099)
Yield: 73%
$^1$H-NMR (DMSO-d$_6$); δ11.41 (brs, 1H), 9.45 (brs, 1H), 8.69 (d, 1H, J=2.31 Hz), 8.41 (d, 1H, J=8.24 Hz), 8.29 (dd, 1H, J=2.64, 8.58 Hz), 7.98 (d, 1H, J=7.92 Hz), 7.67 (dd, 1H, J=7.25, 7.59 Hz), 7.25 (t, 1H, J=7.26 Hz), 7.11 (d, 1H, J=8.58 Hz), 7.00 (d, 2H, J=8.91 Hz), 6.80 (d, 2H, J=8.91 Hz), 3.86 (s, 3H).

Example 3

Synthesis of 2-(2-(6-(4-benzyloxyphenoxy)-3-pyridylacetylamino)benzoic acid (Compound No. 986)

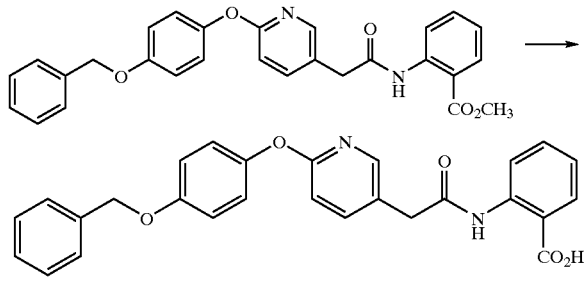

2-(2-(6-(4-Benzyloxyphenoxy)-3-pyridyl)acetylamino) benzoic acid methyl ester (87 mg, 0.186 mmol) obtained by the Example 1 was dissolved in a 2:1 mixed solvent (6 ml) of THF and methanol, 4N-lithium hydroxide (1 ml) was added thereto and the mixture was stirred for 1 hour at room temperature. After completing the reaction, the pH of the product was adjusted to about 4 with 10% aqueous solution of citric acid and the reaction product was extracted with ethyl acetate, washed with water, dried with magnesium sulfate and concentrated, and the residue was recrystallized from acetonitrile (20 ml) to obtain the subject compound (66 mg, 0.145 mmol). The result of $^1$H-NMR was consistent with the above structure.
Yield: 78%
$^1$H-NMR (DMSO-d$_6$); δ13.56 (br, 1H), 11.18 (brs, 1H), 8.47 (d, 1H, J=8.25 Hz), 8.09 (d, 1H, J=1.98 Hz), 7.96 (dd, 1H, J=1.65, 7.92 Hz), 7.80 (d, 1H, J=8.58 Hz), 7.57 (t, 1H, J=7.92 Hz), 7.48–7.31 (m, 5H), 7.14 (t, 1H, J=7.59 Hz), 7.05 (s, 4H), 6.95 (d, 1H, J=8.25 Hz), 5.11 (s, 2H), 3.76 (s, 2H).

Example 4

The following compounds were synthesized by a method similar to the Example 3 using corresponding substrates.
2-(2-(6-(4-(1-Ethylpropylthio)phenoxy)-3-pyridyl)
acetylamino)benzoic acid (Compound No. 1027)
Yield: 75%
$^1$H-NMR (DMSO-d$_6$); δ13.55 (br, 1H), 11.18 (brs, 1H), 8.47 (d, 1H, J=8.25 Hz), 8.13 (s, 1H), 7.96 (d, 1H, J=7.91 Hz), 7.85 (d, 1H, J=8.58 Hz), 7.57 (t, 1H, J=7.92 Hz), 7.42 (d, 2H, J=8.58 Hz), 7.17–7.02 (m, 4H), 3.79 (s, 2H), 3.04 (m, 1H), 1.54 (m, 4H), 0.99 (t, 6H, J=7.26 Hz).
2-(2-(6-(2-Methyl-4-benzyloxyphenoxy)-3-pyridyl)
acetylamino)benzoic acid (Compound No. 1039)
Yield: 83%
$^1$H-NMR (DMSO-d$_6$); δ11.26 (brs, 1H), 8.45 (d, 1H, J=8.58 Hz), 8.04 (s, 1H), 7.95 (d, 1H, J=7.92 Hz), 7.78 (d, 1H, J=8.58 Hz), 7.56 (dd, 1H, J=7.26, 8.57 Hz), 7.48–7.31 (m, 5H), 7.13 (dd, 1H, J=7.26, 7.92 Hz), 6.98–6.83 (m, 4H), 5.09 (s, 2H), 3.74 (s, 2H), 2.05 (s, 3H).
2-(2-(6-(3-Methyl-4-benzyloxyphenoxy)-3-pyridyl)
acetylamino)benzoic acid (Compound No. 1040)
Yield: 59%
$^1$H-NMR (DMSO-d$_6$); δ13.70–13.40 (br, 1H), 11.24 (brs, 1H), 8.46 (d, 1H, J=8.25 Hz), 8.09 (d, 1H, J=2.31 Hz), 7.96 (d, 1H, J=7.92 Hz), 7.80 (dd, 1H, J=2.31, 8.25 Hz), 7.57 (dd, 1H, J=7.26, 8.58 Hz), 7.50–7.31 (m, 5H), 7.14 (dd, 1H, J=7.26, 7.92 Hz), 7.03 (d, 1H, J=8.58 Hz), 6.97–6.88 (m, 3H), 5.13 (s, 2H), 3.76 (s, 2H), 2.20 (s, 3H).
2-(2-(6-(4-Benzyloxyphenylthio)-3-pyridyl)acetylamino)
benzoic acid (Compound No. 1053)
Yield: 91%
$^1$H-NMR (DMSO-d$_6$); δ13.57 (br, 1H), 11.16 (brs, 1H), 8.46 (d, 1H, J=8.25 Hz), 8.12 (d, 1H, J=1.98 Hz), 7.95 (d, 1H, J=7.92 Hz), 7.84 (dd, 1H, J=2.31, 8.24 Hz), 7.57 (dd, 1H, J=7.26, 8.25 Hz), 7.38–7.21 (m, 7H), 7.14 (dd, 1H, J=7.26, 7.91 Hz), 7.06 (d, 2H, J=8.57 Hz), 7.01 (d, 1H, J=8.25 Hz), 4.22 (s, 2H), 3.78 (s, 2H).
4-Nitro-2-(2-(6-(4-benzyloxyphenoxy)-3-pyridyl)
acetylamino)benzoic acid (Compound No. 1071)
Yield: 85%
$^1$H-NMR (DMSO-d$_6$); δ11.28 (brs, 1H), 9.28 (s, 1H), 8.18 (d, 1H, J=8.91 Hz), 8.10 (s, 1H), 7.95 (d, 1H, J=8.91 Hz), 7.82 (d, 1H, J=8.58 Hz), 7.48–7.30 (m, 5H), 7.05 (s, 4H), 6.96 (d, 1H, J=8.58 Hz), 5.10 (s, 2H), 3.83 (s, 2H).
5- Chloro-2-(2-(6-(4-benzyloxyphenoxy)-3-pyridyl)
acetylamino)benzoic acid (Compound No. 1111)
Yield: 72%
$^1$H-NMR (DMSO-d$_6$); δ11.08 (brs, 1H), 8.47 (d, 1H, J=8.91 Hz), 8.08 (d, 1H, J=2.31 Hz), 7.89 (d, 1H, J=2.64 Hz), 7.80 (dd, 1H, J=1.98, 8.25 Hz), 7.64 (dd, 1H, J=2.31, 8.91 Hz), 7.48–7.31 (m, 5H), 7.05 (s, 4H), 6.95 (d, 1H, J=8.53 Hz), 5.11 (s, 2H), 3.77 (s, 2H).
2-(2-(N-Methyl-6-(4-benzyloxyphenoxy)-3-pyridyl)
acetylamino)benzoic acid (Compound No. 1114)
Yield: 54%
$^1$H-NMR (DMSO-d$_6$); δ10.35 (br, 1H), 8.07 (d, 1H, J=1.65 Hz), 8.05 (dd, 1H, J=1.32, 8.25 Hz), 7.78 (dd, 1H, J=2.31, 8.58 Hz), 7.66 (dd, 1H, J=7.58, 7.92 Hz), 7.54–7.26 (m, 7H), 7.11 (d, 2H, J=9.24 Hz), 7.09 (d, 2H, J=9.56 Hz), 7.00 (d, 1H, J=8.58 Hz), 5.12 (s, 2H), 3.61 (s, 3H), 3.32 (s, 2H).

2-(2-(6-(6-Benzyloxy-2-naphthoxy)-3-pyridyl)acetylamino) benzoic acid (Compound No. 1120)

Yield: 97%

$^1$H-NMR (CDCl$_3$); δ3.71 (s, 2H), 5.19 (s, 2H), 6.93 (d, 1H, J=8.41 Hz), 7.04–7.77 (m, 14H), 8.06 (dd, 1H, J=1.57, 8.00 Hz), 8.18 (d, 1H, J=2.31 Hz), 8.67 (d, 1H, J=9.24 Hz), 11.51 (br, 1H).

Example 5

Synthesis of 2-(2-(4-(6-(2-ethoxyethoxy)-2-naphthyloxy)phenyl)-acetylamino)benzoic acid methyl ester (methyl ester of the Compound No. 1)

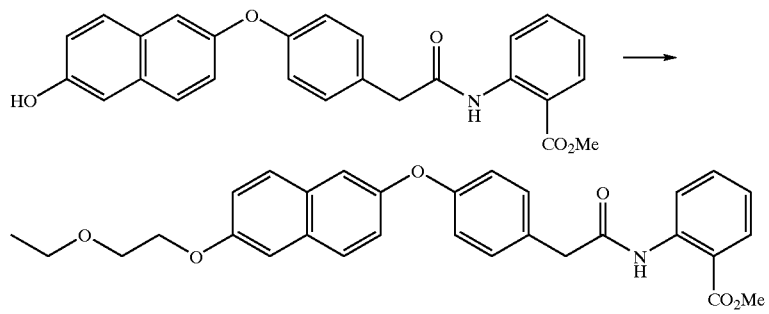

2-(2-(4-(6-Hydroxy-2-naphthyloxy)phenyl)acetylamino) benzoic acid methyl ester (214 mg, 0.50 mmol) obtained by the Reference Example 23 was dissolved in 5 ml of dry DMF under nitrogen atmosphere, potassium carbonate (104 mg, 0.75 mmol) was added to the solution and the mixture was stirred as it is for 1 hour at room temperature. The reaction liquid was added with 2-ethoxyethyl bromide (84 mg, 0.55 mmol) and stirred for 3.5 hours at room temperature and for 4 hours at 80° C. The obtained reaction liquid was added with water and extracted twice with ethyl acetate. The organic layer was washed with saturated aqueous solution of sodium chloride and dried with anhydrous sodium sulfate, and the solvent was distilled out under reduced pressure. The residue was purified by silica gel column chromatography (hexane:ethyl acetate=6:1 to 5:1) to obtain the subject compound (199 mg, 0.398 mmol). The result of $^1$H-NMR was consistent with the above structure. Colorless oil.

Yield: 80%

$^1$H-NMR (CDCl$_3$); 1.27 (t, J=6.9 Hz, 3H), 3.64 (q, J=6.9 Hz, 2H), 3.75 (s, 2H), 3.84–3.88 (m, 2H), 3.88 (s, 3H), 4.24 (t, J=4.6 Hz, 2H), 7.02–7.25 (m, 6H), 7.31–7.37 (m, 3H), 7.50–7.57 (m, 1H), 7.60 (d, J=8.9 Hz, 1H), 7.69 (d, J=8.9 Hz, 1H), 8.01 (dd, J=1.7, 8.3 Hz, 1H), 8.73 (dd, J=1.0, 8.6 Hz, 1H), 11.07 (br.s, 1H).

Example 6

The compounds described as the Example No. 6 in the Tables 44 to 72 and the methyl ester of the Compound No.88 were synthesized by a method similar to the Example 5 using corresponding substrates. The compounds were identified by $^1$H-NMR and the data were consistent with the structures. These data are described in the Tables 44 to 72 and the Table 74. The Table 74 only describes the yield.

Example 7

Synthesis of 2-(2-(4-(6-(2-ethoxyethoxy)-2-naphthyloxy)phenyl)-acetylamino)benzoic acid (Compound No. 1)

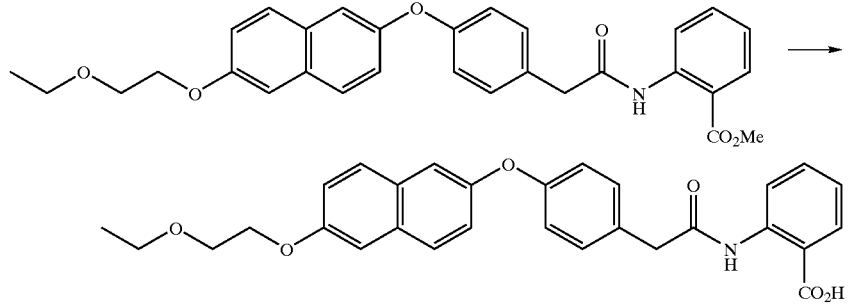

2-(2-(4-(6-(2-Ethoxyethoxy)-2-naphthyloxy)phenyl) acetylamino)-benzoic acid methyl ester (187 mg, 0.37 mmol) obtained by the Example 5 was dissolved in a mixed solvent composed of methanol/THF (3 ml/6 ml), 4N aqueous solution of lithium hydroxide (0.94 ml, 3.7 mmol) was added to the solution and the mixture was stirred at room temperature for a night. After completing the reaction, 5N hydrochloric acid was added to adjust the pH of the system to about 1 and the system was stirred for 0.5 hour at room temperature. Water was added to the reaction liquid and the product was extracted twice with ethyl acetate. The organic layer was washed with saturated aqueous solution of sodium chloride and dried with anhydrous sodium sulfate, and the solvent was distilled off. The residue was recrystallized from acetonitrile (1 ml) to obtain the subject compound (123 mg, 0.253 mmol). The result of $^1$H-NMR was consistent with the structure. Colorless plate crystal.

Yield: 68%

$^1$H-NMR (DMSO-d$_6$); δ1.13 (t, J=6.9 Hz, 3H), 3.52 (q, J=6.9 Hz, 2H), 3.73–3.76 (m, 4H), 4.18 (t, J=4.3 Hz, 2H), 7.02 (d, J=8.6Hz, 2H), 7.10–7.18 (m, 2H), 7.22–7.26 (m, 1H), 7.34–7.39 (m, 4H), 7.57 (t, J=8.9 Hz, 1H), 7.73 (d, J=8.9 Hz, 1H), 7.83 (d, J=8.9 Hz, 1H), 7.95 (dd, J=1.7, 7.9 Hz, 1H), 8.50 (d, J=8.3 Hz, 1H), 11.12 (brs, 1H), 13.57 (brs, 1H).

Example 8

The compounds described as the Example No. 8 in the Tables 44 to 72 and the compounds shown in the Table 74 were synthesized by a method similar to the Example 7 using corresponding substrates. The compounds were identified by $^1$H-NMR or LC-MS and the results were consistent with the above structures. These data are described in the Tables 44 to 72 and the Table 74.

Example 9

Synthesis of 2-(2-(4-(4-((2-furanyl)methoxy) phenoxy)phenyl)acetylamino)-benzoic acid methyl ester (methyl ester of the Compound No.428)

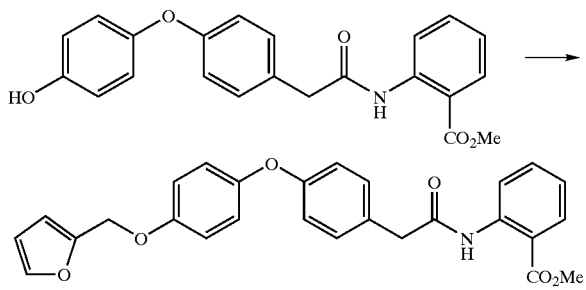

Triphenylphosphine (216 mg, 0.83 mmol), 2-furanylmethanol (81 mg, 0.83 mmol) and 40% toluene solution of diethyl azodicarboxylate (360 mg, 0.83 mmol) were added to 2-(2-(4-(4-hydroxyphenoxy)phenyl)-acetylamino)benzoic acid methyl ester (100 mg, 0.28 mmol) obtained by the Reference Example 24 in nitrogen atmosphere and stirred for 2 hours at room temperature. After completing the reaction, the reaction liquid was concentrated and the obtained crude product was purified by silica gel column chromatography to obtain the subject compound (73 mg, 0.16 mmol). The result of $^1$H-NMR was consistent with the above structure.

Yield: 57%

$^1$H-NMR (CDCl$_3$); δ3.73 (2H, s), 3.87 (3H, s), 4.98 (2H, s), 6.37–6.43 (2H, m), 6.87–7.01 (6H, m), 7.07 (1H, t, J=7.0 Hz), 7.31 (2H, d, J=8.6 Hz), 7.45–7.56 (2H, m), 7.99 (1H, dd, J=7.9, 1.7 Hz), 8.71 (1H, d, J=8.3 Hz), 11.03 (1H, brs).

Example 10

The compounds described as the Example No.10 in the Tables 44 to 72 and the methyl esters of the compounds described in the Table 73 were synthesized by a method similar to the Example 9 using corresponding substrates. The compounds were identified by $^1$H-NMR and the results were consistent with the above structures. These data are shown in the Tables 44 to 72 and the Table 74. The Table 73 only describes the yield.

Example 11

The compounds described as the Example No.11 in the Tables 44 to 72 and the compounds described in the Table 73 were synthesized by a method similar to the Example 7 using corresponding substrates obtained by the Examples 2, 9 and 10. The compounds were identified by $^1$H-NMR or LC-MS and the results were consistent with the above structures. These data are shown in the Tables 44 to 72 and the Table 73.

Example 12

Synthesis of 2-(2-(6-(4-benzyloxyphenylsulfinyl)-3-pyridyl)acetylamino)-benzoic acid methyl ester (Compound No.1097)

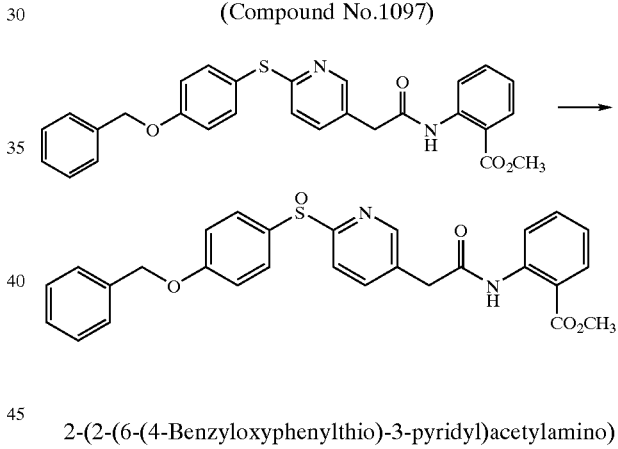

2-(2-(6-(4-Benzyloxyphenylthio)-3-pyridyl)acetylamino) benzoic acid methyl ester (62 mg, 0.128 mmol) obtained by the Example 1 was dissolved in a mixed solvent (5 ml) composed of methanol and methylene chloride (3:2) and the solution was cooled with ice. The solution was added with N-bromosuccinimide (45 mg, 0.256 mmol) and stirred for 1.5 hours under ice cooling. After completing the reaction, the reaction liquid was concentrated and purified by silica gel chromatography to obtain the subject compound (36 mg, 0.0719 mmol) as the objective product. The compound was identified by $^1$H-NMR and the result was consistent with the above structure.

Yield: 56%

$^1$H-NMR (CDCl$_3$); δ11.21 (brs, 1H), 8.69 (d, 1H, J=8.25 Hz), 8.20 (d, 1H, J=2.31 Hz), 8.02 (dd, 1H, J=1.32, 8.25 Hz), 7.79 (dd, 1H, J=2.31, 8.58 Hz), 7.54 (ddd, 1H, J=1.32, 7.25, 8.58 Hz), 7.39 (d, 2H, J=8.90 Hz), 7.30–7.20 (m, 5H), 7.12–7.02 (m, 3H), 6.97 (d, 1H, J=8.92 Hz), 4.11 (d, 1H, J=15.22 Hz), 3.99 (d, 1H, J=12.54 Hz), 3.89 (s, 3H), 3.74 (s, 2H).

Example 13

Synthesis of 2-(2-(6-(4-benzyloxyphenylsulfinyl)-3-pyridyl)acetylamino)-benzoic acid (Compound No.1054)

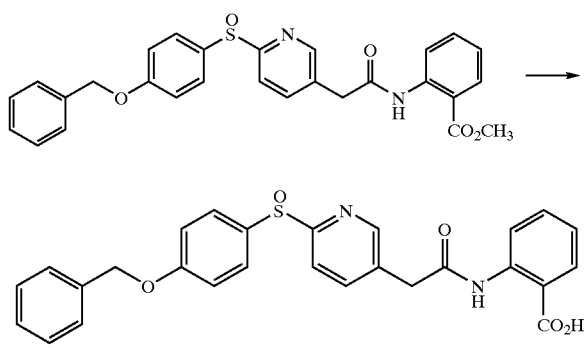

2-(2-(6-(4-Benzyloxyphenylsulfinyl)-3-pyridyl)acetylamino)benzoic acid methyl ester (51 mg, 0.102 mmol) obtained by the Example 12 was dissolved in a mixed solvent (6 ml) composed of THF and methanol (2:1), added with 4N lithium hydroxide (1 ml) and stirred for 1 hour at room temperature. After completing the reaction, the pH of the reaction liquid was adjusted to about 7 using 1N aqueous solution of hydrochloric acid and a phosphate buffer solution, and the liquid was extracted with ethyl acetate, washed with water, dried with magnesium sulfate and concentrated. The residue was dissolved in a mixture of ethyl acetate and methanol (1:1) and hexane was added to the solution to precipitate a solid component and obtain the subject compound (35 mg, 0.0179 mmol) as the objective product. The compound was identified by $^1$H-NMR and the result was consistent with the above structure.

Yield: 70%

$^1$H-NMR (DMSO-$d_6$); δ13.58 (br, 1H), 11.19 (brs, 1H), 8.47 (d, 1H, J=8.25 Hz), 8.18 (d, 1H, J=1.65 Hz), 7.96 (d, 1H, J=7.92 Hz), 7.90 (dd, 1H, J=2.31, 8.58 Hz), 7.57 (m, 3H), 7.25 (s, 5H), 7.17–7.07 (m, 4H), 4.27 (d, 1H, J=12.87 Hz), 4.10 (d, 1H, J=12.54 Hz), 3.81 (s, 2H).

Example 14

Synthesis of 2-(2-(1-hydroxy-6-(4-(1-ethylpropoxy)phenoxy)-3-pyridyl)acetylamino)benzoic acid (Compound No.1246)

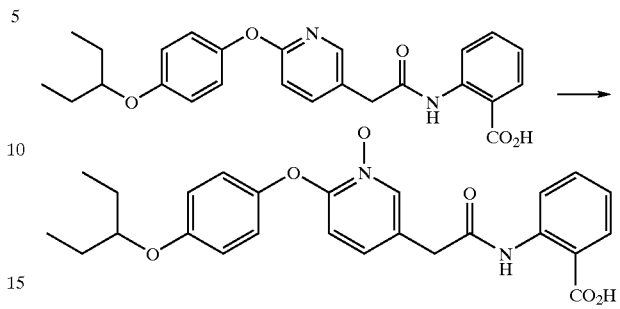

2-(2-(6-(4-(1-Ethylpropoxy)phenoxy)-3-pyridyl)acetylamino)benzoic acid (1.0 g, 2.30 mmol) obtained by the Example 11 was dissolved in a mixed solvent consisting of methylene chloride (30 ml) and methanol (10 ml) and m-chloroperbenzoic acid (50–60%, 0.99 g) was added to the solution in an ice bath. The reaction was continued as it is for 2 days, m-chloroperbenzoic acid (50–60%, 0.99 g) was added to the product in an ice bath and the reaction was continued for 2.5 hours. After completing the reaction, the system was added with excessive amount of saturated aqueous solution of sodium thiosulfate and stirred, the solvent was concentrated and the reaction product was extracted from the residue with methylene chloride. The organic solvent was washed with saturated aqueous solution of magnesium thiosulfate and water in the order, dried with anhydrous magnesium sulfate and concentrated. A small amount of ethyl acetate was added to the obtained residue to effect the dissolution of the residue, and hexane was added to the solution to precipitate a solid component and obtain the subject compound (0.18 g, 0.40 mmol) as the objective product. The compound was identified by $^1$H-NMR and the result was consistent with the above structure.

Yield: 17%

$^1$H-NMR (DMSO-$d_6$); δ14.80–13.50 (br, 1H), 11.18 (brs, 1H), 8.45 (d, 1H, J=8.58 Hz), 8.39 (d, 1H, J=1.98 Hz), 7.97 (dd, 1H, J=1.65, 7.92 Hz), 7.58 (ddd, 1H, J=1.65, 7.26, 8.58 Hz), 7.33 (dd, 1H, J=1.98, 8.58 Hz), 7.16 (dd, 1H, J=7.26, 7.92 Hz), 7.10 (d, 1H, J=8.58 Hz), 6.96 (s, 4H), 4.16 (qui, 1H, J=5.94 Hz), 3.81 (s, 2H), 1.60 (dq, 4H, J=5.94, 7.59 Hz), 0.90 (t, 6H, J=7.59 Hz).

Example 15

Synthesis of 2-(2-(4-(4-(cis-4-(N,N-dibenzylamino)cyclohexyloxy)phenoxy)-phenyl)acetyl amino)benzoic acid methyl ester

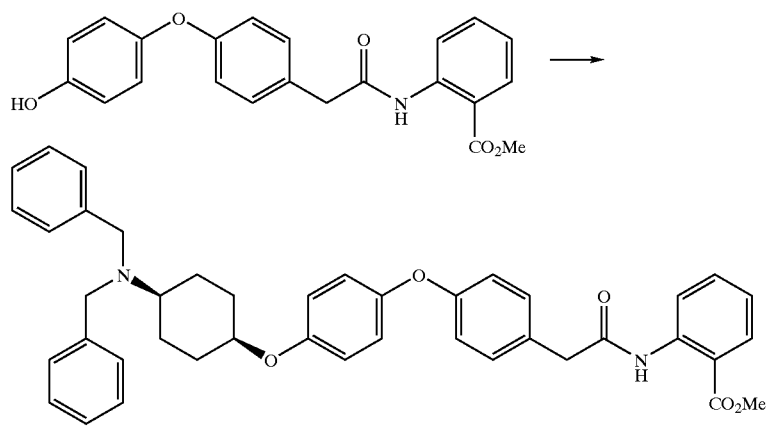

2-(2-(4-(4-Hydroxyphenoxy)phenyl)acetylamino)benzoic acid methyl ester (5.66 g, 15.0 mmol) obtained by the Reference Example 24 was dissolved together with trans-4-(N,N-dibenzylamino)cyclohexanol (8.73 g, 29.6 mmol) and PPh3 (7.87 g, 30.0 mmol) in N-methylmorpholine (90 ml) and cooled with ice. Azodicarboxylic acid diethyl ester (13.1 ml, 40% in PhMe, 30.0 mmol) was dropped into the solution spending 10 minutes. The mixture was stirred for a night at room temperature and the reaction liquid was concentrated. The obtained residue was purified by silica gel chromatography (hexane:ethyl acetate=20:1 to 7:1) to obtain the subject compound (7.03 g, 10.7 mmol). The $^1$H-NMR of the product was consistent with the above structure. Colorless foam.

Yield: 72%

$^1$H-NMR (CDCl$_3$); δ1.3–1.5 (m, 2H), 1.6–1.8 (m, 2H), 1.8–1.9 (m, 2H), 2.0–2.2 (m, 2H), 2.5–2.7 (m, 1H), 3.68 (s, 4H), 3.72 (s, 2H), 3.87 (s, 3H), 4.39 (br, 1H), 6.86 (d, J=9.1 Hz, 2H), 6.95–6.98 (m, 4H), 7.06 (t, J=7.3 Hz, 1H), 7.17–7.23 (m, 2H), 7.26–7.32 (m, 6H), 7.37–7.40 (m, 4H), 7.52 (t, J=7.3 Hz, 1H), 7.99 (dd, J=1.8, 8.1 Hz, 1H), 8.72 (d, J=8.7 Hz, 1H), 11.03 (brs, 1H).

Example 16

The following compounds were synthesized by a method similar to the Example 15 using corresponding substrates. The results of $^1$H-NMR were consistent with the structures of respective compounds.

2-(2-(4-(6-(cis-4-(N,N-Dibenzylamino)cyclohexyloxy)-2-naphthyloxy)-phenyl)acetylamino)benzoic acid methyl ester Yield: 81%

$^1$H-NMR (CDCl$_3$); δ11.07 (brs, 1H), 8.72 (d, 1H, J=7.56 Hz), 8.00 (dd, 1H, J=8.10, 1.35 Hz), 7.68–7.49 (m, 2H), 7.40–7.02 (m, 20H), 4.59 (br, 1H), 3.88 (s, 3H), 3.74 (s, 2H), 3.69 (s, 4H), 2.61 (m, 1H), 2.21–2.16 (m, 2H), 2.04–1.69 (m, 4H), 1.50–1.42 (m, 2H).

2-((4-(6-(cis-4-(N,N-Dibenzylamino)cyclohexyloxy)-2-naphthyloxy)phenyl)-carbonylamino)benzoic acid methyl ester Yield: 64%

$^1$H-NMR (CDCl$_3$); δ12.00 (s, 1H), 8.92 (d, 1H, J=8.58 Hz), 8.06 (m, 2H), 7.66 (m, 2H), 7.09–7.41 (m, 19H), 4.62 (s, 1H), 3.95 (s, 3H), 3.71 (s, 4H), 2.62 (m, 1H), 2.21 (m, 2H), 1.89 (m, 2H), 1.73 (m, 2H), 1.45 (m, 2H).

2-(2-(4-(7-(cis-4-(N,N-Dibenzylamino)cyclohexyloxy)-2-naphthyloxy)-phenyl)acetylamino)benzoic acid methyl ester Yield: 71%

$^1$H-NMR (CDCl$_3$); δ11.10 (brs, 1H), 8.74 (d, 1H, J=8.25 Hz), 7.99 (dd, 1H, J=7.91, 1.32 Hz), 7.72–7.67 (m, 3H), 7.52 (dd, 1H, J=8.58, 7.25 Hz), 7.49–6.98 (m, 18H), 4.56 (br, 1H), 3.88 (s, 3H), 3.75 (s, 2H), 3.68 (s, 4H), 2.59 (m, 1H), 2.04 (m, 2H), 1.88–1.68 (m, 4H), 1.43 (m, 2H).

2-((4-(4-(cis-4-(N,N-Dibenzylamino)cyclohexyloxy)phenoxy)phenyl)-carbonylamino)benzoic acid methyl ester Yield: 93%

$^1$H-NMR (CDCl$_3$); δ11.97 (brs, 1H), 8.91 (d, 1H, J=8.58 Hz), 8.07 (dd, 1H, J=7.75, 1.32 Hz), 8.00 (d, 2H, J=8.91 Hz), 7.59 (ddd, 1H, J=8.58, 7.09, 1.65 Hz), 7.40–6.90 (m, 17H), 4.43 (br, 1H), 3.95 (s, 3H), 3.69 (s, 4H), 2.60 (m, 1H), 2.11–1.23 (m, 8H).

2-(2-(4-(4-(1-Benzylpiperidin-2-ylmethyloxy)phenyloxy)phenyl)-acetylamino)benzoic acid methyl ester Yield: 27%

$^1$H-NMR (CDCl$_3$); δ11.03 (s, 1H), 8.71 (dd, 1H, J=8.4, 1.1 Hz), 7.98 (dd, 1H, J=8.1, 1.6 Hz), 7.52 (ddd, 1H, J=8.4, 7.3, 1.6 Hz), 7.23–7.37 (m, 7H), 7.06 (ddd, 1H, J=8.1, 7.3, 1.1 Hz), 6.92 (d, 2H, J=8.9 Hz), 6.82 (d, 2H, J=8.9 Hz), 6.55 (d, 2H, J=8.9 Hz), 3.86 (s, 3H), 3.72 (d, 1H, J=13.5 Hz), 3.72 (s, 2H), 3.59 (d, 1H, J=13.5 Hz), 2.89–2.99 (brm, 1H), 2.76–2.88 (brm, 1H), 2.60–2.68 (m, 2H), 2.04–2.13 (br, 1H), 1.67–1.78 (brm, 6H).

2-(2-(4-(4-(1-Benzylpiperidin-3-ylmethyloxy)phenyloxy)phenyl)-acetylamino)benzoic acid methyl ester Yield: 60%

$^1$H-NMR (CDCl$_3$); δ11.03 (s, 1H), 8.71 (d, 1H, J=8.4 Hz), 7.99 (dd, 1H, J=8.1 Hz, 1.6 Hz), 7.52 (ddd, 1H, J=8.4 Hz, 7.3 Hz, 1.6 Hz), 7.24–7.32 (m, 7H), 7.06 (dd, 1H, J=8.1 Hz, 7.3 Hz), 6.93–6.98 (m, 4H), 6.82 (d, 2H, J=8.9 Hz), 3.87 (s, 3H), 3.72 (s, 2H), 3.56 (d, 1H, J=13.2 Hz), 3.48 (d, 1H, J=13.2 Hz), 2.14 (brm, 2H), 1.95–2.02 (m, 2H), 1.75–1.89 (m, 1H), 1.66–1.69 (brm, 6H).

2-(2-(4-(4-(2-Dibenzylaminocyclohexyloxy)phenyloxy)phenyl)acetylamino)-benzoic acid methyl ester Yield: 13%

$^1$H-NMR (CDCl$_3$); δ11.05 (s, 1H), 8.72 (d, 1H, J=8.6 Hz), 8.00 (dd, 1H, J=8.1 Hz, 1.6 Hz), 7.52 (ddd, 1H, J=8.6 Hz, 7.0 Hz, 1.6 Hz), 7.15–7.38 (m, 12H), 7.06 (dd, 1H, J=8.1 Hz, 7.0 Hz), 6.91–7.02 (m, 6H), 4.26 (brm, 1H), 3.87 (s, 3H), 3.81 (s, 2H), 3.73 (s, 2H), 3.69 (s, 2H), 2.83 (brm, 1H), 2.16 (br, 1H), 2.00 (br, 1H), 1.70 (brm, 2H), 1.61 (brs, 1H), 1.30–1.50 (brm, 1H), 1.18–1.26 (m, 2H).

Example 17

Synthesis of 2-(2-(4-(4-(cis-4-aminocyclohexyloxy)phenoxy)phenyl)-acetylamino)benzoic acid methyl ester

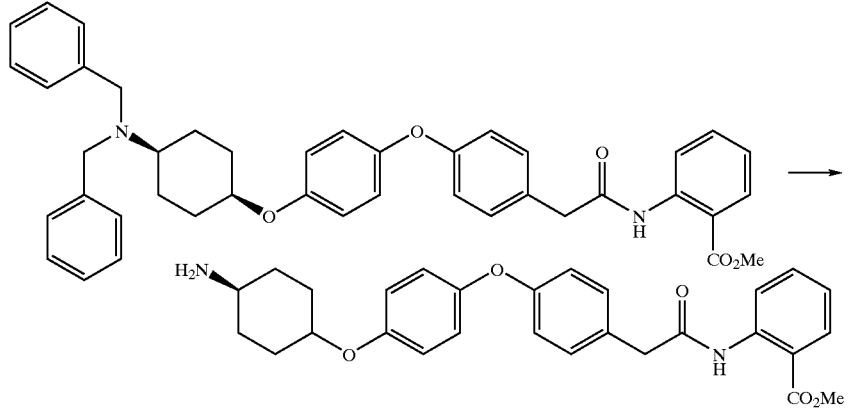

2-(2-(4-(4-cis-4-(N,N-Dibenzylamino)cyclohexyloxy) phenoxy)phenyl)-acetylamino)benzoic acid methyl ester (7.03 g, 10.74 mmol) obtained by the Example 15 was dissolved in a mixed solvent consisting of methanol (60 ml) and methylene chloride (60 ml), formic acid (5.3 ml, 0.14 mol) and Pd-Black (3.6 g) were added to the solution and the obtained mixture was stirred for 8 hours at room temperature. The reaction liquid was filtered with Celite and the filtrate was concentrated. The residue was dissolved in ethyl acetate and adjusted to pH>13 by the addition of concentrated ammonia water. The solution was extracted twice with ethyl acetate, and the organic layer was washed with saturated saline water, dried with anhydrous sodium sulfate and concentrated. The obtained residue was purified by silica gel column chromatography (hexane:ethyl acetate=2:1→simple ethyl acetate→chloroform:methanol:triethylamine= 100:10:1) to obtain the subject compound (4.60 g, 9.69 mmol). The $^1$H-NMR of the product was consistent with the above structure. Pale yellow viscous liquid.

Yield: 90%

$^1$H-NMR (CDCl$_3$); δ1.35 (br, 2H), 1.5–1.7 (m, 6H), 1.95–2.15 (m, 2H), 2.78 (br, 1H), 3.72 (s, 2H), 3.88 (s, 3H), 4.39 (br, 1H), 6.85–6.89 (m, 2H), 6.95–6.98 (m, 4H), 7.06 (t, J=7.4 Hz, 1H), 7.31 (d, J=8.2 Hz, 2H), 7.52 (t, J=7.3 Hz, 1H), 7.99 (dd, J=1.7, 8.1 Hz, 1H), 8.71 (d, J=8.7 Hz, 1H), 11.03 (brs, 1H).

Example 18

The following compounds were synthesized by a method similar to the Example 17 using corresponding substrates. The results of $^1$H-NMR were consistent with the structures of respective compounds.

2-((4-(4-(cis-4-Aminocyclohexyloxy)phenoxy)phenyl carbonylamino)benzoic acid methyl ester Yield: 57%

$^1$H-NMR (CDCl$_3$); δ11.98 (brs, 1H), 8.91 (d, 1H, J=8.37 Hz), 8.07 (d, 1H, J=7.83 Hz), 8.00 (d, 2H, J=8.64 Hz), 7.59 (dd, 1H, J=8.37, 7.56 Hz), 7.10 (dd, 1H, J=7.56, 7.29 Hz), 7.05–6.91 (m, 6H), 4.43 (br, 1H), 3.95 (s, 3H), 2.80 (br, 1H), 2.00 (m, 2H), 1.80–1.63 (m, 4H), 1.32 (m, 2H).

2-(2-(4-(6-(cis-4-Aminocyclohexyloxy)-2-naphthyloxy) phenyl)acetylamino)benzoic acid methyl ester (methyl ester of the compound No.18)

Yield: 66%

$^1$H-NMR (CDCl$_3$); δ11.07 (brs, 1H), 8.72 (d, 1H, J=8.41 Hz), 8.00 (dd, 1H, J=8.08, 1.65 Hz), 7.68–7.49 (m, 3H), 7.36–7.02 (m, 9H), 4.58 (br, 1H), 3.88 (s, 3H), 3.74 (s, 2H), 2.80 (m, 1H), 2.09–2.04 (m, 2H), 1.70–1.46 (m, 6H).

2-((4-(6-(cis-4-Aminocyclohexyloxy)-2-naphthyloxy) phenyl)carbonylamino)-benzoic acid methyl ester Yield: 99%

$^1$H-NMR (CDCl$_3$); δ12.00 (s, 1H), 8.92 (d, 1H, J=8.58 Hz), 8.09 (m, 3H), 7.66 (m, 3H), 7.42 (s, 1H), 7.09–7.25 (m, 6H), 4.62 (s, 1H), 3.95 (s, 3H), 2.83 (m, 1H), 2.11 (m, 2H), 1.67 (m, 4H), 1.50 (br, 2H).

2-(2-(4-(7-(cis-4-Aminocyclohexyloxy)-2-naphthyloxy) phenyl)acetylamino)-benzoic acid methyl ester (methyl ester of the compound No. 19)

Yield: 44%

$^1$H-NMR (CDCl$_3$); δ11.10 (brs, 1H), 8.72 (d, 1H, J=8.58 Hz), 7.99 (dd, 1H, J=7.91, 1.65 Hz), 7.68–7.63 (m, 2H), 7.52 (dd, 1H, J=7.26, 6.92 Hz), 7.36 (d, 2H, J=8.58 Hz), 7.16–6.97 (m, 7H), 4.60 (br, 1H), 3.87 (s, 3H), 3.75 (s, 2H). 3.27 (m, 1H), 2.21–2.16 (m, 1H), 2.02 (m, 1H), 1.61 (m, 2H).

(R)-2-(2-(4-(4-(Pyrrolidin-2-ylmethyloxy)phenyloxy) phenyl)acetylamino)-benzoic acid methyl ester Yield: 32% (yield of two steps from the reaction similar to the Example 15)

$^1$H-NMR (CDCl$_3$); δ11.04 (s, 1H), 8.71 (dd, 1H, J=8.6, 1.1 Hz), 7.99 (dd, 1H, J=8.1, 1.6 Hz), 7.52 (ddd, 1H, J=8.6, 7.3, 1.6 Hz), 7.30 (d, 2H, J=8.6 Hz), 7.06 (ddd, 1H, J=8.1, 7.3, 1.1 Hz), 6.85–6.99 (m, 6H), 4.11–4.18 (m, 1H), 4.04 (d, 1H, J=5.7 Hz), 3.88 (s, 3H), 3.72 (s, 2H), 3.09–3.41 (br, 1H), 3.12–3.19 (m, 2H), 2.89–2.94 (m, 1H), 1.75–2.08 (m, 4H).

2-(2-(4-(4-(1-Aminocyclopentan-1-ylmethyloxy) phenyloxy)phenyl)-acetylamino)benzoic acid methyl ester Yield: 39% (yield of two steps from the reaction similar to the Example 15)

$^1$H-NMR (CDCl$_3$); δ11.04 (s, 1H), 8.71 (d, 1H, J=8.4 Hz), 7.98 (dd, 1H, J=8.1 Hz, 1.6 Hz), 7.51 (ddd, 1H, J=8.4 Hz, 7.3 Hz, 1.6 Hz), 7.32 (d, 2H, J=8.6 Hz), 7.06 (dd, 1H, J=8.1 Hz, 7.3 Hz), 6.97 (d, 2H, J=8.6 Hz), 6.93 (s, 4H), 3.98–4.16 (br, 4H), 3.87 (s, 3H), 3.73 (s, 2H), 3.12 (s, 1H), 1.97–2.08 (brm, 2H), 1.63–1.73 (m, 6H).

(S)-2-(2-(4-(4-(Pyrrolidin-2-ylmethyloxy)phenyloxy) phenyl)acetylamino)-benzoic acid methyl ester Yield: 32% (yield of two steps from the reaction similar to the Example 15)

$^1$H-NMR (CDCl$_3$); δ11.04 (s, 1H), 8.71 (dd, 1H, J=8.6, 1.1 Hz), 7.99 (dd, 1H, J=8.1, 1.6 Hz), 7.52 (ddd, 1H, J=8.6, 7.3, 1.6 Hz), 7.30 (d, 2H, J=8.6 Hz), 7.06 (ddd, 1H, J=8.1, 7.3, 1.1 Hz), 6.85–6.99 (m, 6H), 4.65–5.55 (br, 1H), 4.11–4.18 (m, 1H), 4.04 (d, 1H, J=5.7 Hz), 3.88 (s, 3H), 3.72 (s, 2H), 3.12–3.19 (m, 2H), 2.89–2.94 (m, 1H), 1.75–2.08 (m, 4H).

2-(2-(4-(4-(Piperidin-2-ylmethyloxy)phenyloxy)phenyl) acetylamino)benzoic acid methyl ester Yield: 37%

$^1$H-NMR (CDCl$_3$); δ11.04 (s, 1H), 8.71 (d, 1H, J=8.4 Hz), 7.99 (dd, 1H, J=8.1, 1.6 Hz), 7.51 (ddd, 1H, J=8.4, 7.3, 1.6 Hz), 7.31 (d, 2H, J=8.4 Hz), 7.06 (dd, 1H, J=8.1, 7.3 Hz), 6.91–6.97 (m, 6H), 5.20–5.75 (br, 1H), 3.87 (s, 3H), 3.72 (s, 2H), 3.35–3.42 (m, 2H), 3.23–3.33 (m, 2H), 1.69–2.04 (brm, 7H).

2-(2-(4-(4-(Piperidin-3-ylmethyloxy)phenyloxy)phenyl) acetylamino)benzoic acid methyl ester Yield: 79%

$^1$H-NMR (CDCl$_3$); δ11.04 (s, 1H), 8.71 (dd, 1H, J=8.4, 1.1 Hz), 7.99 (dd, 1H, J=7.8, 1.6 Hz), 7.52 (ddd, 1H, J=8.4, 7.3, 1.6 Hz), 7.30 (d, 2H, J=8.9 Hz), 7.06 (ddd, 1H, J=7.8, 7.3, 1.1 Hz), 6.97 (d, 2H, J=8.9 Hz), 6.95 (d, 2H, J=8.9 Hz), 6.83 (d, 2H, J=8.9 Hz), 3.88 (s, 3H), 3.72 (s, 2H), 3.86–3.75 (m, 2H), 3.38–3.41 (brm, 1H), 3.21–3.26 (brm, 1H), 2.61–2.76 (brm, 2H), 2.16–2.28 (br, 2H), 1.90–1.97 (brm, 1H), 1.82 (br, 2H).

2-(2-(4-(4-(2-Aminocyclohexyloxy)phenyloxy)phenyl) acetylamino)benzoic acid methyl ester Yield: 58%

$^1$H-NMR (CDCl$_3$); δ11.04 (s, 1H), 8.70 (dd, 1H, J=8.6, 1.1 Hz), 7.98 (dd, 1H, J=8.1, 1.6 Hz), 7.51 (ddd, 1H, J=8.6, 7.0, 1.6 Hz), 7.30 (d, 2H, J=8.6 Hz), 7.05 (ddd, 1H, J=8.1, 7.0, 1.1 Hz), 6.90–6.99 (m, 6H), 6.72 (br, 2H), 4.18 (brm, 1H), 3.86 (s, 3H), 3.71 (m, 2H), 2.95–3.01 (m, 1H), 2.17 (brm, 1H), 2.08 (brm, 1H), 1.71 (brm, 1H), 1.65 (brm, 1H), 1.33–1.43 (m, 2H), 1.21–1.26 (m, 2H).

Example 19

Compounds described in the Tables 48 and 49 as the Example No.19 and corresponding to respective starting raw materials were synthesized from 2-(2-(4-(6-(cis-4-aminocyclohexyloxy)-2-naphthyloxy)-phenyl)acetylamino) benzoic acid methyl ester and 2-(2-(4-(7-(cis-4- aminocyclohexyloxy-2-naphthyloxy)phenyl)acetylamino)benzoic acid methyl ester obtained by the Example 18 by the method similar to the Example 7. The yields and $^1$H-NMR data are shown in the Tables 48 and 49.

Example 20

Synthesis of 2-(2-(4-(6-(cis-4-(benzoylamino)cyclohexyloxy)-2-naphthyloxy)-phenyl)acetylamino)benzoic acid (compound No.96)

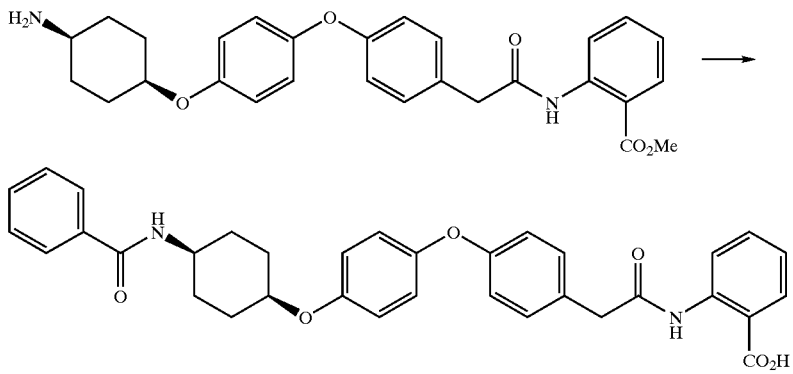

Step 1

A reactor was charged with 358 μl (1.7 eq, 179 μmol) of 0.5M triethylamine-chloroform solution containing 420 μl (105 μl mol, 50 mg) of 2-(2-(4-(4-(cis-4-aminocyclohexyloxy)phenoxy)phenyl)acetylamino)benzoic acid methyl ester (0.25M-CHCl$_3$) obtained by the Example 17, benzoyl chloride (1.5 eq, 22 mg) was added thereto and the mixture was stirred for 2.5 hours. After completing the reaction, 139 mg (157.5 μmol) of an aminomethylated polystyrene resin (product of Novabiochem) was added to the system and stirred for 12 hours. The solution was put on a Silica cartridge (product of Waters) and developed with a hexane/ethyl acetate mixture (1/2) and the obtained solution was distilled to remove the solvent.

Step 2

The compound obtained by the step 1 was dissolved in a mixture of tetrahydrofuran (1 ml) and methanol (0.5 ml), 4N lithium hydroxide solution (0.25 ml) was added thereto and the mixture was stirred over a night. After completing the reaction, the product was acidified with 6N-hydrochloric acid (0.25 ml), water (1 ml) was added, the obtained mixture was extracted with ethyl acetate (2 ml×3) and the organic layer was passed through a sodium sulfate cartridge (product of Waters). The solvent was distilled out and the residue was dried in a desiccator. The compound was identified from the molecular weight using LC-MS and the obtained molecular weight was consistent with the above structure. The data are described in the Table 76.

Example 21

The compounds described as the Example No.21 in the Tables 75 to 89 were synthesized by a method similar to the Example 20 using corresponding substrates. The compounds were identified by the molecular weight using LC-MS and the results were consistent with the structures. The results are shown in the Tables 75 to 89.

Example 22

Synthesis of 2-(2-(4-(4-(cis-4-(2-pyridylcarbonylamino)cyclohexyloxy)-phenoxy)phenyl)acetylamino)benzoic acid (Compound No. 254)

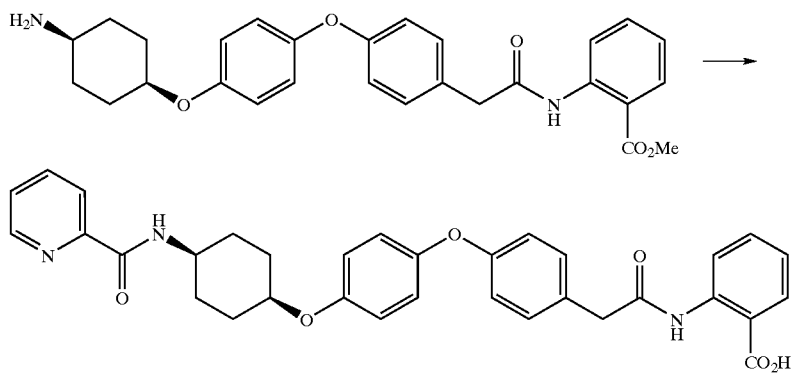

Step 1

2-(2-(4-(4-(cis-4-Aminocyclohexyloxy)phenoxy)phenyl)acetylamino)-benzoic acid methyl ester (47 mg, 0.1 mmol) obtained by the Example 17 was dissolved in preparatorily dried chloroform (0.5 ml) and the solution was added with HOBT (0.12 mmol, 16 mg) and picolinic acid (0.12 mmol, 15 mg). t-BuOH (0.4 ml) and chloroform (1.3 ml) were poured into the mixture, EDCI (0.12 mmol, 23 mg) was added thereto and the mixture was stirred over a night at room temperature. The obtained solution was put on a Silica cartridge (product of Waters) and developed with a mixture of hexane/ethyl acetate (1/2), and the obtained solution was distilled to remove the solvent.

Step 2

The compound obtained by the step 1 was dissolved in a mixture of tetrahydrofuran (1 ml) and methanol (0.5 ml), and the solution was added with 4N aqueous solution of lithium hydroxide (0.25 ml) and stirred over a night. After completing the reaction, the product was acidified with 6N hydrochloric acid (0.25 ml), added with water (1 ml) and extracted with ethyl acetate (2 ml×3), and the organic layer was passed through a sodium sulfate cartridge (product of Waters). The solvent was distilled off and the residue was dried in a desiccator. The obtained compound was identified by the molecular weight using LC-MS and the result was consistent with the above structure. The data are shown in the Table 83.

Example 23

The compounds described as the Example No.23 in the Tables 75 to 89 were synthesized by a method similar to the Example 22 using corresponding substrates. The compounds were identified by the molecular weight using LC-MS and the results were consistent with the above structures. The results are shown in the Tables 75 to 89.

Example 24

Synthesis of 2-(2-(4-(4-(N-acetyl-4-piperidyloxy) phenoxy)l)phenyl)-acetylamino)benzoic acid (Compound No.78)

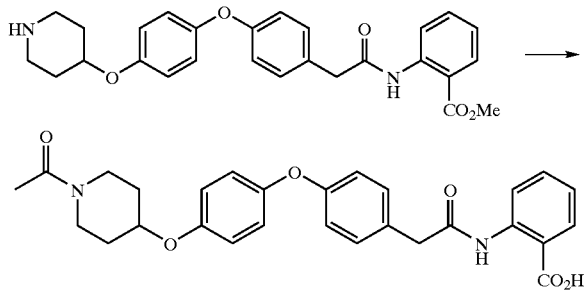

Step 1

A reactor was charged with 2-(2-(4-(4-(4-piperidyloxy) phenoxy)-phenyl)acetylamino)benzoic acid methyl ester (120 mg, 0.26 mmol), preparatorily dried dichloromethane was poured thereto, triethylamine (47 μl, 1.3 eq., 338 μmol) was charged to the reactor, subsequently acetyl chloride (24 μl, 1.3 eq., 338 μmol) was added thereto and the mixture was stirred for 2.5 hours. After completing the reaction, the reaction product was added with water, extracted with dichloromethane and dried with sodium sulfate, and the solvent was removed by distillation. The residue was purified by silica gel column chromatography.

Step 2

The compound produced by the step 1 was dissolved in the mixture of tetrahydrofuran (1 ml) and methanol (0.5 ml), mixed with 4N aqueous solution of lithium hydroxide (0.25 ml) and stirred over a night. After completing the reaction, the product was acidified with 6N hydrochloric acid (0.25 ml), extracted with ethyl acetate and dried with sodium sulfate. The produced compound was identified by the molecular weight using LC-MS and the result was consistent with the above structure. The data are shown in the Table 76.

Example 25

The compounds described as the Example No.25 in the Tables 75 to 89 were synthesized by a method similar to the Example 24 using corresponding substrates. The compounds were identified by the molecular weight using LC-MS and the results were consistent with the structures. The results are shown in the Tables 75 to 89.

Example 26

The compound of the compound No.17 was synthesized by using the compound No.26 of the Table 1 by a method similar to the Referential Example 23. The compound was identified by $^1$H-NMR, and the results are shown in the Table 48.

Example 27

Synthesis of 2-(2-(4-(4-(t-butoxycarbonylmethoxy) phenoxy)phenyl)-acetylamino)benzoic acid methyl ester

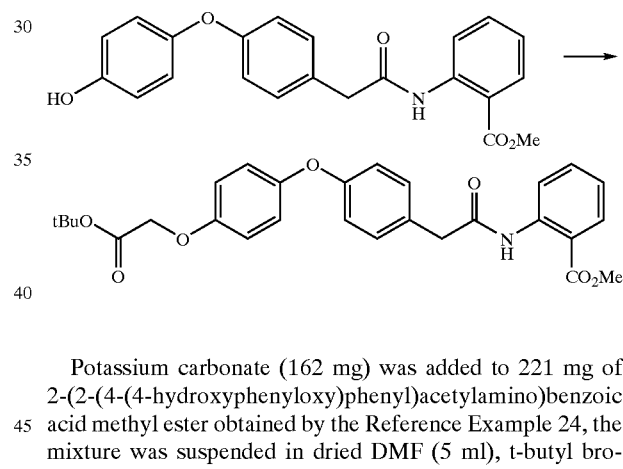

Potassium carbonate (162 mg) was added to 221 mg of 2-(2-(4-(4-hydroxyphenyloxy)phenyl)acetylamino)benzoic acid methyl ester obtained by the Reference Example 24, the mixture was suspended in dried DMF (5 ml), t-butyl bromoacetate (130 μl) was added little by little to the suspension at room temperature, and the mixture was stirred as it is over a night at room temperature. After completing the reaction, DMF was distilled out under reduced pressure and the product was extracted with ethyl acetate. The organic layer was washed with saturated aqueous solution of potassium bisulfate and dried with anhydrous magnesium sulfate. After removing the solvent by distillation, the residue was purified by silica gel column chromatography (developing liquid: hexane:ethyl acetate 4:1 to 1:1) to obtain 174 mg of the subject compound. The $^1$H-NMR of the compound was consistent with the above structure.

Yield: 60%

$^1$H-NMR (CDCl$_3$); δ11.04 (brs, 1H), 8.71 (dd, 1H, J=8.6, 1.0 Hz), 7.91 (dd, 1H, J=8.2 Hz, 1.7 Hz), 7.52 (ddd, 1H, J=8.6, 7.3, 1.7 Hz), 7.31 (d, 2H, J=8.6 Hz), 7.06 (ddd, 1H, J=8.2, 7.3, 1.0 Hz), 6.98 (d, 2H, J=9.2 Hz), 6.96 (d, 2H, J=8.6 Hz), 6.86 (d, 2H, J=9.2 Hz), 4.49 (s, 2H), 3.87 (s, 3H), 3.73 (s, 2H), 1.49 (s, 9H).

Example 28

Synthesis of 2-(2-(4-(4-(hydroxycarbonylmethoxy)phenoxy)phenyl)-acetylamino)benzoic acid methyl ester

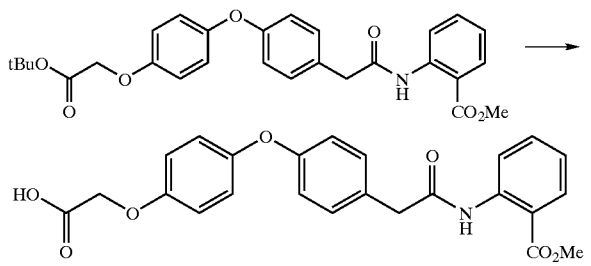

TFA (4 ml) was added to 2-(2-(4-(4-(t-butoxycarbonylmethoxy)-phenoxy)phenyl)acetylamino)benzoic acid methyl ester produced by the Example 27 and the mixture was stirred for 2 hours at room temperature. After the reaction, TFA was distilled out under reduced pressure and the product was dissolved in ethyl acetate. The organic layer was washed with water and dried with anhydrous magnesium sulfate, and the solvent was distilled out under reduced pressure to quantitatively obtain the subject compound (164 mg). The result of $^1$H-NMR was consistent with the above structure.

Yield: 100%

$^1$H-NMR (CDCl$_3$); δ11.09 (brs, 1H), 9.91 (brs, 1H), 8.68 (dd, 1H, J=8.6 Hz), 7.98 (dd, 1H, J=8.2, 1.7 Hz), 7.52 (ddd, 1H, J=8.6, 7.3, 1.7 Hz), 7.31 (d, 2H, J=8.6 Hz), 7.08 (dd, 1H, J=8.2, 7.3 Hz), 6.99 (d, 2H, J=9.2 Hz), 6.96 (d, 2H, J=8.6 Hz), 6.89 (d, 2H, J=9.2 Hz), 4.65 (s, 2H), 3.86 (s, 3H), 3.76 (s, 2H).

Example 29

Synthesis of 2-(2-(4-(4-(piperidinamidomethyloxy)phenoxy)phenyl)-acetylamino)benzoic acid methyl ester (methyl ester of the compound No.42)

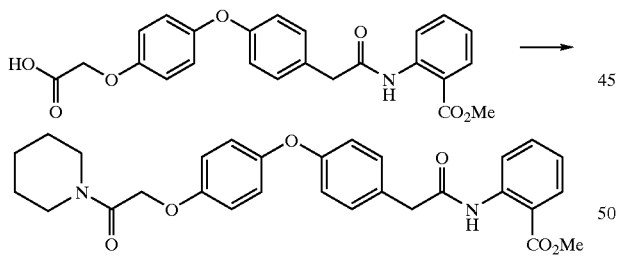

2-(2-(4-(4-(Hydroxycarbonylmethoxy)phenoxy)phenyl)acetylamino)-benzoic acid methyl ester (164 mg, 0.377 mmol) obtained by the Example 28 was suspended in methylene chloride (10 ml) and oxalyl chloride (34 μl) was added to the suspension at room temperature. The product was changed to transparent brown color under foaming by the addition of about 2 drops of dried DMF. After stirring at room temperature for 2 hours, the solvent and excess oxalyl chloride were distilled off under reduced pressure, and the residue was dissolved in methylene chloride (10 ml). Piperidine (35 μl) and triethylamine (54 μl) were added to the solution and reacted over a night at room temperature. The product was extracted with methylene chloride, and the organic layer was washed with saturated aqueous solution of potassium bisulfate and dried with anhydrous magnesium sulfate. The product was subjected to silica gel column chromatography (developing liquid; hexane:ethyl acetate= 1:1) to obtain the subject compound (118 mg, 0.234 mg). The result of $^1$H-NMR was consistent with the above structure.

Yield: 62%

$^1$H-NMR (CDCl$_3$); δ11.04 (brs, 1H), 8.71 (dd, 1H, J=8.6 Hz, 1.0 Hz), 7.99 (dd, 1H, J=7.9 Hz, 1.7 Hz), 7.52 (ddd, 1H, J=8.6, 7.3, 1.7 Hz), 7.31 (dd, 2H, J=8.6, 2.0 Hz), 7.06 (ddd, 1H, J=7.9, 7.3, 1.0 Hz), 6.98 (d, 2H, J=9.2, 2.6 Hz), 6.96 (dd, 2H, J=9.2, 2.6 Hz), 6.92 (dd, 2H, J=8.6, 2.0 Hz), 4.66 (s, 2H), 3.87 (S, 3H), 3.72 (S, 2H), 3.55–3.58 (br, 2H), 3.46–3.50 (br, 2H), 1.57–1.68 (br, 6H).

Example 30

The compound of the compound No.42 of the Table 2 was synthesized by a method similar to the Example 7 using the compound obtained by the Example 29. The result of $^1$H-NMR was consistent with the above structure. The data are shown in the Table 55.

Example 31

Synthesis of 2-(2-(4-(4-(3-(tert-butoxycarbonylamino)benzyloxy)phenoxy)-phenyl)acetylamino)benzoic acid methyl ester

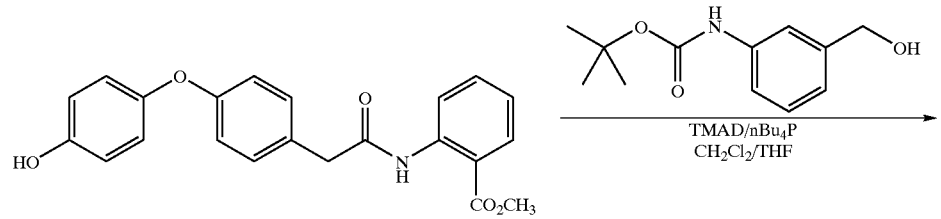

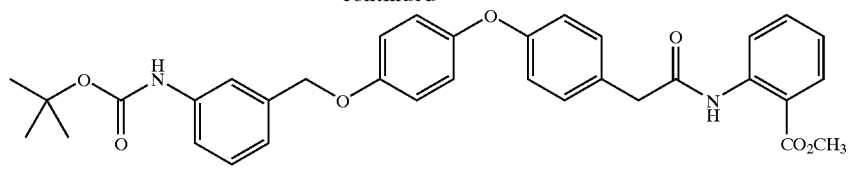

TMAD = 1,1'-Azobis(N,N'-dimethylformamide)

2-(2-(4-(4-Hydroxyphenoxy)phenyl)acetylamino)benzoic acid methyl ester obtained by the Reference Example 24 (315 mg, 0.83 mmol) was dissolved in 20 ml of methylene chloride-THF mixture (1:1 v/v), added with 3-(tert-butoxycarbonylamino)benzyl alcohol (465 mg, 2.1 mmol), 1,1'-azobis(N,N'-dimethylformamide) (359 mg, 2.08 mmol) and tri-n-butyl phosphine (520 ml, 2.1 mmol) and the reaction mixture was stirred over a night. After completing the reaction, the solvent was removed under reduced pressure and the obtained crude residue was purified by silica gel chromatography (elution solvent; hexane:ethyl acetate 75:25 v/v) to obtain the subject compound (404 mg, 0.693 mmol) in the form of a colorless gummy substance. The result of $^1$H-NMR was consistent with the above structure.

Yield: 83%

$^1$H-NMR (CDCl$_3$); δ11.03 (brs, 1H), 8.72 (dd, 1H, J=1.08, 8.64 Hz), 7.99 (dd, 1H, J=1.89, 8.10 Hz), 7.55–7.49 (m, 2H), 7.34–7.26 (m, 6H), 7.04–6.90 (m, 6H), 7.51 (brs, 1H), 5.02 (s, 2H), 3.87 (s, 3H), 3.73 (s, 2H), 1.52 (s, 9H).

Example 32

The following compound was synthesized by a method similar to the Example 31 using the corresponding substrate. The result of $^1$H-NMR was consistent with the structure.

2-(2-(4-(4-(4-(tert-Butoxycarbonylamino)benzyloxy)phenoxy)phenyl)-acetylamino)benzoic acid methyl ester Yield: 46%

$^1$H-NMR (CDCl$_3$); δ11.03 (brs, 1H), 8.71 (d, 1H, J=7.56 Hz), 7.99 (dd, 1H, J=1.62, 7.83 Hz), 7.51 (dt, 1H, J=1.35, 8.64 Hz), 7.34–7.30 (m, 4H), 7.28–7.25 (m, 2H), 7.07 (t, 1H, J=8.37 Hz), 7.00–6.90 (m, 6H), 6.49 (s, 1H), 4.98 (s, 2H), 3.87 (s, 3H), 3.72 (s, 2H), 1.52 (s, 9H).

Example 33

Synthesis 2-(2-(4-(4-(2-(tert-butoxycarbonylamino)benzyloxy)phenoxy)-phenyl)acetylamino)benzoic acid methyl ester

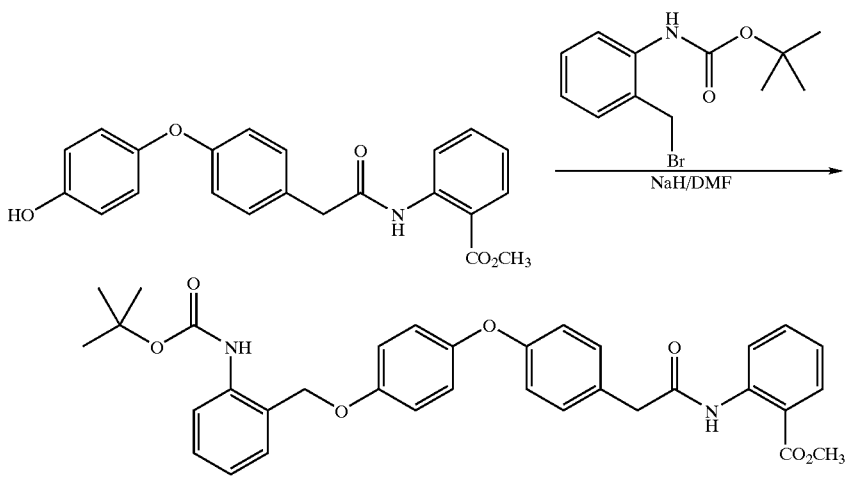

2-(2-(4-(4-Hydroxyphenoxy)phenyl)acetylamino)benzoic acid methyl ester (300 mg, 0.82 mmol) obtained by the Reference Example 24 was dissolved in anhydrous N-dimethylformamide (10 ml), added with sodium hydride (30 mg, abt. 60%), stirred for 15 minutes and added with N-tert-butoxycarbonyl-2-bromomethylaniline (540 mg, 1.9 mmol). The reaction mixture was stirred over a night at room temperature, water (150 ml) was added thereto, the mixture was extracted with ethyl acetate (50 ml×2) and washed with water (100 ml×3), the organic solvent was dried with anhydrous magnesium sulfate and the solvent was removed under reduced pressure. The obtained residue was purified by silica gel chromatography (elution solvent; hexane:ethyl acetate 75:25 v/v) to obtain the subject compound (234 mg, 0.402 mmol) in the form of a colorless gummy substance. The result of $^1$H-NMR was consistent with the above structure.

Yield: 49%

$^1$H-NMR (CDCl$_3$); δ11.05 (brs, 1H), 8.72 (dd, 1H, J=1.03, 8.37 Hz), 7.99 (dd, 1H, J=1.62, 8.10 Hz), 7.93 (d, 1H, J=8.37 Hz), 7.52 (dt, 1H, J=1.62, 7.29 Hz), 7.42–7.25 (m, 6H), 7.09–6.94 (m, 7H), 5.05 (s, 2H), 3.89 (s, 3H), 3.73 (s, 2H), 1.51 (s, 9H).

Example 34

Synthesis of 2-(2-(4-(4-(3-(acetylamino)benzyloxy)phenoxy)phenyl)-acetylamino)benzoic acid methyl ester (methyl ester of the compound No.50)

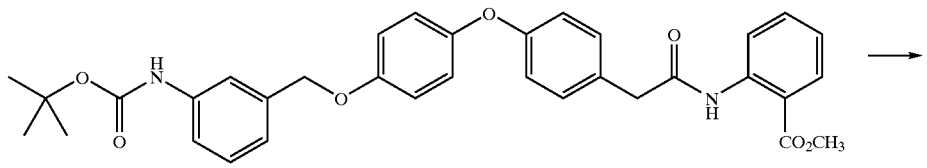

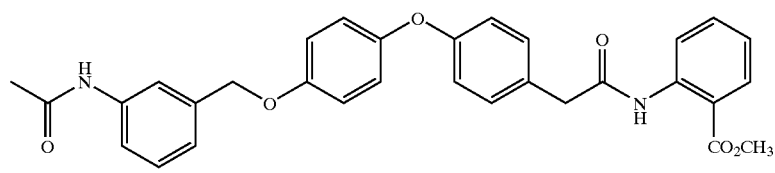

2-(2-(4-(4-(3-(tert-Butoxycarbonylamino)benzyloxy)phenoxy)-phenyl)acetylamino)benzoic acid methyl ester (155 mg, 0.266 mmol) obtained by the Example 31 was dissolved in 4N hydrochloric acid-1,4-dioxane solution (5.0 ml) and stirred for 30 minutes at room temperature. The solvent was quickly removed under reduced pressure and the residue was dried under reduced pressure. The dried residue was dissolved in methylene chloride (10 ml) and triethylamine (0.11 ml, 0.789 mmol), added with acetyl chloride (0.025 ml) and stirred for a night at room temperature. After completing the reaction, the reaction liquid was added with water (100 ml) and immediately extracted with ethyl acetate (20 ml×2). The collected ethyl acetate layer was dried with anhydrous magnesium sulfate and filtered, and the solvent was removed under reduced pressure. The obtained residue was purified by silica gel chromatography (elution, hexane-:ethyl acetate 6:4 v/v) to obtain the subject compound (110 mg, 0.215 mmol) in the form of a colorless gummy substance. The result of $^1$H-NMR was consistent with the above structure.

Yield: 81%

$^1$H-NMR (CDCl$_3$); δ11.04 (brs, 1H), 8.71 (d, 1H, J=8.37 Hz), 7.99 (dd, 1H, J=1.62, 8.10 Hz), 7.60 (brs, 1H), 7.53 (dd, 2H, J=1.62, 8.64 Hz), 7.45–7.23 (m, 4H), 7.17 (d, 1H, J=7.56 Hz), 7.06 (t, 1H, J=7.02 Hz), 7.00–8.89 (m, 6H), 5.02 (s, 2H), 3.87 (s, 3H), 3.72 (s, 2H), 2.17 (s, 3H).

Example 35

The following compounds were synthesized by a method similar to the Example 34 using the compounds obtained by the Examples 32 and 33 and reacting with respective corresponding substrates. The results of $^1$H-NMR were consistent with the structures.

2-(2-(4-(4-(3-(Benzoylamino)benzyloxy)phenoxy)phenyl)acetylamino)benzoic acid methyl ester (methyl ester of the compound No.51)

Yield: 49%

$^1$H-NMR (CDCl$_3$); δ11.03 (brs, 1H), 8.70 (d, 1H, J=8.37 Hz), 8.16 (brs, 1H), 7.99 (dd, 1H, J=1.62, 8.10 Hz), 7.88 (dd, 2H, J=1.62, 6.76 Hz), 7.78 (brs, 1H), 7.64 (d, 1H, J=7.56 Hz), 7.55–7.20 (m, 9H), 7.09–6.91 (m, 6H), 5.05 (s, 2H), 3.86 (s, 3H).

2-(2-(4-(4-(2-(Acetylamino)benzyloxy)phenoxy)phenyl)acetylamino)benzoic acid methyl ester (methyl ester of the compound No.46)

Yield: 68%

$^1$H-NMR (CDCl$_3$); δ11.06 (brs, 1H), 8.71 (d, 1H, J=8.64 Hz), 8.14 (brs, 1H), 8.07 (d, 1H, J=8.37 Hz), 8.00 (dd, 1H, J=1.62, 8.10 Hz), 7.54 (dt, 1H, J=1.62, 8.91 Hz), 7.38–7.26 (m, 5H), 7.16–7.93 (m, 7H), 5.06 (s, 2H), 3.87 (s, 3H), 3.73 (s, 2H), 2.13 (s, 3H).

2-(2-(4-(4-(2-(Methoxycarbonylamino)benzyloxy)phenoxy)phenyl)-acetylamino)benzoic acid methyl ester (methyl ester of the compound No.48)

Yield: 80%

$^1$H-NMR (CDCl$_3$); δ11.04 (brs, 1H), 8.72 (d, 1H, J=8.73 Hz), 8.00 (d, 1H, J=8.10 Hz), 7.52 (t, 1H, J=8.00 Hz), 7.40–7.90 (m, 13H), 6.78–6.60 (m, 1H), 5.00 (s, 2H), 3.86 (s, 3H), 3.73 (s, 2H), 3.59 (s,3H).

2-(2-(4-(4-(2-(Benzoylamino)benzyloxy)phenoxy)phenyl)acetylamino)benzoic acid methyl ester (methyl ester of the compound No.49)

Yield: 63%

$^1$H-NMR (CDCl$_3$); δ11.06 (brs, 1H), 9.16 (brs, 1H), 8.73 (d, 1H, J=8.37 Hz), 8.33 (d, 1H, J=8.37 Hz), 8.11 (d, 1H, J=7.12 Hz), 8.00 (dd, 2H, J=1.89, 6.21 Hz), 7.88–7.60 (m, 4H), 7.60–7.15 (m, 7H), 7.10–6.91 (m, 5H), 5.16 (s, 2H), 3.86 (s, 3H), 3.73 (s, 2H).

Example 36

The compounds described in the Table 90 as example No.36 were synthesized by a method similar to the Example 7 using the corresponding substrates obtained by the Examples 34 and 35. The produced compounds were confirmed by LC-MS and the results were consistent with the structures. The results are shown in the Table 90.

Example 37

Synthesis of 2-((4-(6-(3-aminopropoxy)-2-naphthyloxy)phenyl)-carbonylamino)benzoic acid (compound No.33)

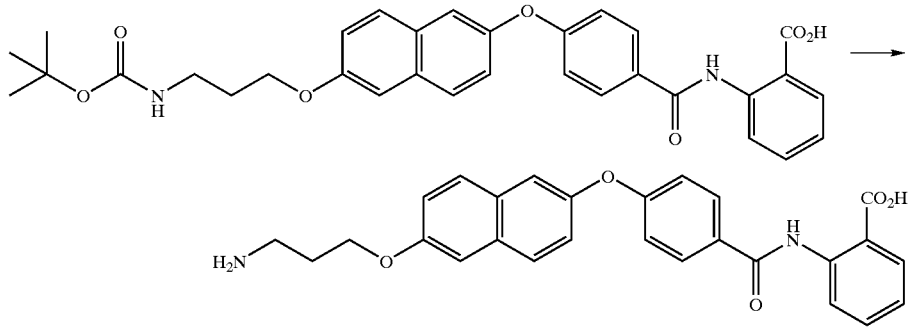

1436 2-((4-(6-(3-(tert-Butoxycarbonylamino)propoxy)-2-naphthyloxy)-phenyl)carbonylamino)benzoic acid (compound No.31, 50 mg, 0.09 mmol) obtained by the Example 8 was dissolved in 3 ml of 4N hydrochloric acid-1,4-dioxane solution and 2.5 ml of 1,4-dioxane, stirred at room temperature for 5.5 hours and at 50 to 60° C. for 7 hours (3 ml of 4N hydrochloric acid-1,4-dioxane solution was added 3 hours after heating) and further stirred at room temperature for a night. After completing the reaction, the reaction liquid was concentrated and the crude product was recrystallized from ethanol (4 ml) to obtain the subject compound (14.5 mg, 0.0317 mmol) in the form of white granular crystal. The result of $^1$H-NMR was consistent with the structure.

Yield: 35%

$^1$H-NMR (DMSO-$d_6$); δ2.07 (quint, J=5.9 Hz, 2H), 2.95–3.10 (m, 2H), 4.18 (t, J=5.9 Hz, 2H), 7.15–7.23 (m, 4H), 7.33 (dd, J=2.3, 8.9 Hz, 1H), 7.38 (d, J=2.0 Hz, 1H), 7.57 (d, J=2.6 Hz, 1H), 7.61–7.64 (m, 1H), 7.82 (d, J=8.9 Hz, 1H), 7.91 (d, J=9.2 Hz, 1H), 7.98 (d, J=8.9 Hz, 2H), 8.04 (d, J=8.3 Hz, 1H), 8.69 (d, J=8.6 Hz, 1H).

TABLE 44

| Compound No. | Yield (%) | $^1$H-NMR (CDCl$_3$): δ | Example No. |
|---|---|---|---|
| 1 | 68 | $^1$H-NMR (DMSO-$d_6$); δ 1.13 (t, J=6.9 Hz, 3H), 3.52 (q, J=6.9 Hz, 2H), 3.73–3.76 (m, 4H), 4.18 (t, J=4.3, 2H), 7.02 (d, J=8.6 Hz, 2H), 7.10–7.18 (m, 2H), 7.22–7.26 (m, 1H), 7.34–7.39 (m, 4H), 7.57 (t, J=8.9 Hz, 1H), 7.73 (d, J=8.9 Hz, 1H), 7.83 (d, J=8.9 Hz, 1H), 7.95 (dd, J=1.7, 7.9 Hz, 1H), 8.50 (d, J=8.3 Hz, 1H), 11.12 (br.s, 1H), 13.57 (br.s, 1H). | 7 |
| 1 methyl ester | 80 | 1.27 (t, J=6.9 Hz, 3H), 3.64 (q, J=6.9 Hz, 2H), 3.75 (s, 2H), 3.84–3.88 (m, 2H), 3.88 (s, 3H), 4.24 (t, J=4.6 Hz, 2H), 7.02–7.25 (m, 6H), 7.31–7.37 (m, 3H), 7.50–7.57 (m, 1H), 7.60 (d, J=8.9 Hz, 1H), 7.69 (d, J=8.9 Hz, 1H), 8.01 (dd, J=1.7, 8.3 Hz, 1H), 8.73 (dd, J=1.0, 8.6 Hz, 1H), 11.07 (br.s, 1H). | 5 |
| 2 | 73 | $^1$H-NMR (DMSO-$d_6$); δ 1.91 (quint, J=6.3 Hz, 2H), 3.20 (q, J=6.3 Hz, 2H), 3.75 (s, 2H), 4.08 (t, J=6.3 Hz, 2H), 5.01 (s, 2H), 7.02 (d, J=8.6 Hz, 2H), 7.07–7.16 (m, 2H), 7.23–7.39 (m, 10H), 7.57 (t, J=8.6 Hz, 1H), 7.72 (d, J=8.9 Hz, 1H), 7.83 (d, J=8.9 Hz, 1H), 7.95 (dd, J=1.7, 7.9 Hz, 1H), 8.50 (d, J=8.3 Hz, 1H), 11.13 (br.s, 1H), 13.57 (br.s, 1H). | 8 |
| 2 methyl ester | 69 | 11.08 (brs, 1H), 8.72 (t, 1H, J=8.3, 1.3 Hz), 8.01 (dd, 1H, J=8.3, 1.3 Hz), 7.69 (d, 1H, J=8.9 Hz), 7.60 (d, 1H, J=9.6 Hz), 7.53 (t, 1H, J=8.3 Hz), 7.37–7.31 (m, 8H), 7.25–7.22 (m, 1H), 7.12–7.03 (m, 5H), 5.11 (s, 2H), 4.14 (t, 2H, J=6.9 Hz), 3.89 (s, 3H), 3.75 (s, 2H), 3.48 (q, 2H, J=6.6 Hz), 2.10–2.05 (m, 2H). | 6 |
| 3 | 69 | $^1$H-NMR (DMSO-$d_6$); δ 1.35–1.65 (m, 4H), 1.77 (quint, J=6.6 Hz, 2H), 2.24 (t, J=7.3 Hz, 2H), 3.74 (s, 2H), 4.05 (t, J=6.6 Hz, 2H), 7.02 (d, J=8.6 Hz, 2H), 7.10–7.15 (m, 2H), 7.23 (dd, J=2.6, 8.9 Hz, 1H), 7.32–7.38 (m, 4H), 7.56 (t, J=8.6 Hz, 1H), 7.72 (d, J=9.2 Hz, 1H), 7.83 (d, J=9.2 Hz, 1H), 7.95 (dd, J=1.7, 7.9 Hz, 1H), 8.50 (d, J=7.6 Hz, 1H), 11.28 (br.s, 1H). | 8 |
| 3 | 100 | 11.07 (brs, 1H), 8.73 (dd, 1H, J=8.6, 1.0 Hz), 8.01 (dd, 1H, J=7.9, 1.7 Hz), 7.69 (d, 1H, J=8.9 Hz), 7.60 (d, 1H, J=9.6 Hz), 7.57–7.50 (m, 1H), 7.37–7.31 (m, 3H), 7.23 (dd, 1H, J=8.9, 2.6 Hz), 7.15–7.02 (m, 5H), 4.14 (q, 2H, J=7.3 Hz), 4.07 (t, 2H, J=6.6 Hz), 3.88 (s, 3H), 3.75 (s, 2H), 2.35 (t, 2H, J=7.3 Hz), 1.95–1.80 (m, 2H), 1.80–1.65 (m, 2H), 1.65–1.45 (m, 2H), 1.26 (t, 3H, J=7.3 Hz). | 6 |

TABLE 45

| | | | |
|---|---|---|---|
| 4 | 53 | ¹H-NMR (DMSO-d₆); δ 13.57 (brs, 2H), 11.17 (s, 1H), 11.13 (s, 1H), 8.51 (d, 1H, J=3.3 Hz), 8.48 (d, 1H, J=3.3 Hz), 7.98–7.93 (m, 2H), 7.82 (d, 1H, J=8.9 Hz), 7.72 (d, 1H, J=9.2 Hz), 7.61–7.54 (m, 2H), 7.38–7.33 (m, 4H), 7.23 (dd, 1H, J=8.9, 2.6 Hz), 7.16–7.11 (m, 3H), 7.02 (d, 2H, J=8.6 Hz), 4.14 (t, 2H, J=6.3 Hz), 3.75 (s, 2H), 2.61 (t, 2H, J=6.9 Hz), 2.12 (quint, 2H, J=6.9 Hz). | 8 |
| 4 methyl ester methyl ester | 41 | 11.05 (brs, 1H), 11.08 (brs, 1H), 8.74 (dd, 1H, J=8.6, 1.0 Hz), 8.73 (dd, 1H, J=8.3, 1.0 Hz), 8.01 (d, 2H, J=7.9 Hz), 7.67 (d, 1H, J=8.9 Hz), 7.60–7.50 (m, 3H), 7.38–7.31 (m, 3H), 7.22 (dd, 1H, J=8.9, 2.6 Hz), 7.15–7.02 (m, 6H), 4.18 (t, 2H, J=6.3 Hz), 3.88 (s, 3H), 3.87 (s, 3H), 3.75 (s, 2H), 2.71 (t, 2H, J=6.9 Hz), 2.30 (quint, 2H, J=6.9 Hz). | 6 |
| 5 | 86 | ¹H-NMR (DMSO-d₆); δ 1.91 (quint, J=6.3 Hz, 2H), 3.59 (t, J=6.3 Hz, 2H), 3.75 (s, 2H), 4.13 (t, J=6.3 Hz, 2H), 5.16 (br.s, 1H), 7.02 (d, J=8.6 Hz, 2H), 7.10–7.16 (m, 2H), 7.24 (dd, J=2.6, 8.6 Hz, 1H), 7.33–7.39 (m, 4H), 7.57 (t, J=8.9 Hz, 1H), 7.72 (d, J=8.9 Hz, 1H), 7.84 (d, J=9.2 Hz, 1H), 7.95 (dd, J=1.3, 8.3 Hz, 1H), 8.49 (d, J=8.6 Hz, 1H), 11.72 (s, 1H), 14.17 (br.s, 1H). | 8 |
| 5 methyl ester | 44 | 11.08 (brs, 1H), 8.73 (dd, 1H, J=8.6, 1.3 Hz), 8.01 (dd, 1H, J=8.2, 1.7 Hz), 7.70 (d, 1H, J=8.9 Hz), 7.61 (d, 1H, J=8.6 Hz), 7.53 (t, 1H, J=8.6 Hz), 7.37–7.32 (m, 3H), 7.25–7.22 (m, 1H), 7.15–7.03 (m, 5H), 4.24 (t, 2H, J=5.9 Hz), 3.99–3.87 (m, 5H), 3.75 (s, 2H), 2.12 (quint, 2H, J=5.9 Hz). | 6 |
| 6 | 50 | ¹H-NMR (DMSO-d₆); δ 3.72 (s, 2H), 5.68 (s, 2H), 7.02 (s, J=8.6 Hz, 2H), 7.08 (t, J=7.5 Hz, 1H), 7.21–7.27 (m, 2H), 7.36–7.39 (m, 4H), 7.49 (t, J=6.9 Hz, 1H), 7.56–7.61 (m, 2H), 7.68–7.81 (m, 3H), 7.96 (dd, J=7.9, 1.5 Hz, 1H), 8.07 (d, J=8.0 Hz, 2H), 8.50 (d, J=8.0 Hz, 1H), 11.91 (brs, 1H). | 8 |
| 6 methyl ester | 95 | 11.08 (brs, 1H), 8.72 (d, 1H, J=8.0 Hz), 8.06–7.98 (m, 3H), 7.69–7.61 (m, 3H), 7.55–7.49 (m, 3H), 7.37–7.32 (m, 3H), 7.26–7.21 (m, 2H), 7.13–7.05 (m, 4H), 5.38 (s, 2H), 3.88 (s, 3H), 3.75 (s, 2H). | 6 |

TABLE 46

| | | | |
|---|---|---|---|
| 7 | 63 | Hydrochloride: ¹H-NMR (DMSO-d₆); δ 3.18 (4H, brs), 3.43 (2H, s br), 3.76 (2H, s), 3.83 (4H, t-like, J=4.6 Hz), 4.45 (2H, t-like, J=5.0 Hz), 7.03 (2H, d, J=8.6 Hz), 7.14 (1H, t-like, J=7.5 Hz), 7.20 (1H, dd, J=8.9, 2.3 Hz), 7.27 (1H, dd, J=8.9, 2.7 Hz), 7.37–7.41 (4H, m), 7.57 (1H, t, J=8 Hz), 7.77 (1H, d, J=9.2 Hz), 7.86 (1H, d, J=8.9 Hz), 7.96 (1H, dd, J=7.9, 1.3 Hz), 8.52 (1H, d, J=8.3 Hz), 11.18 (1H, brs). | 8 |
| 7 methyl ester | 21 | 11.08 (brs, 1H), 8.73 (dd, 1H, J=8.6, 0.7 Hz), 8.00 (dd, 1H, J=8.1, 1.3 Hz), 7.69 (d, 1H, J=8.9 Hz), 7.60 (d, 1H, J=9.6 Hz), 7.53 (t, 1H, J=8.5 Hz), 7.37–7.03 (m, 9H), 4.22 (t, 2H, J=5.6 Hz), 3.89 (s, 3H), 3.75 (t, 4H, J=4.6 Hz), 3.75 (s, 2H), 2.87 (t, 2H, J=5.6 Hz), 2.62 (t, 4H, J=4.6 Hz). | 6 |
| 9 | 40 | ¹H-NMR (DMSO-d₆); δ 13.58 (brs, 1H), 11.16 (s, 1H), 8.53 (d, 1H, J=8.6 Hz), 7.96 (dd, 1H, J=7.9, 1.7 Hz), 7.84 (d, 1H, J=8.6 Hz), 7.78 (d, 1H, J=8.9 Hz), 7.58 (m, 1H), 7.41 (d, 2H, J=8.6 Hz), 7.26–7.02 (m, 7H), 4.53 (brs, 1H), 4.11 (t, 2H, J=6.3 Hz), 3.78 (s, 2H), 3.58 (t, 2H, J=6.0 Hz), 1.90 (quint, 2H, J=6.3 Hz). | 8 |
| 9 methyl ester | 47 | 11.10 (brs, 1H), 8.72 (dd, 1H, J=8.58, 0.99 Hz), 8.00 (dd, 1H, J=8.24, 1.65 Hz), 7.71 (d, 1H, J=8.25 Hz), 7.68 (d, 1H, J=7.91 Hz), 7.52 (ddd, 1H, J=8.58, 7.25, 1.65 Hz), 7.37 (d, 2H, J=8.57 Hz), 7.20 (d, 1H, J=2.31 Hz), 7.12–6.99 (m, 6H), 4.18 (t, 2H, J=5.93 Hz), 3.88 (s, 3H), 3.88 (t, 2H, J=4.95 Hz), 3.75 (s, 2H), 2.08 (m, 2H). | 6 |
| 10 | 81 | ¹H-NMR (DMSO-d₆); δ 13.56 (brs, 1H), 11.19 (s, 1H), 8.54 (d, 1H, J=8.6 Hz), 7.96 (dd, 1H, J=7.9, 1.7 Hz), 7.85 (d, 1H, J=8.6 Hz), 7.79 (d, 1H, J=8.9 Hz), 7.57 (m, 1H), 7.41 (d, 2H, J=8.6 Hz), 7.23–7.04 (m, 7H), 4.15 (t, 2H, J=4.6 Hz), 3.78 (s, 2H), 3.73 (t, 2H, J=4.6 Hz), 3.51 (q, 2H, J=7.0 Hz), 1.14 (t, 3H, J=7.0 Hz). | 8 |

TABLE 46-continued

| | | | |
|---|---|---|---|
| 10 methyl ester | 93 | 11.10 (brs, 1H), 8.73 (d, 1H, J=8.25 Hz), 7.99 (dd, 1H, J=7.91, 1.65 Hz), 7.70 (d, 1H, J=8.25 Hz), 7.67 (d, 1H, J=8.24 Hz), 7.52 (ddd, 1H, J=8.58, 7.25, 1.32 Hz), 7.37 (d, 2H, J=8.57 Hz), 7.21 (d, 1H, J=1.98 Hz), 7.13–7.03 (m, 5H), 6.99 (d, 1H, J=2.64 Hz), 4.18 (t, 2H, J=4.61 Hz), 3.87 (s, 3H), 3.82 (t, 2H, J=4.62 Hz), 3.75 (s, 2H), 3.60 (q, 2H, J=6.93 Hz), 1.24 (t, 3H, J=6.93 Hz). | 6 |

TABLE 47

| | | | |
|---|---|---|---|
| 11 | 33 | ¹H-NMR (DMSO-d₆); δ 14.05 (brs, 1H), 8.46 (d, 1H, J=8.2 Hz), 7.95 (dd, 1H, J=7.8, 1.5 Hz), 7.82 (d, 1H, J=8.9 Hz), 7.74 (d, 1H, J=9.2 Hz), 7.40 (d, 2H, J=8.6 Hz), 7.30–7.20 (m, 3H), 7.14–6.94 (m, 5H), 4.13 (t, 2H, J=5.5 Hz), 3.64 (s, 2H), 3.07 (brm, 4H), 2.74 (brm, 2H), 2.70 (brs, 4H). | 11 |
| 11 methyl ester | 48 | 11.10 (brs, 1H), 8.73 (dd, 1H, J=8.58, 0.99 Hz), 8.01 (dd, 1H, J=8.35, 1.65 Hz), 7.71 (d, 1H, J=8.58 Hz), 7.68 (d, 1H, J=7.91 Hz), 7.53 (ddd, 1H, J=8.57, 7.26, 1.32 Hz), 7.38 (d, 2H, J=8.90 Hz), 7.21 (d, 1H, J=1.98 Hz), 7.13–7.04 (m, 5H), 6.99 (d, 1H, J=2.31 Hz), 4.18 (t, 2H, J=5.94 Hz), 3.89 (s, 3H), 3.76 (s, 2H), 2.92 (t, 4H, J=4.62 Hz), 2.84 (t, 2H, J=5.94 Hz), 2.56 (brm, 4H). | 10 |
| 12 | 32 | ¹H-NMR (DMSO-d₆); δ 8.48 (d, 1H, J=8.6 Hz), 7.95 (d, 1H, J=7.9 Hz), 7.84 (d, 1H, J=8.9 Hz), 7.78 (d, 1H, J=8.9 Hz), 7.66–7.57 (m, 1H), 7.45–7.38 (m, 2H), 7.28–7.02 (m, 7H), 4.17 (t, 2H, J=5.7 Hz), 3.72 (s, 2H), 3.61–3.56 (m, 8H), 2.75 (t, 2H, J=5.7 Hz). | 11 |
| 12 methyl ester | 78 | 11.11 (brs, 1H), 8.73 (dd, 1H, J=8.58, 0.66 Hz), 8.01 (dd, 1H, J=8.25, 1.65 Hz), 7.72 (d, 1H, J=8.25 Hz), 7.69 (d, 1H, J=7.91 Hz), 7.53 (ddd, 1H, J=8.57, 7.26, 1.65 Hz), 7.38 (d, 2H, J=8.57 Hz), 7.21 (d, 1H, J=2.31 Hz), 7.13–7.04 (m, 5H), 6.99 (d, 1H, J=2.31 Hz), 4.19 (t, 2H, J=5.93 Hz), 3.89 (s, 3H), 3.76 (s, 2H), 3.74 (t, 4H, J=4.62 Hz), 2.85 (t, 2H, J=5.94 Hz), 2.60 (t, 4H, J=4.62 Hz). | 10 |
| 13 | 69 | ¹H-NMR (DMSO-d₆); δ 8.57 (dd, 2H, J=4.5, 1.5 Hz), 8.48 (d, 1H, J=8.3 Hz), 7.97 (dd, 1H, J=7.9, 1.6 Hz), 7.85 (t, 2H, J=9.2 Hz), 7.65–7.54 (m, 2H), 7.47–7.36 (m, 5H), 7.24–7.05 (m, 5H), 5.27 (s, 2H), 3.71 (s, 2H). | 11 |
| 13 methyl ester | 85 | 11.12 (brs, 1H), 8.73 (d, 1H, J=8.58 Hz), 8.62 (dd, 2H, J=4.62, 1.65 Hz), 8.01 (dd, 1H, J=8.25, 1.65 Hz), 7.75–7.36 (m, 8H), 7.19–7.01 (m, 6H), 5.17 (s, 2H), 3.89 (s, 3H), 3.76 (s, 2H). | 10 |
| 14 | 10 | ¹H-NMR (DMSO-d₆); δ 13.19 (brs, 1H), 8.49 (d, 1H, J=7.6 Hz), 7.97 (d, 1H, J=7.9 Hz), 7.84 (d, 1H, J=8.9 Hz), 7.78 (d, 1H, J=8.9 Hz), 7.37 (d, 2H, J=8.6 Hz), 7.40–7.33 (m, 2H), 7.25 (s, 1H), 7.13 (dd, 1H, J=8.9, 2.5 Hz), 7.05–6.96 (m, 2H), 7.05 (d, 2H, J=8.6 Hz), 4.37 (2H, m), 3.67 (s, 2H), 3.22 (brs, 2H), 2.98 (brs, 4H), 1.67 (brs, 4H), 1.5–1.4 (brs, 2H). | 11 |

TABLE 48

| | | | |
|---|---|---|---|
| 14 methyl ester | 60 | 11.10 (brs, 1H), 8.73 (d, 1H, J=8.25 Hz), 8.01 (dd, 1H, J=8.25, 1.65 Hz), 7.71 (d, 1H, J=8.58 Hz), 7.68 (d, 1H, J=8.24 Hz), 7.53 (dd, 1H, J=8.57, 7.26 Hz), 7.37 (d, 2H, J=8.24 Hz), 7.21 (d, 1H, J=1.98 Hz), 7.12–7.04 (m, 5H), 6.99 (d, 1H, J=2.31 Hz), 4.18 (t, 2H, J=5.93 Hz), 3.89 (s, 3H), 3.76 (s, 2H), 2.81 (t, 2H, J=5.94 Hz), 2.52 (t, 4H, J=4.95 Hz), 1.65–1.56 (brm, 4H), 1.47–1.43 (brm, 2H). | 10 |
| 16 | 100 | ¹H-NMR (DMSO-d₆); δ 11.20 (brs, 1H), 8.51 (d, 1H, J=8.6 Hz), 7.96 (dd, 1H, J=7.6, 1.7 Hz), 7.84 (d, 1H, J=8.9 Hz), 7.73 (d, 1H, J=8.9 Hz), 7.57 (dd, 1H, J=8.6, 7.6 Hz), 7.21–7.39 (m, 10H), 7.11–7.16 (m, 2H), 7.02 (d, 2H, J=8.6 Hz), 4.52 (brs, 3H), 3.75 (s, 2H), 3.49 (brm, 1H), 2.03–2.09 (brm, 4H), 1.47–1.54 (m, 4H). | 11 |

TABLE 48-continued

| | | | |
|---|---|---|---|
| 16 methyl ester | 29 | 11.08 (brs, 1H), 8.72 (dd, 1H, J=8.6, 1.0 Hz), 8.00 (dd, 1H, J=7.9, 1.7 Hz), 7.69 (d, 1H, J=8.9 Hz), 7.60 (d, 1H, J=8.9 Hz), 7.53 (ddd, 1H, J=8.6, 7.3, 1.7 Hz), 7.24–7.37 (m, 9H), 7.03–7.22 (m, 3H), 7.04 (d, 2H, J=8.6 Hz), 4.57 (s, 2H), 4.43 (brm, 1H), 3.88 (s, 3H), 3.75 (s, 2H), 3.54 (brm, 1H), 2.14–2.17 (brm, 4H), 1.55–1.64 (m, 4H). | 10 |
| 17 | 96 | $^1$H-NMR (DMSO-d$_6$); δ 13.90 (br, 1H), 8.44 (d, 1H, J=8.2 Hz), 7.99 (d, 1H, J=7.6 Hz), 7.82 (d, 1H, J=8.9 Hz), 7.74 (d, 1H, J=8.9 Hz), 7.27–7.37 (m, 6H), 7.22 (dd, 1H, J=8.9, 2.3 Hz), 7.11 (d, 1H, J=8.9, 23 Hz), 7.00 (d, 2H, J=8.6 Hz), 6.95 (d, 1H, J=7.3 Hz), 4.59 (d, 1H, J=3.6 Hz), 4.43 (brm, 1H), 3.62 (s, 2H), 3.56 (brm, 1H), 2.05 (brm, 2H), 1.88 (brm, 2H), 1.30–1.52 (m, 4H). | 26 |
| 18 | — | $^1$H-NMR (DMSO-d$_6$); δ 11.27 (brs, 1H), 8.50 (d, 1H, J=8.58 Hz), 7.99–7.94 (m, 3H), 7.83 (d, 1H, J=8.90 Hz), 7.76 (d, 1H, J=8.91 Hz), 7.56 (d, 1H, J=8.25, 7.59 Hz), 7.39–7.10 (m, 5H), 7.02 (d, 2H, J=8.58 Hz), 4.71 (br, 1H), 3.75 (s, 2H), 3.17 (brm, 1H), 2.06–1.91 (m, 2H), 1.78–1.60 (m, 6H). | 19 |
| 18 methyl ester | 66 | 11.07 (brs, 1H), 8.72 (d, 1H, J=8.41 Hz), 8.00 (dd, 1H, J=8.08, 1.65 Hz), 7.68–7.49 (m, 3H), 7.36–7.02 (m, 9H), 4.58 (br, 1H), 3.88 (s, 3H), 3.74 (s, 2H), 2.80 (m, 1H), 2.09–2.04 (m, 2H), 1.70–1.46 (m, 6H). | 18 |

TABLE 49

| | | | |
|---|---|---|---|
| 19 | 34 | $^1$H-NMR (DMSO-d$_6$); δ 13.58 (br, 1H), 11.27 (brs, 1H), 8.51 (d, 1H, J=8.25 Hz), 7.97–7.80 (m, 5H), 7.57 (dd, 1H, J=8.25, 7.59 Hz), 7.41 (d, 2H, J=7.26 Hz), 7.26–7.05 (m, 5H), 4.68 (br, 1H), 3.77 (s, 2H), 3.13 (brm, 1H), 2.07–2.02 (m, 2H), 1.75–1.60 (m, 6H). | 19 |
| 19 methyl ester | 71 | 11.10 (brs, 1H), 8.72 (d, 1H, J=8.58 Hz), 7.99 (dd, 1H, J=7.91, 1.65 Hz), 7.68–7.63 (m, 2H), 7.52 (dd, 1H, J=7.26, 6.92 Hz), 7.36 (d, 2H, J=8.58 Hz), 7.16–6.97 (m, 7H), 4.60 (br, 1H), 3.87 (s, 3H), 3.75 (s, 2H), 3.27 (m, 1H), 2.21–2.16 (m, 2H), 2.02 (m, 4H), 1.61 (m, 2H). | 18 |
| 20 | 42% (yield form Ex. 6) | $^1$H-NMR (DMSO-d$_6$); δ 9.87 (brs, 1H), 8.43 (d, 1H, J=8.37 Hz), 8.00 (d, 1H, J=7.83 Hz), 7.82 (d, 1H, J=9.45 Hz), 7.75 (d, 1H, J=8.91 Hz), 7.51 (d, 2H, J=7.83 Hz), 7.35 (d, 4H, J=8.37 Hz), 7.24 (m, 4H), 7.11 (d, 1H, J=9.45 Hz), 6.94 (m, 3H), 4.24 (t, 2H, J=6.48 Hz), 3.59 (s, 2H), 3.03 (t, 2H, J=6.21 Hz), 2.02 (s, 3H). | 11 |
| 20 methyl ester | — | 11.10 (brs, 1H), 8.71 (d, 1H, J=8.64 Hz), 8.23 (brs, 1H), 7.99 (d, 1H, J=8.10 Hz), 7.69–7.02 (m, 16H), 4.22 (t, 2H, J=7.02 Hz), 3.87 (s, 3H), 3.74 (s, 2H), 3.09 (t, 2H, J=7.02 Hz), 2.12 (s, 3H). | 10 |
| 21 | 87 | $^1$H-NMR (DMSO-d$_6$); δ 3.36 (3H, s), 3.74 (2H, t, J=4.6 Hz), 4.23 (2H, t, J=4.6 Hz), 7.16–7.21 (4H, m), 7.30 (1H, dd, J=8.9, 2.3 Hz), 7.38 (1H, s), 7.49 (1H, s), 7.64 (1H, t, J=8.6 Hz), 7.85 (1H, d, J=8.9 Hz), 7.90 (1H, d, J=8.9 Hz), 7.99 (2H, d, J=8.6 Hz), 8.23 (1H, d, J=7.6 Hz), 8.73 (1H, d, J=8.2 Hz), 12.21 (1H, brs). | 8 |
| 21 methyl ester | 44 | 12.00 (brs, 1H), 8.93 (d, 1H, J=8.9 Hz), 8.23–8.00 (m, 3H), 7.75 (d, 1H, J=8.9 Hz), 7.66 (d, 1H, J=8.9 Hz), 7.59 (t, 1H, J=7.9 Hz), 7.41 (d, 1H, J=2.3 Hz), 7.23–7.08 (m, 6H), 4.23 (t, 2H, J=4.7 Hz), 3.92 (s, 3H), 3.82 (t, 2H, J=4.7 Hz), 3.48 (s, 3H). | 6 |
| 22 | 82 | $^1$H-NMR (DMSO-d$_6$); δ 1.14 (3H, t, J=6.9 Hz), 3.52 (2H, q, J=6.9 Hz), 3.76 (2H, t, J=4.3 Hz), 4.20 (2H, t, J=4.3 Hz), 7.16–7.22 (4H, m), 7.31 (1H, dd, J=2.3, 8.9 Hz), 7.39 (1H, d, J=2.3 Hz), 7.57 (1H, d, J=2.6 Hz), 7.65 (1H, dt, J=1.6, 8.6 Hz), 7.81 (1H, | 8 |

TABLE 49-continued

| | | | |
|---|---|---|---|
| | | d, J=9.2 Hz), 7.90 (1H, d, J=8.9 Hz), 7.97 (2H, d, J=8.6 Hz), 8.04 (1H, dd, J=7.9, 1.7 Hz), 8.69 (1H, d, J=7.6 Hz), 12.15 (1H, s), 13.7 (1H, br s). | |

TABLE 50

| | | | |
|---|---|---|---|
| 22 methyl ester | 61 | 12.01 (brs, 1H), 8.93 (d, 1H, J=8.6 Hz), 8.10–8.01 (m, 3H), 7.76 (d, 1H, J=8.9 Hz), 7.68–7.58 (m, 2H), 7.42 (d, 1H, J=2.3 Hz), 7.25–7.09 (m, 6H), 4.26 (t, 2H, J=4.6 Hz), 3.95 (s, 3H), 3.88 (t, 2H, J=4.6 Hz), 3.65 (q, 2H, J=6.9 Hz), 1.28 (t, 3H, J=69 Hz). | 6 |
| 23 | 93 | $^1$H-NMR (DMSO-d$_6$); δ 1.51–1.61 (2H, m), 1.70 (2H, quint, J=7.4 Hz), 1.83 (2H, quint, J=7.6 Hz), 2.36 (2H, t, J=7.3 Hz), 4.10 (2H, t, J=6.6 Hz), 7.01 (1H, t, J=7.3 Hz), 7.15–7.37 (8H, m), 7.56–7.68 (m, 4H), 7.79 (1H, d, J=8.6 Hz), 7.90 (1H, d, J=8.6 Hz), 7.98 (1H, d, J=8.9 Hz), 8.05 (1H, d, J=7.9 Hz), 8.72 (1H, d, J=8.6 Hz), 9.86 (1H, s br), 12.16 (1H, s br). | 8 |
| 23 methyl ester | 89 | 12.01 (brs, 1H), 8.92 (d, 1H, J=8.1 Hz), 8.10–8.01 (m, 3H), 7.75 (d, 1H, J=8.9 Hz), 7.67–7.59 (m, 2H), 7.50 (d, 2H, J=7.9 Hz), 7.40 (t, 1H, J=2.3 Hz), 7.32 (t, 1H, J=8.3 Hz), 7.26–7.08 (m, 9H), 4.10 (t, 2H, J=6.2 Hz), 3.95 (s, 3H), 2.42 (t, 2H, J=7.3 Hz), 1.94–1.80 (m, 4H), 1.68–1.58 (m, 2H). | 6 |
| 24 | 88 | $^1$H-NMR (DMSO-d$_6$); δ 3.39 (2H, t, J=5.6 Hz), 4.06 (2H, t, J=5.6 Hz), 4.98 (2H, s), 7.09–7.16 (4H, m), 7.23–7.34 (2H, m), 7.28 (5H, s), 7.51–7.56 (2H, m), 7.75 (1H, d, J=8.1 Hz), 7.83 (1H, d, J=8.1 Hz), 7.92 (2H, d, J=8.2 Hz), 7.98 (1H, d, J=8.3 Hz), 8.63 (1H, d, J=8.2 Hz), 12.11 (1H, s br). | 8 |
| 24 methyl ester | 97 | 11.77 (s, 1H), 8.67 (d, 1H, J=7.9 Hz), 8.10–7.99 (m, 3H), 7.76 (d, 1H, J=8.9 Hz), 7.64 (d, 1H, J=2.3 Hz), 7.50–7.44 (m, 2H), 7.44–7.36 (m, 5H), 7.32–7.16 (m, 6H), 5.14 (s, 2H), 4.23 (t, 2H, J=6.0 Hz), 3.99 (s, 3H), 3.55 (dt, 2H, J=7.6, 6.0 Hz). | 6 |
| 25 | 31 | $^1$H-NMR (DMSO-d$_6$); δ 12.32 (brs, 1H), 8.70 (d, 1H, J=8.2 Hz), 8.12 (d, 1H, J=8.7 Hz), 7.99 (d, 2H, J=8.6 Hz), 7.94 (d, 1H, J=8.6 Hz), 7.82 (d, 1H, J=8.9 Hz), 7.64 (t, 1H, J=7.3 Hz), 7.56 (s, 1H), 7.40 (d, 1H, J=2.3 Hz), 7.32 (dd, 1H, J=8.9, 2.3 Hz), 7.22–7.16 (m, 4H), 4.19 (m, 2H), 3.86 (m, 4H), 3.25–3.19 (m, 6H), 2.23 (m, 2H). | 8 |
| 25 methyl ester | 94 | 12.01 (brs, 1H), 8.93 (d, 1H, J=8.6 Hz), 8.23–8.01 (m, 3H), 7.75 (d, 1H, J=8.9 Hz), 7.64 (d, 1H, J=8.9 Hz), 7.60 (t, 1H, J=7.3 Hz), 7.41 (d, 1H, J=2.3 Hz), 7.17–7.09 (m, 6H), 4.16 (t, 2H, J=6.9 Hz), 3.95 (s, 3H), 3.74 (t, 4H, J=4.6 Hz), 2.58 (t, 2H, J=6.9 Hz), 2.50 (t, 4H, J=4.6 Hz), 2.05 (tt, 2H, J=6.9, 6.9 Hz). | 6 |

TABLE 51

| | | | |
|---|---|---|---|
| 26 | 98 | $^1$H-NMR (DMSO-d$_6$); δ 8.79 (d, 1H, J=8.3 Hz), 8.14 (d, 1H, J=7.9 Hz), 8.07 (d, 2H, J=7.9 Hz), 7.99 (d, 1H, J=8.9 Hz), 7.90 (d, 1H, J=9.2 Hz), 7.74 (t, 1H, J=7.6 Hz), 7.66 (d, 1H, J=2.3 Hz), 7.48–7.39 (m, 7H), 7.27 (d, 4H, J=8.6 Hz), 5.11 (s, 2H), 4.20 (t, 2H, J=5.9 Hz), 3.31 (q, 2H, J=6.3 Hz), 2.08–2.00 (m, 2H). | 8 |
| 26 methyl ester | 66 | 12.01 (brs, 1H), 8.93 (dd, 1H, J=8.6, 1.0 Hz), 8.10–8.01 (m, 3H), 7.75 (d, 1H, J=8.9 Hz), 7.70–7.57 (m, 2H), 7.42–7.31 (m, 5H), 7.23–7.09 (m, 7H), 5.12 (s, 2H), 4.13 (t, 2H, J=6.3 Hz), 3.95 (s, 3H), 3.47 (q, 2H, J=6.6 Hz), 2.09 (t, 2H, J=6.6 Hz). | 6 |
| 27 | 68 | $^1$H-NMR (DMSO-d$_6$); δ 2.14 (quint, J=6.6 Hz, 2H), 2.62 (t, J=7.3 Hz, 2H), 4.16 (t, J=6.3 Hz, 2H), 7.11–7.22 (m, 5H), 7.30 (dd, J=2.6, 8.9 Hz, 1H), 7.39 (d, J=2.3 Hz, 1H), 7.55–7.68 (m, 3H), 7.79 (d, J=9.2 Hz, 1H), 7.89 (d, J=8.9 Hz, 1H), 7.98 (d, J=8.9 Hz, 1H), 8.04 (dd, J=1.0, 8.3 Hz, 1H), 8.49 (d, J=8.6 Hz, 1H), 8.69 (d, J=7.9 Hz, 1H), 11.18 (s, 1H), 12.15 (s, 1H), 13.4–13.8 (br, 2H). | 8 |
| 27 methyl | 82 | 12.01 (brs, 1H), 11.16 (brs, 1H), 8.92 (dd, 1H, J=8.6, 1.0 Hz), 8.75 (dd, 1H, J=8.6, 1.0 Hz), 8.10–8.00 (m, | 6 |

TABLE 51-continued

| | | | |
|---|---|---|---|
| ester methyl ester | | 4H), 7.74 (d, 1H, J=8.9 Hz), 7.66–7.52 (m, 3H), 7.41 (d, 1H, J=2.3 Hz), 7.25–7.05 (m, 7H), 4.21 (t, 2H, J=5.9 Hz), 3.95 (s, 3H), 3.88 (s, 3H), 2.73 (t, 2H, J=6.9 Hz), 2.32 (quint, 2H, J=6.3 Hz). | |
| 28 | 74 | $^1$H-NMR (DMSO-$d_6$); δ 1.93 (quint, J=5.9 Hz, 2H), 3.59 (t, J=5.9 Hz, 2H), 4.15 (t, J=6.3 Hz, 2H), 4.58 (m, 1H), 7.15–7.21 (m, 4H), 7.31 (dd, J=2.6, 8.9 Hz, 1H), 7.39 (d, J=2.0 Hz, 1H), 7.56 (d, J=2.3 Hz, 1H), 7.64 (t, J=7.6 Hz, 1H), 7.80 (d, J=9.2 Hz, 1H), 7.91 (d, J=9.2 Hz, 1H), 7.97 (d, J=8.9 Hz, 2H), 8.04 (dd, J=1.7, 7.9 Hz, 1H), 8.69 (d, J=7.6 Hz, 1H), 12.21 (br.s, 1H), 13.79 (br.s, 1H). | 8 |
| 28 methyl ester | 31 | 12.02 (brs, 1H), 8.93 (d, 1H, J=7.9 Hz), 8.09 (dd, 1H, J=7.9, 1.3 Hz), 8.04 (d, 2H, J=8.6 Hz), 7.77 (d, 1H, J=8.9 Hz), 7.67 (d, 1H, J=8.2 Hz), 7.64–7.59 (m, 1H), 7.42 (d, 1H, J=2.6 Hz), 7.24–7.10 (m, 6H), 4.27 (t, 2H, J=5.9 Hz), 3.96 (s, 3H), 3.93 (t, 2H, J=5.9 Hz), 2.14 (quint, 2H, J=5.9 Hz). | 6 |

TABLE 52

| | | | |
|---|---|---|---|
| 29 | 21 | $^1$H-NMR (DMSO-$d_6$); δ 3.15–3.50 (br, 4H), 3.50–3.70 (br, 2H), 3.80–4.00 (br, 4H), 4.50 (t-like, 2H), 7.16–7.28 (m, 4H), 7.35 (dd, J=2.6, 8.9 Hz, 1H), 7.48 (d, J=2.0 Hz, 1H), 7.59 (d, J=2.3 Hz, 1H), 7.66 (t, J=8.9 Hz, 1H), 7.86 (d, J=9.2 Hz, 1H), 7.93 (d, J=8.9 Hz, 1H), 7.98 (d, J=8.9 Hz, 2H), 8.05 (dd, J=1.7, 7.9 Hz, 1H), 8.69 (d, J=7.9 Hz, 1H), 12.14 (s, 1H). | 8 |
| 29 methyl ester | 15 | 12.02 (brs, 1H), 8.93 (dd, 1H, J=8.6, 1.0 Hz), 8.09 (dd, 1H, J=7.9, 1.7 Hz), 8.04 (d, 2H, J=8.9 Hz), 7.76 (d, 1H, J=8.9 Hz), 7.67 (d, 1H, J=8.2 Hz), 7.64–7.58 (m, 1H), 7.42 (d, 1H, J=2.3 Hz), 7.26–7.09 (m, 6H), 4.25 (t, 2H, J=5.6 Hz), 3.95 (s, 3H), 3.79–3.75 (m, 4H), 2.89 (t, 2H, J=5.6 Hz), 2.64 (t, 4H, J=4.6 Hz). | 6 |
| 30 | 82 | $^1$H-NMR (DMSO-$d_6$); δ 1.33–1.52 (6H, m), 1.76–1.82 (2H, m), 3.37–3.43 (2H, m), 4.08 (2H, t, J=6.6 Hz), 7.15–7.22 (4H, m), 7.30 (1H, dd, J=8.9, 2.3 Hz), 7.37 (1H, s), 7.55 (1H, d, J=2.3 Hz), 7.66 (1H, t, J=7.4 Hz), 7.80 (1H, d, J=9.2 Hz), 7.91 (1H, d, J=8.9 Hz), 7.98 (2H, d, J=8.9 Hz), 8.05 (1H, d, J=8.3 Hz), 8.71 (1H, d, J=8.6 Hz), 12.18 (1H, s br). | 8 |
| 31 | 71 | $^1$H-NMR (DMSO-$d_6$); δ 12.33 (brs, 1H), 8.79 (d, 1H, J=8.3 Hz), 8.14 (dd, 1H, J=7.9, 1.3 Hz), 8.07 (d, 2H, J=8.9 Hz), 7.99 (d, 1H, J=9.2 Hz), 7.90 (d, 1H, J=9.2 Hz), 7.74 (t, 1H, J=8.6 Hz), 7.66 (d, 1H, J=2.3 Hz), 7.46 (d, 1H, J=2.3 Hz), 7.41 (dd, 1H, J=8.9, 2.3 Hz), 7.27 (d, 4H, J=8.9 Hz), 7.05 (t, 1H, J=5.9 Hz), 4.18 (t, 2H, J=6.6 Hz), 3.21 (q, 2H, J=6.6 Hz), 1.99 (t, 2H, J=6.6 Hz), 1.47 (s, 9H). | 8 |
| 31 methyl ester | 100 | 12.02 (brs, 1H), 8.93 (d, 1H, J=8.9 Hz), 8.10–8.07 (m, 1H), 8.04 (d, 2H, J=8.6 Hz), 7.76 (d, 1H, J=8.9 Hz), 7.67 (d, 1H, J=9.9 Hz), 7.61 (t, 1H, J=8.9 Hz), 7.42 (d, 1H, J=2.3 Hz), 7.24–7.10 (m, 6H), 4.79 (brs, 1H), 4.15 (t, 2H, J=6.3 Hz), 3.96 (s, 3H), 3.39 (q, 2H, J=6.3 Hz), 2.10–2.05 (m, 2H), 1.46 (s, 9H). | 6 |
| 32 | 91 | $^1$H-NMR (DMSO-$d_6$); δ 1.40–1.53 (m, 2H), 1.53–1.65 (m, 2H), 1.78 (quint, J=6.3 Hz, 2H), 2.25 (t, J=7.3 Hz, 2H), 4.07 (t, J=6.3 Hz, 2H), 7.15–7.22 (m, 4H), 7.30 (dd, J=2.3, 8.9 Hz, 1H), 7.38 (d, J=2.3 Hz, 1H), 7.56 (d, J=2.3 Hz, 1H), 7.65 (t, J=8.6 Hz, 1H), 7.79 (d, J=9.2 Hz, 1H), 7.90 (d, J=8.9 Hz, 1H), 7.97 (d, J=8.9 Hz, 2H), 8.04 (dd, J=1.7, 7.9 Hz, 1H), 8.69 (d, J=8.6 Hz, 1H), 12.05 (br.s, 1H), 12.17 (s, 1H). | 8 |

TABLE 53

| | | | |
|---|---|---|---|
| 32 methyl | 67 | 12.02 (brs, 1H), 8.93 (d, 1H, J=8.3 Hz), 8.09 (dd, 1H, J=8.3, 1.7 Hz), 8.04 (d, 2H, J=8.6 Hz), 7.76 (d, | 6 |

TABLE 53-continued

| | | | |
|---|---|---|---|
| ester ethyl ester | | 1H, J=8.9 Hz), 7.68–7.58 (m, 2H), 7.42 (d, 1H, J=2.3 Hz), 7.25–7.10 (m, 6H), 4.14 (q, 2H, J=7.3 Hz), 4.09 (t, 2H, J=7.3 Hz), 3.95 (s, 3H), 2.37 (t, 2H, J=7.3 Hz), 1.89 (quint, 2H, J=7.3 Hz), 1.75 (quint, 2H, J=7.3 Hz), 1.62–1.51 (m, 2H), 1.27 (t, 3H, J=7.3 Hz). | |
| 33 | 33 | $^1$H-NMR (DMSO-$d_6$); δ 2.07 (quint, J=5.9 Hz, 2H), 2.95–3.10 (m, 2H), 4.18 (t, J=5.9 Hz, 2H), 7.15–7.23 (m, 4H), 7.33 (dd, J=2.3, 8.9 Hz, 1H), 7.38 (d, J=2.0 Hz, 1H), 7.57 (d, J=2.6 Hz, 1H), 7.61–7.64 (m, 1H), 7.82 (d, J=9.2 Hz, 1H), 7.91 (d, J=9.2 Hz, 1H), 7.98 (d, J=8.9 Hz, 2H), 8.04 (d, J=8.3 Hz, 1H), 8.69 (d, J=8.6 Hz, 1H). | 37 |
| 34 | 58 | $^1$H-NMR (DMSO-$d_6$); δ 1.13 (t, 3H, J=6.92 Hz), 3.50 (q, 2H, J=6.93 Hz), 3.69 (t, 2H, J=4.62 Hz), 3.72 (s, 2H), 4.06 (t, 2H, J=4.62 Hz), 6.91 (d, 2H, J=8.59 Hz), 6.97 (s, 4H), 7.13 (ddd, 1H, J=1.32, 7.59, 7.92 Hz), 7.32 (d, 2H, J=8.58 Hz), 7.57 (ddd, 1H, J=1.65, 6.93, 8.58 Hz), 7.95 (dd, 1H, J=1.32, 7.91 Hz), 8.50 (d, 1H, J=8.25 Hz), 11.13 (s, 1H), 13.56 (br, 1H). | 11 |
| 34 methyl ester | 103 | 11.04 (brs, 1H), 8.71 (d, 1H, J=8.58 Hz), 7.98 (dd, 1H, J=7.91, 1.65 Hz), 7.50 (ddd, 1H, J=8.58, 7.26, 1.65 Hz), 7.30 (d, 2H, J=8.58 Hz), 7.05 (ddd, 1H, J=7.92, 7.26, 0.99 Hz), 7.00–6.87 (m, 6H), 4.09 (t, 2H, J=4.62 Hz), 3.86 (s, 3H), 3.77 (t, 2H, J=4.62 Hz), 3.71 (s, 2H), 3.60 (q, 2H, J=6.91 Hz), 1.24 (t, 3H, J=6.91 Hz). | 10 |
| 35 | 58 | $^1$H-NMR (DMSO-$d_6$); δ 3.39 (s, 3H), 3.72 (s, 2H), 5.16 (s, 2H), 6.92 (d, J=8.6 Hz, 2H), 6.99 (d, J=9.2 Hz, 2H), 7.04 (d, J=9.2 Hz, 2H), 7.13 (ddd, J=6.9, 7.9 Hz, 1H), 7.33 (d, J=8.6 Hz, 2H), 7.57 (ddd, J=1.7, 6.9, 8.6 Hz, 1H), 7.95 (dd, J=1.7, 7.9 Hz, 1H), 8.50 (d, J=8.6 Hz, 1H), 11.17 (s, 1H). | 8 |
| 35 methyl ester | 86 | 11.04 (brs, 1H), 8.72 (dd, 1H, J=8.6 Hz, 1.0 Hz), 7.98 (dd, 1H, J=8.2, 1.7 Hz), 7.51 (ddd, 1H, J=8.6, 6.9, 1.7 Hz), 7.31 (d, 2H, J=8.6 Hz), 7.04 (ddd, 1H, J=8.2, 6.9, 1.0 Hz), 7.00 (d, 2H, J=6.3 Hz), 6.98 (d, 2H, J=6.3 Hz), 6.97 (d, 2H, J=8.6 Hz), 5.13 (s, 2H), 3.86 (s, 3H), 3.72 (s, 2H), 3.48 (s, 3H). | 6 |

TABLE 54

| | | | |
|---|---|---|---|
| 36 | 39 | 1.91–2.13 (m, 4H), 2.76 (s, 3H), 2.94–3.33 (m, 4H), 3.73 (s, 2H), 4.62 (br, 1H), 6.93 (d, J=8.6 Hz, 2H), 6.99 (d, J=9.2 Hz, 2H), 7.04 (d, J=9.2 Hz, 2H), 7.13 (dd, J=6.9, 8.3 Hz, 1H), 7.34 (d, J=8.6 Hz, 2H), 7.56 (ddd, J=1.3, 6.9, 8.3 Hz, 1H), 7.95 (dd, J=1.3, 8.3 Hz, 1H), 8.50 (d, J=8.3 Hz, 1H). | 11 |
| 36 methyl ester | 100 | 11.04 (brs, 1H), 8.72 (d, 1H, J=8.6 Hz), 7.99 (dd, 1H, J=7.9, 1.7 Hz), 7.52 (ddd, 1H, J=8.6, 7.3, 1.7 Hz), 7.31 (d, 2H, J=8.6 Hz), 7.06 (dd, 1H, J=7.9, 7.3 Hz), 6.97 (d, 2H, J=9.2 Hz), 6.96 (d, 2H, J=8.6 Hz), 6.87 (d, 2H, J=9.2 Hz), 4.16–4.26 (m, 1H), 3.87 (s, 3H), 3.72 (s, 2H), 2.54–2.70 (m, 2H), 2.30 (s, 3H), 1.96–2.03 (m, 2H), 1.77–1.90 (m, 2H), 1.23–1.30 (m, 2H). | 10 |
| 37 | 58 yield from Ex. 6 | $^1$H-NMR (DMSO-$d_6$); δ 3.71 (s, 2H), 5.16 (s, 2H), 6.90 (d, 2H, J=8.24 Hz), 7.02 (d, 2H, J=4.95 Hz), 7.02 (d, 2H, J=4.95 Hz), 7.11 (dd, 1H, J=6.93, 7.92 Hz), 7.32 (d, 2H, J=8.56 Hz), 7.43 (d, 2H, J=5.61 Hz), 7.56 (dd, 1H, J=6.93, 8.58 Hz), 7.94 (d, 1H, J=7.59 Hz), 8.49 (d, 1H, J=8.25 Hz), 8.57 (d, 2H, J=5.93 Hz), 11.17 (br, 1H). | 11 |
| 37 methyl ester | 100 | 11.07 (br, 1H), 8.73 (d, 1H, J=8.58 Hz), 8.58 (d, 2H, J=5.94 Hz), 7.97 (dd, 1H, J=8.24, 1.65 Hz), 7.71–7.30 (m, 5H), 7.05–6.89 (m, 7H), 5.03 (s, 2H), 3.83 (s, 3H), 3.71 (s, 2H). | 10 |
| 38 | 50 | $^1$H-NMR (DMSO-$d_6$); δ 3.34 (br, 4H), 3.53 (t, 2H, J=4.95 Hz), 3.72 (s, 2H), 3.87 (br, 4H), 4.37 (t, 2H, J=4.95 Hz), 6.91 (d, 2H, J= | 11 |

TABLE 54-continued

| | | | |
|---|---|---|---|
| | | 8.58 Hz), 7.03 (s, 4H), 7.13 (ddd, 1H, J= 1.32, 7.26, 7.59 Hz), 7.33 (d, 2H, J=8.91 Hz), 7.57 (ddd, 1H, J=1.32, 7.26, 8.58 Hz), 7.95 (dd, 1H, J=1.65, 7.91 Hz), 8.49 (d, 1H, J=7.59 Hz), 11.11 (s, 1H). | |
| 38 methyl ester | 72 | 11.04 (brs, 1H), 8.72 (d, 1H, J=8.58 Hz), 7.99 (dd, 1H, J=7.91, 1.32 Hz), 7.51 (ddd, 1H, J=8.58, 7.25, 1.32 Hz), 7.31 (d, 2H, J=8.58 Hz), 7.05 (dd, 1H, J=7.91, 7.59 Hz), 7.00–6.85 (m, 6H), 4.08 (t, 2H, J=5.94 Hz, 2H), 3.87 (s, 3H), 3.73 (t, 4H, J=4.52 Hz), 3.72 (s, 2H), 2.79 (t, 2H, J=5.94 Hz), 2.58 (t, 4H, J=4.62 Hz). | 10 |
| 39 | 40 | $^1$H-NMR (DMSO-d$_6$); δ 2.16 (br, 4H), 3.41 (br, 4H), 3.65 (t, 2H, J=4.62 Hz), 3.82 (s, 2H), 4.40 (t, 2H, J=4.97 Hz), 7.01 (d, 2H, J=8.58 Hz), 7.12 (s, 4H), 7.22 (dd, 2H, J=7.26, 8.54 Hz), 7.43 (d, 2H, J=8.58 Hz), 7.66 (dd, 1H, J=7.26, 8.24 Hz), 8.04 (d, 1H, J=7.92 Hz), 8.58 (d, 1H, J=8.25 Hz), 11.26 (s, 1H). | 11 |

TABLE 55

| | | | |
|---|---|---|---|
| 39 methyl ester | 63 | 11.03 (brs, 1H), 8.71 (dd, 1H, J=8.58, 0.99 Hz), 7.99 (dd, 1H, J=8.25, 1.65 Hz), 7.52 (m, 1H), 7.31 (d, 2H, J=8.59 Hz), 7.06 (m, 1H), 7.01–6.85 (m, 6H), 4.09 (t, 2H, J=5.94 Hz), 3.87 (s, 3H), 3.72 (s, 2H), 2.91 (t, 2H, J=5.94 Hz), 2.65 (br, 4H), 1.82 (t, 4H, J=3.63 Hz). | 10 |
| 40 | 50 | $^1$H-NMR (DMSO-d$_6$); δ 1.39–1.41 (m, 2H), 1.51–1.55 (m, 4H), 2.50–2.53 (m, 4H), 2.74 (t, J=5.9 Hz, 2H), 3.56 (s, 2H), 4.07 (t, J=5.9 Hz, 2H), 6.86 (d, J=8.6 Hz, 2H), 6.91–6.97 (m, 5H), 7.24–7.28 (m, 2H), 7.30 (d, J=8.6 Hz, 2H), 8.00 (dd, J=1.7, 7.6 Hz, 1H), 8.42 (d, J=8.3 Hz, 1H), 11.20 (s, 1H). | 11 |
| 40 methyl ester | 69 | 11.04 (brs, 1H), 8.72 (d, 1H, J=8.3 Hz), 7.98 (dd, 1H, J=8.3 Hz, 1.3 Hz), 7.51 (ddd, 1H, J=8.3, 7.3, 1.3 Hz), 7.30 (d, 2H, J=8.6 Hz), 7.05 (dd, 1H, J=8.3, 7.3 Hz), 6.97 (d, 2H, J=9.2 Hz), 6.95 (d, 2H, J=8.6 Hz), 6.87 (d, 2H, J=9.2 Hz), 4.08 (t, 2H, J=6.3 Hz), 3.87 (s, 3H), 3.72 (s, 2H), 2.76 (t, 2H, J=6.3 Hz), 2.51–2.52 (m, 4H), 1.54–1.64 (m, 6H). | 10 |
| 41 | 15 | $^1$H-NMR (DMSO-d$_6$); δ 2.82 (s, 3H), 3.50 (br, 10H), 3.73 (s, 2H), 4.33 (br, 2H), 6.91 (d, J=8.6 Hz, 2H), 7.03 (s, 4H), 7.14 (dd, J=7.3, 7.9 Hz, 1H), 7.34 (d, J=8.6 Hz, 2H), 7.57 (dd, J=7.3, 8.6 Hz, 1H), 7.95 (d, J=7.9 Hz, 1H), 8.50 (d, J=8.6 Hz, 1H), 11.12 (s, 1H). | 8 |
| 41 methyl ester | 38 | 11.04 (brs, 1H), 8.71 (dd, 1H, J=8.6, 0.7 Hz), 7.99 (dd, 1H, J=7.9, 1.7 Hz), 7.52 (ddd, 1H, J=8.6, 8.3, 1.7 Hz), 7.31 (d, 2H, J=8.9 Hz), 7.07 (dd, 1H, J=8.3, 7.9, 0.7 Hz), 6.98 (d, 2H, J=7.3 Hz), 6.95 (d, 2H, J=7.3 Hz), 6.86 (d, 2H, J=8.9 Hz), 4.08 (t, 2H, J=5.9 Hz), 3.88 (s, 3H), 3.72 (S, 2H), 2.82 (t, 2H, J=5.9 Hz), 2.64 (br, 4H), 2.51 (br, 4H), 2.31 (s, 3H). | 6 |
| 42 | | $^1$H-NMR (DMSO-d$_6$); δ 1.43–1.56 (m, 6H), 3.40 (brm, 4H), 3.57 (s, 2H), 4.76 (s, 2H), 6.86–6.99 (m, 7H), 7.24–7.32 (m, 3H), 8.00 (dd, J=1.7, 7.6 Hz, 1H), 8.42 (d, J=7.9 Hz, 1H), 14.13 (brs, 1H). | 30 |
| 42 methyl ester | 67 | 11.04 (brs, 1H), 8.71 (dd, 1H, J=8.6, 1.0 Hz), 7.99 (dd, 1H, J=7.9, 1.7 Hz), 7.52 (ddd, 1H, J=8.6, 7.3, 1.7 Hz), 7.31 (dd, 2H, J=8.6, 2.0 Hz), 7.06 (ddd, 1H, J=7.9, 7.3, 1.0 Hz), 6.98 (d, 2H, J=9.2, 2.6 Hz), 6.96 (dd, 2H, J=9.2, 2.6 Hz), 6.92 (d, 2H, J=8.6, 2.0 Hz), 4.66 (s, 2H), 3.87 (s, 3H), 3.72 (s, 2H), 3.55–3.58 (br, 2H), 3.46–3.50 (br, 2H), 1.57–1.68 (br, 6H). | 29 |

TABLE 56

| | | | |
|---|---|---|---|
| 43 | 37 | $^1$H-NMR (DMSO-d$_6$); δ 3.72 (2H, s), 4.30 (4H, s), 6.91 (2H, d, J=8.6 Hz), 6.92–7.01 (8H, m), 7.12 (1H, dd, J=7.9, 7.3 Hz), 7.30 (1H, t, J=7.3 Hz), 7.32 (2H, d, J=8.6 Hz), 7.56 (1H, ddd, J=8.6, 7.3, 1.7 Hz), 7.95 (1H, dd, J=7.9, 1.7 Hz), 8.50 (1H, d, J=8.6 Hz), 11.24 (1H, brs), 13.50–13.60 (1H, br). | 11 |
| 43 methyl ester | 68 | 11.04 (brs, 1H), 8.71 (dd, 1H, J=8.6, 1.0 Hz), 7.99 (dd, 1H, J=8.2, 1.7 Hz), 7.52 (ddd, 1H, J=8.6, 7.3, 1.7 Hz), 7.25–7.33 (m, 4H), 7.06 (ddd, 1H, J=8.2, 7.3, 1.0 Hz), 6.90–7.02 (m, 9H), 4.31 (s, 4H), 3.87 (S, 3H), 3.72 (S, 2H). | 10 |
| 44 | 44 Yield from Ex. 6 | $^1$H-NMR (DMSO-d$_6$); δ 1.59 (m, 2H), 1.92 (m, 2H), 3.46 (m, 2H), 3.58 (s, 2H), 3.86 (m, 2H), 4.48 (m, 1H), 6.88 (d, 2H, J=8.58 Hz), 6.92 (m, 1H), 6.95 (s, 4H), 7.26 (m, 2H), 7.30 (d, 2H, J=8.25 Hz), 8.01 (dd, 1H, J=1.65, 7.92 Hz), 8.43 (d, 1H, J=8.24 Hz), 13.84 (br, 1H). | 11 |
| 44 methyl ester | — | 11.04 (brs, 1H), 8.70 (d, 1H, J=8.58 Hz), 7.99 (dd, 1H, J=7.91, 1.65 Hz), 7.52 (ddd, 1H, J=8.57, 7.26, 1.65 Hz), 7.31 (d, 2H, J=8.25 Hz), 7.06 (ddd, 1H, J=8.25, 7.25, 0.99 Hz), 6.99–6.91 (m, 4H), 6.88 (d, 2H, J=9.24 Hz), 4.40 (quint, 1H, J=3.96 Hz), 3.97 (m, 2H), 3.87 (s, 3H), 3.72 (s, 2H), 3.56 (m, 2H), 2.06–1.96 (m, 2H), 1.84–1.72 (m, 2H). | 10 |
| 45 | 70 | $^1$H-NMR (DMSO-d$_6$); δ 11.15 (brs, 1H), 9.85 (s, 1H), 8.50 (d, 1H, J=8.57 Hz), 7.79 (dd, 1H, J=7.91, 1.48 Hz), 7.56 (dd, 1H, J=7.09, 6.76 Hz), 7.49 (d, 2H, J=8.24 Hz), 7.31 (d, 2H, J=8.57 Hz), 7.22 (d, 2H, J=8.24 Hz), 7.12 (dd, 1H, J=8.08, 7.09 Hz), 6.95 (s, 4H), 6.89 (d, 2H, J=8.57 Hz), 4.12 (t, 2H, J=6.76 Hz), 3.71 (s, 2H), 2.96 (t, 2H, J=6.76 Hz), 2.01 (s, 3H). | 11 |
| 45 methyl ester | 79 | 11.03 (brs, 1H), 8.69 (dd, 1H, J=8.64, 1.08 Hz), 7.97 (dd, 1H, J=8.10, 1.62 Hz), 7.67–7.42 (m, 4H), 7.29 (d, 2H, J=8.64 Hz), 7.21 (d, 2H, J=8.37 Hz), 7.05 (ddd, J=8.10, 7.29, 1.08 Hz), 6.97–6.80 (m, 5H), 4.10 (t, 2H, J=7.02 Hz), 3.86 (s, 3H), 3.71 (s, 2H), 3.03 (t, 2H, J=7.02 Hz), 2.14 (s, 3H). | 10 |
| 47 | 55 Yield from Ex 6 | $^1$H-NMR (DMSO-d$_6$); δ 2.61 (s, 6H), 3.15 (t, 2H, J=4.95 Hz), 3.60 (s, 2H), 4.20 (t, 2H, J=5.28 Hz), 6.87 (d, 2H, J=7.92 Hz), 6.98–7.02 (m, 5H), 7.28–7.39 (m, 3H), 7.95 (d, 1H, J=6.92 Hz), 8.44 (d, 1H, J=8.25 Hz), 13.11 (br, 1H). | 11 |

TABLE 57

| | | | |
|---|---|---|---|
| 47 methyl ester | — | 11.03 (br, 1H), 8.71 (dd, 1H, J=8.58, 0.99 Hz), 7.98 (dd, 1H, J=8.24, 1.65 Hz), 7.51 (ddd, 1H, J=8.58, 7.25, 1.65 Hz), 7.31 (d, 2H, J=8.58 Hz), 7.05 (ddd, 1H, J=8.24, 7.26, 0.99 Hz), 7.01–6.86 (m, 6H), 4.04 (t, 2H, J=5.61 Hz), 3.87 (s, 3H), 3.72 (s, 2H), 2.73 (t, 2H, J=5.61 Hz), 2.34 (s, 6H). | 10 |
| 89 | 32 | $^1$H-NMR (DMSO-d$_6$); δ 3.35 (s, 6H), 4.12 (t, 2H, J=4.29 Hz), 4.54 (t, 2H, J=4.62 Hz), 7.09–7.25 (m, 7H), 7.68 (dd, 1H, J=7.25, 7.53 Hz), 7.98 (d, 2H, J=8.56 Hz), 8.08 (d, 1H, J=7.91 Hz), 8.71 (d, 1H, J=8.26 Hz), 12.20 (s, 1H). | 11 |
| 89 methyl ester | 105 | 11.98 (brs, 1H), 8.91 (d, 1H, J=8.57 Hz), 8.06 (dd, 1H, J=7.92, 1.65 Hz), 8.00 (d, 2H, J=8.57 Hz), 7.59 (ddd, 1H, J=8.58, 7.26, 1.65 Hz), 7.09 (dd, 1H, J=7.59, 7.58 Hz), 7.03–6.92 (m, 6H), 4.07 (t, 2H, J=5.61 Hz), 3.94 (s, 3H), 2.75 (t, 2H, J=5.61 Hz), 2.36 (s, 6H). | 10 |
| 90 | 54 | $^1$H-NMR (DMSO-d$_6$); δ 12.37 (s, 1H), 8.78 (d, 1H, J=8.58 Hz), 8.14 (d, 1H, J=7.91 Hz), 8.04 (d, 2H, J=8.58 Hz), 7.73 (dd, 1H, J=8.58, 6.93 Hz), 7.28 (dd, 1H, J=7.92, 7.59 Hz), 7.23–7.14 (m, 6H), 4.36 (t, 2H, J=4.95 Hz), 3.84 (t, 4H, J=4.95 Hz), 3.26 (br, 2H), 3.04 (br, 4H). | 11 |

TABLE 57-continued

| | | | |
|---|---|---|---|
| 90 methyl ester | 83 | 11.98 (s, 1H), 8.92 (d, 1H, J=8.24 Hz), 8.06 (dd, 1H, J=7.91, 1.32 Hz), 8.00 (d, 2H, J=8.56 Hz), 7.59 (ddd, 1H, J=8.58, 7.26, 1.32 Hz), 7.10 (dd, 1H, J=7.92, 7.25 Hz), 7.04–6.91 (m, 6H), 4.11 (t, 2H, J=5.62 Hz), 3.94 (s, 3H), 3.75 (t, 4H, J=4.62 Hz), 2.82 (t, 2H, J=5.62 Hz), 2.59 (t, 4H, J=4.62 Hz). | 10 |
| 91 | 13 yield from Ex. 6 | ¹H-NMR (DMSO-d₆); δ 3.20–3.90 (br, 10H), 4.48 (s, 2H), 7.15–7.32 (m, 7H), 7.74 (t, 1H, J=7.26 Hz), 8.04 (d, 2H, J=8.91 Hz), 8.14 (dd, 1H, J=1.32, 7.92 Hz), 8.78 (d, 1H, J=7.92 Hz), 9.61 (br, 1H), 12.19 (s, 1H). | 11 |
| 92 | 50 | ¹H-NMR (DMSO-d₆); δ 1.96 (br, 4H), 2.80–3.80 (br, 4H), 3.58 (t, 2H, J=4.94 Hz), 4.35 (t, 2H, J=4.94 Hz), 7.06–7.21 (m, 7H), 7.64 (ddd, 1H, J=1.65, 7.26, 8.24 Hz), 7.95 (d, 2H, J=8.90 Hz), 8.05 (dd, 1H, J=1.65, 8.25 Hz), 8.69 (d, 1H, J=7.92 Hz), 10.55 (br, 1H), 12.24 (s, 1H). | 11 |

TABLE 58

| | | | |
|---|---|---|---|
| 92 methyl ester | 54 | 11.98 (brs; 1H), 8.92 (d, 1H, J=8.26 Hz), 8.06 (dd, 1H, J=7.91, 1.32 Hz), 8.00 (d, 1H, J=8.91 Hz), 7.58 (dd, 1H, J=7.26, 6.93 Hz), 7.09 (dd, 1H, J=7.91, 7.59 Hz), 7.04–6.92 (m, 6H), 4.11 (t, 2H, J=5.94 Hz), 3.94 (s, 3H), 2.91 (t, 2H, J=5.94 Hz), 2.64 (brm, 4H), 1.82 (brm, 4H). | 10 |
| 93 | 31 | ¹H-NMR (DMSO-d₆); δ 1.42–1.83 (br, 6H), 3.03 (br, 2H), 3.33 (br, 2H), 3.48 (br, 2H), 4.42 (t, J=5.0 Hz, 2H), 7.08 (d, J=8.6 Hz, 2H), 7.09 (d, J=8.9 Hz, 2H), 7.14 (d, J=8.9 Hz, 2H), 7.19 (dd, J=7.6, 8.6 Hz, 1H), 7.65 (ddd, J=1.3, 7.6, 7.9 Hz, 1H), 7.95 (d, J=8.6 Hz, 2H), 8.06 (dd, J=1.3, 7.9 Hz, 1H), 8.70 (d, J=8.6 Hz, 1H), 10.37 (br, 1H) 12.15 (s, 1H), 13.76 (br, 1H). | 11 |
| 93 methyl ester | 100 | 11.98 (s, 1H), 8.92 (d, 1H, J=8.6 Hz), 8.06 (dd, 1H, J=8.2, 1.7 Hz), 8.00 (d, 2H, J=8.9 Hz), 7.58 (ddd, 1H, J=8.6, 7.3, 1.7 Hz), 7.09 (dd, 1H, J=8.2, 7.3 Hz), 6.99–7.03 (m, 4H), 6.93 (d, 2H, J=9.2 Hz), 4.10 (t, 2H, J=5.9 Hz), 3.94 (S, 3H), 2.78 (t, 2H, J=5.9 Hz), 2.50–2.54 (m, 4H), 1.54–1.64 (m, 4H), 1.42–1.52 (m, 2H). | 10 |
| 94 | 100 | ¹H-NMR (DMSO-d₆); δ 2.83 (s, 3H), 3.46 (br, 12H), 4.37 (br, 2H), 7.06–7.14 (m, 6H), 7.19 (dd, J=7.9, 8.6 Hz, 1H), 7.66 (dd, J=7.3, 8.6 Hz, 1H), 7.95 (d, J=8.9 Hz, 2H), 8.06 (dd, J=1.7, 7.9 Hz, 1H), 8.70 (d, J=7.3 Hz, 1H), 12.12 (s, 1H). | 8 |
| 94 methyl ester | 54 | 11.98 (brs, 1H), 8.91 (d, 1H, J=8.2 Hz), 8.06 (dd, 1H, J=8.2, 1.7 Hz), 8.00 (d, 2H, J=8.9 Hz), 7.59 (ddd, 1H, J=8.2, 7.3, 1.7 Hz), 7.10 (dd, 1H, J=8.2, 7.3 Hz), 7.00–7.03 (m, 4H), 6.93 (d, 2H, J=9.2 Hz), 4.11 (t, 2H, J=5.9 Hz), 3.94 (S, 3H), 2.84 (t, 2H, J=5.9 Hz), 2.65 (br, 4H), 2.52, (br, 4H), 2.32 (s, 3H). | 6 |
| 121 | 98 | ¹H-NMR (DMSO-d₆); δ 11.20 (s, 1H), 8.57 (d, 1H, J=8.4 Hz), 7.99 (d, 1H, J=7.6 Hz), 7.87–7.90 (m, 2H), 7.75 (d, 1H, J=6.8 Hz), 7.54–7.65 (m, 4H), 7.35 (d, 2H, J=8.4 Hz), 7.13 (t, 1H, J=7.6 Hz), 6.92–6.99 (m, 6H), 4.33 (brs, 1H), 3.74 (s, 2H), 3.14 (br, 1H), 1.71–1.82 (brm, 2H), 1.45–1.61 (brm, 6H). | 21 |
| 121 methyl ester | 60 | 11.04 (brs, 1H), 8.71 (d, 1H, J=7.3 Hz), 8.00 (dd, 1H, J=7.8, 1.4 Hz), 7.90 (dd, 2H, J=8.1, 1.4 Hz), 7.49–7.58 (m, 4H), 7.23–7.32 (m, 3H), 7.07 (ddd, 1H, J=8.1, 7.3, 1.4 Hz), 6.93–6.96 (m, 4H), 6.80–6.87 (d, 2H, J=92 Hz), 4.47 (d, 1H, J=7.6 Hz), 4.31 (br, 1H), 3.88 (s, 3H), 3.72 (s, 2H), 3.31 (brm, 1H), 1.90–1.93 (m, 2H), 1.58–1.66 (m, 6H). | 21 |

TABLE 59

| | | | |
|---|---|---|---|
| 124 | 93 | ¹H-NMR (DMSO-d₆); δ 11.20(s, 1H), 8.56(d, 1H, J=8.4 Hz), 8.04(d, 1H, J=0.8Hz), 7.96–7.99(m, 2H), 7.80–7.85(m, 2H), 7.56(dd, 1H, J=7.8, 7.6Hz), 7.34(d, 2H, J=8.4Hz), 7.13(dd, 1H, J=8.4, 7.6Hz), 6.92–6.99(m, 6H), 4.36(brs, 1H), 3.74(s, 2H), 3.20(br, 1H), 1.80–1.84(brm, 2H), 1.50–1.60(brm, 6H). | 21 |
| 124 methyl ester | 44 | 11.05(brs, 1H), 8.71(d, 1H, J=8.4Hz), 7.96–8.01(m, 2H), 7.71(dd, 1H, J=8.4, 1.9Hz), 7.59(d, 1H, J=8.4Hz), 7.52(ddd, 1H, J=8.4, 7.3, 1.9Hz); 7.30(d, 2H, J=8.4Hz), 7.07(ddd, 1H, J=7.8, 7.3, 1.1Hz), 6.94–6.97(m, 4H), 6.82(d, 2H, J=9.2Hz), 4.61(d, 1H, J=7.8Hz), 4.34(br, 1H), 3.88(s, 3H), 3.72(s, 2H), 3.29(brm, 1H), 1.94–1.98(m, 2H), 1.58–1.69(m, 6H). | 21 |
| 207 | 82 | ¹H-NMR (DMSO-d₆); δ 13.56(br, 1H), 11.13(s, 1H), 8.51(d, 1H, J=8.4Hz), 7.95(dd, 1H, J=7.8, 1.6Hz), 7.86(d, 1H, J=7.3Hz), 7.47–7.71(m, 5H), 7.33(dd, 2H, J=8.4Hz), 7.13(dd, 1H, J=7.8, 7.3Hz), 6.90–6.97(m, 6H), 4.35(brs, 1H), 3.72(s, 2H), 3.16(br, 1H), 1.78(brm, 2H), 1.45–1.58(brm, 6H). | 21 |
| 207 methyl ester | 77 | 11.05(brs, 1H), 8.71(d, 1H, J=8.4Hz), 7.99(dd, 1H, J=8.1, 1.6Hz), 7.70(d, 1H, J=7.8Hz), 7.46–7.63(m, 3H), 7.24–7.32(m, 4H), 7.07(dd; 1H, J=8.1, 7.3Hz), 6.93–6.97(m, 4H), 6.82(d, 2H, J=9.2Hz), 4.32(br, 1H), 3.87(s, 3H), 3.72(s, 2H), 3.28–3.36(m, 1H), 1.93–1.96(m, 2H), 1.55–1.68(m, 6H). | 21 |
| 214 | 77 | ¹H-NMR (DMSO-d₆); δ 13.54(br, 1H), 11.13(s, 1H), 8.51(d, 1H, J=8.4Hz), 7.94–8.07(m, 6H), 7.57(ddd, 1H, J=8.4, 7.3, 1.4Hz), 7.32(d, 2H, J=8.4Hz), 7.13(dd, 1H, J=7.8, 7.3Hz), 6.90–6.98(m, 6H), 4.35(brs, 1H), 3.73(s, 2H), 3.18(br, 1H), 1.79–1.80(brm, 2H), 1.46–1.59(m, 6H). | 21 |
| 214 methyl ester | 90 | 11.05(s, 1H), 8.71(dd, 1H, J=8.4, 0.8Hz), 8.03(d, 2H, J=8.4Hz), 7.99(d, 1H, J=8.1, 1.4Hz), 7.77(d, 2H, J=8.4 Hz); 7.52(ddd, 1H, J=8.4, 7.3, 1.4Hz), 7.31(d, 2H, J=8.9 Hz), 7.07(ddd, 1H, J=8.1, 7.3, 0.8Hz), 6.91–7.04(m, 4H), 6.81(d, 2H, J=6.8Hz), 4.93(d, 1H, J=7.6Hz), 4.32(br, 1H), 3.87(s, 3H), 3.73(s, 2H), 3.27–3.33(m, 1H), 1.93–1.97(m, 2H), 1.57–1.69(m, 6H). | 21 |

TABLE 60

| | | | |
|---|---|---|---|
| 215 | 80 | ¹H-NMR (DMSO-d₆); δ 8.49(d, 1H, J=8.1Hz), 7.97(s, 1H), 7.96(d, 2H, J=8.6Hz), 7.87(d, 1H, J=7.0Hz), 7.58(d, 2H, J=8.6Hz), 7.51–7.57(m, 1H), 7.32(d, 2H, J=8.6Hz), 7.11(dd, 1H, J=8.1, 7.3Hz), 6.89–6.97(m, 6H), 4.34(br, 1H), 3.70(s, 2H), 3.15(br, 1H), 1.79(brm, 2H), 1.45–1.58(m, 6H). | 21 |
| 215 methyl ester | 93 | 11.05(s, 1H), 8.71(d, 1H, J=8.4Hz), 8.11(d, 1H, J=7.0 Hz), 7.95–8.01(m, 3H), 7.51(ddd, 1H, J=8.4, 7.3, 1.6Hz), 7.43(d, 1H, J=8.6Hz), 7.32(d, 2H, J=8.9Hz), 7.31(d, 2H, J=8.4Hz), 7.06(dd, 1H, J=7.3, 7.0Hz) 6.88–6.93(m, 4H), 6.81(d, 2H, J=8.9Hz), 5.21(d, 1H, J=7.6Hz), 4.31(br, 1H), 3.86(s, 3H), 3.73(s, 2H), 3.27–3.33(m, 1H), 1.92–1.97(m, 2H), 1.57–1.71(m, 6H). | 21 |
| 217 methyl ester | 88 | 11.05(brs, 1H), 8.70(dd, 1H, J=8.3, 0.9Hz), 8.21(t, 1H, J=1.4Hz), 8.13(ddd, 1H, J=7.8, 1.6, 1.4Hz), 7.99(dd, 1H, J=8.1, 1.6Hz), 7.83(ddd, 1H, J=8.1, 1.6, 1.4Hz), 7.64(dd, 1H J=8.1, 7.8Hz), 7.51(ddd, 1H, J=8.3, 7.3, 1.6Hz), 7.31(d, 2H, J=8.3Hz), 7.06(ddd, 1H, J=8.1, 7.3, 0.9Hz), 6.92–6.97(m, 4H), 6.81(d, 2H, J=7.0Hz), 5.32(d, 1H, J=7.6Hz), 4.32(brs, 1H), 3.87(s, 3H), 3.73(s, 2H), 3.26–3.39(m, 1H), 1.93–1.98(m, 1H), 1.57–1.67(m, 6H). | 21 |
| 410 | 37 | ¹H-NMR (DMSO-d₆); δ 11.13(s, 1H), 8.45(d, 1H, J=8.57 Hz), 8.08(s, 1H), 7.96(d, 1H, J=7.92Hz), 7.81(d, 1H, J=8.25Hz), 7.57(dd, 1H, J=7.59, 7.92Hz), 7.18–7.03(m, 5H), 6.97(d, 1H, J=8.25Hz), 4.39–4.37(m, 2H), 4.00–3.70(brm, 4H), 3.80–3.77(m, 2H), 3.60–3.49(m, 2H), 3.32(br, 4H). | 11 |
| 410 methyl ester | 44 | 11.17(brs, 1H), 8.68(d, 1H, J=8.58Hz), 8.16(d, 1H, J=2.31Hz), 8.01(dd, 1H, J=1.32, 7.92Hz), 7.71(dd, 1H, J=2.31, 8.58Hz), 7.53(ddd, 1H, J=1.32, 7.26, 8.58Hz), 7.11–7.05(m, 3H), 6.93–6.87(m, 3H), 4.12(t, 2H, J=5.61 Hz), 3.89(s, 3H), 3.76–3.73(m, 4H), 3.70(s, 2H), 2.82(t, 2H, J=5.61Hz), 2.61–2.58(m, 4H). | 10 |
| 411 | 45 | ¹H-NMR (DMSO-d₆); δ 14.13(br, 1H), 8.41(d, 1H, J=8.25Hz), 8.06(d, 1H, J=2.31Hz), 8.00(dd, 1H, J=1.65, 7.92Hz), 7.79(dd, 1H, J=2.31, 8.58Hz), 7.70(d, 1H, J=1.65Hz), 7.28(ddd, 1H, J=1.65, 7.26, 8.25Hz), 7.04(s, 4H), 6.98–6.92(m, 2H), 6.59(d, 1H, J=3.30 Hz), 6.48(dd, 1H, J=1.98, 2.97Hz), 5.05(s, 2H), 3.62(s, 2H). | 11 |

TABLE 61

| | | | |
|---|---|---|---|
| 411 methyl ester | 50 | 11.17(brs, 1H), 8.68(d, 1H, J=8.25Hz), 8.16(d, 1H, J=1.98Hz), 8.00(dd, 1H, J=1.32, 7.92Hz), 7.72(dd, 1H, J=2.31, 8.58Hz), 7.53(ddd, 1H, J=1.65, 7.25, 8.58Hz), 7.45(dd, 1H, J=0.99, 1.98Hz), 7.13–6.97(m, 5H), 6.88(d, 1H, J=8.58Hz), 6.43(d, 1H, J=2.97Hz), 6.38(dd, 1H, J=1.98, 2.97Hz), 4.99(s, 2H), 3.89(s, 3H), 3.70(s, 2H). | 10 |
| 412 | 15 | ¹H-NMR (DMSO-d₆); δ 11.32(brs, 1H), 8.69(brs, 1H), 8.56(brs, 1H), 8.45(d, 1H, J=8.25Hz), 8.09(s, 1H), 7.96(d, 1H, J=7.92Hz), 7.89(d, 1H, J=7.92Hz), 7.81(d, 1H, J=8.58Hz), 7.63–7.52(m, 2H), 7.44(dd, 1H, J=7.25, 7.59 Hz), 7.16–7.07(m, 5H), 6.96(d, 1H, J=8.58Hz), 5.16(s, 2H), 3.76(s, 2H). | 11 |
| 413 | 35 | ¹H-NMR (DMSO-d₆); δ 14.00–13.00(br, 1H), 11.90–11.30(br, 1H), 11.12(brs, 1H), 8.45(d, 1H, J=8.25 Hz), 8.08(s, 1H), 7.95(d; 1H, J=7.92Hz), 7.81(d, 1H, J=8.25Hz), 7.58(dd, 1H, J=7.59, 7.92Hz), 7.18–6.96(m, 6H), 4.39(s, 2H), 3.77–3.44(br, 12H), 2.83(s, 3H). | 11 |
| 413 methyl ester | 72 | 11.17(brs, 1H), 8.68(d, 1H, J=8.58Hz), 8.16(d, 1H, J=2.64Hz), 8.01(dd, 1H; J=1.65, 7.92Hz), 7.71(dd, 1H, J=2.64, 8.58Hz), 7.53(ddd, 1H, J=1.65, 7.26, 8.57Hz), 7.11–7.04(m, 3H), 6.94–6.86(m, 3H), 4.10(t, 2H, J=5.61 Hz), 3.89(s, 3H), 3.70(s, 2H), 2.82(t, 2H, J=5.61Hz), 2.63(br, 4H), 2.49(br, 4H), 2.30(s, 3H). | 10 |
| 414 | 56 | ¹H-NMR (DMSO-d₆); δ 13.90–13.30(br, 1H), 11.16(s, 1H), 10.12–9.71(br, 1H), 8.45(d, 1H, J=8.25Hz), 8.08(d, 1H, J=2.31Hz), 7.96(d, 1H, J=7.92Hz), 7.82(dd, 1H, J=2.31, 8.25Hz), 7.57(dd, 1H, J=7.26, 8.58Hz), 7.17–6.96(m, 6H), 4.38(brt, 2H, J=4.95Hz), 3.77(s, 2H), 3.58–3.38(brm, 4H), 3.15–2.86(m, 2H), 1.87–1.28(m, 6H). | 11 |
| 414 methyl ester | 72 | 11.16(brs, 1H), 8.68(d, 1H, J=8.58Hz), 8.16(d, 1H, J=2.64Hz), 8.00(dd, 1H, J=1.65, 7.92Hz), 7.71(dd, 1H, J=2.64, 8.58Hz), 7.52(ddd, 1H, J=1.65, 7.26, 8.91Hz), 7.10–7.03(m, 3H), 6.94–6.86(m, 3H), 4.10(t, 2H, J=5.94 Hz), 3.89(s, 3H), 3.69(s, 2H), 2.77(t, 2H, J=5.94Hz), 2.53–2.49(m, 4H), 1.57–1.65(m, 4H), 1.48–1.42(m, 2H). | 10 |

TABLE 62

| 415 | 43 | ¹H-NMR (DMSO-d₆); δ 13.56(br, 1H), 11.16(brs, 1H), 8.47(d, 1H, J=8.58Hz), 8.09(s, 1H), 7.96(d, 1H, J=7.92 Hz), 7.80(d, 1H, J=8.25Hz), 7.57(dd, 1H, J=7.59, 8.25 Hz), 7.14(dd, 1H, J=7.59, 7.92Hz), 7.06–6.93(m, 5H), 4.08(t, 2H, J=3.96Hz), 3.76(s, 2H), 3.70(t, 2H, J=3.66 Hz), 3.52(q, 2H, J=6.93Hz), 1.14(t, 3H, J=6.93Hz). | 11 |
|---|---|---|---|
| 415 methyl ester | 47 | 11.16(brs, 1H), 8.68(d, 1H, J=8.58Hz), 8.16(d, 1H, J=2.31Hz), 8.01(dd, 1H, J=1.65, 7.92Hz), 7.71(dd, 1H, J=2.31, 8.58Hz), 7.53(ddd, 1H, J=1.65, 7.25, 8.53Hz), 7.11–7.05(m, 3H), 6.94(d, 2H, J=8.90Hz), 6.87(d, 1H, J=8.58Hz), 4.12(t, 2H, J=4.62Hz), 3.89(s, 3H), 3.79(t, 2H, J=4.29Hz), 3.70(s, 2H), 3.61(q, 2H, J=6.93Hz), 1.25(t, 3H, J=6.93Hz). | 10 |
| 416 | 41 | ¹H-NMR (DMSO-d₆); δ 14.00–13.00(br, 1H), 11.20(brs, 1H), 8.46(d, 1H, J=8.58Hz), 8.09(d, 1H, J=2.31Hz), 7.95(d, 1H, J=8.25Hz), 7.80(dd, 1H, J=2.31, 8.58Hz), 7.57(dd, 1H, J=7.59, 8.25Hz), 7.14(dd, 1H, J=7.59, 7.59 Hz), 6.91–7.07(m, 5H), 4.56–4.50(m, 1H), 3.90–3.82(m, 2H), 3.76(s, 2H), 3.52–3.44(m, 2H), 1.99–1.94(m, 2H), 1.66–1.52(m, 2H). | 11 |
| 416 methyl ester | 31 | 11.18(brs, 1H), 8.68(d, 1H, J=8.58Hz), 8.16(d, 1H, J=2.31Hz), 8.01(dd, 1H, J=1.65, 7.92Hz), 7.72(dd, 1H, J=2.31, 8.58Hz), 7.54(ddd, 1H, J=1.65, 6.93, 8.58Hz), 7.12–7.05(m, 3H), 6.95–6.87(m, 3H), 4.48–4.39(m, 1H), 4.03–3.92(m, 2H), 3.90(s, 3H), 3.70(s, 2H), 3.62–3.53(m, 2H), 2.06–1.99(m, 2H), 1.85–1.74(m, 2H). | 10 |
| 417 | 68 | ¹H-NMR (DMSO-d₆); δ 11.18(brs, 1H), 8.46(d, 1H, J=7.59Hz), 8.09(d, 1H, J=1.98Hz), 7.95(d, 1H, J=7.92 Hz), 7.80(dd, 1H, J=8.58, 1.65Hz), 7.56(dd, 1H, J=8.25, 7.59Hz), 7.28(dd, 2H, J=7.92; 7.26Hz), 7.14(dd, 1H, J=7.92, 7.26Hz), 7.07–6.89(m, 8H), 4.13(t, 4H, J=6.27 Hz), 3.76(s, 2H), 2.17(m, 2H). | 11 |
| 417 methyl ester | 61 | 11.16(brs, 1H), 8.68(dd, 1H, J=8.58, 0.99Hz), 8.16(d, 1H, J=2.31Hz), 8.00(dd, 1H, J=7.92, 1.65Hz), 7.70(dd, 1H, J=8.25, 2.64Hz), 7.53(ddd, 1H, J=8.58, 7.25, 1.65Hz), 7.27(m, 2H), 7.08(m, 1H), 7.06(d, 2H, J=8.90Hz), 6.96–6.77(m, 6H), 4.16(t, 2H, J=5.94Hz), 4.15(t, 2H, J=5.94Hz), 3.88(s, 3H), 3.69(s, 2H), 2.26(quint, 2H, J=5.94Hz). | 10 |

TABLE 63

| 418 | 17 yield from Ex. 6 | ¹H-NMR (DMSO-d₆); δ 11.33(brs, 1H), 8.45(d, 1H, J=8.57Hz), 8.08(s, 1H), 7.95(d, 1H, J=7.59Hz), 7.79(d, 1H, J=8.25Hz), 7.55(dd, 1H, J=8.25, 7.58Hz), 7.12(dd, 1H, J=7.59, 7.26Hz), 7.06–6.92(m, 5H), 4.05(t, 2H, J=4.62Hz), 3.75(s, 2H), 3.69(t, 2H, J=3.96Hz), 3.63(m, 1H), 1.11(d, 6H, J=5.94Hz). | 11 |
|---|---|---|---|
| 419 | 23 yield from Ex. 6 | ¹H-NMR (DMSO-d₆); δ 11.19(brs, 1H), 8.46(d, 1H, J=8.25Hz), 8.09(d, 1H, J=2.31Hz), 7.95(dd, 1H, J=7.92, 1.65Hz), 7.80(dd, 1H, J=8.58, 1.98Hz), 7.56(dd, 1H, J=8.25, 7.26Hz), 7.13(dd, 1H, J=7.59, 7.59Hz), 7.05(d, 2H, J=8.91Hz), 6.97(d, 2H, J=8.91Hz), 6.92(d, 1H, J=4.95Hz), 4.11(t, 2H, J=4.95Hz), 3.80(t, 2H, J=4.62Hz), 3.75(br, 6H). | 11 |
| 420 | 50 | ¹H-NMR (DMSO-d₆); δ 11.93(brs, 1H), 8.45(d, 1H, J=8.24Hz), 8.08(s, 1H), 7.96(d, 1H, J=7.92Hz), 7.79(dd, 1H, J=8.25, 1.65Hz), 7.49(dd, 1H, J=7.92, 7.92Hz), 7.12–6.91(m, 6H), 4.06(t, 2H, J=4.29Hz), 3.74(t, 2H), 3.72(s, 2H), 3.32(m, 1H), 1.85(m, 2H), 1.66(m, 2H), 1.21(m, 6H). | 11 |
| 420 methyl ester | 86 | 11.16(brs, 1H), 8.67(d, 1H, J=8.58Hz), 8.16(d, 1H, J=2.31Hz), 8.00(dd, 1H, J=7.91, 1.65Hz), 7.71(dd, 1H, J=8.58, 2.31Hz), 7.52(ddd, 1H, J=8.58, 7.25, 1.65Hz), 7.07(m, 1H), 7.06(d, 2H, J=8.91Hz), 6.93(d, 2H, J=9.23 Hz), 6.86(d, 1H, J=8.25Hz), 4.10(t, 2H, J=4.95Hz), 3.89(s, 3H), 3.80(t, 2H, J=4.62Hz), 3.69(s, 2H), 3.29(m, 1H), 1.92–1.80(m, 2H), 1.75–1.60(m, 2H), 1.34–1.20(m, 6H). | 10 |
| 421 | 65 | ¹H-NMR (DMSO-d₆); δ 11.23(brs, 1H), 8.46(d, 1H, J=8.41Hz), 8.09(s, 1H), 7.95(d, 1H, J=7.75Hz), 7.80(dd, 1H, J=8.58, 2.64Hz), 7.56(dd, 1H, J=7.75, 7.26Hz), 7.10(dd, 1H, J=7.75, 7.59Hz), 7.05–6.93(m, 5H), 4.36(m, 1H), 3.75(s, 2H), 3.24(s, 3H), 3.21(m, 1H), 1.98(m, 2H), 1.67(m, 4H), 1.42(m, 2H). | 11 |
| 421 methyl ester | 71 | 11.16(brs, 1H), 8.68(d, 1H, J=8.41Hz), 8.16(d, 1H, J=2.31Hz), 8.00(dd, 1H, J=7.92, 1.65Hz), 7.71(dd, 1H, J=8.41, 2.48Hz), 7.52(ddd, 1H, J=8.74, 7.09, 1.65Hz), | 10 |

TABLE 63-continued

|   |   |   |   |
|---|---|---|---|
|   |   | 7.16–7.02(m, 3H), 6.97–6.82(m, 3H), 4.30(m, 1H); 3.88(s, 3H), 3.69(s, 2H), 3.33(s, 3H), 3.30(m, 1H), 2.09–1.25(m, 8H). |   |

TABLE 64

| | | | |
|---|---|---|---|
| 422 | 43 | ¹H-NMR (DMSO-d₆); δ 11.19(brs, 1H), 8.46(d, 1H, J=8.08Hz), 8.08(s, 1H), 7.95(dd, 1H, J=7.92, 1.65Hz), 7.80(dd, 1H, J=8.58, 2.31Hz), 7.56(dd, 1H, J=8.58, 7.26 Hz), 7.13(dd, 1H, J=7.59, 7.59Hz), 7.07–6.92(m, 5H), 4.08(t, 2H, J=4.45Hz), 3.76(s, 2H), 3.72(t, 2H), 3.59(t, 2H, J=3.29Hz), 3.50(t, 2H, J=2.64Hz), 3.44(q; 2H, J=7.09Hz), 1.10(t, 3H, J=7.09Hz). | 11 |
| 422 methyl ester | 80 | 11.16(brs, 1H), 8.68(dd, 1H, J=8.58, 0.99Hz), 8.16(d, 1H, J=2.47Hz), 8.00(dd, 1H, J=7.92, 1.65Hz), 7.71(dd, 1H, J=8.41, 2.47Hz), 7.51(ddd, 1H, J=8.58, 7.25, 1.65Hz), 7.10–7.02(m, 3H), 6.95–6.85(m, 3H), 4.13(t, 2H, J=5.11 Hz), 3.89(s, 3H), 3.86(m, 2H), 3.71(m, 2H), 3.69(s, 2H), 3.61(m, 2H), 3.54(q, 2H, J=6.93Hz), 1.21(t, 3H, J=6.93 Hz). | 10 |
| 423 | 50 | ¹H-NMR (DMSO-d₆); δ 11.66(brs, 1H), 8.66(d, 1H, J=8.74Hz), 8.46(s, 1H), 8.01(d, 1H, J=8.24Hz), 7.91(dd, 1H, J=8.74, 2.64Hz), 7.51(dd, 1H, J=8.90, 7.25Hz), 7.10–6.97(m, 3H), 6.93(d, 2H, J=9.07Hz), 6.83(d, 1H, J=8.57Hz), 4.07(t, 2H, J=4.61Hz), 3.75(t, 2H), 3.72(s, 2H), 3.44(s, 3H). | 11 |
| 423 methyl ester | 86 | 11.15(brs, 1H), 8.67(d, 1H, J=8.57Hz), 8.16(d, 1H, J=2.14Hz), 7.98(dd, 1H, J=7.92, 2.80Hz), 7.70(dd, 1H, J=8.41, 2.31Hz), 7.51(ddd, 1H, J=8.58, 7.25, 1.65Hz), 7.09–7.05(m, 3H), 6.97–6.79(m, 3H), 4.10(dd, 2H, J=6.10, 4.62Hz), 3.88(s, 3H), 3.73(dd, 2H, J=5.77, 4.78Hz), 3.69(s, 2H), 3.44(s, 3H). | 10 |
| 424 | 62 | 11.11(brs, 1H), 8.45(d, 1H, J=8.74Hz), 8.09(s, 1H), 7.95(d, 1H, J=7.91Hz), 7.79(dd, 1H, J=8.57, 2.47Hz), 7.56(dd, 1H, J=8.08, 7.75Hz), 7.13(dd, 1H, J=7.91, 6.26 Hz), 7.06–6.90(m, 5H), 4.08(t, 2H, J=4.45Hz), 3.75(s, 2H), 3.69(t, 2H, J=3.95Hz), 3.46(t, 2H, J=6.26Hz), 1.50(m, 2H), 1.34(m, 2H), 0.88(t, 3H, J=7.26Hz). | 11 |
| 424 methyl ester | 75 | 11.16(brs, 1H), 8.67(d, 1H, J=8.41Hz), 8.16(d, 1H, J=2.47Hz), 8.00(dd, 1H, J=7.92, 1.65Hz), 7.71(dd, 1H, J=8.41, 2.31Hz), 7.52(ddd, 1H, J=8.58, 7.56, 1.65Hz), 7.10–7.04(m, 3H), 6.93(d, 2H, J=9.07Hz), 6.87(d, 1H, J=8.41Hz), 4.11(t, 2H, J=4.62Hz), 3.88(s, 3H), 3.77(t, 2H, J=4.45Hz), 3.69(s, 2H), 3.53(t, 2H, J=6.60Hz), 1.59(m, 2H), 1.37(m, 2H), 0.92(t, 3H, J=7.26Hz). | 10 |

TABLE 65

| | | | |
|---|---|---|---|
| 425 | 76 | ¹H-NMR (DMSO-d₆); δ 11.12(brs, 1H), 8.46(d, 1H, J=8.24Hz), 8.09(d, 1H, J=2.64Hz), 7.95(dd, 1H, J=7.91, 1.81Hz), 7.80(dd, 1H, J=8.41, 2.63Hz), 7.57(dd, 1H, J=8.74, 7.25Hz), 7.13(dd, 1H, J=7.91, 7.25Hz), 7.06–6.92(m, 5H), 4.08(t, 2H, J=4.28Hz), 3.76(s, 2H), 3.74(t, 2H, J=4.28Hz), 3.59(t, 2H, J=3.13Hz), 3.47(t, 2H, J=2.80Hz), 3.25(s, 3H). | 11 |
| 425 methyl ester | 83 | 11.15(brs, 1H), 8.67(d, 1H, J=8.58Hz), 8.16(d, 1H, J=2.47Hz), 7.99(dd, 1H, J=7.92, 1.32Hz), 7.68(m, 1H), 7.51(m, 1H), 7.28–7.01(m, 3H), 6.95–6.77(m, 3H), 4.13(t, 2H, J=5.11Hz), 3.88(s, 3H), 3.87(t, 2H, J=5.60Hz), 3.72(t, 2H, J=5.11Hz), 3.69(s, 2H), 3.57(t, 2H, J=5.11 Hz), 3.39(s, 3H). | 10 |
| 426 | 86 | ¹H-NMR (DMSO-d₆); δ 11.19(brs, 1H), 8.45(d, 1H, J=8.57Hz), 8.08(s, 1H), 7.95(d, 1H, J=7.92Hz), 7.80(dd, 1H; J=8.57, 2.63Hz), 7.56(dd, 1H, J=8.90, 6.76Hz), 7.13(dd, 1H, J=7.75, 7.42Hz), 7.06–6.92(m, 5H), 4.08(t, 2H, J=4.28Hz), 3.75(s, 2H), 3.69(t, 2H, J=3.46Hz), 3.41(t, 2H, J=6.59Hz), 1.52(m, 2H), 0.87(t, 3H, J=7.25 Hz). | 11 |
| 426 methyl ester | 80 | 11.16(brs, 1H), 8.68(d, 1H, J=8.41Hz), 8.16(d, 1H, J=2.31Hz), 8.00(dd, 1H, J=7.92, 1.65Hz), 7.71(dd, 1H, J=8.41, 2.47Hz), 7.52(m, 1H), 7.10–7.03(m, 3H), 6.93(d, 2H, J=8.91Hz), 6.87(d, 1H, J=8.41Hz), 4.11(t, 2H, J=5.11Hz), 3.89(s, 3H), 3.78(t, 2H, J=5.11Hz), 3.69(s, 2H), 3.49(t, 2H, J=6.59Hz), 1.62(m, 2H), 0.93(t, 3H, J=7.42Hz). | 10 |

TABLE 65-continued

| 427 | 79 | 11.69(brs, 1H), 8.46(d, 1H, J=8.4Hz), 8.11(d, 1H, J=2.2 Hz), 7.96(dd, 1H, J=7.8Hz), 7.77–7.87(m, 3H), 7.56(d, 1H, J=2.4Hz), 7.52(dd, 1H, J=7.8, 7.3Hz), 7.39(d, 1H, J=2.4Hz), 7.27(dd, 1H, J=8.6, 2.2Hz), 7.18(dd, 1H, J=8.9, 2.4Hz), 7.11(dd, 1H, J=8.4, 7.3Hz), 7.04(d, 1H, J=8.1Hz), 4.23(t, 2H, J=5.7Hz), 3.76(s, 2H), 3.60–3.63(m, 4H), 2.83(t, 2H, J=5.7Hz), 2.56–2.59(m, 4H). | 11 |
|---|---|---|---|
| 427 methyl ester | 56 | 11.17(brs, 1H), 8.69(d, 1H, J=8.6Hz), 8.17(s, 1H), 7.98–8.02(m, 1H), 7.64–7.76(m, 3H), 7.49–7.52(m, 2H), 7.25–7.30(m, 1H), 7.07–7.17(m, 3H), 6.93–6.96(m, 1H), 4.20–4.24(m, 2H), 3.89(s, 3H) 3.73–3.77(m, 4H), 3.71(s, 2H), 2.84–2.88(m, 2H), 2.59–2.62(m, 4H). | 10 |

TABLE 66

| 428 | 57 | 10.76(brs, 1H), 8.76(d, 1H, J=7.58Hz), 8.10(dd, 1H, J=7.92, 1.65Hz), 7.59(ddd, 1H, J=8.58, 7.26, 1.65Hz), 7.44(dd, 1H, J=1.98, 0.99Hz), 7.29(d, 2H, J=8.58Hz), 7.09(ddd, 1H, J=7.91, 7.26, 0.99Hz), 6.98(d, 2H, J=8.58 Hz), 6.94–6.84(m, 4H), 6.42–6.37(m, 2H), 4.93(s, 2H), 3.76(s, 2H). | 11 |
|---|---|---|---|
| 428 methyl ester | 35 | 11.03(brs, 1H), 8.71(d, 1H, J=8.25Hz), 7.99(dd, 1H, J=7.91, 1.65Hz), 7.52(ddd, 1H, J=8.58, 7.25, 1.65Hz), 7.45(dd, 1H, J=1.65, 0.66Hz), 7.31(d, 2H, J=8.58Hz), 7.06(dd, 1H, J=7.26, 6.92Hz), 7.01–6.87(m, 6H), 6.43–6.37(m, 2H), 4.98(s, 2H), 3.87(s, 3H), 3.73(s, 2H). | 10 |
| 981 | 75 | 13.51(br, 1H), 11.16(brs, 1H), 9.31(brs, 1H), 8.47(d, 1H, J=7.6Hz), 8.08(s, 1H), 7.95(d, 1H, J=7.9Hz), 7.77(d, 1H, J=8.6Hz), 7.56(t, 1H, J=7.9Hz), 7.13(t, 1H, J=7.9Hz), 6.94–6.87(m, 3H), 6.77(d, 2H, J=8.9Hz), 3.75(s, 2H). | 11 |
| 982 | 30 | 11.77(brs, 1H), 8.66(d, 1H, J=8.3Hz), 8.02(d, J=7.9Hz), 7.94(d, 1H, J=8.9Hz), 7.51(t, 1H, J=7.1 Hz), 7.01–7.09(m, 3H), 6.83–6.88(m, 3H), 4.68(brm, 1H), 3.73(s, 2H), 1.4–2.0(brm, 8H). | 11 |
| 983 | 41 | $^1$H-NMR (DMSO-$d_6$); δ 11.27(brs, 1H), 8.55(d, 1H, J=8.25Hz), 8.18(d, 1H, J=1.98Hz), 8.04(dd; 1H, J=1.32, 7.92Hz), 7.89(dd, 1H, J=2.31, 8.25Hz), 7.66(ddd, 1H, J=1.32; 6.92, 8.58Hz), 7.23(dd, 1H, J=6.93, 7.59Hz), 7.12(d, 2H, J=9.24Hz), 7.03(d, 1H, J=8.24Hz), 6.99(d, 2H, J=8.91Hz), 4.53(m, 1H), 3.85(s, 2H), 2.01–1.50(m, 14H). | 11 |
| 984 | 38 | $^1$H-NMR (DMSO-$d_6$); δ 13.66(br, 1H), 11.27(brs, 1H), 8.55(d, 1H, J=8.25Hz), 8.18(d, 1H, J=2.31Hz), 8.05(dd, 1H, J=1.32, 7.92Hz), 7.89(dd, 1H, J=2.31, 8.25Hz), 7.66(dd, 1H, J=6.93, 7.25Hz), 7.23(t, 1H, J=7.26Hz), 7.12(d, 2H, J=8.91Hz), 7.04(d, 1H, J=8.57Hz), 7.03(d, 2H, J=8.80Hz), 4.25(m, 1H), 3.85(s, 2H), 1.70(m, 4H), 1.00(t, 6H, J=7.26Hz). | 11 |
| 985 | 35 | $^1$H-NMR (DMSO-$d_6$); δ 14.15(brs, 1H) 8.40(d, 1H, J=7.92Hz), 8.05(d, 1H, J=1.98Hz), 8.00(d, 1H, J=7.59 Hz), 7.77(dd, 1H, J=2.31, 8.58Hz), 7.27(dd, 1H, J=7.26, 7.92Hz), 7.02–6.89(m, 6H), 4.27(m, 1H), 3.60(s, 2H), 1.89(m, 2H), 1.72(m, 2H), 1.53–1.23(m, 6H). | 11 |

TABLE 67

| 987 | 23 | 11.64(brs, 1H), 8.65(d, 1H, J=8.6Hz), 8.45(s, 1H), 8.04(d, 1H, J=7.9Hz), 7.91(d, 1H, J=8.6Hz), 7.51(t, 1H, J=7.6 Hz), 7.06(m, 1H), 7.03(d, 2H, J=8.9Hz), 6.90–6.82(m, 3H), 3.86(m, 1H), 3.74(s, 2H), 1.80–1.60(brm, 4H), 1.55–1.20(br, 18H). | 11 |
|---|---|---|---|
| 990 | 86 | 11.72(brs, 1H), 8.66(d, 1H, J=8.3Hz), 8.48(d, 1H, J=2.0 Hz), 8.01(dd, 1H, J=1.3, 7.9Hz), 7.93(dd, 1H, J=2.3, 8.6 Hz), 7.51(dt, 1H, J=1.3, 7.9Hz), 7.93–7.07(m, 1H), 7.04(d, 2H, J=9.2Hz), 6.89(d, 2H, J=8.9Hz), 6.83(d, 1H, J=8.6Hz), 5.19(t, 1H, J=7.1Hz), 3.88(t, 2H, J=7.1Hz), 3.73(s, 2H), 2.46(q, 2H, J=6.9Hz), 1.73(s, 3H), 1.66(s, 3H). | 11 |
| 991 | 97 | 11.71(brs, 1H), 8.66(d, 1H, J=8.6Hz), 8.48(s, 1H), 8.01(d, 1H, J=1.6, 7.9Hz), 7.93(dd, 1H, J=2.3, 8.6Hz), 7.51(t, 1H, J=7.2Hz), 7.09–7.06(m, 1H), 7.05(d, 2H, J=8.9Hz), 6.92(d, 2H, J=9.2Hz), 6.85(d, 1H, J=8.6Hz), 6.10–5.96(m, 1H), 5.40(m, 1H), 5.28(m, 1H), 4.48(dd, 2H, | 11 |

TABLE 67-continued

| | | | |
|---|---|---|---|
| 992 | 69 | J=1.3, 4.8Hz), 3.73(s, 2H).<br>11.68(sbr, 1H), 8.66(d, 1H, J=8.3Hz), 8.48(d, 1H, J=2.3 Hz), 8.01(d, 1H, J=7.9Hz), 7.92(dd, 1H, J=2.6, 8.6Hz), 7.51(t, 1H, J=7.2Hz), 7.06(m, 1H), 7.04(d, 2H, J=8.9 Hz), 6.90(d, 2H, J=9.2Hz), 6.84(d, 1H, J=8.6Hz), 5.67–5.89(m, 2H), 4.40(d, 2H, J=5.9Hz), 3.73(s, 2H), 1.75(d, 3H, J=6.3Hz). | 11 |
| 993 | 42 | 11.71(brs, 1H), 8.66(d, 1H, J=8.3Hz), 8.49(d, 1H, J=2.0 Hz), 8.01(dd, 1H, J=1.7, 7.9Hz), 7.93(dd, 1H, J=2.0, 8.6 Hz), 7.50(t, 1H, J=7.6Hz), 7.09–7.06(m, 1H), 7.04(d, 2H, J=9.2Hz), 6.92(d, 2H, J=9.2Hz), 6.84(d, 1H, J=8.6Hz); 5.08(s, 1H), 4.98(s, 1H), 4.38(s, 2H), 3.73(s, 2H), 1.81(s, 3H). | 11 |
| 994 | 86 | 11.70(brs, 1H), 8.65(d, 1H, J=8.3Hz), 8.48(d, 1H, J=2.0 Hz), 8.03(d, 1H, J=7.9Hz), 7.91(dd, 1H, J=2.3, 8.6Hz), 7.51(t, 1H, J=7.2Hz), 7.06–7.00(m, 1H), 7.01(d, 2H, J=8.3Hz), 6.91(d, 2H, J=9.2Hz), 6.83(d, 1H, J=8.6Hz), 5.47(t, 1H, J=6.2Hz), 5.09(t, 1H, J=6.2Hz), 4.49(d, 2H, J=6.2Hz), 3.73(s, 2H), 2.09(brm, 4H), 1.71(s, 3H), 1.68(s, 3H), 1.60(s, 3H). | 11 |
| 1002 | 10 | 11.67(brs, 1H), 8.66(d, 1H, J=8.6Hz), 8.45(s, 1H), 8.02(dd, 1H, J=1.3, 7.9Hz), 7.91(dd, 1H, J=2.0, 8.6Hz), 7.54(t, 1H, J=7.2Hz), 7.09–6.82(m, 6H), 6.40–6.32(m, 1H), 5.97–5.84(m, 2H), 5.37–5.05(m, 3H), 4.52(d, J=4.3 Hz, 1H), 3.72(s, 2H). | 11 |

TABLE 68

| | | | |
|---|---|---|---|
| 1017 | 60 | $^1$H-NMR (DMSO-$d_6$); δ 13.56(br, 1H), 11.18(brs, 1H), 8.46(d, 1H, J=8.57Hz), 8.08(s, 1H), 7.95(d, 1H, J=7.92 Hz), 7.79(d, 1H, J=8.25Hz), 7.57(dd, 1H, J=7.26, 8.58 Hz), 7.37(m, 2H), 7.16–6.92(m, 8H), 4.17(t, 2H, J=6.60 Hz), 3.76(s, 2H), 3.03(t, 2H, J=6.60Hz). | 11 |
| 1019 | 34 | $^1$H-NMR (DMSO-$d_6$); δ 14.26(br, 1H), 8.40(d, 1H, J=7.92Hz), 8.19(d, 2H, J=7.26Hz), 8.05(s, 1H), 8.00(d, 1H, J=7.58Hz), 7.78(d, 1H, J=6.27Hz), 7.64(d, 2H, J=7.92Hz), 7.26(dd, 1H, J=6.93, 8.25Hz), 7.04–6.85(m, 5H), 6.77(d, 1H, J=7.91Hz), 4.26(t, 2H, J=6.6Hz), 3.61(s, 2H), 3.20(t, 2H, J=6.27Hz). | 11 |
| 1021 | 82 | 13.56(br, 1H), 11.18(brs, 1H), 8.46(d, 1H, J=7.58Hz); 8.08(d, 1H, J=1.98Hz), 7.95(d, 1H, J=7.92Hz), 7.80(dd, 1H, J=1.98, 8.58Hz), 7.57(dd, 1H, J=7.59, 8.25Hz), 7.33–7.21(m, 5H), 7.13(dd, 1H, J=7.26, 7.92Hz), 7.06–6.92(m, 5H), 4.19(t, 2H, J=6.93Hz), 3.75(s, 2H), 3.04(t, 2H, J=6.93Hz). | 11 |
| 1059 | 35 | $^1$H-NMR (DMSO-$d_6$); δ 8.81(d, 1H, J=1.65Hz), 8.70(d, 1H, J=7.91.Hz), 8.43(dd; 1H, J=1.31, 8.24Hz), 8.14(d, 1H, J=7.59Hz), 7.53(m, 1H), 7.23–7.14(m, 4H), 7.06(d, 2H, J=9.24Hz), 4.30(m, 1H), 1.72(m, 4H), 1.02(t, 6H, J=7.26Hz). | 11 |
| 1060 | 35 | $^1$H-NMR (DMSO-$d_6$); δ 8.80(d, 1H, J=2.31Hz), 8.71(d, 1H, J=8.57Hz), 8.41(dd, 1H, J=2.31, 8.57Hz), 8.14(d, 1H, J=8.58Hz), 7.64(dd, 1H, J=7.59, 7.91Hz), 7.27–7.10(m, 4H), 7.07(d, 2H, J=9.24Hz), 4.40(m, 1H), 2.08–1.36(m, 10H). | 11 |
| 1061 | 25 | $^1$H-NMR (DMSO-$d_6$); δ 12.28(br; 1H), 8.78(d, 1H, J=2.31Hz), 8.71(d, 1H, J=8.57Hz), 8.39(dd, 1H, J=2.96, 8.58Hz), 8.14(dd, 1H, J=1.65, 7.92Hz), 7.75(dd, 1H J=7.26, 8.25Hz), 7.31(dd, 1H, J=6.60, 7.59Hz), 7.24(d, 1H, J=8.58Hz), 7.20(d, 2H, J=8.90Hz), 7.03(d, 2H, J=9.23Hz), 4.56(m, 1H), 2.00–1.55(m, 14H). | 11 |
| 1077 | 100 | 11.16(brs, 1H), 8.69(d, 1H, J=8.58Hz), 8.18(d, 1H, J=2.31Hz), 8.01(dd, 1H, J=1.65, 7.92Hz), 7.72(dd, 1H, J=2.31, 8.58Hz), 7.53(ddd, 1H, J=1.65, 7.26; 8.57Hz), 7.11–6.98(m, 3H), 6.92–6.86(m, 3H), 4.10(m, 1H), 3.89(s, 3H), 3.71(s, 2H); 1.68(m, 4H), 0.96(t, 6H, J=7.25Hz). | 10 |

TABLE 69

| | | | |
|---|---|---|---|
| 1079 | 89 | 11.16(brs, 1H), 8.69(d, 1H, J=8.3Hz), 8.17(d, 1H, J=2.3 8.00(dd, 1H, J=1.7, 7.9Hz), 7.70(dd, 1H, J=2.3, 8.9 Hz), 7.50(t, 1H, J=7.1Hz), 7.06–7.10(m, 1H), 7.05(d, 2H, J=8.9Hz), 6.85–6.90(m, 3H), 4.72(brm, 1H), 3.89(s, 3H), 3.70(s, 2H), 1.8–2.0(brm, 4H), 1.5–1.75(brm, 4H). | 10 |

TABLE 69-continued

| 1080 | 85 | 11.16(brs, 1H), 8.68(d, 1H, J=8.25Hz), 8.17(d, 1H, J=2.64Hz), 8.01(dd, 1H, J=1.65, 8.25Hz), 7.71(dd, 1H, J=2.31, 8.58Hz), 7.53(ddd, 1H, J=1.65, 7.25, 8.58Hz), 7.27–7.02(m, 3H), 6.93–6.86(m, 3H), 3.97(m, 1H), 3.89(s, 3H), 3.70(s, 2H), 2.04–1.05(m, 10H). | 10 |
| --- | --- | --- | --- |
| 1081 | 100 | 11.16(brs, 1H), 8.68(d, 1H, J=8.58Hz), 8.17(d, 1H, J=2.31Hz), 8.01(dd, 1H, J=1.65, 7.92Hz), 7.71(dd, 1H, J=2.31, 8.58Hz), 7.53(ddd, 1H, J=1.65, 7.26, 8.57Hz), 7.11–7.03(m, 3H), 6.88–6.84(m, 3H), 4.36(m, 1H), 3.89(s, 3H), 3.70(s, 2H), 2.01–1.54(m, 14H). | 10 |
| 1082 | 92 | 11.16(brs, 1H), 8.68(d, 1H, J=8.6Hz), 8.17(d, 1H, J=2.4 Hz), 8.00(d, 1H, J=7.9Hz), 7.71(dd, 1H, J=2.3, 8.6Hz), 7.53(t, 1H, J=7.3Hz), 7.10–7.03(m, 3H), 6.92–6.86(m, 3H), 3.89(s, 3H), 3.84(m, 1H), 3.70(s, 2H), 1.80–1.60(brm, 4H), 1.55–1.20(br, 18H). | 10 |
| 1083 | 33 | 11.16(brs, 1H), 8.68(d, 1H, J=8.58Hz), 8.16(d, 1H, J=2.31Hz), 8.01(dd, 1H, J=1.65, 7.92Hz), 7.71(dd 1H, J=2.64, 8.58Hz), 7.53(ddd, 1H, J=1.65, 7.26, 8.57Hz), 7.11–7.04(m, 3H), 6.93–6.86(m, 3H), 3.89(s, 3H), 3.81(dd, 2H, J=5.61, 10.23Hz), 3.70(s, 2H), 1.56–1.23(m, 7H), 1.03–0.84(m, 6H). | 10 |
| 1084 | 38 | 11.16(brs, 1H), 8.68(d, 1H, J=8.6Hz), 8.16(d, 1H, J=2.3 Hz), 8.00(d, 1H, J=1.6, 7.9Hz), 7.71(dd, 1H, J=2.3, 8.6 Hz), 7.52(t, 1H, J=7.2Hz), 7.11–7.05(m, 3H), 6.92(d, 2H, J=6.9Hz), 6.88(d, 1H, J=8.6Hz), 6.11–5.99(m, 1H), 5.46–5.37(m, 1H), 5.32–5.26(m, 1H), 4.52(d, 2H, J=5.9 Hz), 3.89(s, 3H), 3.69(s, 2H). | 6 |

TABLE 70

| 1085 | 34 | 11.17(brs, 1H), 8.68(d, 1H, J=8.6Hz), 8.16(d, 1, J=2.3 Hz, H), 8.00(dd, 1H, J=1.6, 7.9Hz), 7.70(dd, 1H, J=2.3, 8.6Hz), 7.53(dt, 1H, J=1.3, 7.9Hz), 7.10–7.06(m, 1H), 7.06(d, 2H, J=9.2Hz), 6.90(d, 2H, J=8.9Hz), 6.89–6.85(m, 1H), 5.21(t, 1H, J=7.1Hz), 3.92(t, 2H, J=7.1 Hz), 3.89(s, 3H), 3.70(s, 2H), 2.46(q, 2H, J=6.9Hz), 1.73(s, 3H), 1.66(s, 3H). | 6 |
| --- | --- | --- | --- |
| 1086 | 39 | 11.17(brs, 1H), 8.68(d, 1H, J=8.6Hz), 8.16(s, 1H), 8.00(d, 1H, J=7.1Hz), 7.71(d, 1H, J=8.3Hz), 7.53(t, 1H, J=7.1 Hz), 7.11–7.03(m, 3H), 6.96–6.85(m, 3H), 6.0–5.8(m, 2H), 5.4–5.1(m, 4H), 4.56(d, 1H, J=5.6Hz), 3.89(s, 3H), 3.70(s, 2H). | 10 |
| 1087 | 41 | 11.16(brs, 1H), 8.68(d, 1H, J=8.6Hz), 8.16(d, 1H, J=2.3 Hz), 8.00(dd, 1H, J=1.6, 7.9Hz), 7.71(dd, 1H, J=2.3, 8.6 Hz), 7.53(t, 1H, J=7.8Hz), 7.11–7.06(m, 1H), 7.06(d, 2H, J=9.2Hz), 6.91(d, 2H, J=8.9Hz), 6.88(d, 1H, J=8.3Hz), 5.91–5.70(m, 2H), 4.44(d, 2H, J=5.6Hz), 3.89(s, 3H), 3.70(s, 2H), 1.76(dd, 3H, J=1.0, 5.3Hz). | 10 |
| 1088 | 42 | 11.16(brs, 1H), 8.68(d, 1H, J=8.6Hz), 8.16(d, 1H, J=2.3 Hz), 8.00(dd, 1H, J=1.6, 7.9Hz), 7.71(dd, 1H, J=2.3, 8.6 Hz), 7.52(dt, 1H, J=1.6, 7.9Hz), 7.10–7.04(m, 3H), 6.93(d, 2H, J=8.9Hz), 6.88(d, 1H, J=8.6Hz), 5.10(s, 1H), 4.99(s, 1H), 4.42(s, 2H), 3.89(s, 3H), 3.70(s, 2H), 1.83(s, 3H). | 10 |
| 1089 | 23 | 11.16(brs, 1H), 8.68(d, 1H, J=8.6Hz), 8.16(d, 1H, J=2.3 Hz), 8.00(d, 1H, J=7.9Hz), 7.71(d, 1H, J=2.3, 8.6Hz), 7.52(t, 1H, J=7.9Hz), 7.08–7.11(m, 1H), 7.06(d, 2H, J=8.9Hz), 6.92(d, 2H, J=8.9Hz), 6.88(d, 1H, J=8.3Hz), 5.50(t, 1H, J=6.3Hz), 5.09(br, 1H), 4.52(d, 2H, J=6.6 Hz), 3.89(s, 3H), 3.70(s, 2H), 2.05(brm, 4H), 1.73(s, 3H), 1.68(s, 3H), 1.60(s, 3H). | 6 |
| 1090 | 49 | 11.16(brs, 1H), 8.68(d, 1H, J=8.25Hz), 8.16(d, 1H, J=2.31Hz), 8.01(dd, 1H, J=1.65, 7.92Hz), 7.71(dd, 1H, J=2.31, 8.58Hz), 7.53(ddd, 1H, J=1.65, 7.26, 8.57Hz), 7.35–7.21(m, 5H), 7.11–7.04(m, 3H), 6.93–6.86(m, 3H), 4.17(t, 2H, J=6.92Hz), 3.89(s, 3H), 3.70(s, 2H), 3.10(t, 2H, J=6.92Hz). | 10 |

TABLE 71

| 1091 | 61 | 11.17(brs, 1H), 8.68(d, 1H, J=8.58Hz), 8.15(d, 1H, J=2.31Hz), 8.01(dd, 1H, J=1.65, 7.92Hz), 7.71(dd, 1H, J=2.31, 8.58Hz), 7.53(ddd, 1H, J=1.32, 7.26, 8.57Hz), 7.25(m, 2H), 7.10–6.86(m, 8H), 4.14(t, 2H, J=6.93Hz), | 10 |
| --- | --- | --- | --- |

TABLE 71-continued

| | | | |
|---|---|---|---|
| | | 3.89(s, 3H) 3.69(s, 2H), 3.06(t, 2H, J=6.93Hz). | |
| 1101 | 92 | 12.07(s, 1H), 8.90(d, 1H, J=2.63Hz), 8.88(d, 1H, J=8.25 Hz), 8.32(dd, 1H, J=2.64, 8.58Hz), 8.08(dd, 1H, J=1.65, 7.92Hz), 7.60(ddd, 1H, J=1.65, 7.26, 8.58Hz), 7.16–6.93(m, 6H), 4.22(m, 1H), 3.94(s, 3H), 2.04–1.26(m, 10H). | 10 |
| 1102 | 89 | 12.07(brs, 1H), 8.90(d, 1H, J=2.63Hz), 8.88(dd, 1H, J=0.66, 8.58Hz), 8.31(dd, 1H, J=2.30, 8.57Hz), 8.07(dd, 1H, J=1.32, 7.92Hz), 7.60(ddd, 1H, J=1.32, 7.26, 8.58 Hz), 7.15–7.06(m, 3H), 6.99(d, 1H, J=8.91), 6.90(d, 2H, J=8.91Hz), 4.39(m, 1H), 3.94(s, 3H); 2.04–1.41(m, 14H). | 10 |
| 1103 | 65 | 12.08(brs, 1H), 8.90(d, 1H, J=2.63Hz), 8.88(dd, 1H, J=0.66, 8.91Hz), 8.32(dd, 1H, J=2.65, 8.58Hz), 8.08(dd, 1H, J=1.65, 7.92Hz), 7.60(ddd, 1H, J=1.65, 7.26, 8.58 Hz), 7.16–6.91(m, 6H), 4.09(m, 1H), 3.94(s, 3H), 1.70(m, 4H), 0.98(t, 6H, J=7.25Hz). | 10 |
| 1105 | 100 | 11.16(brs, 1H), 8.69(d, 1H, J=8.58Hz), 8.18(d, 1H, J=2.31Hz), 8.01(dd, 1H, J=1.65, 7.92Hz), 7.72(dd, 1H, J=2.31, 8.58Hz), 7.53(ddd, 1H, J=1.65, 7.26, 8.57Hz), 7.11–6.98(m, 3H), 6.92–6.86(m, 3H), 4.10(m, 1H), 3.89(s, 3H), 3.71(s, 2H), 1.68(m, 4H), 0.96(t, 6H, J=7.25Hz). | 10 |
| 1108 | 30 | 11.16(brs, 1H), 8.67(d, 1H, J=8.25Hz), 8.15(d, 1H, J=2.31Hz), 7.99(dd, 1H, J=1.32, 7.91Hz), 7.71(dd, 1H, J=2.31, 8.25Hz), 7.51(ddd, 1H, J=1.32, 7.25, 8.57Hz), 7.10–7.03(m, 3H), 6.94–6.87(m, 3H), 4.26(t, 2H, J=6.27 Hz), 3.88(s, 3H), 3.69(s, 2H), 3.62(t, 2H, J=6.27Hz). | 10 |
| 1118 | 60 | $^1$H-NMR (DMSO-$d_6$); δ 0.93(6H, t, J=7.81Hz), 1.67(4H, dq, J=5.86, 7.81Hz), 3.77(2H, s), 4.37(1H, tt, J=5.86, 5.86Hz), 7.03(1H, d, J=7.81Hz), 7.15(2H, m), 7.25(1H, m), 7.35(1H, s), 7.54(1H, s), 7.57(1H, dd, J=7.81, 7.81 Hz), 7.76(1H, d, J=9.76Hz), 7.83(2H, m), 7.95(1H, d, J=7.81Hz), 8.11(1H, s), 8.45(1H, d, J=9.76Hz), 11.13(1H, s), 13.56(1H, br). | 11 |

TABLE 72

| | | | |
|---|---|---|---|
| 1205 | 35 | 1.00(6H, t, J=7.51Hz), 1.74(4H, m), 3.71(2H, s), 3.90(3H, s), 4.21(1H, m), 6.94(1H, d, J=6.94Hz), 7.11(3H, m), 7.26(1H, m), 7.50(2H, m), 7.70(3H, m), 8.02(1H, ,dd, J=1.73, 8.00Hz), 8.18(1H, d, J=2.47Hz), 8.69(1H, dd, J=0.91, 8.50Hz), 11.19(1H,s). | 10 |
| 1243 | 41 | 11.16(brs, 1H), 8.68(d, 1H, J=8.6Hz), 8.16(d, 1H, J=2.3 Hz), 8.00(dd, 1H, J=1.6, 7.9Hz), 7.71(dd, 1H, J=2.3, 8.6 Hz), 7.53(t, 1H, J=7.8Hz), 7.11–7.06(m, 1H), 7.06(d, 2H, J=9.2Hz), 6.91(d, 2H, J=8.9Hz), 6.88(d, 1H, J—8.3Hz), 5.91–5.70(m, 2H), 4.44(d, 2H, J=5.6Hz), 3.89(s, 3H), 3.70(s, 2H), 1.76(dd, 3H, J—1.0, 5.3Hz). | 10 |
| 1244 | 55 | $^1$H-NMR (DMSO-$d_6$); δ 14.25(brs, 1H), 8.41(d, 1H, J=8.25Hz), 8.06(s, 1H), 8.00(d, 1H, J=7.91), 7.78(d, 1H, J=8.58Hz), 7.27(dd, 1H, J=7.26, 8.25Hz), 7.05–6.90(m, 6H), 3.83(dd, 2H, J=6.27, 10.23Hz), 3.61(s, 2H), 1.47–1.28(m, 7H), 1.00–0.89(m, 6H). | 11 |
| 1245 | 41 | $^1$H-NMR (DMSO-$d_6$); δ 14.00–13.00(br, 1H), 11.20(brs, 1H), 8.46(d, 1H, J=8.58Hz), 8.09(d, 1H, J=2.31Hz), 7.95(d, 1H, J=8.25Hz), 7.80(dd, 1H, J—2.31, 8.58Hz), 7.57(dd, 1H, J=7.59, 8.25Hz), 7.14(dd, 1H, J=7.59, 7.59 Hz), 6.91–7.07(m, 5H), 4.56–4.50(m, 1H), 3.90–3.82(m, 2H), 3.76(s, 2H), 3.52–3.44(m, 2H), 1.99–1.94(m, 2H), 1.65–1.52(m, 2H). | 11 |

Note:
In the above tables, "methyl ester" means the carboxylic acid ester at the anthranilic acid site, and "methyl ester" and "ethyl ester" shown in the lower column mean carboxylic acid esters at the other site.

TABLE 73

| Compound No. | M | Measured value $(M + 1)^+$ | Yield of Example 10 | Yield of Example 11 |
|---|---|---|---|---|
| 80 | 461.18 | 462.2 | 100 | 100 |
| 81 | 503.23 | 504.2 | 24 | 46 |
| 82 | 475.2 | 476.2 | 27 | 100 |
| 83 | 529.25 | 530.2 | 11 | 100 |
| 84 | 475.2 | 476.2 | 4 | 100 |
| 85 | 489.22 | 490.2 | 39 | 100 |

TABLE 74

| Compound No. | M | Measured value (M + 1)+ | Yield of Example 6 | Yield of Example 8 |
|---|---|---|---|---|
| 88 | 513.18 | 514.2 | 48 | 76 |

TABLE 75

| Compound No. | M | Measured value (M + 1)+ | Acylation yield (%) 1st stage | Hydrolysis yield (%) 2nd stage | Yield (%) 1st and 2nd stages | Example No. |
|---|---|---|---|---|---|---|
| 52 | 474.18 | 475.2 | 73 | 100 | 73 | 25 |
| 53 | 490.17 | 491.2 | 87 | 100 | 87 | 25 |
| 54 | 536.19 | 537.4 | 84 | 100 | 84 | 25 |
| 55 | 474.18 | 475.2 | 67 | 100 | 67 | 25 |
| 56 | 490.17 | 491.2 | 55 | 100 | 55 | 25 |
| 57 | 536.19 | 537.4 | 58 | 100 | 58 | 25 |
| 58 | 488.19 | 489 | 73 | 91 | 66 | 25 |
| 59 | 504.19 | 505 | 75 | 88 | 66 | 25 |
| 60 | 550.21 | 551 | 30 | 44 | 13 | 25 |
| 61 | 488.19 | 489 | 56 | 58 | 29 | 25 |
| 62 | 504.19 | 505 | 61 | 77 | 47 | 25 |
| 63 | 550.21 | 551 | 82 | 81 | 66 | 25 |
| 64 | 502.21 | 503 | 65 | 63 | 41 | 25 |
| 65 | 564.23 | 565 | 76 | 52 | 40 | 25 |
| 66 | 518.21 | 519 | 56 | 65 | 36 | 25 |
| 67 | 502.21 | 503 | 41 | 84 | 34 | 25 |
| 68 | 564.23 | 565 | 87 | 85 | 74 | 25 |
| 69 | 518.21 | 519 | 71 | 77 | 55 | 25 |
| 70 | 502.21 | 503 | 59 | 96 | 56 | 25 |
| 71 | 564.23 | 565 | 72 | 88 | 63 | 25 |
| 72 | 518.21 | 519 | 78 | 99 | 77 | 25 |

TABLE 76

| 73 | 502.21 | 503 | 51 | 91 | 46 | 25 |
|---|---|---|---|---|---|---|
| 74 | 564.23 | 565 | 70 | 94 | 66 | 25 |
| 75 | 518.21 | 519 | 71 | 61 | 43 | 25 |
| 76 | 488.19 | 489.2 | 70 | 100 | 70 | 25 |
| 77 | 550.21 | 551.2 | 45 | 100 | 45 | 25 |
| 78 | 488.19 | 489.2 | 61 | 100 | 61 | 24 |
| 79 | 504.19 | 505.2 | 59 | 100 | 59 | 25 |
| 95 | 502.21 | 503.3 | 78 | 51 | 39 | 21 |
| 96 | 564.23 | 565.3 | 100 | 50 | 51 | 20 |
| 97 | 578.24 | 579.3 | 100 | 63 | 63 | 21 |
| 98 | 594.24 | 595.3 | 100 | 65 | 65 | 21 |
| 99 | 598.19 | 599.3 | 99 | 46 | 45 | 21 |
| 100 | 632.52 | 633.3 | 100 | 60 | 60 | 21 |
| 101 | 565.22 | 566.3 | 82 | 45 | 37 | 21 |
| 102 | 565.22 | 566.3 | 56 | 22 | 13 | 21 |
| 103 | 516.23 | 517.3 | 72 | 32 | 23 | 21 |
| 104 | 530.24 | 531.3 | 70 | 57 | 40 | 21 |
| 105 | 560.24 | 531.3 | 79 | 63 | 50 | 21 |
| 106 | 544.26 | 545.3 | 98 | 77 | 76 | 21 |
| 107 | 544.26 | 545.3 | 84 | 47 | 40 | 21 |
| 108 | 544.26 | 545.3 | 89 | 63 | 56 | 21 |
| 109 | 586.3 | 587.3 | 94 | 94 | 89 | 21 |

TABLE 77

| 110 | 570.27 | 571.3 | 83 | 76 | 64 | 21 |
|---|---|---|---|---|---|---|
| 111 | 609.21 | 610.3 | 100 | 32 | 32 | 21 |
| 112 | 578.24 | 579.3 | 78 | 45 | 35 | 21 |
| 113 | 594.24 | 595.3 | 86 | 94 | 81 | 21 |
| 114 | 592.26 | 593.3 | 89 | 60 | 53 | 21 |
| 115 | 554.21 | 555.0 | 96 | 51 | 49 | 21 |
| 116 | 567.2 | 568.3 | 26 | 27 | 7 | 21 |
| 117 | 538.18 | 539.3 | 96 | 63 | 61 | 21 |
| 118 | 552.19 | 553.3 | 88 | 54 | 48 | 21 |
| 119 | 566.21 | 567.3 | 90 | 43 | 39 | 21 |
| 120 | 580.22 | 581.3 | 68 | 50 | 34 | 21 |

TABLE 77-continued

| 121 | 600.19 | 601.3 | 100 | 63 | 63 | 21 |
|---|---|---|---|---|---|---|
| 122 | 614.21 | 615.3 | 88 | 68 | 61 | 21 |
| 123 | 634.15 | 635.3 | 92 | 65 | 60 | 21 |
| 124 | 668.12 | 669.3 | 93 | 52 | 49 | 21 |
| 125 | 645.18 | 646.3 | 96 | 2 | 2 | 21 |
| 126 | 614.21 | 615.3 | 34 | 13 | 5 | 21 |
| 127 | 518.21 | 519.3 | 30 | 71 | 21 | 21 |
| 128 | 532.22 | 533.3 | 62 | 48 | 30 | 21 |
| 129 | 546.24 | 547.3 | 38 | 14 | 5 | 21 |
| 130 | 546.24 | 547.3 | 31 | 61 | 19 | 21 |
| 131 | 560.25 | 561.3 | 49 | 45 | 22 | 21 |
| 132 | 560.25 | 561.3 | 14 | 16 | 2 | 21 |

TABLE 78

| 133 | 560.25 | 561.3 | 35 | 49 | 17 | 21 |
|---|---|---|---|---|---|---|
| 134 | 594.24 | 595.3 | 41 | 65 | 27 | 21 |
| 135 | 573.25 | 574.3 | 27 | 72 | 20 | 21 |
| 136 | 545.25 | 546.3 | 45 | 69 | 31 | 21 |
| 137 | 545.25 | 546.3 | 32 | 67 | 22 | 21 |
| 138 | 579.24 | 580.3 | 19 | 69 | 13 | 21 |
| 139 | 593.25 | 594.3 | 6 | 99 | 6 | 21 |
| 140 | 609.25 | 610.3 | 13 | 79 | 11 | 21 |
| 141 | 613.2 | 614.3 | 19 | 89 | 17 | 21 |
| 142 | 647.16 | 648.3 | 27 | 61 | 17 | 21 |
| 143 | 624.22 | 625.3 | 21 | 60 | 13 | 21 |
| 144 | 593.25 | 594.3 | 34 | 95 | 32 | 21 |
| 145 | 629.25 | 630.3 | 40 | 62 | 25 | 21 |
| 146 | 579.24 | 580.3 | 78 | 54 | 42 | 23 |
| 147 | 593.25 | 594.3 | 72 | 60 | 43 | 23 |
| 148 | 607.27 | 608.3 | 67 | 50 | 34 | 23 |
| 149 | 588.17 | 589.3 | 88 | 61 | 54 | 23 |
| 150 | 553.22 | 554.3 | 78 | 88 | 69 | 23 |
| 151 | 580.22 | 581.3 | 69 | 61 | 42 | 23 |
| 152 | 580.22 | 581.3 | 98 | 61 | 60 | 23 |
| 153 | 580.22 | 581.3 | 87 | 77 | 67 | 23 |
| 154 | 579.24 | 580.3 | 83 | 40 | 33 | 23 |
| 155 | 579.24 | 580.3 | 76 | 73 | 55 | 23 |

TABLE 79

| 156 | 593.25 | 594.3 | 78 | 69 | 54 | 23 |
|---|---|---|---|---|---|---|
| 157 | 607.27 | 608.3 | 79 | 34 | 27 | 23 |
| 158 | 607.27 | 608.3 | 70 | 60 | 42 | 23 |
| 159 | 621.25 | 622.3 | 100 | 66 | 66 | 23 |
| 160 | 621.25 | 622.3 | 100 | 59 | 59 | 23 |
| 161 | 606.24 | 607.3 | 89 | 72 | 64 | 23 |
| 162 | 610.21 | 611.3 | 81 | 73 | 59 | 23 |
| 163 | 622.13 | 623.3 | 100 | 54 | 54 | 23 |
| 164 | 604.22 | 605.3 | 88 | 62 | 55 | 23 |
| 165 | 567.24 | 568.3 | 61 | 57 | 35 | 23 |
| 166 | 603.24 | 604.3 | 100 | 62 | 62 | 23 |
| 167 | 617.25 | 618.3 | 71 | 57 | 40 | 23 |
| 168 | 603.24 | 604.3 | 46 | 17 | 8 | 23 |
| 169 | 603.24 | 604.3 | 71 | 74 | 53 | 23 |
| 170 | 603.24 | 604.3 | 67 | 53 | 36 | 23 |
| 171 | 554.22 | 555 | 74 | 74 | 55 | 23 |
| 172 | 604.24 | 605.3 | 85 | 56 | 48 | 23 |
| 173 | 605.23 | 606.3 | 34 | 66 | 22 | 23 |
| 174 | 604.14 | 605 | 81 | 64 | 52 | 23 |
| 175 | 578.24 | 579.3 | — | — | 14 | 21 |
| 176 | 578.24 | 579.3 | 57 | 71 | 40 | 21 |
| 177 | 594.24 | 595.3 | 31 | 55 | 17 | 21 |
| 178 | 608.22 | 609.3 | 29 | 63 | 18 | 21 |

TABLE 80

| 179 | 582.22 | 583.3 | 43 | 62 | 27 | 21 |
|---|---|---|---|---|---|---|
| 180 | 582.22 | 583.3 | 59 | 75 | 44 | 21 |
| 181 | 598.19 | 599.3 | 43 | 73 | 31 | 21 |
| 182 | 598.19 | 599.3 | 61 | 85 | 52 | 21 |
| 183 | 642.16 | 645.3 | 63 | 62 | 39 | 21 |

TABLE 80-continued

| | | | | | | |
|---|---|---|---|---|---|---|
| 184 | 632.21 | 633.3 | 69 | 49 | 34 | 21 |
| 185 | 632.21 | 633.3 | 66 | 64 | 42 | 21 |
| 186 | 648.21 | 649.3 | 59 | 61 | 36 | 21 |
| 187 | 648.21 | 649.3 | 46 | 62 | 29 | 21 |
| 188 | 648.21 | 649.3 | 48 | 37 | 18 | 21 |
| 189 | 608.64 | 609 | 54 | 60 | 32 | 21 |
| 190 | 589.22 | 590.3 | 29 | 77 | 22 | 21 |
| 191 | 589.22 | 590.3 | 22 | 46 | 10 | 21 |
| 192 | 640.26 | 641.3 | 53 | 71 | 38 | 21 |
| 193 | 614.24 | 615.3 | 47 | 72 | 34 | 21 |
| 194 | 614.24 | 615.3 | 43 | 68 | 29 | 21 |
| 195 | 632.15 | 633 | 53 | 75 | 40 | 21 |
| 196 | 599.18 | 600 | 17 | 89 | 15 | 21 |
| 197 | 570.18 | 571 | 43 | 65 | 28 | 21 |
| 198 | 620.20 | 621.3 | 50 | 69 | 35 | 21 |
| 199 | 528.23 | 529 | 57 | 85 | 48 | 21 |
| 200 | 528.23 | 529.3 | 20 | 77 | 15 | 21 |
| 201 | 542.24 | 543.3 | 27 | 66 | 18 | 21 |

TABLE 81

| | | | | | | |
|---|---|---|---|---|---|---|
| 202 | 614.21 | 615.3 | 44 | 65 | 29 | 21 |
| 203 | 614.21 | 615.3 | 41 | 69 | 28 | 21 |
| 204 | 660.21 | 661.3 | 36 | 72 | 26 | 21 |
| 205 | 660.21 | 661.3 | 35 | 73 | 26 | 21 |
| 206 | 618.18 | 619.3 | 46 | 59 | 27 | 21 |
| 207 | 618.18 | 619.3 | 43 | 78 | 33 | 21 |
| 208 | 618.18 | 619.3 | 39 | 69 | 27 | 21 |
| 209 | 634.15 | 635 | 42 | 65 | 27 | 21 |
| 210 | 631.15 | 635 | 43 | 45 | 19 | 21 |
| 211 | 678.12 | 681 | 47 | 56 | 26 | 21 |
| 212 | 668.18 | 669.3 | 46 | 80 | 37 | 21 |
| 213 | 668.18 | 669.3 | 41 | 81 | 33 | 21 |
| 214 | 668.18 | 669.3 | 47 | 37 | 17 | 21 |
| 215 | 684.18 | 685 | 63 | 39 | 25 | 21 |
| 216 | 614.21 | 626.3 | 46 | 85 | 39 | 21 |
| 217 | 625.19 | 626.3 | 86 | 14 | 12 | 21 |
| 218 | 678.17 | 679.3 | 24 | 6 | 1 | 21 |
| 219 | 593.25 | 594.3 | 23 | 42 | 10 | 21 |
| 220 | 593.25 | 594.3 | 38 | 6 | 2 | 21 |
| 221 | 597.23 | 598.3 | 47 | 58 | 27 | 21 |
| 222 | 597.23 | 598.3 | 31 | 36 | 11 | 21 |
| 223 | 597.23 | 598.3 | 18 | 46 | 8 | 21 |
| 224 | 613.2 | 614.3 | 48 | 71 | 34 | 21 |

TABLE 82

| | | | | | | |
|---|---|---|---|---|---|---|
| 225 | 613.2 | 614.3 | 29 | 66 | 19 | 21 |
| 226 | 657.17 | 660 | 19 | 44 | 8 | 21 |
| 227 | 609.25 | 610.3 | 38 | 38 | 14 | 21 |
| 228 | 609.25 | 610.3 | 20 | 71 | 14 | 21 |
| 229 | 647.22 | 648.3 | 57 | 34 | 19 | 21 |
| 230 | 647.22 | 648.3 | 48 | 28 | 13 | 21 |
| 231 | 663.22 | 664.3 | 49 | 29 | 14 | 21 |
| 232 | 663.22 | 664.3 | 39 | 37 | 14 | 21 |
| 233 | 604.23 | 605 | 7 | 15 | 1 | 21 |
| 234 | 625.22 | 626.3 | 35 | 18 | 6 | 21 |
| 235 | 625.22 | 626.3 | — | — | 23 | 21 |
| 236 | 621.25 | 622.3 | 12 | 66 | 8 | 21 |
| 237 | 621.25 | 622.3 | 10 | 71 | 7 | 21 |
| 238 | 632.21 | 633.3 | 39 | 80 | 31 | 21 |
| 239 | 514.21 | 515.3 | — | — | 7 | 21 |
| 240 | 599.18 | 600.3 | 35 | 20 | 7 | 21 |
| 241 | 633.14 | 630.3 | 40 | 100 | 40 | 21 |
| 242 | 633.14 | 630.3 | 50 | 54 | 27 | 21 |
| 243 | 611.21 | 612.3 | 19 | 43 | 8 | 21 |
| 244 | 657.25 | 658.3 | 58 | 69 | 40 | 21 |
| 245 | 667.22 | 664.3 | 73 | 45 | 33 | 21 |
| 246 | 599.18 | 600.3 | 11 | 100 | 11 | 21 |
| 247 | 613.2 | 614.3 | 35 | 97 | 34 | 21 |

TABLE 83

| | | | | | | |
|---|---|---|---|---|---|---|
| 248 | 714.15 | 715 | 77 | 86 | 66 | 21 |
| 249 | 638.1 | 639 | 77 | 83 | 64 | 21 |
| 250 | 648.15 | 649.3 | 20 | 59 | 12 | 21 |
| 251 | 633.14 | 634 | 100 | 58 | 58 | 21 |
| 252 | 629.19 | 630.3 | 97 | 57 | 55 | 21 |
| 254 | 565.22 | 566.3 | 100 | 90 | 90 | 22 |
| 255 | 618.13 | 619.3 | 90 | 88 | 79 | 21 |
| 256 | 586.18 | 587.3 | 68 | 95 | 65 | 21 |
| 257 | 654.1 | 655 | 66 | 84 | 55 | 21 |
| 258 | 633.14 | 634.3 | 83 | 87 | 72 | 21 |
| 259 | 646.2 | 647.3 | 76 | 82 | 62 | 21 |
| 260 | 604.17 | 605.3 | 78 | 92 | 72 | 21 |
| 261 | 604.17 | 605.3 | 74 | 87 | 64 | 21 |
| 262 | 654.16 | 655.3 | 81 | 91 | 74 | 21 |
| 263 | 670.16 | 671.3 | 79 | 91 | 72 | 21 |
| 264 | 611.17 | 612.3 | 86 | 85 | 73 | 21 |
| 265 | 579.24 | 580.3 | 100 | 96 | 96 | 21 |
| 266 | 603.24 | 604.3 | 100 | 82 | 82 | 21 |
| 267 | 632.15 | 633.3 | 100 | 88 | 88 | 21 |
| 268 | 600.19 | 601.3 | 91 | 99 | 90 | 21 |
| 269 | 668.12 | 669.3 | 91 | 86 | 78 | 21 |
| 270 | 647.16 | 648.3 | 88 | 88 | 77 | 21 |
| 271 | 660.21 | 661.3 | 92 | 84 | 77 | 21 |

TABLE 84

| | | | | | | |
|---|---|---|---|---|---|---|
| 272 | 618.18 | 619.3 | 85 | 89 | 76 | 21 |
| 273 | 618.18 | 619.3 | 81 | 86 | 70 | 21 |
| 274 | 668.18 | 669.3 | 95 | 86 | 82 | 21 |
| 275 | 684.18 | 685.3 | 87 | 92 | 80 | 21 |
| 276 | 625.19 | 626.3 | 92 | 87 | 80 | 21 |
| 277 | 593.25 | 594.3 | 100 | 94 | 94 | 23 |
| 278 | 617.25 | 618.3 | 100 | 98 | 98 | 23 |
| 279 | 564.23 | 565.3 | 99 | 76 | 75 | 21 |
| 280 | 584.17 | 585.3 | 100 | 88 | 88 | 21 |
| 281 | 618.13 | 619.3 | 100 | 86 | 86 | 21 |
| 282 | 580.22 | 581.3 | 69 | 80 | 55 | 21 |
| 283 | 572.29 | 573.3 | 100 | 80 | 80 | 21 |
| 284 | 580.22 | 581.3 | 100 | 85 | 85 | 21 |
| 285 | 551.21 | 552.3 | 71 | 64 | 45 | 21 |
| 286 | 551.21 | 552.3 | 72 | 65 | 47 | 21 |
| 287 | 516.23 | 517.3 | 45 | 60 | 27 | 21 |
| 288 | 530.24 | 531.3 | 39 | 59 | 23 | 21 |
| 289 | 530.24 | 531.3 | — | — | 68 | 21 |
| 290 | 628.14 | 631.3 | 100 | 75 | 75 | 21 |
| 291 | 618.2 | 619.3 | 100 | 82 | 82 | 21 |
| 292 | 634.19 | 635.3 | 100 | 78 | 78 | 21 |
| 293 | 606.18 | 607.3 | 100 | 83 | 83 | 21 |
| 294 | 600.19 | 601.3 | 99 | 37 | 37 | 21 |

TABLE 85

| | | | | | | |
|---|---|---|---|---|---|---|
| 295 | 620.14 | 621.3 | 98 | 74 | 73 | 21 |
| 296 | 654.1 | 655.3 | 93 | 69 | 64 | 21 |
| 297 | 566.21 | 567.3 | 96 | 71 | 68 | 21 |
| 298 | 586.18 | 587.3 | 95 | 72 | 68 | 21 |
| 299 | 646.2 | 647.3 | 88 | 92 | 81 | 21 |
| 300 | 646.2 | 647.3 | 89 | 81 | 72 | 21 |
| 301 | 604.17 | 605.3 | 87 | 93 | 81 | 21 |
| 302 | 654.16 | 655.3 | 88 | 88 | 77 | 21 |
| 303 | 670.16 | 671.3 | 85 | 100 | 85 | 21 |
| 304 | 611.17 | 612.3 | 88 | 100 | 88 | 21 |
| 306 | 595.23 | 596.3 | 59 | 100 | 59 | 21 |
| 308 | 610.21 | 611.3 | 86 | 100 | 86 | 21 |
| 309 | 599.18 | 600.3 | 78 | 98 | 76 | 21 |
| 310 | 531.24 | 532.3 | 60 | 81 | 49 | 21 |
| 311 | 643.15 | 644.3 | 85 | 89 | 76 | 21 |
| 312 | 649.2 | 650.3 | 89 | 100 | 89 | 21 |
| 313 | 590.22 | 591.3 | — | — | 52 | 21 |
| 314 | 546.24 | 547.3 | 82 | 100 | 82 | 21 |
| 315 | 566.21 | 567.3 | 100 | 82 | 82 | 23 |
| 316 | 579.24 | 580.3 | 81 | 92 | 74 | 23 |
| 317 | 593.25 | 594 | 46 | 99 | 45 | 23 |
| 318 | 608.11 | 609 | 100 | 82 | 82 | 23 |
| 319 | 603.24 | 604.3 | 63 | 100 | 63 | 23 |

TABLE 86

| | | | | | | |
|---|---|---|---|---|---|---|
| 320 | 590.13 | 591.3 | 74 | 96 | 71 | 23 |
| 321 | 649.13 | 616.3 | 77 | 100 | 77 | 21 |
| 322 | 619.13 | 616.3 | 87 | 82 | 71 | 21 |
| 323 | 643.23 | 644.3 | 100 | 76 | 76 | 21 |
| 324 | 585.17 | 586 | — | — | 92 | 21 |
| 325 | 599.18 | 600.3 | — | — | 80 | 21 |
| 326 | 700.14 | 701 | — | — | 84 | 21 |
| 327 | 634.14 | 635 | 75 | 88 | 66 | 21 |
| 328 | 619.13 | 620.3 | 100 | 85 | 85 | 21 |
| 329 | 682.16 | 683.3 | 97 | 56 | 54 | 21 |
| 330 | 630.24 | 631.3 | 70 | 58 | 41 | 21 |
| 331 | 650.21 | 651.3 | 98 | 32 | 31 | 21 |
| 332 | 664.22 | 665.3 | 8 | 37 | 3 | 21 |
| 333 | 684.17 | 685.3 | 10 | 66 | 7 | 21 |
| 334 | 718.13 | 719 | 100 | 43 | 43 | 21 |
| 335 | 643.27 | 644.5 | 9 | 49 | 4 | 21 |
| 336 | 697.17 | 698.3 | 100 | 57 | 57 | 21 |
| 337 | 674.24 | 675.3 | 8 | 25 | 2 | 21 |
| 338 | 615.24 | 616.3 | 75 | 51 | 38 | 21 |
| 339 | 615.24 | 616.3 | 89 | 45 | 40 | 21 |
| 340 | 566.24 | 567.3 | 4 | 68 | 3 | 21 |
| 341 | 580.26 | 581.3 | 86 | 53 | 46 | 21 |
| 342 | 594.69 | 595.3 | 90 | 37 | 33 | 21 |

TABLE 87

| | | | | | | |
|---|---|---|---|---|---|---|
| 343 | 594.27 | 595.3 | 100 | 41 | 41 | 21 |
| 344 | 636.32 | 637.3 | 100 | 62 | 62 | 21 |
| 345 | 644.25 | 645.3 | 100 | 18 | 18 | 21 |
| 346 | 616.22 | 617.3 | 7 | 28 | 2 | 21 |
| 347 | 610.27 | 611.3 | 100 | 48 | 48 | 21 |
| 348 | 623.26 | 624.3 | 2 | 94 | 2 | 21 |
| 349 | 595.27 | 596.3 | 21 | 55 | 12 | 21 |
| 350 | 649.2 | 650.3 | 93 | 57 | 53 | 21 |
| 352 | 661.22 | 662 | 59 | 73 | 43 | 21 |
| 353 | 707.26 | 708.3 | 95 | 59 | 56 | 21 |
| 354 | 649.2 | 650.3 | 96 | 49 | 47 | 21 |
| 355 | 663.21 | 664.3 | 100 | 49 | 49 | 21 |
| 356 | 764.17 | 765.3 | 55 | 56 | 31 | 21 |
| 357 | 698.17 | 699.3 | — | — | 16 | 21 |
| 358 | 683.16 | 684.3 | — | — | 17 | 21 |
| 359 | 679.21 | 680.3 | 89 | 52 | 46 | 21 |
| 360 | 614.24 | 615.3 | 100 | 14 | 14 | 21 |
| 361 | 634.19 | 635.3 | 46 | 58 | 27 | 21 |
| 362 | 668.15 | 669.3 | 83 | 50 | 42 | 21 |
| 363 | 630.24 | 631.3 | 62 | 84 | 52 | 21 |
| 364 | 622.3 | 623.3 | 64 | 95 | 61 | 21 |
| 365 | 630.24 | 631.3 | 73 | 83 | 61 | 21 |
| 366 | 601.22 | 602.3 | 49 | 57 | 28 | 21 |

TABLE 88

| | | | | | | |
|---|---|---|---|---|---|---|
| 367 | 601.22 | 602.3 | 52 | 87 | 45 | 21 |
| 368 | 566.24 | 567.3 | 69 | 46 | 32 | 21 |
| 369 | 580.26 | 581.3 | 59 | 82 | 48 | 21 |
| 370 | 580.26 | 581.3 | 64 | 92 | 59 | 21 |
| 371 | 678.16 | 681.3 | 98 | 66 | 65 | 21 |
| 372 | 668.21 | 669.3 | 76 | 51 | 39 | 21 |
| 373 | 684.21 | 685.3 | 100 | 83 | 83 | 21 |
| 374 | 656.2 | 657.3 | 100 | 76 | 76 | 21 |
| 375 | 616.22 | 617.3 | 100 | 73 | 73 | 23 |
| 376 | 629.25 | 630.3 | 82 | 64 | 52 | 23 |
| 377 | 643.27 | 644.3 | 46 | 78 | 36 | 23 |
| 378 | 658.13 | 659 | 100 | 80 | 80 | 23 |
| 379 | 653.25 | 684.3 | 97 | 63 | 61 | 23 |
| 380 | 640.14 | 641.3 | 100 | 60 | 60 | 23 |
| 381 | 650.21 | 651.3 | 90 | 60 | 54 | 21 |
| 382 | 670.15 | 671.3 | 76 | 90 | 68 | 21 |
| 383 | 704.12 | 705.2 | 67 | 89 | 60 | 21 |
| 384 | 616.22 | 617.3 | 82 | 47 | 39 | 21 |
| 385 | 636.19 | 637.3 | 85 | 59 | 50 | 21 |
| 386 | 696.21 | 697.2 | 79 | 93 | 73 | 21 |
| 387 | 696.21 | 697.4 | 96 | 74 | 71 | 21 |
| 388 | 654.18 | 655.3 | 97 | 75 | 73 | 21 |
| 389 | 704.18 | 705.2 | 82 | 78 | 64 | 21 |

TABLE 89

| | | | | | | |
|---|---|---|---|---|---|---|
| 390 | 720.18 | 721.4 | 90 | 79 | 71 | 21 |
| 391 | 661.19 | 663.3 | 93 | 76 | 71 | 21 |
| 392 | 629.25 | 630.3 | 93 | 72 | 67 | 21 |
| 393 | 645.25 | 646.3 | 76 | 90 | 68 | 21 |
| 394 | 683.16 | 684.3 | 69 | 51 | 35 | 21 |
| 395 | 660.22 | 661.3 | 40 | 34 | 14 | 21 |
| 396 | 649.2 | 650.3 | 56 | 64 | 36 | 21 |
| 397 | 581.25 | 582.3 | 64 | 43 | 28 | 21 |
| 398 | 693.17 | 696.4 | 30 | 63 | 19 | 21 |
| 399 | 699.22 | 700.4 | 63 | 66 | 42 | 21 |
| 400 | 640.23 | 641.5 | 18 | 34 | 6 | 21 |
| 401 | 596.25 | 597.4 | 75 | 60 | 45 | 21 |
| 402 | 669.14 | 666.3 | 100 | 78 | 78 | 21 |
| 403 | 669.14 | 666.3 | 96 | 79 | 76 | 21 |
| 404 | 693.25 | 694.3 | 100 | 82 | 82 | 21 |
| 405 | 635.18 | 636.3 | 100 | 82 | 82 | 21 |
| 406 | 649.2 | 650.3 | 100 | 80 | 80 | 21 |
| 407 | 750.15 | 751.4 | 93 | 86 | 80 | 21 |
| 408 | 684.15 | 687 | 100 | 80 | 80 | 21 |
| 409 | 669.14 | 670.3 | 100 | 100 | 100 | 21 |

TABLE 90

| Compound No. | M | Measured value (M + 1)$^+$ | Hydrolysis yield (%) | Example No. |
|---|---|---|---|---|
| 46 | 510.18 | 511.4 | 73 | 36 |
| 48 | 526.17 | 527.2 | 82 | 36 |
| 49 | 572.19 | 573.2 | 88 | 36 |
| 50 | 510.18 | 511.4 | 82 | 36 |
| 51 | 572.19 | 573.2 | 83 | 36 |

Example 38

Human in vitro IgE Antibody Production Suppressing Activity

The concentrations of IgE and IgG antibodies were measured by the following method according to the method described in the Journal of Immunology vol.146, pp.1836–1842, 1991 and the Journal of Immunology vol. 147, pp.8–13, 1991.

Concretely, lymphocyte was separated from the peripheral venous blood of healthy person by density gradient centrifugation. The obtained lymphocyte was washed, suspended in a culture liquid (RPMI-1640 (product of Gibco Co.)+10% heat-inactivated FCS (product of Whittaker Co.)+100 μg/ml streptomycin+100 U/ml penicillin G+2 mM L-glutamine) and cultured for a week in the presence of interleukin 4 (IL-4, product of GENZYME Co.) (0.1 μg/ml), anti-CD40 antibody (antiCD40Aab, product of BIO-SOURCE Co.), clone B-B20) (2 μg/ml) and interleukin 10 (IL-10, product of GENZYME Co.) (0.2 μg/ml) in the presence or absence of the compounds of the present invention described in the Tables 10 to 15 at various concentrations as test drugs.

The culture liquid was added to the culture system, the culture was continued for additional one week, and the concentrations of IgE and IgG antibodies in the supernatant were measured by sandwich ELISA method.

The measurement by ELISA method was carried out according to the known ELISA method by using rabbit anti-human IgE(ε) antibody (product of ICN Co.) as the primary antibody and biotin.anti-human IgE monoclonal antibody (G7-26, product of PharMingen Co.) as the secondary antibody for the measurement of IgE antibody concentration and anti-human IgG monoclonal antibody (G18-145, product of PharMingen Co.) as the primary antibody and biotin-donkey anti-human IgG antibody (H+L) (product of Jackson Co.) as the secondary antibody for the measurement of IgG antibody concentration, and using avidin-biotin-hourse radish peroxidase (ABC kit, product of Vector Lab.) as the enzyme and TMB (3,3',5,5'-tetramethyl-benzidine) microwell peroxidase substrate system (product of Kirkegaard & Perry Laboratories Inc.) as the substrate.

The value of IC50 and the suppressing ratio (%) at the test drug concentration of 1 μM were calculated based on the concentration attained in the absence of the compound of the present invention (reference: Ueshimna, et al. American Academy of Allergy & Immunology, 1995 Annual Meeting, Program No.818).

The results are shown in the Table 91.

TABLE 91

Antibody production suppressing action of the compound of the present invention (1 μM)

| Compound No. | IgE production suppressing ratio (%) | IgG production suppressing ratio (%) | IC50 (μM) (IgE) | IC50 (μM) (IgG) |
|---|---|---|---|---|
| 93 | 56.2 | 57.9 (−91.5) | 0.738 | >10 |
| 415 | 100 | −85.8 | 0.028 | 9.76 |
| 121 | 100 | 77.5 | 0.027 | 0.543 |
| 100 | 100 | 100 | 0.028 | 0.244 |
| 142 | 100 | 93.7 | 0.034 | 0.141 |
| 427 | 96.4 | >10 | 0.040 | >10 |
| 351 | 100 | 71.7 | <0.01 | 0.662 |
| 370 | 94.7 | −45.5 | 0.027 | >1 |
| 133 | 100 | 98.2 | 0.042 | 0.228 |
| 79 | 100 | 92.4 | 0.040 | 0.489 |
| 45 | 99.4 | −178.7 | 0.305 | 0.631 |
| 44 | 100 | 88.5 | 0.221 | 0.404 |

It has been recognized from the results shown in the Table 91 that the compounds of the present invention have IgE antibody production suppresing activity.

According, these compounds are expectable as preventives and/or therapeutic agents for allergic diseases, etc., caused by the production of IgE antibody such as bronchial asthma, allergic rhinitis, allergic conjunctivitis, atopic dermatitis, anaphylactic shock, mite allergy, pollinosis, food allergy, urticaria, ulcerative colitis, eosinophilic gastroenteritis and drug-induced rash.

Example 39

Measurement of Cytotoxicity Using Mouse Tumor Cell L929

[Procedure] The cytotoxicity action on tumor cell was measured by neutral red assay (the method described in the Journal of Tissue Culture Methodology vol.9, p.7 (1984) and Toxicology Letters, vol.24, p.119 (1985)). Concretely, L929 cells ($5 \times 10^4$ cells/ml, 10% FCS/RPMI) were added to the wells of a 96 well ELISA plate at a rate of 100 μL each and cultured for a night, and the testing compounds of respective measurement concentrations were dissolved in DMSO solution and added to the above cells. The culture was continued for 3 days, and 2.0 μL of Neutral Red was added to attain the final concentration of 0.01%. The mixture was incubated for 1 hour at 37° C., the supernatant of the cell culture product was removed and the residue was washed twice with 200 μL of PBS to remove excess Neutral Red. Thereafter, the dye taken into the cell was extracted by adding 100 μL of 50% ethanol-1% acetic acid aqueous solution and the amount of the dye was determined by measuring the absorbance at 490 nm. The cytotoxicity was determined at each concentration of the test compound taking the cytotoxicity free from the drug as 100%. The cytotoxicity at each concentration was plotted against the concentration of each test compound and the concentration of the test compound exhibiting 50% cytotoxicity (LD50) was determined. Two sets of measurement were performed for each test under the same condition and the average value was used as the test result. The results are shown in the Table 92.

TABLE 92

Cytotoxic activity of the compounds of the present invention against L929

| Compound No. | LD50 (μM) |
|---|---|
| 4 | 0.375 |
| 6 | 2.4 |
| 37 | 1.02 |
| 44 | 1.16 |
| 45 | 0.22 |
| 47 | 0.2 |
| 59 | 2.4 |
| 73 | >5 |
| 74 | >5 |
| 79 | 0.98 |
| 100 | 0.95 |
| 121 | 1.8 |
| 124 | 0.14 |
| 133 | 0.33 |
| 138 | 0.13 |
| 142 | 0.54 |
| 156 | 0.30 |
| 167 | 0.18 |
| 192 | 0.26 |
| 248 | 0.085 |
| 264 | 0.156 |
| 268 | 0.16 |
| 351 | 0.31 |
| 370 | 6.8 |

It has been recognized from the results shown in the Table 92 that the compounds of the present invention have cytotoxic action on L929.

Example 40

Carcinostatic Action on Cultured Human Cancer Cell

[Procedure] Cultured human cancer cells (39 kinds) were scattered on a 96 well plate, a solution of the testing substance (5-stage concentrations starting from $10^{-4}$ M and diluted 10 times to $10^{-8}$ M) was added thereto on the next day and the cells were cultured for 2 days. The number of the proliferated cells on each plate was determined by colorimetric quantitative analysis with sulforhodamine B. The concentration to suppress the proliferation of cell by 50% (GI50) compared with a control (free from the testing substance) was calculated and the following values (concentrations) were calculated based on the number of cells immediately before the addition of the testing substance.

TGI: concentration to suppress the proliferation to a standard cell number (free from the change of apparent number of cells)

LC50: concentration to decrease the number of cells to 50% of the standard cell number (cytocidal activity)

The proliferation-suppressing results of three testing substances 124, 257 and 983 on 9 representative cancer cell strains are collectively shown in the Tables 93 to 95.

TABLE 93

| Compound No. | Cancer cell strain | GI50 ($\mu$M) | TGI ($\mu$M) | LC50 ($\mu$M) |
|---|---|---|---|---|
| 983 | HBC-4 | 0.59 | 76 | >100 |
| | SF-539 | 0.6 | 20 | 51 |
| | HCT-15 | 0.1 | 30 | >100 |
| | NCI-H460 | 0.33 | 16 | 95 |
| | LOX-IMVI | 0.26 | 3.4 | 50 |
| | OVCAR-8 | 4.2 | 40 | >100 |
| | RXF-631L | 0.4 | 18 | 96 |
| | MKN-74 | 0.46 | 25 | >100 |
| | PC-3 | 4.5 | 31 | >100 |

TABLE 94

| Compound No. | Cancer cell strain | GI50 ($\mu$M) | TGI ($\mu$M) | LC50 ($\mu$M) |
|---|---|---|---|---|
| 124 | HBC-4 | 0.25 | 18 | 57 |
| | SF-539 | 0.13 | 26 | 57 |
| | HCT-15 | 0.17 | 17 | 58 |
| | NCI-H460 | 0.091 | 14 | 69 |
| | LOX-IMVI | 0.09 | 10 | 45 |
| | OVCAR-8 | 3.1 | 23 | 57 |
| | RXF-631L | 0.13 | 12 | 38 |
| | MKN-74 | 0.086 | 16 | >100 |
| | PC-3 | 10 | 24 | 55 |

TABLE 95

| Compound No. | Cancer cell strain | GI50 ($\mu$M) | TGI ($\mu$M) | LC50 ($\mu$M) |
|---|---|---|---|---|
| 257 | HBC-4 | <0.01 | 18 | 58 |
| | SF-539 | <0.01 | 17 | 51 |
| | HCT-15 | <0.01 | 17 | 53 |
| | NCI-H460 | <0.01 | 11 | 44 |
| | LOX-IMVI | <0.01 | 10 | 44 |
| | OVCAR-8 | <0.01 | 23 | 59 |
| | RXF-631L | <0.01 | 14 | 42 |
| | MKN-74 | <0.01 | 16 | >100 |
| | PC-3 | 10 | 26 | 69 |

It has been recognized from the results shown in the Tables 93 to 95 that the compounds of the present invention have proliferation suppressing action on main cultured human cancer cells.

The results of the Examples 39 and 40 show that the compounds of the present invention are useful also as carcinostatic agents.

POSSIBILITY OF INDUSTRIAL UTILIZATION

The anthranilic acid derivatives of the present invention or their medically permissible salts or solvates exhibit strong cytotoxic activity and IgE antibody production suppressing action. Accordingly, the anthranilic acid derivatives of the present invention are clinically applicable as a therapeutic agent for cancer or a preventive or therapeutic agent for allergic diseases.

What is claimed is:

1. The anthranilic acid derivative expressed by the following formula (1) or its pharmacologically permissible salt or solvate:

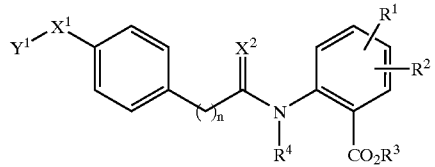
(1)

wherein, $Y^1$ is the group of the following formula (3)-1 or (3)-2:

(3)-1

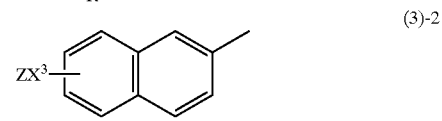
(3)-2

{in the formulas (3)-1 or (3)-2, Z is a straight-chain, branched or cyclic saturated, unsaturated or aromatic C1 to C12 hydrocarbon group substituted by one or more —$NR^{10}R^{11}$, —$COOR^{12}$, —$(C=O)NR^{13}R^{14}$, or —$(C=O)R^{15}$ (the C1 to C12 hydrocarbon group is optionally substituted by a substituent L (L is a C1 to C6 alkyl group, a halogen atom, —$NO_2$ or —CN)), a 3 to 8-membered saturated ring containing one or plural —$NR^{17}$—,—O— or —S— in the ring and optionally containing one or more —C(=O)— groups in the ring, a C1 to C4 straight or branched-chain saturated or unsaturated hydrocarbon group having one or two double bonds or triple bonds and optionally substituted by the above 3 to 8-membered ring, or a C5 to C10 straight or branched-chain saturated or unsaturated hydrocarbon group substituted by a monocyclic or bicyclic aromatic ring containing one or more heteroatoms selected from the group consisting of an oxygen, nitrogen and sulfur atom in the ring (the aromatic ring is optionally substituted by the substituent L), the groups $R^{10}$, $R^{11}$, $R^{12}$, $R^{13}$, $R^{14}$, $R^{15}$, and $R^{17}$ are each independently hydrogen atom, a straight or branched-chain C1 to C6 alkyl group which is optionally substituted, a C7 to C11 aralkyl group which is optionally substituted, a C6 to C10 aryl group which is optionally substituted (the substituent is a halogen atom, —OH, a C1 to C4 alkoxy group, —CN, —$NO_2$ or —$COOR^{18}$), or a group selected from the following formulas (4)-1, (4)-2 and (4)-3; the groups $R^{10}$ and $R^{11}$, or $R^{13}$ and $R^{14}$ may together form a 3 to 12-membered ring optionally containing one or more —O—, —S—, —$NR^{18}$— or —(C=O)— groups;

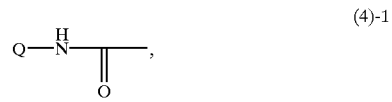
(4)-1

(4)-2

-continued (4)-3

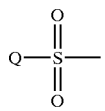

(in the formulas, Q is a C1 to C10 alkyl group which is optionally substituted, a C2 to C6 alkenyl group which is optionally substituted, a C1 to C6 alkoxy group which is optionally substituted, a C7 to C11 aralkyl group which is optionally substituted, a C7 to C11 aralkyloxy group which is optionally substituted (the substituent is a halogen atom, —OH, —CN, —NO$_2$, —COOR$^{19}$ or phenoxy group), dimethylamino group, morpholino group or a monocyclic or bicyclic aromatic hydrocarbon group which may have one or more hetero-atoms selected from oxygen, nitrogen and sulfur atoms (when a monocyclic or bicyclic aromatic hydrocarbon group which may have one or more hetero-atoms is selected in the above case, the ring is optionally substituted at arbitrary positions independently by one or plural substituents selected from the group consisting of halogen atom, —OH, —NO$_2$, —CN, —COOR$^{19}$, —NR$^{19}$R$^{20}$, straight or branched-chain C1 to C6 alkyl group, straight or branched-chain C1 to C6 alkoxy group (in this case, the substituents at adjacent positions may form an acetal bond), straight or branched-chain C1 to C6 alkylthio group, straight or branched-chain C1 to C6 alkylsulfonyl group, straight or branched-chain C1 to C6 acyl group, straight or branched-chain C1 to C6 acylamino group, trihalomethyl group, trihalomethoxy group, phenyl group, and phenoxy group which is optionally substituted by one or more halogen atoms), the groups R$^{19}$ and R$^{20}$ are each independently hydrogen atom or a C1 to C4 alkyl group), the group R$^{18}$ is hydrogen atom or a C1 to C4 alkyl group, the group X$^3$ is —(C=O)—, —O—, —S—, —(S=O)—, SO$_2$, —NR$^{21}$, *—NR$^{21}$C=O) or *—(C=O)NR$^{21}$ (the sign (*—) representing a bond means the bonding to the benzene ring or the naphthalene ring in the formula (3)-1 or the formula (3)-2), the group R$^{21}$ is hydrogen atom or a C1 to C4 hydrocarbon group which is optionally substituted by a halogen, the groups R$^5$ and R$^6$ are each independently hydrogen atom, a halogen atom, —NO$_2$, —CO$_2$H, —CN, —OR$^{22}$, —NH(C=O)R$^{22}$, —(C=O)NHR$^{22}$ or a C1 to C4 straight or branched-chain saturated or unsaturated hydrocarbon group which is optionally substituted by halogen atom, the group R$^{22}$ is hydrogen atom or a C1 to C3 hydrocarbon group which is optionally substituted by halogen atom}, the group X$^1$ is —(C=O)—, —O—, —S—, —(S=O)—, —(O=S=O)— or —CH$_2$—, the group X$^2$ is O or S, the groups R$^1$ and R$^2$ are each independently hydrogen atom, a halogen atom, —NO$_2$, —CO$_2$H, —CN, —OR$^{25}$, —NH(C=O)R$^{25}$, —(CO)NHR$^{25}$ or a C1 to C4 straight or branched-chain saturated or unsaturated hydrocarbon group which is optionally substituted by halogen atom, the group R$^{25}$ is hydrogen atom or a C1 to C3 hydrocarbon group which is optionally substituted by halogen atom, the groups R$^3$ and R$^4$ are each independently hydrogen atom or a C1 to C4 hydrocarbon group, and n is an integer of 0 to 3.

2. The anthranilic acid derivative described in claim 1 wherein the group Y$^1$ is expressed by the following formula (9)-1, (9)-2 or (9)-3, or its pharmacologically permissible salt or solvate:

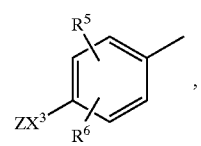

(9)-1

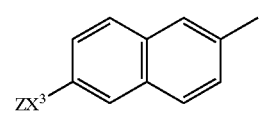

(9)-2

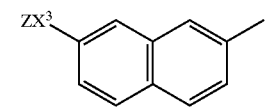

(9)-3 wherein the definitions of Z, X$^3$, R$^5$ and R$^6$ are same as those of the formula (3)-1 or the formula (3)-2.

3. The anthranilic acid derivative described in claim 1 wherein the group Z is a straight-chain, branched or cyclic saturated, unsaturated or aromatic C1 to C12 hydrocarbon group substituted by one or more —NR$^{10}$R$^{11}$, —COOR$^{12}$, —(C=O)NR$^{13}$R$^{14}$, or —(C=O)R$^{15}$ (the C1 to C12 hydrocarbon group is optionally further substituted by substituent L (L is a C1 to C6 alkyl group, halogen atom, —NO$_2$ or —CN)), or its pharmacologically permissible salt or solvate.

4. The anthranilic acid derivative described in claim 1 wherein the group Z is a saturated 3 to 8-membered ring containing one or plural —NR$^{17}$—, —O— or —S— groups and optionally containing one or more —C(=O)— groups in the ring, or a C1 to C4 straight or branched-chain saturated or unsaturated hydrocarbon group having one or two double bonds or triple bonds and optionally substituted by the above 3 to 8-membered ring, or its pharmacologically permissible salt or solvate.

5. The anthranilic acid derivative described in claim 1 wherein the group Z is a C5 to C10 straight or branched-chain saturated or unsaturated hydrocarbon group substituted by a monocyclic or bicyclic aromatic ring containing one or more hetero-atoms selected from oxygen, nitrogen and sulfur atom in the ring (the aromatic ring is optionally substituted by a substituent L), or its pharmacologically permissible salt or solvate.

6. A pharmaceutical composition composed of an anthranilic acid derivative described in any one of claims 1–5 or its pharmacologically permissible salt or solvate, and a pharmacologically permissible carrier.

7. A pharmaceutical composition described in claim 6 and having cytotoxic activity.

8. A therapeutic agent for cancer composed of the pharmaceutical composition described in claim 6.

9. A pharmaceutical composition described in claim 6 and having IgE antibody production suppressing action.

10. A preventive or therapeutic agent for allergic diseases composed of the pharmaceutical composition described in claim 6 or 9.

11. A preventive or therapeutic agent described in the claim 10 wherein said allergic diseases are bronchial asthma, allergic rhinitis, allergic conjunctivitis, atopic dermatitis, anaphylactic shock, mite allergy, pollinosis, food allergy, urticaria, ulcerative colitis, eosinophilic gastroenteritis or drug-induced rash.

* * * * *